US012435046B2

(12) United States Patent
Lucas et al.

(10) Patent No.: US 12,435,046 B2
(45) Date of Patent: Oct. 7, 2025

(54) ALKYNYL QUINAZOLINE COMPOUNDS

(71) Applicant: Black Diamond Therapeutics, Inc., Cambridge, MA (US)

(72) Inventors: Matthew C. Lucas, Lexington, MA (US); Fernando Padilla, Arlington, MA (US); Alexander Flohr, Basel (CH); Luca Arista, Riehen (CH); Elizabeth Buck, Huntington, NY (US)

(73) Assignee: Black Diamond Therapeutics, Inc., Cambridge, MA (US)

( * ) Notice: Subject to any disclaimer, the term of this patent is extended or adjusted under 35 U.S.C. 154(b) by 833 days.

(21) Appl. No.: 17/635,578

(22) PCT Filed: Aug. 14, 2020

(86) PCT No.: PCT/US2020/046425
§ 371 (c)(1),
(2) Date: Feb. 15, 2022

(87) PCT Pub. No.: WO2021/030711
PCT Pub. Date: Feb. 18, 2021

(65) Prior Publication Data

US 2022/0298120 A1 Sep. 22, 2022

Related U.S. Application Data

(60) Provisional application No. 63/065,028, filed on Aug. 13, 2020, provisional application No. 62/887,392, filed on Aug. 15, 2019.

(51) Int. Cl.

| | |
|---|---|
| ***C07D 239/94*** | (2006.01) |
| ***A61P 35/00*** | (2006.01) |
| ***C07D 401/10*** | (2006.01) |
| ***C07D 401/14*** | (2006.01) |
| ***C07D 403/10*** | (2006.01) |
| ***C07D 403/14*** | (2006.01) |
| ***C07D 405/10*** | (2006.01) |
| ***C07D 405/14*** | (2006.01) |
| ***C07D 471/04*** | (2006.01) |
| ***C07D 471/08*** | (2006.01) |
| ***C07D 491/10*** | (2006.01) |
| ***C07D 498/08*** | (2006.01) |

(52) U.S. Cl.

CPC ............ *C07D 239/94* (2013.01); *A61P 35/00* (2018.01); *C07D 401/10* (2013.01); *C07D 401/14* (2013.01); *C07D 403/10* (2013.01); *C07D 403/14* (2013.01); *C07D 405/10* (2013.01); *C07D 405/14* (2013.01); *C07D 471/04* (2013.01); *C07D 471/08* (2013.01); *C07D 491/10* (2013.01); *C07D 498/08* (2013.01)

(58) Field of Classification Search

None

See application file for complete search history.

(56) References Cited

U.S. PATENT DOCUMENTS

| | | | | |
|---|---|---|---|---|
| 6,127,374 | A | 10/2000 | Bridges | |
| 6,867,201 | B2 | 3/2005 | Kath et al. | |
| 7,294,629 | B2 * | 11/2007 | Kitano ................ | C07D 401/06 514/266.4 |
| 8,735,409 | B2 | 5/2014 | Zhang et al. | |
| 8,987,284 | B2 | 3/2015 | Shen et al. | |
| 9,090,588 | B2 | 7/2015 | Shen et al. | |
| 9,187,459 | B2 | 11/2015 | Shen et al. | |
| 9,890,187 | B2 | 2/2018 | Odysseos et al. | |
| 10,221,191 | B2 | 3/2019 | Hadari et al. | |
| 10,309,966 | B2 | 6/2019 | Sibilia | |
| 10,640,524 | B2 | 5/2020 | Odysseos et al. | |

(Continued)

FOREIGN PATENT DOCUMENTS

| | | | |
|---|---|---|---|
| CN | 1492860 | A | 4/2004 |
| CN | 101010304 | A | 8/2007 |

(Continued)

OTHER PUBLICATIONS

Sattler, M. et al., "A Closer Look at EGFR Inhibitor Resistance in Non-Small Cell Lung Cancer through the Lens of Precision Medicine," J Clin Med. Mar. 1, 2023;12(5):1936, 13 pages, doi: 10.3390/jcm12051936.

(Continued)

*Primary Examiner* — Kortney L. Klinkel
*Assistant Examiner* — Donna M Nestor
(74) *Attorney, Agent, or Firm* — Fenwick & West LLP; Heidi A. Erlacher; Christine McCain

(57) ABSTRACT

The present disclosure relates to compounds of Formula (I'):

I'

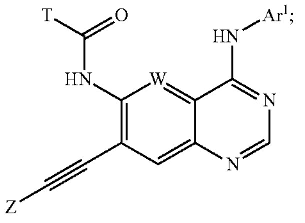

and pharmaceutically acceptable salts and stereoisomers thereof. The present disclosure also relates to methods of preparation these compounds, compositions comprising these compounds, and methods of using them in the prevention or treatment of abnormal cell growth in mammals, especially humans.

20 Claims, No Drawings

Specification includes a Sequence Listing.

(56) References Cited

U.S. PATENT DOCUMENTS

| | | | |
|---|---|---|---|
| 10,870,657 | B2 | 12/2020 | Hadari et al. |
| 11,034,672 | B1 | 6/2021 | Flohr et al. |
| 2008/0200433 | A1 | 8/2008 | Suzuki et al. |
| 2010/0087482 | A1 | 4/2010 | Haber et al. |
| 2013/0035350 | A1 | 2/2013 | Zhang et al. |
| 2015/0126537 | A1 | 5/2015 | Zhang |
| 2016/0039838 | A1 | 2/2016 | Zhang et al. |
| 2019/0382382 | A1 | 12/2019 | Shen et al. |
| 2020/0299315 | A1 | 9/2020 | Shen et al. |
| 2022/0041613 | A1 | 2/2022 | Flohr et al. |
| 2022/0273665 | A1 | 9/2022 | McGovern et al. |
| 2022/0340523 | A1 | 10/2022 | Dakin et al. |
| 2022/0363666 | A1 | 11/2022 | Flohr et al. |
| 2024/0075042 | A1 | 3/2024 | Buck et al. |
| 2024/0425492 | A1 | 12/2024 | Zhang |

FOREIGN PATENT DOCUMENTS

| | | | |
|---|---|---|---|
| CN | 101679384 | A | 3/2010 |
| CN | 102382065 | A | 3/2012 |
| CN | 102452989 | A | 5/2012 |
| CN | 102516232 | A | 6/2012 |
| CN | 102731485 | A | 10/2012 |
| CN | 103797006 | A | 5/2014 |
| CN | 103965120 | A | 8/2014 |
| CN | 103998040 | A | 8/2014 |
| CN | 104119350 | A | 10/2014 |
| CN | 105348271 | A | 2/2016 |
| CN | 108473464 | A | 8/2018 |
| CN | 109265449 | A | 1/2019 |
| CN | 113382986 | A | 9/2021 |
| EP | 1249451 | A2 | 10/2002 |
| EP | 1369418 | A1 | 12/2003 |
| EP | 1000039 | B1 | 6/2004 |
| EP | 1506962 | A2 | 2/2005 |
| EP | 1792898 | A1 | 6/2007 |
| EP | 2612860 | A1 | 7/2013 |
| JP | 5155391 | B2 | 3/2013 |
| JP | 2014518544 | A | 7/2014 |
| WO | WO-9630347 | A1 | 10/1996 |
| WO | WO-9738983 | A1 | 10/1997 |
| WO | WO-9906378 | A1 | 2/1999 |
| WO | WO-9909016 | A1 | 2/1999 |
| WO | WO-0044728 | A1 | 8/2000 |
| WO | WO-0047212 | A1 | 8/2000 |
| WO | WO-0078735 | A1 | 12/2000 |
| WO | WO-0177104 | A1 | 10/2001 |
| WO | WO-0218370 | A1 | 3/2002 |
| WO | WO-0250043 | A1 | 6/2002 |
| WO | WO-02066445 | A1 | 8/2002 |
| WO | WO-03045939 | A1 | 6/2003 |
| WO | WO-03089439 | A1 | 10/2003 |
| WO | WO-2004069791 | A2 | 8/2004 |
| WO | WO-2005026157 | A1 | 3/2005 |
| WO | WO-2005107758 | A1 | 11/2005 |
| WO | WO-2006025490 | A1 | 3/2006 |
| WO | WO-2007013950 | A2 | 2/2007 |
| WO | WO-2007055513 | A1 | 5/2007 |
| WO | WO-2007055514 | A1 | 5/2007 |
| WO | WO-2008020711 | A1 | 2/2008 |
| WO | WO-2008033749 | A2 | 3/2008 |
| WO | WO-2008150118 | A2 | 12/2008 |
| WO | WO-2008157500 | A1 | 12/2008 |
| WO | WO-2010036629 | A2 | 4/2010 |
| WO | WO-2012122058 | A2 | 9/2012 |
| WO | WO-2012136099 | A1 | 10/2012 |
| WO | WO-2013008217 | A1 | 1/2013 |
| WO | WO-2013013640 | A1 | 1/2013 |
| WO | WO-2013131424 | A1 | 9/2013 |
| WO | WO-2013173254 | A1 | 11/2013 |
| WO | WO-2014007951 | A2 | 1/2014 |
| WO | WO-2014071824 | A1 | 5/2014 |
| WO | WO-2014177038 | A1 | 11/2014 |
| WO | WO-2015043515 | A1 | 4/2015 |
| WO | WO-2015054572 | A1 | 4/2015 |
| WO | WO-2016023217 | A1 | 2/2016 |
| WO | WO-2016055982 | A1 | 4/2016 |
| WO | WO-2016105582 | A1 | 6/2016 |
| WO | WO-2016203406 | A1 | 12/2016 |
| WO | WO-2017055859 | A1 | 4/2017 |
| WO | WO-2020068867 | A1 | 4/2020 |
| WO | WO-2020068873 | A1 | 4/2020 |
| WO | WO-2021030711 | A1 | 2/2021 |
| WO | WO-2021154997 | A1 | 8/2021 |
| WO | WO-2021195206 | A1 | 9/2021 |
| WO | WO-2021213800 | A1 | 10/2021 |
| WO | WO-2022040377 | A1 | 2/2022 |
| WO | WO-2022076671 | A1 | 4/2022 |
| WO | WO-2022094464 | A1 | 5/2022 |
| WO | WO-2023049168 | A1 | 3/2023 |
| WO | WO-2025038731 | A1 | 2/2025 |

OTHER PUBLICATIONS

Wang, D.D. et al., "Personalized prediction of EGFR mutation-induced drug resistance in lung cancer," Scientific Reports, 2013;3:2855, DOI: 10.1038/srep02855, 8 pages.

Argiris, A et al., "Phase III Randomized, Placebo-Controlled Trial of Docetaxel With or Without Gefitinib in Recurrent or Metastatic Head and Neck Cancer: An Eastern Cooperative Oncology Group Trial," Journal of Clinical Oncology, 31(11):1405-1414 (2013).

Asadollahi-Baboli, M., "In silica evaluation, molecular docking and QSAR analysis of quinazoline—based EGFR-T790M inhibitors," Mol Divers, 20:729-739 (2016).

Blair et al., "Structure-guided development of affinity probes for tyrosine kinases using chemical genetics," Nature Chemical Biology, Apr. 2007, 3:229-238.

Caira, M. R., "Crystalline Polymorphism of Organic Compounds", Topics in Current Chemistry (Jan. 1, 1998); 198:163-208.

Carmi, C. et al. "Irreversible Inhibition of Epidermal Growth Factor Receptor Activity by 3-Aminopropanamides," J. Med. Chem., Jan. 26, 2012, 55:2251-2264 (including Supporting Information, 25 pages total).

CAS Registry No. 1012054-59-9, dated Apr. 4, 2008, 1 page.

CAS Registry No. 1092364-38-9, dated Dec. 31, 2008, 1 page.

CAS Registry No. 1110813-31-4, dated Feb. 23, 2009, 1 page.

CAS Registry No. 1131863-89-2, dated Apr. 3, 2009, 1 page.

CAS Registry No. 1197953-54-0, dated Dec. 17, 2009, 1 page.

CAS Registry No. 1213269-23-8, dated Mar. 23, 2010, 1 page.

CAS Registry No. 1214265-56-1, dated Mar. 24, 2010, 1 page.

CAS Registry No. 1214265-57-2, dated Mar. 24, 2010, 1 page.

CAS Registry No. 1374640-70-6, dated May 29, 2012, 1 page.

CAS Registry No. 1398833-56-1, dated Oct. 3, 2012, 1 page.

CAS Registry No. 1421373-65-0, dated Feb. 19, 2013, 1 page.

CAS Registry No. 183319-69-9, dated Nov. 22, 1996, 1 page.

CAS Registry No. 184475-35-2, dated Dec. 26, 1996, 1 page.

CAS Registry No. 187724-61-4, dated Mar. 28, 1997, 1 page.

CAS Registry No. 194423-15-9, dated Sep. 24, 1997, 1 page.

CAS Registry No. 196612-93-8, dated Oct. 31, 1997, 1 page.

CAS Registry No. 212141-54-3, dated Oct. 4, 1998, 1 page.

CAS Registry No. 231277-92-2, dated Aug. 7, 1999, 1 page.

CAS Registry No. 257933-82-7, dated Mar. 3, 2000, 1 page.

CAS Registry No. 267243-28-7, dated May 30, 2000, 1 page.

CAS Registry No. 439081-18-2, dated Jul. 17, 2002, 1 page.

CAS Registry No. 443913-73-3, dated Aug. 14, 2002, 1 page.

CAS Registry No. 451493-31-5, dated Sep. 16, 2002, 1 page.

CAS Registry No. 497839-62-0, dated Mar. 11, 2003, 1 page.

CAS Registry No. 610798-31-7, dated Oct. 30, 2003, 1 page.

CAS Registry No. 692737-80-7, dated Jun. 14, 2004, 1 page.

CAS Registry No. 698387-09-6, dated Jun. 24, 2004, 1 page.

CAS Registry No. 714971-09-2, dated Jul. 23, 2004, 1 page.

CAS Registry No. 781613-23-8, dated Nov. 16, 2004, 1 page.

CAS Registry No. 848133-17-5, dated Apr. 8, 2005, 1 page.

CAS Registry No. 848942-61-0, dated Apr. 21, 2005, 1 page.

CAS Registry No. 871026-44-7, dated Jan. 3, 2006, 1 page.

CAS Registry No. 897383-62-9, dated Jul. 28, 2006, 1 page.

CAS Registry No. 934660-93-2, dated May 13, 2007, 1 page.

(56) References Cited

OTHER PUBLICATIONS

Dermer, G.B., "Another Anniversary for the War on Cancer," Bio/Technology, 12:320, 1 page (Mar. 1994).
Freshney R.I., et al., "Culture of Animal Cells," A Manual of Basic Technique, 1983, Alan R. Liss, Inc., New York, p. 4.
Golub, T. R., et al., "Molecular classification of cancer: class discovery and class prediction by gene expression monitoring", Science (1999); 286: 531-537.
Martins, R. G. et al., "Cisplatin and Radiotherapy With or Without Erlotinib in Locally Advanced Squamous Cell Carcinoma of the Head and Neck: A Randomized Phase II Trial," Journal of Clinical Oncology, 31(11):1415-1421 (2013).
Peereboom, D. M. et al., "Phase II trial of erlotinib with temozolomide and radiation in patients with newly diagnosed glioblastoma multiforme," J Neurooncol, 98:93-99 (2010).
Petrylak, D. P. et al., "Results of the Southwest Oncology Group phase II evaluation (study S0031) of ZD1839 for advanced transitional cell carcinoma of the urothelium," Southwest Oncology Group, 105:317-321 (2009); doi:10.1111/j.1464-41OX.2009.08799.x.
Philips, G. K. et al., "A phase II trial of cisplatin (C), gemcitabine (G) and gefitinib for advanced urothelial tract carcinoma: results of Cancer and Leukemia Group B (CALGB) 90102," Annals of Oncology, 20:1074-1079 (2009).
Reardon, D.A. et al., "Phase I/randomized phase II study of afatinib, an irreversible ErbB family blocker, with or without protracted temozolomide in adults with recurrent glioblastoma," Neuro-Oncology, Advance Access published Aug. 19, 2014, 10 pages; final publication in Neuro Oncol., Mar. 2015;17(3):430-9. doi: 10.1093/neuonc/nou160.
Shen, W. et al. "A41 EO1001: A First-in-Class Irreversible Pan-ErbB Inhibitor with Excellent Brain Penetration," Journal of Thoracic Oncology, 15(2 Suppl):S26, Abstract A41 (Feb. 2020).
Shen, W. et al. "NT113, a potent and selective pan-ErbB inhibitor, is efficacious in vivo and has high brain penetrance," [abstract]. In: Proceedings of the 104th Annual Meeting of the American Association for Cancer Research; Apr. 6-10, 2013; Washington, DC. Philadelphia (PA): AACR; Cancer Res., 73(8 Suppl):Abstract nr 2089 (2013); doi:10.1158/1538-7445.AM2013-2089.
Simone, J. V. (1996) "Introduction" in Cecil Textbook of Medicine. 20th Ed., vol. I . J. Claude Bennet and F. Plum (Eds.) W.B. Sauders Co.; pp. 1004-1010.
Van Den Bent, M. J. et al., "Randomized Phase II Trial of Erlotinib Versus Temozolomide or Carmustine in Recurrent Glioblastoma: EORTC Brain Tumor Group Study 26034," J Clin Oncol, 27:1268-1274 (2009).
Yin, D. et al. "Studying the Conformation of a Receptor Tyrosine Kinase in Solution by Inhibitor-Based Spin Labeling," Angew Chem Int Ed Engl., 56(29):8417-8421, with Supporting Information, 24 pages (Jul. 10, 2017). doi: 10.1002/anie.201703154. Epub Jun. 19, 2017.
Yoshida, Y. et al. "NT113, a pan-ERBB Inhibitor with High Brain Penetrance, Inhibits the Growth of Glioblastoma Xenografts with EGFR Amplification," Mol. Cancer Ther., Dec. 2014, 13(12):2919-29.

* cited by examiner

SEQUENCE LISTING

<160> NUMBER OF SEQ ID NOS: 8

<210> SEQ ID NO 1
<211> LENGTH: 1210
<212> TYPE: PRT
<213> ORGANISM: Homo sapien

<400> SEQUENCE: 1

```
Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365
```

-continued

```
Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Lys Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
    690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
        755                 760                 765

Val Asp Asn Pro His Val Cys Arg Leu Leu Gly Ile Cys Leu Thr Ser
    770                 775                 780

Thr Val Gln Leu Ile Thr Gln Leu Met Pro Phe Gly Cys Leu Leu Asp
```

-continued

```
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
        835                 840                 845

Gln His Val Lys Ile Thr Asp Phe Gly Leu Ala Lys Leu Leu Gly Ala
    850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
        915                 920                 925

Lys Gly Glu Arg Leu Pro Gln Pro Pro Ile Cys Thr Ile Asp Val Tyr
    930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala  Leu Met Asp Glu Glu  Asp Met Asp
        995                 1000                1005

Asp Val  Val Asp Ala Asp Glu  Tyr Leu Ile Pro Gln  Gln Gly Phe
    1010                1015                1020

Phe Ser  Ser Pro Ser Thr Ser  Arg Thr Pro Leu Leu  Ser Ser Leu
    1025                1030                1035

Ser Ala  Thr Ser Asn Asn Ser  Thr Val Ala Cys Ile  Asp Arg Asn
    1040                1045                1050

Gly Leu  Gln Ser Cys Pro Ile  Lys Glu Asp Ser Phe  Leu Gln Arg
    1055                1060                1065

Tyr Ser  Ser Asp Pro Thr Gly  Ala Leu Thr Glu Asp  Ser Ile Asp
    1070                1075                1080

Asp Thr  Phe Leu Pro Val Pro  Glu Tyr Ile Asn Gln  Ser Val Pro
    1085                1090                1095

Lys Arg  Pro Ala Gly Ser Val  Gln Asn Pro Val Tyr  His Asn Gln
    1100                1105                1110

Pro Leu  Asn Pro Ala Pro Ser  Arg Asp Pro His Tyr  Gln Asp Pro
    1115                1120                1125

His Ser  Thr Ala Val Gly Asn  Pro Glu Tyr Leu Asn  Thr Val Gln
    1130                1135                1140

Pro Thr  Cys Val Asn Ser Thr  Phe Asp Ser Pro Ala  His Trp Ala
    1145                1150                1155

Gln Lys  Gly Ser His Gln Ile  Ser Leu Asp Asn Pro  Asp Tyr Gln
    1160                1165                1170

Gln Asp  Phe Phe Pro Lys Glu  Ala Lys Pro Asn Gly  Ile Phe Lys
    1175                1180                1185

Gly Ser  Thr Ala Glu Asn Ala  Glu Tyr Leu Arg Val  Ala Pro Gln
    1190                1195                1200
```

```
Ser Ser  Glu Phe Ile Gly Ala
    1205                 1210


<210> SEQ ID NO 2
<211> LENGTH: 1255
<212> TYPE: PRT
<213> ORGANISM: Homo sapien

<400> SEQUENCE: 2

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
```

```
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
            660                 665                 670

Ile Leu Ile Lys Arg Arg Gln Gln Lys Ile Arg Lys Tyr Thr Met Arg
        675                 680                 685

Arg Leu Leu Gln Glu Thr Glu Leu Val Glu Pro Leu Thr Pro Ser Gly
    690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
        755                 760                 765

Asp Glu Ala Tyr Val Met Ala Gly Val Gly Ser Pro Tyr Val Ser Arg
    770                 775                 780
```

-continued

```
Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
        835                 840                 845

Arg Asn Val Leu Val Lys Ser Pro Asn His Val Lys Ile Thr Asp Phe
    850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
        915                 920                 925

Arg Glu Ile Pro Asp Leu Leu Glu Lys Gly Glu Arg Leu Pro Gln Pro
    930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu  Asp Ser Thr Phe Tyr  Arg Ser Leu
        995                 1000                1005

Leu Glu  Asp Asp Asp Met Gly  Asp Leu Val Asp Ala  Glu Glu Tyr
    1010                1015                1020

Leu Val  Pro Gln Gln Gly Phe  Phe Cys Pro Asp Pro  Ala Pro Gly
    1025                1030                1035

Ala Gly  Gly Met Val His His  Arg His Arg Ser Ser  Ser Thr Arg
    1040                1045                1050

Ser Gly  Gly Gly Asp Leu Thr  Leu Gly Leu Glu Pro  Ser Glu Glu
    1055                1060                1065

Glu Ala  Pro Arg Ser Pro Leu  Ala Pro Ser Glu Gly  Ala Gly Ser
    1070                1075                1080

Asp Val  Phe Asp Gly Asp Leu  Gly Met Gly Ala Ala  Lys Gly Leu
    1085                1090                1095

Gln Ser  Leu Pro Thr His Asp  Pro Ser Pro Leu Gln  Arg Tyr Ser
    1100                1105                1110

Glu Asp  Pro Thr Val Pro Leu  Pro Ser Glu Thr Asp  Gly Tyr Val
    1115                1120                1125

Ala Pro  Leu Thr Cys Ser Pro  Gln Pro Glu Tyr Val  Asn Gln Pro
    1130                1135                1140

Asp Val  Arg Pro Gln Pro Pro  Ser Pro Arg Glu Gly  Pro Leu Pro
    1145                1150                1155

Ala Ala  Arg Pro Ala Gly Ala  Thr Leu Glu Arg Pro  Lys Thr Leu
    1160                1165                1170

Ser Pro  Gly Lys Asn Gly Val  Val Lys Asp Val Phe  Ala Phe Gly
    1175                1180                1185
```

```
Gly Ala  Val Glu Asn Pro Glu  Tyr Leu Thr Pro Gln  Gly Gly Ala
    1190                 1195                 1200

Ala Pro  Gln Pro His Pro Pro  Pro Ala Phe Ser Pro  Ala Phe Asp
    1205                 1210                 1215

Asn Leu  Tyr Tyr Trp Asp Gln  Asp Pro Pro Glu Arg  Gly Ala Pro
    1220                 1225                 1230

Pro Ser  Thr Phe Lys Gly Thr  Pro Thr Ala Glu Asn  Pro Glu Tyr
    1235                 1240                 1245

Leu Gly  Leu Asp Val Pro Val
    1250                 1255


<210> SEQ ID NO 3
<211> LENGTH: 1225
<212> TYPE: PRT
<213> ORGANISM: Homo sapien

<400> SEQUENCE: 3

Met Lys Leu Arg Leu Pro Ala Ser Pro Glu Thr His Leu Asp Met Leu
1               5                   10                  15

Arg His Leu Tyr Gln Gly Cys Gln Val Val Gln Gly Asn Leu Glu Leu
            20                  25                  30

Thr Tyr Leu Pro Thr Asn Ala Ser Leu Ser Phe Leu Gln Asp Ile Gln
        35                  40                  45

Glu Val Gln Gly Tyr Val Leu Ile Ala His Asn Gln Val Arg Gln Val
    50                  55                  60

Pro Leu Gln Arg Leu Arg Ile Val Arg Gly Thr Gln Leu Phe Glu Asp
65                  70                  75                  80

Asn Tyr Ala Leu Ala Val Leu Asp Asn Gly Asp Pro Leu Asn Asn Thr
                85                  90                  95

Thr Pro Val Thr Gly Ala Ser Pro Gly Gly Leu Arg Glu Leu Gln Leu
            100                 105                 110

Arg Ser Leu Thr Glu Ile Leu Lys Gly Gly Val Leu Ile Gln Arg Asn
        115                 120                 125

Pro Gln Leu Cys Tyr Gln Asp Thr Ile Leu Trp Lys Asp Ile Phe His
    130                 135                 140

Lys Asn Asn Gln Leu Ala Leu Thr Leu Ile Asp Thr Asn Arg Ser Arg
145                 150                 155                 160

Ala Cys His Pro Cys Ser Pro Met Cys Lys Gly Ser Arg Cys Trp Gly
                165                 170                 175

Glu Ser Ser Glu Asp Cys Gln Ser Leu Thr Arg Thr Val Cys Ala Gly
            180                 185                 190

Gly Cys Ala Arg Cys Lys Gly Pro Leu Pro Thr Asp Cys Cys His Glu
        195                 200                 205

Gln Cys Ala Ala Gly Cys Thr Gly Pro Lys His Ser Asp Cys Leu Ala
    210                 215                 220

Cys Leu His Phe Asn His Ser Gly Ile Cys Glu Leu His Cys Pro Ala
225                 230                 235                 240

Leu Val Thr Tyr Asn Thr Asp Thr Phe Glu Ser Met Pro Asn Pro Glu
                245                 250                 255

Gly Arg Tyr Thr Phe Gly Ala Ser Cys Val Thr Ala Cys Pro Tyr Asn
            260                 265                 270

Tyr Leu Ser Thr Asp Val Gly Ser Cys Thr Leu Val Cys Pro Leu His
        275                 280                 285

Asn Gln Glu Val Thr Ala Glu Asp Gly Thr Gln Arg Cys Glu Lys Cys
    290                 295                 300
```

```
Ser Lys Pro Cys Ala Arg Val Cys Tyr Gly Leu Gly Met Glu His Leu
305                 310                 315                 320

Arg Glu Val Arg Ala Val Thr Ser Ala Asn Ile Gln Glu Phe Ala Gly
                325                 330                 335

Cys Lys Lys Ile Phe Gly Ser Leu Ala Phe Leu Pro Glu Ser Phe Asp
            340                 345                 350

Gly Asp Pro Ala Ser Asn Thr Ala Pro Leu Gln Pro Glu Gln Leu Gln
        355                 360                 365

Val Phe Glu Thr Leu Glu Glu Ile Thr Gly Tyr Leu Tyr Ile Ser Ala
    370                 375                 380

Trp Pro Asp Ser Leu Pro Asp Leu Ser Val Phe Gln Asn Leu Gln Val
385                 390                 395                 400

Ile Arg Gly Arg Ile Leu His Asn Gly Ala Tyr Ser Leu Thr Leu Gln
                405                 410                 415

Gly Leu Gly Ile Ser Trp Leu Gly Leu Arg Ser Leu Arg Glu Leu Gly
            420                 425                 430

Ser Gly Leu Ala Leu Ile His His Asn Thr His Leu Cys Phe Val His
        435                 440                 445

Thr Val Pro Trp Asp Gln Leu Phe Arg Asn Pro His Gln Ala Leu Leu
    450                 455                 460

His Thr Ala Asn Arg Pro Glu Asp Glu Cys Val Gly Glu Gly Leu Ala
465                 470                 475                 480

Cys His Gln Leu Cys Ala Arg Gly His Cys Trp Gly Pro Gly Pro Thr
                485                 490                 495

Gln Cys Val Asn Cys Ser Gln Phe Leu Arg Gly Gln Glu Cys Val Glu
            500                 505                 510

Glu Cys Arg Val Leu Gln Gly Leu Pro Arg Glu Tyr Val Asn Ala Arg
        515                 520                 525

His Cys Leu Pro Cys His Pro Glu Cys Gln Pro Gln Asn Gly Ser Val
    530                 535                 540

Thr Cys Phe Gly Pro Glu Ala Asp Gln Cys Val Ala Cys Ala His Tyr
545                 550                 555                 560

Lys Asp Pro Pro Phe Cys Val Ala Arg Cys Pro Ser Gly Val Lys Pro
                565                 570                 575

Asp Leu Ser Tyr Met Pro Ile Trp Lys Phe Pro Asp Glu Glu Gly Ala
            580                 585                 590

Cys Gln Pro Cys Pro Ile Asn Cys Thr His Ser Cys Val Asp Leu Asp
        595                 600                 605

Asp Lys Gly Cys Pro Ala Glu Gln Arg Ala Ser Pro Leu Thr Ser Ile
    610                 615                 620

Ile Ser Ala Val Val Gly Ile Leu Leu Val Val Val Leu Gly Val Val
625                 630                 635                 640

Phe Gly Ile Leu Ile Lys Arg Arg Gln Gln Lys Ile Arg Lys Tyr Thr
                645                 650                 655

Met Arg Arg Leu Leu Gln Glu Thr Glu Leu Val Glu Pro Leu Thr Pro
            660                 665                 670

Ser Gly Ala Met Pro Asn Gln Ala Gln Met Arg Ile Leu Lys Glu Thr
        675                 680                 685

Glu Leu Arg Lys Val Lys Val Leu Gly Ser Gly Ala Phe Gly Thr Val
    690                 695                 700

Tyr Lys Gly Ile Trp Ile Pro Asp Gly Glu Asn Val Lys Ile Pro Val
705                 710                 715                 720
```

```
Ala Ile Lys Val Leu Arg Glu Asn Thr Ser Pro Lys Ala Asn Lys Glu
                725                 730                 735

Ile Leu Asp Glu Ala Tyr Val Met Ala Gly Val Gly Ser Pro Tyr Val
            740                 745                 750

Ser Arg Leu Leu Gly Ile Cys Leu Thr Ser Thr Val Gln Leu Val Thr
        755                 760                 765

Gln Leu Met Pro Tyr Gly Cys Leu Leu Asp His Val Arg Glu Asn Arg
    770                 775                 780

Gly Arg Leu Gly Ser Gln Asp Leu Leu Asn Trp Cys Met Gln Ile Ala
785                 790                 795                 800

Lys Gly Met Ser Tyr Leu Glu Asp Val Arg Leu Val His Arg Asp Leu
                805                 810                 815

Ala Ala Arg Asn Val Leu Val Lys Ser Pro Asn His Val Lys Ile Thr
            820                 825                 830

Asp Phe Gly Leu Ala Arg Leu Leu Asp Ile Asp Glu Thr Glu Tyr His
        835                 840                 845

Ala Asp Gly Gly Lys Val Pro Ile Lys Trp Met Ala Leu Glu Ser Ile
    850                 855                 860

Leu Arg Arg Arg Phe Thr His Gln Ser Asp Val Trp Ser Tyr Gly Val
865                 870                 875                 880

Thr Val Trp Glu Leu Met Thr Phe Gly Ala Lys Pro Tyr Asp Gly Ile
                885                 890                 895

Pro Ala Arg Glu Ile Pro Asp Leu Leu Glu Lys Gly Glu Arg Leu Pro
            900                 905                 910

Gln Pro Pro Ile Cys Thr Ile Asp Val Tyr Met Ile Met Val Lys Cys
        915                 920                 925

Trp Met Ile Asp Ser Glu Cys Arg Pro Arg Phe Arg Glu Leu Val Ser
    930                 935                 940

Glu Phe Ser Arg Met Ala Arg Asp Pro Gln Arg Phe Val Val Ile Gln
945                 950                 955                 960

Asn Glu Asp Leu Gly Pro Ala Ser Pro Leu Asp Ser Thr Phe Tyr Arg
                965                 970                 975

Ser Leu Leu Glu Asp Asp Asp Met Gly Asp Leu Val Asp Ala Glu Glu
            980                 985                 990

Tyr Leu Val Pro Gln Gln Gly Phe  Phe Cys Pro Asp Pro  Ala Pro Gly
        995                 1000                1005

Ala Gly  Gly Met Val His His  Arg His Arg Ser Ser  Ser Thr Arg
    1010                1015                1020

Ser Gly  Gly Gly Asp Leu Thr  Leu Gly Leu Glu Pro  Ser Glu Glu
    1025                1030                1035

Glu Ala  Pro Arg Ser Pro Leu  Ala Pro Ser Glu Gly  Ala Gly Ser
    1040                1045                1050

Asp Val  Phe Asp Gly Asp Leu  Gly Met Gly Ala Ala  Lys Gly Leu
    1055                1060                1065

Gln Ser  Leu Pro Thr His Asp  Pro Ser Pro Leu Gln  Arg Tyr Ser
    1070                1075                1080

Glu Asp  Pro Thr Val Pro Leu  Pro Ser Glu Thr Asp  Gly Tyr Val
    1085                1090                1095

Ala Pro  Leu Thr Cys Ser Pro  Gln Pro Glu Tyr Val  Asn Gln Pro
    1100                1105                1110

Asp Val  Arg Pro Gln Pro Pro  Ser Pro Arg Glu Gly  Pro Leu Pro
    1115                1120                1125

Ala Ala  Arg Pro Ala Gly Ala  Thr Leu Glu Arg Pro  Lys Thr Leu
```

```
    1130                1135                1140

Ser Pro  Gly Lys Asn Gly Val  Val Lys Asp Val Phe  Ala Phe Gly
    1145                1150                1155

Gly Ala  Val Glu Asn Pro Glu  Tyr Leu Thr Pro Gln  Gly Gly Ala
    1160                1165                1170

Ala Pro  Gln Pro His Pro Pro  Pro Ala Phe Ser Pro  Ala Phe Asp
    1175                1180                1185

Asn Leu  Tyr Tyr Trp Asp Gln  Asp Pro Pro Glu Arg  Gly Ala Pro
    1190                1195                1200

Pro Ser  Thr Phe Lys Gly Thr  Pro Thr Ala Glu Asn  Pro Glu Tyr
    1205                1210                1215

Leu Gly  Leu Asp Val Pro Val
    1220                1225


<210> SEQ ID NO 4
<211> LENGTH: 1240
<212> TYPE: PRT
<213> ORGANISM: Homo sapien

<400> SEQUENCE: 4

Met Pro Arg Gly Ser Trp Lys Pro Gln Val Cys Thr Gly Thr Asp Met
1               5                   10                  15

Lys Leu Arg Leu Pro Ala Ser Pro Glu Thr His Leu Asp Met Leu Arg
            20                  25                  30

His Leu Tyr Gln Gly Cys Gln Val Val Gln Gly Asn Leu Glu Leu Thr
        35                  40                  45

Tyr Leu Pro Thr Asn Ala Ser Leu Ser Phe Leu Gln Asp Ile Gln Glu
    50                  55                  60

Val Gln Gly Tyr Val Leu Ile Ala His Asn Gln Val Arg Gln Val Pro
65                  70                  75                  80

Leu Gln Arg Leu Arg Ile Val Arg Gly Thr Gln Leu Phe Glu Asp Asn
                85                  90                  95

Tyr Ala Leu Ala Val Leu Asp Asn Gly Asp Pro Leu Asn Asn Thr Thr
            100                 105                 110

Pro Val Thr Gly Ala Ser Pro Gly Gly Leu Arg Glu Leu Gln Leu Arg
        115                 120                 125

Ser Leu Thr Glu Ile Leu Lys Gly Gly Val Leu Ile Gln Arg Asn Pro
    130                 135                 140

Gln Leu Cys Tyr Gln Asp Thr Ile Leu Trp Lys Asp Ile Phe His Lys
145                 150                 155                 160

Asn Asn Gln Leu Ala Leu Thr Leu Ile Asp Thr Asn Arg Ser Arg Ala
                165                 170                 175

Cys His Pro Cys Ser Pro Met Cys Lys Gly Ser Arg Cys Trp Gly Glu
            180                 185                 190

Ser Ser Glu Asp Cys Gln Ser Leu Thr Arg Thr Val Cys Ala Gly Gly
        195                 200                 205

Cys Ala Arg Cys Lys Gly Pro Leu Pro Thr Asp Cys Cys His Glu Gln
    210                 215                 220

Cys Ala Ala Gly Cys Thr Gly Pro Lys His Ser Asp Cys Leu Ala Cys
225                 230                 235                 240

Leu His Phe Asn His Ser Gly Ile Cys Glu Leu His Cys Pro Ala Leu
                245                 250                 255

Val Thr Tyr Asn Thr Asp Thr Phe Glu Ser Met Pro Asn Pro Glu Gly
            260                 265                 270
```

```
Arg Tyr Thr Phe Gly Ala Ser Cys Val Thr Ala Cys Pro Tyr Asn Tyr
        275                 280                 285

Leu Ser Thr Asp Val Gly Ser Cys Thr Leu Val Cys Pro Leu His Asn
    290                 295                 300

Gln Glu Val Thr Ala Glu Asp Gly Thr Gln Arg Cys Glu Lys Cys Ser
305                 310                 315                 320

Lys Pro Cys Ala Arg Val Cys Tyr Gly Leu Gly Met Glu His Leu Arg
                325                 330                 335

Glu Val Arg Ala Val Thr Ser Ala Asn Ile Gln Glu Phe Ala Gly Cys
            340                 345                 350

Lys Lys Ile Phe Gly Ser Leu Ala Phe Leu Pro Glu Ser Phe Asp Gly
        355                 360                 365

Asp Pro Ala Ser Asn Thr Ala Pro Leu Gln Pro Glu Gln Leu Gln Val
    370                 375                 380

Phe Glu Thr Leu Glu Glu Ile Thr Gly Tyr Leu Tyr Ile Ser Ala Trp
385                 390                 395                 400

Pro Asp Ser Leu Pro Asp Leu Ser Val Phe Gln Asn Leu Gln Val Ile
                405                 410                 415

Arg Gly Arg Ile Leu His Asn Gly Ala Tyr Ser Leu Thr Leu Gln Gly
            420                 425                 430

Leu Gly Ile Ser Trp Leu Gly Leu Arg Ser Leu Arg Glu Leu Gly Ser
        435                 440                 445

Gly Leu Ala Leu Ile His His Asn Thr His Leu Cys Phe Val His Thr
    450                 455                 460

Val Pro Trp Asp Gln Leu Phe Arg Asn Pro His Gln Ala Leu Leu His
465                 470                 475                 480

Thr Ala Asn Arg Pro Glu Asp Glu Cys Val Gly Glu Gly Leu Ala Cys
                485                 490                 495

His Gln Leu Cys Ala Arg Gly His Cys Trp Gly Pro Gly Pro Thr Gln
            500                 505                 510

Cys Val Asn Cys Ser Gln Phe Leu Arg Gly Gln Glu Cys Val Glu Glu
        515                 520                 525

Cys Arg Val Leu Gln Gly Leu Pro Arg Glu Tyr Val Asn Ala Arg His
    530                 535                 540

Cys Leu Pro Cys His Pro Glu Cys Gln Pro Gln Asn Gly Ser Val Thr
545                 550                 555                 560

Cys Phe Gly Pro Glu Ala Asp Gln Cys Val Ala Cys Ala His Tyr Lys
                565                 570                 575

Asp Pro Pro Phe Cys Val Ala Arg Cys Pro Ser Gly Val Lys Pro Asp
            580                 585                 590

Leu Ser Tyr Met Pro Ile Trp Lys Phe Pro Asp Glu Glu Gly Ala Cys
        595                 600                 605

Gln Pro Cys Pro Ile Asn Cys Thr His Ser Cys Val Asp Leu Asp Asp
    610                 615                 620

Lys Gly Cys Pro Ala Glu Gln Arg Ala Ser Pro Leu Thr Ser Ile Ile
625                 630                 635                 640

Ser Ala Val Val Gly Ile Leu Leu Val Val Val Leu Gly Val Val Phe
                645                 650                 655

Gly Ile Leu Ile Lys Arg Arg Gln Gln Lys Ile Arg Lys Tyr Thr Met
            660                 665                 670

Arg Arg Leu Leu Gln Glu Thr Glu Leu Val Glu Pro Leu Thr Pro Ser
        675                 680                 685

Gly Ala Met Pro Asn Gln Ala Gln Met Arg Ile Leu Lys Glu Thr Glu
```

```
    690                 695                 700

Leu Arg Lys Val Lys Val Leu Gly Ser Gly Ala Phe Gly Thr Val Tyr
705                 710                 715                 720

Lys Gly Ile Trp Ile Pro Asp Gly Glu Asn Val Lys Ile Pro Val Ala
                725                 730                 735

Ile Lys Val Leu Arg Glu Asn Thr Ser Pro Lys Ala Asn Lys Glu Ile
            740                 745                 750

Leu Asp Glu Ala Tyr Val Met Ala Gly Val Gly Ser Pro Tyr Val Ser
        755                 760                 765

Arg Leu Leu Gly Ile Cys Leu Thr Ser Thr Val Gln Leu Val Thr Gln
    770                 775                 780

Leu Met Pro Tyr Gly Cys Leu Leu Asp His Val Arg Glu Asn Arg Gly
785                 790                 795                 800

Arg Leu Gly Ser Gln Asp Leu Leu Asn Trp Cys Met Gln Ile Ala Lys
                805                 810                 815

Gly Met Ser Tyr Leu Glu Asp Val Arg Leu Val His Arg Asp Leu Ala
            820                 825                 830

Ala Arg Asn Val Leu Val Lys Ser Pro Asn His Val Lys Ile Thr Asp
        835                 840                 845

Phe Gly Leu Ala Arg Leu Leu Asp Ile Asp Glu Thr Glu Tyr His Ala
    850                 855                 860

Asp Gly Gly Lys Val Pro Ile Lys Trp Met Ala Leu Glu Ser Ile Leu
865                 870                 875                 880

Arg Arg Arg Phe Thr His Gln Ser Asp Val Trp Ser Tyr Gly Val Thr
                885                 890                 895

Val Trp Glu Leu Met Thr Phe Gly Ala Lys Pro Tyr Asp Gly Ile Pro
            900                 905                 910

Ala Arg Glu Ile Pro Asp Leu Leu Glu Lys Gly Glu Arg Leu Pro Gln
        915                 920                 925

Pro Pro Ile Cys Thr Ile Asp Val Tyr Met Ile Met Val Lys Cys Trp
    930                 935                 940

Met Ile Asp Ser Glu Cys Arg Pro Arg Phe Arg Glu Leu Val Ser Glu
945                 950                 955                 960

Phe Ser Arg Met Ala Arg Asp Pro Gln Arg Phe Val Val Ile Gln Asn
                965                 970                 975

Glu Asp Leu Gly Pro Ala Ser Pro Leu Asp Ser Thr Phe Tyr Arg Ser
            980                 985                 990

Leu Leu Glu Asp Asp Asp Met Gly  Asp Leu Val Asp Ala  Glu Glu Tyr
        995                 1000                1005

Leu Val  Pro Gln Gln Gly Phe  Phe Cys Pro Asp Pro  Ala Pro Gly
    1010                1015                1020

Ala Gly  Gly Met Val His His  Arg His Arg Ser Ser  Ser Thr Arg
    1025                1030                1035

Ser Gly  Gly Gly Asp Leu Thr  Leu Gly Leu Glu Pro  Ser Glu Glu
    1040                1045                1050

Glu Ala  Pro Arg Ser Pro Leu  Ala Pro Ser Glu Gly  Ala Gly Ser
    1055                1060                1065

Asp Val  Phe Asp Gly Asp Leu  Gly Met Gly Ala Ala  Lys Gly Leu
    1070                1075                1080

Gln Ser  Leu Pro Thr His Asp  Pro Ser Pro Leu Gln  Arg Tyr Ser
    1085                1090                1095

Glu Asp  Pro Thr Val Pro Leu  Pro Ser Glu Thr Asp  Gly Tyr Val
    1100                1105                1110
```

```
Ala Pro  Leu Thr Cys Ser Pro  Gln Pro Glu Tyr Val  Asn Gln Pro
    1115                 1120                 1125

Asp Val  Arg Pro Gln Pro Pro  Ser Pro Arg Glu Gly  Pro Leu Pro
    1130                 1135                 1140

Ala Ala  Arg Pro Ala Gly Ala  Thr Leu Glu Arg Pro  Lys Thr Leu
    1145                 1150                 1155

Ser Pro  Gly Lys Asn Gly Val  Val Lys Asp Val Phe  Ala Phe Gly
    1160                 1165                 1170

Gly Ala  Val Glu Asn Pro Glu  Tyr Leu Thr Pro Gln  Gly Gly Ala
    1175                 1180                 1185

Ala Pro  Gln Pro His Pro Pro  Pro Ala Phe Ser Pro  Ala Phe Asp
    1190                 1195                 1200

Asn Leu  Tyr Tyr Trp Asp Gln  Asp Pro Pro Glu Arg  Gly Ala Pro
    1205                 1210                 1215

Pro Ser  Thr Phe Lys Gly Thr  Pro Thr Ala Glu Asn  Pro Glu Tyr
    1220                 1225                 1230

Leu Gly  Leu Asp Val Pro Val
    1235                 1240


<210> SEQ ID NO 5
<211> LENGTH: 1055
<212> TYPE: PRT
<213> ORGANISM: Homo sapien

<400> SEQUENCE: 5

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
```

-continued

```
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655
```

```
Ala Val Val Gly Ile Leu Leu Val Val Val Leu Gly Val Val Phe Gly
            660                 665                 670

Ile Leu Ile Lys Arg Arg Gln Gln Lys Ile Arg Lys Tyr Thr Met Arg
        675                 680                 685

Arg Leu Leu Gln Glu Thr Glu Leu Val Glu Pro Leu Thr Pro Ser Gly
    690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
        755                 760                 765

Asp Glu Ala Tyr Val Met Ala Gly Val Gly Ser Pro Tyr Val Ser Arg
    770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
        835                 840                 845

Arg Asn Val Leu Val Lys Ser Pro Asn His Val Lys Ile Thr Asp Phe
    850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
        915                 920                 925

Arg Glu Ile Pro Asp Leu Leu Glu Lys Gly Glu Arg Leu Pro Gln Pro
    930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu  Asp Ser Thr Phe Tyr  Arg Ser Leu
        995                 1000                1005

Leu Glu  Asp Asp Asp Met Gly  Asp Leu Val Asp Ala  Glu Glu Tyr
    1010                1015                1020

Leu Val  Pro Gln Gln Gly Phe  Phe Cys Pro Asp Pro  Ala Pro Gly
    1025                1030                1035

Ala Gly  Gly Met Val His His  Arg His Arg Ser Ser  Ser Thr Arg
    1040                1045                1050

Asn Met
    1055
```

<210> SEQ ID NO 6
<211> LENGTH: 603
<212> TYPE: PRT
<213> ORGANISM: Homo sapien

<400> SEQUENCE: 6

Met Lys Leu Arg Leu Pro Ala Ser Pro Glu Thr His Leu Asp Met Leu
1 5 10 15

Arg His Leu Tyr Gln Gly Cys Gln Val Val Gln Gly Asn Leu Glu Leu
20 25 30

Thr Tyr Leu Pro Thr Asn Ala Ser Leu Ser Phe Leu Gln Asp Ile Gln
35 40 45

Glu Val Gln Gly Tyr Val Leu Ile Ala His Asn Gln Val Arg Gln Val
50 55 60

Pro Leu Gln Arg Leu Arg Ile Val Arg Gly Thr Gln Leu Phe Glu Asp
65 70 75 80

Asn Tyr Ala Leu Ala Val Leu Asp Asn Gly Asp Pro Leu Asn Asn Thr
85 90 95

Thr Pro Val Thr Gly Ala Ser Pro Gly Gly Leu Arg Glu Leu Gln Leu
100 105 110

Arg Ser Leu Thr Glu Ile Leu Lys Gly Gly Val Leu Ile Gln Arg Asn
115 120 125

Pro Gln Leu Cys Tyr Gln Asp Thr Ile Leu Trp Lys Asp Ile Phe His
130 135 140

Lys Asn Asn Gln Leu Ala Leu Thr Leu Ile Asp Thr Asn Arg Ser Arg
145 150 155 160

Ala Cys His Pro Cys Ser Pro Met Cys Lys Gly Ser Arg Cys Trp Gly
165 170 175

Glu Ser Ser Glu Asp Cys Gln Ser Leu Thr Arg Thr Val Cys Ala Gly
180 185 190

Gly Cys Ala Arg Cys Lys Gly Pro Leu Pro Thr Asp Cys Cys His Glu
195 200 205

Gln Cys Ala Ala Gly Cys Thr Gly Pro Lys His Ser Asp Cys Leu Ala
210 215 220

Cys Leu His Phe Asn His Ser Gly Ile Cys Glu Leu His Cys Pro Ala
225 230 235 240

Leu Val Thr Tyr Asn Thr Asp Thr Phe Glu Ser Met Pro Asn Pro Glu
245 250 255

Gly Arg Tyr Thr Phe Gly Ala Ser Cys Val Thr Ala Cys Pro Tyr Asn
260 265 270

Tyr Leu Ser Thr Asp Val Gly Ser Cys Thr Leu Val Cys Pro Leu His
275 280 285

Asn Gln Glu Val Thr Ala Glu Asp Gly Thr Gln Arg Cys Glu Lys Cys
290 295 300

Ser Lys Pro Cys Ala Arg Val Cys Tyr Gly Leu Gly Met Glu His Leu
305 310 315 320

Arg Glu Val Arg Ala Val Thr Ser Ala Asn Ile Gln Glu Phe Ala Gly
325 330 335

Cys Lys Lys Ile Phe Gly Ser Leu Ala Phe Leu Pro Glu Ser Phe Asp
340 345 350

Gly Asp Pro Ala Ser Asn Thr Ala Pro Leu Gln Pro Glu Gln Leu Gln
355 360 365

Val Phe Glu Thr Leu Glu Glu Ile Thr Gly Tyr Leu Tyr Ile Ser Ala
370 375 380

-continued

```
Trp Pro Asp Ser Leu Pro Asp Leu Ser Val Phe Gln Asn Leu Gln Val
385                 390                 395                 400

Ile Arg Gly Arg Ile Leu His Asn Gly Ala Tyr Ser Leu Thr Leu Gln
                405                 410                 415

Gly Leu Gly Ile Ser Trp Leu Gly Leu Arg Ser Leu Arg Glu Leu Gly
            420                 425                 430

Ser Gly Leu Ala Leu Ile His His Asn Thr His Leu Cys Phe Val His
        435                 440                 445

Thr Val Pro Trp Asp Gln Leu Phe Arg Asn Pro His Gln Ala Leu Leu
    450                 455                 460

His Thr Ala Asn Arg Pro Glu Asp Glu Cys Val Gly Glu Gly Leu Ala
465                 470                 475                 480

Cys His Gln Leu Cys Ala Arg Gly His Cys Trp Gly Pro Gly Pro Thr
                485                 490                 495

Gln Cys Val Asn Cys Ser Gln Phe Leu Arg Gly Gln Glu Cys Val Glu
            500                 505                 510

Glu Cys Arg Val Leu Gln Gly Leu Pro Arg Glu Tyr Val Asn Ala Arg
        515                 520                 525

His Cys Leu Pro Cys His Pro Glu Cys Gln Pro Gln Asn Gly Ser Val
    530                 535                 540

Thr Cys Phe Gly Pro Glu Ala Asp Gln Cys Val Ala Cys Ala His Tyr
545                 550                 555                 560

Lys Asp Pro Pro Phe Cys Val Ala Arg Cys Pro Ser Gly Val Lys Pro
                565                 570                 575

Asp Leu Ser Tyr Met Pro Ile Trp Lys Phe Pro Asp Glu Glu Gly Ala
            580                 585                 590

Cys Gln Pro Cys Pro Ile Asn Cys Thr His Ser
        595                 600


<210> SEQ ID NO 7
<211> LENGTH: 21
<212> TYPE: PRT
<213> ORGANISM: Artificial sequence
<220> FEATURE:
<223> OTHER INFORMATION: EGFR insertion encoding exon 20

<400> SEQUENCE: 7

Lys Glu Ile Leu Asp Glu Ala Tyr Val Met Ala Ser Val Asp Asn Pro
1               5                   10                  15

His Val Cys Ala Arg
            20


<210> SEQ ID NO 8
<211> LENGTH: 20
<212> TYPE: PRT
<213> ORGANISM: Artificial sequence
<220> FEATURE:
<223> OTHER INFORMATION: HER2 receptor insertion encoding exon 20

<400> SEQUENCE: 8

Lys Glu Ile Leu Asp Glu Ala Tyr Val Met Ala Gly Val Gly Ser Pro
1               5                   10                  15

Tyr Val Ser Arg
            20
```

ALKYNYL QUINAZOLINE COMPOUNDS

RELATED APPLICATIONS

This application is a U.S. National Phase application, filed under U.S.C. § 371, of International Application No. PCT/US2020/046425, filed Aug. 14, 2020, which claims priority to, and the benefit of, U.S. Application Nos. 63/065,028, filed Aug. 13, 2020, and 62/887,392, filed Aug. 15, 2019, the entire contents of each of which are incorporated herein by reference.

SEQUENCE LISTING

The instant application contains a Sequence Listing which has been submitted via Patent Center and is hereby incorporated by reference in its entirety. Said ASCII copy, created on May 7, 2025, is named 02102US_SeqList, and is 57,851 bytes in size.

FIELD OF DISCLOSURE

The present disclosure relates to new compounds as inhibitors of receptor tyrosine kinases (RTK), in particular oncogenic mutants of ErbB-receptors. The disclosure also relates to methods of preparation these compounds, compositions comprising these compounds, and methods of using them in the prevention or treatment of abnormal cell growth in mammals, especially humans.

BACKGROUND

Mutations affecting either the intracellular catalytic domain or extracellular ligand binding domain of an ErbB receptor can generate oncogenic activity (the ErbB protein family consists of 4 members including ErbB-1, also named epidermal growth factor receptor (EGFR) and Erb-2, also named HER2 in humans). ErbB inhibitors are a known treatment for a number of cancers. However, not every patient is responsive satisfactorily to this treatment. Thus, there is a long-felt need in the art for new therapies that are able to address the variable responsiveness of cancer patients to known therapies. The present disclosure provides compositions and methods for preventing or treating cancer in patients with these oncogenic mutations without the variable responsiveness observed when patients having these ErbB mutants are treated using the existing standard of care.

SUMMARY OF DISCLOSURE

In some aspects, the present disclosure provides a compound of Formula (I'):

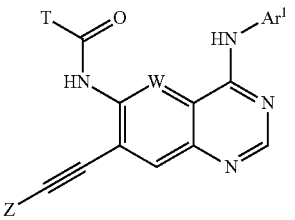

I' or a pharmaceutically acceptable salt or stereoisomer thereof, wherein:

W is CH or N;

Z is 3- to 12-membered heterocycloalkyl optionally substituted with one or more $R^Z$;

each $R^Z$ independently is halogen, CN, —OH, —$NH_2$, —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 10-membered heterocycloalkyl, or 5- to 10-membered heteroaryl; wherein the —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 10-membered heterocycloalkyl, or 5- to 10-membered heteroaryl is optionally substituted with one or more $R^{Za}$;

each $R^{Za}$ independently is halogen, CN, —OH, —$NH_2$, —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 10-membered heterocycloalkyl, or 5- to 10-membered heteroaryl;

T is —O—($C_1$-$C_6$ alkyl), —NH—($C_1$-$C_6$ alkyl), $C_1$-$C_6$ alkyl, $C_2$-$C_6$ alkenyl, or $C_2$-$C_6$ alkynyl; wherein the —O—($C_1$-$C_6$ alkyl), —NH—($C_1$-$C_6$ alkyl), $C_1$-$C_6$ alkyl, $C_2$-$C_6$ alkenyl, or $C_2$-$C_6$ alkynyl is optionally substituted with one or more $R^T$;

each $R^T$ independently is halogen, CN, —OH, —$NH_2$, —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 10-membered heterocycloalkyl, or 5- to 10-membered heteroaryl; wherein the —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 10-membered heterocycloalkyl, or 5- to 10-membered heteroaryl is optionally substituted with one or more $R^{Ta}$;

each $R^{Ta}$ independently is halogen, CN, —OH, —$NH_2$, —C(═O)OH, —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 10-membered heterocycloalkyl, or 5- to 10-membered heteroaryl;

$Ar^1$ is $C_6$-$C_{10}$ aryl optionally substituted with one or more $R^{A1}$;

each $R^{A1}$ independently is halogen, CN, —OH, —$NH_2$, —$OR^{A1a}$, —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 10-membered heterocycloalkyl, or 5- to 10-membered heteroaryl; wherein the —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 10-membered heterocycloalkyl, or 5- to 10-membered heteroaryl is optionally substituted with one or more $R^{A1a}$; and each $R^{A1a}$ independently is halogen, CN, —OH, —$NH_2$, —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 10-membered heterocycloalkyl, or 5- to 10-membered heteroaryl; wherein the —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 10-membered heterocycloalkyl, or 5- to 10-membered heteroaryl is optionally substituted with one or more $R^{A1b}$; and each $R^{A1b}$ independently is halogen, CN, —OH, or —$NH_2$.

In some aspects, the present disclosure provides a compound or pharmaceutically acceptable salts or stereoisomers thereof of formula I

I

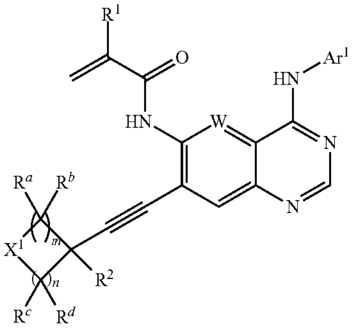

wherein

W is CH or N, preferably CH;

$X^1$ is —O—, —S—, or —$NR^3$—;

$R^a$, $R^b$ are independently of each other hydrogen or $C_{1-4}$ alkyl or one of $R^a$ is —$(CH_2)_p$— which forms a ring with $X^1$ if $X^1$ is $NR^3$ or one of $R^a$ is —$(CH_2)_p$— which forms a ring with $R^2$;

$R^c$, $R^d$ are independently of each other hydrogen or $C_{1-4}$ alkyl;

$R^1$ is H or F;

$R^2$ is hydrogen or $C_{1-4}$ alkyl, or is —$(CH_2)_q$— which forms a ring with $R^3$ or with one of $R^a$;

$R^3$ is hydrogen or $C_{1-4}$ alkyl, preferably hydrogen or methyl, or is —$(CH_2)_p$— which forms a ring with $R^2$;

m is 1, 2 or 3;

n is 0, 1 or 2;

p is 1 or 2;

q is 0, 1 or 2; and $Ar^1$ is a 6-membered aryl, which is unsubstituted or substituted with one or more of a group selected from halogen, —$CF_3$, $C_{1-6}$ alkyl, $C_{1-6}$ alkoxy, $C_{3-7}$ cycloalkyl, hydroxy $C_{1-5}$ alkyl, $C_{1-6}$ alkoxy-$C_{1-6}$ alkyl, $C_{1-6}$ alkoxy-$C_6$ aryl, $C_{1-6}$ alkoxy-$C_{5*6}$ heteroaryl, amino, amino $C_{1-4}$ alkyl, $C_{1-6}$ alkylamino, $C_{1-6}$ aminoalkyl-$C_6$ aryl, $C_{1-6}$ aminoalkyl-$C_{5-6}$ heteroaryl, $C_{1-6}$ alkoxycarbonyl, $C_{1-6}$ alkoxyaminocarbonyl, aryl $C_{1-6}$ alkoxy, or $C_6$ aryl.

In some embodiments, when $X^1$ is —$NR^3$—, $R^2$ is not hydrogen.

In some embodiments, when $X^1$ is —$NR^3$—, $R^2$ is $C_{1-4}$ alkyl, or is —$(CH_2)_q$— which forms a ring with $R^3$ or with one of $R^a$.

In some embodiments, $X^1$ is —$NR^3$—, and $R^2$ is not hydrogen.

In some embodiments, $X^1$ is —$NR^3$—, and $R^2$ is $C_{1-4}$ alkyl, or is —$(CH_2)_q$— which forms a ring with $R^3$ or with one of $R^a$.

In some embodiments, $X^1$ is $NR^3$ or 0 and wherein $R^3$ is methyl, ethyl, n-propyl or n-butyl-.

In some embodiments, $R^1$ is hydrogen.

In some embodiments, $R^2$ is methyl, ethyl, n-propyl or n-butyl-, preferably methyl or $R^2$ is —$(CH_2)$— or —$(CH_2)_2$— which forms a ring with $R^3$, or $R^2$ is —$(CH_2)$— or —$(CH_2)_2$— which forms a ring with one of $R^a$.

In some embodiments in which one of $R^a$ forms a ring with $R^3$, the ring formed is a 4, 5, or 6-membered ring, or a 5 or 6 membered ring, or a 5 membered ring.

In some embodiments in which one of $R^a$ forms a ring with $R^3$, the ring formed is a 3, 4, 5, or 6-membered ring.

In some embodiments in which one of $R^2$ forms a ring with $R^3$, the ring formed is a 4, 5, or 6-membered ring or a 5 or 6 membered ring, or a 6 membered ring.

In some embodiments, $Ar^1$ is of formula i or pharmaceutically acceptable salts or stereoisomers thereof i

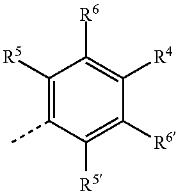

wherein $R^4$ is hydrogen, halogen, $C_{1-6}$ alkyl, $C_{1-6}$ alkoxy, $C_{3-7}$ cycloalkyl, hydroxy $C_{1-5}$ alkyl, $C_{1-6}$ alkoxy-$C_{1-6}$ alkyl, $C_{1-6}$ alkoxy-$C_6$ aryl, $C_{1-6}$ alkoxy-$C_{5*6}$ heteroaryl, amino $C_{1-4}$ alkyl, $C_{1-6}$ alkylamino, $C_{1-6}$ aminoalkyl-$C_6$ aryl, $C_{1-6}$ aminoalkyl-$C_{5-6}$ heteroaryl, $C_{1-6}$ alkoxycarbonyl, $C_{1-6}$ alkoxyaminocarbonyl, aryl $C_{1-6}$ alkoxy, or $C_6$ aryl;

$R^5$, $R^{5'}$, $R^6$, $R^{6'}$ are independently of each other hydrogen, —$CF_3$ or halogen, preferably F, Cl.

In some embodiments, $R^1$ is hydrogen.

In some embodiments, $R^c$ and $R^d$ are hydrogen. In some embodiments, $R^b$, $R^c$ and $R^d$ are hydrogen.

In some embodiments, $R^2$ is methyl or $R^2$ is —$(CH_2)$— or —$(CH_2)_2$— which forms a ring with $R^3$, or $R^2$ is —$(CH_2)$— or —$(CH_2)_2$— which forms a ring with one of $R^a$.

In some embodiments, $Ar^1$ is of formula ii-1, ii-2, ii-3 or ii-4 or pharmaceutically acceptable salts or stereoisomers thereof ii-1

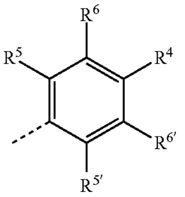

ii-2

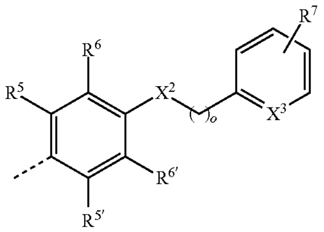

ii-3

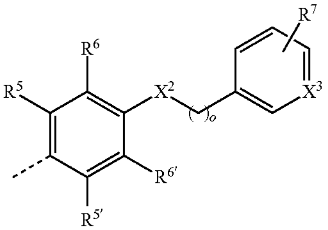

-continued iii-4

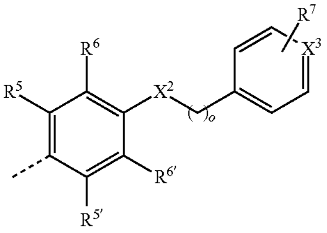

wherein $X^2$ is O, NH or NMe;

$X^3$ is CH or N;

is 0 or 1;

$R^4$ is hydrogen or halogen, preferably F or Cl;

$R^5$, $R^{5'}$, $R^6$, $R^{6'}$ are independently of each other hydrogen, —$CF_3$ or halogen, preferably F or Cl;

$R^7$ is hydrogen or halogen, preferably F.

In some embodiments, $R^5$ is F and/or $R^6$ is F or Cl.

In some embodiments, $R^1$ is hydrogen.

In some embodiments, $R^2$ is methyl or $R^2$ is —$(CH_2)$— or —$(CH_2)_2$— which forms a ring with $R^3$, or $R^2$ is —$(CH_2)$— or —$(CH_2)_2$— which forms a ring with one of $R^a$.

In some embodiments, $R^c$ and $R^d$ are hydrogen. In some embodiments, $R^b$, $R^c$ and $R^d$ are hydrogen.

In some embodiments, $Ar^1$ is of formula iii-1, iii-3 or iii-4, iii-6 or iii-7 or pharmaceutically acceptable salts or stereoisomers thereof iii-1

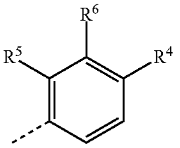

iii-2

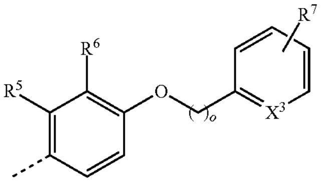

iii-3

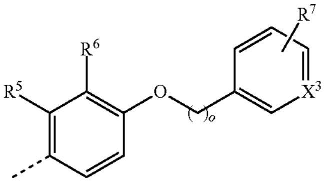

iii-4

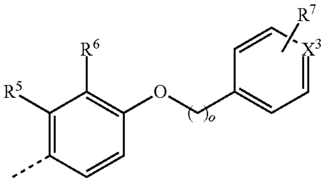

-continued iii-5

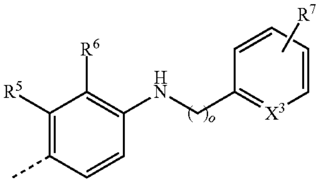

iii-6

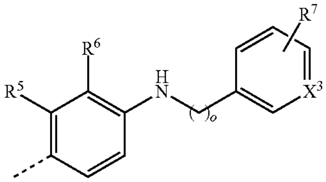

iii-7

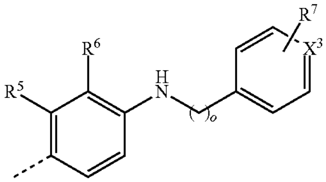

wherein $X^3$ is CH or N;

is 0 or 1;

$R^4$ is hydrogen or halogen, preferably F or Cl;

$R^5$, $R^6$ are independently of each other hydrogen, —$CF_3$ or halogen, preferably F or Cl;

$R^7$ is hydrogen or halogen, preferably F.

In some embodiments, $R^5$ is F and/or $R^6$ is F or Cl.

In some embodiments, $R^1$ is hydrogen.

In some embodiments, $R^c$ and $R^d$ are hydrogen. In some embodiments, $R^b$, $R^c$ and $R^d$ are hydrogen.

In some embodiments, $R^2$ is methyl or $R^2$ is —$(CH_2)$— or —$(CH_2)_2$— which forms a ring with $R^3$, or $R^2$ is —$(CH_2)$— or —$(CH_2)_2$— which forms a ring with one of $R^a$.

In some embodiments, $Ar^1$ is of formula iii-1, iii-3 or iii-4, iii-6 or iii-7 or pharmaceutically acceptable salts or stereoisomers thereof iii-1

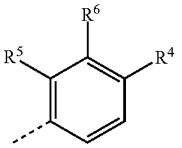

iii-2

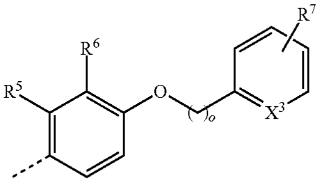

iii-3

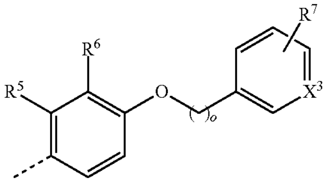

-continued iii-4

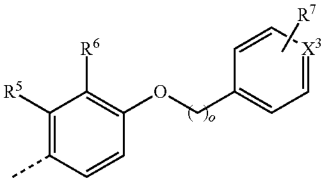

iii-5

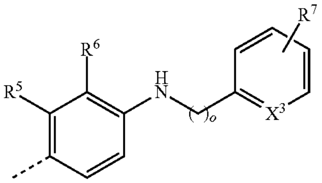

iii-6

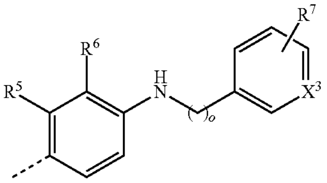

iii-7

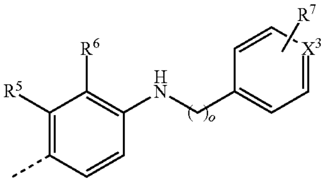

wherein $X^3$ is C or N, preferably N;

is 0 or 1;

$R^4$ is hydrogen or halogen, preferably F or Cl;

$R^5$, $R^6$ are independently of each other hydrogen, —$CF_3$ or halogen, preferably F or Cl;

$R^7$ is hydrogen or halogen, preferably F.

In some embodiments, $R^5$ is F and/or wherein $R^6$ is F or Cl.

In some embodiments, $R^1$ is hydrogen.

In some embodiments, $R^c$ and $R^d$ are hydrogen. In some embodiments, $R^b$, $R^c$ and $R^d$ are hydrogen.

In some embodiments, $R^2$ is methyl or $R^2$ is —$(CH_2)$— or —$(CH_2)_2$— which forms a ring with $R^3$, or $R^2$ is —$(CH_2)$— or —$(CH_2)_2$— which forms a ring with one of $R^a$.

In some embodiments, $Ar^1$ is of formula iv-1, iv-2, iv-3 or iv-4, iv-5, iv-6, iv-7, iv-8 or iv-9 or pharmaceutically acceptable salts or stereoisomers thereof iv-1

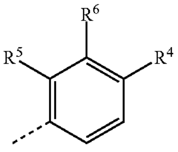

iv-2

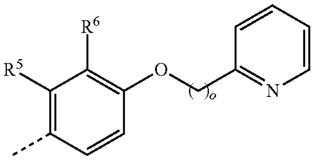

-continued iv-3

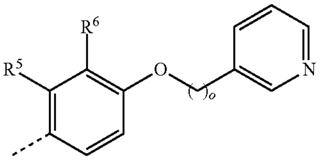

iv-4

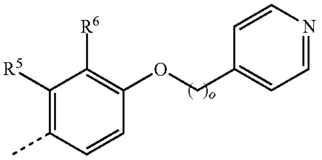

iv-5

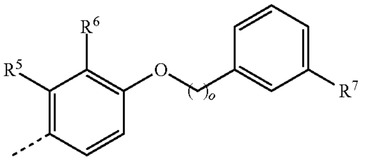

iv-6

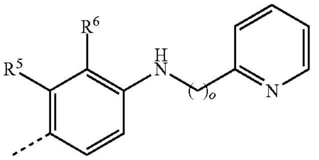

iv-7

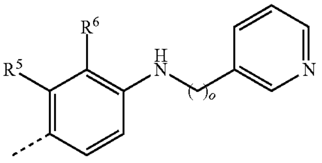

iv-8

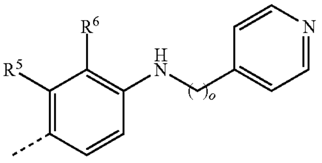

iv-9

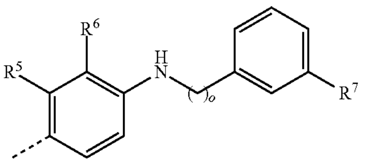

wherein is 0 or 1;

$R^4$ is hydrogen or halogen, preferably F or Cl;

$R^5$, $R^6$ are independently of each other hydrogen, —$CF_3$ or halogen, preferably F or Cl;

$R^7$ is hydrogen or halogen, preferably F.

In some embodiments, $R^5$ is F and/or $R^6$ is F or Cl.

In some embodiments, $R^1$ is hydrogen.

In some embodiments, $R^c$ and $R^d$ are hydrogen. In some embodiments, $R^b$, $R^c$ and $R^d$ are hydrogen.

In some embodiments, $R^2$ is methyl or $R^2$ is —$(CH_2)$— or —$(CH_2)_2$— which forms a ring with $R^3$, or $R^2$ is —$(CH_2)$— or —$(CH_2)_2$— which forms a ring with one of $R^a$. In some embodiments $R^7$ is F.

In some embodiments, the present disclosure provides a compound or pharmaceutically acceptable salts or stereoisomers thereof of formula IIa or IIb IIa

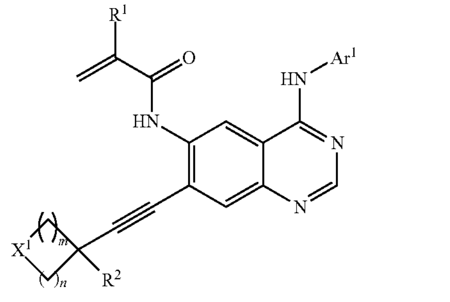

IIb

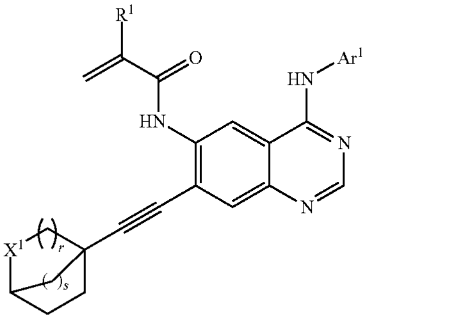

wherein $X^1$ is —O— or —$NR^3$—;

$R^1$ is H or F;

$R^2$ is hydrogen or $C_{1-4}$ alkyl, preferably methyl or is —$(CH_2)_q$— which forms a ring with $R^3$;

$R^3$ is hydrogen or $C_{1-4}$ alkyl, preferably hydrogen or methyl, or is —$(CH_2)_p$— which forms a ring with $R^2$;

m is 1, 2 or 3;

n is 0, 1 or 2;

p is 1 or 2;

q is 0, 1 or 2;

r is 0 or 1;

s is 1 or 2; and $Ar^1$ is a 6-membered aryl, which is unsubstituted or substituted with one or more of a group selected from halogen, —$CF_3$, $C_{1-6}$ alkyl, $C_{1-6}$ alkoxy, $C_{3-7}$ cycloalkyl, hydroxy $C_{1-5}$ alkyl, $C_{1-6}$ alkoxy-$C_{1-6}$ alkyl, $C_{1-6}$ alkoxy-$C_6$ aryl, $C_{1-6}$ alkoxy-$C_{5*6}$ heteroaryl, amino, amino $C_{1-4}$ alkyl, $C_{1-6}$ alkylamino, $C_{1-6}$ aminoalkyl-$C_6$ aryl, $C_{1-6}$ aminoalkyl-$C_{5-6}$ heteroaryl, $C_{1-6}$ alkoxycarbonyl, $C_{1-6}$ alkoxyaminocarbonyl, aryl $C_{1-6}$ alkoxy, or $C_6$ aryl.

In some embodiments, $R^1$ is hydrogen.

In some embodiments, $R^2$ is methyl or $R^2$ is —$(CH_2)$— or —$(CH_2)_2$— which forms a ring with $R^3$.

In some embodiments, when $X^1$ is —$NR^3$—, $R^2$ is not hydrogen.

In some embodiments, when $X^1$ is —$NR^3$—, $R^2$ is $C_{1-4}$ alkyl, or is —$(CH_2)_q$— which forms a ring with $R^3$ or with one of $R^a$.

In some embodiments, $X^1$ is —$NR^3$—, and $R^2$ is not hydrogen.

In some embodiments, $X^1$ is —$NR^3$—, and $R^2$ is $C_{1-4}$ alkyl, or is —$(CH_2)_q$— which forms a ring with $R^3$ or with one of $R^a$.

In some embodiments, the present disclosure provides a compound or pharmaceutically acceptable salts or stereoisomers thereof of formula III

III

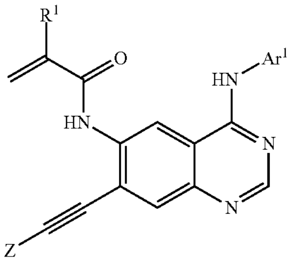

wherein $R^1$ is H or F;

$Ar^1$ is a 6-membered aryl, which is unsubstituted or substituted with one or more of a group selected from halogen, —$CF_3$, $C_{1-6}$ alkyl, $C_{1-6}$ alkoxy, $C_{3-7}$ cycloalkyl, hydroxy $C_{1-5}$ alkyl, $C_{1-6}$ alkoxy-$C_{1-6}$ alkyl, $C_{1-6}$ alkoxy-$C_6$ aryl, $C_{1-6}$ alkoxy-$C_{5*6}$ heteroaryl, amino, amino $C_{1-4}$ alkyl, $C_{1-6}$ alkylamino, $C_{1-6}$ aminoalkyl-$C_6$ aryl, $C_{1-6}$ aminoalkyl-$C_{5-6}$ heteroaryl, $C_{1-6}$ alkoxy carbonyl, $C_{1-6}$ alkoxyaminocarbonyl, or $C_6$ aryl; and Z is selected from

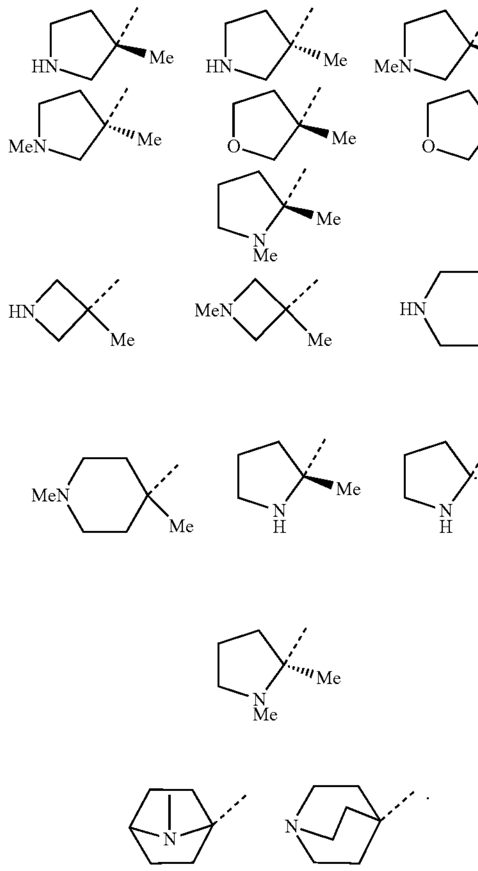

.

In some embodiments, $R^1$ is hydrogen.

In some embodiments, the present disclosure provides a compound or pharmaceutically acceptable salts or stereoisomers thereof of formula IV

IV

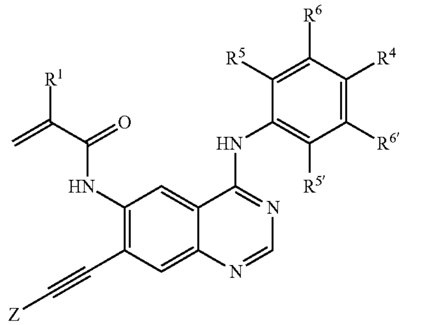

wherein $R^1$ is H or F;

$R^4$ is hydrogen, halogen, $C_{1-6}$ alkyl, $C_{1-6}$ alkoxy, $C_{3-7}$ cycloalkyl, hydroxy $C_{1-5}$ alkyl, $C_{1-6}$ alkoxy-$C_{1-6}$ alkyl, $C_{1-6}$ alkoxy-$C_6$ aryl, $C_{1-6}$ alkoxy-$C_{5*6}$ heteroaryl, amino $C_{1-4}$ alkyl, $C_{1-6}$ alkylamino, $C_{1-6}$ aminoalkyl-$C_6$ aryl, $C_{1-6}$ aminoalkyl-$C_{5-6}$ heteroaryl, $C_{1-6}$ alkoxycarbonyl, $C_{1-6}$ alkoxyaminocarbonyl or $C_6$ aryl;

$R^5$, $R^{5'}$, $R^6$, $R^{6'}$ are independently of each other hydrogen, —$CF_3$ or halogen, preferably F or Cl; and Z is selected from

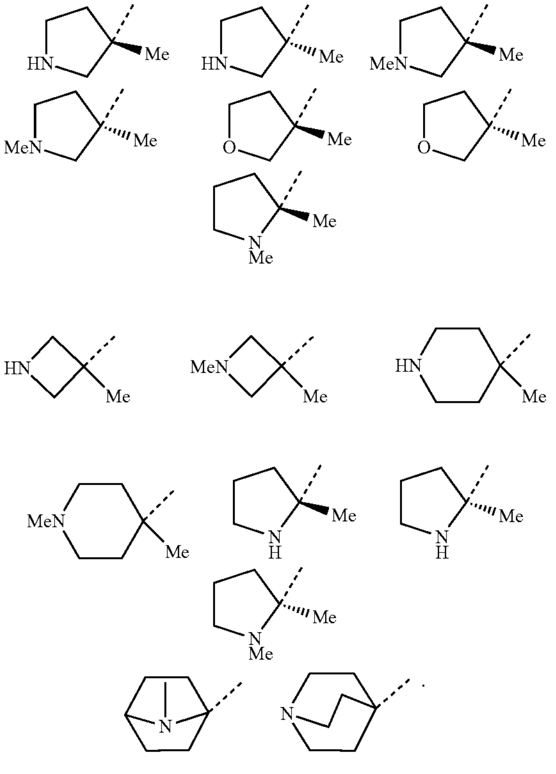

In some embodiments, $R^5$ is F and/or $R^6$ is F or Cl.

In some embodiments, $R^1$ is hydrogen.

In some embodiments, the present disclosure provides a compound or pharmaceutically acceptable salts or stereoisomers thereof of formula V-1, V-2, V-3 or V-4

V-1

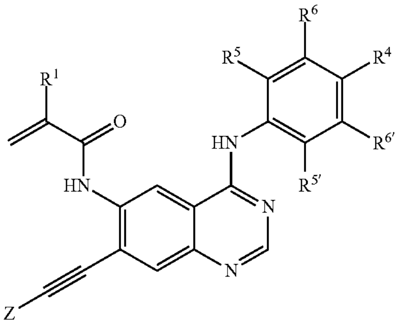

V-2

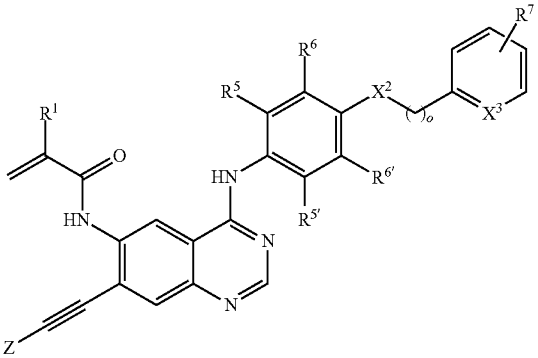

V-3

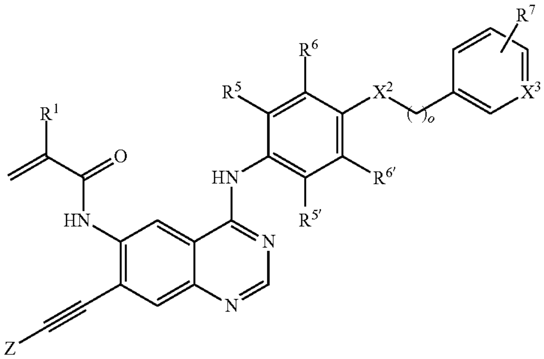

V-4

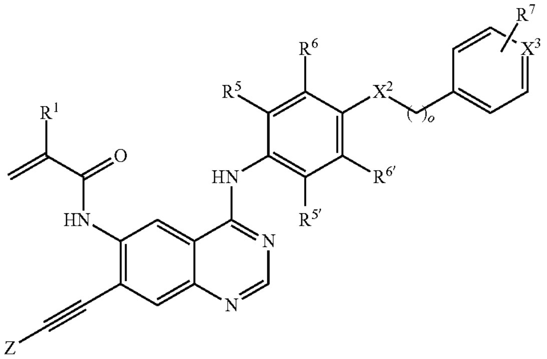

wherein $X^2$ is O, NH or NMe;

$X^3$ is C or N;

$R^1$ is H or F;

$R^4$ is hydrogen or halogen, preferably F or Cl;

$R^5$, $R^{5'}$, $R^6$, $R^{6'}$ are independently of each other hydrogen, —$CF_3$ or halogen, preferably F or Cl;

is 0 or 1;

$R^7$ is hydrogen or halogen, preferably F; and

Z is selected from

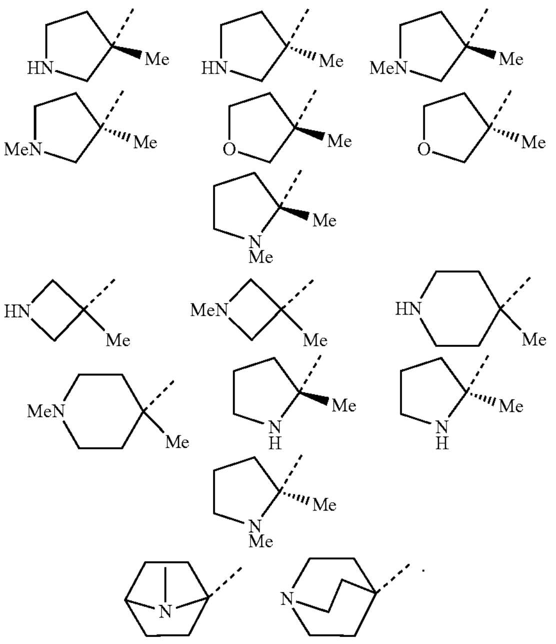

In some embodiments, $R^5$ is F and/or $R^6$ is F or Cl.

In some embodiments, $R^1$ is hydrogen.

In some embodiments, the present disclosure provides a compound or pharmaceutically acceptable salts or stereoisomers thereof of formula VI-1, VI-2, VI-3 or VI-4

VI-1

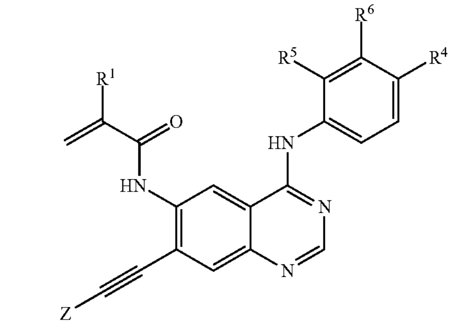

VI-2

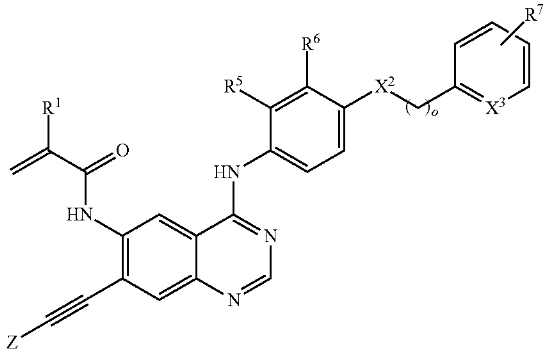

-continued

VI-3

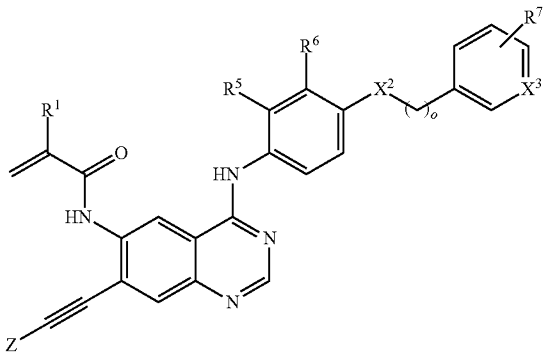

VI-4

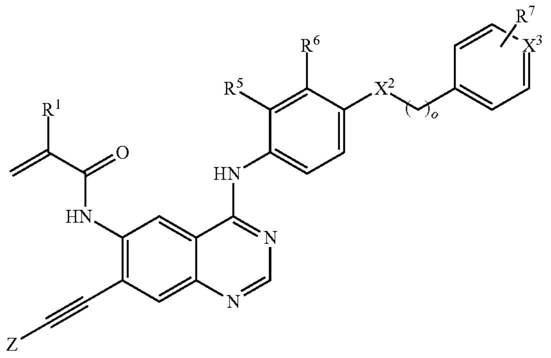

wherein $X^2$ is O, NH or NMe;

$X^3$ is C or N;

$R^1$ is H or F;

is 0 or 1;

$R^4$ is hydrogen or halogen, preferably F or Cl;

$R^5$, $R^6$ are independently of each other hydrogen, —$CF_3$ or halogen, preferably F or Cl;

$R^7$ is hydrogen or halogen, preferably F; and

Z is selected from

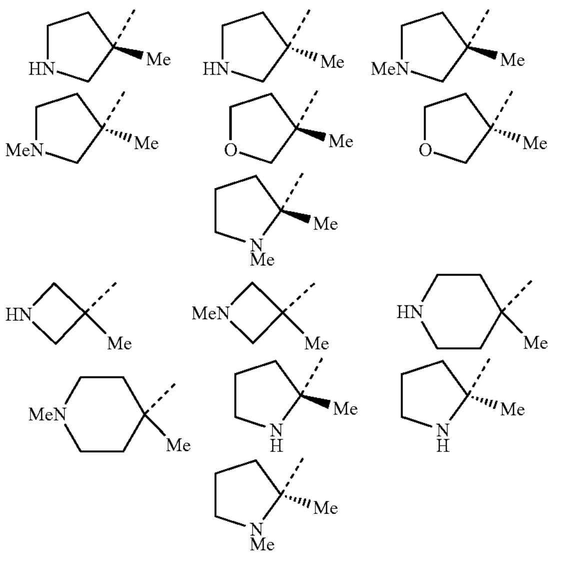

-continued
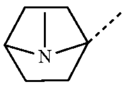 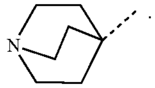
In some embodiments, $R^5$ is F and/or $R^6$ is F or Cl.
In some embodiments, $R^1$ is hydrogen.
In some embodiments, the present disclosure provides a compound or pharmaceutically acceptable salts or stereoisomers thereof of formula VII-1, VII-2, VII-3 or VII-4, VII-5, VII-6 VII-7, VII-8 or VII-9
VII-1
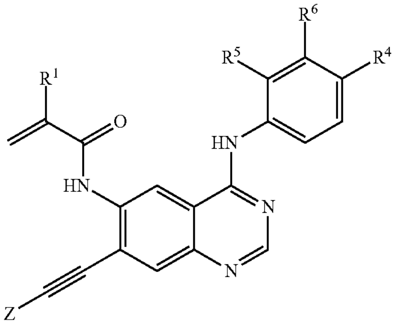
VII-2
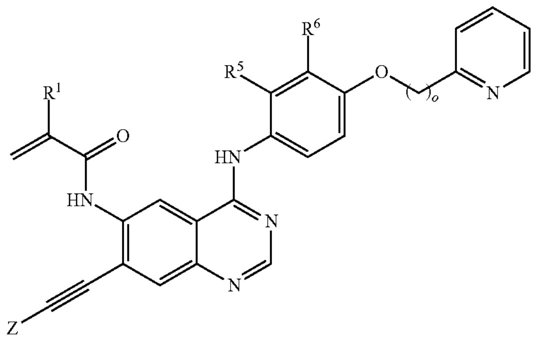
VII-3
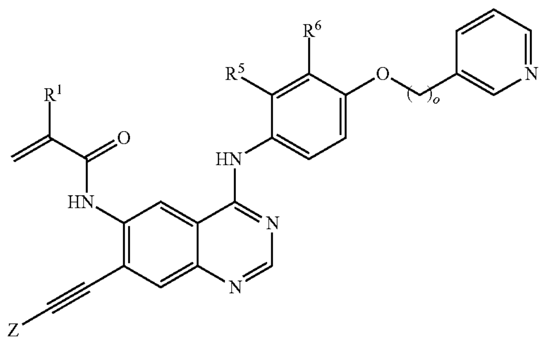
-continued
VII-4
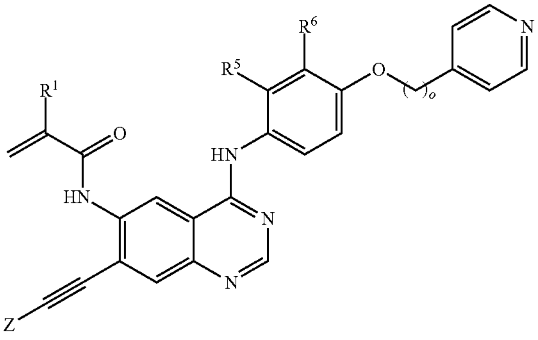
VII-5
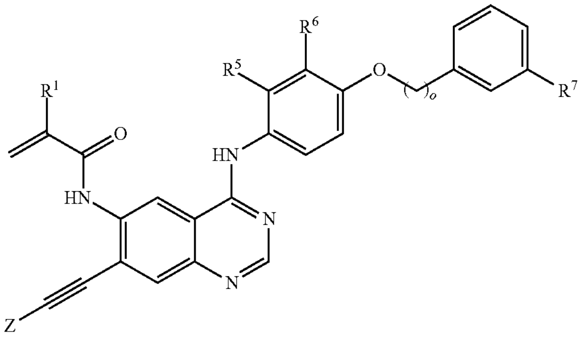
VII-6
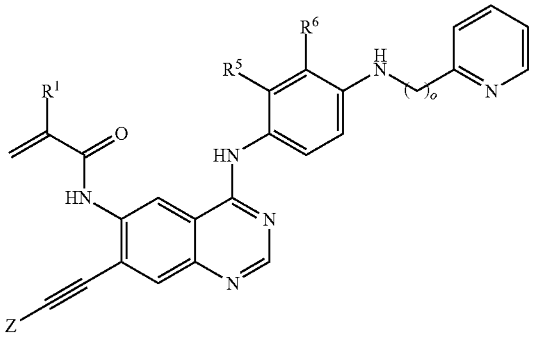
VII-7
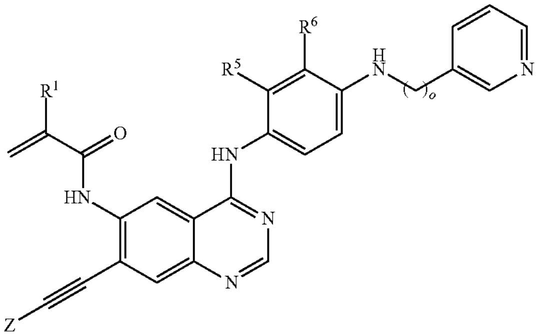

-continued

VII-8

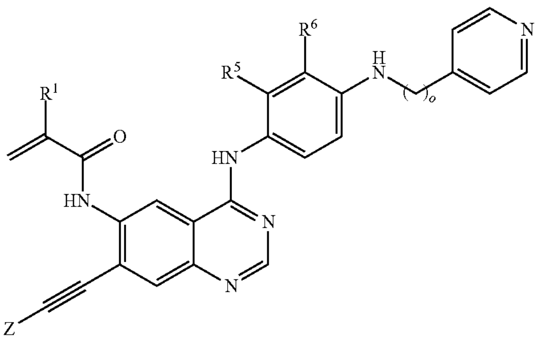

VII-9

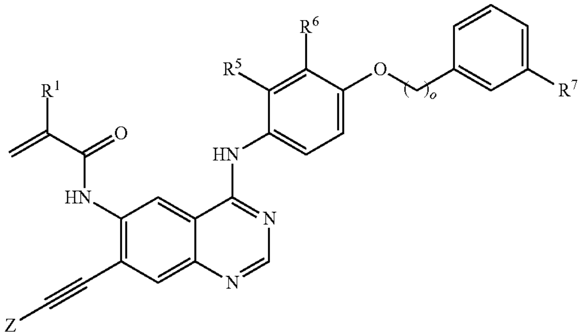

wherein $R^1$ is H or F;

is 0 or 1;

$R^4$ is hydrogen or halogen, preferably F or Cl;

$R^5$, $R^6$ are independently of each other hydrogen, $-CF_3$ or halogen, preferably F or Cl;

$R^7$ is hydrogen or halogen, preferably F;

Z is selected from

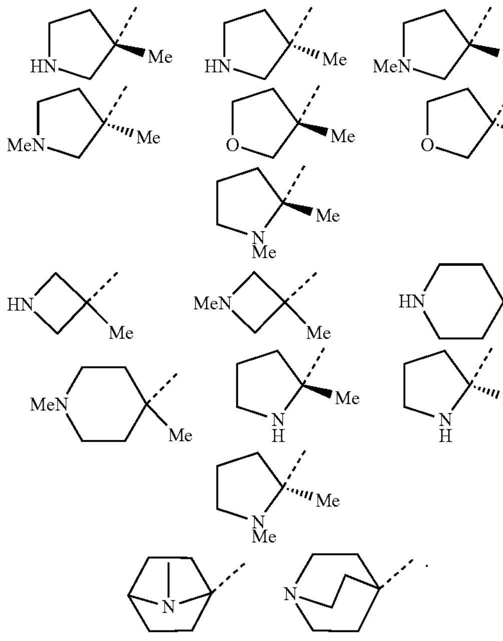

In some embodiments, $R^5$ is F and/or $R^6$ is F or Cl.

In some embodiments, $R^1$ is hydrogen. In certain embodiments, $R^7$ is F.

In some aspects, the present disclosure is directed to a composition comprising a compound according to any of the embodiments described herein or pharmaceutically acceptable salts or stereoisomers thereof.

In some embodiments, the composition comprises a pharmaceutically acceptable carrier.

In some embodiments, the composition comprises a second therapeutically active agent.

In some aspects, the present disclosure is directed to a method of inhibiting an oncogenic variant of an ErbB receptor (e.g., an oncogenic variant of an EGFR), comprising administering the subject in need thereof a therapeutically effective amount of a compound described herein.

In some aspects, the present disclosure is directed to a method of inhibiting an oncogenic variant of an ErbB receptor (e.g., an oncogenic variant of an EGFR), comprising administering the subject in need thereof a composition described herein.

In some aspects, the present disclosure is directed to a method of preventing or treating cancer, comprising administering the subject in need thereof a therapeutically effective amount of a compound described herein.

In some aspects, the present disclosure is directed to a method of preventing or treating cancer, comprising administering the subject in need thereof a composition described herein.

In some aspects, the present disclosure is directed to a compound described herein for use in the inhibition of an oncogenic variant of an ErbB receptor (e.g., an oncogenic variant of an EGFR).

In some aspects, the present disclosure is directed to a compound described herein for use in the prevention or treatment of cancer.

In some aspects, the present disclosure is directed to a composition described herein for use in the inhibition of an oncogenic variant of an ErbB receptor (e.g., an oncogenic variant of an EGFR).

In some aspects, the present disclosure is directed to a composition described herein for use in the prevention or treatment of cancer.

In some aspects, the present disclosure is directed to use of a compound described herein in the manufacture of a medicament for inhibiting an oncogenic variant of an ErbB receptor (e.g., an oncogenic variant of an EGFR).

In some aspects, the present disclosure is directed to use of a compound described herein in the manufacture of a medicament for preventing or treating cancer.

In some embodiments, the cancer is glioblastoma.

In some aspects, the present disclosure is directed to a method of preventing or treating glioblastoma, comprising administering the subject in need thereof a therapeutically effective amount of a compound according to any of the embodiments described herein.

In some aspects, the present disclosure is directed to a compound according to any of the embodiments described herein for use in the prevention or treatment of glioblastoma.

In some aspects, the present disclosure is directed to a method of preventing or treating glioblastoma, comprising administering the subject in need thereof a composition according to any of the embodiments described herein.

In some aspects, the present disclosure is directed to a composition according to any of the embodiments described herein for use in the prevention or treatment of glioblastoma.

DETAILED DESCRIPTION

The present disclosure relates to compounds useful as inhibitors of receptor tyrosine kinases (RTK), in particular oncogenic mutants of ErbB-receptors. In some embodiments of the invention, oncogenic mutants of ErbB-receptors are also allosteric mutants of ErbB-receptors. In some embodiments, allosteric mutants may comprise or consist of an ErbB receptor variant having a mutation in a sequence outside of an ATP-binding site. In some embodiments, allosteric mutants may comprise or consist of an ErbB receptor variant having a mutation in a sequence within one or more of exon 19, exon 20 or a $C_1$-$C_2$ extracellular dimerization interface.

Mutations affecting either the intracellular catalytic domain or extracellular ligand binding domain of an ErbB receptor can generate oncogenic activity (the ErbB protein family consists of 4 members including ErbB-1, also named epidermal growth factor receptor (EGFR) and Erb-2, also named HER2 in humans). Extracellular mutants of ErbB receptors in cancer, including EGFR-Viii (also EGFR-V3) and HER2-S310F, are constitutively activated in the absence of ligand, exhibit sustained signaling that is resistant to downregulation, and are both transforming and tumorigenic (Nishikawa, Ji et al. 1994, 2013, Francis, Zhang et al. 2014). Their expression is associated with metastasis and with poor long term overall survival.

In glioblastoma (also glioblastoma multiforma or GBM), EGFR-Viii is expressed by 20% of tumors (Sugawa, Ekstrand et al. 1990, Brennan, Verhaak et al. 2013). Expression of EGFR-Viii in GBM tends to be mutually exclusive with expression of other RTK oncogenes, which are co-expressed with EGFR variants in only 7% of GBM tumors (Furnari, Cloughesy et al. 2015). These data demonstrate how EGFR-Viii in GBM has a dominant and mutually exclusive expression pattern compared with other oncogenic drivers. EGFR-Viii is also expressed by approximately 30% of SCCHN tumors (Sok, Coppelli et al. 2006, Keller, Shroyer et al. 2010, Wheeler, Suzuki et al. 2010, Tinhofer, Klinghammer et al. 2011, Wheeler, Egloff et al. 2015) and 10% of squamous NSCLC (Ji, Zhao et al. 2006, Sasaki, Kawano et al. 2007), and is associated with resistance to current therapeutics including the anti-EGFR antibody cetuximab (Sok, Coppelli et al. 2006, Tinhofer, Klinghammer et al. 2011). Normal tissues do not express this oncogenic receptor variants.

RNA sequencing data has revealed that EGFR-Viii is just one of several aberrantly spliced variants of EGFR expressed in GBM tumors. Two others result in truncation of exons 12-13 (EGFR-Vvi) and 14-15 (EGFR-Vii). Like EGFR-Viii, EGFR-Vii is both transforming and tumorigenic. In addition to splice variants, GBM tumors also express a collection of EGFR point mutations including C620Y, A289V and G598V, which are transforming and tumorigenic.

HER2-S310F is the most common mutation of HER2 expressed in human tumors, expressed by approximately 0.5% of all tumors. HER2-S310F expression is mutually exclusive with expression of HER2 amplification. HER2-S310F is highly oncogenic, transforming BaF3 cells (a murine interleukin-3 (IL-3) dependent pro-B cell line) to IL-3 independence and promoting tumor growth in vivo.

Short insertions of within Exon 20 of EGFR and HER2 are expressed by lung adenocarcinoma tumors and other tumor groups. ErbB Exon 20 insertion mutants are expressed by 4-5% of lung adenocarcinoma tumors. Examples include HER2-YVMA, EGFR-SVD, and EGFR-NPH. These ErbB Exon 20 insertion mutants are highly oncogenic, transforming BaF3 cells to IL-3 independence and promoting tumor growth in vivo.

ErbB inhibitors are a known treatment for a number of cancers. However, not every patient is responsive satisfactorily to this treatment. Thus, there is a long-felt need in the art for new therapies that are able to address the variable responsiveness of cancer patients to known therapies. The present invention is able to overcome some of these drawbacks of the standard of care, as it existed prior to the development of the compositions and methods disclosed herein.

Paradoxic ErbB Receptor Activation

Although the mechanisms described herein apply to any form of cancer in which these EGFR variants of the disclosure are expressed, the prevalence of these variants in glioblastoma (GBM) are provide by way of example. Other cancers expressing the EGFR variants of the disclosure include, but are not limited to, solid cancers, epithelial cancers and/or cancers of epithelial origin, bladder cancer, breast cancer, cervical cancer, colorectal cancer, endometrial cancer, gastric cancer, glioblastoma (GBM), head and neck cancer, lung cancer, and non-small cell lung cancer (NSCLC).

In GBM tumors EGFR is frequently the target of genomic mutations and alternative splicing events that result in alteration of the extracellular dimer interface. Many tumors express more than one aberrant isoform. The disclosure provides the mechanism of activation for the most commonly occurring variants, EGFR-Viii, EGFR-Vii, EGFR-Vvi, EGFR-G598V and EGFR-A289V. Although each isoform/point mutant is the result of a distinct ectodomain alteration, all are activated by a common mechanism involving covalent ligand-independent dimerization.

AMG-595 (Amgen) is an EGFR-Viii isoform selective antibody that has no activity against wild type EGFR or other splice-activated variants. Rindopepimut (Celldex) is a vaccine the produces an immunological response selectively against tumor cells expressing EGFR-Viii but not wild type EGFR or other splice-activated isoforms. Other EGFR isoforms expressed in GBM tumors (EGFR-Vii and EGFR-Vvi) are constitutively active covalent receptors and their expression may limit the breadth and duration of treatment benefit for an ErbB inhibitor that is selective only for EGFR-Viii. Therefore, it may be useful to exclude patients whose tumors express EGFR-Vii, EGFR-Vvi, or EGFR ectodomain point mutants from treatment with an EGFR-Viii selective therapy.

The heterogenic expression pattern for multiple ectodomain variants of ErbB receptors in tumors indicates that a small molecule inhibitor that inhibits all variants is preferred. The family of covalently-activated EGFR isoforms responds very differently to small molecule ErbB inhibitors compared to EGFR catalytic domain mutations observed in NSCLC. Importantly, Type I inhibitors, including erlotinib, all induce the formation of covalent EGFR dimers and increase EGFR phosphorylation at sub-saturating concentrations, an activity that is further enhanced when ErbB inhibitor is washed away. This manifests in paradoxical activation of proliferation at sub-saturating concentrations.

The discovery of paradoxical activation of proliferation at sub-saturating concentrations of Type I ErbB inhibitors is further demonstrated for a series of extracellular variants of HER2, prevalent in a number of cancers including breast and bladder. All variants existed as covalently activated receptors, and levels of covalent dimers increased following treatment with Type I inhibitors including sapitinib and afatinib. As with covalently-activated EGFR variants, sub-saturating doses of Type I inhibitors paradoxically increased phosphorylation of HER2 variants, increasing the proliferation of cells expressing them.

In contrast to Type I inhibitors, the disclosure demonstrates that Non-Type I (e.g. Type II) inhibitors including neratinib are devoid of paradoxical activation for cells expressing ErbB ectodomain variants. Neratinib is found to exemplify a preferred molecule that is both potent and selective for each member of the covalently-activated EGFR family versus wild type EGFR.

Collectively, the disclosure provides a structure/functional relationship for predicting how structural variations affecting receptor regions distal to the active site can confer dramatically different responses to small molecule active site inhibitors. The discovery described herein of paradoxical activation of covalently-activated ErbB receptor variants by Type I inhibitors has important clinical implications. The data of the disclosure provide a mechanistic explanation for the failed clinical studies for Type I inhibitors in tumor types where expression of covalently-activated ErbB receptors is prevalent. This includes erlotinib and gefitinib in GBM tumors, erlotinib in SCCHN tumors, and sapitinib in breast tumors.

Glioblastoma

Glioblastoma (GBM), grade IV astrocytoma, is the most common form of brain cancer. The outcome for this disease is dismal. Surgery followed by a therapeutic regimen of radiation and temozolomide is standard of care, however this produces a median overall survival (OS) of only 14.6 months and few patients survive for five years. There has been little progress made in extending survival for GBM patients over the past decade. Although bevacizumab showed an improved progression free survival benefit in the recurrent setting, the addition of bevacizumab to standard of care therapy in the front-line setting did not result in an OS benefit.

EGFR is the most frequently altered oncogene in GBM. In addition to EGFR gene amplification, many tumors express variants generated by aberrant splicing or genomic mutation. The first recognized variant is EGFR-Viii, resulting from truncation of exons 2-7 and expressed by approximately 20% of GBM tumors. EGFR-Viii is oncogenic. EGFR-Viii is constitutively activated in the absence of EGF ligand, exhibiting sustained signaling that is resistant to downregulation. Therefore, EGFR-Viii is both transforming and tumorigenic. Expression of EGFR-Viii is associated with poor long term overall survival in GBM.

RNA sequencing data has revealed that EGFR-Viii is just one of several aberrantly spliced variants of EGFR expressed in GBM tumors. Two others result in truncation of exons 12-13 (EGFR-Vvi and 14-15 (EGFR-Vii). Like EGFR-Viii, EGFR-Vii is both transforming and tumorigenic. In addition to splice variants, GBM tumors also express a collection of EGFR point mutations including C620Y, A289V and G598V, which are transforming and tumorigenic. The complex landscape of EGFR alterations in GBM is further compounded by the observation that many tumors express more than one receptor variant.

Because the expression of multiple EGFR variants in GBM gives rise to transforming and tumorigenic activity and because EGFR is the most frequently altered oncogene present in GBM tumors, EGFR is an especially attractive target for small molecule ErbB inhibitors. Following the success for small molecule EGFR therapeutics against NSCLC tumors harboring activating mutations in EGFR (erlotinib, gefitinib, and afatinib), these drugs were tested in GBM. Despite intense clinical investigation of this group of ErbB inhibitors in GBM, involving >30 clinical trials and >1500 patients, all failed to produce any benefit, even for those tumors that expressed EGFR-Viii. Strikingly, some evidence suggests that erlotinib promoted disease progression. A phase 2 study evaluating erlotinib in combination with radiation and temozolomide showed median PFS (mPFS) and median OS (mOS) of 2.8 months and 8.6 months, as compared to 6.9 months and 14.6 months for patients receiving radiation and temozolomide alone. Another randomized phase II trial with erlotinib showed that patients who received erlotinib, including those whose tumors expressed EGFR-Viii, progressed more poorly as compared to those patients who received standard of care therapy. The clinical failures for ErbB inhibitors such as erlotinib in GBM tumors has cast doubt on the role of EGFR as a driver of tumor growth in GBM and led to inquiry as to why ErbB inhibitors that were so effective in treating EGFR mutations in lung cancer were so ineffective in treating EGFR variants in GBM.

A distinctive feature for the EGFR variants expressed in GBM is their location within the extracellular domain. This is in contrast to activating mutations of EGFR found in lung cancer, which often reside in the intracellular catalytic domain. EGFR is composed of four extracellular domains (two ligand binding domains and two cysteine rich regions), a transmembrane domain, and an intracellular catalytic domain. Ligand binding promotes dimerization of the extracellular cysteine rich domains (CR1 and CR2), an event that confers dimerization of the intracellular domain and activation of receptor catalytic activity. Nearly all EGFR splicing events and mutations in GBM affect the extracellular region, specifically two cysteine rich regions (CR1 and CR2) that form the extracellular dimer interface. The CR regions contain >40 cysteine residues, all of which form intramolecular disulfide bonds. In EGFR-Viii, truncation of exons 2-7 results in partial loss of sequence encoding the CR1 region. A consequence is loss of one cysteine from the Cys295-Cys307 pair, leaving Cys307 as a free unpaired cysteine. For EGFR-Viii, this cysteine can form an intermolecular disulfide bond with another EGFR monomer to drive a covalently dimerized and constitutively activated receptor. Mutation of Cysteine 307 to a Serine (C307S) prevents the formation of covalently dimerized EGFR-Viii and is inactive.

Although several recent preclinical studies have suggested that EGFR kinase inhibitors such as erlotinib are quite ineffective at inhibiting EGFR-Viii, there has been no mechanism proposed for this effect. There is also a lack in current understanding for the mechanism responsible for activation of other ectodomain variants in GBM, including EGFR-Vii and EGFR-A289V. The disclosure provides a mechanism of receptor activation and impact on ErbB inhibitor activity for a group of four of the most common ectodomain variants in GBM, EGFR-Viii, EGFR-Vii, EGFR-Vvi, EGFR-G598V and EGFR-A289V.

The disclosure demonstrates that like EGFR-Viii, an additional group of commonly occurring EGFR variants in GBM (EGFR-Vii, EGFR-Vvi, EGFR-G598V and EGFR-A289V) all exist as constitutively active covalent dimers and together form a family of EGFR isoforms that are activated by this common mechanism. Furthermore, the disclosure shows that the propensity of these variants to covalently dimerize is coupled to the conformation of the intracellular catalytic site, conferring distinct activity for classes of small molecules inhibitors binding to this distal site. Inhibitors that stabilize the active conformation of the kinase (Type I inhibitors, including erlotinib) induce the formation of covalent dimers for all covalently-activated EGFR isoforms. This is associated with the propensity of Type I inhibitors to increase EGFR phosphorylation at sub-saturating concentrations and to paradoxically stimulate the proliferation of cells expressing covalently-activated EGFR isoforms.

Neither enhanced dimerization nor paradoxical activation of EGFR is seen with small molecule inhibitors that stabilize the inactive kinase conformation (Type II inhibitors, including lapatinib and neratinib). Examples of Type II inhibitors were identified that were potent inhibitors of covalently-activated EGFR isoforms and which were selective for this family compared to WT-EGFR.

Similar to the mutations identified for EGFR, the disclosure identifies a group of splice events and mutations affecting the CR domains of HER2 and HER4. The disclosure demonstrates that this group of splice events and mutations affecting the CR domains of HER2 and HER4 exists as covalent dimers and are paradoxically activated by agents with a Type I binding mode. These data provide a mechanistic explanation for the failure of multiple clinical trials involving Type I inhibitors, including >30 clinical trials of Type I ErbB inhibitors in GBM. Collectively these data indicate that tumors expressing covalently-activated EGFR isoforms should be excluded from treatment with Type I ErbB inhibitors such as erlotinib because of paradoxical activation. These data further demonstrate the utility for optimizing Type II ErbB inhibitors against the covalently-activated ErbB family.

Definitions

Unless specified otherwise the following general definitions apply to all compounds of the disclosure according to the description.

The term "compound of the disclosure," as used herein, refers to compounds represented by any of the formulas described herein (e.g. Formulae (I')-(IV') and (I) to (VII)) and any of the specific examples disclosed herein.

It will be understood that while compounds disclosed herein may be presented in one particular configuration. Such particular configuration is not to be construed as limiting the disclosure to one or another isomer, tautomer, regioisomer or stereoisomer, nor does it exclude mixtures of isomers, tautomers, regioisomers or stereoisomers. In some embodiments, the presentation of a compound herein in a particular configuration intends to encompass, and to refer to, each of the available isomers, tautomers, regioisomers, and stereoisomers of the compound, or any mixture thereof; while the presentation further intends to refer to the specific configuration of the compound.

Further, it will be understood that while compounds disclosed herein may be presented without specified configuration (e.g., without specified stereochemistry). Such presentation intends to encompass all available isomers, tautomers, regioisomers, and stereoisomers of the compound. In some embodiments, the presentation of a compound herein without specified configuration intends to refer to each of the available isomers, tautomers, regioisomers, and stereoisomers of the compound, or any mixture thereof.

As used herein, the term "isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

As used herein, the term "chiral centre" refers to a carbon atom bonded to four nonidentical substituents.

As used herein, the term "chiral isomer" means a compound with at least one chiral centre. Compounds with more than one chiral centre may exist either as an individual diastereomer or as a mixture of diastereomers, termed "diastereomeric mixture." When one chiral centre is present, a stereoisomer may be characterised by the absolute configuration (R or S) of that chiral centre. Absolute configuration refers to the arrangement in space of the substituents attached to the chiral centre. The substituents attached to the chiral centre under consideration are ranked in accordance with the *Sequence Rule* of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

As used herein, the term "geometric isomer" means the diastereomers that owe their existence to hindered rotation about double bonds or a cycloalkyl linker (e.g., 1,3-cyclobutyl). These configurations are differentiated in their names by the prefixes cis and trans, or Z and E, which indicate that the groups are on the same or opposite side of the double bond in the molecule according to the Cahn-Ingold-Prelog rules.

It is understood that "independently of each other" means that when a group is occurring more than one time in any compound, its definition on each occurrence is independent from any other occurrence.

It is further understood that a dashed line (or a wave being transverse to a bond) depicts the site of attachment of a residue (i.e. a partial formula).

The term "halogen" or "hal" as used herein may be fluoro, chloro, bromo or iodo preferably fluoro, chloro.

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intends to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, i-pentyl or n-hexyl. In some embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms. In some embodiments, the term "alkyl" as used herein refers to a fully saturated branched or unbranched hydrocarbon moiety. The term "$C_{1-4}$alkyl" refers to a fully saturated branched or unbranched hydrocarbon moiety having 1, 2, 3 or 4 carbon atoms. Representative examples of alkyl include, but are not limited to, methyl, ethyl, n-propyl, iso-propyl, n-butyl, sec-butyl, isobutyl, tert-butyl.

As used herein, the term "optionally substituted alkyl" refers to unsubstituted alkyl or alkyl having designated substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulphhydryl, alkylthio, arylthio, thiocarboxylate, sulphates, alkylsulphinyl, sulphonato, sulphamoyl, sulphonamido, nitro, trifluoromethyl, cyano, azido, heterocyclyl, alkylaryl, or an aromatic or heteroaromatic moiety.

As used herein, the term “alkenyl” includes unsaturated aliphatic groups analogous in length and possible substitution to the alkyls described above, but that contain at least one double bond. For example, the term “alkenyl” includes straight chain alkenyl groups (e.g., ethenyl, propenyl, butenyl, pentenyl, hexenyl, heptenyl, octenyl, nonenyl, decenyl), and branched alkenyl groups. In certain embodiments, a straight chain or branched alkenyl group has six or fewer carbon atoms in its backbone (e.g., $C_2$-$C_6$ for straight chain, $C_3$-$C_6$ for branched chain). The term “$C_2$-$C_6$” includes alkenyl groups containing two to six carbon atoms. The term “$C_3$-$C_6$” includes alkenyl groups containing three to six carbon atoms.

As used herein, the term “optionally substituted alkenyl” refers to unsubstituted alkenyl or alkenyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulphhydryl, alkylthio, arylthio, thiocarboxylate, sulphates, alkylsulphinyl, sulphonato, sulphamoyl, sulphonamido, nitro, trifluoromethyl, cyano, heterocyclyl, alkylaryl, or an aromatic or heteroaromatic moiety.

As used herein, the term “alkynyl” includes unsaturated aliphatic groups analogous in length and possible substitution to the alkyls described above, but which contain at least one triple bond. For example, “alkynyl” includes straight chain alkynyl groups (e.g., ethynyl, propynyl, butynyl, pentynyl, hexynyl, heptynyl, octynyl, nonynyl, decynyl), and branched alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term “$C_2$-$C_6$” includes alkynyl groups containing two to six carbon atoms. The term “$C_3$-$C_6$” includes alkynyl groups containing three to six carbon atoms. As used herein, “$C_2$-$C_6$ alkenylene linker” or “$C_2$-$C_6$ alkynylene linker” is intended to include $C_2$, $C_3$, $C_4$, $C_5$ or $C_6$ chain (linear or branched) divalent unsaturated aliphatic hydrocarbon groups. For example, $C_2$-$C_6$ alkenylene linker is intended to include $C_2$, $C_3$, $C_4$, $C_5$ and $C_6$ alkenylene linker groups.

As used herein, the term “optionally substituted alkynyl” refers to unsubstituted alkynyl or alkynyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulphhydryl, alkylthio, arylthio, thiocarboxylate, sulphates, alkylsulphinyl, sulphonato, sulphamoyl, sulphonamido, nitro, trifluoromethyl, cyano, azido, heterocyclyl, alkylaryl, or an aromatic or heteroaromatic moiety.

Other optionally substituted moieties (such as optionally substituted cycloalkyl, heterocycloalkyl, aryl, or heteroaryl) include both the unsubstituted moieties and the moieties having one or more of the designated substituents. For example, substituted heterocycloalkyl includes those substituted with one or more alkyl groups, such as 2,2,6,6-tetramethyl-piperidinyl and 2,2,6,6-tetramethyl-1,2,3,6-tetrahydropyridinyl.

The term “alkoxy” or “alkoxyl” as used herein includes substituted and unsubstituted alkyl groups covalently linked to an oxygen atom. Examples of alkoxy groups or alkoxyl radicals include, but are not limited to, methoxy, ethoxy, isopropyloxy, propoxy, butoxy and pentoxy groups.

The term “cycloalkyl” as used herein refers to a saturated or partially unsaturated hydrocarbon monocyclic or polycyclic (e.g., fused, bridged, or spiro rings) system having 3 to 30 carbon atoms (e.g., C3-C12, C3-C10, or C3-C8). Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, 1,2,3,4-tetrahydronaphthalenyl, adamantly, hexahydroindacenyl. It is understood that for polycyclic (e.g., fused, bridged, or spiro rings) system, only one of the rings therein needs to be non-aromatic.

The term “aryl” as used herein refers to groups with aromaticity, including “conjugated,” or multicyclic systems with one or more aromatic rings and do not contain any heteroatom in the ring structure. The term aryl includes both monovalent species and divalent species. Examples of aryl groups include, but are not limited to, phenyl, biphenyl, naphthyl and the like. In some embodiments, the aryl is phenyl.

As used herein, the term “heterocycloalkyl” refers to a saturated or partially unsaturated 3-8 membered monocyclic, 7-12 membered bicyclic (fused, bridged, or spiro rings), or 11-14 membered tricyclic ring system (fused, bridged, or spiro rings) having one or more heteroatoms (such as O, N, S, P, or Se), e.g., 1 or 1-2 or 1-3 or 1-4 or 1-5 or 1-6 heteroatoms, or e.g. 1, 2, 3, 4, 5, or 6 heteroatoms, independently selected from the group consisting of nitrogen, oxygen and sulphur, unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, oxiranyl, azetidinyl, oxetanyl, thietanyl, 1,2,3,6-tetrahydropyridinyl, tetrahydropyranyl, dihydropyranyl, pyranyl, morpholinyl, tetrahydrothiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, 1,4-dioxa-8-azaspiro[4.5]decanyl, 1,4-dioxaspiro[4.5]decanyl, 1-oxaspiro[4.5]decanyl, 1-azaspiro[4.5]decanyl, 3'H-spiro[cyclohexane-1,1'-isobenzofuran]-yl, 7'H-spiro[cyclohexane-1,5'-furo[3,4-b]pyridin]-yl, 3'H-spiro[cyclohexane-1,1'-furo[3,4-c]pyridin]-yl, 3-azabicyclo[3.1.0]hexanyl, 3-azabicyclo[3.1.0]hexan-3-yl, 1,4,5,6-tetrahydropyrrolo[3,4-c]pyrazolyl, 3,4,5,6,7,8-hexahydropyrido[4,3-d]pyrimidinyl, 4,5,6,7-tetrahydro-1H-pyrazolo[3,4-c]pyridinyl, 5,6,7,8-tetrahydropyrido[4,3-d]pyrimidinyl, 2-azaspiro[3.3]heptanyl, 2-methyl-2-azaspiro[3.3]heptanyl, 2-azaspiro[3.5]nonanyl, 2-methyl-2-azaspiro[3.5]nonanyl, 2-azaspiro[4.5]decanyl, 2-methyl-2-azaspiro[4.5]decanyl, 2-oxa-azaspiro[3.4]octanyl, 2-oxa-azaspiro

[3.4]octan-6-yl, and the like. In the case of multicyclic heterocycloalkyl, only one of the rings in the heterocycloalkyl needs to be non-aromatic. In some embodiments, the heterocycloalkyl is oxetanyl, tetrahydrofuranyl, pyrrolidinyl, piperidinyl, morpholinyl, 3-oxabicyclo[3.1.0]hexanyl, 3-azabicyclo[3.1.0]hexanyl, 2-azaspiro[3.3]heptanyl, 2-oxa-5-azaspiro[3.4]octanyl, wherein the oxetanyl, tetrahydrofuranyl, pyrrolidinyl, piperidinyl, morpholinyl, 3-oxabicyclo[3.1.0]hexanyl, 3-azabicyclo[3.1.0]hexanyl, 2-azaspiro[3.3]heptanyl, or 2-oxa-5-azaspiro[3.4]octanyl.

As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulphur. The nitrogen atom may be substituted or unsubstituted (i.e., N or NR wherein R is H or other substituents, as defined). The nitrogen and sulphur heteroatoms may optionally be oxidised (i.e., N→O and $S(O)_p$, where p=1 or 2). It is to be noted that total number of S and O atoms in the aromatic heterocycle is not more than 1. In some embodiments, the term "heteroaryl", refers to a (fully) aromatic ring system having 3, 4, 5, or 6 ring atoms, preferably 6 ring atoms, selected from C, N, O, or S, preferably C, N, or O, more preferably C, N, with the number of N atoms preferably being 0, 1, 2 or 3 and the number of O and S atoms each being 0, 1 or 2. Examples of "heteroaryl" include furyl, imidazolyl, isoxazolyl, oxazolyl, pyrazinyl, pyrazolyl (pyrazyl), pyridazinyl, pyridinyl, pyrimidinyl, pyrrolyl, thiazolyl, thienyl, and the like. Preferred examples of "heteroaryl" include pyridinyl.

In some embodiments, the cycloalkyl, heterocycloalkyl, aryl, or heteroaryl is substituted at one or more ring positions (e.g., the ring-forming carbon or heteroatom such as N) with such substituents as described above, for example, alkyl, alkenyl, alkynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkyl carbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. In some embodiments, the cycloalkyl, heterocycloalkyl, aryl, or heteroaryl is substituted with halogen (e.g., F or Cl).

As used herein, the term "substituted," means that any one or more hydrogen atoms on the designated atom is replaced with a selection from the indicated groups, provided that the designated atom's normal valency is not exceeded, and that the substitution results in a stable compound. When a substituent is oxo or keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N).

The terms "nucleic acid" and "polynucleotide" are used interchangeably herein to refer to single- or double-stranded RNA, DNA, or mixed polymers. Polynucleotides may include genomic sequences, extra-genomic and plasmid sequences, and smaller engineered gene segments that express, or may be adapted to express polypeptides.

An "isolated nucleic acid" is a nucleic acid that is substantially separated from other genome DNA sequences as well as proteins or complexes such as ribosomes and polymerases, which naturally accompany a native sequence. The term embraces a nucleic acid sequence that has been removed from its naturally occurring environment, and includes recombinant or cloned DNA isolates and chemically synthesized analogues or analogues biologically synthesized by heterologous systems. A substantially pure nucleic acid includes isolated forms of the nucleic acid. Of course, this refers to the nucleic acid as originally isolated and does not exclude genes or sequences later added to the isolated nucleic acid by the hand of man.

The term "polypeptide" is used in its conventional meaning, i.e., as a sequence of amino acids. The polypeptides are not limited to a specific length of the product. Peptides, oligopeptides, and proteins are included within the definition of polypeptide, and such terms may be used interchangeably herein unless specifically indicated otherwise. This term also does not refer to or exclude post-expression modifications of the polypeptide, for example, glycosylations, acetylations, phosphorylations and the like, as well as other modifications known in the art, both naturally occurring and non-naturally occurring. A polypeptide may be an entire protein, or a subsequence thereof.

An "isolated polypeptide" is one that has been identified and separated and/or recovered from a component of its natural environment. In preferred embodiments, the isolated polypeptide will be purified (1) to greater than 95% by weight of polypeptide as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or, preferably, silver stain. Isolated polypeptide includes the polypeptide in situ within recombinant cells since at least one component of the polypeptide's natural environment will not be present. Ordinarily, however, isolated polypeptide will be prepared by at least one purification step.

A "native sequence" polynucleotide is one that has the same nucleotide sequence as a polynucleotide derived from nature. A "native sequence" polypeptide is one that has the same amino acid sequence as a polypeptide (e.g. EGFR) derived from nature (e.g., from any species). Such native sequence polynucleotides and polypeptides can be isolated from nature or can be produced by recombinant or synthetic means.

A polynucleotide "variant," as the term is used herein, is a polynucleotide that typically differs from a polynucleotide specifically disclosed herein in one or more substitutions, deletions, additions and/or insertions.

A polypeptide "variant," as the term is used herein, is a polypeptide that typically differs from a polypeptide specifically disclosed herein in one or more substitutions, deletions, additions and/or insertions, or inversions. Such variants may be naturally occurring, non-naturally occurring, or may be synthetically generated.

EGFR mutations (or variants) of the disclosure may comprise one or more substitutions, deletions, additions and/or insertions, or inversions of the amino acid sequence that are alter the function of the resultant protein. Mutations may be detected, for example, by comparison or alignment of a nucleic or amino acid sequence with a wild type sequence.

When comparing polynucleotide and polypeptide sequences, two sequences are said to be "identical" if the sequence of nucleotides or amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNAS TAR, Inc., Madison, WI), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington DC Vol. 5, Suppl. 3, pp. 345-358; Hein J. (1990) Unified Approach to Alignment and Phylogenes pp. 626-645 *Methods in Enzymology* vol. 183, Academic Press, Inc., San Diego, CA; Higgins, D. G. and Sharp, P. M. (1989) *CABIOS* 5: 151-153; Myers, E. W. and Muller W. (1988) *CABIOS* 4:11-17; Robinson, E. D. (1971) *Comb. Theor* 11:105; Santou, N. Nes, M. (1987) *Mol. Biol. Evol.* 4:406-425; Sneath, P. H. A. and Sokal, R. R. (1973) *Numerical Taxonomy—the Principles and Practice of Numerical Taxonomy*, Freeman Press, San Francisco, CA; Wilbur, W. J. and Lipman, D. J. (1983) *Proc. Natl. Acad., Sci. USA* 80: 726-730.

Alternatively, optimal alignment of sequences for comparison may be conducted by the local identity algorithm of Smith and Waterman (1981) *Add. APL. Math* 2:482, by the identity alignment algorithm of Needleman and Wunsch (1970)*J. Mol. Biol.* 48:443, by the search for similarity methods of Pearson and Lipman (1988) *Proc. Natl. Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, WI), or by inspection.

One preferred example of algorithms that are suitable for determining percent sequence identity and sequence similarity are the BLAST and BLAST 2.0 algorithms, which are described in Altschul et al. (1977) *Nucl. Acids Res.* 25:3389-3402 and Altschul et al. (1990) *J. Mol. Biol.* 215:403-410, respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information.

In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) *Proc. Natl. Acad. Sci. USA* 89:10915) alignments, (B) of 50, expectation (E) of 10, M=5, N=−4 and a comparison of both strands.

For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one approach, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residues occur in both sequences to yield the number of matched positions, dividing the number of matched positions by the total number of positions in the reference sequence (i.e., the window size) and multiplying the results by 100 to yield the percentage of sequence identity.

A wild type EGFR sequence of the disclosure may comprise or consist of the amino acid sequence of:

(SEQ ID NO: 1, corresponding to epidermal growth factor receptor [*Homo sapiens*] and Genbank Accession No. CAA25240)

```
  1  mrpsgtagaa llallaalcp asraleekkv cqgtsnkltq lgtfedhfls lqrmfnncev

 61  vlgnleityv qrnydlsflk tiqevagyvl ialntverip lenlqiirgn myyensyala

121  vlsnydankt glkelpmrnl qeilhgavrf snnpalcnve siqwrdivss dflsnmsmdf

181  qnhlgscqkc dpscpngscw gageencqkl tkiicaqqcs grcrgkspsd cchnqcaagc

241  tgpresdclv crkfrdeatc kdtcpplmly npttyqmdvn pegkysfgat cvkkcprnyv

301  vtdhgscvra cgadsyemee dgvrkckkce gperkvcngi gigefkdsls inatnikhfk

361  nctsisgdlh ilpvafrgds fthtppldpq eldilktvke itgflliqaw penrtdlhaf

421  enleiirgrt kqhgqfslav vslnitslgl rslkeisdgd viisgnknlc yantinwkkl
```

-continued

```
 481  fgtsgqktki isnrgensck atgqvchalc spegcwgpep rdcvscrnvs rgrecvdkck
 541  llegeprefv enseciqchp eclpqamnit ctgrgpdnci qcahyidgph cvktcpagvm
 601  genntlvwky adaghvchlc hpnctygctg pglegcptng pkipsiatgm vgalllllvv
 661  algiglfmrr rhivrkrtlr rllqerelve pltpsgeapn qallrilket efkkikvlgs
 721  gafgtvykgl wipegekvki pvaikelrea tspkankeil deayvmasvd nphvcrllgi
 781  cltstvqlit qlmpfgclld yvrehkdnig sqyllnwcvq iakgmnyled rrlvhrdlaa
 841  rnvlvktpqh vkitdfglak llgaeekeyh aeggkvpikw malesilhri ythqsdvwsy
 901  gvtvwelmtf gskpydgipa seissilekg erlpqppict idvymimvkc wmidadsrpk
 961  freliiefsk mardpqrylv iqgdermhlp sptdsnfyra lmdeedmddv vdadeylipq
1021  qgffsspsts rtpllsslsa tsnnstvaci drnglqscpi kedsflqrys sdptgalted
1081  siddtflpvp eyinqsvpkr pagsvqnpvy hnqplnpaps rdphyqdphs tavgnpeyln
1141  tvqptcvnst fdspahwaqk gshqisldnp dyqqdffpke akpngifkgs taenaeylrv
1201  apqssefiga.
```

A wild type HER2 Receptor sequence of the disclosure may comprise or consist of the amino acid sequence of:

(SEQ ID NO: 2, corresponding to receptor tyrosine-protein kinase erbB-2 isoform a precursor [*Homo sapiens*] and GenBank Accession No. NP_004439)

```
   1  melaalcrwg lllallppga astqvctgtd mklrlpaspe thldmlrhly qgcqvvqgnl
  61  eltylptnas lsflqdiqev qgyvliahnq vrqvplqrlr ivrgtqlfed nyalavldng
 121  dplnnttpvt gaspgglrel qlrslteilk ggvliqrnpq lcyqdtilwk difhknnqla
 181  ltlidtnrsr achpcspmck gsrcwgesse dcqsltrtvc aggcarckgp lptdccheqc
 241  aagctgpkhs dclaclhfnh sgicelhcpa lvtyntdtfe smpnpegryt fgascvtacp
 301  ynylstdvgs ctlvcplhnq evtaedgtqr cekcskpcar vcyglgmehl revravtsan
 361  iqefagckki fgslaflpes fdgdpasnta plqpeqlqvf etleeitgyl yisawpdslp
 421  dlsvfqnlqv irgrilhnga ysltlqglgi swlglrslre lgsglalihh nthlcfvhtv
 481  pwdqlfrnph qallhtanrp edecvgegla chqlcarghc wgpgptqcvn csqflrgqec
 541  veecrvlqgl preyvnarhc lpchpecqpq ngsvtcfgpe adqcvacahy kdppfcvarc
 601  psgvkpdlsy mpiwkfpdee gacqpcpinc thscvdlddk gcpaeqrasp ltsiisavvg
 661  illvvvlgvv fgilikrrqq kirkytmrrl lqetelvepl tpsgampnqa qmrilketel
 721  rkvkvlgsga fgtvykgiwi pdgenvkipv aikvlrents pkankeilde ayvmagvgsp
 781  yvsrllgicl tstvqlvtql mpygclldhv renrgrlgsq dllnwcmqia kgmsyledvr
 841  lvhrdlaarn vlvkspnhvk itdfglarll dideteyhad ggkvpikwma lesilrrrft
 901  hqsdvwsygv tvwelmtfga kpydgipare ipdllekger lpqppictid vymimvkcwm
 961  idsecrprfr elvsefsrma rdpqrfvviq nedlgpaspl dstfyrslle dddmgdlvda
1021  eeylvpqqgf fcpdpapgag gmvhhrhrss strsgggdlt lglepseeea prsplapseg
1081  agsdvfdgdl gmgaakglqs lpthdpsplq rysedptvpl psetdgyvap ltcspqpeyv
1141  nqpdvrpqpp spregplpaa rpagatlerp ktlspgkngv vkdvfafgga venpeyltpq
1201  ggaapqphpp pafspafdnl yywdqdpper gappstfkgt ptaenpeylg ldvpv.
```

A wild type HER2 Receptor sequence of the disclosure may comprise or consist of the amino acid sequence of:

(SEQ ID NO: 3, corresponding to receptor tyrosine-protein kinase erbB-2 isoform b [*Homo sapiens*] and GenBank Accession No. NP_001005862)

```
   1 mklrlpaspe thldmlrhly qgcqvvqgnl eltylptnas lsflqdiqev qgyvliahnq
  61 vrqvplqrlr ivrgtqlfed nyalavldng dplnnttpvt gaspgglrel qlrslteilk
 121 ggvliqrnpq lcyqdtilwk difhknnqla ltlidtnrsr achpcspmck gsrcwgesse
 181 dcqsltrtvc aggcarckgp lptdccheqc aagctgpkhs dclaclhfnh sgicelhcpa
 241 lvtyntdtfe smpnpegryt fgascvtacp ynylstdvgs ctlvcplhnq evtaedgtqr
 301 cekcskpcar vcyglgmehl revravtsan iqefagckki fgslaflpes fdgdpasnta
 361 plqpeqlqvf etleeitgyl yisawpdslp dlsvfqnlqv irgrilhnga ysltlqglgi
 421 swlglrslre lgsglalihh nthlcfvhtv pwdqlfrnph qallhtanrp edecvgegla
 481 chqlcarghc wgpgptqcvn csqflrgqec veecrvlqgl preyvnarhc lpchpecqpq
 541 ngsvtcfgpe adqcvacahy kdppfcvarc psgvkpdlsy mpiwkfpdee gacqpcpinc
 601 thscvdlddk gcpaeqrasp ltsiisavvg illvvvlgvv fgilikrrqq kirkytmrrl
 661 lqetelvepl tpsgampnqa qmrilketel rkvkvlgsga fgtvykgiwi pdgenvkipv
 721 aikvlrents pkankeilde ayvmagvgsp yvsrllgicl tstvqlvtql mpygclldhv
 781 renrgrlgsq dllnwcmqia kgmsyledvr lvhrdlaarn vlvkspnhvk itdfglarll
 841 dideteyhad ggkvpikwma lesilrrrft hqsdvwsygv tvwelmtfga kpydgipare
 901 ipdllekger lpqppictid vymimvkcwm idsecrprfr elvsefsrma rdpqrfvviq
 961 nedlgpaspl dstfyrslle dddmgdlvda eeylvpqqgf fcpdpapgag gmvhhrhrss
1021 strsgggdlt lglepseeea prsplapseg agsdvfdgdl gmgaakglqs lpthdpsplq
1081 rysedptvpl psetdgyvap ltcspqpeyv nqpdvrpqpp spregplpaa rpagatlerp
1141 ktlspgkngv vkdvfafgga venpeyltpq ggaapqphpp pafspafdnl yywdqdpper
1201 gappstfkgt ptaenpeylg ldvpv.
```

A wild type HER2 Receptor sequence of the disclosure may comprise or consist of the amino acid sequence of:

(SEQ ID NO: 4, corresponding to receptor tyrosine-protein kinase erbB-2 isoform c [*Homo sapiens*] and GenBank Accession No. NP_001276865)

```
   1 mprgswkpqv ctgtdmklrl paspethldm lrhlyqgcqv vqgnleltyl ptnaslsflq
  61 diqevqgyvl iahnqvrqvp lqrlrivrgt qlfednyala vldngdplnn ttpvtgaspg
 121 glrelqlrsl teilkggvli qrnpqlcyqd tilwkdifhk nnqlaltlid tnrsrachpc
 181 spmckgsrcw gessedcqsl trtvcaggca rckgplptdc cheqcaagct gpkhsdclac
 241 lhfnhsgice lhcpalvtyn tdtfesmpnp egrytfgasc vtacpynyls tdvgsctlvc
 301 plhnqevtae dgtqrcekcs kpcarvcygl gmehlrevra vtsaniqefa gckkifgsla
 361 flpesfdgdp asntaplqpe qlqvfetlee itgylyisaw pdslpdlsvf qnlqvirgri
 421 lhngaysltl qglgiswlgl rslrelgsgl alihhnthlc fvhtvpwdql frnphqallh
 481 tanrpedecv geglachqlc arghcwgpgp tqcvncsqfl rgqecveecr vlqglpreyv
 541 narhclpchp ecqpqngsvt cfgpeadqcv acahykdppf cvarcpsgvk pdlsympiwk
 601 fpdeegacqp cpincthscv dlddkgcpae qraspltsii savvgillvv vlgvvfgili
 661 krrqqkirky tmrrllqete lvepltpsga mpnqaqmril ketelrkvkv lgsgafgtvy
 721 kgiwipdgen vkipvaikvl rentspkank eildeayvma gvgspyvsrl lgicltstvq
```

-continued

```
 781  lvtqlmpygc lldhvrenrg rlgsqdllnw cmqiakgmsy ledvrlvhrd laarnvlvks

 841  pnhvkitdfg larlldidet eyhadggkvp ikwmalesil rrrfthqsdv wsygvtvwel

 901  mtfgakpydg ipareipdll ekgerlpqpp ictidvymim vkcwmidsec rprfrelvse

 961  fsrmardpqr fvviqnedlg paspldstfy rsllededdmg dlvdaeeylv pqqgffcpdp

1021  apgaggmvhh rhrssstrsg ggdltlglep seeeaprspl apsegagsdv fdgdlgmgaa

1081  kglqslpthd psplqrysed ptvplpsetd gyvapltcsp qpeyvnqpdv rpqppspreg

1141  plpaarpaga tlerpktlsp gkngvvkdvf afggavenpe yltpqggaap qphpppafsp

1201  afdnlyywdq dppergapps tfkgtptaen peylgldvpv.
```

A wild type HER2 Receptor sequence of the disclosure may comprise or consist of the amino acid sequence of:

(SEQ ID NO: 5, corresponding to receptor tyrosine-protein kinase erbB-2 isoform d precursor [*Homo sapiens*] and GenBank Accession No. NP_001276866)

```
   1  melaalcrwg lllallppga astqvctgtd mklrlpaspe thldmlrhly qgcqvvqgnl

  61  eltylptnas lsflqdiqev qgyvliahnq vrqvplqrlr ivrgtqlfed nyalavldng

 121  dplnnttpvt gaspgglrel qlrslteilk ggvliqrnpq lcyqdtilwk difhknnqla

 181  ltlidtnrsr achpcspmck gsrcwgesse dcqsltrtvc aggcarckgp lptdccheqc

 241  aagctgpkhs dclaclhfnh sgicelhcpa lvtyntdtfe smpnpegryt fgascvtacp

 301  ynylstdvgs ctivcplhnq evtaedgtqr cekcskpcar vcyglgmehl revravtsan

 361  iqefagckki fgslaflpes fdgdpasnta plqpeqlqvf etleeitgyl yisawpdslp

 421  dlsvfqnlqv irgrilhnga ysltlqglgi swlglrslre lgsglalihh nthlcfvhtv

 481  pwdqlfrnph qallhtanrp edecvgegla chqlcarghc wgpgptqcvn csqflrgqec

 541  veecrvlqgl preyvnarhc lpchpecqpq ngsvtcfgpe adqcvacahy kdppfcvarc

 601  psgvkpdlsy mpiwkfpdee gacqpcpinc thscvdlddk gcpaeqrasp ltsiisavvg

 661  illvvvlgvv fgilikrrqq kirkytmrrl lqetelvepl tpsgampnqa qmrilketel

 721  rkvkvlgsga fgtvykgiwi pdgenvkipv aikvlrents pkankeilde ayvmagvgsp

 781  yvsrllgicl tstvqlvtql mpygclldhv renrgrlgsq dllnwcmqia kgmsyledvr

 841  lvhrdlaarn vlvkspnhvk itdfglarll dideteyhad ggkvpikwma lesilrrrft

 901  hqsdvwsygv tvwelmtfga kpydgipare ipdllekger lpqppictid vymimvkcwm

 961  idsecrprfr elvsefsrma rdpqrfvviq nedlgpaspl dstfyrslle dddmgdlvda

1021  eeylvpqqgf fcpdpapgag gmvhhrhrss strnm.
```

A wild type HER2 Receptor sequence of the disclosure may comprise or consist of the amino acid sequence of:

(SEQ ID NO: 6, corresponding to receptor tyrosine-protein kinase erbB-2 isoform e [*Homo sapiens*] and GenBank Accession No. NP_001276867)

```
   1  mklrlpaspe thldmlrhly qgcqvvqgnl eltylptnas lsflqdiqev qgyvliahnq

  61  vrqvplqrlr ivrgtqlfed nyalavldng dplnnttpvt gaspgglrel qlrslteilk

 121  ggvliqrnpq lcyqdtilwk difhknnqla ltlidtnrsr achpcspmck gsrcwgesse

 181  dcqsltrtvc aggcarckgp lptdccheqc aagctgpkhs dclaclhfnh sgicelhcpa

 241  lvtyntdtfe smpnpegryt fgascvtacp ynylstdvgs ctivcplhnq evtaedgtqr

 301  cekcskpcar vcyglgmehl revravtsan iqefagckki fgslaflpes fdgdpasnta

 361  plqpeqlqvf etleeitgyl yisawpdslp dlsvfqnlqv irgrilhnga ysltlqglgi
```

-continued

```
421   swlglrslre lgsglalihh nthlcfvhtv pwdqlfrnph qallhtanrp edecvgegla
481   chqlcarghc wgpgptqcvn csqflrgqec veecrvlqgl preyvnarhc lpchpecqpq
541   ngsvtcfgpe adqcvacahy kdppfcvarc psgvkpdlsy mpiwkfpdee gacqpcpinc
601   ths.
```

Based on the definitions given throughout the application the skilled person knows which combinations are synthetically feasible and realistic, e.g. typically combinations of groups leading to heteroatoms directly linked to each other are not contemplated.

Compounds of the Present Disclosure

In some aspects, the present disclosure provides a compound of Formula (I'):

I'

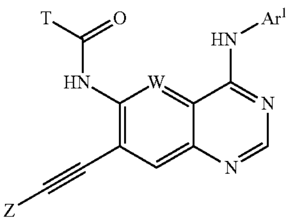

or a pharmaceutically acceptable salt or stereoisomer thereof, wherein:

W is CH or N;

Z is 3- to 12-membered heterocycloalkyl optionally substituted with one or more $R^Z$;

each $R^Z$ independently is halogen, CN, —OH, —$NH_2$, —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 10-membered heterocycloalkyl, or 5- to 10-membered heteroaryl; wherein the —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 10-membered heterocycloalkyl, or 5- to 10-membered heteroaryl is optionally substituted with one or more $R^{Za}$;

each $R^{Za}$ independently is halogen, CN, —OH, —$NH_2$, —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 10-membered heterocycloalkyl, or 5- to 10-membered heteroaryl;

T is —O—($C_1$-$C_6$ alkyl), —NH—($C_1$-$C_6$ alkyl), $C_1$-$C_6$ alkyl, $C_2$-$C_6$ alkenyl, or $C_2$-$C_6$ alkynyl; wherein the —O—($C_1$-$C_6$ alkyl), —NH—($C_1$-$C_6$ alkyl), $C_1$-$C_6$ alkyl, $C_2$-$C_6$ alkenyl, or $C_2$-$C_6$ alkynyl is optionally substituted with one or more $R^T$;

each $R^T$ independently is halogen, CN, —OH, —$NH_2$, —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 10-membered heterocycloalkyl, or 5- to 10-membered heteroaryl; wherein the —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 10-membered heterocycloalkyl, or 5- to 10-membered heteroaryl is optionally substituted with one or more $R^{Ta}$;

each $R^{Ta}$ independently is halogen, CN, —OH, —$NH_2$, —C(=O)OH, —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 10-membered heterocycloalkyl, or 5- to 10-membered heteroaryl;

$Ar^1$ is $C_6$-$C_{10}$ aryl optionally substituted with one or more $R^{A1}$;

each $R^{A1}$ independently is halogen, CN, —OH, —$NH_2$, —$OR^{A1a}$, —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 10-membered heterocycloalkyl, or 5- to 10-membered heteroaryl; wherein the —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 10-membered heterocycloalkyl, or 5- to 10-membered heteroaryl is optionally substituted with one or more $R^{A1a}$; and each $R^{A1a}$ independently is halogen, CN, —OH, —$NH_2$, —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 10-membered heterocycloalkyl, or 5- to 10-membered heteroaryl; wherein the —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 10-membered heterocycloalkyl, or 5- to 10-membered heteroaryl is optionally substituted with one or more $R^{A1b}$; and each $R^{A1b}$ independently is halogen, CN, —OH, or —$NH_2$.

In some aspects, the compound is of Formula (I') or a pharmaceutically acceptable salt or stereoisomer thereof, wherein:

W is CH or N;

Z is 3- to 12-membered heterocycloalkyl optionally substituted with one or more $R^Z$;

each $R^Z$ independently is halogen, CN, —OH, —$NH_2$, —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, or 5- to 10-membered heteroaryl; wherein the —O—($C_1$-$C_6$ alkyl), —NH($C_1$-$C_6$ alkyl), —N($C_1$-$C_6$alkyl)$_2$, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3 or 5- to 10-membered heteroaryl is optionally substituted with one or more $R^{Za}$;

each $R^{Za}$ independently is halogen, CN, —OH, —$NH_2$, —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 10-membered heterocycloalkyl, or 5- to 10-membered heteroaryl;

T is —O—($C_1$-$C_6$ alkyl), —NH—($C_1$-$C_6$ alkyl), $C_1$-$C_6$ alkyl, $C_2$-$C_6$ alkenyl, or $C_2$-$C_6$ alkynyl; wherein the —O—($C_1$-$C_6$ alkyl), —NH—($C_1$-$C_6$ alkyl), $C_1$-$C_6$ alkyl, $C_2$-$C_6$ alkenyl, or $C_2$-$C_6$ alkynyl is optionally substituted with one or more $R^T$;

each $R^T$ independently is halogen, CN, —OH, —$NH_2$, —O—($C_1$-$C_6$ alkyl), $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 7-membered heterocycloalkyl, or 5- to 10-membered heteroaryl; wherein the —O—($C_1$-$C_6$ alkyl), $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 7-membered heterocycloalkyl, or 5- to 10-membered heteroaryl is optionally substituted with one or more $R^{Ta}$;

each $R^{Ta}$ independently is halogen, CN, —OH, —$NH_2$, —C(═O)OH, —O—($C_1$-$C_6$ alkyl$C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 10-membered heterocycloalkyl, or 5- to 10-membered heteroaryl;

$Ar^1$ is $C_6$-$C_{10}$ aryl optionally substituted with one or more $R^{A1}$;

each $R^{A1}$ independently is halogen, CN, —OH, —$NH_2$, —$OR^{A1a}$, —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl; wherein the —O—($C_1$-$C_6$ alkyl), —NH ($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl is optionally substituted with one or more $R^{A1a}$; and each $R^{A1a}$ independently is halogen, CN, —OH, —$NH_2$, —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl; wherein the —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl is optionally substituted with one or more $R^{A1b}$; and each $R^{A1b}$ independently is halogen, CN, —OH, or —$NH_2$;

provided that when Z is

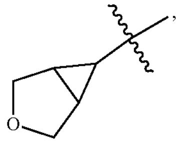 [SMILES: *C1C2COCC12]

then $Ar^1$ is $C_6$-$C_{10}$ aryl optionally substituted with one or more halogen.

In some aspects, the compound is of Formula (I') or a pharmaceutically acceptable salt or stereoisomer thereof, wherein:

W is CH or N;

Z is 3- to 12-membered heterocycloalkyl optionally substituted with one or more $R^Z$;

each $R^Z$ independently is halogen, CN, —OH, —$NH_2$, —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, or 5- to 10-membered heteroaryl; wherein the —O—($C_1$-$C_6$ alkyl), —NH($C_1$-$C_6$ alkyl), —N($C_1$-$C_6$alkyl)$_2$, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3 or 5- to 10-membered heteroaryl is optionally substituted with one or more $R^{Za}$;

each $R^{Za}$ independently is halogen, CN, —OH, —$NH_2$, —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 10-membered heterocycloalkyl, or 5- to 10-membered heteroaryl;

T is —O—($C_1$-$C_6$ alkyl), —NH—($C_1$-$C_6$ alkyl), $C_1$-$C_6$ alkyl, $C_2$-$C_6$ alkenyl, or $C_2$-$C_6$ alkynyl; wherein the —O—($C_1$-$C_6$ alkyl), —NH—($C_1$-$C_6$ alkyl), $C_1$-$C_6$ alkyl, $C_2$-$C_6$ alkenyl, or $C_2$-$C_6$ alkynyl is optionally substituted with one or more $R^T$;

each $R^T$ independently is halogen, CN, —OH, —$NH_2$, —O—($C_1$-$C_6$ alkyl), $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 7-membered monocyclic heterocycloalkyl, or 5- to 10-membered heteroaryl; wherein the —O—($C_1$-$C_6$ alkyl), $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 7-membered heterocycloalkyl, or 5- to 10-membered heteroaryl is optionally substituted with one or more $R^{Ta}$;

each $R^{Ta}$ independently is halogen, CN, —OH, —$NH_2$, —C(═O)OH, —O—($C_1$-$C_6$ alkyl$C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 10-membered heterocycloalkyl, or 5- to 10-membered heteroaryl;

$Ar^1$ is $C_6$-$C_{10}$ aryl optionally substituted with one or more $R^{A1}$;

each $R^{A1}$ independently is halogen, CN, —OH, —$NH_2$, —$OR^{A1a}$, —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl; wherein the —O—($C_1$-$C_6$ alkyl), —NH ($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl is optionally substituted with one or more $R^{A1a}$; and each $R^{A1a}$ independently is halogen, CN, —OH, —$NH_2$, —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl; wherein the —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl is optionally substituted with one or more $R^{A1b}$, and each $R^{A1b}$ independently is halogen, CN, —OH, or —$NH_2$;

provided that when Z is

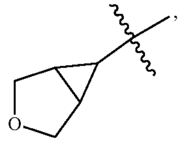 [SMILES: *C1C2COCC12]

then $Ar^1$ is $C_6$-$C_{10}$ aryl optionally substituted with one or more halogen.

In some embodiments, the compound is of Formula (I') or a pharmaceutically acceptable salt or stereoisomer thereof, wherein:

W is CH;

Z is 3- to 12-membered heterocycloalkyl optionally substituted with one or more $R^Z$;

each $R^Z$ independently is halogen, —O—($C_1$-$C_6$ alkyl), $C_1$-$C_6$ alkyl, or 3- to 10-membered heterocycloalkyl; wherein the —O—($C_1$-$C_6$ alkyl), $C_1$-$C_6$ alkyl, or 3- to 10-membered heterocycloalkyl is optionally substituted with one or more halogen;

T is —O—($C_1$-$C_6$ alkyl), —NH—($C_1$-$C_6$ alkyl), $C_1$-$C_6$ alkyl, $C_2$-$C_6$ alkenyl, or $C_2$-$C_6$ alkynyl; wherein the $C_1$-$C_6$ alkyl, $C_2$-$C_6$ alkenyl, or $C_2$-$C_6$ alkynyl is optionally substituted with one or more $R^T$;

each $R^T$ independently is halogen, —OH, —O—($C_1$-$C_6$ alkyl), —N($C_1$-$C_6$ alkyl)$_2$, or 3- to 7-membered heterocycloalkyl; wherein the —O—($C_1$-$C_6$ alkyl), —N($C_1$-$C_6$ alkyl)$_2$, or 3- to 7-membered heterocycloalkyl is optionally substituted with one or more —C(═O)OH;

$Ar^1$ is $C_6$-$C_{10}$ aryl optionally substituted with one or more $R^{A1}$;

each $R^{A1}$ independently is halogen, —$OR^{A1a}$, or —O—($C_1$-$C_6$ alkyl) optionally substituted with one or more $R^{A1a}$; and each $R^{A1a}$ independently is $C_6$-$C_{10}$ aryl or 5- to 10-membered heteroaryl; wherein the $C_6$-$C_{10}$ aryl or 5- to 10-membered heteroaryl is optionally substituted with one or more halogen.

In some embodiments, the compound is of Formula (I') or a pharmaceutically acceptable salt or stereoisomer thereof, wherein:

W is CH;

Z is 3- to 12-membered heterocycloalkyl optionally substituted with one or more $R^Z$;

each $R^Z$ independently is halogen, —O—($C_1$-$C_6$ alkyl), $C_1$-$C_6$ alkyl, or 3- to 10-membered heterocycloalkyl; wherein the —O—($C_1$-$C_6$ alkyl), $C_1$-$C_6$ alkyl, or 3- to 10-membered heterocycloalkyl is optionally substituted with one or more halogen;

T is —O—($C_1$-$C_6$ alkyl), —NH—($C_1$-$C_6$ alkyl), $C_1$-$C_6$ alkyl, $C_2$-$C_6$ alkenyl, or $C_2$-$C_6$ alkynyl; wherein the $C_1$-$C_6$ alkyl, $C_2$-$C_6$ alkenyl, or $C_2$-$C_6$ alkynyl is optionally substituted with one or more $R^T$;

each $R^T$ independently is halogen, —OH, —O—($C_1$-$C_6$ alkyl), —N($C_1$-$C_6$ alkyl)$_2$, or 3- to 7-membered monocyclic heterocycloalkyl; wherein the —O—($C_1$-$C_6$ alkyl), —N($C_1$-$C_6$ alkyl)$_2$, or 3- to 7-membered monocyclic heterocycloalkyl is optionally substituted with one or more —C(═O)OH;

$Ar^1$ is $C_6$-$C_{10}$ aryl optionally substituted with one or more $R^{A1}$;

each $R^{A1}$ independently is halogen, —$OR^{A1a}$, or —O—($C_1$-$C_6$ alkyl) optionally substituted with one or more $R^{A1a}$; and each $R^{A1a}$ independently is $C_6$-$C_{10}$ aryl or 5- to 10-membered heteroaryl; wherein the $C_6$-$C_{10}$ aryl or 5- to 10-membered heteroaryl is optionally substituted with one or more halogen.

In some embodiments, the compound is of Formula (I') or a pharmaceutically acceptable salt or stereoisomer thereof, wherein:

W is CH;

Z is 3- to 12-membered heterocycloalkyl optionally substituted with one or more $R^Z$;

each $R^Z$ independently is halogen, —O—($C_1$-$C_6$ alkyl), or $C_1$-$C_6$ alkyl; wherein the —O—($C_1$-$C_6$ alkyl) or $C_1$-$C_6$ alkyl is optionally substituted with one or more halogen;

T is —O—($C_1$-$C_6$ alkyl), —NH—($C_1$-$C_6$ alkyl), $C_1$-$C_6$ alkyl, $C_2$-$C_6$ alkenyl, or $C_2$-$C_6$ alkynyl; wherein the $C_1$-$C_6$ alkyl, $C_2$-$C_6$ alkenyl, or $C_2$-$C_6$ alkynyl is optionally substituted with one or more $R^T$;

each $R^T$ independently is halogen, —OH, —O—($C_1$-$C_6$ alkyl), or 3- to 7-membered heterocycloalkyl; wherein the —O—($C_1$-$C_6$ alkyl), or 3- to 7-membered heterocycloalkyl is optionally substituted with one or more —C(═O)OH;

$Ar^1$ is $C_6$-$C_{10}$ aryl optionally substituted with one or more $R^{A1}$;

each $R^{A1}$ independently is halogen, —$OR^{A1a}$, or —O—($C_1$-$C_6$ alkyl) optionally substituted with one or more $R^{A1a}$; and each $R^{A1a}$ independently is $C_6$-$C_{10}$ aryl or 5- to 10-membered heteroaryl; wherein the $C_6$-$C_{10}$ aryl or 5- to 10-membered heteroaryl is optionally substituted with one or more halogen;

provided that when Z is

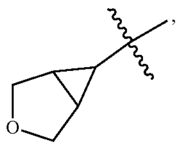 [SMILES: *C1C2COCC12]

then $Ar^1$ is $C_6$-$C_{10}$ aryl optionally substituted with one or more halogen.

In some embodiments, the compound is of Formula (I') or a pharmaceutically acceptable salt or stereoisomer thereof, wherein:

W is CH;

Z is 3- to 12-membered heterocycloalkyl optionally substituted with one or more $R^Z$;

each $R^Z$ independently is halogen, —O—($C_1$-$C_6$ alkyl), or $C_1$-$C_6$ alkyl; wherein the —O—($C_1$-$C_6$ alkyl) or $C_1$-$C_6$ alkyl is optionally substituted with one or more halogen;

T is —O—($C_1$-$C_6$ alkyl), —NH—($C_1$-$C_6$ alkyl), $C_1$-$C_6$ alkyl, $C_2$-$C_6$ alkenyl, or $C_2$-$C_6$ alkynyl; wherein the $C_1$-$C_6$ alkyl, $C_2$-$C_6$ alkenyl, or $C_2$-$C_6$ alkynyl is optionally substituted with one or more $R^T$;

each $R^T$ independently is halogen, —OH, —O—($C_1$-$C_6$ alkyl), or 3- to 7-membered monocyclic heterocycloalkyl; wherein the —O—($C_1$-$C_6$ alkyl), or 3- to 7-membered monocyclic heterocycloalkyl is optionally substituted with one or more —C(═O)OH;

$Ar^1$ is $C_6$-$C_{10}$ aryl optionally substituted with one or more $R^{A1}$;

each $R^{A1}$ independently is halogen, —$OR^{A1a}$, or —O—($C_1$-$C_6$ alkyl) optionally substituted with one or more $R^{A1a}$; and each $R^{A1a}$ independently is $C_6$-$C_{10}$ aryl or 5- to 10-membered heteroaryl; wherein the $C_6$-$C_{10}$ aryl or 5- to 10-membered heteroaryl is optionally substituted with one or more halogen;

provided that when Z is

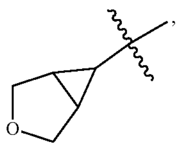 [SMILES: *C1C2COCC12]

then $Ar^1$ is $C_6$-$C_{10}$ aryl optionally substituted with one or more halogen.

In some embodiments, the compound is of Formula (I') or a pharmaceutically acceptable salt or stereoisomer thereof, wherein:

W is CH;

Z is 3- to 12-membered heterocycloalkyl optionally substituted with one or more $R^Z$;

each $R^Z$ independently is halogen, —O—($C_1$-$C_6$ alkyl), or $C_1$-$C_6$ alkyl; wherein the —O—($C_1$-$C_6$ alkyl) or $C_1$-$C_6$ alkyl is optionally substituted with one or more halogen;

T is —O—($C_1$-$C_6$ alkyl), —NH—($C_1$-$C_6$ alkyl), $C_1$-$C_6$ alkyl, $C_2$-$C_6$ alkenyl, or $C_2$-$C_6$ alkynyl; wherein the $C_1$-$C_6$ alkyl, $C_2$-$C_6$ alkenyl, or $C_2$-$C_6$ alkynyl is optionally substituted with one or more $R^T$;

each $R^T$ independently is halogen, —OH, —O—($C_1$-$C_6$ alkyl), or 3- to 7-membered heterocycloalkyl; wherein the —O—($C_1$-$C_6$ alkyl), or 3- to 7-membered heterocycloalkyl is optionally substituted with one or more —C(=O)OH;

$Ar^1$ is $C_6$-$C_{10}$ aryl optionally substituted with one or more halogen.

In some embodiments, the compound is of Formula (I') or a pharmaceutically acceptable salt or stereoisomer thereof, wherein:

W is CH;

Z is 3- to 12-membered heterocycloalkyl optionally substituted with one or more $R^Z$;

each $R^Z$ independently is halogen, —O—($C_1$-$C_6$ alkyl), or $C_1$-$C_6$ alkyl; wherein the —O—($C_1$-$C_6$ alkyl) or $C_1$-$C_6$ alkyl is optionally substituted with one or more halogen;

T is —O—($C_1$-$C_6$ alkyl), —NH—($C_1$-$C_6$ alkyl), $C_1$-$C_6$ alkyl, $C_2$-$C_6$ alkenyl, or $C_2$-$C_6$ alkynyl; wherein the $C_1$-$C_6$ alkyl, $C_2$-$C_6$ alkenyl, or $C_2$-$C_6$ alkynyl is optionally substituted with one or more $R^T$;

each $R^T$ independently is halogen, —OH, —O—($C_1$-$C_6$ alkyl), or 3- to 7-membered monocyclic heterocycloalkyl; wherein the —O—($C_1$-$C_6$ alkyl), or 3- to 7-membered monocyclic heterocycloalkyl is optionally substituted with one or more —C(=O)OH;

$Ar^1$ is $C_6$-$C_{10}$ aryl optionally substituted with one or more halogen.

In some embodiments, the compound is of Formula (I') or a pharmaceutically acceptable salt or stereoisomer thereof, wherein:

W is CH;

Z is 3- to 12-membered heterocycloalkyl optionally substituted with one or more $C_1$-$C_6$ alkyl;

T is $C_2$-$C_6$ alkenyl optionally substituted with one or more 6-membered heterocycloalkyl; and $Ar^1$ is $C_6$ aryl optionally substituted with one or more halogen.

In some embodiments, the compound is of Formula (I') or a pharmaceutically acceptable salt or stereoisomer thereof, wherein:

W is CH;

Z is 3- to 12-membered heterocycloalkyl optionally substituted with one or more $C_1$-$C_6$ alkyl;

T is $C_2$-$C_6$ alkenyl optionally substituted with one or more 6-membered monocyclic heterocycloalkyl; and $Ar^1$ is $C_6$ aryl optionally substituted with one or more halogen.

Variable W

In some embodiments, W is CH.

In some embodiments, W is N.

Variables Z, $R^Z$, and $R^{Za}$

In some embodiments, Z is 3- to 12-membered heterocycloalkyl optionally substituted with one or more $R^Z$; and each $R^Z$ independently is halogen, —O—($C_1$-$C_6$ alkyl), $C_1$-$C_6$ alkyl, or 3- to 10-membered heterocycloalkyl; wherein the —O—($C_1$-$C_6$ alkyl), $C_1$-$C_6$ alkyl, or 3- to 10-membered heterocycloalkyl is optionally substituted with one or more halogen.

In some embodiments, Z is 3- to 12-membered heterocycloalkyl.

In some embodiments, Z is 3- to 12-membered heterocycloalkyl substituted with one or more $R^Z$.

In some embodiments, Z is oxetanyl, tetrahydrofuranyl, pyrrolidinyl, piperidinyl, morpholinyl, 3-oxabicyclo[3.1.0]hexanyl, 3-azabicyclo[3.1.0]hexanyl, 2-azaspiro[3.3]heptanyl, 2-oxa-5-azaspiro[3.4]octanyl, wherein the oxetanyl, tetrahydrofuranyl, pyrrolidinyl, piperidinyl, morpholinyl, 3-oxabicyclo[3.1.0]hexanyl, 3-azabicyclo[3.1.0]hexanyl, 2-azaspiro[3.3]heptanyl, or 2-oxa-5-azaspiro[3.4]octanyl is optionally substituted with one or more $R^Z$.

In some embodiments, Z is oxetanyl, tetrahydrofuranyl, pyrrolidinyl, piperidinyl, morpholinyl, 3-oxabicyclo[3.1.0]hexanyl, 3-azabicyclo[3.1.0]hexanyl, 2-azaspiro[3.3]heptanyl, 2-oxa-5-azaspiro[3.4]octanyl, wherein the oxetanyl, tetrahydrofuranyl, pyrrolidinyl, piperidinyl, morpholinyl, 3-azabicyclo[3.1.0]hexanyl, 2-azaspiro[3.3]heptanyl, or 2-oxa-5-azaspiro[3.4]octanyl is optionally substituted with one or more $R^Z$.

In some embodiments, Z is

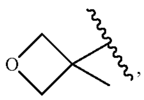, 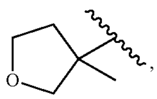 [SMILES: *C1(C)CCOC1], 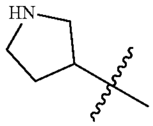,

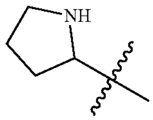, 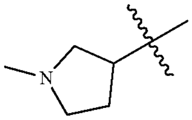, 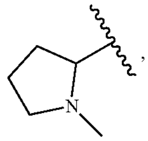,

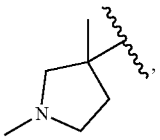, 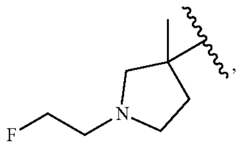,

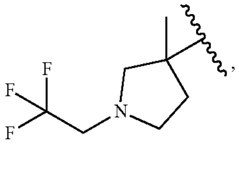, 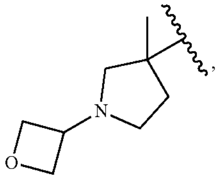,

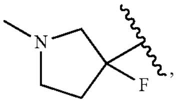, 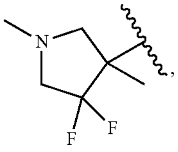,

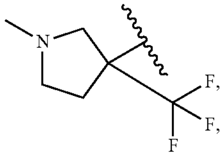, 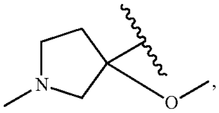,

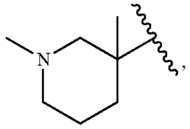, 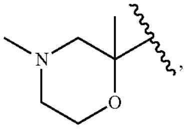,

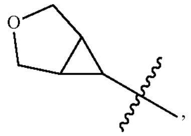, 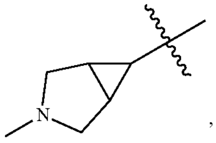,

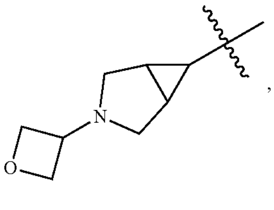, 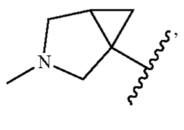,

-continued
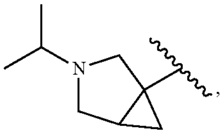,
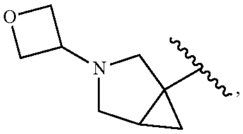,
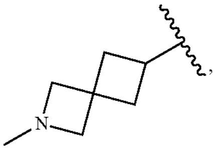, or
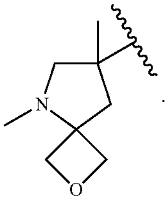.
In some embodiments, Z is
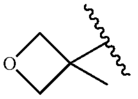,
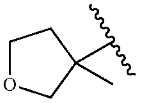,
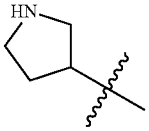,
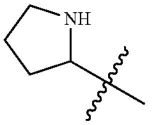,
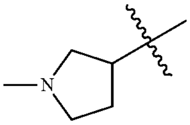,
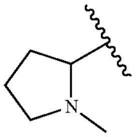,
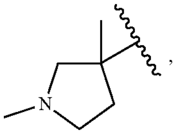,
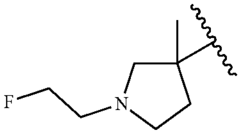,
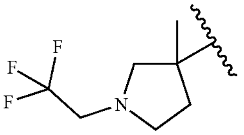,
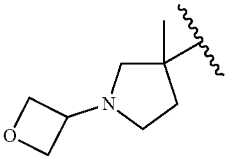,
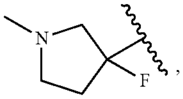,
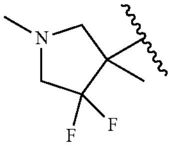,
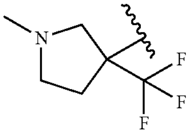,
-continued
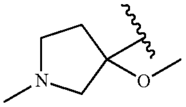,
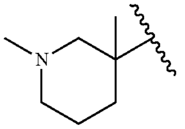,
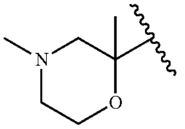,
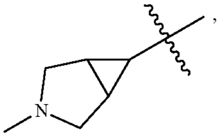,
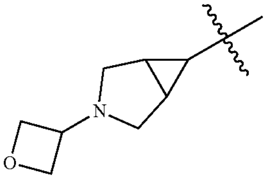,
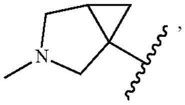,
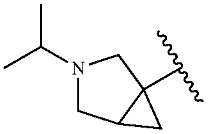,
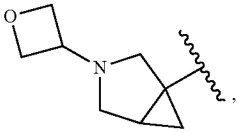,
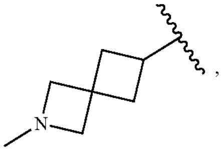, or
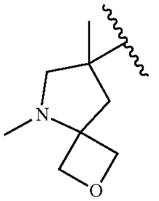.
In some embodiments, Z is
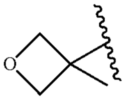
In some embodiments, Z is
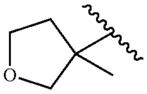.
In some embodiments, Z is
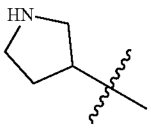, -continued

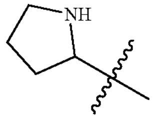, 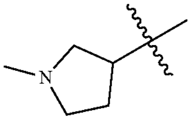, 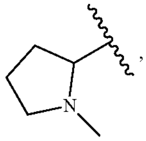,

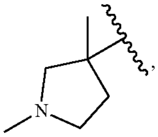, 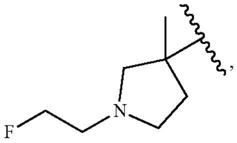,

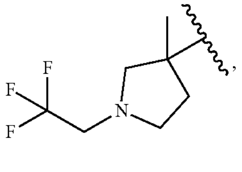, 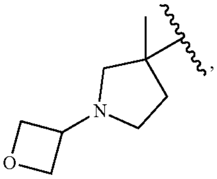,

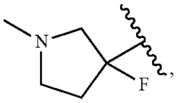, 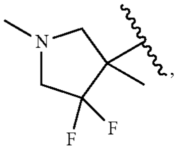,

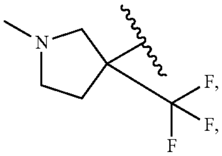 or 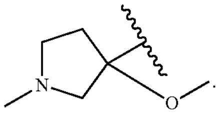.

In some embodiments, Z is

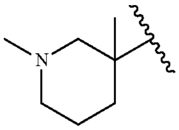 or 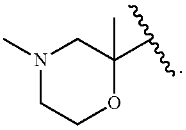.

In some embodiments, Z is

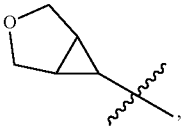, 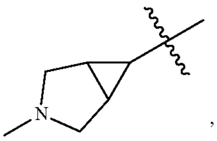,

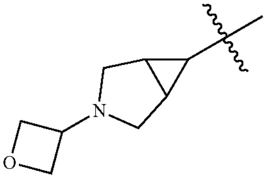, 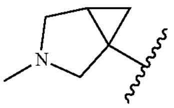,

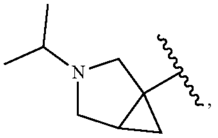, or 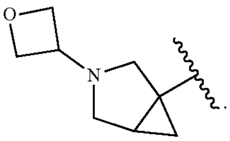.

In some embodiments, Z is

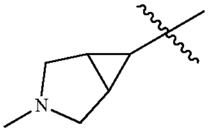, 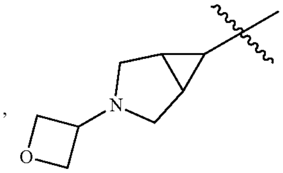,

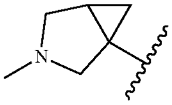, 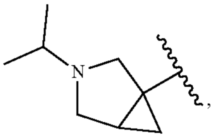, or

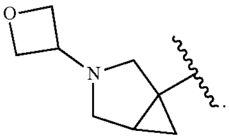.

In some embodiments, Z is

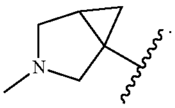 [SMILES: *C12CC1CN(C)C2].

In some embodiments, Z is

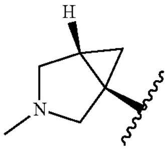 or 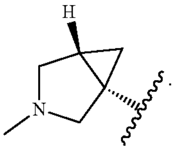.

In some embodiments, Z is

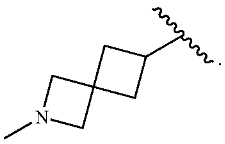.

In some embodiments, Z is

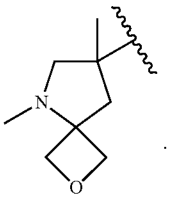 [SMILES: *C1(C)CN(C)C2(COC2)C1].

In some embodiments, at least one $R^Z$ is halogen.

In some embodiments, at least one $R^Z$ is F or Cl.

In some embodiments, at least one $R^Z$ is F.

In some embodiments, at least one $R^Z$ is Cl.

In some embodiments, at least one $R^Z$ is F, and at least one $R^Z$ is Cl.

In some embodiments, at least one $R^Z$ is CN, —OH, or —$NH_2$.

In some embodiments, at least one $R^Z$ is —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 10-membered heterocycloalkyl, or 5- to 10-membered heteroaryl; wherein the —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 10-membered heterocycloalkyl, or 5- to 10-membered heteroaryl is optionally substituted with one or more $R^{Za}$.

In some embodiments, at least one $R^Z$ is —O—($C_1$-$C_6$ alkyl) optionally substituted with one or more $R^{Za}$.

In some embodiments, at least one $R^Z$ is —O—($C_1$-$C_6$ alkyl).

In some embodiments, at least one $R^Z$ is —$OCH_3$.

In some embodiments, at least one $R^Z$ is —O—($C_1$-$C_6$ alkyl) substituted with one or more $R^{Za}$.

In some embodiments, at least one $R^Z$ is —O—($C_1$-$C_6$ alkyl) substituted with one or more halogen (e.g., F or Cl).

In some embodiments, at least one $R^Z$ is —NH($C_1$-$C_6$ alkyl) or —N($C_1$-$C_6$ alkyl)$_2$, wherein the —NH($C_1$-$C_6$ alkyl) or —N($C_1$-$C_6$ alkyl)$_2$ is optionally substituted with one or more $R^{Za}$.

In some embodiments, at least one $R^Z$ is $C_1$-$C_6$ alkyl optionally substituted with one or more $R^{Za}$.

In some embodiments, at least one $R^Z$ is $C_1$-$C_6$ alkyl.

In some embodiments, at least one $R^Z$ is methyl, ethyl, or propyl (e.g., i-propyl).

In some embodiments, at least one $R^Z$ is $C_1$-$C_6$ alkyl substituted with one or more $R^{Za}$.

In some embodiments, at least one $R^Z$ is $C_1$-$C_6$ alkyl substituted with one or more halogen (e.g., F or Cl).

In some embodiments, at least one $R^Z$ is $C_1$-$C_6$ alkyl substituted with one or more F.

In some embodiments, at least one $R^Z$ is $CF_3$.

In some embodiments, at least one $R^Z$ is $C_2$-$C_6$ alkenyl or $C_2$-$C_6$ alkynyl, wherein the $C_2$-$C_6$ alkenyl or $C_2$-$C_6$ alkynyl is optionally substituted with one or more $R^{Za}$.

In some embodiments, at least one $R^Z$ is $C_3$-$C_{10}$ cycloalkyl, $C_6$-$C_{10}$ aryl, 3- to 10-membered heterocycloalkyl, or 5- to 10-membered heteroaryl; wherein the $C_3$-$C_{10}$ cycloalkyl, $C_6$-$C_{10}$ aryl, 3- to 10-membered heterocycloalkyl, or 5- to 10-membered heteroaryl is optionally substituted with one or more $R^{Za}$.

In some embodiments, at least one $R^Z$ is $C_3$-$C_{10}$ cycloalkyl optionally substituted with one or more $R^{Za}$.

In some embodiments, at least one $R^Z$ is $C_6$-$C_{10}$ aryl optionally substituted with one or more $R^{Za}$.

In some embodiments, at least one $R^Z$ is 3- to 10-membered heterocycloalkyl optionally substituted with one or more $R^{Za}$.

In some embodiments, at least one $R^Z$ is 4-membered heterocycloalkyl optionally substituted with one or more $R^{Za}$.

In some embodiments, at least one $R^Z$ is 4-membered heterocycloalkyl.

In some embodiments, at least one $R^Z$ is oxetanyl.

In some embodiments, at least one $R^Z$ is 5- to 10-membered heteroaryl optionally substituted with one or more $R^{Za}$.

In some embodiments, at least one $R^{Za}$ is halogen.

In some embodiments, at least one $R^{Za}$ is F or Cl.

In some embodiments, at least one $R^{Za}$ is F.

In some embodiments, at least one $R^{Za}$ is Cl.

In some embodiments, at least one $R^{Za}$ is CN, —OH, —$NH_2$, —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 10-membered heterocycloalkyl, or 5- to 10-membered heteroaryl.

Variables T, $R^T$, and $R^{Ta}$

In some embodiments, T is —O—($C_1$-$C_6$ alkyl), —NH—($C_1$-$C_6$ alkyl), $C_1$-$C_6$ alkyl, $C_2$-$C_6$ alkenyl, or $C_2$-$C_6$ alkynyl; wherein the —O—($C_1$-$C_6$ alkyl), —NH—($C_1$-$C_6$ alkyl), $C_1$-$C_6$ alkyl, $C_2$-$C_6$ alkenyl, or $C_2$-$C_6$ alkynyl is optionally substituted with one or more $R^T$;

each $R^T$ independently is halogen, CN, —OH, —$NH_2$, —O—($C_1$-$C_6$ alkyl), $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 7-membered heterocycloalkyl, or 5- to 10-membered heteroaryl; wherein the —O—($C_1$-$C_6$ alkyl), $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 7-membered heterocycloalkyl, or 5- to 10-membered heteroaryl is optionally substituted with one or more $R^{Ta}$; and each $R^{Ta}$ independently is halogen, CN, —OH, —$NH_2$, —C(═O)OH, —O—($C_1$-$C_6$ alkyl), $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 10-membered heterocycloalkyl, or 5- to 10-membered heteroaryl.

In some embodiments, T is —O—($C_1$-$C_6$ alkyl), —NH—($C_1$-$C_6$ alkyl), $C_1$-$C_6$ alkyl, $C_2$-$C_6$ alkenyl, or $C_2$-$C_6$ alkynyl; wherein the —O—($C_1$-$C_6$ alkyl), —NH—($C_1$-$C_6$ alkyl), $C_1$-$C_6$ alkyl, $C_2$-$C_6$ alkenyl, or $C_2$-$C_6$ alkynyl is optionally substituted with one or more $R^T$;

each $R^T$ independently is halogen, CN, —OH, —$NH_2$, —O—($C_1$-$C_6$ alkyl), $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 7-membered monocyclic heterocycloalkyl, or 5- to 10-membered heteroaryl; wherein the —O—($C_1$-$C_6$ alkyl), $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 7-membered monocyclic heterocycloalkyl, or 5- to 10-membered heteroaryl is optionally substituted with one or more $R^{Ta}$; and each $R^{Ta}$ independently is halogen, CN, —OH, —$NH_2$, —C(═O)OH, —O—($C_1$-$C_6$ alkyl), $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 10-membered heterocycloalkyl, or 5- to 10-membered heteroaryl.

In some embodiments, T is —O—($C_1$-$C_6$ alkyl), —NH—($C_1$-$C_6$ alkyl), $C_1$-$C_6$ alkyl, $C_2$-$C_6$ alkenyl, or $C_2$-$C_6$ alkynyl; wherein the $C_1$-$C_6$ alkyl, $C_2$-$C_6$ alkenyl, or $C_2$-$C_6$ alkynyl is optionally substituted with one or more $R^T$; and each $R^T$ independently is halogen, —OH, —O—($C_1$-$C_6$ alkyl), —N($C_1$-$C_6$ alkyl)$_2$, or 3- to 7-membered heterocycloalkyl; wherein the —O—($C_1$-$C_6$ alkyl), —N($C_1$-$C_6$ alkyl)$_2$, or 3- to 7-membered heterocycloalkyl is optionally substituted with one or more —C(═O)OH.

In some embodiments, T is —O—($C_1$-$C_6$ alkyl), —NH—($C_1$-$C_6$ alkyl), $C_1$-$C_6$ alkyl, $C_2$-$C_6$ alkenyl, or $C_2$-$C_6$ alkynyl; wherein the $C_1$-$C_6$ alkyl, $C_2$-$C_6$ alkenyl, or $C_2$-$C_6$ alkynyl is optionally substituted with one or more $R^T$; and each $R^T$ independently is halogen, —OH, —O—($C_1$-$C_6$ alkyl), or 3- to 7-membered heterocycloalkyl; wherein the —O—($C_1$-$C_6$ alkyl), or 3- to 7-membered heterocycloalkyl is optionally substituted with one or more —C(═O)OH.

In some embodiments, T is —O—($C_1$-$C_6$ alkyl), —NH—($C_1$-$C_6$ alkyl), $C_1$-$C_6$ alkyl, $C_2$-$C_6$ alkenyl, or $C_2$-$C_6$ alkynyl; wherein the $C_1$-$C_6$ alkyl, $C_2$-$C_6$ alkenyl, or $C_2$-$C_6$ alkynyl is optionally substituted with one or more $R^T$; and each $R^T$ independently is halogen, —OH, —O—($C_1$-$C_6$ alkyl), —N($C_1$-$C_6$ alkyl)$_2$, or 3- to 7-membered monocyclic heterocycloalkyl; wherein the —O—($C_1$-$C_6$ alkyl), —N($C_1$-

$C_6$ alkyl)$_2$, or 3- to 7-membered monocyclic heterocycloalkyl is optionally substituted with one or more —C(═O)OH.

In some embodiments, T is —O—($C_1$-$C_6$ alkyl), —NH—($C_1$-$C_6$ alkyl), $C_1$-$C_6$ alkyl, $C_2$-$C_6$ alkenyl, or $C_2$-$C_6$ alkynyl; wherein the $C_1$-$C_6$ alkyl, $C_2$-$C_6$ alkenyl, or $C_2$-$C_6$ alkynyl is optionally substituted with one or more $R^T$; and each $R^T$ independently is halogen, —OH, —O—($C_1$-$C_6$ alkyl), or 3- to 7-membered heterocycloalkyl; wherein the —O—($C_1$-$C_6$ alkyl), or 3- to 7-membered heterocycloalkyl is optionally substituted with one or more —C(═O)OH.

In some embodiments, T is —O—($C_1$-$C_6$ alkyl) optionally substituted with one or more $R^T$.

In some embodiments, T is —O—($C_1$-$C_6$ alkyl).

In some embodiments, T is —$OCH_3$.

In some embodiments, T is —NH—($C_1$-$C_6$ alkyl) optionally substituted with one or more $R^T$.

In some embodiments, T is —NH—($C_1$-$C_6$ alkyl).

In some embodiments, T is —$NHCH_3$.

In some embodiments, T is $C_1$-$C_6$ alkyl optionally substituted with one or more $R^T$.

In some embodiments, T is $C_1$-$C_6$ alkyl.

In some embodiments, T is methyl or ethyl.

In some embodiments, T is methyl.

In some embodiments, T is ethyl.

In some embodiments, T is $C_1$-$C_6$ alkyl substituted with one or more $R^T$.

In some embodiments, T is $C_1$-$C_6$ alkyl substituted with one or more halogen (e.g., F or $C_1$).

In some embodiments, T is methyl substituted with one or more halogen (e.g., F or Cl).

In some embodiments, T is —CHFCl.

In some embodiments, T is $C_1$-$C_6$ alkyl substituted with one or more CN.

In some embodiments, T is —$CH_2CN$.

In some embodiments, T is $C_2$-$C_6$ alkenyl optionally substituted with one or more $R^T$.

In some embodiments, T is $C_2$-$C_6$ alkenyl.

In some embodiments, T is ethenyl (i.e., —CH═$CH_2$).

In some embodiments, T is propenyl (e.g., —C($CH_3$)═$CH_2$ or —CH═CH—$CH_3$).

In some embodiments, T is pentenyl (e.g., —CH═CH—C($CH_3$)$_2$).

In some embodiments, T is $C_2$-$C_6$ alkenyl substituted with one or more $R^T$.

In some embodiments, T is $C_2$-$C_6$ alkenyl substituted with one or more —OH, —O—($C_1$-$C_6$ alkyl), —N($C_1$-$C_6$ alkyl)$_2$, or 3- to 10-membered heterocycloalkyl; wherein the 3- to 10-membered heterocycloalkyl is optionally substituted with one or more —C(═O)OH.

In some embodiments, T is $C_2$-$C_6$ alkenyl substituted with one or more —OH

In some embodiments, T is $C_2$-$C_6$ alkenyl substituted with one or more —O—($C_1$-$C_6$ alkyl).

In some embodiments, T is $C_2$-$C_6$ alkenyl substituted with one or more —$OCH_3$.

In some embodiments, T is $C_2$-$C_6$ alkenyl substituted with one or more —N($C_1$-$C_6$ alkyl)$_2$.

In some embodiments, T is $C_2$-$C_6$ alkenyl substituted with one or more —N($CH_3$)$_2$.

In some embodiments, T is $C_2$-$C_6$ alkenyl substituted with one or more 3- to 10-membered heterocycloalkyl.

In some embodiments, T is $C_2$-$C_6$ alkenyl substituted with one or more 3- to 10-membered heterocycloalkyl; wherein the 3- to 10-membered heterocycloalkyl is optionally substituted with one or more —C(═O)OH.

In some embodiments, T is $C_2$-$C_6$ alkenyl substituted with one or more 3- to 7-membered heterocycloalkyl.

In some embodiments, T is $C_2$-$C_6$ alkenyl substituted with one or more 3- to 7-membered heterocycloalkyl; wherein the 3- to 7-membered heterocycloalkyl is optionally substituted with one or more —C(═O)OH.

In some embodiments, T is $C_2$-$C_6$ alkenyl substituted with one or more 3- to 7-membered heterocycloalkyl.

In some embodiments, T is $C_2$-$C_6$ alkenyl substituted with one or more 3- to 7-membered monocyclic heterocycloalkyl.

In some embodiments, T is $C_2$-$C_6$ alkenyl substituted with one or more 3- to 7-membered monocyclic heterocycloalkyl; wherein the 3- to 7-membered monocyclic heterocycloalkyl is optionally substituted with one or more —C(═O)OH.

In some embodiments, T is $C_2$-$C_6$ alkenyl substituted with one or more 3- to 7-membered monocyclic heterocycloalkyl.

In some embodiments, T is $C_2$-$C_6$ alkenyl substituted with one or more 6-membered heterocycloalkyl; wherein the 6-membered heterocycloalkyl is optionally substituted with one or more —C(═O)OH.

In some embodiments, T is $C_2$-$C_6$ alkenyl substituted with one or more 6-membered heterocycloalkyl.

In some embodiments, T is $C_2$-$C_6$ alkenyl substituted with one or more 6-membered monocyclic heterocycloalkyl; wherein the 6-membered monocyclic heterocycloalkyl is optionally substituted with one or more —C(═O)OH.

In some embodiments, T is $C_2$-$C_6$ alkenyl substituted with one or more 6-membered monocyclic heterocycloalkyl.

In some embodiments, T is $C_2$-$C_6$ alkynyl optionally substituted with one or more $R^T$.

In some embodiments, T is $C_2$-$C_6$ alkynyl.

In some embodiments, T is propynyl (e.g., —C≡C—$CH_3$).

In some embodiments, T is $C_2$-$C_6$ alkynyl substituted with one or more $R^T$.

In some embodiments, T is propynyl substituted with one or more $R^T$.

In some embodiments, T is —C≡C—$CH_2$—$R^T$.

In some embodiments, T is $C_2$-$C_6$ alkynyl substituted with one or more 3- to 10-membered heterocycloalkyl.

In some embodiments, T is propynyl substituted with one or more 3- to 10-membered heterocycloalkyl.

In some embodiments, T is $C_2$-$C_6$ alkynyl substituted with one or more 3- to 7-membered heterocycloalkyl.

In some embodiments, T is propynyl substituted with one or more 3- to 7-membered heterocycloalkyl.

In some embodiments, T is

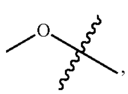 [SMILES: *OC],
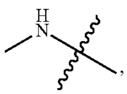 [SMILES: *NC],
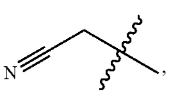,
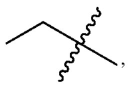,
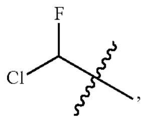,
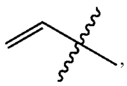,
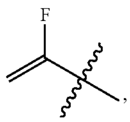,
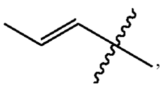,
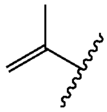,
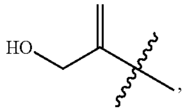,
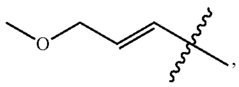,
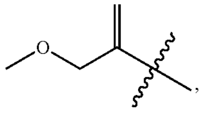,
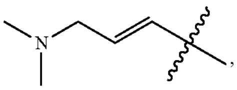, -continued
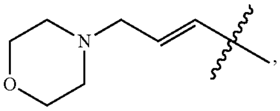,
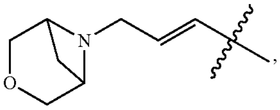,
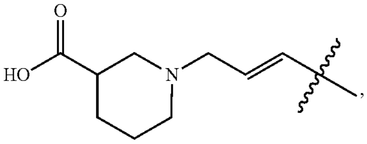,
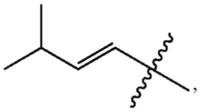, 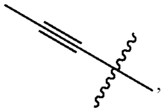, or
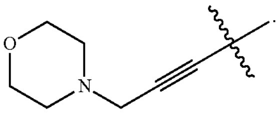.
In some embodiments, T is
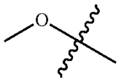, 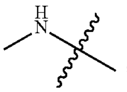,
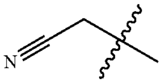, 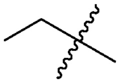,
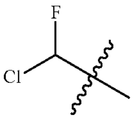, 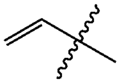,
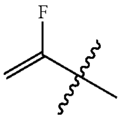,
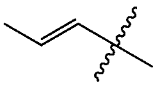, 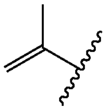,
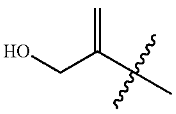,
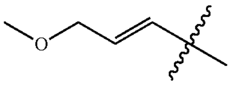,
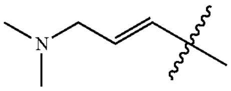,
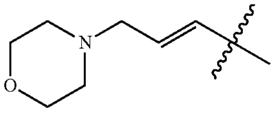,
-continued
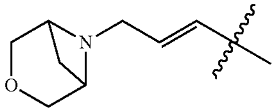,
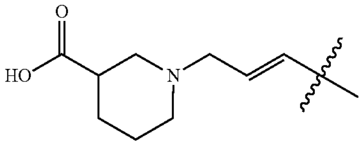,
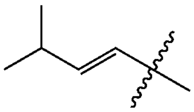,
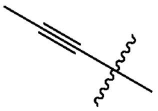, or
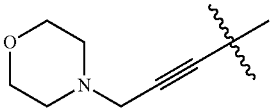.
In some embodiments, T is
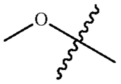.
In some embodiments, T is
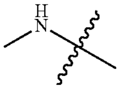.
In some embodiments, T is
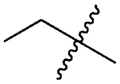 or 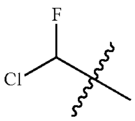.
In some embodiments, T is
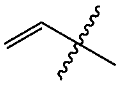, 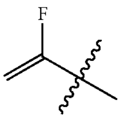,
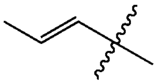, 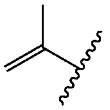,
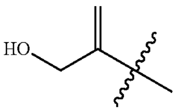, -continued

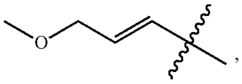
,
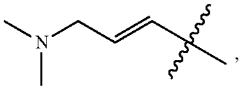
,
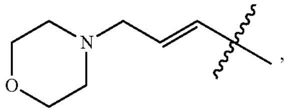
,
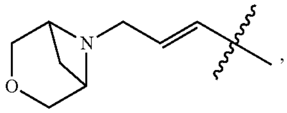
,
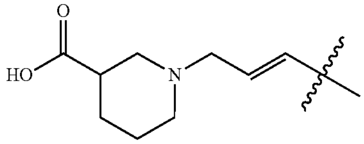
, or
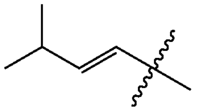
.

In some embodiments, T is

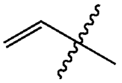
,
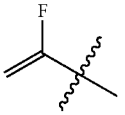
,
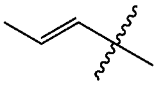
,
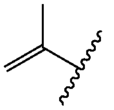
,
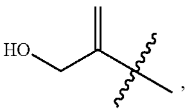
,
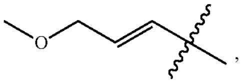
,
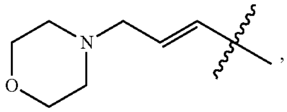
,
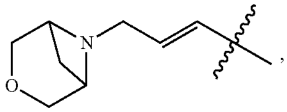
,
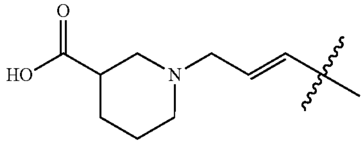
, or
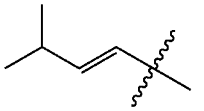
.

In some embodiments, T is

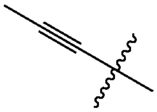
or
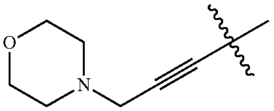
.

In some embodiments, at least one $R^T$ is halogen (e.g., F or Cl).

In some embodiments, at least one $R^T$ is F.

In some embodiments, at least one $R^T$ is Cl.

In some embodiments, at least one $R^T$ is CN, —OH, or —$NH_2$.

In some embodiments, at least one $R^T$ is CN.

In some embodiments, at least one $R^T$ is —OH.

In some embodiments, at least one $R^T$ is —O—($C_1$-$C_6$ alkyl), —NH($C_1$-$C_6$ alkyl), or —N($C_1$-$C_6$ alkyl)$_2$; wherein the O—($C_1$-$C_6$ alkyl), —NH($C_1$-$C_6$ alkyl), or —N($C_1$-$C_6$ alkyl)$_2$ is optionally substituted with one or more $R^{Ta}$.

In some embodiments, at least one $R^T$ is —O—($C_1$-$C_6$ alkyl) or —N($C_1$-$C_6$ alkyl)$_2$; wherein the O—($C_1$-$C_6$ alkyl) or —N($C_1$-$C_6$ alkyl)$_2$ is optionally substituted with one or more $R^{Ta}$.

In some embodiments, at least one $R^T$ is —O—($C_1$-$C_6$ alkyl) or —N($C_1$-$C_6$ alkyl)$_2$.

In some embodiments, at least one $R^T$ is —O—($C_1$-$C_6$ alkyl).

In some embodiments, at least one $R^T$ is —N($C_1$-$C_6$ alkyl)$_2$.

In some embodiments, at least one $R^T$ is $C_1$-$C_6$ alkyl, $C_2$-$C_6$ alkenyl, or $C_2$-$C_6$ alkynyl; wherein the $C_1$-$C_6$ alkyl, $C_2$-$C_6$ alkenyl, or $C_2$-$C_6$ alkynyl is optionally substituted with one or more $R^{Ta}$.

In some embodiments, at least one $R^T$ is $C_3$-$C_{10}$ cycloalkyl, $C_6$-$C_{10}$ aryl, 3- to 10-membered heterocycloalkyl, or 5- to 10-membered heteroaryl; wherein the $C_3$-$C_{10}$ cycloalkyl, $C_6$-$C_{10}$ aryl, 3- to 10-membered heterocycloalkyl, or 5- to 10-membered heteroaryl is optionally substituted with one or more $R^{Ta}$.

In some embodiments, at least one $R^T$ is 3- to 10-membered heterocycloalkyl optionally substituted with one or more $R^{Ta}$.

In some embodiments, at least one $R^T$ is 3- to 10-membered heterocycloalkyl substituted with one or more $R^{Ta}$.

In some embodiments, at least one $R^T$ is 3- to 10-membered heterocycloalkyl substituted with one or more C(=O)OH.

In some embodiments, at least one $R^T$ is 3- to 7-membered heterocycloalkyl optionally substituted with one or more $R^{Ta}$.

In some embodiments, at least one $R^T$ is 3- to 7-membered heterocycloalkyl.

In some embodiments, at least one $R^T$ is 3- to 7-membered heterocycloalkyl substituted with one or more $R^{Ta}$.

In some embodiments, at least one $R^T$ is 3- to 7-membered heterocycloalkyl substituted with one or more C(=O)OH.

In some embodiments, at least one $R^T$ is 6-membered heterocycloalkyl optionally substituted with one or more $R^{Ta}$.

In some embodiments, at least one $R^T$ is 6-membered heterocycloalkyl.

In some embodiments, at least one $R^T$ is 6-membered heterocycloalkyl substituted with one or more $R^{Ta}$.

In some embodiments, at least one $R^T$ is 6-membered heterocycloalkyl substituted with one or more C(=O)OH.

In some embodiments, at least one $R^T$ is 3- to 7-membered monocyclic heterocycloalkyl optionally substituted with one or more $R^{Ta}$.

In some embodiments, at least one $R^T$ is 3- to 7-membered monocyclic heterocycloalkyl.

In some embodiments, at least one $R^T$ is 3- to 7-membered monocyclic heterocycloalkyl substituted with one or more $R^{Ta}$.

In some embodiments, at least one $R^T$ is 3- to 7-membered monocyclic heterocycloalkyl substituted with one or more C(═O)OH.

In some embodiments, at least one $R^T$ is 6-membered monocyclic heterocycloalkyl optionally substituted with one or more $R^{Ta}$.

In some embodiments, at least one $R^T$ is 6-membered monocyclic heterocycloalkyl.

In some embodiments, at least one $R^T$ is 6-membered monocyclic heterocycloalkyl substituted with one or more $R^{Ta}$.

In some embodiments, at least one $R^T$ is 6-membered monocyclic heterocycloalkyl substituted with one or more C(═O)OH.

In some embodiments, at least one $R^{Ta}$ is C(═O)OH.

In some embodiments, at least one $R^{Ta}$ is halogen, CN, —OH, —$NH_2$, —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 10-membered heterocycloalkyl, or 5- to 10-membered heteroaryl.

Variables $Ar^1$, $R^{A1}$, $R^{A1a}$, and $R^{A1b}$

In some embodiments, $Ar^1$ is $C_6$-$C_{10}$ aryl optionally substituted with one or more $R^{A1}$;

each $R^{A1}$ independently is halogen, CN, —OH, —$NH_2$, —$OR^{A1a}$, —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl; wherein the —O—($C_1$-$C_6$ alkyl), —NH ($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl is optionally substituted with one or more $R^{A1a}$;

each $R^{A1a}$ independently is halogen, CN, —OH, —$NH_2$, —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl; wherein the —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl is optionally substituted with one or more $R^{A1b}$; and each $R^{A1b}$ independently is halogen, CN, —OH, or —$NH_2$.

In some embodiments, $Ar^1$ is $C_6$-$C_{10}$ aryl.

In some embodiments, $Ar^1$ is $C_6$-$C_{10}$ aryl substituted with one or more $R^{A1}$.

In some embodiments, $Ar^1$ is phenyl substituted with one or more $R^{A1}$.

In some embodiments, $Ar^1$ is phenyl substituted with one or more halogen, —$OR^{A1a}$, or —O—($C_1$-$C_6$ alkyl); wherein the —O—($C_1$-$C_6$ alkyl) is optionally substituted with one or more $R^{A1a}$; and each $R^{A1a}$ independently is $C_6$-$C_{10}$ aryl or 5- to 10-membered heteroaryl; wherein the $C_6$-$C_{10}$ aryl or 5- to 10-membered heteroaryl is optionally substituted with one or more halogen.

In some embodiments, $Ar^1$ is phenyl substituted with one or more halogen

In some embodiments, $Ar^1$ is phenyl substituted with one or more F or Cl.

In some embodiments, $Ar^1$ is phenyl substituted with one F and one $C_1$.

In some embodiments, $Ar^1$ is phenyl optionally substituted with one or more halogen, wherein the phenyl is further substituted with —O—($C_6$-$C_{10}$ aryl) or —O-(5- to 10-membered heteroaryl); wherein the —O—($C_6$-$C_{10}$ aryl) or —O-(5- to 10-membered heteroaryl) is optionally substituted with one or more halogen.

In some embodiments, $Ar^1$ is phenyl optionally substituted with one or more halogen, wherein the phenyl is further substituted with —O-phenyl or —O-pyridinyl; wherein the —O-phenyl or —O-pyridinyl is optionally substituted with one or more halogen.

In some embodiments, $Ar^1$ is phenyl optionally substituted with one or more halogen, wherein the phenyl is further substituted with —O-phenyl; wherein the —O-phenyl is optionally substituted with one or more halogen.

In some embodiments, $Ar^1$ is phenyl optionally substituted with one or more halogen, wherein the phenyl is further substituted with —O-pyridinyl; wherein the —O-pyridinyl is optionally substituted with one or more halogen.

In some embodiments, $Ar^1$ is

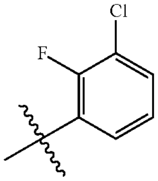
,
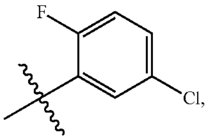

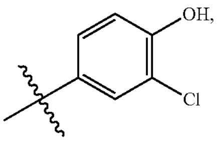

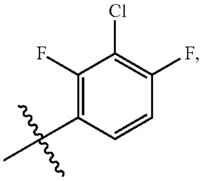
or

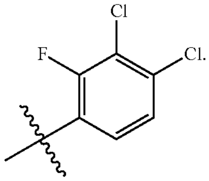

In some embodiments, $Ar^1$ is

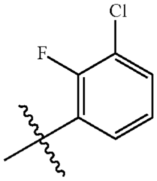
.

In some embodiments, $Ar^1$ is

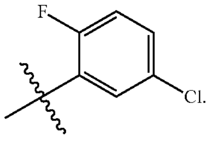 [SMILES: *c1cc(Cl)ccc1F]

In some embodiments, $Ar^1$ is
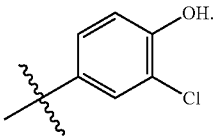 [SMILES: *c1ccc(O)c(Cl)c1]
In some embodiments, $Ar^1$ is
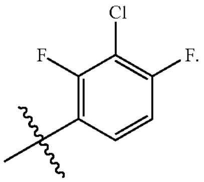 [SMILES: *c1ccc(F)c(Cl)c1F]
In some embodiments, $Ar^1$ is
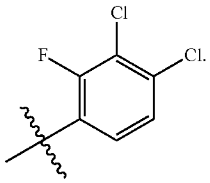 [SMILES: *c1ccc(Cl)c(Cl)c1F]
In some embodiments, $Ar^1$ is
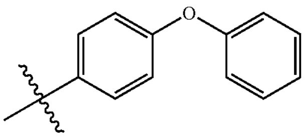
,
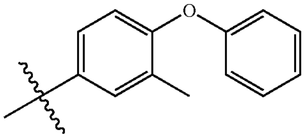
, or
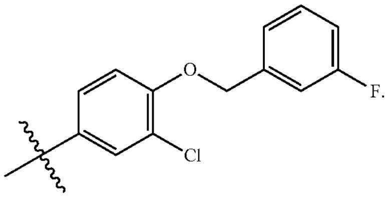
In some embodiments, $Ar^1$ is
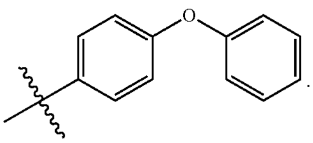 [SMILES: *c1ccc(Oc2ccccc2)cc1]
In some embodiments, $Ar^1$ is
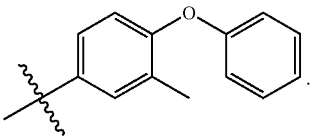 [SMILES: *c1ccc(Oc2ccccc2)c(C)c1]
In some embodiments, $Ar^1$ is
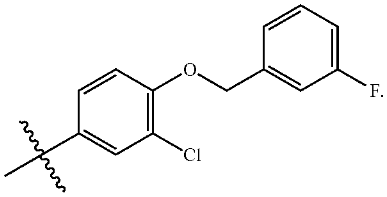 [SMILES: *c1ccc(OCc2cccc(F)c2)c(Cl)c1]
In some embodiments, $Ar^1$ is
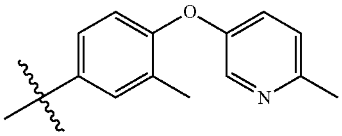
or
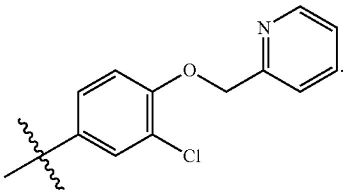
In some embodiments, $Ar^1$ is
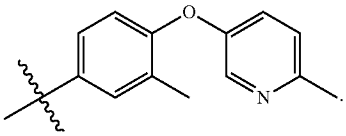 [SMILES: *c1ccc(Oc2ccc(C)nc2)c(C)c1]
In some embodiments, $Ar^1$ is
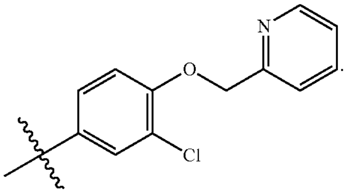 [SMILES: *c1ccc(OCc2ccccn2)c(Cl)c1]

In some embodiments, $Ar^1$ is

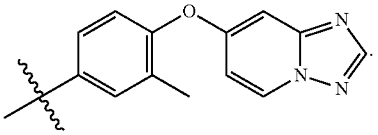 [SMILES: *c1ccc(Oc2ccn3ncnc3c2)c(C)c1]

In some embodiments, at least one $R^{A1}$ is halogen (e.g., F or Cl).

In some embodiments, at least one $R^{A1}$ is F.

In some embodiments, at least one $R^{A1}$ is Cl.

In some embodiments, at least one $R^{A1}$ is F, and at least one $R^{A1}$ is Cl.

In some embodiments, at least one $R^{A1}$ is CN, —OH, or —$NH_2$.

In some embodiments, at least one $R^{A1}$ is —$OR^{A1a}$.

In some embodiments, at least one $R^{A1}$ is —O—($C_6$-$C_{10}$ aryl) or —O-(5- to 10-membered heteroaryl); wherein the —O—($C_6$-$C_{10}$ aryl) or —O-(5- to 10-membered heteroaryl) is optionally substituted with one or more $R^{Ab}$.

In some embodiments, at least one $R^{A1}$ is —O—($C_6$-$C_{10}$ aryl) or —O-(5- to 10-membered heteroaryl); wherein the —O—($C_6$-$C_{10}$ aryl) or —O-(5- to 10-membered heteroaryl) is optionally substituted with one or more halogen.

In some embodiments, at least one $R^{A1}$ is —O-phenyl or —O-pyridinyl; wherein the —O-phenyl or —O-pyridinyl is optionally substituted with one or more halogen.

In some embodiments, at least one $R^{A1}$ is —O-phenyl optionally substituted with one or more halogen.

In some embodiments, at least one $R^{A1}$ is —O-pyridinyl optionally substituted with one or more halogen.

In some embodiments, at least one $R^{A1}$ is —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl, wherein the —O—($C_1$-$C_6$ alkyl), —NH($C_1$-$C_6$ alkyl), —N($C_1$-$C_6$alkyl)$_2$, $C_1$-$C_6$ alkyl, $C_2$-$C_6$ alkenyl, or $C_2$-$C_6$ alkynyl is optionally substituted with one or more $R^{A1a}$.

In some embodiments, at least one $R^{A1}$ is —O—($C_1$-$C_6$ alkyl) optionally substituted with one or more $R^{A1a}$.

In some embodiments, at least one $R^{A1}$ is —O—($C_1$-$C_6$ alkyl) substituted with one or more $R^{A1a}$.

In some embodiments, at least one $R^{A1}$ is —O—($C_1$-$C_6$ alkyl) substituted with one or more $C_6$-$C_{10}$ aryl or 5- to 10-membered heteroaryl, wherein the $C_6$-$C_{10}$ aryl or 5- to 10-membered heteroaryl is optionally substituted with one or more halogen.

In some embodiments, at least one $R^{A1}$ is —O—$CH_2$—$R^{A1a}$.

In some embodiments, at least one $R^{A1}$ is —O—$CH_2$—($C_6$-$C_{10}$ aryl) or —O—$CH_2$—(5- to 10-membered heteroaryl), wherein the —O—$CH_2$—($C_6$-$C_{10}$ aryl) or —O—$CH_2$—(5- to 10-membered heteroaryl) is optionally substituted with one or more halogen.

In some embodiments, at least one $R^{A1}$ is —O—$CH_2$-phenyl or —O—$CH_2$-pyridinyl, wherein the —O—$CH_2$-phenyl or —O—$CH_2$-pyridinyl is optionally substituted with one or more halogen.

In some embodiments, at least one $R^{A1}$ is —O—$CH_2$-phenyl optionally substituted with one or more halogen.

In some embodiments, at least one $R^{A1}$ is —O—$CH_2$-pyridinyl optionally substituted with one or more halogen.

In some embodiments, at least one $R^{A1}$ is $C_3$-$C_{10}$ cycloalkyl, $C_6$-$C_{10}$ aryl, 3- to 10-membered heterocycloalkyl, or 5- to 10-membered heteroaryl; wherein the $C_3$-$C_{10}$ cycloalkyl, $C_6$-$C_{10}$ aryl, 3- to 10-membered heterocycloalkyl, or 5- to 10-membered heteroaryl is optionally substituted with one or more $R^{A1a}$.

In some embodiments, at least one $R^{A1a}$ is halogen, CN, —OH, —$NH_2$, —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl, wherein the —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl is optionally substituted with one or more $R^{A1b}$.

In some embodiments, at least one $R^{A1a}$ is $C_3$-$C_{10}$ cycloalkyl, $C_6$-$C_{10}$ aryl, 3- to 10-membered heterocycloalkyl, or 5- to 10-membered heteroaryl; wherein the $C_3$-$C_{10}$ cycloalkyl, $C_6$-$C_{10}$ aryl, 3- to 10-membered heterocycloalkyl, or 5- to 10-membered heteroaryl is optionally substituted with one or more $R^{A1b}$.

In some embodiments, at least one $R^{A1a}$ is $C_3$-$C_{10}$ cycloalkyl, $C_6$-$C_{10}$ aryl, 3- to 10-membered heterocycloalkyl, or 5- to 10-membered heteroaryl; wherein the $C_3$-$C_{10}$ cycloalkyl, $C_6$-$C_{10}$ aryl, 3- to 10-membered heterocycloalkyl, or 5- to 10-membered heteroaryl is optionally substituted with one or more halogen.

In some embodiments, at least one $R^{A1a}$ is $C_6$-$C_{10}$ aryl or 5- to 10-membered heteroaryl; wherein the $C_6$-$C_{10}$ aryl or 5- to 10-membered heteroaryl is optionally substituted with one or more halogen.

In some embodiments, at least one $R^{A1a}$ is phenyl or pyridinyl; wherein the phenyl or pyridinyl is optionally substituted with one or more halogen.

In some embodiments, at least one $R^{A1a}$ is phenyl optionally substituted with one or more halogen.

In some embodiments, at least one $R^{A1a}$ is pyridinyl optionally substituted with one or more halogen.

In some embodiments, at least one $R^{A1b}$ is halogen.

In some embodiments, at least one $R^{A1b}$ is F.

In some embodiments, at least one $R^{A1b}$ is Cl.

In some embodiments, at least one $R^{A1b}$ is F, and at least one $R^{A1b}$ is Cl.

In some embodiments, at least one $R^{A1b}$ is CN, —OH, or —$NH_2$.

Exemplary Embodiments of the Compounds

In some embodiments, when Z is

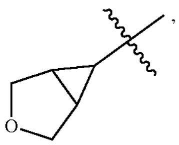 [SMILES: *C1C2COCC12]

then

T is —O—($C_1$-$C_6$ alkyl), —NH—($C_1$-$C_6$ alkyl), $C_1$-$C_6$ alkyl, $C_2$-$C_6$ alkenyl, or $C_2$-$C_6$ alkynyl; wherein the —O—($C_1$-$C_6$ alkyl), —NH—($C_1$-$C_6$ alkyl), $C_1$-$C_6$ alkyl, or $C_2$-$C_6$ alkynyl is optionally substituted with one or more $R^T$; and wherein the $C_2$-$C_6$ alkenyl is substituted with one or more $R^T$ each $R^T$ independently is halogen, CN, —OH, —$NH_2$, —O—($C_1$-$C_6$ alkyl), —$C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 10-membered heterocycloalkyl, or 5- to 10-membered heteroaryl; wherein the —O—($C_1$-$C_6$ alkyl), $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 10-membered heterocycloalkyl, or 5- to 10-membered heteroaryl is optionally substituted with one or more $R^{Ta}$; and each $R^{Ta}$ independently is halogen, CN, —OH, —$NH_2$, —C(═O)OH, —O—($C_1$-$C_6$ alkyl), $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 10-membered heterocycloalkyl, or 5- to 10-membered heteroaryl.

In some embodiments, when Z is

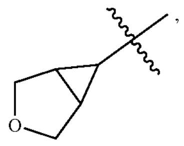 [SMILES: *C1C2COCC12]

then T is not

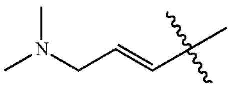

or

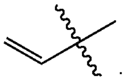

In some embodiments, when Z is

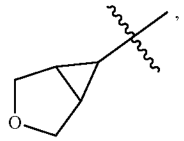 [SMILES: *C1C2COCC12]

then $Ar^1$ is $C_6$-$C_{10}$ aryl optionally substituted with one or more halogen.

In some embodiments, Z is not

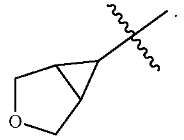 [SMILES: *C1C2COCC12]

In some embodiments, Z is not

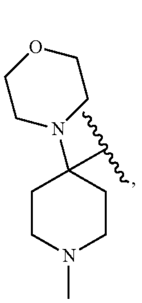

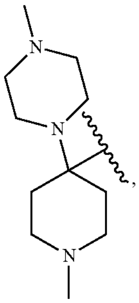

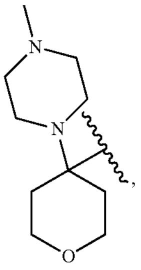

or

-continued

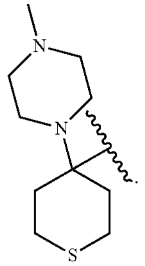

In some embodiments, T is not

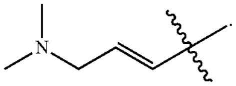 [SMILES: */C=C/CN(C)C]

In some embodiments, the compound is of formula (II'):

(II')

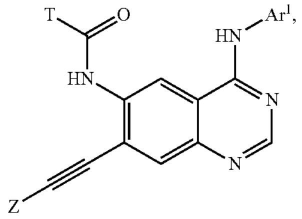

or a pharmaceutically acceptable salt or stereoisomer thereof.

In some embodiments, the compound is of formula (II'):

(II')

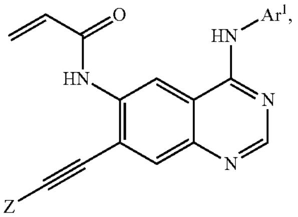

or a pharmaceutically acceptable salt or stereoisomer thereof.

In some embodiments, the compound is of formula (III') or (III'-a):

(III')

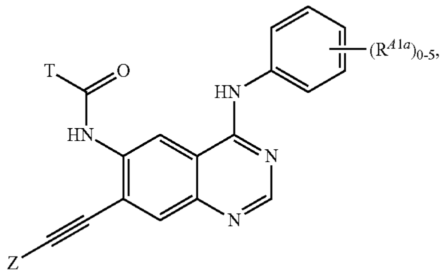

(III-a')

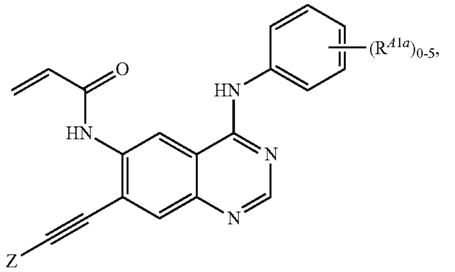

or a pharmaceutically acceptable salt or stereoisomer thereof.

In some embodiments, the compound is of formula (IV') or (IV'-a):

(IV')

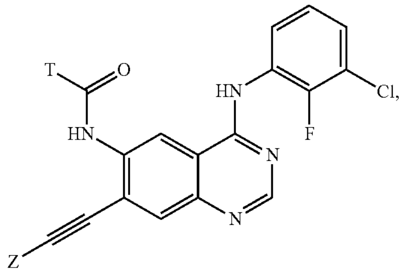

(IV-a')

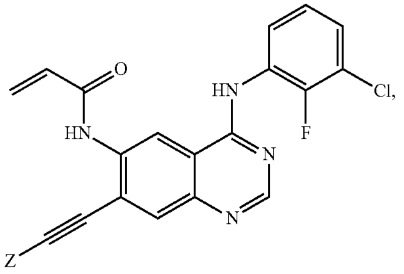

or a pharmaceutically acceptable salt or stereoisomer thereof.

In some aspects, the disclosure provides a compound or pharmaceutically acceptable salts or stereoisomers thereof of formula I

I

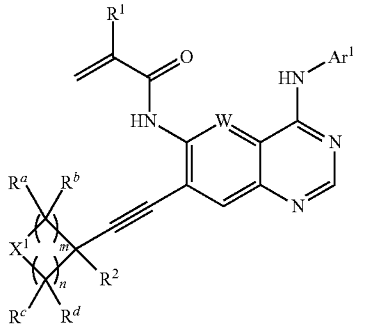

wherein

W is CH or N, preferably CH;

$X^1$ is —O—, —S—, —$NR^3$—.

$R^a$, $R^b$ are independently of each other hydrogen or $C_{1-4}$ alkyl or one of $R^a$ is —$(CH_2)_p$— which forms a ring with $X^1$ if $X^1$ is NW or one of $R^a$ is —$(CH_2)_p$— which forms a ring with $R^2$;

$R^c$, $R^d$ are independently of each other hydrogen or $C_{1-4}$ alkyl;

$R^1$ is H or F;

$R^2$ is hydrogen or $C_{1-4}$ alkyl, or is —$(CH_2)_q$— which forms a ring with $R^3$ or with one of $R^a$;

$R^3$ is hydrogen or $C_{1-4}$ alkyl, preferably hydrogen or methyl, or is —$(CH_2)_p$— which forms a ring with $R^2$;

m is 1, 2 or 3;

n is 0, 1 or 2;

p is 1 or 2;

q is 0, 1 or 2; and $Ar^1$ is a 6-membered aryl, which is unsubstituted or substituted with one or more of a group selected from halogen, —$CF_3$, $C_{1-6}$ alkyl, $C_{1-6}$ alkoxy, $C_{3-7}$ cycloalkyl, hydroxy $C_{1-5}$ alkyl, $C_{1-6}$ alkoxy-$C_{1-6}$ alkyl, $C_{1-6}$ alkoxy-$C_6$ aryl, $C_{1-6}$ alkoxy-$C_{5*6}$ heteroaryl, amino, amino $C_{1-4}$ alkyl, $C_{1-6}$ alkylamino, $C_{1-6}$ aminoalkyl-$C_6$ aryl, $C_{1-6}$ aminoalkyl-$C_{5-6}$ heteroaryl, $C_{1-6}$ alkoxycarbonyl, $C_{1-6}$ alkoxyaminocarbonyl, aryl $C_{1-6}$ alkoxy, or $C_6$ aryl.

In some embodiments of a compound of formula I, W is CH.

In some embodiments, when n is 0, $R^2$ is —$(CH_2)_q$— which forms a ring with $R^3$ or with one of $R^a$.

In some embodiments, when n is 0, $R^2$ is —$(CH_2)_q$— which forms a ring with $R^3$.

In some embodiments, n is 0, and $R^2$ is —$(CH_2)_q$— which forms a ring with $R^3$ or with one of $R^a$.

In some embodiments, n is 0, and $R^2$ is —$(CH_2)_q$— which forms a ring with $R^3$.

In some embodiments of a compound of formula I, $X^1$ is —O— or —$NR^3$—, more preferably —$NR^3$—.

In some embodiments of a compound of formula I, $R^b$ is always hydrogen, such that only $R^a$ may be not hydrogen. For example, $R^b$ may be hydrogen and $R^a$ may be selected from methyl, ethyl, n-propyl, i-propyl, n-butyl, i-butyl or t-butyl, or —$(CH_2)$— or —$(CH_2)_2$— which forms a ring with $R^2$. Preferably, $R^b$ may be hydrogen and $R^a$ may be methyl or —$(CH_2)$— or —$(CH_2)_2$— which forms a ring with $R^2$. Furthermore, both $R^a$ and $R^b$ may be hydrogen.

In some embodiments the ring of which $X^1$ is part of is a monocycle or bicycle.

In some embodiments of a compound of formula I, $R^c$ is always hydrogen, such that only $R^d$ may be not hydrogen.

For example, $R^c$ may be hydrogen and $R^d$ may be selected from methyl, ethyl, n-propyl, i-propyl, n-butyl, i-butyl or t-butyl. Preferably, $R^c$ may be hydrogen and $R^d$ may be methyl. Furthermore, both $R^c$ and $R^d$ may be hydrogen.

In some embodiments of a compound of formula I, $R^1$ is hydrogen.

In some embodiments of a compound of formula I, $R^c$ and $R^d$ are hydrogen. In some embodiments of a compound of formula I, $R^b$, $R^c$ and $R^d$ are hydrogen. In some embodiments of a compound of formula I, $R^1$, $R^b$, $R^c$ and $R^d$ are hydrogen.

In some embodiments of a compound of formula I in which one of $R^a$ forms a ring with $R^3$, the ring formed is a 4, 5, or 6-membered ring, or a 5 or 6 membered ring, or a 5 membered ring.

In some embodiments of a compound of formula I in which one of $R^a$ forms a ring with $R^3$, the ring formed is a 3, 4, 5, or 6-membered ring.

In some embodiments of a compound of formula I in which one of $R^2$ forms a ring with $R^3$, the ring formed is a 4, 5, or 6-membered ring or a 5 or 6 membered ring, or a 6 membered ring. In some embodiments of a compound of formula I, $R^2$ is $C_{1-4}$ alkyl, or is $—(CH_2)_q—$ which forms a ring with $R^3$ or $R^a$. For example, $R^2$ may be selected from methyl, ethyl, n-propyl, i-propyl, n-butyl, i-butyl or t-butyl or $R^2$ is $—(CH_2)—$ or $—(CH_2)_2—$ which forms a ring with $R^3$, or $R^2$ is $—(CH_2)—$ or $—(CH_2)_2—$ which forms a ring with one of $R^a$. Preferably, $R^2$ may be selected from methyl, ethyl, n-propyl, i-propyl, n-butyl or i-butyl or $R^2$ is $—(CH_2)—$ or $—(CH_2)_2—$ which forms a ring with $R^3$, or $R^2$ is $—(CH_2)—$ or $—(CH_2)_2—$ which forms a ring with one of $R^a$. More preferably, $R^2$ may be methyl.

In some embodiments of a compound of formula I, $R^3$ is hydrogen or methyl or $R^3$ is $—(CH_2)—$ or $—(CH_2)_2—$ which forms a ring with $R^2$.

In some embodiments of a compound of formula I, n is 0 and m is 1, 2 or 3; or n is 0 and m is 1 or 2; or n is 1 and m is 1, 2 or 3; or n is 1 and m is 1 or 2; or n is 2 and m is 1, 2, or 3; or n is 2 and m is 1 or 2; or n is 0, 1 or 2 and m is 1 or 2; or n is 0, 1 or 2 and m is 1; or n is 1 or 2 and m is 1, 2 or 3; or n is 1 or 2 and m is 1 or 2; or n is 1 or 2 and m is 1 or 3; or n is 1 or 2 and m is 2 or 3.

In some embodiments of a compound of formula I, $X^1$ may form a heterocycle with the carbon to which $R^2$ is directly bound. For example, $X^1$ may form a 4, 5, 6 or 7 membered heterocycle. In some embodiments of a compound of formula I, $X^1$ may form a substituted or unsubstituted oxetanyl, thiatanyl, azetidinyl, pyrrolidinyl, tetrahydrofuranyl, tetrahydrothiopyranyl, dihydropyranyl, tetrahydropyranyl, piperidinyl, oxepanyl, thiepanyl, azepanyl, azabicyclo[2.2.1]heptane or azabicyclo[2.2.2]octane, preferably azetidinyl, pyrrolidinyl, tetrahydrofuranyl, piperidinyl, more preferably azetidinyl, pyrrolidinyl or piperidinyl.

In some embodiments of a compound of formula I, $Ar^1$ is of formula i or pharmaceutically acceptable salts or stereoisomers thereof

I

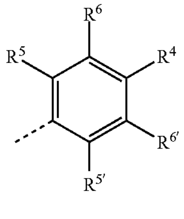

wherein $R^4$ hydrogen, halogen, $C_{1-6}$ alkyl, $C_{1-6}$ alkoxy, $C_{3-7}$ cycloalkyl, hydroxy $C_{1-5}$ alkyl, $C_{1-6}$ alkoxy-$C_{1-6}$ alkyl, $C_{1-6}$ alkoxy-$C_6$ aryl, $C_{1-6}$ alkoxy-$C_{5*6}$ heteroaryl, amino $C_{1-4}$ alkyl, $C_{1-6}$ alkylamino, $C_{1-6}$ aminoalkyl-$C_6$ aryl, $C_{1-6}$ aminoalkyl-$C_{5-6}$ heteroaryl, $C_{1-6}$ alkoxycarbonyl, $C_{1-6}$ alkoxyaminocarbonyl, aryl $C_{1-6}$ alkoxy, or $C_6$ aryl;

$R^5$, $R^{5'}$, $R^6$, $R^{6'}$ are independently of each other hydrogen, $—CF_3$ or halogen, preferably F, Cl.

In some embodiments of a compound of formula I, wherein $Ar^1$ is of formula i, $R^4$ is hydrogen, fluoro, chloro, $C_{1-4}$ alkyl, $C_{1-4}$ alkoxy, $C_{3-6}$ cycloalkyl, hydroxy $C_{1-5}$ alkyl, $C_{1-4}$ alkoxy-$C_{1-4}$ alkyl, $C_{1-4}$ alkoxy-$C_6$ aryl, $C_{1-4}$ alkoxy-$C_{5-6}$ heteroaryl, amino $C_{1-4}$ alkyl, $C_{1-4}$ alkylamino, $C_{1-4}$ aminoalkyl-$C_6$ aryl, $C_{1-4}$ aminoalkyl-$C_6$ heteroaryl, $C_{1-4}$ alkoxycarbonyl, $C_{1-4}$ alkoxyaminocarbonyl or $C_6$ aryl.

In some embodiments of a compound of formula I, wherein $Ar^1$ is of formula i, $R^4$ is hydrogen, fluoro, chloro, $C_{1-4}$ alkyl, $C_{1-4}$ alkoxy, $C_{3-6}$ cycloalkyl, $C_{1-4}$ alkoxy-$C_{1-4}$ alkyl, $C_{1-4}$ alkoxy-$C_6$ aryl, $C_{1-4}$ alkoxy-$C_{5*6}$ heteroaryl or $C_6$ aryl.

In some embodiments of a compound of formula I, wherein $Ar^1$ is of formula i, $R^4$ is in general hydrogen, fluoro, chloro, methyl, ethyl, n-propyl, i-propyl, n-butyl, i-butyl, t-butyl, n-pentyl, i-pentyl, n-hexyl, i-hexyl, methoxy, ethoxy, n-propoxy, i-propoxy, n-propoxy, n-butoxy, i-butoxy, n-pentoxy, i-pentoxy, n-hexoxy, i-hexoxy, cyclopropyl, cyclobutyl, cyclopentyl, cyclohexyl, cyclopheptyl, hydroxy methyl, hydroxy ethyl, hydroxyl propyl, hydroxyl butyl, hydroxyl pentyl, methoxy methyl, method ethyl, methoxy propyl, methoxy butyl, methoxy pentyl, mehoxy hexyl, ethoxy methyl, ethoxy ethyl, ethoxy propyl, ethoxy butyl, ethoxy pentyl, ethoxy hexyl, propoxy methyl, propoxy ethyl, propoxy propyl, propoxy butyl, propoxy pentyl, propoxy hexyl, butoxy methyl, butoxy ethyl, butoxy propyl, butoxy butyl, butoxy pentyl, butoxy hexyl, pentoxy methyl, pentoxy ethyl, pentoxy propyl, pentoxy butyl, pentoxy pentyl, pentoxy hexyl, hexoxy methyl, hexoxy ethyl, hexoxy propyl, hexoxy butyl, hexoxy pentyl, hexoxy hexyl, amino methyl, amino ethyl, amino propyl, amino butyl, amino pentyl, amino hexyl, methylamino ethylamino, propylamino, butylamino, pentylamino, hexylamino, methoxy carbonyl, ethoxy carbonyl, propoxy carbonyl, butoxy carbonyl, pentoxy carbonyl, hexoxy carbonyl, methoxyamino carbonyl, ethoxyamino carbonyl, propoxyamino carbonyl, butoxyamino carbonyl, pentoxyamino carbonyl, hexoxyamino carbonyl, phenyl methoxy, phenyl ethoxy, phenyl propoxy, phenyl butoxy, phenyl pentoxy, phenyl hexoxy, m-fluorophenyl methoxy, m-fluorophenylphenyl ethoxy, m-fluorophenylphenyl propoxy, m-fluorophenylphenyl butoxy, m-fluorophenylphenyl pentoxy, m-fluorophenylphenyl hexoxy, pyridinyl methoxy, pyridinyl ethoxy, pyridinyl propoxy, pyridinyl butoxy, pyridinyl pentoxy, pyridinyl hexoxy, phenyl, pyridinyl or naphtyl.

In some embodiments of a compound of formula I, wherein $Ar^1$ is of formula i, $R^5$ and $R^6$ are independently of each other hydrogen, $—CF_3$, F or Cl and $R^{5'}$ and $R^{6'}$ are hydrogen. Preferably, $R^4$ hydrogen, halogen, $C_{1-6}$ alkyl, $C_{1-6}$ alkoxy, $C_{3-7}$ cycloalkyl, hydroxy $C_{1-5}$ alkyl, $C_{1-6}$ alkoxy-$C_{1-6}$ alkyl, $C_{1-6}$ alkoxy-$C_6$ aryl, $C_{1-6}$ alkoxy-$C_{5*6}$ heteroaryl, amino $C_{1-4}$ alkyl, $C_{1-6}$ alkylamino, $C_{1-6}$ aminoalkyl-$C_6$ aryl, $C_{1-6}$ aminoalkyl-$C_{5-6}$ heteroaryl, $C_{1-6}$ alkoxycarbonyl, $C_{1-6}$ alkoxyaminocarbonyl, aryl $C_{1-6}$ alkoxy, or $C_6$ aryl.

In some embodiments of a compound of formula I, wherein $Ar^1$ is of formula i, $R^5$ and $R^6$ are independently of each other hydrogen, —$CF_3$, F or Cl and $R^{5'}$ and $R^{6'}$ are hydrogen. Preferably, $R^4$ is hydrogen, fluoro, chloro, $C_{1-4}$ alkyl, $C_{1-4}$ alkoxy, $C_{3-6}$ cycloalkyl, hydroxy $C_{1-5}$ alkyl, $C_{1-4}$ alkoxy-$C_{1-4}$ alkyl, $C_{1-4}$ alkoxy-$C_6$ aryl, $C_{1-4}$ alkoxy-$C_{5*6}$ heteroaryl, amino $C_{1-4}$ alkyl, $C_{1-4}$ alkylamino, $C_{1-4}$ aminoalkyl-$C_6$ aryl, $C_{1-4}$ aminoalkyl-$C_6$ heteroaryl, $C_{1-4}$ alkoxycarbonyl, $C_{1-4}$ alkoxyaminocarbonyl or $C_6$ aryl.

In some embodiments of a compound of formula I, wherein $Ar^1$ is of formula i, comprises only 1, 2 or 3 substituents which are not hydrogen. Thus, at least two of $R^4$, $R^5$. $R^{5'}$, $R^6$ or $R^{6'}$ may be hydrogen.

In some embodiments of a compound of formula I, wherein $Ar^1$ is of formula i, $R^1$ may be hydrogen and/or $R^2$ may be methyl or $R^2$ is —$(CH_2)$— or —$(CH_2)_2$— which forms a ring with $R^3$, or $R^2$ is —$(CH_2)$— or —$(CH_2)_2$— which forms a ring with one of $R^a$.

In some embodiments of a compound of formula I, wherein $Ar^1$ is of formula i, $R^c$ and $R^d$ are hydrogen. In some embodiments of a compound of formula I, wherein $Ar^1$ is of formula I, $R^b$, $R^c$ and $R^d$ are hydrogen.

In some embodiments compound of formula I wherein $Ar^1$ is of formula i, in which with one of $R^a$ forms a ring with $R^3$, the ring formed is a 4, 5, or 6-membered ring, or a 5 or 6 membered ring, or a 5 membered ring.

In some embodiments compound of formula I wherein $Ar^1$ is of formula i, in which with one of $R^a$ forms a ring with $R^3$, the ring formed is a 3, 4, 5, or 6-membered ring.

In some embodiments compound of formula I wherein $Ar^1$ is of formula i, in which one of $R^2$ forms a ring with $R^3$, the ring formed is a 4, 5, or 6-membered ring or a 5 or 6 membered ring, or a 6 membered ring.

In some embodiments of a compound of formula I, $Ar^1$ is of formula ii-1 or pharmaceutically acceptable salts or stereoisomers thereof ii-1

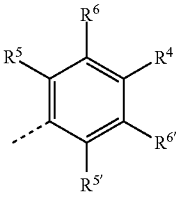

wherein $R^4$ is hydrogen, F or Cl;

$R^5$, $R^{5'}$, $R^6$, $R^{6'}$ are independently of each other hydrogen, —$CF_3$ or halogen, preferably F, Cl.

In some embodiments of a compound of formula I, $Ar^1$ is of formula ii-2, ii-3 or ii-4 or pharmaceutically acceptable salts or stereoisomers thereof ii-2

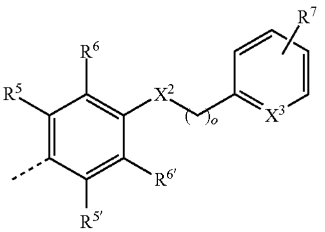

-continued ii-3

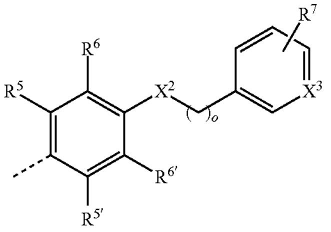

ii-4

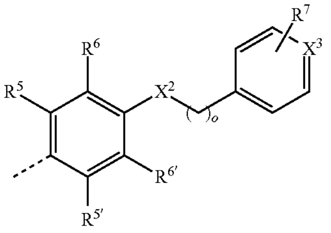

wherein $X^2$ is O, NH or NMe;

$X^3$ is CH or N;

is 0 or 1;

$R^5$, $R^{5'}$, $R^6$, $R^{6'}$ are independently of each other hydrogen, —$CF_3$ or halogen, preferably F or Cl;

$R^7$ is hydrogen or halogen, preferably F.

The skilled person understands that if $X^3$ stands for CH, $R^7$ may in general also be bound to this carbon, such that $X^3$ may be $CR^7$. Preferably, the corresponding aryl or heteroaryl is substituted only with a single $R^7$. Furthermore, it is understood that when $X^3$ is N, $R^7$ can in general not be bound to N.

In some embodiments of a compound of formula I, wherein $Ar^1$ is of formula ii-1, ii-2, ii-3 or ii-4, $R^5$ and $R^6$ are independently of each other hydrogen, —$CF_3$, F or Cl and $R^{5'}$ and $R^{6'}$ are hydrogen.

In some embodiments of a compound of formula I, wherein $Ar^1$ is of formula ii-1, ii-2, ii-3 or ii-4, $R^7$ is hydrogen if $X^3$ is N and/or $R^7$ is F if $X^3$ is CH.

In some embodiments of a compound of formula I, wherein $Ar^1$ is of formula ii-1, ii-2, ii-3 or ii-4, o is 1.

In some embodiments of a compound of formula I, wherein $Ar^1$ is of formula ii-1, ii-2, ii-3 or ii-4, $R^5$ is F and/or $R^6$ is F or Cl.

In some embodiments of a compound of formula I, wherein $Ar^1$ is of formula ii-1, ii-2, ii-3 or ii-4, $R^c$ and $R^d$ are hydrogen. In some embodiments of a compound of formula I, wherein $Ar^1$ is of formula ii-1, ii-2, ii-3 or ii-4, $R^b$, $R^c$ and $R^d$ are hydrogen.

In some embodiments compound of formula I wherein $Ar^1$ is of formula ii-1, ii-2, ii-3 or ii-4, in which with one of $R^a$ forms a ring with $R^3$, the ring formed is a 4, 5, or 6-membered ring, or a 5 or 6 membered ring, or a 5 membered ring.

In some embodiments compound of formula I wherein $Ar^1$ is of formula ii-1, ii-2, ii-3 or ii-4, in which with one of $R^a$ forms a ring with $R^3$, the ring formed is a 3, 4, 5, or 6-membered ring.

In some embodiments compound of formula I wherein $Ar^1$ is of formula ii-1, ii-2, ii-3 or ii-4, in which one of $R^2$ forms a ring with $R^3$, the ring formed is a 4, 5, or 6-membered ring or a 5 or 6 membered ring, or a 6 membered ring.

In some embodiments of a compound of formula I, wherein $Ar^1$ is of formula ii-1, ii-2, ii-3 or ii-4, $R^2$ is methyl or $R^2$ is —$(CH_2)$— or —$(CH_2)_2$— which forms a ring with $R^3$, or $R^2$ is —$(CH_2)$— or —$(CH_2)_2$— which forms a ring with one of $R^a$.

In some embodiments, $X^2$ is O, such that $Ar^1$ is of formula ii-1a or pharmaceutically acceptable salts or stereoisomers thereof ii-1a

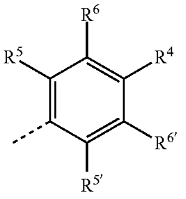

wherein $R^4$ is hydrogen, F or Cl;

$R^5$, $R^{5'}$, $R^6$, $R^{6'}$ are independently of each other hydrogen, —$CF_3$ or halogen, preferably F, Cl.

In some embodiments, $X^2$ is O, such that $Ar^1$ is of formula ii-2a, ii-3a or ii-4a or pharmaceutically acceptable salts or stereoisomers thereof ii-2a

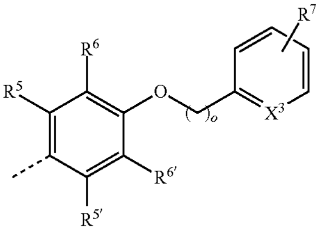

ii-3a

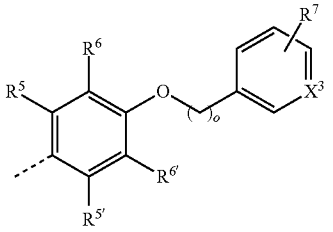

ii-4a

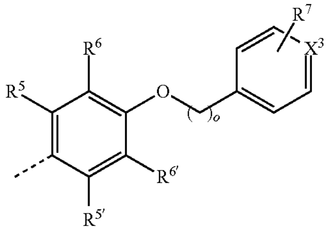

wherein $X^3$ is CH or N, preferably N;

is 0 or 1;

$R^5$, $R^{5'}$, $R^6$, $R^{6'}$ are independently of each other hydrogen, —$CF_3$ or halogen, preferably F or Cl;

$R^7$ is hydrogen or halogen, preferably F.

In some embodiments of a compound of formula I, wherein $Ar^1$ is of formula ii-1a, ii-2a, ii-3a or ii-4a, $R^5$ and $R^6$ are independently of each other hydrogen, —$CF_3$, F or Cl and $R^{5'}$ and $R^{6'}$ are hydrogen.

In some embodiments of a compound of formula I, wherein $Ar^1$ is of formula ii-1a, ii-2a, ii-3a or ii-4a, o is 1.

In some embodiments of a compound of formula I, wherein $Ar^1$ is of formula ii-1a, ii-2a, ii-3a or ii-4a, $R^5$ is F and/or $R^6$ is F or Cl.

In some embodiments of a compound of formula I, wherein $Ar^1$ is of formula ii-1a, ii-2a, ii-3a or ii-4a, $R^7$ is hydrogen if $X^3$ is N and/or $R^7$ is F if $X^3$ is CH.

In some embodiments of a compound of formula I, wherein $Ar^1$ is of formula ii-1a, ii-2a, ii-3a or ii-4a, $R^2$ is methyl or $R^2$ is —$(CH_2)$— or —$(CH_2)_2$— which forms a ring with $R^3$, or $R^2$ is —$(CH_2)$— or —$(CH_2)_2$— which forms a ring with one of $R^a$.

In some embodiments of a compound of formula I, wherein $Ar^1$ is of formula ii-1a, ii-2a, ii-3a or ii-4a, $R^c$ and $R^d$ are hydrogen. In some embodiments of a compound of formula I, wherein $Ar^1$ is of formula ii-1a, ii-2a, ii-3a or ii-4a, $R^b$, $R^c$ and $R^d$ are hydrogen.

In some embodiments compound of formula I wherein $Ar^1$ is of formula ii-1a, ii-2a, ii-3a or ii-4a, in which with one of $R^a$ forms a ring with $R^3$, the ring formed is a 4, 5, or 6-membered ring, or a 5 or 6 membered ring, or a 5 membered ring.

In some embodiments compound of formula I wherein $Ar^1$ is of formula ii-1a, ii-2a, ii-3a or ii-4a, in which with one of $R^a$ forms a ring with $R^3$, the ring formed is a 3, 4, 5, or 6-membered ring.

In some embodiments compound of formula I wherein $Ar^1$ is of formula ii-1a, ii-2a, ii-3a or ii-4a, in which one of $R^2$ forms a ring with $R^3$, the ring formed is a 4, 5, or 6-membered ring or a 5 or 6 membered ring, or a 6 membered ring.

In some embodiments, $X^3$ is N, such that $Ar^1$ is of formula ii-1b or pharmaceutically acceptable salts or stereoisomers thereof ii-1b

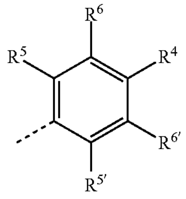

wherein $R^4$ is hydrogen, F or Cl;

$R^5$, $R^{5'}$, $R^6$, $R^{6'}$ are independently of each other hydrogen, —$CF_3$ or halogen, preferably F, Cl.

In some embodiments, $X^3$ is N, such that $Ar^1$ is of formula ii-2b, ii-3b, ii-4b, ii-5b or pharmaceutically acceptable salts or stereoisomers thereof ii-2b

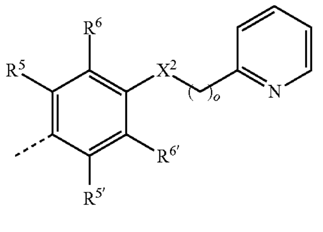

-continued ii-3b

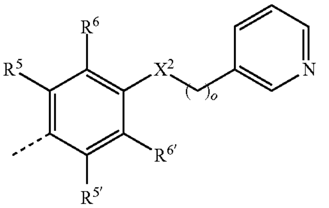

ii-4b

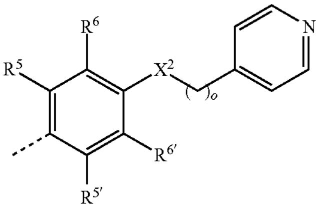

ii-5b

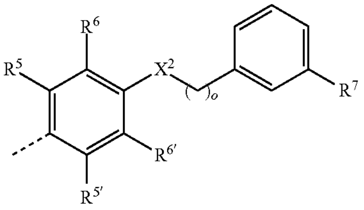

wherein $X^2$ is O, NH or NMe, preferably O;

is 0 or 1;

$R^5$, $R^{5'}$, $R^6$, $R^{6'}$ are independently of each other hydrogen, $—CF_3$ or halogen, preferably F, Cl $R^7$ is hydrogen or halogen, preferably F.

In some embodiments of a compound of formula I, wherein $Ar^1$ is of formula ii-1b, ii-2b, ii-3b, ii-4b or ii-5b, $R^5$ and $R^6$ are independently of each other hydrogen, $—CF_3$, F or Cl and $R^{5'}$ and $R^{6'}$ are hydrogen.

In some embodiments of a compound of formula I, wherein $Ar^1$ is of formula ii-1b, ii-2b, ii-3b, ii-4b or ii-5b, o is 1.

In some of a compound of formula I, wherein $Ar^1$ is of ii-1b, ii-2b, ii-3b, ii-4b or ii-5b, $R^5$ is F and/or $R^6$ is F or Cl.

In some of a compound of formula I, wherein $Ar^1$ is ii-1b, ii-2b, ii-3b, ii-4b or ii-5b, $R^7$ is F.

In some of a compound of formula I, wherein $Ar^1$ is of formula ii-1b, ii-2b, ii-3b, ii-4b or ii-5b, $R^2$ is methyl or $R^2$ is $—(CH_2)—$ or $—(CH_2)_2—$ which forms a ring with $R^3$, or $R^2$ is $—(CH_2)—$ or $—(CH_2)_2—$ which forms a ring with one of $R^a$.

In some embodiments of a compound of formula I, wherein $Ar^1$ is of formula ii-1b, ii-2b, ii-3b or ii-4b, $R^c$ and $R^d$ are hydrogen. In some embodiments of a compound of formula I, wherein $Ar^1$ is of formula ii-1b, ii-2b, ii-3b or ii-4b, $R^b$, $R^c$ and $R^d$ are hydrogen.

In some embodiments compound of formula I wherein $Ar^1$ is of formula ii-1b, ii-2b, ii-3b or ii-4b, in which one of $R^a$ forms a ring with $R^3$, the ring formed is a 4, 5, or 6-membered ring, or a 5 or 6 membered ring, or a 5 membered ring.

In some embodiments compound of formula I wherein $Ar^1$ is of formula ii-1b, ii-2b, ii-3b or ii-4b, in which one of $R^a$ forms a ring with $R^3$, the ring formed is a 3, 4, 5, or 6-membered ring.

In some embodiments compound of formula I wherein $Ar^1$ is of ii-1b, ii-2b, ii-3b or ii-4b, in which one of $R^2$ forms a ring with $R^3$, the ring formed is a 4, 5, or 6-membered ring or a 5 or 6 membered ring, or a 6 membered ring.

In some embodiments, $X^2$ is 0 and $X^3$ is N, such that $Ar^1$ is of formula ii-1c or pharmaceutically acceptable salts or stereoisomers thereof ii-1c

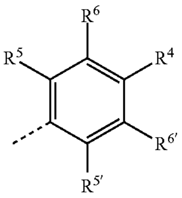

wherein $R^4$ is hydrogen, F or Cl;

$R^5$, $R^{5'}$, $R^6$, $R^{6'}$ are independently of each other hydrogen, $—CF_3$ or halogen, preferably F, Cl.

In some embodiments, $X^2$ is O and $X^3$ is N, such that $Ar^1$ is of formula ii-2c, ii-3c, ii-4c, ii-5c or pharmaceutically acceptable salts or stereoisomers thereof ii-2c

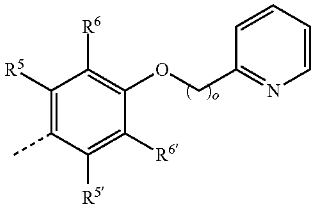

ii-3c

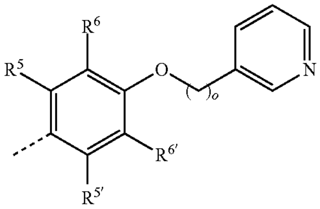

ii-4c

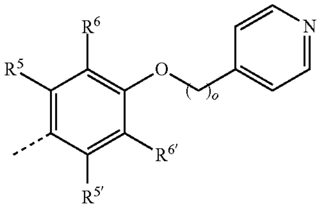

ii-5c

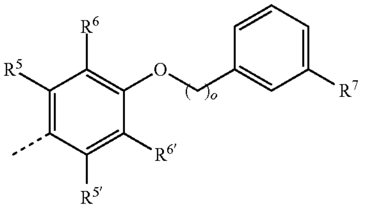

wherein is 0 or 1;

$R^4$ is hydrogen, F or Cl;

$R^5$, $R^{5'}$, $R^6$, $R^{6'}$ are independently of each other hydrogen, $—CF_3$ or halogen, preferably F or Cl;

$R^7$ is hydrogen or halogen, preferably F.

In some embodiments of a compound of formula I, wherein $Ar^1$ is of formula ii-1c, ii-2c, ii-3c, ii-4c or ii-5c, $R^5$ and $R^6$ are independently of each other hydrogen, $—CF_3$, F or Cl and $R^{5'}$ and $R^{6'}$ are hydrogen.

In some embodiments of a compound of formula I, wherein $Ar^1$ is of formula ii-1c, ii-2c, ii-3c, ii-4c or ii-5c, o is 1.

In some embodiments of a compound of formula I, wherein $Ar^1$ is of formula ii-1c, ii-2c, ii-3c, ii-4c or ii-5c, $R^5$ is F and/or $R^6$ is F or Cl.

In some embodiments of a compound of formula I, wherein $Ar^1$ is of formula ii-1c, ii-2c, ii-3c, ii-4c or ii-5c, $R^7$ is F.

In some embodiments of a compound of formula I, wherein $Ar^1$ is of ii-1c, ii-2c, ii-3c, ii-4c or ii-5c, $R^2$ is methyl or $R^2$ is $—(CH_2)—$ or $—(CH_2)_2—$ which forms a ring with $R^3$, or $R^2$ is $—(CH_2)—$ or $—(CH_2)_2—$ which forms a ring with one of $R^a$.

In some embodiments of a compound of formula I, wherein $Ar^1$ is of formula ii-1c, ii-2c, ii-3c or ii-4c, $R^c$ and $R^d$ are hydrogen. In some embodiments of a compound of formula I, wherein $Ar^1$ is of formula ii-1c, ii-2c, ii-3c or ii-4c, $R^b$, $R^c$ and $R^d$ are hydrogen.

In some embodiments compound of formula I wherein $Ar^1$ is of formula ii-1c, ii-2c, ii-3c or ii-4c, in which one of $R^a$ forms a ring with $R^3$, the ring formed is a 4, 5, or 6-membered ring, or a 5 or 6 membered ring, or a 5 membered ring.

In some embodiments compound of formula I wherein $Ar^1$ is of formula ii-1c, ii-2c, ii-3c or ii-4c, in which one of $R^a$ forms a ring with $R^3$, the ring formed is a 3, 4, 5, or 6-membered ring.

In some embodiments compound of formula I wherein $Ar^1$ is of ii-1c, ii-2c, ii-3c or ii-4c, in which one of $R^2$ forms a ring with $R^3$, the ring formed is a 4, 5, or 6-membered ring or a 5 or 6 membered ring, or a 6 membered ring.

In some embodiments of a compound of formula I, $Ar^1$ is of formula iii-1 or pharmaceutically acceptable salts or stereoisomers thereof iii-1

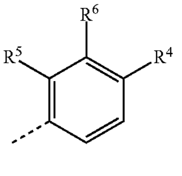

wherein $R^4$ is hydrogen or halogen, preferably F or Cl;

$R^5$, $R^6$ are independently of each other hydrogen, $—CF_3$ or halogen, preferably F, $C_1$.

In some embodiments of a compound of formula I, $Ar^1$ is of formula iii-2, iii-3 or iii-4, iii-5, iii-6 or iii-7 or pharmaceutically acceptable salts or stereoisomers thereof iii-2

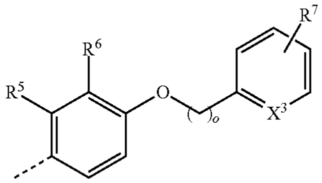

iii-3

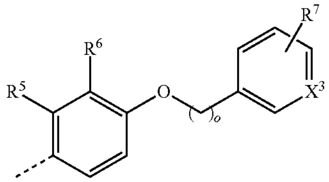

iii-4

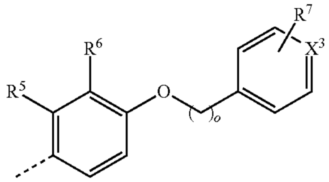

iii-5

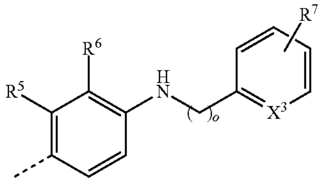

iii-6

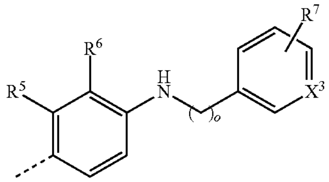

iii-7

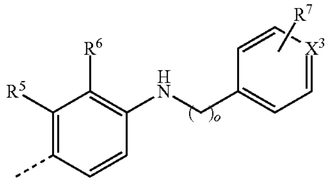

wherein $X^3$ is CH or N, preferably N;

is 0 or 1;

$R^5$, $R^6$ are independently of each other hydrogen, $—CF_3$ or halogen, preferably F or Cl;

$R^7$ is hydrogen or halogen, preferably F.

In some embodiments a compound of formula I, wherein $Ar^1$ is of formula iii-1, iii-3 or iii-4, iii-6 or iii-7, $R^5$ and $R^6$ are independently of each other hydrogen, $—CF_3$, F or Cl and $R^{5'}$ and $R^{6'}$ are hydrogen.

In some embodiments a compound of formula I, wherein $Ar^1$ is of formula iii-1, iii-3 or iii-4, iii-6 or iii-7, o is 1.

In some embodiments a compound of formula I, wherein $Ar^1$ is of formula iii-1, iii-3 or iii-4, iii-6 or iii-7, $R^5$ is F and/or $R^6$ is F or Cl.

In some embodiments of a compound of formula I, wherein $Ar^1$ is of formula iii-1, iii-3 or iii-4, $R^7$ is hydrogen if $X^3$ is N and/or $R^7$ is F if $X^3$ is CH.

In some embodiments a compound of formula I, wherein $Ar^1$ is of formula iii-1, iii-3 or iii-4, iii-6 or iii-7, $R^2$ is methyl or $R^2$ is —$(CH_2)$— or —$(CH_2)_2$— which forms a ring with $R^3$, or $R^2$ is —$(CH_2)$— or —$(CH_2)_2$— which forms a ring with one of $R^a$.

In some embodiments of a compound of formula I, wherein $Ar^1$ is of formula iii-1, iii-3 or iii-4, iii-6 or iii-7, $R^c$ and $R^d$ are hydrogen. In some embodiments of a compound of formula I, wherein $Ar^1$ is of formula iii-1, iii-3 or iii-4, iii-6 or iii-7, $R^b$, $R^c$ and $R^d$ are hydrogen.

In some embodiments compound of formula I wherein $Ar^1$ is of formula iii-1, iii-3 or iii-4 iii-5 iii-6 or iii-7, in which one of $R^a$ forms a ring with $R^3$, the ring formed is a 4, 5, or 6-membered ring, or a 5 or 6 membered ring, or a 5 membered ring.

In some embodiments compound of formula I wherein $Ar^1$ is of iii-1, iii-3 or iii-4, iii-5, iii-6 or iii-7, in which one of $R^a$ forms a ring with $R^3$, the ring formed is a 3, 4, 5, or 6-membered ring.

In some embodiments compound of formula I wherein $Ar^1$ is of iii-1, iii-3 or iii-4, iii-5, iii-6 or iii-7, in which one of $R^2$ forms a ring with $R^3$, the ring formed is a 4, 5, or 6-membered ring or a 5 or 6 membered ring, or a 6 membered ring.

In some embodiments, $X^3$ is N, such that $Ar^1$ is of formula iv-2, iv-3 or iv-4, iv-5, iv-6 or iv-7, or $X^3$ is C such that $Ar^1$ is of formula iv-8 or iv-9 iv-2

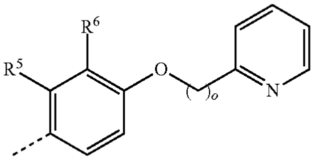

iv-3

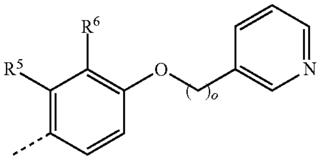

iv-4

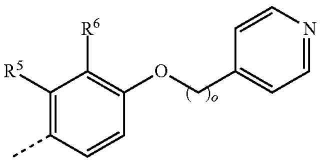

iv-5

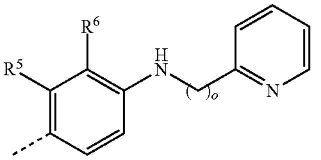

iv-6

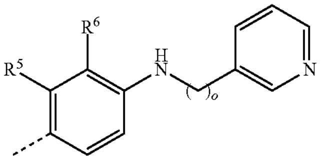

-continued iv-7

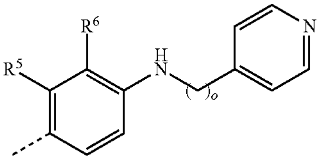

iv-8

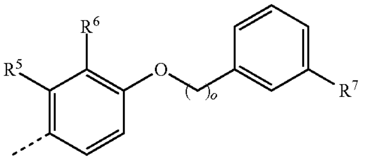

iv-9

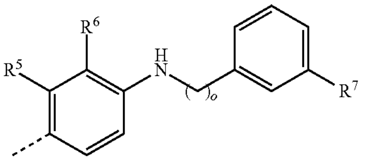

wherein is 0 or 1;

$R^5$, $R^6$ are independently of each other hydrogen, —$CF_3$ or halogen, preferably F or Cl;

$R^7$ is hydrogen or halogen, preferably F.

In some embodiments of a compound of formula I, wherein $Ar^1$ is of formula iv-2, iv-3 or iv-4, iv-5, iv-6, iv-7, iv-8 or iv-9, $R^5$ and $R^6$ are independently of each other hydrogen, —$CF_3$, F or $C_1$ and $R^{5'}$ and $R^{6'}$ are hydrogen.

In some embodiments of a compound of formula I, wherein $Ar^1$ is of iv-2, iv-3 or iv-4, iv-5, iv-6, iv-7, iv-8 or iv-9, o is 1.

In some embodiments of a compound of formula I, wherein $Ar^1$ is of formula iv-2, iv-3 or iv-4, iv-5, iv-6, iv-7, iv-8 or iv-9, $R^5$ is F and/or $R^6$ is F or Cl.

In some embodiments of a compound of formula I, wherein $Ar^1$ is of iiv-2, iv-3 or iv-4, iv-5, iv-6, iv-7, iv-8 or iv-9, $R^7$ is F.

In some embodiments of a compound of formula I, wherein $Ar^1$ is of iv-2, iv-3 or iv-4, iv-5, iv-6, iv-7, iv-8 or iv-9, $R^2$ is methyl or $R^2$ is —$(CH_2)$— or —$(CH_2)_2$— which forms a ring with $R^3$, or $R^2$ is —$(CH_2)$— or —$(CH_2)_2$— which forms a ring with one of $R^a$.

In some embodiments of a compound of formula I, wherein $Ar^1$ is of iv-2, iv-3 or iv-4, iv-5, iv-6, iv-7, iv-8 or iv-9, $R^c$ and $R^d$ are hydrogen. In some embodiments of a compound of formula I, wherein $Ar^1$ is of formula iv-1, iv-2, iv-3 or iv-4, iv-5, iv-6, iv-7, iv-8 or iv-9, $R^b$, $R^c$ and $R^d$ are hydrogen.

In some embodiments compound of formula I wherein $Ar^1$ is of formula iv-2, iv-3 or iv-4, iv-5, iv-6, iv-7, iv-8 or iv-9, in which one of $R^a$ forms a ring with $R^3$, the ring formed is a 4, 5, or 6-membered ring, or a 5 or 6 membered ring, or a 5 membered ring.

In some embodiments compound of formula I wherein $Ar^1$ is of iv-2, iv-3 or iv-4, iv-5, iv-6, iv-7, iv-8 or iv-9, in which one of $R^a$ forms a ring with $R^3$, the ring formed is a 3, 4, 5, or 6-membered ring.

In some embodiments compound of formula I wherein $Ar^1$ is of iv-2, iv-3 or iv-4, iv-5, iv-6, iv-7, iv-8 or iv-9, in which one of $R^2$ forms a ring with $R^3$, the ring formed is a 4, 5, or 6-membered ring or a 5 or 6 membered ring, or a 6 membered ring.

In some embodiments, the present disclosure provides a compound or pharmaceutically acceptable salts or stereoisomers thereof of formula IIa or IIb IIa

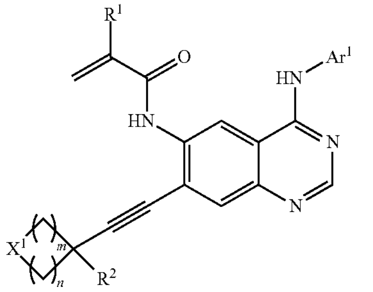

IIb

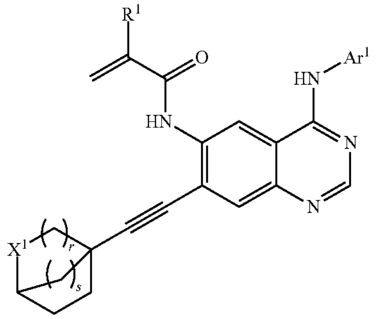

wherein
- $X^1$ is —O—, —$NR^3$—;
- $R^1$ is H or F;
- $R^2$ is hydrogen or $C_{1-4}$ alkyl, preferably methyl or is —$(CH_2)_q$— which forms a ring with $R^3$;
- $R^3$ is hydrogen or $C_{1-4}$ alkyl, preferably hydrogen or methyl, or is —$(CH_2)_p$— which forms a ring with $R^2$;
- m is 1, 2 or 3;
- n is 0, 1 or 2;
- p is 1 or 2;
- q is 0, 1 or 2;
- r is 0 or 1;
- s is 1 or 2; and
- $Ar^1$ is a 6-membered aryl, which is unsubstituted or substituted with one or more of a group selected from halogen, —$CF_3$, $C_{1-6}$ alkyl, $C_{1-6}$ alkoxy, $C_{3-7}$ cycloalkyl, hydroxy $C_{1-5}$ alkyl, $C_{1-6}$ alkoxy-$C_{1-6}$ alkyl, $C_{1-6}$ alkoxy-$C_6$ aryl, $C_{1-6}$ alkoxy-$C_{5*6}$ heteroaryl, amino, amino $C_{1-4}$ alkyl, $C_{1-6}$ alkylamino, $C_{1-6}$ aminoalkyl-$C_6$ aryl, $C_{1-6}$ aminoalkyl-$C_{5-6}$ heteroaryl, $C_{1-6}$ alkoxycarbonyl, $C_{1-6}$ alkoxyaminocarbonyl, aryl $C_{1-6}$ alkoxy, or $C_6$ aryl.

In some embodiments of a compound of formula IIa or IIb, $X^1$ is —$NR^3$—.

In some embodiments of a compound of formula IIa or IIb, $R^1$ is hydrogen.

In some embodiments of a compound of formula IIa or IIb, $R^2$ is $C_{1-4}$ alkyl or is —$(CH_2)_q$— which forms a ring with $R^3$. For example, $R^2$ may be selected from methyl, ethyl, n-propyl, propyl, n-butyl, i-butyl or t-butyl $R^2$ is —$(CH_2)$— or —$(CH_2)_2$— which forms a ring with $R^3$. Preferably, $R^2$ may be selected from methyl, ethyl, n-propyl, i-propyl, n-butyl or i-butyl $R^2$ is —$(CH_2)$— or —$(CH_2)_2$— which forms a ring with $R^3$. More preferably, $R^2$ may be methyl $R^2$ is —$(CH_2)$— or —$(CH_2)_2$— which forms a ring with $R^3$.

In some embodiments of a compound of formula IIa or IIb, $R^3$ is hydrogen or methyl is —$(CH_2)$— or —$(CH_2)_2$— which forms a ring with $R^2$.

In some embodiments of a compound of formula IIa or IIb, $X^1$ is $NR^3$.

In some embodiments of a compound of formula Ha, n is 0 and m is 1, 2 or 3; or n is 0 and m is 1 or 2; or n is 1 and m is 1, 2 or 3; or n is 1 and m is 1 or 2; or n is 2 and m is 1, 2, or 3; or n is 2 and m is 1 or 2; or n is 0, 1 or 2 and m is 1 or 2; or n is 0, 1 or 2 and m is 1; or n is 1 or 2 and m is 1, 2 or 3; or n is 1 or 2 and m is 1 or 2; or n is 1 or 2 and m is 1 or 3; or n is 1 or 2 and m is 2 or 3.

In some embodiments of a compound of formula IIb, r is 0 and s is 1 or 2, or r is 1 and s is 1 or 2, or r is 0 or 1 and s is 1, or r is 0 or 1 and s is 2.

In some embodiments of a compound of formula IIa or IIb, $X^1$ may form a heterocycle with the carbon to which $R^2$ is directly bound. For example, $X^1$ may form a 4, 5, 6 or 7 membered heterocycle or a heterobicycle. In some embodiments of a compound of formula I, $X^1$ may form a substituted or unsubstituted oxetanyl, thiatanyl, azetidinyl, pyrrolidinyl, tetrahydrofuranyl, tetrahydrothiopyranyl, dihydropyranyl, tetrahydropyranyl, piperidinyl, oxepanyl, thiepanyl, azepanyl, azabicyclo[2.2.1]heptane or azabicyclo [2.2.2]octane, preferably azetidinyl, pyrrolidinyl, tetrahydrofuranyl, piperidinyl, more preferably azetidinyl, pyrrolidinyl or piperidinyl.

In some embodiments of a compound of formula IIa or IIb, $Ar^1$ is of formula i or pharmaceutically acceptable salts or stereoisomers thereof i

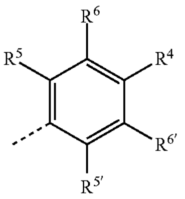

wherein
- $R^4$ is hydrogen, halogen, $C_{1-6}$ alkyl, $C_{1-6}$ alkoxy, $C_{3-7}$ cycloalkyl, hydroxy $C_{1-5}$ alkyl, $C_{1-6}$ alkoxy-$C_{1-6}$ alkyl, $C_{1-6}$ alkoxy-$C_6$ aryl, $C_{1-6}$ alkoxy-$C_{5*6}$ heteroaryl, amino $C_{1-4}$ alkyl, $C_{1-6}$ alkylamino, $C_{1-6}$ aminoalkyl-$C_6$ aryl, $C_{1-6}$ aminoalkyl-$C_{5-6}$ heteroaryl, $C_{1-6}$ alkoxycarbonyl, $C_{1-6}$ alkoxyaminocarbonyl, aryl $C_{1-6}$ alkoxy, or $C_6$ aryl;
- $R^5$, $R^{5'}$, $R^6$, $R^{6'}$ are independently of each other hydrogen, —$CF_3$ or halogen, preferably F, Cl.

In some embodiments of a compound of formula IIa or IIb, wherein $Ar^1$ is of formula i, $R^4$ is hydrogen, fluoro, chloro, $C_{1-4}$ alkyl, $C_{1-4}$ alkoxy, $C_{3-6}$ cycloalkyl, hydroxy $C_{1-5}$ alkyl, $C_{1-4}$ alkoxy-$C_{1-4}$ alkyl, $C_{1-4}$ alkoxy-$C_6$ aryl, $C_{1-4}$ alkoxy-$C_{5*6}$ heteroaryl, amino $C_{1-4}$ alkyl, $C_{1-4}$ alkylamino, $C_{1-4}$ aminoalkyl-$C_6$ aryl, $C_{1-4}$ aminoalkyl-$C_6$ heteroaryl, $C_{1-4}$ alkoxycarbonyl, $C_{1-4}$ alkoxyaminocarbonyl or $C_6$ aryl.

In some embodiments of a compound of formula IIa or IIb, wherein $Ar^1$ is of formula i, $R^4$ is hydrogen, fluoro, chloro, $C_{1-4}$ alkyl, $C_{1-4}$ alkoxy, $C_{3-6}$ cycloalkyl, $C_{1-4}$ alkoxy-$C_{1-4}$ alkyl, $C_{1-4}$ alkoxy-$C_6$ aryl, $C_{1-4}$ alkoxy-$C_{5*6}$ heteroaryl or $C_6$ aryl.

In some embodiments of a compound of formula IIa or IIb, wherein $Ar^1$ is of formula i, $R^4$ is in general hydrogen, fluoro, chloro, methyl, ethyl, n-propyl, i-propyl, n-butyl, i-butyl, t-butyl, n-pentyl, i-pentyl, n-hexyl, i-hexyl, methoxy, ethoxy, n-propoxy, i-propoxy, n-propoxy, n-butoxy, i-butoxy, n-pentoxy, i-pentoxy, n-hexoxy, i-hexoxy, cyclopropyl, cyclobutyl, cyclopentyl, cyclohexyl, cyclopheptyl, hydroxy methyl, hydroxy ethyl, hydroxyl propyl, hydroxyl butyl, hydroxyl pentyl, methoxy methyl, method ethyl, methoxy propyl, methoxy butyl, methoxy pentyl, mehoxy hexyl, ethoxy methyl, ethoxy ethyl, ethoxy propyl, ethoxy butyl, ethoxy pentyl, ethoxy hexyl, propoxy methyl, propoxy ethyl, propoxy propyl, propoxy butyl, propoxy pentyl, propoxy hexyl, butoxy methyl, butoxy ethyl, butoxy propyl, butoxy butyl, butoxy pentyl, butoxy hexyl, pentoxy methyl, pentoxy ethyl, pentoxy propyl, pentoxy butyl, pentoxy pentyl, pentoxy hexyl, hexoxy methyl, hexoxy ethyl, hexoxy propyl, hexoxy butyl, hexoxy pentyl, hexoxy hexyl, amino methyl, amino ethyl, amino propyl, amino butyl, amino pentyl, amino hexyl, methylamino ethylamino, propylamino, butylamino, pentylamino, hexylamino, methoxy carbonyl, ethoxy carbonyl, propoxy carbonyl, butoxy carbonyl, pentoxy carbonyl, hexoxy carbonyl, methoxyamino carbonyl, ethoxyamino carbonyl, propoxyamino carbonyl, butoxyamino carbonyl, pentoxyamino carbonyl, hexoxyamino carbonyl, phenyl methoxy, phenyl ethoxy, phenyl propoxy, phenyl butoxy, phenyl pentoxy, phenyl hexoxy, m-fluorophenyl methoxy, m-fluorophenylphenyl ethoxy, m-fluorophenylphenyl propoxy, m-fluorophenylphenyl butoxy, m-fluorophenylphenyl pentoxy, m-fluorophenylphenyl hexoxy, pyridinyl methoxy, pyridinyl ethoxy, pyridinyl propoxy, pyridinyl butoxy, pyridinyl pentoxy, pyridinyl hexoxy, phenyl, pyridinyl or naphtyl.

In some embodiments of a compound of formula IIa or IIb, wherein $Ar^1$ is of formula i, and $R^6$ are independently of each other hydrogen, —$CF_3$, F or Cl and $R^{5'}$ and $R^{6'}$ are hydrogen. Preferably, $R^4$ is hydrogen, halogen, $C_{1-6}$ alkyl, $C_{1-6}$ alkoxy, $C_{3-7}$ cycloalkyl, hydroxy $C_{1-5}$ alkyl, $C_{1-6}$ alkoxy-$C_{1-6}$ alkyl, $C_{1-6}$ alkoxy-$C_6$ aryl, $C_{1-6}$ alkoxy-$C_{5*6}$ heteroaryl, amino $C_{1-4}$ alkyl, $C_{1-6}$ alkylamino, $C_{1-6}$ aminoalkyl-$C_6$ aryl, $C_{1-6}$ aminoalkyl-$C_{5-6}$ heteroaryl, $C_{1-6}$ alkoxycarbonyl, $C_{1-6}$ alkoxyaminocarbonyl, aryl $C_{1-6}$ alkoxy, or $C_6$ aryl.

In some embodiments of a compound of formula IIa or IIb, wherein $Ar^1$ is of formula i, $R^5$ and $R^6$ are independently of each other hydrogen, —$CF_3$, F or Cl and $R^{5'}$ and $R^{6'}$ are hydrogen. Preferably, $R^4$ is hydrogen, fluoro, chloro, $C_{1-4}$ alkyl, $C_{1-4}$ alkoxy, $C_{3-6}$ cycloalkyl, hydroxy $C_{1-5}$ alkyl, $C_{1-4}$ alkoxy-$C_{1-4}$ alkyl, $C_{1-4}$ alkoxy-$C_6$ aryl, $C_{1-4}$ alkoxy-$C_{5*6}$ heteroaryl, amino $C_{1-4}$ alkyl, $C_{1-4}$ alkylamino, $C_{1-4}$ aminoalkyl-$C_6$ aryl, $C_{1-4}$ aminoalkyl-$C_6$ heteroaryl, $C_{1-4}$ alkoxycarbonyl, $C_{1-4}$ alkoxyaminocarbonyl or $C_6$ aryl.

In some embodiments of a compound of formula IIa or IIb, wherein $Ar^1$ is of formula i, $Ar^1$ comprises only 1, 2 or 3 substituents which are not hydrogen. Thus, at least two of $R^4$, $R^5$. $R^{5'}$, $R^6$ or $R^{6'}$ may be hydrogen.

In some embodiments of a compound of formula IIa or IIb, wherein $Ar^1$ is of formula i, $R^1$ may be hydrogen and/or $R^2$ may be methyl or may be —$(CH_2)$— or —$(CH_2)_2$— which forms a ring with $R^3$.

In some embodiments of a compound of formula IIa or IIb, $Ar^1$ is of formula ii-1 or pharmaceutically acceptable salts or stereoisomers thereof ii-1

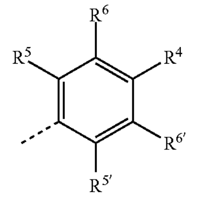

wherein $R^4$ is hydrogen, F or Cl;

$R^5$, $R^{5'}$, $R^6$, $R^{6'}$ are independently of each other hydrogen, —$CF_3$ or halogen, preferably F, Cl.

In some embodiments of a compound of formula IIa or IIb, $Ar^1$ is of formula ii-2, ii-3 or ii-4 or pharmaceutically acceptable salts or stereoisomers thereof ii-2

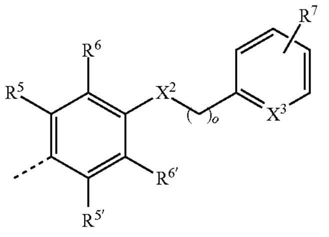

ii-3

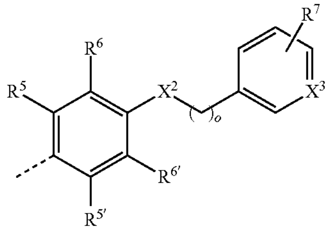

ii-4

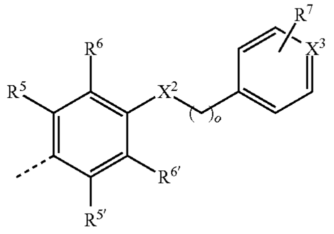

wherein $X^2$ is O, NH or NMe;

$X^3$ is C or N;

is 0 or 1;

$R^5$, $R^{5'}$, $R^6$, $R^{6'}$ are independently of each other hydrogen, —$CF_3$ or halogen, preferably F or Cl;

$R^7$ is hydrogen or halogen, preferably F.

In some embodiments of a compound of formula IIa or IIb, wherein $Ar^1$ is of formula ii-1, ii-2, ii-3 or ii-4, $R^5$ and $R^6$ are independently of each other hydrogen, —$CF_3$, F or Cl and $R^{5'}$ and $R^{6'}$ are hydrogen.

In some embodiments of a compound of formula IIa or IIb, wherein $Ar^1$ is of formula ii-1, ii-2, ii-3 or ii-4, o is 1.

In some embodiments of a compound of formula IIa or lib, wherein $Ar^1$ is of formula ii-1, ii-2, ii-3 or ii-4, $R^5$ is F and/or $R^6$ is F or Cl.

In some embodiments of a compound of formula IIa or IIb, wherein $Ar^1$ is of formula ii-1, ii-2, ii-3 or ii-4, $R^2$ is methyl or is —($CH_2$)— or —$(CH_2)_2$— which forms a ring with $R^3$.

In some embodiments of a compound of formula IIa or IIb, wherein $Ar^1$ is of formula ii-1, ii-2, ii-3 or ii-4, $R^7$ is hydrogen if $X^3$ is N and/or $R^7$ is F if $X^3$ is CH.

In some embodiments of a compound of formula Ha, wherein $Ar^1$ is of formula ii-1, ii-2, ii-3 or ii-4, n is 0 and m is 1, 2 or 3; or n is 0 and m is 1 or 2; or n is 1 and m is 1, 2 or 3; or n is 1 and m is 1 or 2; or n is 2 and m is 1, 2, or 3; or n is 2 and m is 1 or 2; or n is 0, 1 or 2 and m is 1 or 2; or n is 0, 1 or 2 and m is 1; or n is 1 or 2 and m is 1, 2 or 3; or n is 1 or 2 and m is 1 or 2; or n is 1 or 2 and m is 1 or 3; or n is 1 or 2 and m is 2 or 3.

In some embodiments of a compound of formula IIb, wherein $Ar^1$ is of formula ii-1, ii-2, ii-3 or ii-4, r is 0 and s is 1 or 2, or r is 1 and s is 1 or 2, or r is 0 or 1 and s is 1, or r is 0 or 1 and s is 2.

In some embodiments, $X^2$ is O, such that $Ar^1$ is of formula ii-1a or pharmaceutically acceptable salts or stereoisomers thereof ii-1a

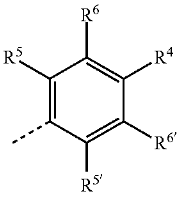

wherein $R^4$ is hydrogen, F or Cl;

$R^5$, $R^{5'}$, $R^6$, $R^{6'}$ are independently of each other hydrogen, —$CF_3$ or halogen, preferably F, Cl.

In some embodiments, $X^2$ is O, such that $Ar^1$ is of formula ii-2a, ii-3a or ii-4a or pharmaceutically acceptable salts or stereoisomers thereof ii-2a

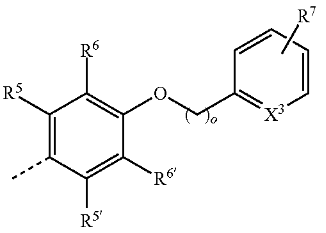

ii-3a

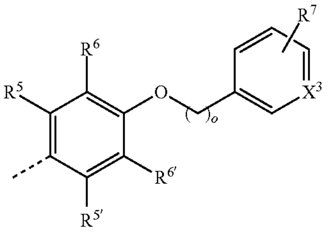

-continued ii-4a

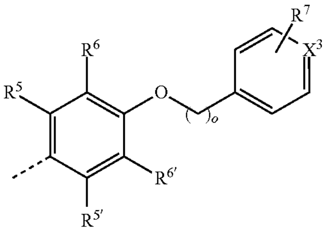

wherein $X^3$ is CH or N, preferably N;

is 0 or 1;

$R^5$, $R^{5'}$, $R^6$, $R^{6'}$ are independently of each other hydrogen, —$CF_3$ or halogen, preferably F or Cl;

$R^7$ is hydrogen or halogen, preferably F.

In some embodiments of a compound of formula IIa or IIb, wherein $Ar^1$ is of formula ii-1a, ii-2a, ii-3a or ii-4a, $R^5$ and $R^6$ are independently of each other hydrogen, —$CF_3$, F or Cl and $R^{5'}$ and $R^{6'}$ are hydrogen.

In some embodiments of a compound of formula IIa or IIb, wherein $Ar^1$ is of formula ii-1a, ii-2a, ii-3a or ii-4a, o is 1.

In some embodiments of a compound of formula IIa or IIb, wherein $Ar^1$ is of formula ii-1a, ii-2a, ii-3a or ii-4a, $R^5$ is F and/or $R^6$ is F or Cl.

In some embodiments of a compound of formula IIa or IIb, wherein $Ar^1$ is of formula ii-1a, ii-2a, ii-3a or ii-4a, $R^7$ is hydrogen if $X^3$ is N and/or $R^7$ is F if $X^3$ is CH.

In some embodiments of a compound of formula IIa or IIb, wherein $Ar^1$ is of formula ii-1a, ii-2a, ii-3a or ii-4a, $R^2$ is methyl or is —($CH_2$)— or —$(CH_2)_2$— which forms a ring with $R^3$.

In some embodiments of a compound of formula Ha, wherein $Ar^1$ is of formula ii-a-1, ii-2a, ii-3a or ii-4a, n is 0 and m is 1, 2 or 3; or n is 0 and m is 1 or 2; or n is 1 and m is 1, 2 or 3; or n is 1 and m is 1 or 2; or n is 2 and m is 1, 2, or 3; or n is 2 and m is 1 or 2; or n is 0, 1 or 2 and m is 1 or 2; or n is 0, 1 or 2 and m is 1; or n is 1 or 2 and m is 1, 2 or 3; or n is 1 or 2 and m is 1 or 2; or n is 1 or 2 and m is 1 or 3; or n is 1 or 2 and m is 2 or 3.

In some embodiments of a compound of formula IIb, wherein $Ar^1$ is of formula ii-1a, ii-2a, ii-3a or ii-4a, r is 0 and s is 1 or 2, or r is 1 and s is 1 or 2, or r is 0 or 1 and s is 1, or r is 0 or 1 and s is 2.

In some embodiments of a compound of formula IIa or IIb, $X^3$ is N, such that $Ar^1$ is of formula ii-1b or pharmaceutically acceptable salts or stereoisomers thereof ii-1b

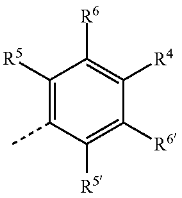

wherein $R^4$ is hydrogen, F or Cl;

$R^5$, $R^{5'}$, $R^6$, $R^{6'}$ are independently of each other hydrogen, —$CF_3$ or halogen, preferably F, Cl.

In some embodiments of a compound of formula IIa or IIb, $X^3$ is N, such that $Ar^1$ is of formula ii-2b, ii-3b, ii-4b, ii-5b or pharmaceutically acceptable salts or stereoisomers thereof ii-2b

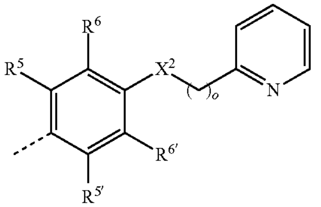

ii-3b

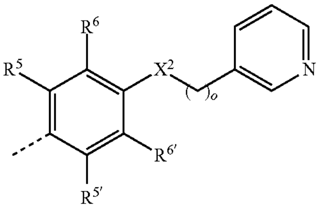

ii-4b

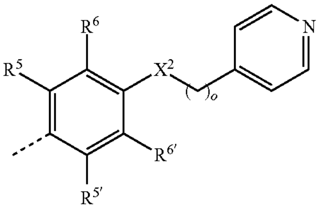

ii-5b

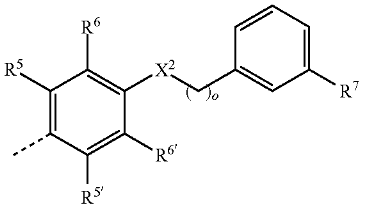

wherein $X^2$ is O, NH or NMe, preferably O;

is 0 or 1;

$R^5$, $R^{5'}$, $R^6$, $R^{6'}$ are independently of each other hydrogen, —$CF_3$ or halogen, preferably F or Cl;

$R^7$ is hydrogen or halogen, preferably F.

In some embodiments of a compound of formula IIa or IIb, wherein $Ar^1$ is of formula ii-1b, ii-2b, ii-3b, ii-4b or ii-5b, $R^5$ and $R^6$ are independently of each other hydrogen, —$CF_3$, F or Cl and $R^{5'}$ and $R^{6'}$ are hydrogen.

In some embodiments of a compound of formula IIa or IIb, wherein $Ar^1$ is of formula ii-1b, ii-2b, ii-3b, ii-4b or ii-5b, o is 1.

In some embodiments of a compound of formula IIa or IIb, wherein $Ar^1$ is of formula ii-1b, ii-2b, ii-3b, ii-4b or ii-5b, $R^5$ is F and/or $R^6$ is F or Cl.

In some embodiments of a compound of formula IIa or IIb, wherein $Ar^1$ is of formula ii-1b, ii-2b, ii-3b, ii-4b or ii-5b, $R^7$ is F.

In some embodiments of a compound of formula IIa or IIb, wherein $Ar^1$ is of formula ii-1b, ii-2b, ii-3b, ii-4b or ii-5b, $R^2$ is methyl or is —$(CH_2)$— or —$(CH_2)_2$— which forms a ring with $R^3$.

In some embodiments of a compound of formula Ha, wherein $Ar^1$ is of formula ii-1b, ii-2b, ii-3b or ii-4b, n is 0 and m is 1, 2 or 3; or n is 0 and m is 1 or 2; or n is 1 and m is 1, 2 or 3; or n is 1 and m is 1 or 2; or n is 2 and m is 1, 2, or 3; or n is 2 and m is 1 or 2; or n is 0, 1 or 2 and m is 1 or 2; or n is 0, 1 or 2 and m is 1; or n is 1 or 2 and m is 1, 2 or 3; or n is 1 or 2 and m is 1 or 2; or n is 1 or 2 and m is 1 or 3; or n is 1 or 2 and m is 2 or 3.

In some embodiments of a compound of formula IIb, wherein $Ar^1$ is of formula ii-1b, ii-2b, ii-3b or ii-4b, r is 0 and s is 1 or 2, or r is 1 and s is 1 or 2, or r is 0 or 1 and s is 1, or r is 0 or 1 and s is 2.

In some embodiments of a compound of formula IIa or IIb $Ar^1$ is of formula ii-1c or pharmaceutically acceptable salts or stereoisomers thereof ii-1c

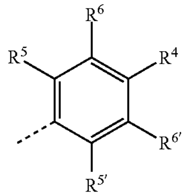

wherein $R^4$ is hydrogen, F or Cl;

$R^5$, $R^{5'}$, $R^6$, $R^{6'}$ are independently of each other hydrogen, —$CF_3$ or halogen, preferably F, Cl.

In some embodiments of a compound of formula IIa or IIb, $X^2$ is 0 and $X^3$ is N, such that $Ar^1$ is of formula ii-2c, ii-3c, ii-4c, ii-5c or pharmaceutically acceptable salts or stereoisomers thereof ii-2b

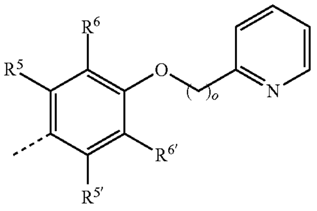

ii-3c

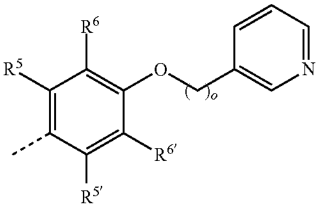

ii-4c

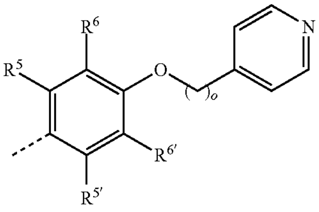

-continued ii-5c

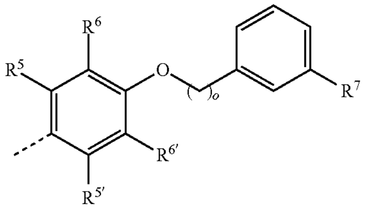

wherein is 0 or 1;

$R^5$, $R^{5'}$, $R^6$, $R^{6'}$ are independently of each other hydrogen, $—CF_3$ or halogen, preferably F or Cl;

$R^7$ is hydrogen or halogen, preferably F.

In some embodiments of a compound of formula IIa or IIb, wherein $Ar^1$ is of formula ii-1c, ii-2c, ii-3c, ii-4c or ii-5c, $R^5$ and $R^6$ are independently of each other hydrogen, $—CF_3$, F or Cl and $R^{5'}$ and $R^{6'}$ are hydrogen.

In some embodiments of a compound of formula IIa or IIb, wherein $Ar^1$ is of formula ii-1c, ii-2c, ii-3c, ii-4c or ii-5c, o is 1.

In some embodiments of a compound of formula IIa or IIb, wherein $Ar^1$ is of formula ii-1c, ii-2c, ii-3c, ii-4c or ii-5c, $R^5$ is F and/or $R^6$ is F or Cl.

In some embodiments of a compound of formula IIa or IIb, wherein $Ar^1$ is of formula ii-1c, ii-2c, ii-3c, ii-4c or ii-5c, $R^7$ is F.

In some embodiments of a compound of formula IIa or IIb, wherein $Ar^1$ is of formula ii-1c, ii-2c, ii-3c, ii-4c or ii-5c, $R^2$ is methyl or is $—(CH_2)—$ or $—(CH_2)_2—$ which forms a ring with $R^3$.

In some embodiments of a compound of formula Ha, wherein $Ar^1$ is of formula ii-1c, ii-2c, ii-3c or ii-4c, n is 0 and m is 1, 2 or 3; or n is 0 and m is 1 or 2; or n is 1 and m is 1, 2 or 3; or n is 1 and m is 1 or 2; or n is 2 and m is 1, 2, or 3; or n is 2 and m is 1 or 2; or n is 0, 1 or 2 and m is 1 or 2; or n is 0, 1 or 2 and m is 1; or n is 1 or 2 and m is 1, 2 or 3; or n is 1 or 2 and m is 1 or 2; or n is 1 or 2 and m is 1 or 3; or n is 1 or 2 and m is 2 or 3.

In some embodiments of a compound of formula IIb, wherein $Ar^1$ is of formula ii-1c, ii-2c, ii-3c or ii-4c, r is 0 and s is 1 or 2, or r is 1 and s is 1 or 2, or r is 0 or 1 and s is 1, or r is 0 or 1 and s is 2.

In some embodiments of a compound of formula IIa or IIb, $Ar^1$ is of formula iii-1 or pharmaceutically acceptable salts or stereoisomers thereof iii-1

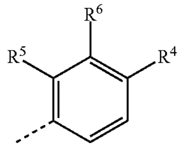

wherein $R^4$ is hydrogen or halogen, preferably F or Cl;

$R^5$, $R^6$ are independently of each other hydrogen, $—CF_3$ or halogen, preferably F, $C_1$.

In some embodiments of a compound of formula IIa or IIb, $Ar^1$ is of formula iii-2, iii-3 or iii-4 iii-5 iii-6 or iii-7 or pharmaceutically acceptable salts or stereoisomers thereof iii-2

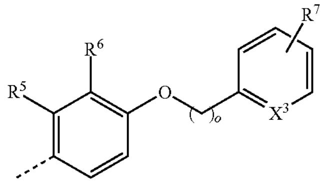

iii-3

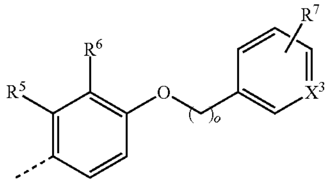

iii-4

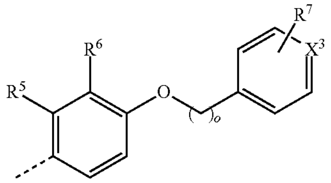

iii-5

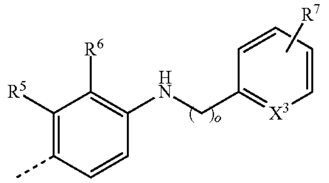

iii-6

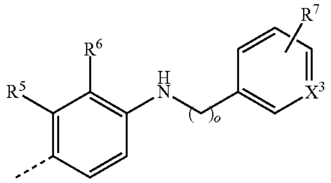

iii-7

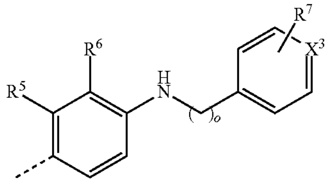

wherein $X^3$ is CH or N, preferably N;

is 0 or 1;

$R^5$, $R^6$ are independently of each other hydrogen, $—CF_3$ or halogen, preferably F or Cl;

$R^7$ is hydrogen or halogen, preferably F.

In some embodiments of a compound of formula IIa or IIb, wherein $Ar^1$ is of formula iii-1, iii-3 or iii-4, iii-6 or iii-7, $R^5$ and $R^6$ are independently of each other hydrogen, $—CF_3$, F or Cl and $R^{5'}$ and $R^{6'}$ are hydrogen.

In some embodiments of a compound of formula IIa or IIb, wherein $Ar^1$ is of formula iii-1, iii-3 or iii-4, iii-6 or iii-7, o is 1.

In some embodiments of a compound of formula IIa or IIb, wherein $Ar^1$ is of formula iii-1, iii-3 or iii-4, iii-6 or iii-7, $R^5$ is F and/or $R^6$ is F or Cl.

In some embodiments of a compound of formula IIa or IIb, wherein $Ar^1$ is of formula iii-1, iii-3 or iii-4, $R^7$ is hydrogen if $X^3$ is N and/or $R^7$ is F if $X^3$ is CH.

In some embodiments a compound of formula IIa or IIb, wherein $Ar^1$ is of formula iii-1, iii-3 or iii-4, iii-6 or iii-7, $R^2$ is methyl or is $-(CH_2)-$ or $-(CH_2)_2-$ which forms a ring with $R^3$.

In some embodiments of a compound of formula Ha, wherein $Ar^1$ is of formula iii-1, ii-3 or iii-4, n is 0 and m is 1, 2 or 3; or n is 0 and m is 1 or 2; or n is 1 and m is 1, 2 or 3; or n is 1 and m is 1 or 2; or n is 2 and m is 1, 2, or 3; or n is 2 and m is 1 or 2; or n is 0, 1 or 2 and m is 1 or 2; or n is 0, 1 or 2 and m is 1; or n is 1 or 2 and m is 1, 2 or 3; or n is 1 or 2 and m is 1 or 2; or n is 1 or 2 and m is 1 or 3; or n is 1 or 2 and m is 2 or 3.

In some embodiments of a compound of formula IIb, wherein $Ar^1$ is of formula iii-1, iii-3 or iii-4, r is 0 and s is 1 or 2, or r is 1 and s is 1 or 2, or r is 0 or 1 and s is 1, or r is 0 or 1 and s is 2.

In some embodiments, $X^3$ is N, such that $Ar^1$ is of formula iv-2, iv-3 or iv-4, iv-5, iv-6 or iv-7, or $X^3$ is C such that $Ar^1$ is of formula iv-8 or iv-9 iv-2

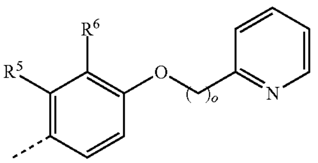

iv-3

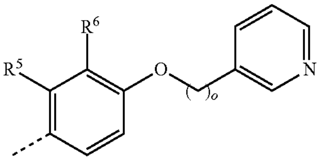

iv-4

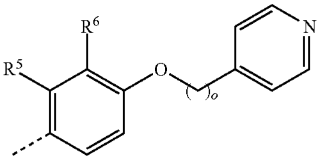

iv-5

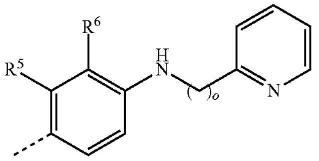

iv-6

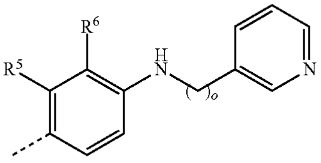

iv-7

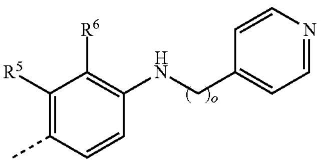

-continued iv-8

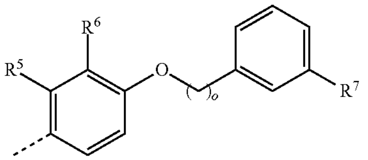

iv-9

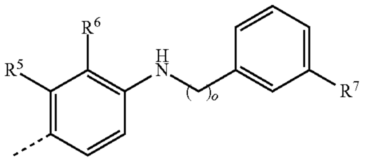

wherein is 0 or 1;

$R^5$, $R^6$ are independently of each other hydrogen, $-CF_3$ or halogen, preferably F or Cl; $R^7$ is hydrogen or halogen, preferably F.

In some embodiments of a compound of formula IIa or IIb, wherein $Ar^1$ is of formula iv-2, iv-3 or iv-4, iv-5, iv-6, iv-7, iv-8 or iv-9, $R^5$ and $R^6$ are independently of each other hydrogen, $-CF_3$, F or Cl and $R^{5'}$ and $R^{6'}$ are hydrogen.

In some embodiments of a compound of formula IIa or IIb, wherein $Ar^1$ is of iv-2, iv-3 or iv-4, iv-5, iv-6, iv-7, iv-8 or iv-9, o is 1.

In some embodiments of a compound of formula IIa or IIb, wherein $Ar^1$ is of formula iv-2, iv-3 or iv-4, iv-5, iv-6, iv-7, iv-8 or iv-9, $R^5$ is F and/or $R^6$ is F or Cl.

In some embodiments of a compound of formula IIa or IIb, wherein $Ar^1$ is of iv-2, iv-3 or iv-4, iv-5, iv-6, iv-7, iv-8 or iv-9, $R^7$ is F.

In some embodiments of a compound of formula IIa or IIb, wherein $Ar^1$ is of formula iv-2, iv-3 or iv-4, iv-5, iv-6, iv-7, iv-8 or iv-9, $R^2$ is methyl or is $-(CH_2)-$ or $-(CH_2)_2-$ which forms a ring with $R^3$.

In some embodiments of a compound of formula Ha, wherein $Ar^1$ is of formula iv-2, iv-3 or iv-4, iv-5, iv-6, iv-7, iv-8 or iv-9, n is 0 and m is 1, 2 or 3; or n is 0 and m is 1 or 2; or n is 1 and m is 1, 2 or 3; or n is 1 and m is 1 or 2; or n is 2 and m is 1, 2, or 3; or n is 2 and m is 1 or 2; or n is 0, 1 or 2 and m is 1 or 2; or n is 0, 1 or 2 and m is 1; or n is 1 or 2 and m is 1, 2 or 3; or n is 1 or 2 and m is 1 or 2; or n is 1 or 2 and m is 1 or 3; or n is 1 or 2 and m is 2 or 3.

In some embodiments of a compound of formula IIb, wherein $Ar^1$ is of formula iv-2, iv-3 or iv-4, iv-5, iv-6, iv-7, iv-8 or iv-9, r is 0 and s is 1 or 2, or r is 1 and s is 1 or 2, or r is 0 or 1 and s is 1, or r is 0 or 1 and s is 2.

In some embodiments, the present disclosure provides a compound or pharmaceutically acceptable salts or stereoisomers thereof of formula III

III

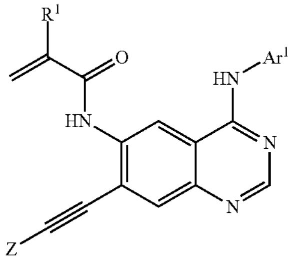

wherein $R^1$ is H or F;

$Ar^1$ is a 6-membered aryl, which is unsubstituted or substituted with one or more of a group selected from halogen, —$CF_3$, $C_{1-6}$ alkyl, $C_{1-6}$ alkoxy, $C_{3-7}$ cycloalkyl, hydroxy $C_{1-5}$ alkyl, $C_{1-6}$ alkoxy-$C_{1-6}$ alkyl, $C_{1-6}$ alkoxy-$C_6$ aryl, $C_{1-6}$ alkoxy-$C_{5*6}$ heteroaryl, amino, amino $C_{1-4}$ alkyl, $C_{1-6}$ alkylamino, $C_{1-6}$ aminoalkyl-$C_6$ aryl, $C_{1-6}$ aminoalkyl-$C_{5-6}$ heteroaryl, $C_{1-6}$ alkoxycarbonyl, $C_{1-6}$ alkoxyaminocarbonyl, aryl $C_{1-6}$ alkoxy, or $C_6$ aryl;

Z is selected from

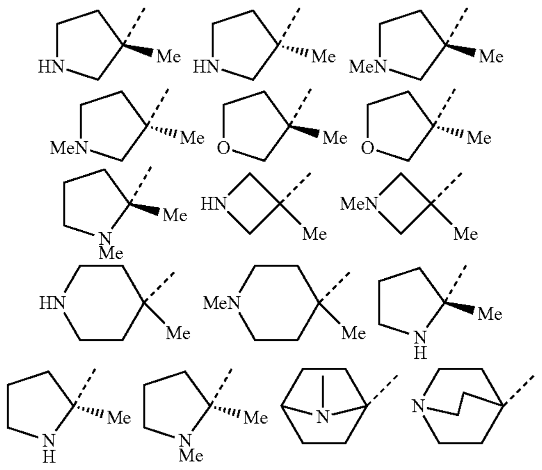

In some embodiments of a compound of formula III, $R^1$ is hydrogen.

In some embodiments, the present disclosure provides a compound or pharmaceutically acceptable salts or stereoisomers thereof of formula IV

IV

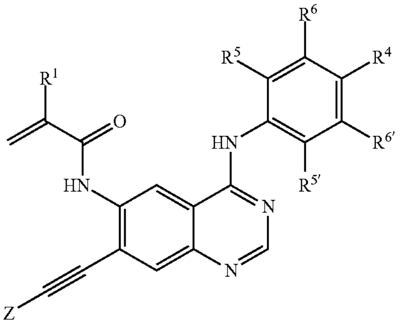

wherein $R^1$ is H or F;

$R^4$ is hydrogen, halogen, $C_{1-6}$ alkyl, $C_{1-6}$ alkoxy, $C_{3-7}$ cycloalkyl, hydroxy $C_{1-5}$ alkyl, $C_{1-6}$ alkoxy-$C_{1-6}$ alkyl, $C_{1-6}$ alkoxy-$C_6$ aryl, $C_{1-6}$ alkoxy-$C_{5*6}$ heteroaryl, amino $C_{1-4}$ alkyl, $C_{1-6}$ alkylamino, $C_{1-6}$ aminoalkyl-$C_6$ aryl, $C_{1-6}$ aminoalkyl-$C_{5-6}$ heteroaryl, $C_{1-6}$ alkoxy carbonyl, $C_{1-6}$ alkoxyaminocarbonyl, aryl $C_{1-6}$ alkoxy, or $C_6$ aryl;

$R^5$, $R^{5'}$, $R^6$, $R^{6'}$ are independently of each other hydrogen, —$CF_3$ or halogen, preferably F or Cl;

Z is selected from

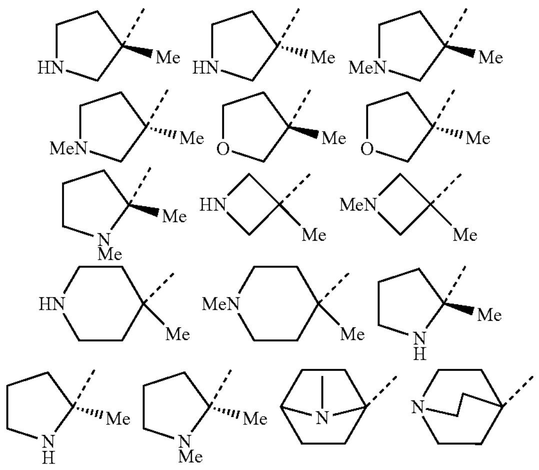

In some embodiments of a compound of formula IV, $R^4$ is hydrogen, fluoro, chloro, $C_{1-4}$ alkyl, $C_{1-4}$ alkoxy, $C_{3-6}$ cycloalkyl, hydroxy $C_{1-5}$ alkyl, $C_{1-4}$ alkoxy-$C_{1-4}$ alkyl, $C_{1-4}$ alkoxy-$C_6$ aryl, $C_{1-4}$ alkoxy-$C_{5*6}$ heteroaryl, amino $C_{1-4}$ alkyl, $C_{1-4}$ alkylamino, $C_{1-4}$ aminoalkyl-$C_6$ aryl, $C_{1-4}$ aminoalkyl-$C_6$ heteroaryl, $C_{1-4}$ alkoxycarbonyl, $C_{1-4}$ alkoxyaminocarbonyl or $C_6$ aryl.

In some embodiments of a compound of formula VI, $R^4$ is hydrogen, fluoro, chloro, $C_{1-4}$ alkyl, $C_{1-4}$ alkoxy, $C_{3-6}$ cycloalkyl, $C_{1-4}$ alkoxy-$C_{1-4}$ alkyl, $C_{1-4}$ alkoxy-$C_6$ aryl, $C_{1-4}$ alkoxy-$C_{5*6}$ heteroaryl or $C_6$ aryl.

In some embodiments of a compound of formula IV, $R^4$ is in general hydrogen, fluoro, chloro, methyl, ethyl, n-propyl, i-propyl, n-butyl, i-butyl, t-butyl, n-pentyl, i-pentyl, n-hexyl, hexyl, methoxy, ethoxy, n-propoxy, i-propoxy, n-propoxy, n-butoxy, i-butoxy, n-pentoxy, i-pentoxy, n-hexoxy, i-hexoxy, cyclopropyl, cyclobutyl, cyclopentyl, cyclohexyl, cyclopheptyl, hydroxy methyl, hydroxy ethyl, hydroxyl propyl, hydroxyl butyl, hydroxyl pentyl, methoxy methyl, method ethyl, methoxy propyl, methoxy butyl, methoxy pentyl, mehoxy hexyl, ethoxy methyl, ethoxy ethyl, ethoxy propyl, ethoxy butyl, ethoxy pentyl, ethoxy hexyl, propoxy methyl, propoxy ethyl, propoxy propyl, propoxy butyl, propoxy pentyl, propoxy hexyl, butoxy methyl, butoxy ethyl, butoxy propyl, butoxy butyl, butoxy pentyl, butoxy hexyl, pentoxy methyl, pentoxy ethyl, pentoxy propyl, pentoxy butyl, pentoxy pentyl, pentoxy hexyl, hexoxy methyl, hexoxy ethyl, hexoxy propyl, hexoxy butyl, hexoxy pentyl, hexoxy hexyl, amino methyl, amino ethyl, amino propyl, amino butyl, amino pentyl, amino hexyl, methylamino ethylamino, propylamino, butylamino, pentylamino, hexylamino, methoxy carbonyl, ethoxy carbonyl, propoxy carbonyl, butoxy carbonyl, pentoxy carbonyl, hexoxy carbonyl, methoxyamino carbonyl, ethoxyamino carbonyl, propoxyamino carbonyl, butoxyamino carbonyl, pentoxyamino carbonyl, hexoxyamino carbonyl, phenyl methoxy, phenyl ethoxy, phenyl propoxy, phenyl butoxy, phenyl pentoxy, phenyl hexoxy, m-fluorophenyl methoxy, m-fluorophenylphenyl ethoxy, m-fluorophenylphenyl propoxy, m-fluorophenylphenyl butoxy, m-fluorophenylphenyl pentoxy, m-fluorophenylphenyl hexoxy, pyridinyl methoxy, pyridinyl ethoxy, pyridinyl propoxy, pyridinyl butoxy, pyridinyl pentoxy, pyridinyl hexoxy, phenyl, pyridinyl or naphtyl.

In some embodiments of a compound of formula IV, $R^5$ and $R^6$ are independently of each other hydrogen, —$CF_3$, F or Cl and $R^{5'}$ and $R^{6'}$ are hydrogen. Preferably, $R^4$ is hydrogen, halogen, $C_{1-6}$ alkyl, $C_{1-6}$ alkoxy, $C_{3-7}$ cycloalkyl, hydroxy $C_{1-5}$ alkyl, $C_{1-6}$ alkoxy-$C_{1-6}$ alkyl, $C_{1-6}$ alkoxy-$C_6$ aryl, $C_{1-6}$ alkoxy-$C_{5*6}$ heteroaryl, amino $C_{1-4}$ alkyl, $C_{1-6}$ alkylamino, $C_{1-6}$ aminoalkyl-$C_6$ aryl, $C_{1-6}$ aminoalkyl-$C_{5-6}$ heteroaryl, $C_{1-6}$ alkoxycarbonyl, $C_{1-6}$ alkoxyaminocarbonyl, aryl $C_{1-6}$ alkoxy, or $C_6$ aryl.

In some embodiments of a compound of formula IV, $R^5$ and $R^6$ are independently of each other hydrogen, —$CF_3$, F or Cl and $R^{5'}$ and $R^{6'}$ are hydrogen. Preferably, $R^4$ is hydrogen, fluoro, chloro, $C_{1-4}$ alkyl, $C_{1-4}$ alkoxy, $C_{3-6}$ cycloalkyl, hydroxy $C_{1-5}$ alkyl, $C_{1-4}$ alkoxy-$C_{1-4}$ alkyl, $C_{1-4}$ alkoxy-$C_6$ aryl, $C_{1-4}$ alkoxy-$C_{5*6}$ heteroaryl, amino $C_{1-4}$ alkyl, $C_{1-4}$ alkylamino, $C_{1-4}$ aminoalkyl-$C_6$ aryl, $C_{1-4}$ aminoalkyl-$C_6$ heteroaryl, $C_{1-4}$ alkoxycarbonyl, $C_{1-4}$ alkoxyaminocarbonyl or $C_6$ aryl.

In some embodiments of a compound of formula IV, $Ar^1$ comprises only 1, 2 or 3 substituents which are not hydrogen. Thus, at least two of $R^4$, $R^5$. $R^{5'}$, $R^6$ or $R^{6'}$ may be hydrogen.

In some embodiments of a compound of formula IV, $R^1$ may be hydrogen.

In some embodiments, the present disclosure provides a compound or pharmaceutically acceptable salts or stereoisomers thereof of formula V-1

V-1

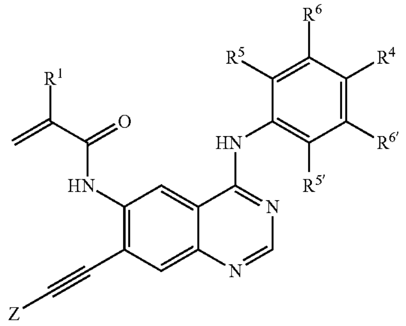

wherein $R^1$ is H or F;

$R^4$ is hydrogen or halogen, preferably F or Cl;

$R^5$, $R^{5'}$, $R^6$, $R^{6'}$ are independently of each other hydrogen, —$CF_3$ or halogen, preferably F or Cl;

Z is selected from

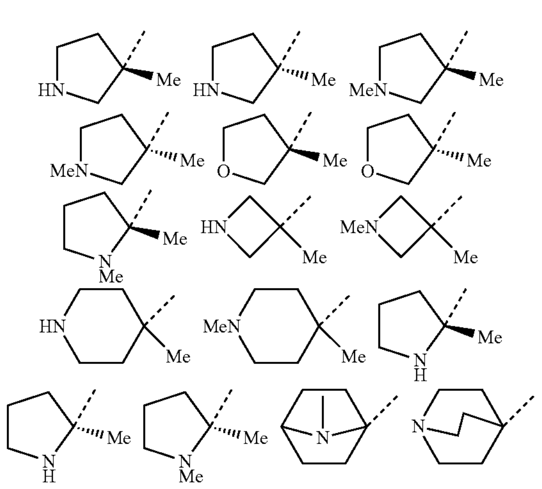

In some embodiments, the present disclosure provides a compound or pharmaceutically acceptable salts or stereoisomers thereof of formula V-2, V-3 or V-4

V-2

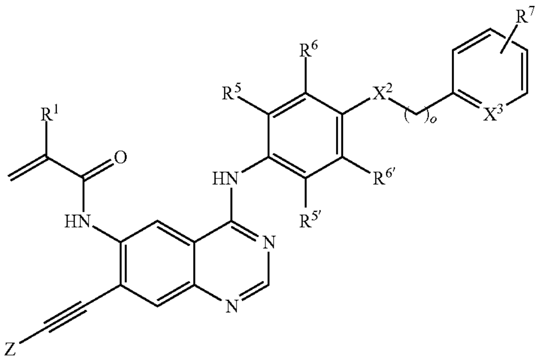

V-3

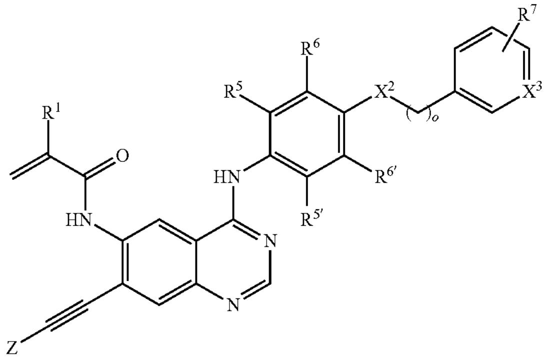

V-4

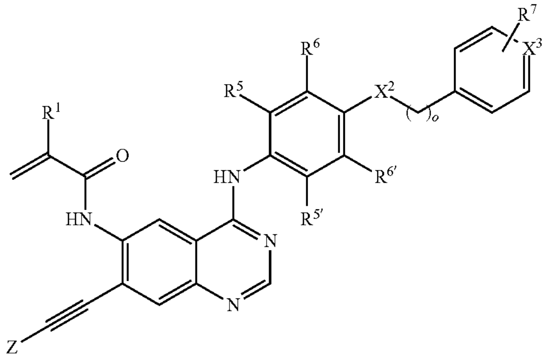

wherein $X^2$ is O or NH or NMe;

$X^3$ is CH or N;

$R^1$ is H or F;

$R^5$, $R^{5'}$, $R^6$, $R^{6'}$ are independently of each other hydrogen, —$CF_3$ or halogen, preferably F or Cl;

is 0 or 1;

$R^7$ is hydrogen or halogen, preferably F;

Z is selected from

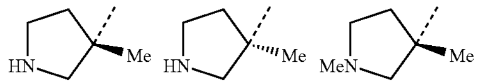

-continued

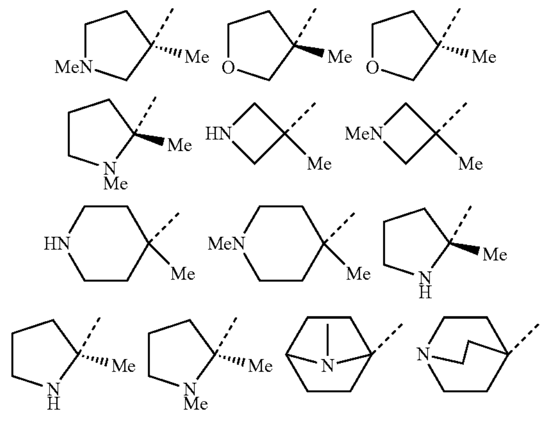

In some embodiments of a compound of formula V-1, V-2, V-3 or V-4, $R^4$ is hydrogen, chloro or fluoro.

In some embodiments of a compound of formula V-1, V-2, V-3 or V-4, $R^5$ and $R^6$ are independently of each other hydrogen, $-CF_3$, F or Cl and $R^{5'}$ and $R^{6'}$ are hydrogen. Preferably, $R^4$ is hydrogen, chloro or fluoro.

In some embodiments of a compound of formula V-1, V-2, V-3 or V-4, $R^5$ and $R^6$ are independently of each other hydrogen, $-CF_3$, F or Cl and $R^{5'}$ and $R^{6'}$ are hydrogen. Preferably, $R^4$ is hydrogen, chloro or fluoro.

In some embodiments of a compound of formula V-1, V-2, V-3 or V-4, $Ar^1$ comprises only 1, 2 or 3 substituents which are not hydrogen. Thus, at least two of $R^4$, $R^5$. $R^{5'}$, $R^6$ or $R^{6'}$ may be hydrogen.

In some embodiments of a compound of formula V-1, V-2, V-3 or V-4, $R^7$ is hydrogen if $X^3$ is N and/or $R^7$ is F if $X^3$ is CH.

In some embodiments of a compound of formula V-1, V-2, V-3 or V-4, o is 1.

In some embodiments of a compound of formula V-1, V-2, V-3 or V-4, $R^1$ may be hydrogen.

In some embodiments of a compound of formula V-2, V-3 or V-4, $X^2$ is O, resulting in a compound or pharmaceutically acceptable salts or stereoisomers thereof of formula V-2a, V-3a or V-4a V-2a

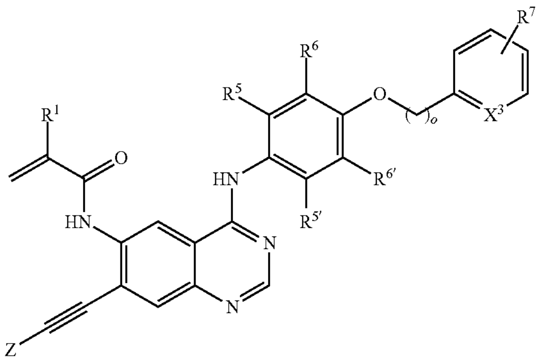

-continued

V-3a

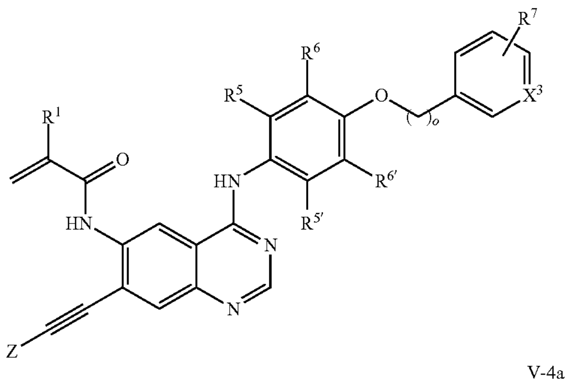

V-4a

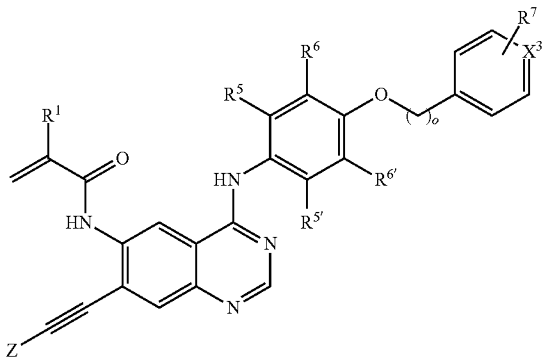

wherein $X^3$ is CH or N;

$R^1$ is H or F;

$R^5$, $R^{5'}$, $R^6$, $R^{6'}$ are independently of each other hydrogen, $-CF_3$ or halogen, preferably F or Cl;

is 0 or 1;

$R^7$ is hydrogen or halogen, preferably F;

Z is selected from

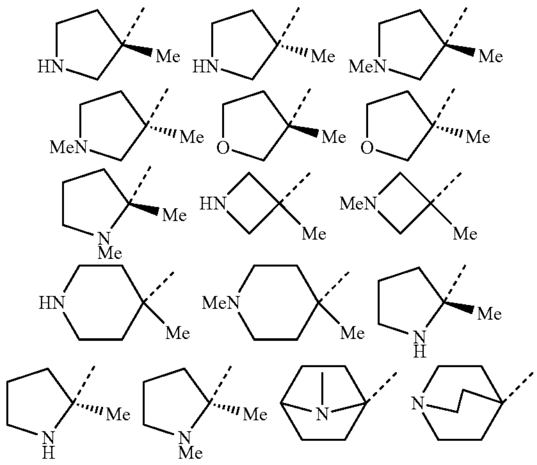

In some embodiments of a compound of formula V-1, V-2a, V-3a or V-4a, $R^4$ is hydrogen, fluoro or chloro.

In some embodiments of a compound of formula V-1, V-2a, V-3a or V-4a, $R^5$ and $R^6$ are independently of each other hydrogen, $-CF_3$, F or Cl and $R^{5'}$ and $R^{6'}$ are hydrogen. Preferably, $R^4$ is hydrogen, chloro or fluoro.

In some embodiments of a compound of formula V-1, V-2a, V-3a or V-4a, $R^5$ and $R^6$ are independently of each other hydrogen, —$CF_3$, F or Cl and $R^{5'}$ and $R^{6'}$ are hydrogen. Preferably, $R^4$ is hydrogen, chloro or fluoro.

In some embodiments of a compound of formula V-1, V-2a, V-3a or V-4a, $Ar^1$ comprises only 1, 2 or 3 substituents which are not hydrogen. Thus, at least two of $R^4$, $R^5$. $R^{5'}$, $R^6$ or $R^{6'}$ may be hydrogen.

In some embodiments of a compound of formula V-1, V-2a, V-3a or V-4a, $R^7$ is hydrogen if $X^3$ is N and/or $R^7$ is F if $X^3$ is CH.

In some embodiments of a compound of formula V-1, V-2a, V-3a or V-4a, o is 1.

In some embodiments of a compound of formula V-1, V-2a, V-3a or V-4a, $R^1$ may be hydrogen.

In some embodiments of a compound of formula V-2, V-3 or V-4, $X^3$ is N, resulting in a compound or pharmaceutically acceptable salts or stereoisomers thereof of formula V-2b, V-3b, V-4b or $X^3$ is C, resulting in a compound or pharmaceutically acceptable salts or stereoisomers thereof of formula V-5b V-2b

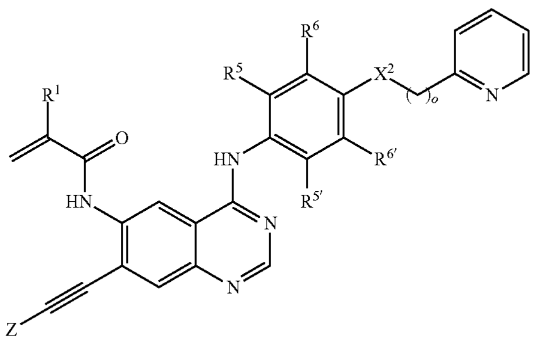

V-3b

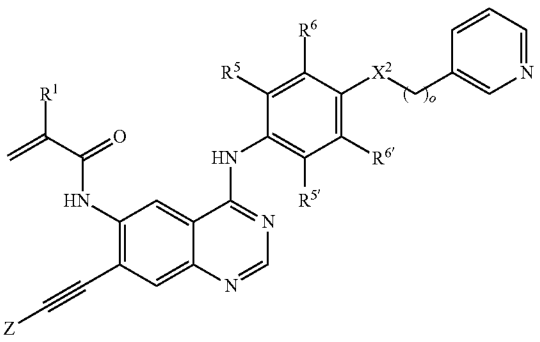

V-4b

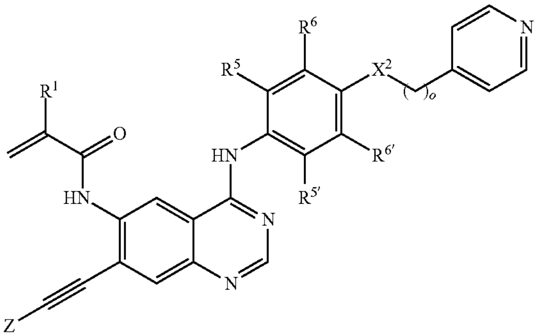

-continued

V-5b

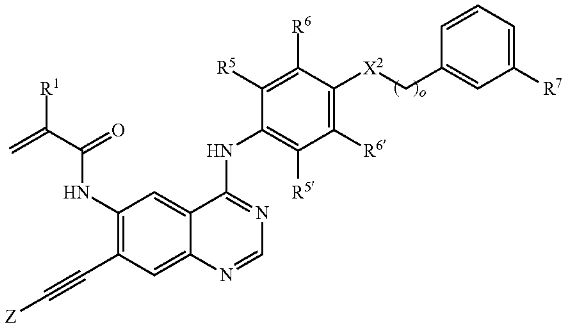

wherein $X^2$ is O, NH or NMe $R^1$ is H or F;

$R^5$, $R^{5'}$, $R^6$, $R^{6'}$ are independently of each other hydrogen, —$CF_3$ or halogen, preferably F or Cl;

is 0 or 1;

$R^7$ is hydrogen or halogen, preferably F;

Z is selected from

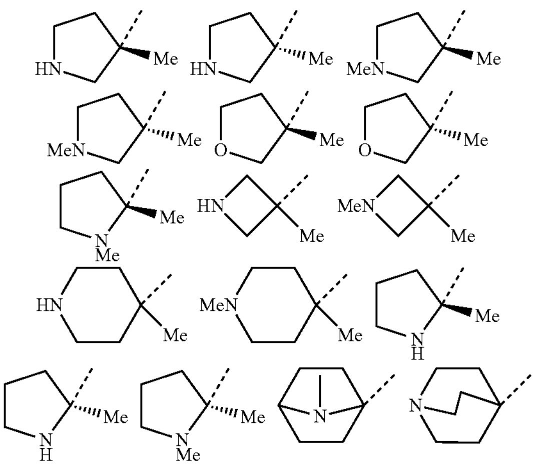

In some embodiments of a compound of formula V-1, V-2b, V-3b, V-4b or V-5b, $R^4$ is hydrogen, fluoro, chloro.

In some embodiments of a compound of formula V-1, V-2b, V-3b, V-4b or V-5b, $R^5$ and $R^6$ are independently of each other hydrogen, —$CF_3$, F or Cl and $R^{5'}$ and $R^{6'}$ are hydrogen. Preferably, $R^4$ is hydrogen, chloro or fluoro.

In some embodiments of a compound of formula V-1, V-2b, V-3b, V-4b or V-5b, $R^5$ and $R^6$ are independently of each other hydrogen, —$CF_3$, F or Cl and $R^{5'}$ and $R^{6'}$ are hydrogen. Preferably, $R^4$ is hydrogen, fluoro, chloro, $C_{1-4}$ alkyl, $C_{1-4}$ alkoxy, $C_{3-6}$ cycloalkyl, hydroxy $C_{1-5}$ alkyl, $C_{1-4}$ alkoxy-$C_{1-4}$ alkyl, amino $C_{1-4}$ alkyl, $C_{1-4}$ alkylamino, $C_{1-4}$ alkoxycarbonyl, $C_{1-4}$ alkoxyaminocarbonyl, aryl $C_{1-4}$ alkoxy, heteroaryl $C_{1-4}$ alkoxy or aryl.

In some embodiments of a compound of formula V-1, V-2b, V-3b, V-4b or V-5b, comprises only 1, 2 or 3 substituents which are not hydrogen. Thus, at least two of $R^4$, $R^5$. $R^{5'}$, $R^6$ or $R^{6'}$ may be hydrogen.

In some embodiments V-2b, V-3b, V-4b or V-5b, o is 1.

In some embodiments of a compound of formula V-1, V-2b, V-3b, V-4b or V-5b, $R^7$ is F.

In some embodiments of a compound of formula V-1, V-2b, V-3b, V-4b or V-5b, $R^1$ may be hydrogen.

In some embodiments, the present disclosure provides a compound or pharmaceutically acceptable salts or stereoisomers thereof of formula VI-1

VI-1

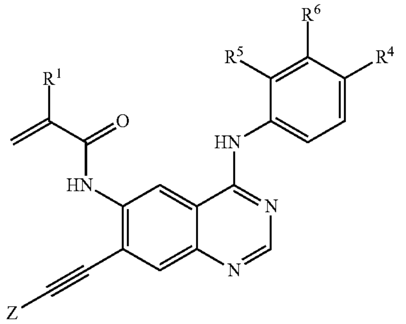

wherein $R^1$ is H or F;

$R^4$ is hydrogen or halogen, preferably F or Cl;

$R^5$, $R^6$ are independently of each other hydrogen, $—CF_3$ or halogen, preferably F or Cl;

$R^7$ is hydrogen or halogen, preferably F;

Z is selected from

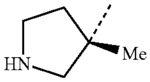 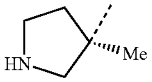 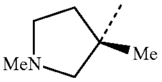

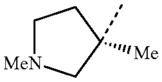 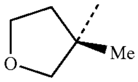 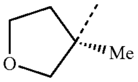

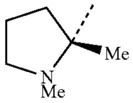 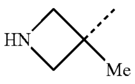 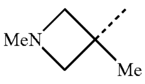

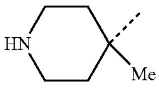 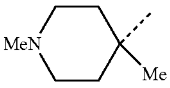 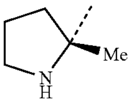

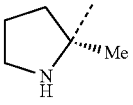 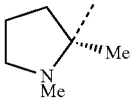 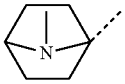 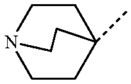

In some embodiments, the present disclosure provides a compound or pharmaceutically acceptable salts or stereoisomers thereof of formula VI-2, VI-3 or VI-4

VI-2

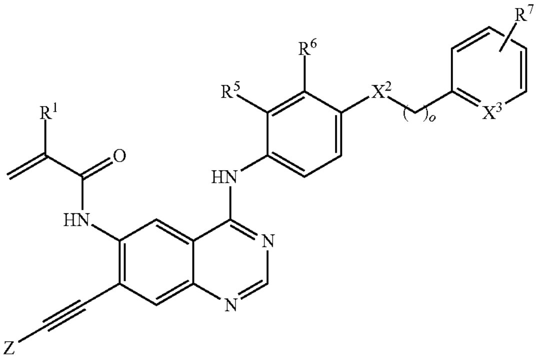

VI-3

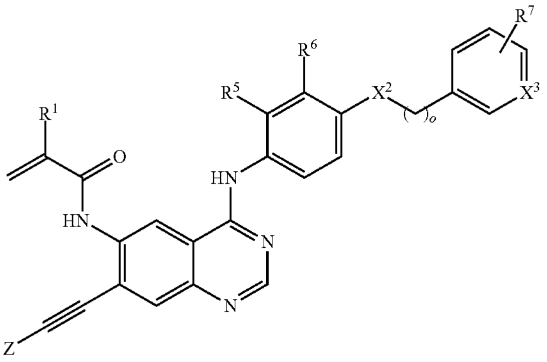

VI-4

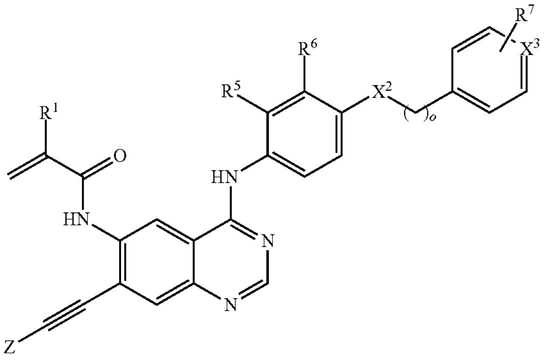

wherein $X^2$ is O, NH or NMe;

$X^3$ is CH or N;

$R^1$ is H or F;

is 0 or 1;

$R^5$, $R^6$ are independently of each other hydrogen, $—CF_3$ or halogen, preferably F or Cl;

$R^7$ is hydrogen or halogen, preferably F;

Z is selected from

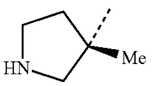 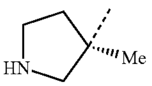 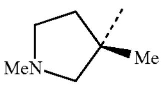

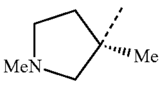 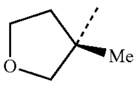 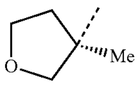

-continued

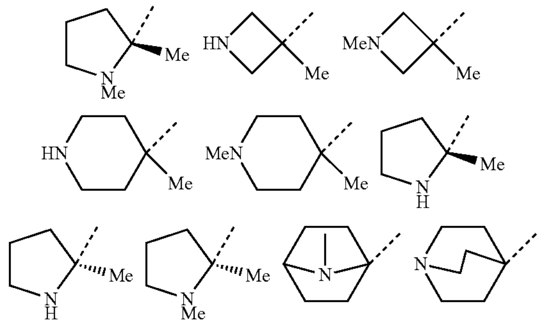

In some embodiments of a compound of formula VI-1, VI-2, VI-3 or VI-4, $R^4$ is hydrogen, chloro or fluoro.

In some embodiments of a compound of formula VI-1, VI-2, VI-3 or VI-4, o is 1.

In some embodiments of a compound of formula VI-1, VI-2, VI-3 or VI-4, $R^5$ is F and/or $R^6$ is F or Cl.

In some embodiments of a compound of formula VI-1, VI-2, VI-3 or VI-4, $R^7$ is hydrogen if $X^3$ is N and/or $R^7$ is F if $X^3$ is CH.

In some embodiments of a compound of formula VI-1, VI-2, VI-3 or VI-4, $R^1$ may be hydrogen.

In some embodiments of a compound of formula VI-2, VI-3 or VI-4, $X^2$ is O, resulting in a compound or pharmaceutically acceptable salts or stereoisomers thereof of formula VI-2a, VI-3a or VI-4a VI-2a

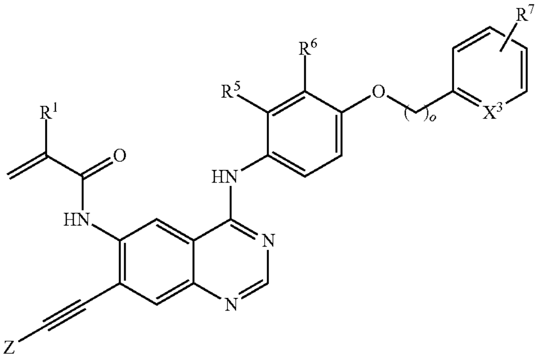

VI-3a

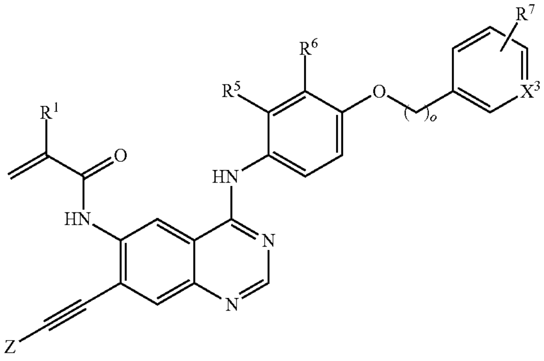

-continued

VI-4a

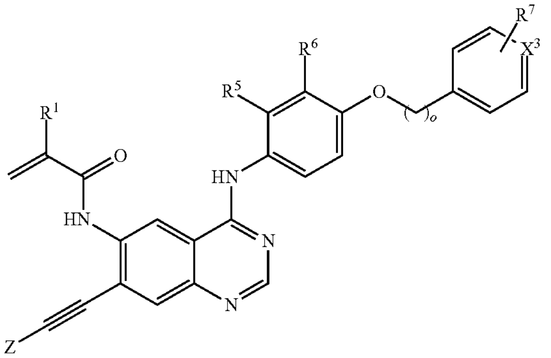

wherein $X^3$ is CH or N;

$R^1$ is H or F;

$R^5$, $R^6$ are independently of each other hydrogen, —$CF_3$ or halogen, preferably F or Cl;

is 0 or 1;

$R^7$ is hydrogen or halogen, preferably F;

Z is selected from

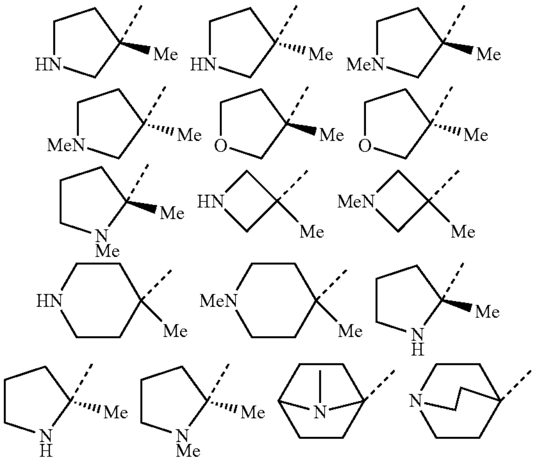

In some embodiments of a compound of formula VI-1, VI-2a, VI-3a or VI-4a, $R^4$ is hydrogen, fluoro or chloro.

In some embodiments of a compound of formula VI-1, VI-2a, VI-3a or VI-4a, o is 1.

In some embodiments of a compound of formula VI-1, VI-2a, VI-3a or VI-4a, $R^5$ is F and/or $R^6$ is F or Cl.

In some embodiments of a compound of formula VI-1, VI-2a, VI-3a or VI-4a, $R^7$ is hydrogen if $X^3$ is N and/or $R^7$ is F if $X^3$ is CH.

In some embodiments of a compound of formula VI-1, VI-2a, VI-3a or VI-4a, $R^1$ may be hydrogen.

In some embodiments of a compound of formula VI-2, VI-3 or VI-4, $X^3$ is N, resulting in a compound or pharmaceutically acceptable salts or stereoisomers thereof of formula VI-2b, VI-3b or VI-4b or $X^3$ is C, resulting in a compound or pharmaceutically acceptable salts or stereoisomers thereof of formula VI-5b VI-2b

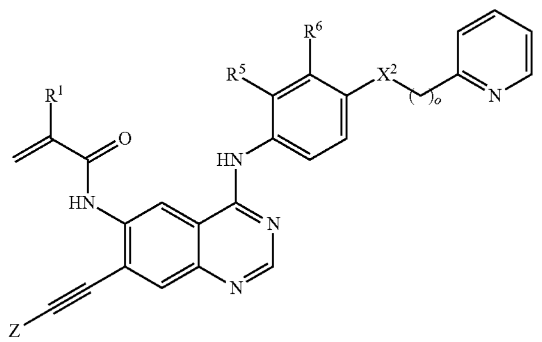

VI-3b

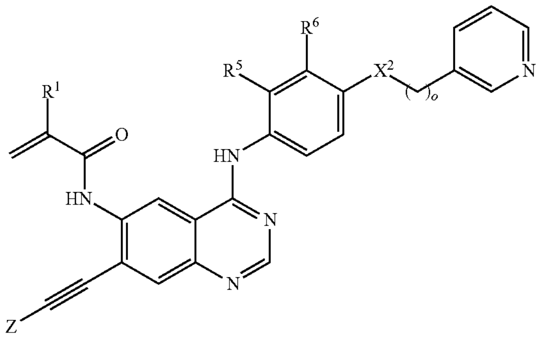

VI-4b

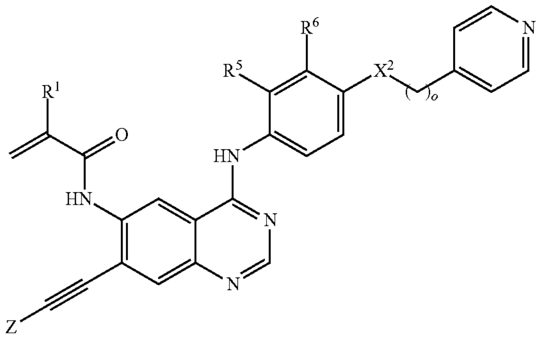

VI-5b

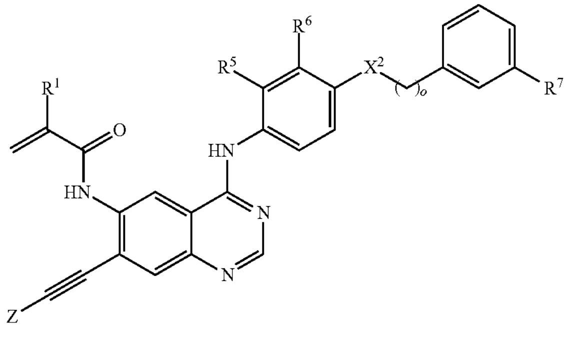

wherein $X^2$ is O, NH or NMe $R^1$ is H or F;

$R^5$, $R^6$ are independently of each other hydrogen, $—CF_3$ or halogen, preferably F or Cl;

is 0 or 1;

$R^7$ is hydrogen or halogen, preferably F;

Z is selected from

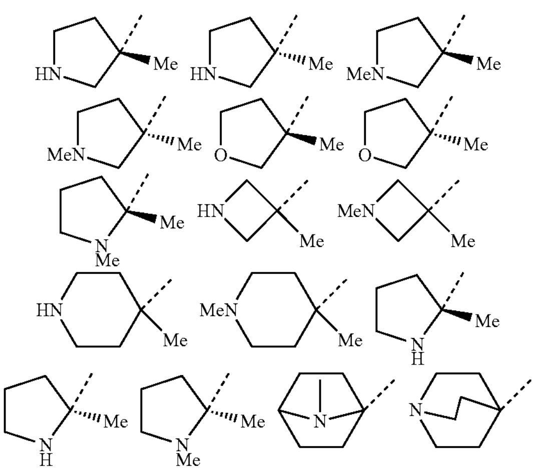

In some embodiments of a compound of formula VI-1, VI-2b, VI-3b, VI-4b or VI-5b, $R^4$ is hydrogen, fluoro or chloro.

In some embodiments of a compound of formula VI-1, VI-2b, VI-3b, VI-4b or VI-5b, o is 1.

In some embodiments of a compound of formula VI-1b, VI-2b, VI-3b, VI-4b or VI-5b, $R^5$ is F and/or $R^6$ is F or Cl.

In some embodiments of a compound of formula VI-1, VI-2b, VI-3b, VI-4b or VI-5b, $R^7$ is F.

In some embodiments of a compound of formula VI-1, VI-2b, VI-3b, VI-4b or VI-5b, $R^1$ may be hydrogen.

In some embodiments, the present disclosure provides a compound or pharmaceutically acceptable salts or stereoisomers thereof of formula VII-1

VII-1

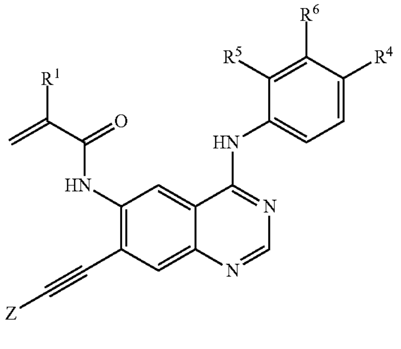

wherein $R^1$ is H or F, preferably H;

$R^4$ is hydrogen or halogen, preferably F or Cl;

$R^5$, $R^6$ are independently of each other hydrogen, $—CF_3$ or halogen, preferably F or Cl;

Z is selected from

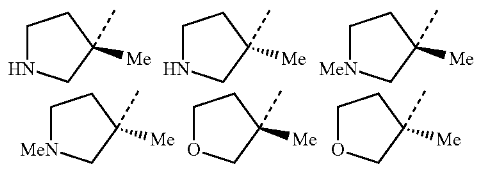

-continued
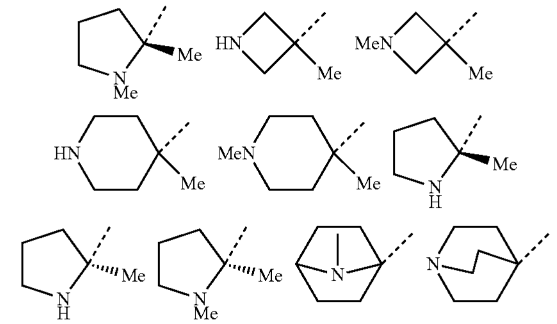
In some embodiments, the present disclosure provides a compound or pharmaceutically acceptable salts or stereoisomers thereof of formula VII-2, VII-3 or VII-4, VII-5, VII-6 VII-7, VII-8 or VII-9
VII-2
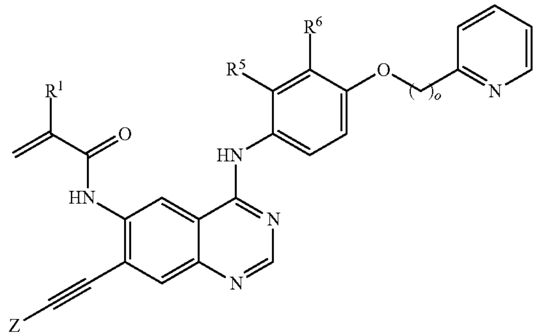
VII-3
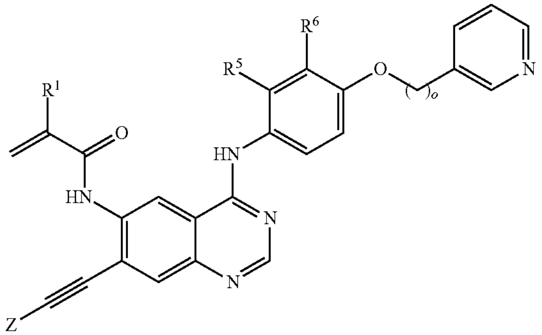
VII-4
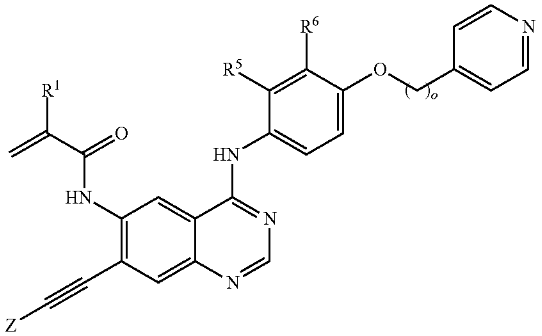
-continued
VII-5
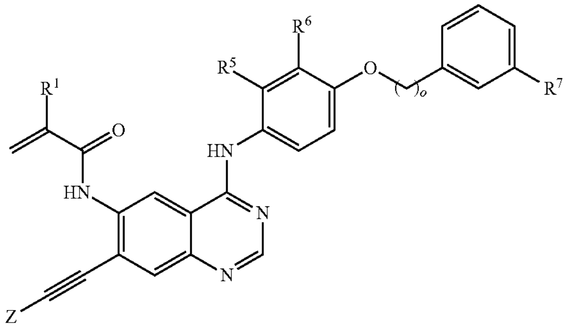
VII-6
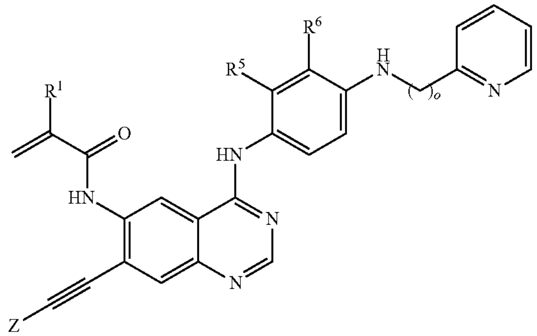
VII-7
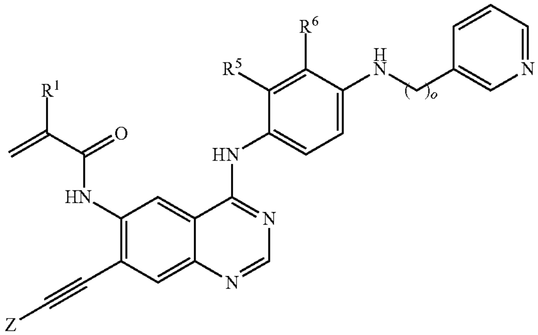
VII-8
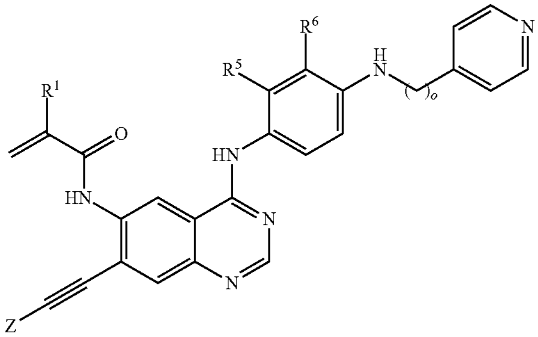

-continued

VII-9

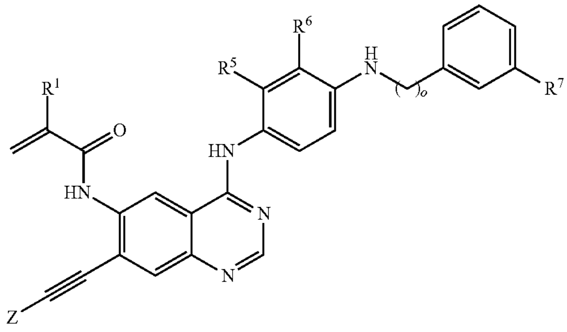

wherein $R^1$ is H or F, preferably H;

is 0 or 1;

$R^5$, $R^6$ are independently of each other hydrogen, $—CF_3$ or halogen, preferably F or Cl;

$R^7$ is hydrogen or halogen, preferably F;

Z is selected from

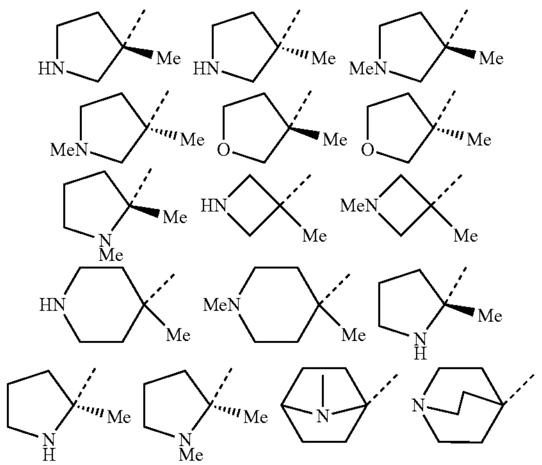

In some embodiments of a compound of formula VII-1, VII-2, VII-3 or VII-4, VII-5, VII-6 VII-7, VII-8 or VII-9, $R^4$ is hydrogen, fluoro or chloro.

In some embodiments of a compound of formula VII-1, VII-2, VII-3 or VII-4, VII-5, VII-6 VII-7, VII-8 or VII-9, o is 1.

In some embodiments of a compound of formula VII-1, VII-2, VII-3 or VII-4, VII-5, VII-6 VII-7, VII-8 or VII-9, $R^5$ is F and/or wherein $R^6$ is F or Cl.

In some embodiments of a compound of formula VII-1, VII-2, VII-3 or VII-4, VII-5, VII-6 VII-7, VII-8 or VII-9, $R^7$ is F.

In some embodiments of a compound of formula VII-1, VII-2, VII-3 or VII-4, VII-5, VII-6 VII-7, VII-8 or VII-9, $R^1$ may be hydrogen.

In some embodiments, the compound is selected from the compounds described in Tables 1 and 2, pharmaceutically acceptable salts thereof, and stereoisomers thereof.

In some embodiments, the compound is selected from the compounds described in Tables 1 and 2 and pharmaceutically acceptable salts thereof.

In some embodiments, the compound is selected from the compounds described in Tables 1 and 2.

In some embodiments, the compound is selected from the compounds described in Table 1, pharmaceutically acceptable salts thereof, and stereoisomers thereof.

In some embodiments, the compound is selected from the compounds described in Table 1 and pharmaceutically acceptable salts thereof.

In some embodiments, the compound is selected from the compounds described in Table 1.

In some embodiments, the compound is selected from the compounds described in Table 2, pharmaceutically acceptable salts thereof, and stereoisomers thereof.

In some embodiments, the compound is selected from the compounds described in Table 2 and pharmaceutically acceptable salts thereof.

In some embodiments, the compound is selected from the compounds described in Table 2.

TABLE 1

| Compound No. | Structure |
|---|---|
| 1 | 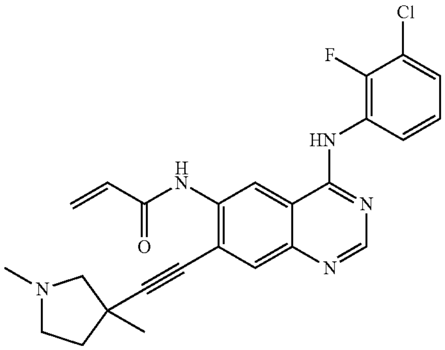 |
| 2 | 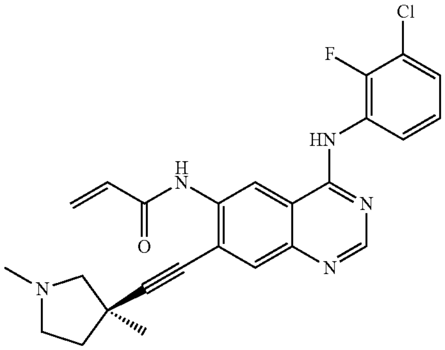 [SMILES: C=CC(=O)Nc1cc2c(Nc3cccc(Cl)c3F)ncnc2cc1C#C[C@@]1(C)CCN(C)C1] |
| 3 | 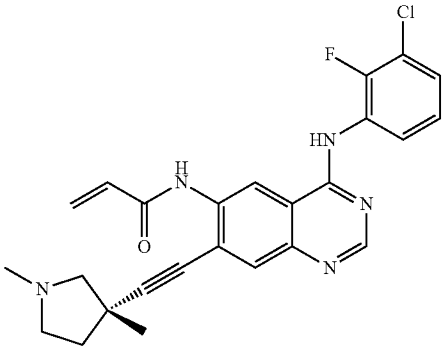 [SMILES: C=CC(=O)Nc1cc2c(Nc3cccc(Cl)c3F)ncnc2cc1C#C[C@]1(C)CCN(C)C1] |

TABLE 1-continued
| Compound No. | Structure |
|---|---|
| 4 | 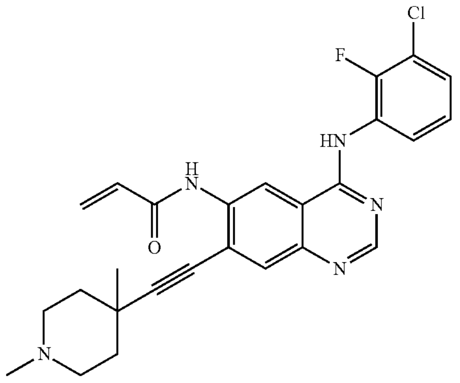 [SMILES: C=CC(=O)Nc1cc2c(Nc3cccc(Cl)c3F)ncnc2cc1C#CC1(C)CCN(C)CC1] |
| 5 | 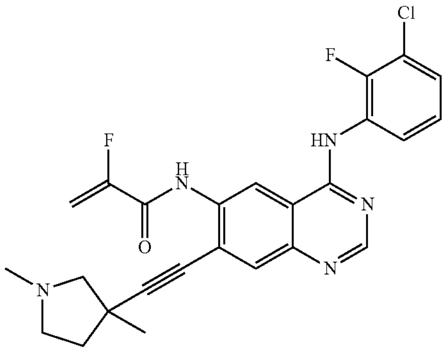 [SMILES: C=C(F)C(=O)Nc1cc2c(Nc3cccc(Cl)c3F)ncnc2cc1C#CC1(C)CCN(C)C1] |
| 6 | 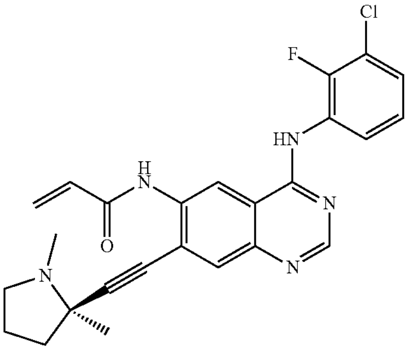 [SMILES: C=CC(=O)Nc1cc2c(Nc3cccc(Cl)c3F)ncnc2cc1C#C[C@@]1(C)CCCN1C] |
| 7 | 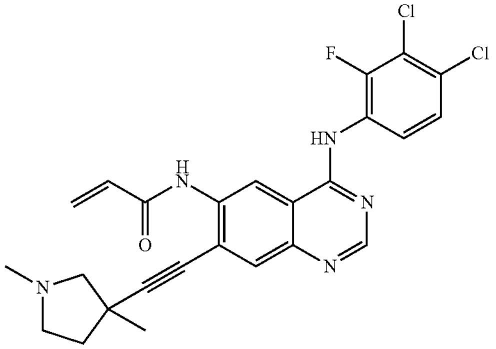 [SMILES: C=CC(=O)Nc1cc2c(Nc3ccc(Cl)c(Cl)c3F)ncnc2cc1C#CC1(C)CCN(C)C1] |
| 8 | 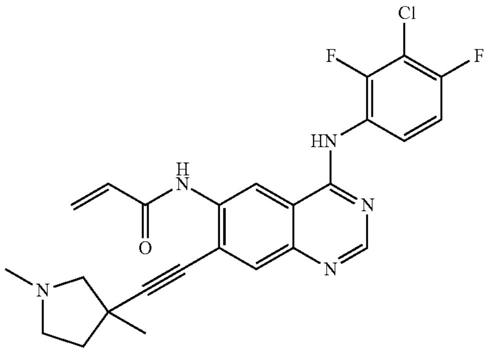 [SMILES: C=CC(=O)Nc1cc2c(Nc3ccc(F)c(Cl)c3F)ncnc2cc1C#CC1(C)CCN(C)C1] |
| 10 | 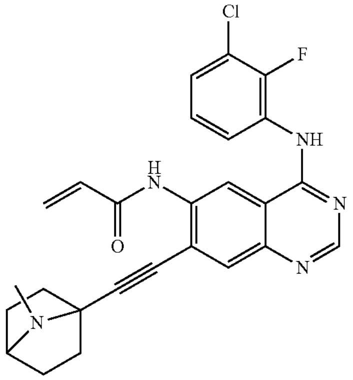 [SMILES: C=CC(=O)Nc1cc2c(Nc3cccc(Cl)c3F)ncnc2cc1C#CC12CCC(CC1)N2C] |
| 11 | 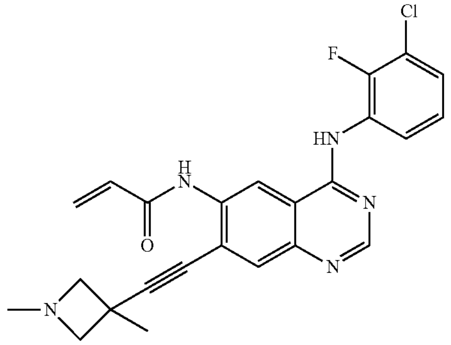 [SMILES: C=CC(=O)Nc1cc2c(Nc3cccc(Cl)c3F)ncnc2cc1C#CC1(C)CN(C)C1] |
| 12 | 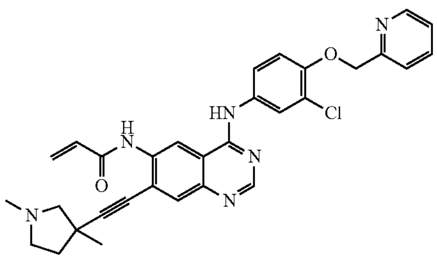 [SMILES: C=CC(=O)Nc1cc2c(Nc3ccc(OCc4ccccn4)c(Cl)c3)ncnc2cc1C#CC1(C)CCN(C)C1] |

TABLE 1-continued
| Compound No. | Structure |
| --- | --- |
| 13 | 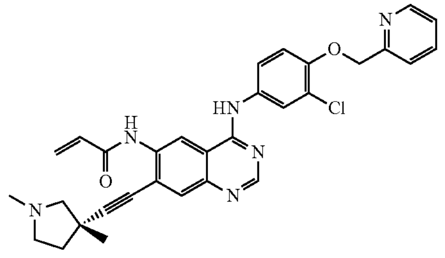 [SMILES: C=CC(=O)Nc1cc2c(Nc3ccc(OCc4ccccn4)c(Cl)c3)ncnc2cc1C#C[C@]1(C)CCN(C)C1] |
| 14 | 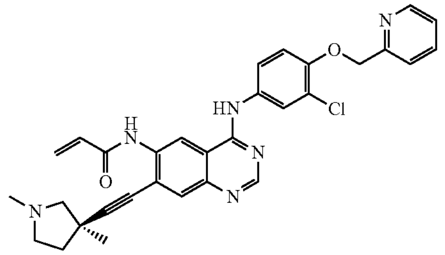 [SMILES: C=CC(=O)Nc1cc2c(Nc3ccc(OCc4ccccn4)c(Cl)c3)ncnc2cc1C#C[C@@]1(C)CCN(C)C1] |
| 16 | 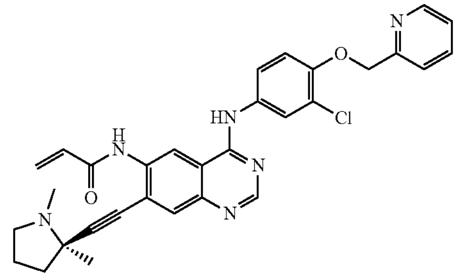 [SMILES: C=CC(=O)Nc1cc2c(Nc3ccc(OCc4ccccn4)c(Cl)c3)ncnc2cc1C#C[C@@]1(C)CCCN1C] |
| 17 | 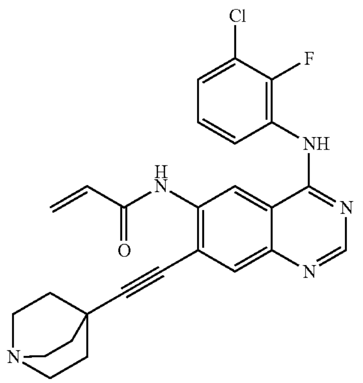 [SMILES: C=CC(=O)Nc1cc2c(Nc3cccc(Cl)c3F)ncnc2cc1C#CC12CCN(CC1)CC2] |
TABLE 2
| Compound No. | Structure |
| --- | --- |
| 18 | 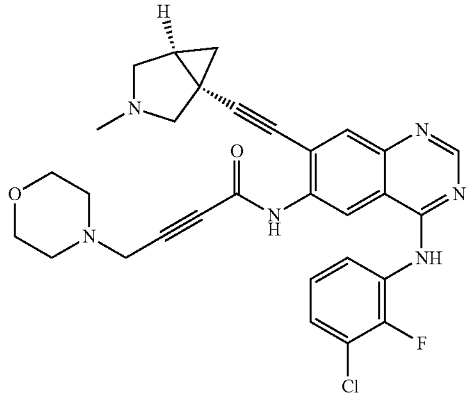 [SMILES: CN1C[C@H]2C[C@@]2(C#Cc2cc3ncnc(Nc4cccc(Cl)c4F)c3cc2NC(=O)C#CCN2CCOCC2)C1] |
| 19 | 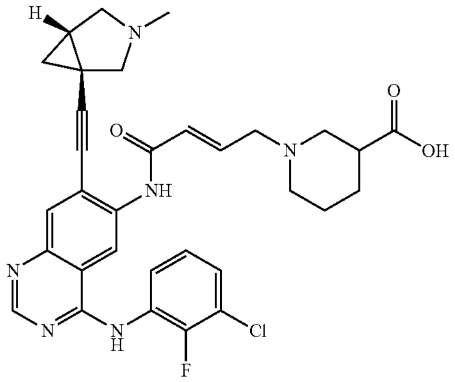 [SMILES: CN1C[C@H]2C[C@@]2(C#Cc2cc3ncnc(Nc4cccc(Cl)c4F)c3cc2NC(=O)/C=C/CN2CCCC(C(=O)O)C2)C1] |
| 20 | 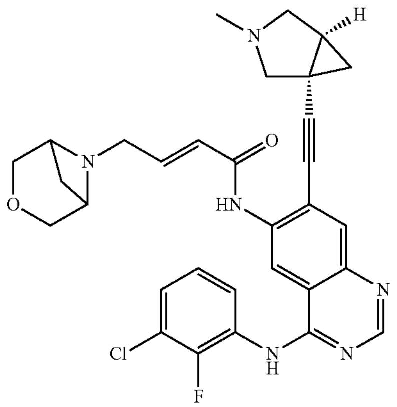 [SMILES: CN1C[C@H]2C[C@@]2(C#Cc2cc3ncnc(Nc4cccc(Cl)c4F)c3cc2NC(=O)/C=C/CN2C3COCC2C3)C1] |

TABLE 2-continued
| Compound No. | Structure |
|---|---|
| 21 | 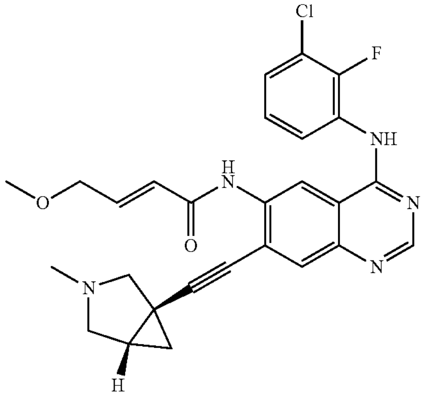 [SMILES: COC/C=C/C(=O)Nc1cc2c(Nc3cccc(Cl)c3F)ncnc2cc1C#C[C@@]12C[C@@H]1CN(C)C2] |
| 22 | 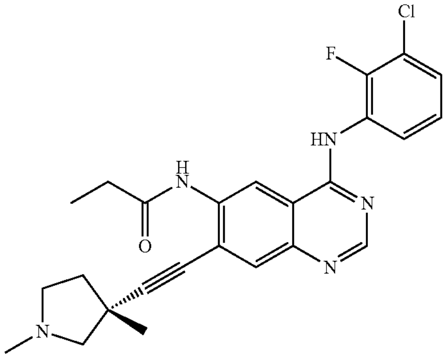 [SMILES: CCC(=O)Nc1cc2c(Nc3cccc(Cl)c3F)ncnc2cc1C#C[C@@]1(C)CCN(C)C1] |
| 23 | 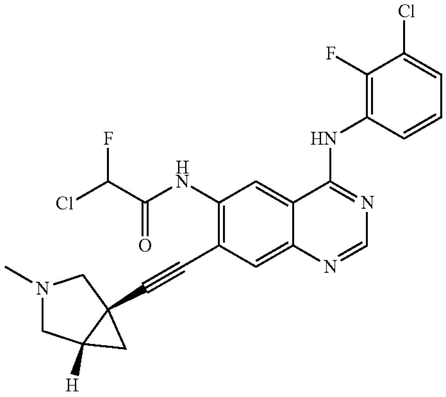 [SMILES: CN1C[C@H]2C[C@@]2(C#Cc2cc3ncnc(Nc4cccc(Cl)c4F)c3cc2NC(=O)C(F)Cl)C1] |
| 24 | 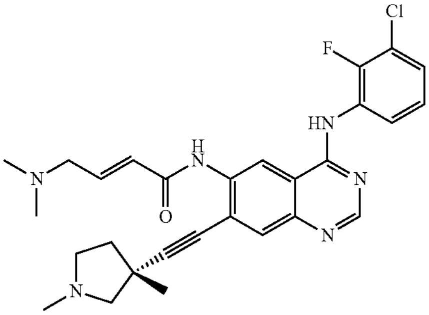 [SMILES: CN(C)C/C=C/C(=O)Nc1cc2c(Nc3cccc(Cl)c3F)ncnc2cc1C#C[C@@]1(C)CCN(C)C1] |
TABLE 2-continued
| Compound No. | Structure |
|---|---|
| 25 | 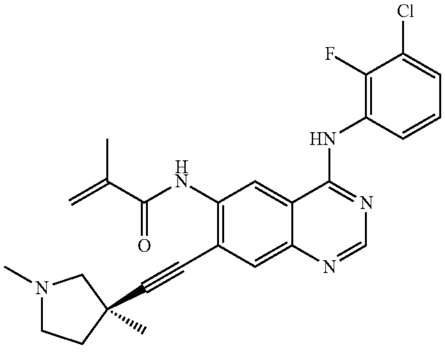 [SMILES: C=C(C)C(=O)Nc1cc2c(Nc3cccc(Cl)c3F)ncnc2cc1C#C[C@@]1(C)CCN(C)C1] |
| 26 | 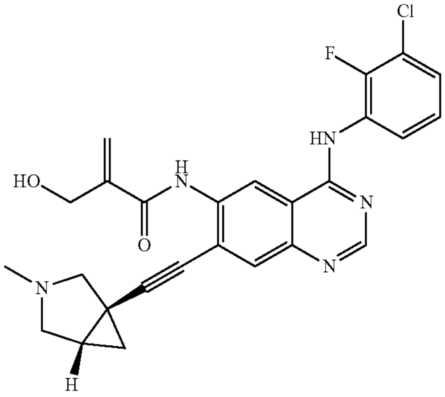 [SMILES: C=C(CO)C(=O)Nc1cc2c(Nc3cccc(Cl)c3F)ncnc2cc1C#C[C@@]12C[C@@H]1CN(C)C2] |
| 27 | 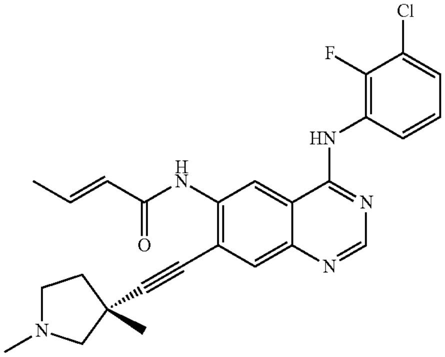 [SMILES: C/C=C/C(=O)Nc1cc2c(Nc3cccc(Cl)c3F)ncnc2cc1C#C[C@@]1(C)CCN(C)C1] |
| 28 | 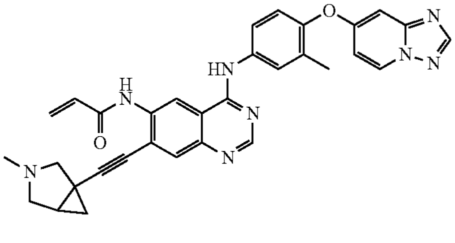 [SMILES: C=CC(=O)Nc1cc2c(Nc3ccc(Oc4ccn5ncnc5c4)c(C)c3)ncnc2cc1C#CC12CC1CN(C)C2] |

TABLE 2-continued
| Compound No. | Structure |
| --- | --- |
| 29 | 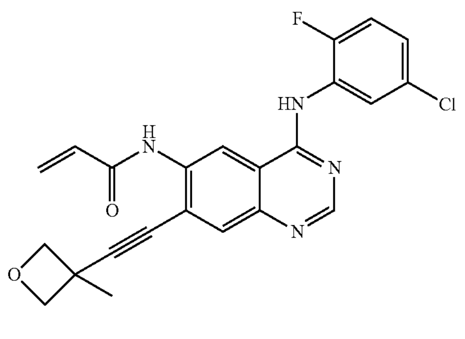 [SMILES: C=CC(=O)Nc1cc2c(Nc3cc(Cl)ccc3F)ncnc2cc1C#CC1(C)COC1] |
| 30 | 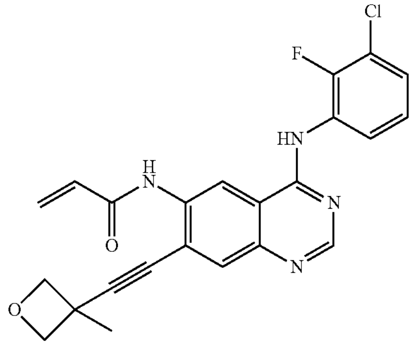 [SMILES: C=CC(=O)Nc1cc2c(Nc3cccc(Cl)c3F)ncnc2cc1C#CC1(C)COC1] |
| 31 | 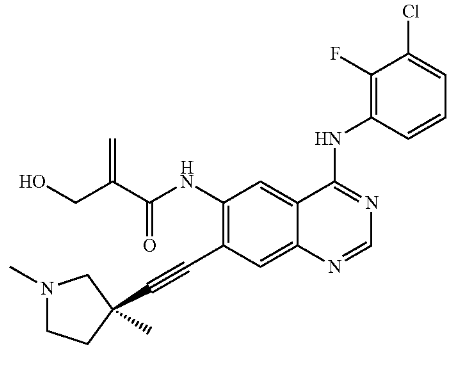 [SMILES: C=C(CO)C(=O)Nc1cc2c(Nc3cccc(Cl)c3F)ncnc2cc1C#C[C@@]1(C)CCN(C)C1] |
| 32 | 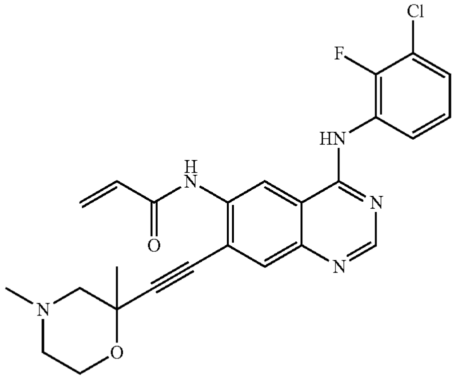 [SMILES: C=CC(=O)Nc1cc2c(Nc3cccc(Cl)c3F)ncnc2cc1C#CC1(C)CN(C)CCO1] |
| 33 | 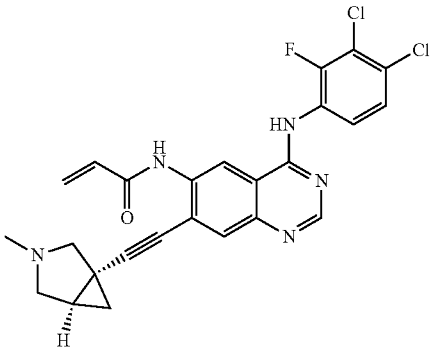 [SMILES: C=CC(=O)Nc1cc2c(Nc3ccc(Cl)c(Cl)c3F)ncnc2cc1C#C[C@]12C[C@H]1CN(C)C2] |
| 34 | 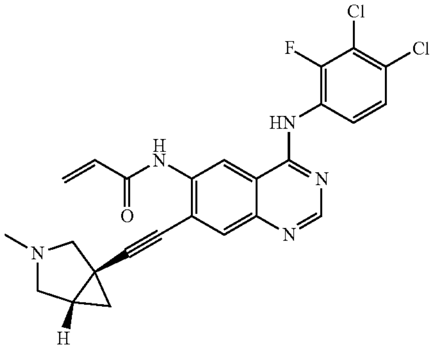 [SMILES: C=CC(=O)Nc1cc2c(Nc3ccc(Cl)c(Cl)c3F)ncnc2cc1C#C[C@@]12C[C@@H]1CN(C)C2] |
| 35 | 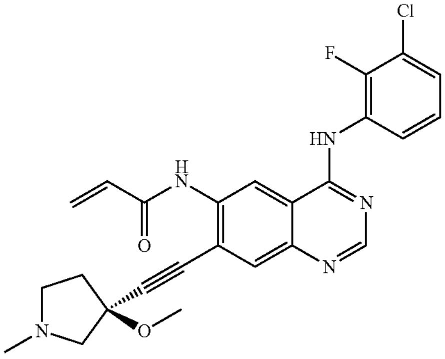 [SMILES: C=CC(=O)Nc1cc2c(Nc3cccc(Cl)c3F)ncnc2cc1C#C[C@@]1(OC)CCN(C)C1] |
| 36 | 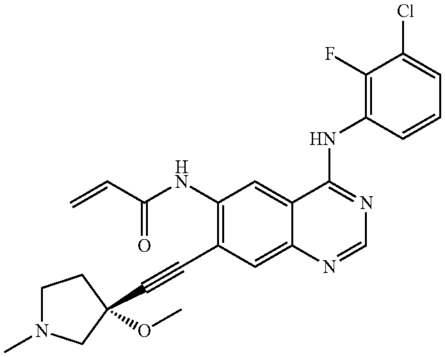 [SMILES: C=CC(=O)Nc1cc2c(Nc3cccc(Cl)c3F)ncnc2cc1C#C[C@]1(OC)CCN(C)C1] |

TABLE 2-continued
| Compound No. | Structure |
|---|---|
| 37 | 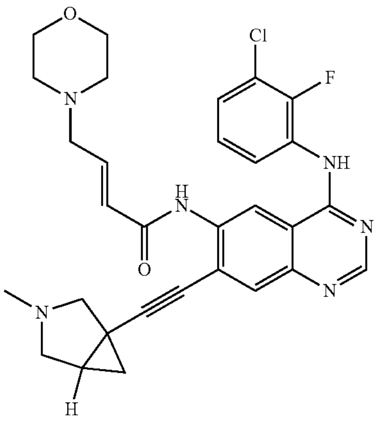 [SMILES: CN1CC2CC2(C#Cc2cc3ncnc(Nc4cccc(Cl)c4F)c3cc2NC(=O)/C=C/CN2CCOCC2)C1] |
| 37A | 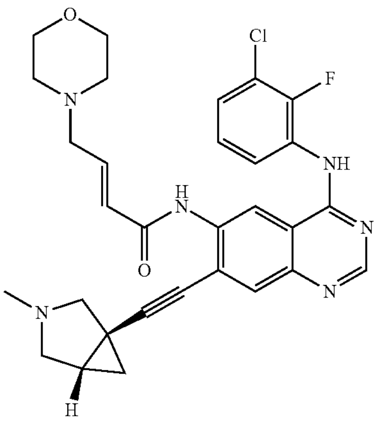 [SMILES: CN1C[C@H]2C[C@@]2(C#Cc2cc3ncnc(Nc4cccc(Cl)c4F)c3cc2NC(=O)/C=C/CN2CCOCC2)C1] |
| 37B | 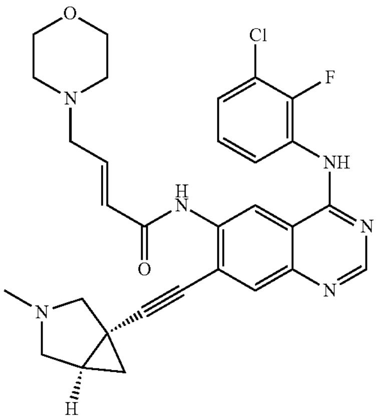 [SMILES: CN1C[C@@H]2C[C@]2(C#Cc2cc3ncnc(Nc4cccc(Cl)c4F)c3cc2NC(=O)/C=C/CN2CCOCC2)C1] |
TABLE 2-continued
| Compound No. | Structure |
|---|---|
| 38 | 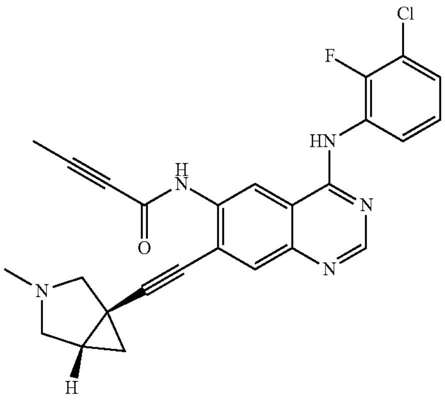 [SMILES: CC#CC(=O)Nc1cc2c(Nc3cccc(Cl)c3F)ncnc2cc1C#C[C@@]12C[C@@H]1CN(C)C2] |
| 39 | 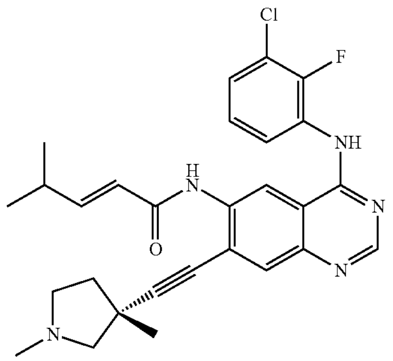 [SMILES: CC(C)/C=C/C(=O)Nc1cc2c(Nc3cccc(Cl)c3F)ncnc2cc1C#C[C@@]1(C)CCN(C)C1] |
| 40 | 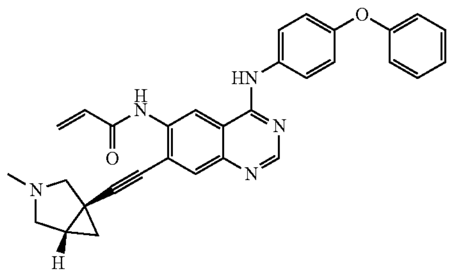 [SMILES: C=CC(=O)Nc1cc2c(Nc3ccc(Oc4ccccc4)cc3)ncnc2cc1C#C[C@@]12C[C@@H]1CN(C)C2] |
| 41 | 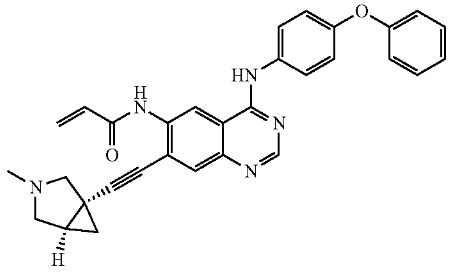 [SMILES: C=CC(=O)Nc1cc2c(Nc3ccc(Oc4ccccc4)cc3)ncnc2cc1C#C[C@]12C[C@H]1CN(C)C2] |

TABLE 2-continued
| Compound No. | Structure |
|---|---|
| 42 | 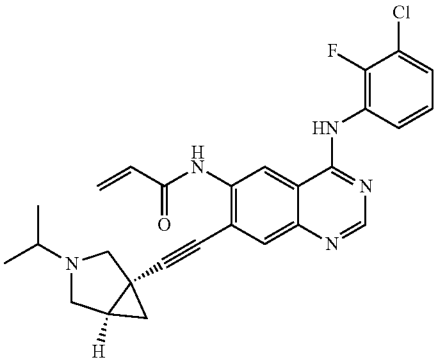 [SMILES: C=CC(=O)Nc1cc2c(Nc3cccc(Cl)c3F)ncnc2cc1C#C[C@]12C[C@H]1CN(C(C)C)C2] |
| 43 | 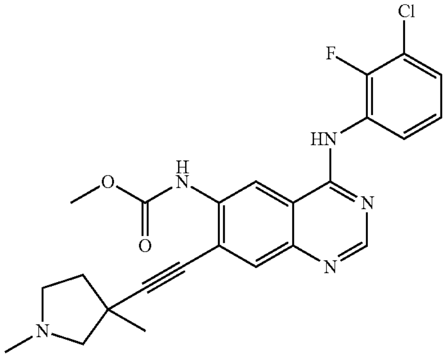 [SMILES: COC(=O)Nc1cc2c(Nc3cccc(Cl)c3F)ncnc2cc1C#CC1(C)CCN(C)C1] |
| 44 | 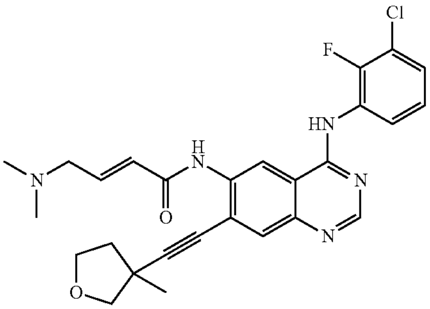 [SMILES: CN(C)C/C=C/C(=O)Nc1cc2c(Nc3cccc(Cl)c3F)ncnc2cc1C#CC1(C)CCOC1] |
| 45 | 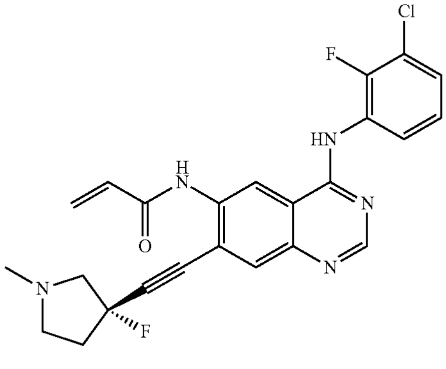 |
| 46 | 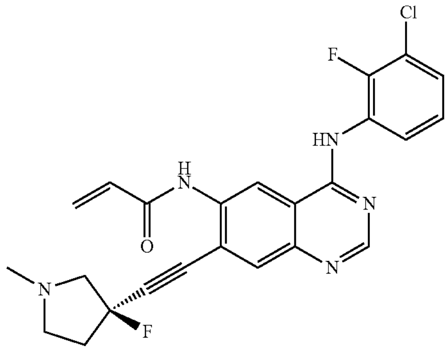 [SMILES: C=CC(=O)Nc1cc2c(Nc3cccc(Cl)c3F)ncnc2cc1C#C[C@]1(F)CCN(C)C1] |
| 47 | 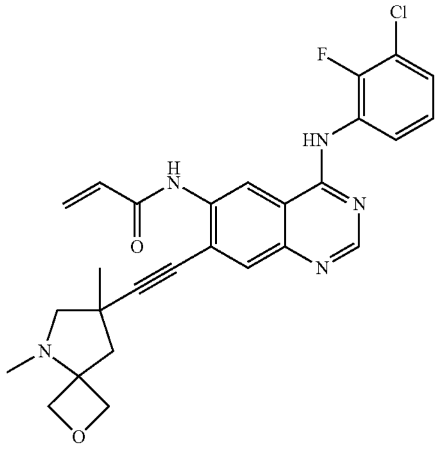 [SMILES: C=CC(=O)Nc1cc2c(Nc3cccc(Cl)c3F)ncnc2cc1C#CC1(C)CN(C)C2(COC2)C1] |
| 48 | 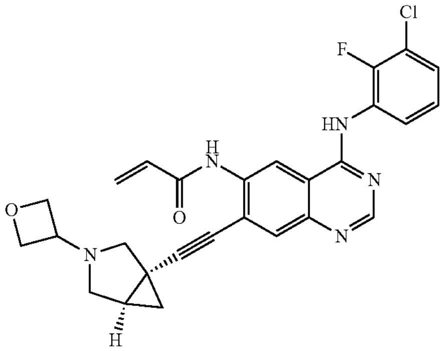 [SMILES: C=CC(=O)Nc1cc2c(Nc3cccc(Cl)c3F)ncnc2cc1C#C[C@]12C[C@H]1CN(C1COC1)C2] |
| 49 | 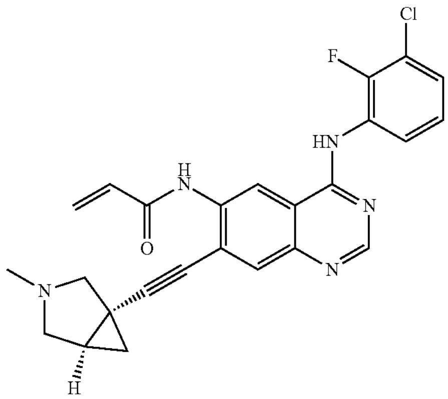 [SMILES: C=CC(=O)Nc1cc2c(Nc3cccc(Cl)c3F)ncnc2cc1C#C[C@]12C[C@H]1CN(C)C2] |

TABLE 2-continued
| Compound No. | Structure |
| --- | --- |
| 50 | 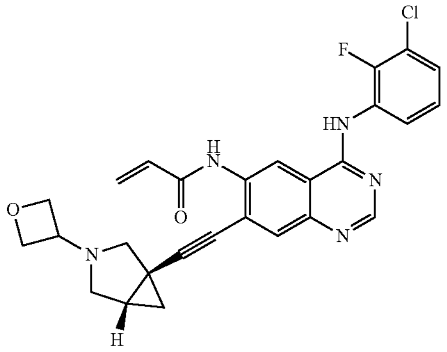 [SMILES: C=CC(=O)Nc1cc2c(Nc3cccc(Cl)c3F)ncnc2cc1C#C[C@@]12C[C@@H]1CN(C1COC1)C2] |
| 51 | 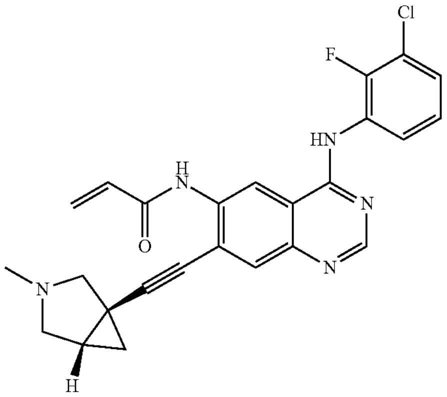 [SMILES: C=CC(=O)Nc1cc2c(Nc3cccc(Cl)c3F)ncnc2cc1C#C[C@@]12C[C@@H]1CN(C)C2] |
| 52 | 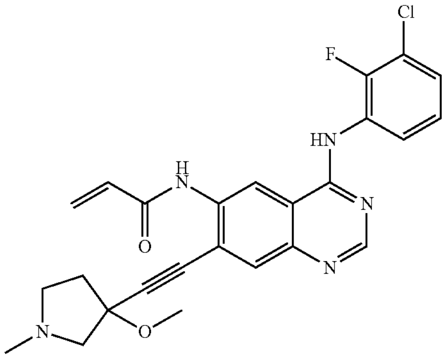 [SMILES: C=CC(=O)Nc1cc2c(Nc3cccc(Cl)c3F)ncnc2cc1C#CC1(OC)CCN(C)C1] |
| 53 | 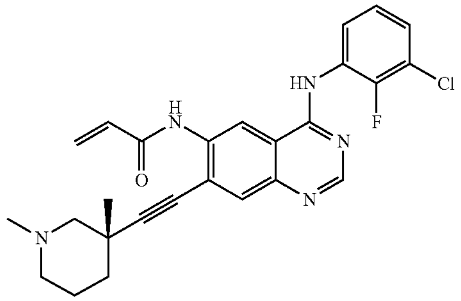 [SMILES: C=CC(=O)Nc1cc2c(Nc3cccc(Cl)c3F)ncnc2cc1C#C[C@]1(C)CCCN(C)C1] |
TABLE 2-continued
| Compound No. | Structure |
| --- | --- |
| 54 | 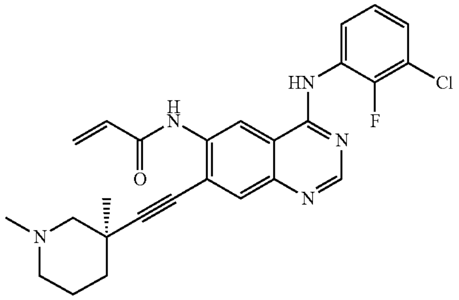 [SMILES: C=CC(=O)Nc1cc2c(Nc3cccc(Cl)c3F)ncnc2cc1C#C[C@@]1(C)CCCN(C)C1] |
| 55 | 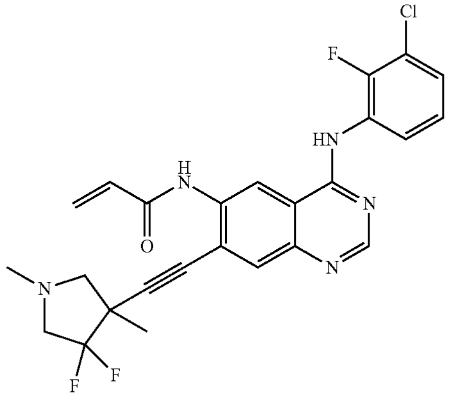 [SMILES: C=CC(=O)Nc1cc2c(Nc3cccc(Cl)c3F)ncnc2cc1C#CC1(C)CN(C)CC1(F)F] |
| 56 | 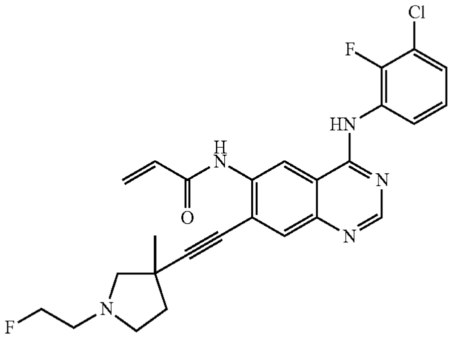 [SMILES: C=CC(=O)Nc1cc2c(Nc3cccc(Cl)c3F)ncnc2cc1C#CC1(C)CCN(CCF)C1] |
| 57 | 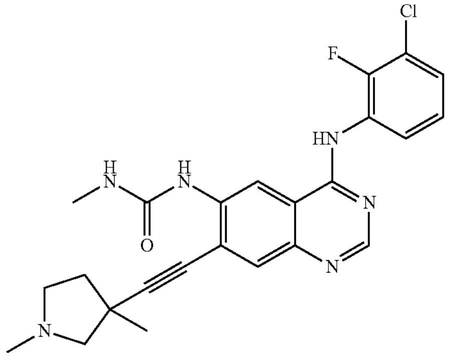 [SMILES: CNC(=O)Nc1cc2c(Nc3cccc(Cl)c3F)ncnc2cc1C#CC1(C)CCN(C)C1] |

TABLE 2-continued
| Compound No. | Structure |
|---|---|
| 58 | 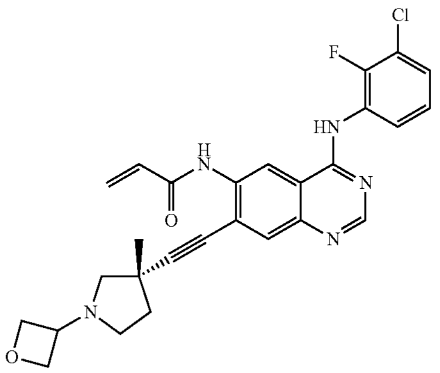 [SMILES: C=CC(=O)Nc1cc2c(Nc3cccc(Cl)c3F)ncnc2cc1C#C[C@]1(C)CCN(C2COC2)C1] |
| 59 | 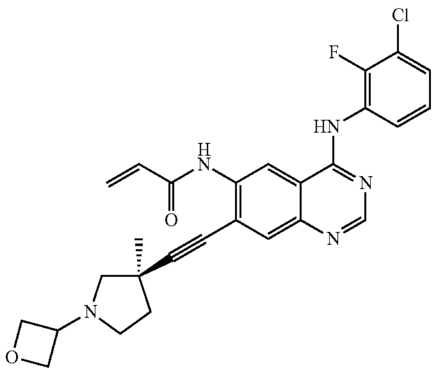 [SMILES: C=CC(=O)Nc1cc2c(Nc3cccc(Cl)c3F)ncnc2cc1C#C[C@@]1(C)CCN(C2COC2)C1] |
| 60 | 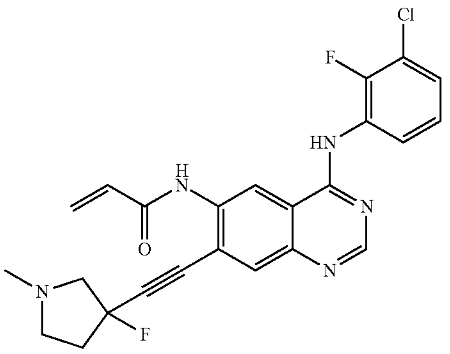 [SMILES: C=CC(=O)Nc1cc2c(Nc3cccc(Cl)c3F)ncnc2cc1C#CC1(F)CCN(C)C1] |
| 61 | 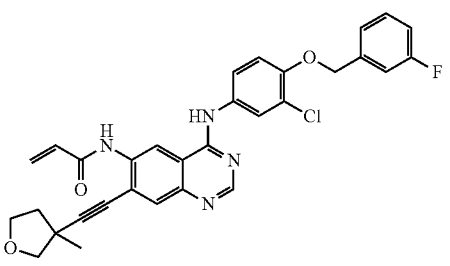 [SMILES: C=CC(=O)Nc1cc2c(Nc3ccc(OCc4cccc(F)c4)c(Cl)c3)ncnc2cc1C#CC1(C)CCOC1] |
TABLE 2-continued
| Compound No. | Structure |
|---|---|
| 62 | 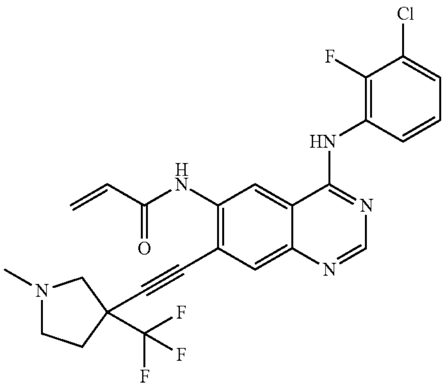 [SMILES: C=CC(=O)Nc1cc2c(Nc3cccc(Cl)c3F)ncnc2cc1C#CC1(C(F)(F)F)CCN(C)C1] |
| 63 | 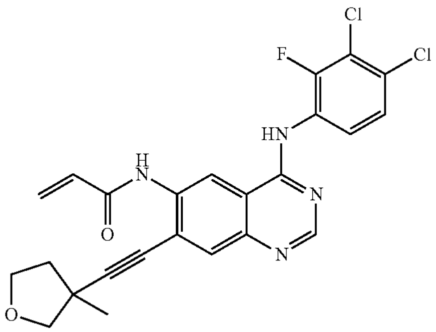 [SMILES: C=CC(=O)Nc1cc2c(Nc3ccc(Cl)c(Cl)c3F)ncnc2cc1C#CC1(C)CCOC1] |
| 64 | 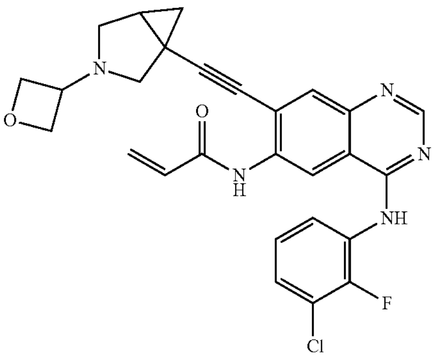 [SMILES: C=CC(=O)Nc1cc2c(Nc3cccc(Cl)c3F)ncnc2cc1C#CC12CC1CN(C1COC1)C2] |
| 65 | 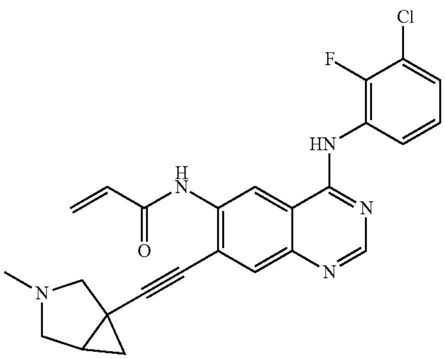 [SMILES: C=CC(=O)Nc1cc2c(Nc3cccc(Cl)c3F)ncnc2cc1C#CC12CC1CN(C)C2] |

TABLE 2-continued
| Compound No. | Structure |
|---|---|
| 66 | 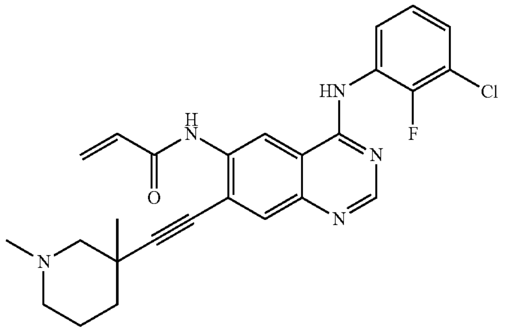 [SMILES: C=CC(=O)Nc1cc2c(Nc3cccc(Cl)c3F)ncnc2cc1C#CC1(C)CCCN(C)C1] |
| 67 | 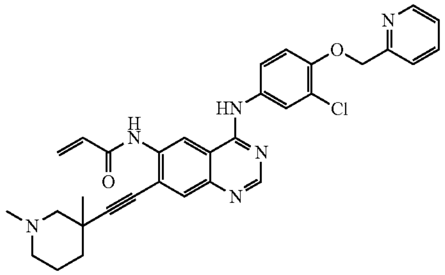 [SMILES: C=CC(=O)Nc1cc2c(Nc3ccc(OCc4ccccn4)c(Cl)c3)ncnc2cc1C#CC1(C)CCCN(C)C1] |
| 68 | 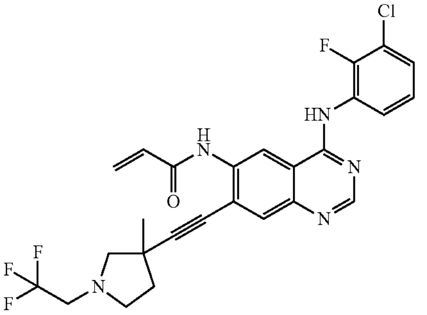 [SMILES: C=CC(=O)Nc1cc2c(Nc3cccc(Cl)c3F)ncnc2cc1C#CC1(C)CCN(CC(F)(F)F)C1] |
| 69 | 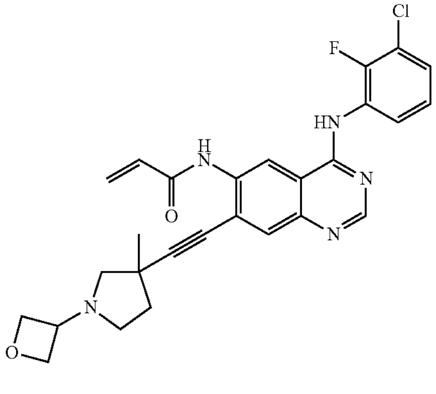 [SMILES: C=CC(=O)Nc1cc2c(Nc3cccc(Cl)c3F)ncnc2cc1C#CC1(C)CCN(C2COC2)C1] |
TABLE 2-continued
| Compound No. | Structure |
|---|---|
| 70 | 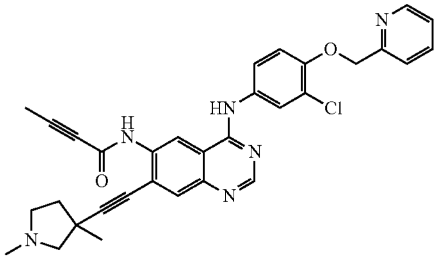 [SMILES: CC#CC(=O)Nc1cc2c(Nc3ccc(OCc4ccccn4)c(Cl)c3)ncnc2cc1C#CC1(C)CCN(C)C1] |
| 71 | 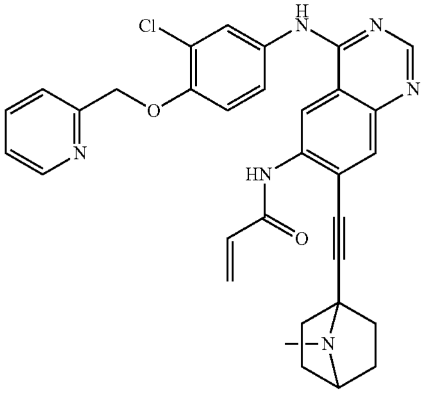 [SMILES: C=CC(=O)Nc1cc2c(Nc3ccc(OCc4ccccn4)c(Cl)c3)ncnc2cc1C#CC12CCC(CC1)N2C] |
| 72 | 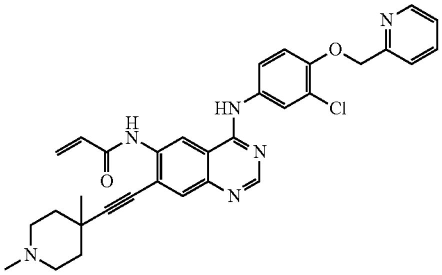 [SMILES: C=CC(=O)Nc1cc2c(Nc3ccc(OCc4ccccn4)c(Cl)c3)ncnc2cc1C#CC1(C)CCN(C)CC1] |
| 73 | 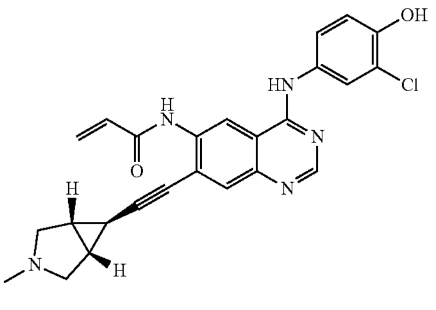 [SMILES: C=CC(=O)Nc1cc2c(Nc3ccc(O)c(Cl)c3)ncnc2cc1C#C[C@@H]1[C@H]2CN(C)C[C@@H]12] |

TABLE 2-continued
| Compound No. | Structure |
|---|---|
| 74 | 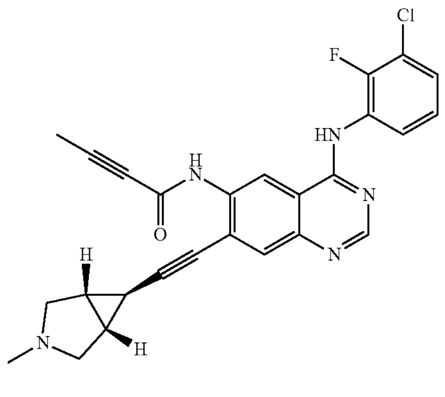 [SMILES: CC#CC(=O)Nc1cc2c(Nc3cccc(Cl)c3F)ncnc2cc1C#C[C@@H]1[C@H]2CN(C)C[C@@H]12] |
| 75 | 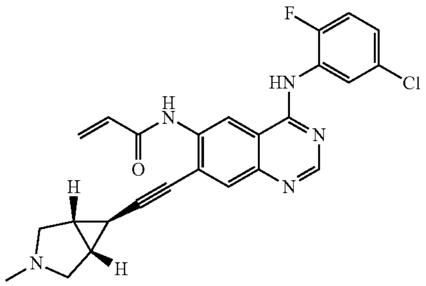 [SMILES: C=CC(=O)Nc1cc2c(Nc3cc(Cl)ccc3F)ncnc2cc1C#C[C@@H]1[C@H]2CN(C)C[C@@H]12] |
| 76 | 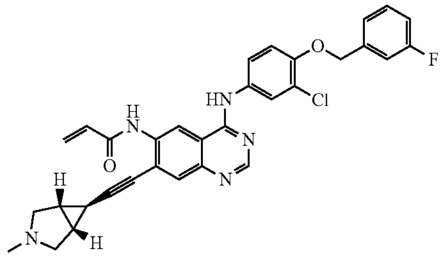 [SMILES: C=CC(=O)Nc1cc2c(Nc3ccc(OCc4cccc(F)c4)c(Cl)c3)ncnc2cc1C#C[C@@H]1[C@H]2CN(C)C[C@@H]12] |
| 77 | 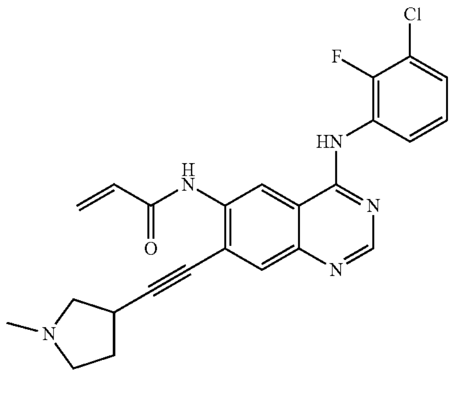 [SMILES: C=CC(=O)Nc1cc2c(Nc3cccc(Cl)c3F)ncnc2cc1C#CC1CCN(C)C1] |
TABLE 2-continued
| Compound No. | Structure |
|---|---|
| 78 | 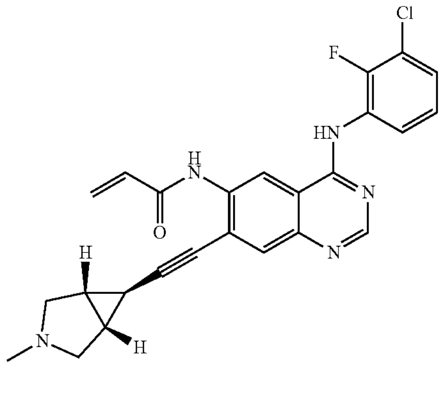 [SMILES: C=CC(=O)Nc1cc2c(Nc3cccc(Cl)c3F)ncnc2cc1C#C[C@@H]1[C@H]2CN(C)C[C@@H]12] |
| 79 | 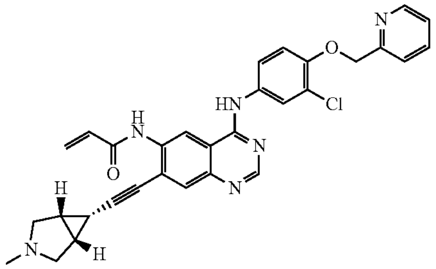 [SMILES: C=CC(=O)Nc1cc2c(Nc3ccc(OCc4ccccn4)c(Cl)c3)ncnc2cc1C#C[C@H]1[C@H]2CN(C)C[C@@H]12] |
| 80 | 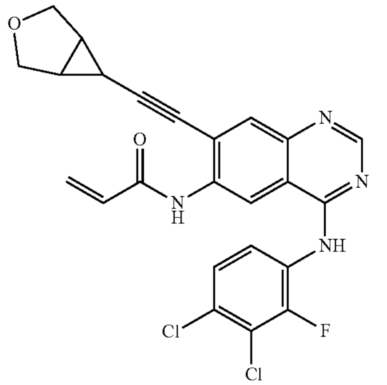 [SMILES: C=CC(=O)Nc1cc2c(Nc3ccc(Cl)c(Cl)c3F)ncnc2cc1C#CC1C2COCC12] |
| 81 | 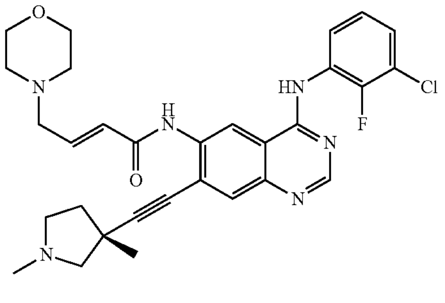 [SMILES: CN1CC[C@](C)(C#Cc2cc3ncnc(Nc4cccc(Cl)c4F)c3cc2NC(=O)/C=C/CN2CCOCC2)C1] |

TABLE 2-continued

| Compound No. | Structure |
|---|---|
| 82 | 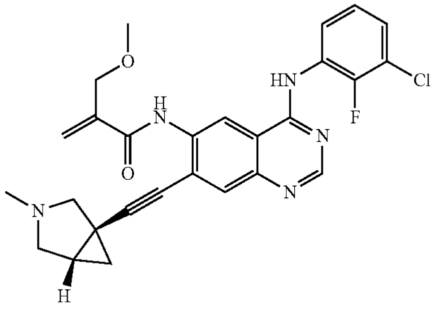 [SMILES: C=C(COC)C(=O)Nc1cc2c(Nc3cccc(Cl)c3F)ncnc2cc1C#C[C@@]12C[C@@H]1CN(C)C2] |
| 83 | 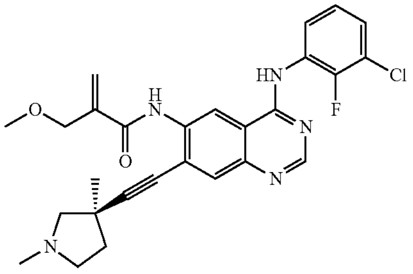 [SMILES: C=C(COC)C(=O)Nc1cc2c(Nc3cccc(Cl)c3F)ncnc2cc1C#C[C@@]1(C)CCN(C)C1] |
| 84 | 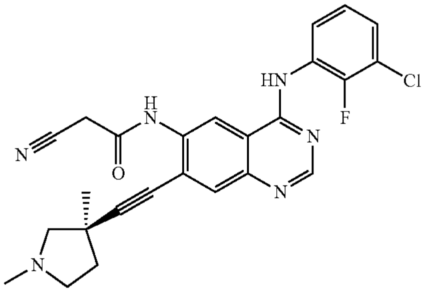 [SMILES: CN1CC[C@](C)(C#Cc2cc3ncnc(Nc4cccc(Cl)c4F)c3cc2NC(=O)CC#N)C1] |

In some aspects, the present disclosure provides a compound being an isotopic derivative (e.g., isotopically labeled compound) of any one of the compounds of the Formulae disclosed herein.

In some embodiments, the compound is an isotopic derivative of any one of the compounds described in Tables 1 and 2, pharmaceutically acceptable salts thereof, and stereoisomers thereof.

In some embodiments, the compound is an isotopic derivative of any one of the compounds described in Tables 1 and 2 and pharmaceutically acceptable salts thereof.

In some embodiments, the compound is an isotopic derivative of any one of the compounds described in Tables 1 and 2.

It is understood that the isotopic derivative can be prepared using any of a variety of art-recognised techniques. For example, the isotopic derivative can generally be prepared by carrying out the procedures disclosed in the Schemes and/or in the Examples described herein, by substituting an isotopically labeled reagent for a non-isotopically labeled reagent.

In some embodiments, the isotopic derivative is a deuterium labeled compound.

In some embodiments, the isotopic derivative is a deuterium labeled compound of any one of the compounds of the Formulae disclosed herein.

In some embodiments, the compound is a deuterium labeled compound of any one of the compounds described in Tables 1 and 2, pharmaceutically acceptable salts thereof, and stereoisomers thereof.

In some embodiments, the compound is a deuterium labeled compound of any one of the compounds described in Tables 1 and 2 and pharmaceutically acceptable salts thereof.

In some embodiments, the compound is a deuterium labeled compound of any one of the compounds described in Tables 1 and 2.

In some embodiments, the compound is selected from the compound described Table 3, pharmaceutically acceptable salts thereof, and stereoisomers thereof.

In some embodiments, the compound is selected from the compound described Table 3 and pharmaceutically acceptable salts thereof.

In some embodiments, the compound is the compound described Table 3.

TABLE 3

| Compound No. | Structure |
|---|---|
| D-1 | 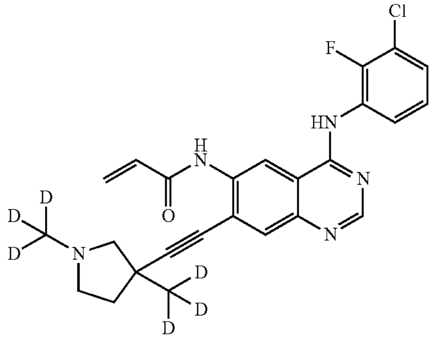 [SMILES: [2H]C([2H])([2H])N1CCC(C#Cc2cc3ncnc(Nc4cccc(Cl)c4F)c3cc2NC(=O)C=C)(C([2H])([2H])[2H])C1] |

It is understood that the deuterium labeled compound comprises a deuterium atom having an abundance of deuterium that is substantially greater than the natural abundance of deuterium, which is 0.015%.

In some embodiments, the deuterium labeled compound has a deuterium enrichment factor for each deuterium atom of at least 3500 (52.5% deuterium incorporation at each deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). As used herein, the term "deuterium enrichment factor" means the ratio between the deuterium abundance and the natural abundance of a deuterium.

It is understood that the deuterium labeled compound can be prepared using any of a variety of art-recognised techniques. For example, the deuterium labeled compound can generally be prepared by carrying out the procedures disclosed in the Schemes and/or in the Examples described herein, by substituting a deuterium labeled reagent for a non-deuterium labeled reagent.

A compound of the invention or a pharmaceutically acceptable salt or solvate thereof that contains the aforementioned deuterium atom(s) is within the scope of the invention. Further, substitution with deuterium (i.e., $^{2}H$)

may afford certain therapeutic advantages resulting from greater metabolic stability, e.g., increased in vivo half-life or reduced dosage requirements.

The compounds of the disclosure can contain one or more asymmetric centers in the molecule. A compound without designation of the stereochemistry is to be understood to include all the optical isomers (e.g., diastereomers, enantiomers, etc) in pure or substantially pure form, as well as mixtures thereof (e.g. a racemic mixture, or an enantiomerically enriched mixture). It is well known in the art how to prepare such optically active forms (e.g. by resolution of the racemic form by recrystallization techniques, by synthesis from optically-active starting materials, by chiral synthesis, by chromatographic separation using a chiral stationary phase, and other methods).

The compounds can be isotopically-labeled compounds, for example, compounds including various isotopes of hydrogen, carbon, nitrogen, oxygen, phosphorous, fluorine, iodine, or chlorine. The disclosed compounds may exist in tautomeric forms and mixtures and separate individual tautomers are contemplated. In addition, some compounds may exhibit polymorphism.

The compounds of the disclosure include the free form as well as the pharmaceutically acceptable salts and stereoisomers thereof. The pharmaceutically acceptable salts include all the typical pharmaceutically acceptable salts. The pharmaceutically acceptable salts of the present compounds can be synthesized from the compounds of this disclosure which contain a basic or acidic moiety by conventional chemical methods, see e.g. Berge et al, "Pharmaceutical Salts," J. Pharm. ScL, 1977: 66:1-19.

For example, conventional pharmaceutically acceptable salts for a basic compound include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like. Conventional pharmaceutically acceptable salts for an acidic compound include those derived from inorganic bases include aluminum, ammonium, calcium, copper, ferric, ferrous, lithium, magnesium, manganic salts, manganous, potassium, sodium, zinc and the like. Salts derived from pharmaceutically acceptable organic bases include salts of primary, secondary and tertiary amines, substituted amines including naturally occurring substituted amines, cyclic amines and basic ion exchange resins, such as arginine, betaine caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

The compounds of the disclosure may exist in solid, i.e. crystalline or noncrystalline form (optionally as solvates) or liquid form. In the solid state, it may exist in, or as a mixture thereof. In crystalline solvates, solvent molecules are incorporated into the crystalline lattice during crystallization. The formation of solvates may include non-aqueous solvents such as, but not limited to, ethanol, isopropanol, DMSO, acetic acid, ethanolamine, or ethyl acetate, or aqueous solvents such as water (also called "hydrates"). It is common knowledge that crystalline forms (and solvates thereof) may exhibit polymorphism, i.e. exist in different crystalline structures known as "polymorphs", that have the same chemical composition but differ in packing, geometrical arrangement, and other descriptive properties of the crystalline solid state. Polymorphs, therefore, may have different physical properties such as shape, density, hardness, deformability, stability, and dissolution properties, and may display different melting points, IR spectra, and X-ray powder diffraction patterns, which may be used for identification. Such different polymorphs may be produced, for example, by changing or adjusting the reaction conditions or reagents, during preparation of the compound of the disclosure.

In some aspects, the disclosure also provides methods of preparation of the compounds of the disclosure. Typically they are prepared according to the syntheses shown in the experimental section.

It is to be understood that the synthetic processes of the disclosure can tolerate a wide variety of functional groups, therefore various substituted starting materials can be used. The processes generally provide the desired final compound at or near the end of the overall process, although it may be desirable in certain instances to further convert the compound to a pharmaceutically acceptable salt thereof.

It is to be understood that compounds of the present disclosure can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure,* 5th edition, John Wiley & Sons: New York, 2001; Greene, T. W., Wuts, P. G. M., *Protective Groups in Organic Synthesis,* 3rd edition, John Wiley & Sons: New York, 1999; R. Larock, *Comprehensive Organic Transformations*, VCH Publishers (1989); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), incorporated by reference herein, are useful and recognised reference textbooks of organic synthesis known to those in the art One of ordinary skill in the art will note that, during the reaction sequences and synthetic schemes described herein, the order of certain steps may be changed, such as the introduction and removal of protecting groups. One of ordinary skill in the art will recognise that certain groups may require protection from the reaction conditions via the use of protecting groups. Protecting groups may also be used to differentiate similar functional groups in molecules. A list of protecting groups and how to introduce and remove these groups can be found in Greene, T. W., Wuts, P. G. M., *Protective Groups in Organic Synthesis,* 3rd edition, John Wiley & Sons: New York, 1999.

Biological Assays

Compounds designed, selected and/or optimised by methods described herein, once produced, can be characterised using a variety of assays known to those skilled in the art to determine whether the compounds have biological activity. For example, the molecules can be characterised by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the molecules described herein for activity, using techniques known in the art. General methodologies for performing high-throughput screening are described, for example, in Devlin (1998) High Throughput Screening, Marcel Dekker; and U.S. Pat. No. 5,763,263. High-throughput assays can use one or more different assay techniques including, but not limited to, those described below.

Various in vitro or in vivo biological assays are may be suitable for detecting the effect of the compounds of the present disclosure. These in vitro or in vivo biological assays can include, but are not limited to, enzymatic activity assays, electrophoretic mobility shift assays, reporter gene assays, in vitro cell viability assays, and the assays described herein.

Pharmaceutical Compositions

In some aspects, the disclosure further provides a pharmaceutical composition comprising a therapeutically-effective amount of one or more of the compounds of the disclosure or pharmaceutically acceptable salt thereof and one or more pharmaceutically acceptable carriers and/or excipients (also referred to as diluents). The excipients are acceptable in the sense of being compatible with the other ingredients of the formulation and not deleterious to the recipient thereof (i.e., the patient). The term "therapeutically-effective amount" as used herein refers to the amount of a compound (as such or in form of a pharmaceutical composition) of the present disclosure which is effective for producing some desired therapeutic effect.

Pharmaceutical compositions may be in unit dose form containing a predetermined amount of a compound of the disclosure per unit dose. Such a unit may contain a therapeutically effective dose of a compound of the disclosure or salt thereof or a fraction of a therapeutically effective dose such that multiple unit dosage forms might be administered at a given time to achieve the desired therapeutically effective dose. Preferred unit dosage formulations are those containing a daily dose or sub-dose, or an appropriate fraction thereof, of a compound of the disclosure or salt thereof.

The compounds of the disclosure may be administered by any acceptable means in solid or liquid form, including (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) nasally; (9) pulmonary; or (10) intrathecally.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical compositions.

Such compositions may contain further components conventional in pharmaceutical preparations, e.g. wetting agents, emulsifiers and lubricants, such as sodium lauryl sulfate and magnesium stearate, as well as coloring agents, release agents, coating agents, sweetening, flavoring and perfuming agents, preservatives and antioxidants, pH modifiers, bulking agents, and further active agents. Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Such compositions may be prepared by any method known in the art, for example, by bringing into association the active ingredient with one or more carriers and/or excipients. Different compositions and examples of carriers and/or excipients are well known to the skilled person and are described in detail in, e.g., Remington: The Science and Practice of Pharmacy. Pharmaceutical Press, 2013; Rowe, Sheskey, Quinn: Handbook of Pharmaceutical Excipients. Pharmaceutical Press, 2009. Excipients that may be used in the preparation of the pharmaceutical compositions may include one or more of buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide a composition suitable for an administration of choice.

As indicated above, the compounds of the present disclosure may be in solid or liquid form and administered by various routes in any convenient administrative form, e.g., tablets, powders, capsules, solutions, dispersions, suspensions, syrups, sprays, suppositories, gels, emulsions, patches, etc.

In solid dosage forms of the disclosure for oral administration (capsules, tablets, pills, dragees, powders, granules, trouches and the like), a compound is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like. A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent. The tablets, and other solid dosage forms of the pharmaceutical compositions of the present disclosure, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the disclosure include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. An oral composition can also include adjuvants such as wetting agents, emulsifying and suspending agents, sweetening, flavoring, coloring, perfuming and preservative agents.

In form of suspensions, a compound may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Dosage forms for rectal or vaginal administration of a compound of the disclosure include a suppository, which may be prepared by mixing one or more compounds of the disclosure with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound. Other suitable forms include pessaries, tampons, creams, gels, pastes, foams or spray formulations containing such carriers as are known in the art to be appropriate.

Dosage forms for the topical or transdermal administration of a compound of the disclosure include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required. Such ointments, pastes, creams and gels may contain, in addition to a compound of the disclosure, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Dosage forms such as powders and sprays for administration of a compound of the disclosure, may contain excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Dosage forms such as transdermal patches for administration of a compound of the disclosure may include absorption enhancers or retarders to increase or decrease the flux of the compound across the skin. The rate of such flux can be controlled by either providing a rate controlling membrane or dispersing the compound in a polymer matrix or gel. Other dosage forms contemplated include ophthalmic formulations, eye ointments, powders, solutions and the like. It is understood that all contemplated compositions must be stable under the conditions of manufacture and storage, and preserved against the contaminating action of microorganisms, such as bacteria and fungi.

The dosage levels of a compound of the disclosure in the pharmaceutical compositions of the disclosure may be adjusted in order to obtain an amount of a compound of the disclosure which is effective to achieve the desired therapeutic response for a particular patient, composition, and mode of administration, without being deleterious to the patient. The dosage of choice will depend upon a variety of factors including the nature of the particular compound of the present disclosure used, the route of administration, the time of administration, the rate of excretion or metabolism of the particular compound used, the rate and extent of absorption, the duration of the prevention or treatment, other drugs, compounds and/or materials used in combination with the particular compound, the age, sex, weight, condition, general health and prior medical history of the patient being treated, and like factors well known in the medical arts. A medical practitioner having ordinary skill in the art can readily determine and prescribe the effective amount of the pharmaceutical composition required.

Typically, a suitable daily dose of a compound of the disclosure will be that amount of the compound which is the lowest dose effective to produce a therapeutic effect. Such an effective dose will generally depend upon the factors described above. Generally, oral, intravenous, intracerebroventricular and subcutaneous doses of the compounds of this disclosure for a patient, when used for the indicated analgesic effects, will range from about 0.0001 to about 100 mg, more usual 0.1 to 100 mg/kg per kilogram of body weight of recipient (patient, mammal) per day. Acceptable daily dosages may be from about 1 to about 1000 mg/day, and for example, from about 1 to about 100 mg/day.

The effective dose of a compound of the disclosure may be administered as two, three, four, five, six or more sub-doses administered separately at appropriate intervals throughout a specified period (per day or per week or per month), optionally, in unit dosage forms. Preferred dosing also depends on factors as indicated above, e.g. on the administration, and can be readily arrived at by one skilled in medicine or the pharmacy art.

Uses of the Compounds and Compositions

The compounds of the disclosure inhibit or modulate the activity of a receptor tyrosine kinase, in particular extracellular mutants of ErbB-receptors, such as, but not limited to, EGFR-Viii, EGFR-Vii, EGFR-Vvi, EGFR-A289V and EGFR-G598V and HER2-S310F. Thus, the compounds and compositions of the disclosure can be useful as a medicament, i.e. as a medicament in therapy, more specifically for the prevention or treatment of cancer, as detailed below. Therefore, in a further aspect, the present disclosure provides a method of prevention or treatment of a mammal, for example, a human, suffering from cancer, as detailed below.

The term "prevention" or "preventing" refers to reducing or eliminating the onset of the symptoms or complications of a disease (e.g., cancer). Such prevention comprises the step of administering a therapeutically effective amount of a compound of Formula I or salt thereof (or of a pharmaceutical composition containing a compound of Formula I or salt thereof) to said mammal, for example, a human.

The term "treatment" or "treating" is intended to encompass therapy and cure. Such treatment comprises the step of administering a therapeutically effective amount of a compound of Formula I or salt thereof (or of a pharmaceutical composition containing a compound of Formula I or salt thereof) to said mammal, for example, a human.

Thus, the disclosure provides the use of the compounds of the disclosure or pharmaceutically acceptable salts or stereoisomers thereof or a pharmaceutical composition thereof for the prevention or treatment of cancer, as detailed below, in a mammal, for example a human.

In some aspects, the present disclosure is directed to a method of inhibiting an oncogenic variant of an ErbB receptor (e.g., an oncogenic variant of an EGFR), comprising administering the subject in need thereof a therapeutically effective amount of a compound described herein.

In some aspects, the present disclosure is directed to a method of inhibiting an oncogenic variant of an ErbB receptor (e.g., an oncogenic variant of an EGFR), comprising administering the subject in need thereof a composition described herein.

In some aspects, the present disclosure is directed to a method of preventing or treating cancer, comprising administering the subject in need thereof a therapeutically effective amount of a compound described herein.

In some aspects, the present disclosure is directed to a method of preventing or treating cancer, comprising administering the subject in need thereof a composition described herein.

In some aspects, the present disclosure is directed to a compound described herein for use in the inhibition of an oncogenic variant of an ErbB receptor (e.g., an oncogenic variant of an EGFR).

In some aspects, the present disclosure is directed to a compound described herein for use in the prevention or treatment of cancer.

In some aspects, the present disclosure is directed to a composition described herein for use in the inhibition of an oncogenic variant of an ErbB receptor (e.g., an oncogenic variant of an EGFR).

In some aspects, the present disclosure is directed to a composition described herein for use in the prevention or treatment of cancer.

In some aspects, the present disclosure is directed to use of a compound described herein in the manufacture of a medicament for inhibiting an oncogenic variant of an ErbB receptor (e.g., an oncogenic variant of an EGFR).

In some aspects, the present disclosure is directed to use of a compound described herein in the manufacture of a medicament for preventing or treating cancer.

In some embodiments, the compound is selected from the compounds described in Tables 1 and 2, pharmaceutically acceptable salts thereof, and stereoisomers thereof.

In some embodiments, the compound is selected from the compounds described in Tables 1 and 2 and pharmaceutically acceptable salts thereof.

In some embodiments, the compound is selected from the compounds described in Tables 1 and 2.

In some embodiments, cancer is a solid tumor.

In some embodiments, the cancer is a bladder cancer, a breast cancer, a cervical cancer, a colorectal cancer, an endometrial cancer, a gastric cancer, a glioblastoma (GBM), a head and neck cancer, a lung cancer, a non-small cell lung cancer (NSCLC), or any subtype thereof.

In some embodiments, the cancer is glioblastoma (GBM) or any subtype thereof.

In some embodiments, the cancer is glioblastoma.

In some embodiments, the cancer, or a tumor or a cell thereof, expresses an oncogenic variant of an ErbB receptor.

In some embodiments, the oncogenic variant of the ErbB receptor comprises an allosteric mutation.

In some embodiments, the oncogenic variant of an ErbB receptor is is an allosteric variant of the ErbB receptor.

In some embodiments, the ErbB receptor is an an epidermal growth factor receptor (EGFR) or a human epidermal growth factor receptor 2 (HER2) receptor.

In some embodiments, the ErbB receptor is an epidermal growth factor receptor (EGFR).

In some embodiments, the ErbB receptor is a HER2 receptor.

In some embodiments, the cancer, or a tumor or a cell thereof, expresses an oncogenic variant of an epidermal growth factor receptor (EGFR).

In some embodiments, the oncogenic variant of EGFR is an allosteric variant of EGFR.

In some embodiments, the oncogenic variant of EGFR comprises an allosteric mutation.

In some embodiments, the cancer, or a tumor or a cell thereof, expresses an oncogenic variant of a HER2 receptor.

In some embodiments, the oncogenic variant of the HER2 receptor is an allosteric variant of the HER2 receptor.

In some embodiments, the oncogenic variant of the HER2 receptor comprises an allosteric mutation.

In some embodiments, the oncogenic variant of an EGFR comprises an EGFR variant III (EGFR-Viii) mutation.

In some embodiments, the oncogenic variant of EGFR comprises an EGFR variant II (EGFR-Vii) mutation.

In some embodiments, the oncogenic variant of EGFR comprises an EGFR variant VI (EGFR-Vvi) mutation.

In some embodiments, the oncogenic variant of an EGFR comprises a substitution of a valine (V) for an alanine (A) at position 289 of SEQ ID NO: 1.

In some embodiments, the oncogenic variant of EGFR comprises a substitution of a valine (V) for a glycine (G) at position 598 of SEQ ID NO: 1.

In some embodiments, the cancer, or a tumor or a cell thereof, expresses an oncogenic variant of an EGFR and wherein the oncogenic variant of EGFR is an allosteric variant of EGFR, the oncogenic variant of an EGFR comprises a modification of a structure of the EGFR, wherein the oncogenic variant of an EGFR is a capable of forming a covalently linked dimer, wherein the covalently linked dimer is constitutively active and wherein the covalently linked dimer enhances an activity of EGFR when contacted to a Type I ErbB inhibitor. In some embodiments, the modification of the structure of the EGFR comprises a modification of one or more of a nucleic acid sequence, an amino acid sequence, a secondary structure, a tertiary structure, and a quaternary structure. In some embodiments, the oncogenic variant comprises a mutation, a splicing event, a post-translational process, a conformational change or any combination thereof. In some embodiments, the modification of the structure of the EGFR occurs within a first cysteine rich (CR1) and/or second cysteine rich (CR2) region of EGFR. In some embodiments, the first cysteine rich (CR1) and/or second cysteine rich (CR2) region of EGFR comprises amino acid residues T211-R334 and/or C526-S645 of SEQ ID NO: 1, respectively. In some embodiments, the oncogenic variant of an EGFR generates a physical barrier to formation of a disulfide bond within the CR1 and/or the CR2 region. In some embodiments, the oncogenic variant of an EGFR removes a physical barrier to formation of a disulfide bond within the CR1 and/or the CR2 region. In some embodiments, the oncogenic variant of an EGFR comprises one or more free or unpaired Cysteine (C) residues located at a dimer interface of the EGFR. In some embodiments, the oncogenic variant of an EGFR comprises one or more free or unpaired Cysteine (C) residues at a site selected from the group consisting of C190-C199, C194-C207, C215-C223, C219-C231, C232-C240, C236-C248, C251-C260, C264-C291, C295-C307, C311-C326, C329-C333, C506-0515, C510-0523, C526-0535, C539-0555, C558-0571, C562-0579, C582-0591, C595-C617, C620-C628 and C624-C636 according to SEQ ID NO: 1. In some embodiments, the modification occurs within 10 angstroms or less of an intramolecular disulfide bond at a site selected from the group consisting of C190-C199, C194-C207, C215-C223, C219-C231, C232-C240, C236-C248, C251-C260, C264-C291, C295-C307, C311-C326, C329-C333, C506-C515, C510-C523, C526-C535, C539-C555, C558-C571, C562-C579, C582-C591, C595-C617, C620-C628 and C624-C636 according to SEQ ID NO: 1.

In some embodiments, the cancer, or a tumor or a cell thereof, expresses an oncogenic variant of EGFR and the oncogenic variant of EGFR is a mutation of EGFR, a nucleotide sequence encoding the oncogenic variant of an EGFR comprises a deletion or the substitution comprises one or more amino acids that encode an adenosine triphosphate (ATP) binding site. In some embodiments, the ATP binding site comprises amino acids E746 to A750 of SEQ ID NO: 1. In some embodiments, the ATP binding site or the deletion or substitution thereof comprises K858 of SEQ ID NO: 1. In some embodiments, the deletion comprises K858 of SEQ ID NO: 1. In some embodiments, an arginine (R) is substituted for the lysine (K) at position 858 (K858R) of SEQ ID NO: 1.

In some embodiments, the cancer, or a tumor or a cell thereof, expresses an oncogenic variant of an EGFR and wherein the oncogenic variant of EGFR is an allosteric variant of EGFR, a nucleotide sequence encoding the oncogenic variant of an EGFR comprises an insertion within a sequence encoding exon 20 or a portion thereof. In some embodiments, the sequence encoding exon 20 or a portion thereof comprises a sequence encoding KEILDEAYV-NIASVDNPHVCAR (SEQ ID NO: 7). In some embodiments, the sequence encoding exon 20 or a portion thereof comprises a sequence encoding a C-helix, a terminal end of the C-helix or a loop following the C-helix. In some embodiments, the insertion comprises the amino acid sequence of ASV, SVD, NPH, or FQEA. In some embodiments, the sequence encoding exon 20 or a portion thereof comprises one or more of: (a) an insertion of the amino acid sequence ASV between positions V769 and D770 of SEQ ID NO: 1; (b) an insertion of the amino acid sequence SVD between positions D770 and N771 of SEQ ID NO: 1; (c) an insertion of the amino acid sequence NPH between positions H773 and V774 of SEQ ID NO: 1; (d) an insertion of the amino acid sequence FQEA between positions A763 and Y764 of SEQ ID NO: 1; (e) an insertion of the amino acid sequence PH between positions H773 and V774 of SEQ ID NO: 1; (f) an insertion of the amino acid G between positions D770 and N771 of SEQ ID NO: 1; (g) an insertion of the amino acid H between positions H773 and V774 of SEQ ID NO: 1; (h) an insertion of the amino acid sequence HV between positions V774 and C775 of SEQ ID NO: 1; (i) an insertion of the amino acid sequence AH between positions H773 and V774 of SEQ ID NO: 1; (j) an insertion of the amino acid sequence SVA between positions A767 and S768 of SEQ ID NO: 1; (k) a substitution of the amino acid sequence GYN for the DN between positions 770 and 771 of SEQ ID NO: 1; (l) an insertion of the amino acid H between positions N771 and P772 of SEQ ID NO: 1; (m) an insertion of the amino acid Y between positions H773 and V774 of SEQ ID NO: 1; (n) an insertion of the amino acid sequence PHVC between positions C775 and R776 of SEQ ID NO: 1; (o) a substitution of the amino acid sequence YNPY for the H at position 773 of SEQ ID NO: 1; (p) an insertion of the amino acid sequence DNP between positions P772 and H773 of SEQ ID NO: 1; (q) an insertion of the amino acid sequence VDS between positions S768 and V769 of SEQ ID NO: 1; (r) an insertion of the amino acid H between positions D770 and N771 of SEQ ID NO: 1; (s) an insertion of the amino acid N between positions N771 and P772 of SEQ ID NO: 1; (t) an insertion of the amino acid sequence PNP between positions P772 and H773 of SEQ ID NO: 1; (u) a substitution of the amino acid sequence GSVDN for the DN between positions 770 and 771 of SEQ ID NO: 1; (v) a substitution of the amino acid sequence GYP for the NP between positions 771 and 772 of SEQ ID NO: 1; (w) an insertion of the amino acid G between positions N771 and P772 of SEQ ID NO: 1; (x) an insertion of the amino acid sequence GNP between positions P772 and H773 of SEQ ID NO: 1; (y) an insertion of the amino acid sequence GSV between positions V769 and D770 of SEQ ID NO: 1; (z) a substitution of the amino acid sequence GNPHVC for the VC between positions 774 and 775 of SEQ ID NO: 1; (aa) an insertion of the amino acid sequence LQEA between positions A763 and Y764 of SEQ ID NO: 1; (bb) an insertion of the amino acid sequence GL between positions D770 and N771 of SEQ ID NO: 1; (cc) an insertion of the amino acid Y between positions D770 and N771 of SEQ ID NO: 1; (dd) an insertion of the amino acid sequence NPY between positions H773 and V774 of SEQ ID NO: 1; (ee) an insertion of the amino acid sequence TH between positions H773 and V774 of SEQ ID NO: 1; (ff) a substitution of the amino acid sequence KGP for the NP between positions 771 and 772 of SEQ ID NO: 1; (gg) a substitution of the amino acid sequence SVDNP for the NP between positions 771 and 772 of SEQ ID NO: 1; (hh) an insertion of the amino acid sequence NN between positions N771 and P772 of SEQ ID NO: 1; (ii) an insertion of the amino acid T between positions N771 and P772 of SEQ ID NO: 1; and (jj) a substitution of the amino acid sequence STLASV for the SV between positions 768 and 769 of SEQ ID NO: 1.

In some embodiments, the cancer, or a tumor or a cell thereof, expresses an oncogenic variant of an EGFR and wherein the oncogenic variant of EGFR is an allosteric variant of EGFR, the oncogenic variant of an EGFR comprises EGFR-Vii, EGFR-Vvi, EGFR-R222C, EGFR-R252C, EGFR-R252P, EGFR-R256Y, EGFR-T263P, EGFR-Y270C, EGFR-A289T, EGFR-A289V, EGFR-A289D, EGFR-H304Y, EGFR-G331R, EGFR-P596S, EGFR-P596L, EGFR-P596R, EGFR-G598V, EGFR-G598A, EGFR-G614D, EGFR-C620Y, EGFR-C614W, EGFR-C628F, EGFR-C628Y, EGFR-C636Y, EGFR-G645C, EGFR-4660, EGFR-4768 or any combination thereof.

In some embodiments, the cancer, or a tumor or a cell thereof, expresses one or more of: (a) a wild type human epidermal growth factor receptor 2 (HER2) receptor or an oncogenic variant of a HER-2 receptor.

In some embodiments, the cancer, or a tumor or a cell thereof, expresses a wild type HER-2 receptor, the wild type HER2 receptor comprises the amino acid sequence of SEQ ID NO: 2, 3, 4, 5, or 6.

In some embodiments, the cancer, or a tumor or a cell thereof, expresses an oncogenic variant of a HER-2 receptor, the oncogenic variant of a HER2 receptor is an allosteric variant of the HER2 receptor.

In some embodiments, the cancer, or a tumor or a cell thereof, expresses an oncogenic variant of a HER-2 receptor and wherein the oncogenic variant of a HER2 receptor is an allosteric variant of the HER2 receptor, the oncogenic variant of a HER2 receptor comprises a substitution of a phenylalanine (F) for a serine (S) at position 310 of SEQ ID NO: 2 or 5.

In some embodiments, the cancer, or a tumor or a cell thereof, expresses an oncogenic variant of a HER-2 receptor and wherein the oncogenic variant of a HER2 receptor is an allosteric variant of the HER2 receptor, the oncogenic variant of a HER2 receptor comprises a substitution of a tyrosine (Y) for a serine (S) at position 310 of SEQ ID NO: 2 or 5.

In some embodiments, the cancer, or a tumor or a cell thereof, expresses an oncogenic variant of a HER-2 receptor and wherein the oncogenic variant of a HER2 receptor is an allosteric variant of the HER2 receptor, the oncogenic variant of a HER2 receptor comprises a substitution of a glutamine (Q) for an arginine (R) at position 678 of SEQ ID NO: 2 or 5.

In some embodiments, the cancer, or a tumor or a cell thereof, expresses an oncogenic variant of a HER-2 receptor and wherein the oncogenic variant of a HER2 receptor is an allosteric variant of the HER2 receptor, the oncogenic variant of a HER2 receptor comprises a substitution of a leucine (L) for a valine (V) at position 777 of SEQ ID NO: 2 or 5.

In some embodiments, the cancer, or a tumor or a cell thereof, expresses an oncogenic variant of a HER-2 receptor and wherein the oncogenic variant of a HER2 receptor is an allosteric variant of the HER2 receptor, the oncogenic variant of a HER2 receptor comprises a substitution of a methionine (M) for a valine (V) at position 777 of SEQ ID NO: 2 or 5.

In some embodiments, the cancer, or a tumor or a cell thereof, expresses an oncogenic variant of a HER-2 receptor and wherein the oncogenic variant of a HER2 receptor is an allosteric variant of the HER2 receptor, the oncogenic variant of a HER2 receptor comprises a substitution of an isoleucine (I) for a valine (V) at position 842 of SEQ ID NO: 2 or 5.

In some embodiments, the cancer, or a tumor or a cell thereof, expresses an oncogenic variant of a HER-2 receptor and wherein the oncogenic variant of a HER2 receptor is an allosteric variant of the HER2 receptor, the oncogenic variant of a HER2 receptor comprises a substitution of an alanine (A) for a leucine (L) at position 755 of SEQ ID NO: 2 or 5.

In some embodiments, the cancer, or a tumor or a cell thereof, expresses an oncogenic variant of a HER-2 receptor and wherein the oncogenic variant of a HER2 receptor is an allosteric variant of the HER2 receptor, the oncogenic variant of a HER2 receptor comprises a substitution of a proline (P) for a leucine (L) at position 755 of SEQ ID NO: 2 or 5.

In some embodiments, the cancer, or a tumor or a cell thereof, expresses an oncogenic variant of a HER-2 receptor and wherein the oncogenic variant of a HER2 receptor is an allosteric variant of the HER2 receptor, the oncogenic variant of a HER2 receptor comprises a substitution of a serine (S) for a leucine (L) at position 755 of SEQ ID NO: 2 or 5.

In some embodiments, the cancer, or a tumor or a cell thereof, expresses an oncogenic variant of a HER-2 receptor and wherein the oncogenic variant of a HER2 receptor is an allosteric variant of the HER2 receptor, a nucleotide sequence encoding the oncogenic variant of a HER2 receptor comprises an insertion within a sequence encoding exon 20 or a portion thereof. In some embodiments, the sequence encoding exon 20 or a portion thereof comprises a sequence encoding KEILDEAYVMAGVGSPYVSR (SEQ ID NO: 8). In some embodiments, the sequence encoding exon 20 or a portion thereof comprises a sequence encoding a C-helix, a terminal end of the C-helix or a loop following the C-helix. In some embodiments, the insertion comprises the amino acid sequence of GSP or YVMA. In some embodiments, the sequence encoding exon 20 or a portion thereof comprises one or more of: (a) an insertion of the amino acid sequence YVMA between positions A775 and G776 of SEQ ID NO: 2; (b) an insertion of the amino acid sequence GSP between positions P780 and Y781 of SEQ ID NO: 2; (c) an insertion of the amino acid sequence YVMA between positions A771 and Y772 of SEQ ID NO: 2; (d) an insertion of the amino acid sequence YVMA between positions A775 and G776 of SEQ ID NO: 2; (e) an insertion of the amino acid V between positions V777 and G778 of SEQ ID NO: 2; (f) an insertion of the amino acid V between positions V777 and G778 of SEQ ID NO: 2; (g) a substitution of the amino acid sequence AVGCV for the GV between positions 776 and 777 of SEQ ID NO: 2; (h) a substitution of the amino acid sequence LC for the G between position 776 of SEQ ID NO: 2; (i) a substitution of the amino acid sequence LCV for the G between position 776 of SEQ ID NO: 2; (j) an insertion of the amino acid sequence GSP between positions V777 and G778 of SEQ ID NO: 2; (k) a substitution of the amino acid sequence PS for the LRE between positions 755 and 757 of SEQ ID NO: 2; (1) a substitution of the amino acid sequence CPGSP for the SP between positions 779 and 780 of SEQ ID NO: 2; (m) an insertion of the amino acid C between positions V777 and G778 of SEQ ID NO: 2; (n) a substitution of the amino acid sequence VVMA for the AG between positions 775 and 776 of SEQ ID NO: 2; (o) a substitution of the amino acid sequence VV for the G at position 776 of SEQ ID NO: 2; (p) a substitution of the amino acid sequence AVCV for the GV between positions 776 and 777 of SEQ ID NO: 2; (q) a substitution of the amino acid sequence VCV for the GV between positions 776 and 777 of SEQ ID NO: 2; (r) an insertion of the amino acid G between positions G778 and S779 of SEQ ID NO: 2; (s) a substitution of the amino acid sequence PK for the LRE between positions 755 and 757 of SEQ ID NO: 2; (t) an insertion of the amino acid V between positions A775 and G776 of SEQ ID NO: 2; (u) an insertion of the amino acid sequence YAMA between positions A775 and G776 of SEQ ID NO: 2; (v) a substitution of the amino acid sequence CV for the G at position 776 of SEQ ID NO: 2; (w) a substitution of the amino acid sequence AVCGG for the GVG between positions 776 and 778 of SEQ ID NO: 2; (x) a substitution of the amino acid sequence CVCG for the GVG between positions 776 and 778 of SEQ ID NO: 2; (y) a substitution of the amino acid sequence VVVG for the GVG between positions 776 and 778 of SEQ ID NO: 2; (z) a substitution of the amino acid sequence SVGG for the GVGS between positions 776 and 779 of SEQ ID NO: 2; (aa) a substitution of the amino acid sequence VVGES for the GVGS between positions 776 and 779 of SEQ ID NO: 2; (bb) a substitution of the amino acid sequence AVGSGV for the GV between positions 776 and 777 of SEQ ID NO: 2; (cc) a substitution of the amino acid sequence CVC for the GV between positions 776 and 777 of SEQ ID NO: 2; (dd) a substitution of the amino acid sequence HVC for the GV between positions 776 and 777 of SEQ ID NO: 2; (ee) a substitution of the amino acid sequence VAAGV for the GV between positions 776 and 777 of SEQ ID NO: 2; (ff) a substitution of the amino acid sequence VAGV for the GV between positions 776 and 777 of SEQ ID NO: 2; (gg) a substitution of the amino acid sequence VVV for the GV between positions 776 and 777 of SEQ ID NO: 2; (hh) an insertion of the amino acid sequence FPG between positions G778 and S779 of SEQ ID NO: 2; (ii) an insertion of the amino acid sequence GS between positions S779 and P780 of SEQ ID NO: 2; (jj) a substitution of the amino acid sequence VPS for the VLRE between positions 754 and 757 of SEQ ID NO: 2; (kk) an insertion of the amino acid E between positions V777 and G778 of SEQ ID NO: 2; (ll) an insertion of the amino acid sequence MAGV between positions V777 and G778 of SEQ ID NO: 2; (mm) an insertion of the amino acid S between positions V777 and G778 of SEQ ID NO: 2; (nn) an insertion of the amino acid sequence SCV between positions V777 and G778 of SEQ ID NO: 2; and (oo) an insertion of the amino acid sequence LMAY between positions Y772 and V773 of SEQ ID NO: 2.

In some embodiments, the cancer, or a tumor or a cell thereof, expresses an oncogenic variant of a HER-2 receptor and wherein the oncogenic variant of a HER2 receptor is an allosteric variant of the HER2 receptor, the oncogenic variant of a HER2 receptor comprises HER2-416, HER2-C311R, HER2-S310F, p95-HER2-M611 or any combination thereof.

In some embodiments, the cancer, or a tumor or a cell thereof, expresses an oncogenic variant of a HER-4 receptor. In some embodiments, the oncogenic variant of the HER-4 receptor is an allosteric variant of the HER4 receptor. In some embodiments, the oncogenic variant of a HER4 receptor comprises deletion of exon 16 (HER4-416).

In some embodiments, the cancer, or a tumor or a cell thereof, expresses an oncogenic variant of an EGFR, wherein the sequence encoding the oncogenic variant of the EGFR comprises a deletion of exon 20 or a portion thereof and wherein the cancer, the tumor or the cell thereof does not comprise a second oncogenic variation in a sequence other than exon 20 of EGFR. In some embodiments, the second oncogenic variation comprises a sequence encoding one or more of an EGFR kinase domain (KD), BRAF, NTRK, and KRAS.

In some embodiments, the cancer, or a tumor or a cell thereof, expresses an oncogenic variant of an EGFR, wherein the sequence encoding the oncogenic variant of the EGFR comprises a deletion of exon 20 or a portion thereof and wherein the cancer, the tumor or the cell thereof does not comprise a marker indicating responsiveness to immunotherapy.

In some embodiments, the oncogenic variant (e.g., allosteric variant) or the oncogenic mutation (e.g., allosteric mutation) is detected by a Food and Drug Administration (FDA)-approved diagnosis.

In some embodiments, prior to the treatment with the compound of the present disclosure, the subject is treated with a therapeutic agent different from the compound of the present disclosure.

In some embodiments, the cancer, or a tumor or a cell thereof, is insensitive or resistant to treatment with a therapeutic agent different from the compound of the present disclosure. In some embodiments, the cancer, or a tumor or a cell thereof, is insensitive or resistant to treatment with a Type I inhibitor. In some embodiments, the cancer, or a tumor or a cell thereof, is insensitive or resistant to treatment with one or more of gefinitinib, erlotinib, afatinib, osimertinib, necitunumab, crizotinib, alectinib, ceritinib, dabrafenib, trametinib, afatinib, sapitinib, dacomitinib, canertinib, pelitinib, WZ4002, WZ8040, WZ3146, CO-1686 and AZD9291.

In some embodiments, the subject has an adverse reaction to treatment with a therapeutic agent different from the compound of the present disclosure. In some embodiments, the subject has an adverse reaction to treatment with a Type I inhibitor. In some embodiments, the subject has an adverse reaction to treatment with one or more of gefinitinib, erlotinib, afatinib, osimertinib, necitunumab, crizotinib, alectinib, ceritinib, dabrafenib, trametinib, afatinib, sapitinib, dacomitinib, canertinib, pelitinib, WZ4002, WZ8040, WZ3146, CO-1686 and AZD9291. In some embodiments, the adverse reaction is an activation of the oncogenic variant of an EGFR and wherein the oncogenic variant comprises a mutation in an extracellular domain of the receptor. In some embodiments, the adverse reaction is an activation of the oncogenic variant of a HER-2 Receptor and wherein the oncogenic variant comprises a mutation in an extracellular domain of the receptor.

In some embodiments, the method further comprises administering to the subject in need thereof a therapeutically effective amount of a non-Type I inhibitor. In some embodiments, the non-Type I inhibitor comprises a small molecule Type II inhibitor.

In some embodiments, the method further comprises administering to the subject in need thereof a therapeutically effective amount of a non-Type I inhibitor. In some embodiments, the non-Type I inhibitor comprises a small molecule Type II inhibitor.

In some embodiments, the compound is used in combination with a therapeutically effective amount of a non-Type I inhibitor. In some embodiments, the non-Type I inhibitor comprises a small molecule Type II inhibitor.

In some embodiments, the composition further comprises a non-Type I inhibitor. In some embodiments, the non-Type I inhibitor comprises a small molecule Type II inhibitor.

In some embodiments, the therapeutically effective amount reduces a severity of a sign or symptom of the cancer.

In some embodiments, the sign of the cancer comprises a tumor grade and wherein a reduction of the severity of the sign comprises a decrease of the tumor grade.

In some embodiments, the sign of the cancer comprises a tumor metastasis and wherein a reduction of the severity of the sign comprises an elimination of the metastasis or a reduction in the rate or extent the metastasis.

In some embodiments, the sign of the cancer comprises a tumor volume and wherein a reduction of the severity of the sign comprises an elimination of the tumor or a reduction in the volume.

In some embodiments, the symptom of the cancer comprises pain and wherein a reduction of the severity of the sign comprises an elimination or a reduction in the pain.

In some embodiments, the therapeutically effective amount induces a period of remission.

In some embodiments, the therapeutically effective amount improves a prognosis of the subject.

Such a use (or method of prevention or treatment) of a subject comprises administering to a subject in need of such prevention or treatment a therapeutically effective amount of a compound of the disclosure or pharmaceutically acceptable salts thereof or a pharmaceutical composition thereof by targeting allosteric and/or oncogenic variants of EGFR and HER-2 receptor.

The present disclosure contemplates administration of a compound of the disclosure alone or in combination with one or more additional therapeutic agents, such as other Tyrosine kinase inhibitors: Erlotinib hydrochloride (e.g. Tarceva® by Genentech/Roche), Linifanib (or ABT 869, by Genentech), sunitinib malate (e.g. Sutent® by Pfizer), bosutinib (or SKI-606, described in U.S. Pat. No. 6,780,996), dasatinib (e.g. Sprycel® by Bristol-Myers Squibb), armala (e.g. pazopanib, e.g. Votrient® by GlaxoSmithKline), imatinib and imatinib mesylate (e.g. Gilvec® and Gleevec® by Novartis); Vascular Endothelial Growth Factor (VEG) receptor inhibitors (Bevacizumab, or Avastin® by Genentech/Roche), axitinib, (or AG013736, described in WO 01/002369), Brivanib Alaninate (or BMS-582664), motesanib (or AMG-706, described in PCT WO 02/066470), pasireotide (e.g. SOM230, described in WO 02/010192), sorafenib (e.g. Nexavar®); HER2 receptor inhibitors: Trastuzumab (e.g. Herceptin® by Genentech/Roche), neratinib (or HKI-272, described WO 05/028443), lapatinib or lapatinib ditosylate (e.g. Tykerb® by GlaxoSmithKline); CD20 antibodies: Rituximab (e.g. Riuxan® and MabThera® by Genentech/Roche), tositumomab (e.g. Bexxar® by GlaxoSmithKline), ofatumumab (e.g. Arzerra® by GlaxoSmithKline); Bcr/Abl kinase inhibitors: nilotinib hydrochloride (e.g. Tasigna® by Novartis); DNA Synthesis inhibitors: Capecitabine (e.g. Xeloda® by Roche), gemcitabine hydrochloride (e.g. Gemzar® by Eli Lilly and Company), nelarabine (or Arranon® and Atriance® by GlaxoSmithKline); Antineoplastic agents: oxaliplatin (e.g. Eloxatin® ay Sanofi-Aventis described in U.S. Pat. No. 4,169,846); Epidermal growth factor receptor (EGFR) inhibitors: Gefitinib (or Iressa®), Afatinib (or Tovok® by Boehringer Ingelheim), cetuximab (e.g. Erbitux® by Bristol-Myers Squibb), panitumumab (e.g. Vectibix® by Amgen); HER dimerization inhibitors: Pertuzumab (e.g. Omnitarg®, by Genentech); Human Granulocyte colony-stimulating factor (G-CSF) modulators: Filgrastim (e.g. Neupogen® by Amgen); Immunomodulators: Afutuzumab (by Roche®), pegfilgrastim (e.g. Neulasta® by Amgen), lenalidomide (e.g. CC-5013, e.g. Revlimid®), thalidomide (e.g. Thalomid®); (m) CD40 inhibitors: Dacetuzumab (e.g. SGN-40 or huS2C$_6$, by Seattle Genetics, Inc); Pro-apoptotic receptor agonists (PARAs): Dulanermin (e.g. AMG-951, by Amgen/Genentech); Hedgehog antagonists: Vismodegib (or GDC-0449, described in WO 06/028958); PI3K inhibitors: Pictilisib (or GDC-0941 described in WO 09/036082 and WO 09/055730), Dactolisib (or BEZ 235 or NVP-BEZ 235, described in WO 06/122806); Phospholipase A2 inhibitors: Anagrelide (e.g. Agrylin®); BCL-2 inhibitors: Navitoclax (or ABT-263, described in WO 09/155386); Mitogen-activated protein kinase kinase (MEK) inhibitors: XL-518 (Cas No. 1029872-29-4, by ACC Corp.); Aromatase inhibitors: Exemestane (e.g. Aromasin® by Pfizer), letrozole (e.g. Femara® by Novartis), anastrozole (e.g. Arimidex®); Topoisomerase I inhibitors: Irinotecan (e.g. Camptosar® by Pfizer), topotecan hydrochloride (e.g. Hycamtin® by GlaxoSmithKline); Topoisomerase II inhibitors: etoposide (e.g. VP-16 and Etoposide phosphate, e.g. Toposar®, VePesid® and Etopophos®), teniposide (e.g. VM-26, e.g. Vumon®); mTOR inhibitors: Temsirolimus (e.g. Torisel® by Pfizer), ridaforolimus (formally known as deferolimus, (or AP23573 and MK8669, described in WO 03/064383), everolimus (e.g. Afinitor® by Novartis); Osteoclastic bone resorption inhibitors: zoledronic acid (or Zometa® by Novartis); CD33 Antibody Drug Conjugates: Gemtuzumab ozogamicin (e.g. Mylotarg® by Pfizer/Wyeth); CD22 Antibody Drug Conjugates: Inotuzumab ozogamicin (also referred to as CMC-544 and WAY-207294, by Hangzhou Sage Chemical Co., Ltd.); CD20 Antibody Drug Conjugates: Ibritumomab tiuxetan (e.g. Zevalin®); Somatostain analogs: octreotide (e.g. octreotide acetate, e.g. Sandostatin® and Sandostatin LAR®); Synthetic Interleukin-11 (IL-11): oprelvekin (e.g. Neumega® by Pfizer/Wyeth); Synthetic erythropoietin: Darbepoetin alfa (e.g. Aranesp® by Amgen); Receptor Activator for Nuclear Factor kappa B (RANK) inhibitors: Denosumab (e.g. Prolia® by Amgen); Thrombopoietin mimetic peptibodies: Romiplostim (e.g. Nplate® by Amgen; Cell growth stimulators: Palifermin (e.g. Kepivance® by Amgen); Anti-Insulin-like Growth Factor-1 receptor (IGF-1R) antibodies: Figitumumab (e.g. CP-751,871, by ACC Corp), robatumumab (CAS No. 934235-44-6); Anti-CS1 antibodies: Elotuzumab (HuLuc63, CAS No. 915296-00-3); CD52 antibodies: Alemtuzumab (e.g. Campath®); CTLA-4 inhibitors: Tremelimumab (IgG2 monoclonal antibody by Pfizer, formerly known as ticilimumab, CP-675,206), ipilimumab (CTLA-4 antibody, e.g. MDX-010, CAS No. 477202-00-9); Histone deacetylase inhibitors (HDI): Voninostat (e.g. Zolinza® by Merck); Alkylating agents: Temozolomide (e.g. Temodar® and Temodal® by Schering-Plough/Merck), dactinomycin (e.g. actinomycin-D and e.g. Cosmegen®), melphalan (e.g.

L-PAM, L-sarcolysin, and phenylalanine mustard, e.g. Alkeran®), altretamine (e.g. hexamethylmelamine (HMM), e.g. Hexalen®), carmustine (e.g. BiCNU®), bendamustine (e.g. Treanda®), busulfan (e.g. Busulfex® and Myleran®), carboplatin (e.g. Paraplatin®), lomustine (e.g. CCNU, e.g. CeeNU®), cisplatin (e.g. CDDP, e.g. Platinol® and Platinol®-AQ), chlorambucil (e.g. Leukeran®), cyclophosphamide (e.g. Cytoxan® and Neosar®), dacarbazine (e.g. DTIC, DIC and imidazole carboxamide, e.g. DTIC-Dome®), altretamine (e.g. hexamethylmelamine (HMM) e.g. Hexalen®), ifosfamide (e.g. Ifex®), procarbazine (e.g. Matulane®), mechlorethamine (e.g. nitrogen mustard, mustine and mechloroethamine hydrochloride, e.g. Mustargen®), streptozocin (e.g. Zanosar®), thiotepa (e.g. thiophosphoamide, TESPA and TSPA, e.g. Thioplex®; Biologic response modifiers: bacillus calmette-guerin (e.g. thera-Cys® and TICE® BCG), denileukin diftitox (e.g. Ontak®); Anti-tumor antibiotics: doxorubicin (e.g. Adriamycin® and Rubex®), bleomycin (e.g. Lenoxane®), daunorubicin (e.g. dauorubicin hydrochloride, daunomycin, and rubidomycin hydrochloride, e.g. Cerubidine®), daunorubicin liposomal (daunorubicin citrate liposome, e.g. DaunoXome®), mitoxantrone (e.g. DHAD, e.g. Novantrone®), epirubicin (e.g. Ellence™), idarubicin (e.g. Idamycin®, Idamycin PFS®), mitomycin C (e.g. Mutamycin®); Anti-microtubule agents: Estramustine (e.g. Emcyl®); Cathepsin K inhibitors: Odanacatib (or MK-0822, by Lanzhou Chon Chemicals, ACC Corp., and ChemieTek, described in WO 03/075836); Epothilone B analogs: Ixabepilone (e.g. Lxempra® by Bristol-Myers Squibb); Heat Shock Protein (HSP) inhibitors: Tanespimycin (17-allylamino-17-demethoxygeldanamycin, e.g. KOS-953 and 17-AAG, by SIGMA, described in U.S. Pat. No. 4,261,989); TpoR agonists: Eltrombopag (e.g. Promacta® and Revolade® by GlaxoSmithKline); Anti-mitotic agents: Docetaxel (e.g. Taxotere® by Sanofi-Aventis); Adrenal steroid inhibitors: aminoglutethimide (e.g. Cytadren®); Anti-androgens: Nilutamide (e.g. Nilandron® and Anandron®), bicalutamide (sold under tradename Casodex®), flutamide (e.g. Fulexin™); Androgens: Fluoxymesterone (e.g. Halotestin®); Proteasome inhibitors: Bortezomib (e.g. Velcade®); CDK1 inhibitors: Alvocidib (e.g. flovopirdol or HMR-1275, described in U.S. Pat. No. 5,621,002); Gonadotropin-releasing hormone (GnRH) receptor agonists: Leuprolide or leuprolide acetate (e.g. Viadure® by Bayer AG, Eligard® by Sanofi-Aventis and Lupron® by Abbott Lab); Taxane anti-neoplastic agents: Cabazitaxel, larotaxel; 5HT1a receptor agonists: Xaliproden (or SR57746, described in U.S. Pat. No. 5,266,573); HPC vaccines: Cervarix® sold by GlaxoSmithKline, Gardasil® sold by Merck; Iron Chelating agents: Deferasinox (e.g. Exjade® by Novartis); Anti-metabolites: Claribine (2-chlorodeoxyadenosine, e.g. Leustatin®), 5-fluorouracil (e.g. Adrucil®), 6-thioguanine (e.g. Purinethol®), pemetrexed (e.g. Alimta®), cytarabine (e.g. arabinosylcytosine (Ara-C), e.g. Cytosar-U®), cytarabine liposomal (e.g. Liposomal Ara-C, e.g. DepoCyt™), decitabine (e.g. Dacogen®), hydroxyurea (e.g. Hydrea®, Droxia™ and Mylocel™), fludarabine (e.g. Fludara®), floxuridine (e.g. FUDR®), cladribine (e.g. 2-chlorodeoxyadenosine (2-CdA) e.g. Leustatin™), methotrexate (e.g. amethopterin, methotrexate sodim (MTX), e.g. Rheumatrex® and Trexall™), pentostatin (e.g. Nipent®); Bisphosphonates: Pamidronate (e.g. Aredia®), zoledronic acid (e.g. Zometa®); Demethylating agents: 5-azacitidine (e.g. Vidaza®), decitabine (e.g. Dacogen®); Plant Alkaloids: Paclitaxel protein-bound (e.g. Abraxane®), vinblastine (e.g. vinblastine sulfate, vincaleukoblastine and VLB, e.g. Alkaban-AQ® and Velban®), vincristine (e.g. vincristine sulfate, LCR, and VCR, e.g. Oncovin® and Vincasar Pfs®), vinorelbine (e.g. Navelbine®), paclitaxel (e.g. Taxol and Onxal™); Retinoids: Alitretinoin (e.g. Panretin®), tretinoin (all-trans retinoic acid, e.g. ATRA, e.g. Vesanoid®), Isotretinoin (13-cis-retinoic acid, e.g. Accutane®, Amnesteem®, Claravis®, *Clarus*®, Decutan®, Isotane®, Izotech®, Oratane®, Isotret®, and Sotret®), bexarotene (e.g. Targretin®); Glucocorticosteroids: Hydrocortisone (e.g. cortisone, hydrocortisone sodium succinate, hydrocortisone sodium phosphate, and e.g. Ala-Cort®, Hydrocortisone Phosphate, Solu-Cortef®, Hydrocort Acetate® and Lanacort®), dexamethasone, prednisolone (e.g. Delta-Cortel®, Orapred®, Pediapred® and Prelone®), prednisone (e.g. Deltasone®, Liquid Red®, Meticorten® and Orasone®), methylprednisolone (e.g. 6-Methylprednisolone, Methylprednisolone Acetate, Methylprednisolone Sodium Succinate, e.g. Duralone®, Medralone®, Medrol®, M-Prednisol® and Solu-Medrol®); Cytokines: interleukin-2 (e.g. aldesleukin and IL-2, e.g. Proleukin®), interleukin-11 (e.g. oprevelkin, e.g. Neumega®), alpha interferon alfa (e.g. IFN-alpha, e.g. Intron® A, and Roferon-A®); Lutinizing hormone releasing hormone (LHRH) agonists: Goserelin (e.g. Zoladex®); Progesterones: megestrol (e.g. megestrol acetate, e.g. Megace®); Miscellaneous cytotoxic agents: Arsenic trioxide (e.g. Trisenox®), asparaginase (e.g. L-asparaginase, Erwinia L-asparaginase, e.g. Elspar® and Kidrolase®); Anti-nausea drugs: NK-1 receptor antagonists: Casopitant (e.g. Rezonic® and Zunrisa® by GlaxoSmithKline); and Cytoprotective agents: Amifostine (e.g. Ethyol®), leucovorin (e.g. calcium leucovorin, citrovorum factor and folinic acid).

EXEMPLARY EMBODIMENTS

Embodiment No. 1

A compound of Formula (I'):

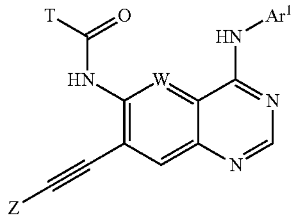

I' or a pharmaceutically acceptable salt or stereoisomer thereof, wherein:

W is CH or N;

Z is 3- to 12-membered heterocycloalkyl optionally substituted with one or more $R^Z$;

each $R^Z$ independently is halogen, CN, —OH, —$NH_2$, —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 10-membered heterocycloalkyl, or 5- to 10-membered heteroaryl; wherein the —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 10-membered heterocycloalkyl, or 5- to 10-membered heteroaryl is optionally substituted with one or more $R^{Za}$;

each $R^{Za}$ independently is halogen, CN, —OH, —$NH_2$, —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 10-membered heterocycloalkyl, or 5- to 10-membered heteroaryl;

T is —O—($C_1$-$C_6$ alkyl), —NH—($C_1$-$C_6$ alkyl), $C_1$-$C_6$ alkyl, $C_2$-$C_6$ alkenyl, or $C_2$-$C_6$ alkynyl; wherein the —O—($C_1$-$C_6$ alkyl), —NH—($C_1$-$C_6$ alkyl), $C_1$-$C_6$ alkyl, $C_2$-$C_6$ alkenyl, or $C_2$-$C_6$ alkynyl is optionally substituted with one or more $R^T$;

each $R^T$ independently is halogen, CN, —OH, —$NH_2$, —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 10-membered heterocycloalkyl, or 5- to 10-membered heteroaryl; wherein the —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 10-membered heterocycloalkyl, or 5- to 10-membered heteroaryl is optionally substituted with one or more $R^{Ta}$;

each $R^{Ta}$ independently is halogen, CN, —OH, —$NH_2$, —C(═O)OH, —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 10-membered heterocycloalkyl, or 5- to 10-membered heteroaryl;

$Ar^1$ is $C_6$-$C_{10}$ aryl optionally substituted with one or more $R^{A1}$;

each $R^{A1}$ independently is halogen, CN, —OH, —$NH_2$, —$OR^{A1a}$, —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 10-membered heterocycloalkyl, or 5- to 10-membered heteroaryl; wherein the —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 10-membered heterocycloalkyl, or 5- to 10-membered heteroaryl is optionally substituted with one or more $R^{A1a}$; and each $R^{A1a}$ independently is halogen, CN, —OH, —$NH_2$, —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 10-membered heterocycloalkyl, or 5- to 10-membered heteroaryl; wherein the —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 10-membered heterocycloalkyl, or 5- to 10-membered heteroaryl is optionally substituted with one or more $R^{A1b}$; and each $R^{A1b}$ independently is halogen, CN, —OH, or —$NH_2$.

Embodiment No. 2

The compound of any one of the preceding Embodiments, wherein the compound is of Formula (I') or a pharmaceutically acceptable salt or stereoisomer thereof, wherein:

W is CH or N;

Z is 3- to 12-membered heterocycloalkyl optionally substituted with one or more $R^Z$;

each $R^Z$ independently is halogen, CN, —OH, —$NH_2$, —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, or 5- to 10-membered heteroaryl; wherein the —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3 or 5- to 10-membered heteroaryl is optionally substituted with one or more $R^{Za}$;

each $R^{Za}$ independently is halogen, CN, —OH, —$NH_2$, —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 10-membered heterocycloalkyl, or 5- to 10-membered heteroaryl;

T is —O—($C_1$-$C_6$ alkyl), —NH—($C_1$-$C_6$ alkyl), $C_1$-$C_6$ alkyl, $C_2$-$C_6$ alkenyl, or $C_2$-$C_6$ alkynyl; wherein the —O—($C_1$-$C_6$ alkyl), —NH—($C_1$-$C_6$ alkyl), $C_1$-$C_6$ alkyl, $C_2$-$C_6$ alkenyl, or $C_2$-$C_6$ alkynyl is optionally substituted with one or more $R^T$;

each $R^T$ independently is halogen, CN, —OH, —$NH_2$, —O—($C_1$-$C_6$ alkyl), $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 7-membered heterocycloalkyl, or 5- to 10-membered heteroaryl; wherein the —O—($C_1$-$C_6$ alkyl), $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 7-membered heterocycloalkyl, or 5- to 10-membered heteroaryl is optionally substituted with one or more $R^{Ta}$;

each $R^{Ta}$ independently is halogen, CN, —OH, —$NH_2$, —C(═O)OH, —O—($C_1$-$C_6$ alkyl$C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 10-membered heterocycloalkyl, or 5- to 10-membered heteroaryl;

$Ar^1$ is $C_6$-$C_{10}$ aryl optionally substituted with one or more $R^{A1}$;

each $R^{A1}$ independently is halogen, CN, —OH, —$NH_2$, —$OR^{A1a}$, —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl; wherein the —O—($C_1$-$C_6$ alkyl), —NH ($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl is optionally substituted with one or more $R^{A1a}$; and each $R^{A1a}$ independently is halogen, CN, —OH, —$NH_2$, —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl; wherein the —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl is optionally substituted with one or more $R^{A1b}$; and each $R^{A1b}$ independently is halogen, CN, —OH, or —$NH_2$;

provided that when Z is

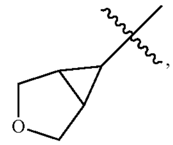 [SMILES: *C1C2COCC12], then $Ar^1$ is $C_6$-$C_{10}$ aryl optionally substituted with one or more halogen.

Embodiment No. 3

The compound of any one of the preceding Embodiments, wherein the compound is of Formula (I') or a pharmaceutically acceptable salt or stereoisomer thereof, wherein:

W is CH or N;

Z is 3- to 12-membered heterocycloalkyl optionally substituted with one or more $R^Z$;

each $R^Z$ independently is halogen, CN, —OH, —$NH_2$, —O—($C_1$-$C_6$ alkyl), —NH($C_1$-$C_6$ alkyl), —N($C_1$-

$C_6$ alkyl)$_2$, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, or 5- to 10-membered heteroaryl; wherein the —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3 or 5- to 10-membered heteroaryl is optionally substituted with one or more $R^{Za}$;

each $R^{Za}$ independently is halogen, CN, —OH, —$NH_2$, —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 10-membered heterocycloalkyl, or 5- to 10-membered heteroaryl;

T is —O—($C_1$-$C_6$ alkyl), —NH—($C_1$-$C_6$ alkyl), $C_1$-$C_6$ alkyl, $C_2$-$C_6$ alkenyl, or $C_2$-$C_6$ alkynyl; wherein the —O—($C_1$-$C_6$ alkyl), —NH—($C_1$-$C_6$ alkyl), $C_1$-$C_6$ alkyl, $C_2$-$C_6$ alkenyl, or $C_2$-$C_6$ alkynyl is optionally substituted with one or more $R^T$;

each $R^T$ independently is halogen, CN, —OH, —$NH_2$, —O—($C_1$-$C_6$ alkyl), $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 7-membered monocyclic heterocycloalkyl, or 5- to 10-membered heteroaryl; wherein the —O—($C_1$-$C_6$ alkyl), $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 7-membered monocyclic heterocycloalkyl, or 5- to 10-membered heteroaryl is optionally substituted with one or more $R^{Ta}$;

each $R^{Ta}$ independently is halogen, CN, —OH, —$NH_2$, —C(═O)OH, —O—($C_1$-$C_6$ alkyl$C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 10-membered heterocycloalkyl, or 5- to 10-membered heteroaryl;

$Ar^1$ is $C_6$-$C_{10}$ aryl optionally substituted with one or more $R^{A1}$;

each $R^{A1}$ independently is halogen, CN, —OH, —$NH_2$, —$OR^{A1a}$, —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl; wherein the —O—($C_1$-$C_6$ alkyl), —NH ($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl is optionally substituted with one or more $R^{A1a}$; and each $R^{A1a}$ independently is halogen, CN, —OH, —$NH_2$, —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl; wherein the —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl is optionally substituted with one or more $R^{A1b}$; and each $R^{A1b}$ independently is halogen, CN, —OH, or —$NH_2$;

provided that when Z is

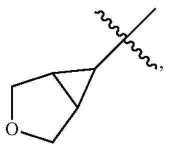 [SMILES: *C1C2COCC12]

then $Ar^1$ is $C_6$-$C_{10}$ aryl optionally substituted with one or more halogen.

Embodiment No. 4

The compound of any one of the preceding Embodiments, wherein the compound is of Formula (I') or a pharmaceutically acceptable salt or stereoisomer thereof, wherein:

W is CH;

Z is 3- to 12-membered heterocycloalkyl optionally substituted with one or more $R^Z$;

each $R^Z$ independently is halogen, —O—($C_1$-$C_6$ alkyl), $C_1$-$C_6$ alkyl, or 3- to 10-membered heterocycloalkyl; wherein the —O—($C_1$-$C_6$ alkyl), $C_1$-$C_6$ alkyl, or 3- to 10-membered heterocycloalkyl is optionally substituted with one or more halogen;

T is —O—($C_1$-$C_6$ alkyl), —NH—($C_1$-$C_6$ alkyl), $C_1$-$C_6$ alkyl, $C_2$-$C_6$ alkenyl, or $C_2$-$C_6$ alkynyl; wherein the $C_1$-$C_6$ alkyl, $C_2$-$C_6$ alkenyl, or $C_2$-$C_6$ alkynyl is optionally substituted with one or more $R^T$;

each $R^T$ independently is halogen, —OH, —O—($C_1$-$C_6$ alkyl), —N($C_1$-$C_6$ alkyl)$_2$, or 3- to 7-membered heterocycloalkyl; wherein the —O—($C_1$-$C_6$ alkyl), —N($C_1$-$C_6$ alkyl)$_2$, or 3- to 7-membered heterocycloalkyl is optionally substituted with one or more —C(═O)OH;

$Ar^1$ is $C_6$-$C_{10}$ aryl optionally substituted with one or more $R^{A1}$;

each $R^{A1}$ independently is halogen, —$OR^{A1a}$, or —O—($C_1$-$C_6$ alkyl) optionally substituted with one or more $R^{A1a}$; and each $R^{A1a}$ independently is $C_6$-$C_{10}$ aryl or 5- to 10-membered heteroaryl; wherein the $C_6$-$C_{10}$ aryl or 5- to 10-membered heteroaryl is optionally substituted with one or more halogen.

Embodiment No. 5

The compound of any one of the preceding Embodiments, wherein the compound is of Formula (I') or a pharmaceutically acceptable salt or stereoisomer thereof, wherein:

W is CH;

Z is 3- to 12-membered heterocycloalkyl optionally substituted with one or more $R^Z$;

each $R^Z$ independently is halogen, —O—($C_1$-$C_6$ alkyl), $C_1$-$C_6$ alkyl, or 3- to 10-membered heterocycloalkyl; wherein the —O—($C_1$-$C_6$ alkyl), $C_1$-$C_6$ alkyl, or 3- to 10-membered heterocycloalkyl is optionally substituted with one or more halogen;

T is —O—($C_1$-$C_6$ alkyl), —NH—($C_1$-$C_6$ alkyl), $C_1$-$C_6$ alkyl, $C_2$-$C_6$ alkenyl, or $C_2$-$C_6$ alkynyl; wherein the $C_1$-$C_6$ alkyl, $C_2$-$C_6$ alkenyl, or $C_2$-$C_6$ alkynyl is optionally substituted with one or more $R^T$;

each $R^T$ independently is halogen, —OH, —O—($C_1$-$C_6$ alkyl), —N($C_1$-$C_6$ alkyl)$_2$, or 3- to 7-membered monocyclic heterocycloalkyl; wherein the —O—($C_1$-$C_6$ alkyl), —N($C_1$-$C_6$ alkyl)$_2$, or 3- to 7-membered monocyclic heterocycloalkyl is optionally substituted with one or more —C(═O)OH;

$Ar^1$ is $C_6$-$C_{10}$ aryl optionally substituted with one or more $R^{A1}$;

each $R^{A1}$ independently is halogen, —$OR^{A1a}$, or —O—($C_1$-$C_6$ alkyl) optionally substituted with one or more $R^{A1a}$; and each $R^{A1a}$ independently is $C_6$-$C_{10}$ aryl or 5- to 10-membered heteroaryl; wherein the $C_6$-$C_{10}$ aryl or 5- to 10-membered heteroaryl is optionally substituted with one or more halogen.

Embodiment No. 6

The compound of any one of the preceding Embodiments, wherein the compound is of Formula (I') or a pharmaceutically acceptable salt or stereoisomer thereof, wherein:

W is CH;

Z is 3- to 12-membered heterocycloalkyl optionally substituted with one or more $R^Z$;

each $R^Z$ independently is halogen, —O—($C_1$-$C_6$ alkyl), or $C_1$-$C_6$ alkyl; wherein the —O—($C_1$-$C_6$ alkyl) or $C_1$-$C_6$ alkyl is optionally substituted with one or more halogen;

T is —O—($C_1$-$C_6$ alkyl), —NH—($C_1$-$C_6$ alkyl), $C_1$-$C_6$ alkyl, $C_2$-$C_6$ alkenyl, or $C_2$-$C_6$ alkynyl; wherein the $C_1$-$C_6$ alkyl, $C_2$-$C_6$ alkenyl, or $C_2$-$C_6$ alkynyl is optionally substituted with one or more $R^T$;

each $R^T$ independently is halogen, —OH, —O—($C_1$-$C_6$ alkyl), or 3- to 7-membered heterocycloalkyl; wherein the —O—($C_1$-$C_6$ alkyl), or 3- to 7-membered heterocycloalkyl is optionally substituted with one or more —C(═O)OH;

$Ar^1$ is $C_6$-$C_{10}$ aryl optionally substituted with one or more $R^{A1}$;

each $R^{A1}$ independently is halogen, —$OR^{A1a}$, or —O—($C_1$-$C_6$ alkyl) optionally substituted with one or more $R^{A1a}$; and each $R^{A1a}$ independently is $C_6$-$C_{10}$ aryl or 5- to 10-membered heteroaryl; wherein the $C_6$-$C_{10}$ aryl or 5- to 10-membered heteroaryl is optionally substituted with one or more halogen;

provided that when Z is

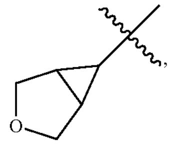 [SMILES: *C1C2COCC12]

then $Ar^1$ is $C_6$-$C_{10}$ aryl optionally substituted with one or more halogen.

Embodiment No. 7

The compound of any one of the preceding Embodiments, wherein the compound is of Formula (I') or a pharmaceutically acceptable salt or stereoisomer thereof, wherein:

W is CH;

Z is 3- to 12-membered heterocycloalkyl optionally substituted with one or more $R^Z$;

each $R^Z$ independently is halogen, —O—($C_1$-$C_6$ alkyl), or $C_1$-$C_6$ alkyl; wherein the —O—($C_1$-$C_6$ alkyl) or $C_1$-$C_6$ alkyl is optionally substituted with one or more halogen;

T is —O—($C_1$-$C_6$ alkyl), —NH—($C_1$-$C_6$ alkyl), $C_1$-$C_6$ alkyl, $C_2$-$C_6$ alkenyl, or $C_2$-$C_6$ alkynyl; wherein the $C_1$-$C_6$ alkyl, $C_2$-$C_6$ alkenyl, or $C_2$-$C_6$ alkynyl is optionally substituted with one or more $R^T$;

each $R^T$ independently is halogen, —OH, —O—($C_1$-$C_6$ alkyl), or 3- to 7-membered monocyclic heterocycloalkyl; wherein the —O—($C_1$-$C_6$ alkyl), or 3- to 7-membered monocyclic heterocycloalkyl is optionally substituted with one or more —C(═O)OH;

$Ar^1$ is $C_6$-$C_{10}$ aryl optionally substituted with one or more $R^{A1}$;

each $R^{A1}$ independently is halogen, —$OR^{A1a}$, or —O—($C_1$-$C_6$ alkyl) optionally substituted with one or more $R^{A1a}$; and each $R^{A1a}$ independently is $C_6$-$C_{10}$ aryl or 5- to 10-membered heteroaryl; wherein the $C_6$-$C_{10}$ aryl or 5- to 10-membered heteroaryl is optionally substituted with one or more halogen;

provided that when Z is

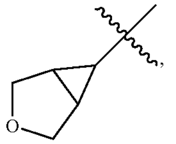 [SMILES: *C1C2COCC12]

then $Ar^1$ is $C_6$-$C_{10}$ aryl optionally substituted with one or more halogen.

Embodiment No. 8

The compound of any one of the preceding Embodiments, wherein the compound is of Formula (I') or a pharmaceutically acceptable salt or stereoisomer thereof, wherein:

W is CH;

Z is 3- to 12-membered heterocycloalkyl optionally substituted with one or more $R^Z$;

each $R^Z$ independently is halogen, —O—($C_1$-$C_6$ alkyl), or $C_1$-$C_6$ alkyl; wherein the —O—($C_1$-$C_6$ alkyl) or $C_1$-$C_6$ alkyl is optionally substituted with one or more halogen;

T is —O—($C_1$-$C_6$ alkyl), —NH—($C_1$-$C_6$ alkyl), $C_1$-$C_6$ alkyl, $C_2$-$C_6$ alkenyl, or $C_2$-$C_6$ alkynyl; wherein the $C_1$-$C_6$ alkyl, $C_2$-$C_6$ alkenyl, or $C_2$-$C_6$ alkynyl is optionally substituted with one or more $R^T$;

each $R^T$ independently is halogen, —OH, —O—($C_1$-$C_6$ alkyl), or 3- to 7-membered heterocycloalkyl; wherein the —O—($C_1$-$C_6$ alkyl), or 3- to 7-membered heterocycloalkyl is optionally substituted with one or more —C(═O)OH;

$Ar^1$ is $C_6$-$C_{10}$ aryl optionally substituted with one or more halogen.

Embodiment No. 9

The compound of any one of the preceding Embodiments, wherein the compound is of Formula (I') or a pharmaceutically acceptable salt or stereoisomer thereof, wherein:

W is CH;

Z is 3- to 12-membered heterocycloalkyl optionally substituted with one or more $R^Z$;

each $R^Z$ independently is halogen, —O—($C_1$-$C_6$ alkyl), or $C_1$-$C_6$ alkyl; wherein the —O—($C_1$-$C_6$ alkyl) or $C_1$-$C_6$ alkyl is optionally substituted with one or more halogen;

T is —O—($C_1$-$C_6$ alkyl), —NH—($C_1$-$C_6$ alkyl), $C_1$-$C_6$ alkyl, $C_2$-$C_6$ alkenyl, or $C_2$-$C_6$ alkynyl; wherein the $C_1$-$C_6$ alkyl, $C_2$-$C_6$ alkenyl, or $C_2$-$C_6$ alkynyl is optionally substituted with one or more $R^T$;

each $R^T$ independently is halogen, —OH, —O—($C_1$-$C_6$ alkyl), or 3- to 7-membered monocyclic heterocycloalkyl; wherein the —O—($C_1$-$C_6$ alkyl), or 3- to 7-membered monocyclic heterocycloalkyl is optionally substituted with one or more —C(═O)OH;

$Ar^1$ is $C_6$-$C_{10}$ aryl optionally substituted with one or more halogen.

Embodiment No. 10

The compound of any one of the preceding Embodiments, wherein the compound is of Formula (I') or a pharmaceutically acceptable salt or stereoisomer thereof, wherein:

W is CH;

Z is 3- to 12-membered heterocycloalkyl optionally substituted with one or more $C_1$-$C_6$ alkyl;

T is $C_2$-$C_6$ alkenyl optionally substituted with one or more 6-membered heterocycloalkyl; and $Ar^1$ is $C_6$ aryl optionally substituted with one or more halogen.

Embodiment No. 11

The compound of any one of the preceding Embodiments, wherein the compound is of Formula (I') or a pharmaceutically acceptable salt or stereoisomer thereof, wherein:

W is CH;

Z is 3- to 12-membered heterocycloalkyl optionally substituted with one or more $C_1$-$C_6$ alkyl;

T is $C_2$-$C_6$ alkenyl optionally substituted with one or more 6-membered monocyclic heterocycloalkyl; and $Ar^1$ is $C_6$ aryl optionally substituted with one or more halogen.

Embodiment No. 12

The compound of any one of the preceding Embodiments, wherein W is CH.

Embodiment No. 13

The compound of any one of the preceding Embodiments, wherein W is N.

Embodiment No. 14

The compound of any one of the preceding Embodiments, wherein Z is 3- to 12-membered heterocycloalkyl optionally substituted with one or more $R^Z$; and each $R^Z$ independently is halogen, —O—($C_1$-$C_6$ alkyl), $C_1$-$C_6$ alkyl, or 3- to 10-membered heterocycloalkyl; wherein the —O—($C_1$-$C_6$ alkyl), $C_1$-$C_6$ alkyl, or 3- to 10-membered heterocycloalkyl is optionally substituted with one or more halogen.

Embodiment No. 15

The compound of any one of the preceding Embodiments, wherein Z is oxetanyl, tetrahydrofuranyl, pyrrolidinyl, piperidinyl, morpholinyl, 3-oxabicyclo[3.1.0]hexanyl, 3-azabicyclo[3.1.0]hexanyl, 2-azaspiro[3.3]heptanyl, 2-oxa-5-azaspiro[3.4]octanyl, wherein the oxetanyl, tetrahydrofuranyl, pyrrolidinyl, piperidinyl, morpholinyl, 3-oxabicyclo[3.1.0]hexanyl, 3-azabicyclo[3.1.0]hexanyl, 2-azaspiro[3.3]heptanyl, or 2-oxa-5-azaspiro[3.4]octanyl is optionally substituted with one or more $R^Z$.

Embodiment No. 16

The compound of any one of the preceding Embodiments, wherein Z is oxetanyl, tetrahydrofuranyl, pyrrolidinyl, piperidinyl, morpholinyl, 3-oxabicyclo[3.1.0]hexanyl, 3-azabicyclo[3.1.0]hexanyl, 2-azaspiro[3.3]heptanyl, or 2-oxa-5-azaspiro[3.4]octanyl is optionally substituted with one or more $R^Z$.

Embodiment No. 17

The compound of any one of the preceding Embodiments, wherein Z is

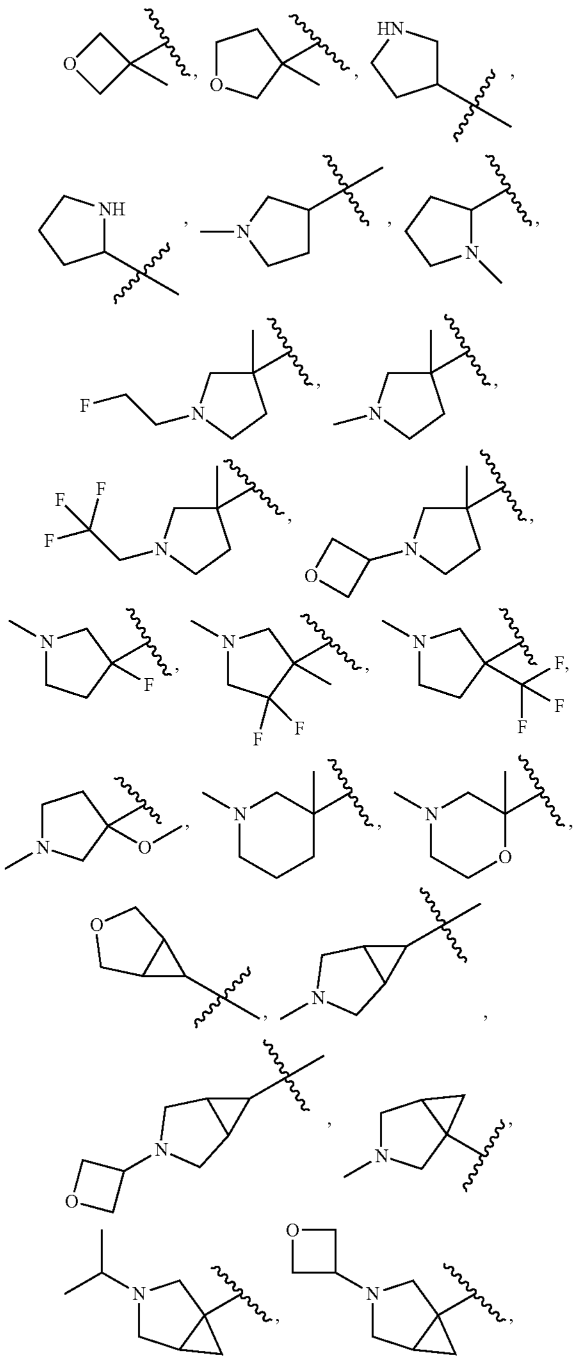

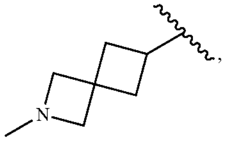

, or

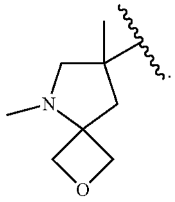

Embodiment No. 18

The compound of any one of the preceding Embodiments, wherein Z is

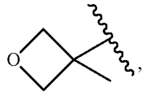, 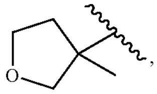, 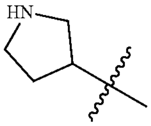,

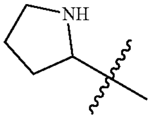, 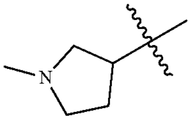, 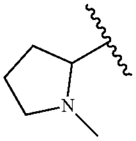,

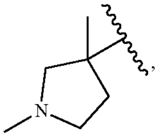, 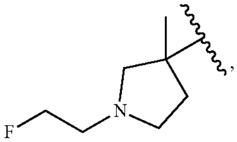,

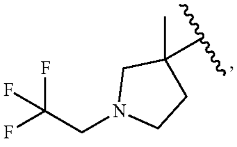, 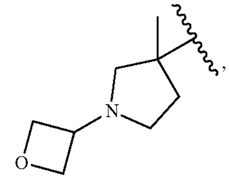,

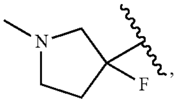, 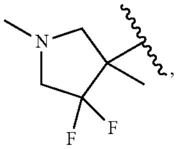,

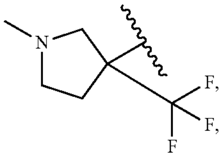 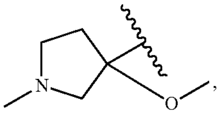,

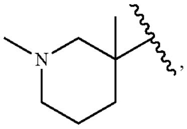, 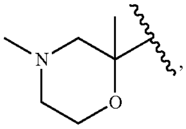,

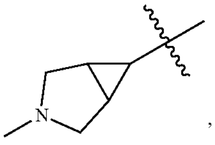,

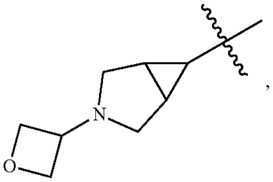, 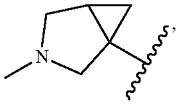,

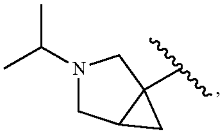, 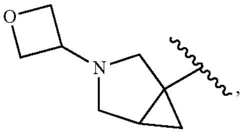,

-continued

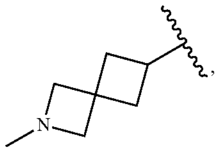, or 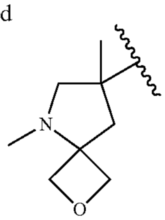.

Embodiment No. 19

The compound of any one of the preceding Embodiments, wherein at least one $R^Z$ is halogen.

Embodiment No. 20

The compound of any one of the preceding Embodiments, wherein at least one $R^Z$ is F or Cl.

Embodiment No. 21

The compound of any one of the preceding Embodiments, wherein at least one $R^Z$ is CN, —OH, or —$NH_2$.

Embodiment No. 22

The compound of any one of the preceding Embodiments, wherein at least one $R^Z$ is —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 10-membered heterocycloalkyl, or 5- to 10-membered heteroaryl; wherein the —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 10-membered heterocycloalkyl, or 5- to 10-membered heteroaryl is optionally substituted with one or more $R^{Za}$.

Embodiment No. 23

The compound of any one of the preceding Embodiments, wherein at least one $R^Z$ is —O—($C_1$-$C_6$ alkyl) optionally substituted with one or more $R^{Za}$.

Embodiment No. 24

The compound of any one of the preceding Embodiments, wherein at least one $R^Z$ is —$OCH_3$.

Embodiment No. 25

The compound of any one of the preceding Embodiments, wherein at least one $R^Z$ is —O—($C_1$-$C_6$ alkyl) substituted with one or more halogen.

Embodiment No. 26

The compound of any one of the preceding Embodiments, wherein at least one $R^Z$ is $C_1$-$C_6$ alkyl.

Embodiment No. 27

The compound of any one of the preceding Embodiments, wherein at least one $R^Z$ is methyl, ethyl, or propyl.

Embodiment No. 28

The compound of any one of the preceding Embodiments, wherein at least one $R^Z$ is $C_1$-$C_6$ alkyl substituted with one or more halogen.

Embodiment No. 29

The compound of any one of the preceding Embodiments, wherein at least one $R^Z$ is $CF_3$.

Embodiment No. 30

The compound of any one of the preceding Embodiments, wherein at least one $R^Z$ is $C_3$-$C_{10}$ cycloalkyl, $C_6$-$C_{10}$ aryl, 3- to 10-membered heterocycloalkyl, or 5- to 10-membered heteroaryl; wherein the $C_3$-$C_{10}$ cycloalkyl, $C_6$-$C_{10}$ aryl, 3- to 10-membered heterocycloalkyl, or 5- to 10-membered heteroaryl is optionally substituted with one or more $R^{Za}$.

Embodiment No. 31

The compound of any one of the preceding Embodiments, wherein at least one $R^Z$ is 3- to 10-membered heterocycloalkyl optionally substituted with one or more $R^{Za}$.

Embodiment No. 32

The compound of any one of the preceding Embodiments, wherein at least one $R^Z$ is 4-membered heterocycloalkyl optionally substituted with one or more $R^{Za}$.

Embodiment No. 33

The compound of any one of the preceding Embodiments, wherein at least one $R^Z$ is oxetanyl.

Embodiment No. 34

The compound of any one of the preceding Embodiments, wherein at least one $R^{Za}$ is halogen.

Embodiment No. 35

The compound of any one of the preceding Embodiments, wherein at least one $R^{Za}$ is F or Cl.

Embodiment No. 36

The compound of any one of the preceding Embodiments, wherein at least one $R^{Za}$ is CN, —OH, —$NH_2$, —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 10-membered heterocycloalkyl, or 5- to 10-membered heteroaryl.

Embodiment No. 37

The compound of any one of the preceding Embodiments, wherein T is —O—($C_1$-$C_6$ alkyl), —NH—($C_1$-$C_6$ alkyl), $C_1$-$C_6$ alkyl, $C_2$-$C_6$ alkenyl, or $C_2$-$C_6$ alkynyl; wherein the —O—($C_1$-$C_6$ alkyl), —NH—($C_1$-$C_6$ alkyl), $C_1$-$C_6$ alkyl, $C_2$-$C_6$ alkenyl, or $C_2$-$C_6$ alkynyl is optionally substituted with one or more $R^T$;

each $R^T$ independently is halogen, CN, —OH, —$NH_2$, —O—($C_1$-$C_6$ alkyl), $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 7-membered heterocycloalkyl, or 5- to 10-membered heteroaryl; wherein the —O—($C_1$-$C_6$ alkyl), $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 7-membered heterocycloalkyl, or 5- to 10-membered heteroaryl is optionally substituted with one or more $R^{Ta}$; and each $R^{Ta}$ independently is halogen, CN, —OH, —$NH_2$, —C(═O)OH, —O—($C_1$-$C_6$ alkyl), $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 10-membered heterocycloalkyl, or 5- to 10-membered heteroaryl.

Embodiment No. 38

The compound of any one of the preceding Embodiments, wherein T is —O—($C_1$-$C_6$ alkyl), —NH—($C_1$-$C_6$ alkyl), $C_1$-$C_6$ alkyl, $C_2$-$C_6$ alkenyl, or $C_2$-$C_6$ alkynyl; wherein the —O—($C_1$-$C_6$ alkyl), —NH—($C_1$-$C_6$ alkyl), $C_1$-$C_6$ alkyl, $C_2$-$C_6$ alkenyl, or $C_2$-$C_6$ alkynyl is optionally substituted with one or more $R^T$;

each $R^T$ independently is halogen, CN, —OH, —$NH_2$, —O—($C_1$-$C_6$ alkyl), $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 7-membered monocyclic heterocycloalkyl, or 5- to 10-membered heteroaryl; wherein the —O—($C_1$-$C_6$ alkyl), $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 7-membered monocyclic heterocycloalkyl, or 5- to 10-membered heteroaryl is optionally substituted with one or more $R^{Ta}$; and each $R^{Ta}$ independently is halogen, CN, —OH, —$NH_2$, —C(═O)OH, —O—($C_1$-$C_6$ alkyl), $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 10-membered heterocycloalkyl, or 5- to 10-membered heteroaryl.

Embodiment No. 39

The compound of any one of the preceding Embodiments, wherein T is —O—($C_1$-$C_6$ alkyl), —NH—($C_1$-$C_6$ alkyl), $C_1$-$C_6$ alkyl, $C_2$-$C_6$ alkenyl, or $C_2$-$C_6$ alkynyl; wherein the $C_1$-$C_6$ alkyl, $C_2$-$C_6$ alkenyl, or $C_2$-$C_6$ alkynyl is optionally substituted with one or more $R^T$; and each $R^T$ independently is halogen, —OH, —O—($C_1$-$C_6$ alkyl), —N($C_1$-$C_6$ alkyl)$_2$, or 3- to 7-membered heterocycloalkyl; wherein the —O—($C_1$-$C_6$ alkyl), —N($C_1$-$C_6$ alkyl)$_2$, or 3- to 7-membered heterocycloalkyl is optionally substituted with one or more —C(═O)OH.

Embodiment No. 40

The compound of any one of the preceding Embodiments, wherein T is —O—($C_1$-$C_6$ alkyl), —NH—($C_1$-$C_6$ alkyl), $C_1$-$C_6$ alkyl, $C_2$-$C_6$ alkenyl, or $C_2$-$C_6$ alkynyl; wherein the $C_1$-$C_6$ alkyl, $C_2$-$C_6$ alkenyl, or $C_2$-$C_6$ alkynyl is optionally substituted with one or more $R^T$; and each $R^T$ independently is halogen, —OH, —O—($C_1$-$C_6$ alkyl), —N($C_1$-$C_6$ alkyl)$_2$, or 3- to 7-membered monocyclic heterocycloalkyl; wherein the —O—($C_1$-$C_6$ alkyl), —N($C_1$-$C_6$ alkyl)$_2$, or 3- to 7-membered monocyclic heterocycloalkyl is optionally substituted with one or more —C(═O)OH.

Embodiment No. 41

The compound of any one of the preceding Embodiments, wherein T is —O—($C_1$-$C_6$ alkyl), —NH—($C_1$-$C_6$ alkyl), $C_1$-$C_6$ alkyl, $C_2$-$C_6$ alkenyl, or $C_2$-$C_6$ alkynyl; wherein the $C_1$-$C_6$ alkyl, $C_2$-$C_6$ alkenyl, or $C_2$-$C_6$ alkynyl is optionally substituted with one or more $R^T$; and each $R^T$ independently is halogen, —OH, —O—($C_1$-$C_6$ alkyl), or 3- to 7-membered heterocycloalkyl; wherein the —O—($C_1$-$C_6$ alkyl), or 3- to 7-membered heterocycloalkyl is optionally substituted with one or more —C(═O)OH.

Embodiment No. 42

The compound of any one of the preceding Embodiments, wherein T is —O—($C_1$-$C_6$ alkyl), —NH—($C_1$-$C_6$ alkyl), $C_1$-$C_6$ alkyl, $C_2$-$C_6$ alkenyl, or $C_2$-$C_6$ alkynyl; wherein the $C_1$-$C_6$ alkyl, $C_2$-$C_6$ alkenyl, or $C_2$-$C_6$ alkynyl is optionally substituted with one or more $R^T$; and each $R^T$ independently is halogen, —OH, —O—($C_1$-$C_6$ alkyl), or 3- to 7-membered monocyclic heterocycloalkyl; wherein the —O—($C_1$-$C_6$ alkyl), or 3- to 7-membered monocyclic heterocycloalkyl is optionally substituted with one or more —C(═O)OH.

Embodiment No. 43

The compound of any one of the preceding Embodiments, wherein T is —O—($C_1$-$C_6$ alkyl) optionally substituted with one or more $R^T$.

Embodiment No. 44

The compound of any one of the preceding Embodiments, wherein T is —$OCH_3$.

Embodiment No. 45

The compound of any one of the preceding Embodiments, wherein T is —NH—($C_1$-$C_6$ alkyl) optionally substituted with one or more $R^T$.

Embodiment No. 46

The compound of any one of the preceding Embodiments, wherein T is —$NHCH_3$.

Embodiment No. 47

The compound of any one of the preceding Embodiments, wherein T is $C_1$-$C_6$ alkyl optionally substituted with one or more $R^T$.

Embodiment No. 48

The compound of any one of the preceding Embodiments, wherein T is $C_1$-$C_6$ alkyl.

Embodiment No. 49

The compound of any one of the preceding Embodiments, wherein T is methyl or ethyl.

Embodiment No. 50

The compound of any one of the preceding Embodiments, wherein T is $C_1$-$C_6$ alkyl substituted with one or more halogen.

Embodiment No. 51

The compound of any one of the preceding Embodiments, wherein T is —CHFCl.

Embodiment No. 52

The compound of any one of the preceding Embodiments, wherein T is $C_2$-$C_6$ alkenyl optionally substituted with one or more $R^T$.

Embodiment No. 53

The compound of any one of the preceding Embodiments, wherein T is $C_2$-$C_6$ alkenyl.

Embodiment No. 54

The compound of any one of the preceding Embodiments, wherein T is ethenyl.

Embodiment No. 55

The compound of any one of the preceding Embodiments, wherein T is propenyl.

Embodiment No. 56

The compound of any one of the preceding Embodiments, wherein T is pentenyl.

Embodiment No. 57

The compound of any one of the preceding Embodiments, wherein T is $C_2$-$C_6$ alkenyl substituted with one or more $R^T$.

Embodiment No. 58

The compound of any one of the preceding Embodiments, wherein T is $C_2$-$C_6$ alkenyl substituted with one or more —OH, —O—($C_1$-$C_6$ alkyl), —N($C_1$-$C_6$ alkyl)$_2$, or 3- to 10-membered heterocycloalkyl; wherein the 3- to 10-membered heterocycloalkyl is optionally substituted with one or more —C(═O)OH.

Embodiment No. 59

The compound of any one of the preceding Embodiments, wherein T is $C_2$-$C_6$ alkynyl.

Embodiment No. 60

The compound of any one of the preceding Embodiments, wherein T is propynyl.

Embodiment No. 61

The compound of any one of the preceding Embodiments, wherein T is $C_2$-$C_6$ alkynyl substituted with one or more $R^T$.

Embodiment No. 62

The compound of any one of the preceding Embodiments, wherein T is propynyl substituted with one or more $R^T$.

Embodiment No. 63

The compound of any one of the preceding Embodiments, wherein T is propynyl substituted with one or more 3- to 10-membered heterocycloalkyl.

Embodiment No. 64

The compound of any one of the preceding Embodiments, wherein T is

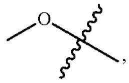, 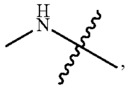, 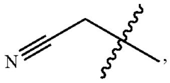,

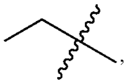, 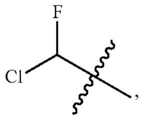, 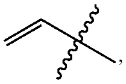,

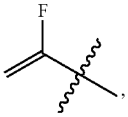, 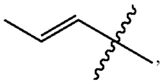, 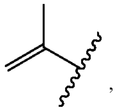,

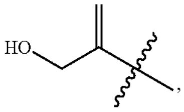, 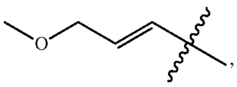,

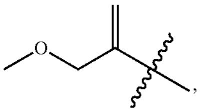, 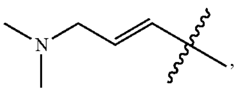,

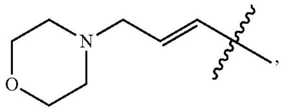,

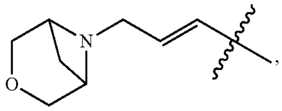,

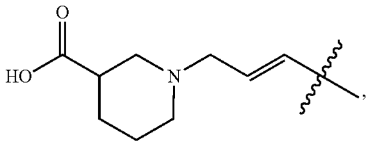,

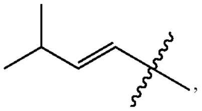, 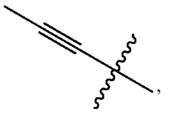, or

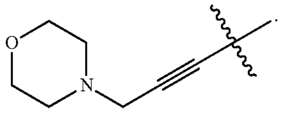.

Embodiment No. 65

The compound of any one of the preceding Embodiments, wherein T is

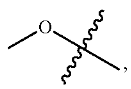, 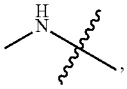, 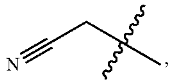, 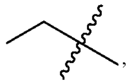,

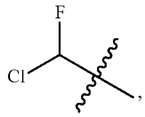, 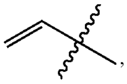, 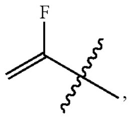, 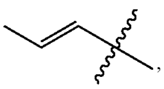,

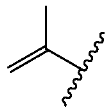, 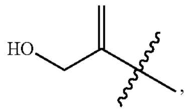, 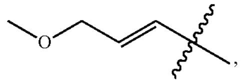,

-continued

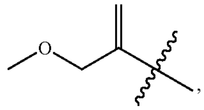, 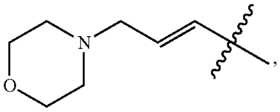,

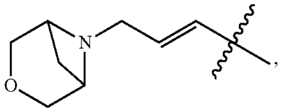,

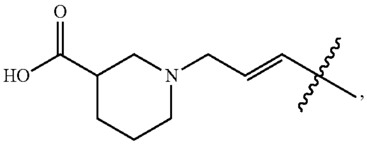, 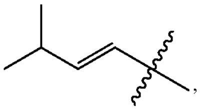,

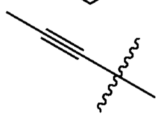, or 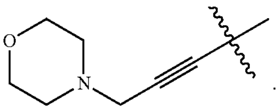.

Embodiment No. 66

The compound of any one of the preceding Embodiments, wherein at least one $R^T$ is halogen.

Embodiment No. 67

The compound of any one of the preceding Embodiments, wherein at least one $R^T$ is CN, —OH, or —$NH_2$.

Embodiment No. 68

The compound of any one of the preceding Embodiments, wherein at least one $R^T$ is —O—($C_1$-$C_6$ alkyl), —NH($C_1$-$C_6$ alkyl), or —N($C_1$-$C_6$ alkyl)$_2$; wherein the O—($C_1$-$C_6$ alkyl), —NH($C_1$-$C_6$ alkyl), or —N($C_1$-$C_6$ alkyl)$_2$ is optionally substituted with one or more $R^{Ta}$.

Embodiment No. 69

The compound of any one of the preceding Embodiments, wherein at least one $R^T$ is —O—($C_1$-$C_6$ alkyl) or —N($C_1$-$C_6$ alkyl)$_2$.

Embodiment No. 70

The compound of any one of the preceding Embodiments, wherein at least one $R^T$ is $C_1$-$C_6$ alkyl, $C_2$-$C_6$ alkenyl, or $C_2$-$C_6$ alkynyl; wherein the $C_1$-$C_6$ alkyl, $C_2$-$C_6$ alkenyl, or $C_2$-$C_6$ alkynyl is optionally substituted with one or more $R^{Ta}$.

Embodiment No. 71

The compound of any one of the preceding Embodiments, wherein at least one $R^T$ is $C_3$-$C_{10}$ cycloalkyl, $C_6$-$C_{10}$ aryl, 3- to 10-membered heterocycloalkyl, or 5- to 10-membered heteroaryl; wherein the $C_3$-$C_{10}$ cycloalkyl, $C_6$-$C_{10}$ aryl, 3- to 10-membered heterocycloalkyl, or 5- to 10-membered heteroaryl is optionally substituted with one or more $R^{Ta}$.

Embodiment No. 72

The compound of any one of the preceding Embodiments, wherein at least one $R^T$ is 3- to 10-membered heterocycloalkyl substituted with one or more C(═O)OH.

Embodiment No. 73

The compound of any one of the preceding Embodiments, wherein at least one $R^{Ta}$ is C(═O)OH.

Embodiment No. 74

The compound of any one of the preceding Embodiments, wherein at least one $R^{Ta}$ is halogen, CN, —OH, —$NH_2$, —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 10-membered heterocycloalkyl, or 5- to 10-membered heteroaryl.

Embodiment No. 75

The compound of any one of the preceding Embodiments, wherein $Ar^1$ is $C_6$-$C_{10}$ aryl optionally substituted with one or more $R^{A1}$;

each $R^{A1}$ independently is halogen, CN, —OH, —$NH_2$, —$OR^{A1a}$, —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl; wherein the —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl is optionally substituted with one or more $R^{A1a}$;

each $R^{A1a}$ independently is halogen, CN, —OH, —$NH_2$, —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl; wherein the —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl is optionally substituted with one or more $R^{A1b}$; and each $R^{A1b}$ independently is halogen, CN, —OH, or —$NH_2$.

Embodiment No. 76

The compound of any one of the preceding Embodiments, wherein $Ar^1$ is $C_6$-$C_{10}$ aryl.

Embodiment No. 77

The compound of any one of the preceding Embodiments, wherein $Ar^1$ is $C_6$-$C_{10}$ aryl substituted with one or more $R^{A1}$.

Embodiment No. 78

The compound of any one of the preceding Embodiments, wherein $Ar^1$ is phenyl substituted with one or more halogen, —$OR^{A1a}$, or —O—($C_1$-$C_6$ alkyl); wherein the -O—($C_1$-$C_6$ alkyl) is optionally substituted with one or more $R^{A1a}$; and each $R^{A1a}$ independently is $C_6$-$C_{10}$ aryl or 5- to 10-membered heteroaryl; wherein the $C_6$-$C_{10}$ aryl or 5- to 10-membered heteroaryl is optionally substituted with one or more halogen.

Embodiment No. 79

The compound of any one of the preceding Embodiments, wherein $Ar^1$ is phenyl substituted with one or more halogen Embodiment No. 80

The compound of any one of the preceding Embodiments, wherein $Ar^1$ is phenyl substituted with one F and one $C_1$.

Embodiment No. 81

The compound of any one of the preceding Embodiments, wherein $Ar^1$ is phenyl optionally substituted with one or more halogen, wherein the phenyl is further substituted with —O—($C_6$-$C_{10}$ aryl) or —O-(5- to 10-membered heteroaryl); wherein the —O—($C_6$-$C_{10}$ aryl) or —O-(5- to 10-membered heteroaryl) is optionally substituted with one or more halogen.

Embodiment No. 82

The compound of any one of the preceding Embodiments, wherein $Ar^1$ is phenyl optionally substituted with one or more halogen, wherein the phenyl is further substituted with —O-phenyl or —O-pyridinyl; wherein the —O-phenyl or —O-pyridinyl is optionally substituted with one or more halogen.

Embodiment No. 83

The compound of any one of the preceding Embodiments, wherein $Ar^1$ is

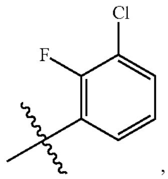
,
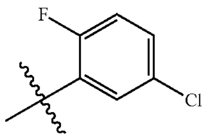
,
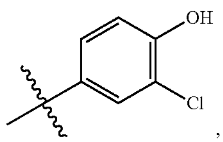
,
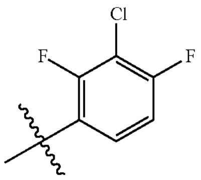
, or
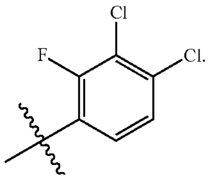

Embodiment No. 84

The compound of any one of the preceding Embodiments, wherein $Ar^1$ is

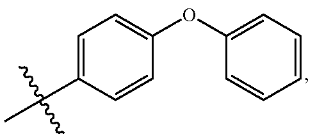
,

-continued

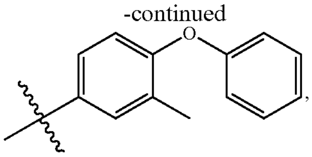

, or

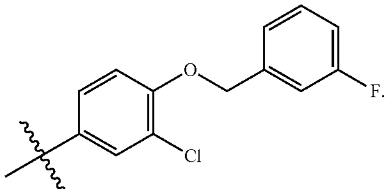

Embodiment No. 85

The compound of any one of the preceding Embodiments, wherein $Ar^1$ is

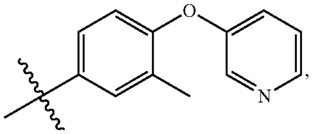

, or

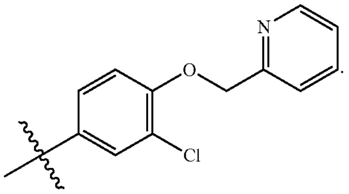

Embodiment No. 86

The compound of any one of the preceding Embodiments, wherein $Ar^1$ is

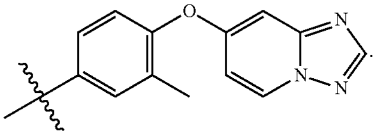 [SMILES: *c1ccc(Oc2ccn3ncnc3c2)c(C)c1]

Embodiment No. 87

The compound of any one of the preceding Embodiments, wherein at least one $R^{A1}$ is halogen.

Embodiment No. 88

The compound of any one of the preceding Embodiments, wherein at least one $R^{A1}$ is F, and at least one $R^{A1}$ is Cl.

Embodiment No. 89

The compound of any one of the preceding Embodiments, wherein at least one $R^{A1}$ is CN, —OH, or —$NH_2$.

Embodiment No. 90

The compound of any one of the preceding Embodiments, wherein at least one $R^{A1}$ is —$OR^{A1a}$.

Embodiment No. 91

The compound of any one of the preceding Embodiments, wherein at least one $R^{A1}$ is —O—($C_6$-$C_{10}$ aryl) or —O-(5- to 10-membered heteroaryl); wherein the —O—($C_6$-$C_{10}$ aryl) or —O-(5- to 10-membered heteroaryl) is optionally substituted with one or more $R^{A1b}$.

Embodiment No. 92

The compound of any one of the preceding Embodiments, wherein at least one $R^{A1}$ is —O—($C_6$-$C_{10}$ aryl) or —O-(5- to 10-membered heteroaryl); wherein the —O—($C_6$-$C_{10}$ aryl) or —O-(5- to 10-membered heteroaryl) is optionally substituted with one or more halogen.

Embodiment No. 93

The compound of any one of the preceding Embodiments, wherein at least one $R^{A1}$ is —O-phenyl or —O-pyridinyl; wherein the —O-phenyl or —O-pyridinyl is optionally substituted with one or more halogen.

Embodiment No. 94

The compound of any one of the preceding Embodiments, wherein at least one $R^{A1}$ is —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl, wherein the —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl is optionally substituted with one or more $R^{A1a}$.

Embodiment No. 95

The compound of any one of the preceding Embodiments, wherein at least one $R^{A1}$ is —O—($C_1$-$C_6$ alkyl) substituted with one or more $C_6$-$C_{10}$ aryl or 5- to 10-membered heteroaryl, wherein the $C_6$-$C_{10}$ aryl or 5- to 10-membered heteroaryl is optionally substituted with one or more halogen.

Embodiment No. 96

The compound of any one of the preceding Embodiments, wherein at least one $R^{A1}$ is —O—$CH_2$—($C_6$-$C_{10}$ aryl) or —O—$CH_2$—(5- to 10-membered heteroaryl), wherein the —O—$CH_2$—($C_6$-$C_{10}$ aryl) or —O—$CH_2$—(5- to 10-membered heteroaryl) is optionally substituted with one or more halogen.

Embodiment No. 97

The compound of any one of the preceding Embodiments, wherein at least one $R^{A1}$ is —O—$CH_2$-phenyl or —O—$CH_2$-pyridinyl, wherein the —O—$CH_2$-phenyl or —O—$CH_2$-pyridinyl is optionally substituted with one or more halogen.

Embodiment No. 98

The compound of any one of the preceding Embodiments, wherein at least one $R^{A1}$ is $C_3$-$C_{10}$ cycloalkyl, $C_6$-$C_{10}$ aryl, 3- to 10-membered heterocycloalkyl, or 5- to 10-membered heteroaryl; wherein the $C_3$-$C_{10}$ cycloalkyl, $C_6$-$C_{10}$ aryl, 3- to 10-membered heterocycloalkyl, or 5- to 10-membered heteroaryl is optionally substituted with one or more $R^{A1a}$.

Embodiment No. 99

The compound of any one of the preceding Embodiments, wherein at least one $R^{A1a}$ is halogen, CN, —OH, —$NH_2$, —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl, wherein the —O—($C_1$-$C_6$ alkyl), —NH($C_1$-$C_6$ alkyl), —N($C_1$-$C_6$ alkyl)$_2$, $C_1$-$C_6$ alkyl, $C_2$-$C_6$ alkenyl, or $C_2$-$C_6$ alkynyl is optionally substituted with one or more $R^{A1b}$.

Embodiment No. 100

The compound of any one of the preceding Embodiments, wherein at least one $R^{A1a}$ is $C_3$-$C_{10}$ cycloalkyl, $C_6$-$C_{10}$ aryl, 3- to 10-membered heterocycloalkyl, or 5- to 10-membered heteroaryl; wherein the $C_3$-$C_{10}$ cycloalkyl, $C_6$-$C_{10}$ aryl, 3- to 10-membered heterocycloalkyl, or 5- to 10-membered heteroaryl is optionally substituted with one or more $R^{A1b}$.

Embodiment No. 101

The compound of any one of the preceding Embodiments, wherein at least one $R^{A1a}$ is $C_6$-$C_{10}$ aryl or 5- to 10-membered heteroaryl; wherein the $C_6$-$C_{10}$ aryl or 5- to 10-membered heteroaryl is optionally substituted with one or more halogen.

Embodiment No. 102

The compound of any one of the preceding Embodiments, wherein at least one $R^{A1a}$ is phenyl or pyridinyl; wherein the phenyl or pyridinyl is optionally substituted with one or more halogen.

Embodiment No. 103

The compound of any one of the preceding Embodiments, wherein at least one $R^{A1b}$ is halogen.

Embodiment No. 104

The compound of any one of the preceding Embodiments, wherein at least one $R^{A1b}$ is F, and at least one $R^{A1b}$ is Cl.

Embodiment No. 105

The compound of any one of the preceding Embodiments, wherein at least one $R^{A1b}$ is CN, —OH, or —$NH_2$.

Embodiment No. 106

The compound of any one of the preceding Embodiments, wherein when Z is

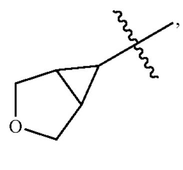 [SMILES: *C1C2COCC12]

, then

T is —O—($C_1$-$C_6$ alkyl), —NH—($C_1$-$C_6$ alkyl), $C_1$-$C_6$ alkyl, $C_2$-$C_6$ alkenyl, or $C_2$-$C_6$ alkynyl; wherein the —O—($C_1$-$C_6$ alkyl), —NH—($C_1$-$C_6$ alkyl), $C_1$-$C_6$ alkyl, or $C_2$-$C_6$ alkynyl is optionally substituted with one or more $R^T$; and wherein the $C_2$-$C_6$ alkenyl is substituted with one or more $R^T$ each $R^T$ independently is halogen, CN, —OH, —$NH_2$, —O—($C_1$-$C_6$ alkyl), —$C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 7-membered heterocycloalkyl, or 5- to 10-membered heteroaryl; wherein the —O—($C_1$-$C_6$ alkyl), $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 7-membered heterocycloalkyl, or 5- to 10-membered heteroaryl is optionally substituted with one or more $R^{Ta}$; and each $R^{Ta}$ independently is halogen, CN, —OH, —$NH_2$, —C(=O)OH, —O—($C_1$-$C_6$ alkyl), $C_1$-$C_6$ alkyl, $C_2$-$C_6$ alkenyl, $C_2$-$C_6$ alkynyl, $C_3$-$C_{10}$ cycloalkyl, $C_6$-$C_{10}$ aryl, 3- to 10-membered heterocycloalkyl, or 5- to 10-membered heteroaryl.

Embodiment No. 107

The compound of any one of the preceding Embodiments, wherein when Z is

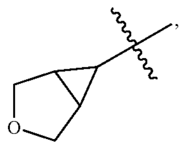 [SMILES: *C1C2COCC12]

, then T is not

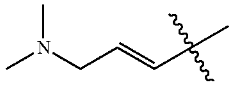

or

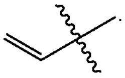

.

Embodiment No. 108

The compound of any one of the preceding Embodiments, wherein when Z is

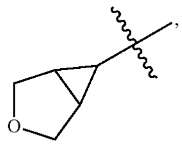 [SMILES: *C1C2COCC12]

, then $Ar^1$ is $C_6$-$C_{10}$ aryl optionally substituted with one or more halogen.

Embodiment No. 109

The compound of any one of the preceding Embodiments, wherein Z is not

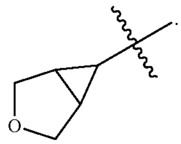 [SMILES: *C1C2COCC12]

Embodiment No. 110

The compound of any one of the preceding Embodiments, wherein Z is not

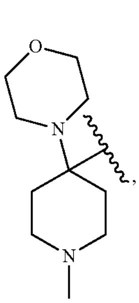, 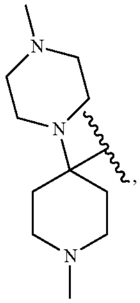,

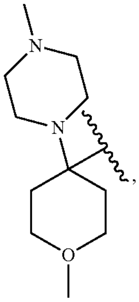, or 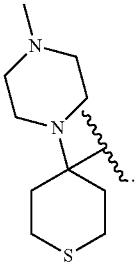.

Embodiment No. 111

The compound of any one of the preceding Embodiments, wherein T is not

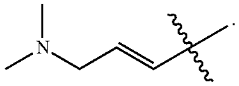 [SMILES: */C=C/CN(C)C]

Embodiment No. 112

The compound of any one of the preceding Embodiments, wherein the compound is of formula (II'):

(II')

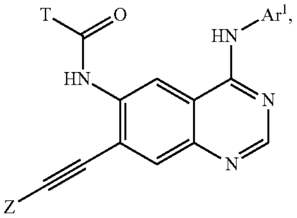

or a pharmaceutically acceptable salt or stereoisomer thereof.

Embodiment No. 113

The compound of any one of the preceding Embodiments, wherein the compound is of formula (II'):

(II')

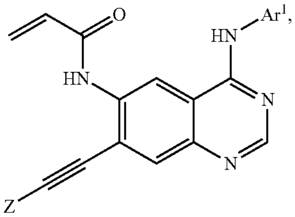

or a pharmaceutically acceptable salt or stereoisomer thereof.

Embodiment No. 114

The compound of any one of the preceding Embodiments, wherein the compound is of formula (III') or (III'-a):

(III')

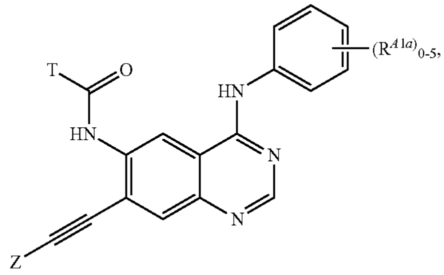

(III-*a*')

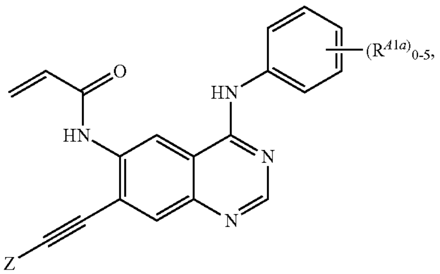

or a pharmaceutically acceptable salt or stereoisomer thereof.

Embodiment No. 115

The compound of any one of the preceding Embodiments, wherein the compound is of formula (IV') or (IV'-a):

(IV')

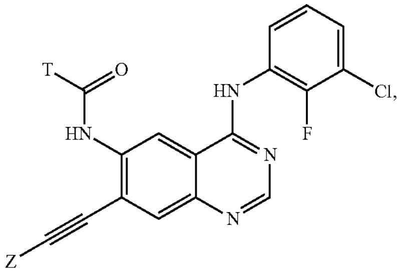

(IV-*a*)

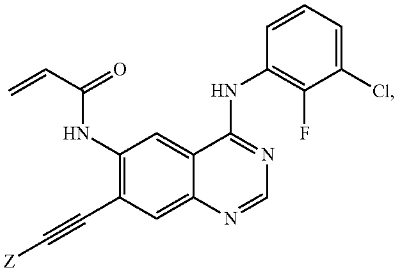

or a pharmaceutically acceptable salt or stereoisomer thereof.

Embodiment No. 116

The compound of any one of the preceding Embodiments, where in the compound is of formula I

I

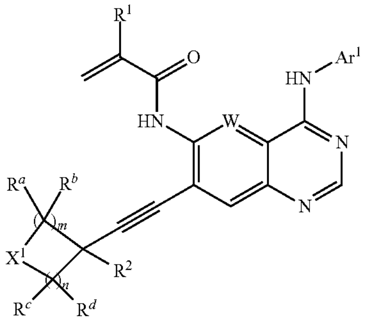

or a pharmaceutically acceptable salt or stereoisomer thereof, wherein

W is CH or N;

$X^1$ is —O—, —S—, —$NR^3$—;

$R^a$, $R^b$ are independently of each other hydrogen, $C_{1-4}$ alkyl or one of $R^a$ is —$(CH_2)_p$— which forms a ring with $X^1$ if $X^1$ is $NR^3$ or one of $R^a$ is —$(CH_2)_p$— which forms a ring with $R^2$ $R^c$, $R^d$ are independently of each other hydrogen or $C_{1-4}$ alkyl;

$R^1$ is H or F;

$R^2$ is hydrogen or $C_{1-4}$ alkyl, or is —$(CH_2)_q$— which forms a ring with $R^3$ or with one of $R^a$;

$R^3$ is hydrogen or $C_{1-4}$ alkyl, preferably hydrogen or methyl, or is —$(CH_2)_p$— which forms a ring with $R^2$;

m is 1, 2 or 3;

n is 0, 1 or 2;

p is 1 or 2;

q is 0, 1 or 2 and $Ar^1$ is a 6-membered aryl, which is unsubstituted or substituted with one or more of a group selected from halogen, —$CF_3$, $C_{1-6}$ alkyl, $C_{1-6}$ alkoxy, $C_{3-7}$ cycloalkyl, hydroxy $C_{1-5}$ alkyl, $C_{1-6}$ alkoxy-$C_{1-6}$ alkyl, $C_{1-6}$ alkoxy-$C_6$ aryl, $C_{1-6}$ alkoxy-$C_{5*6}$ heteroaryl, amino, amino $C_{1-4}$ alkyl, $C_{1-6}$ alkylamino, $C_{1-6}$ aminoalkyl-$C_6$ aryl, $C_{1-6}$ aminoalkyl-$C_{5-6}$ heteroaryl, $C_{1-6}$ alkoxycarbonyl, $C_{1-6}$ alkoxyaminocarbonyl, aryl $C_{1-6}$ alkoxy, or $C_6$ aryl.

Embodiment No. 117

The compound of any one of the preceding Embodiments, wherein when $X^1$ is —$NR^3$—, $R^2$ is not hydrogen.

Embodiment No. 118

The compound of any one of the preceding Embodiments, wherein when $X^1$ is —$NR^3$—, $R^2$ is $C_{1-4}$ alkyl, or is —$(CH_2)_q$— which forms a ring with $R^3$ or with one of $R^a$.

Embodiment No. 119

The compound of any one of the preceding Embodiments, wherein $X^1$ is —$NR^3$—, and $R^2$ is not hydrogen.

Embodiment No. 120

The compound of any one of the preceding Embodiments, wherein $X^1$ is —$NR^3$—, and $R^2$ is $C_{1-4}$ alkyl, or is —$(CH_2)_q$— which forms a ring with $R^3$ or with one of $R^a$.

Embodiment No. 121

The compound of any one of the preceding Embodiments, wherein when n is 0, $R^2$ is —$(CH_2)_q$— which forms a ring with $R^3$ or with one of $R^a$.

Embodiment No. 122

The compound of any one of the preceding Embodiments, wherein when n is 0, $R^2$ is —$(CH_2)_q$— which forms a ring with $R^3$.

Embodiment No. 123

The compound of any one of the preceding Embodiments, wherein n is 0, and $R^2$ is —$(CH_2)_q$— which forms a ring with $R^3$ or with one of $R^a$.

Embodiment No. 124

The compound of any one of the preceding Embodiments, wherein n is 0, and $R^2$ is —$(CH_2)_q$— which forms a ring with $R^3$.

Embodiment No. 125

The compound of any one of the preceding Embodiments, wherein $X^1$ is $NR^3$ or 0 and wherein $R^3$ is methyl, ethyl, n-propyl or n-butyl.

Embodiment No. 126

The compound of any one of the preceding Embodiments, wherein $R^1$ is hydrogen.

Embodiment No. 127

The compound of any one of the preceding Embodiments, wherein $R^2$ is methyl, ethyl, n-propyl or n-butyl-, preferably methyl or wherein $R^2$ is —$(CH_2)$— or —$(CH_2)_2$— which forms a ring with $R^3$, or wherein $R^2$ is —$(CH_2)$— or —$(CH_2)_2$— which forms a ring with one of $R^a$.

Embodiment No. 128

The compound of any one of the preceding Embodiments, wherein $Ar^1$ is of formula i or pharmaceutically acceptable salts or stereoisomers thereof i

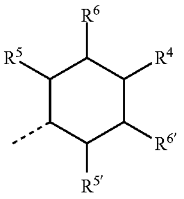

wherein $R^4$ is hydrogen, halogen, $C_{1-6}$ alkyl, $C_{1-6}$ alkoxy, $C_{3-7}$ cycloalkyl, hydroxy $C_{1-5}$ alkyl, $C_{1-6}$ alkoxy-$C_{1-6}$ alkyl, $C_{1-6}$ alkoxy-$C_6$ aryl, $C_{1-6}$ alkoxy-$C_{5*6}$ heteroaryl, amino $C_{1-4}$ alkyl, $C_{1-6}$ alkylamino, $C_{1-6}$ aminoalkyl-$C_6$ aryl, $C_{1-6}$ aminoalkyl-$C_{5-6}$ heteroaryl, $C_{1-6}$ alkoxycarbonyl, $C_{1-6}$ alkoxyaminocarbonyl, aryl $C_{1-6}$ alkoxy, or $C_6$ aryl;

$R^5$, $R^{5'}$, $R^6$, $R^{6'}$ are independently of each other hydrogen, —$CF_3$ or halogen, preferably F or Cl.

Embodiment No. 129

The compound of any one of the preceding Embodiments, wherein $R^5$ is F and/or wherein $R^6$ is F or Cl.

Embodiment No. 130

The compound of any one of the preceding Embodiments, wherein $R^1$ is hydrogen.

Embodiment No. 131

The compound of any one of the preceding Embodiments, wherein $R^2$ is methyl or wherein $R^2$ is —$(CH_2)$— or —$(CH_2)_2$— which forms a ring with $R^3$, or wherein $R^2$ is —$(CH_2)$— or —$(CH_2)_2$— which forms a ring with one of $R^a$.

Embodiment No. 132

The compound of any one of the preceding Embodiments, wherein $Ar^1$ is of formula ii-1, ii-2, ii-3 or ii-4 or pharmaceutically acceptable salts or stereoisomers thereof ii-1

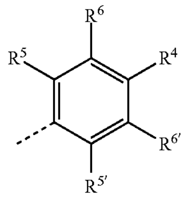

-continued ii-2

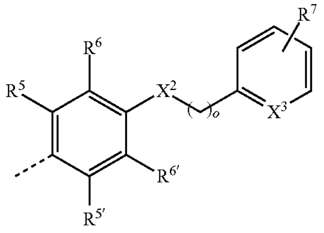

ii-3

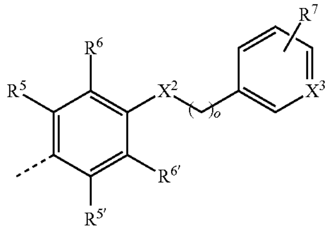

ii-4

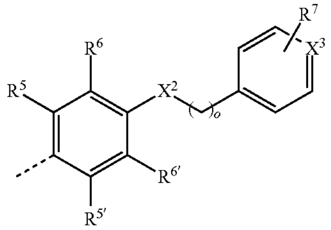

wherein $X^2$ is O, NH or NMe;

$X^3$ is CH or N;

is 0 or 1;

$R^4$ is hydrogen or halogen, preferably F or Cl;

$R^5$, $R^{5'}$, $R^6$, $R^{6'}$ are independently of each other hydrogen, —$CF_3$ or halogen, preferably F or Cl;

$R^7$ is hydrogen or halogen, preferably F.

Embodiment No. 133

The compound of any one of the preceding Embodiments, wherein $R^5$ is F and/or wherein $R^6$ is F or Cl.

Embodiment No. 134

The compound of any one of the preceding Embodiments, wherein $R^1$ is hydrogen.

Embodiment No. 135

The compound of any one of the preceding Embodiments, wherein $R^2$ is methyl or wherein $R^2$ is —$(CH_2)$— or —$(CH_2)_2$— which forms a ring with $R^3$ wherein $R^2$ is —$(CH_2)$— or —$(CH_2)_2$— which forms a ring with one of $R^a$.

Embodiment No. 136

The compound of any one of the preceding Embodiments, wherein $Ar^1$ is of formula iii-1, iii-3 or iii-4, iii-6 or iii-7 or pharmaceutically acceptable salts or stereoisomers thereof iii-1

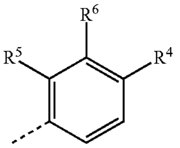

iii-2

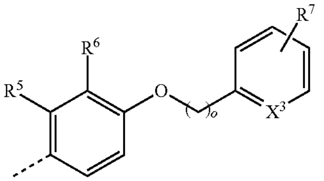

iii-3

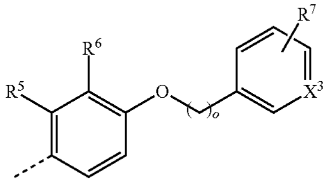

iii-4

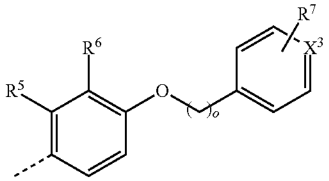

iii-5

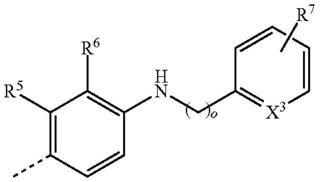

iii-6

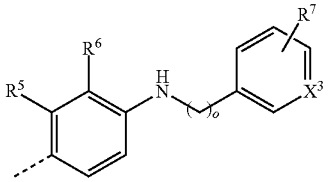

iii-7

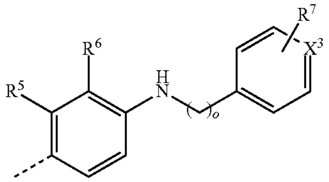

wherein $X^3$ is CH or N, preferably N;

is 0 or 1;

$R^4$ is hydrogen or halogen, preferably F or Cl;

$R^5$, $R^6$ are independently of each other hydrogen, $—CF_3$ or halogen, preferably F or Cl;

$R^7$ is hydrogen or halogen, preferably F.

Embodiment No. 137

The compound of any one of the preceding Embodiments, wherein $R^5$ is F and/or wherein $R^6$ is F or Cl.

Embodiment No. 138

The compound of any one of the preceding Embodiments, wherein $R^1$ is hydrogen.

Embodiment No. 139

The compound of any one of the preceding Embodiments, wherein $R^2$ is methyl or wherein $R^2$ is $—(CH_2)—$ or $—(CH_2)_2—$ which forms a ring with $R^3$ wherein $R^2$ is $—(CH_2)—$ or $—(CH_2)_2—$ which forms a ring with one of $R^a$.

Embodiment No. 140

The compound of any one of the preceding Embodiments, wherein $Ar^1$ is of formula iv-1, iv-2, iv-3 or iv-4, iv-5, iv-6, iv-7, iv-8 or iv-9 or pharmaceutically acceptable salts or stereoisomers thereof iv-1

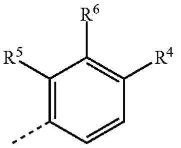

iv-2

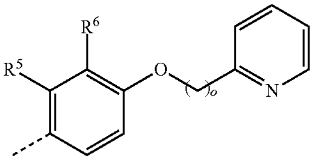

iv-3

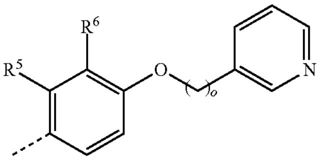

iv-4

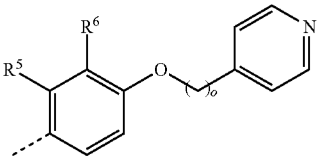

iv-5

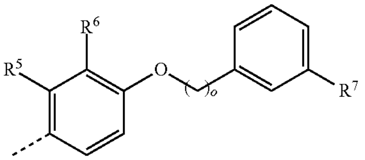

iv-6

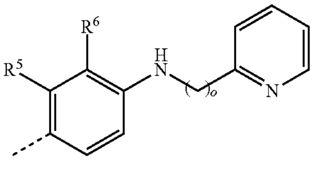

-continued iv-7

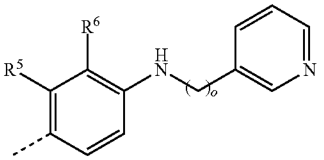

iv-8

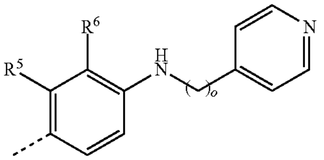

iv-9

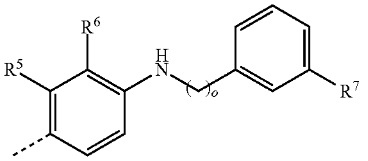

wherein is 0 or 1;

$R^4$ is hydrogen or halogen, preferably F or Cl;

$R^5$, $R^{5'}$, $R^6$, $R^{6'}$ are independently of each other hydrogen, —$CF_3$ or halogen, preferably F or Cl;

$R^7$ is hydrogen or halogen, preferably F.

Embodiment No. 141

The compound of any one of the preceding Embodiments, wherein $R^5$ is F and/or wherein $R^6$ is F or Cl.

Embodiment No. 142

The compound of any one of the preceding Embodiments, wherein $R^1$ is hydrogen.

Embodiment No. 143

The compound of any one of the preceding Embodiments, wherein $R^2$ is methyl or wherein $R^2$ is —$(CH_2)$— or —$(CH_2)_2$— which forms a ring with $R^3$ wherein $R^2$ is —$(CH_2)$— or —$(CH_2)_2$— which forms a ring with one of $R^a$.

Embodiment No. 144

The compound of any one of the preceding Embodiments, being of formula IIa or IIb IIa

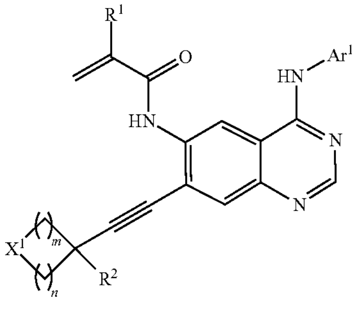

-continued

IIb

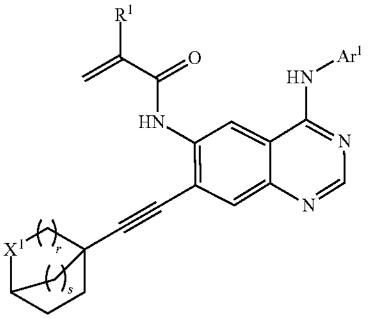

or a pharmaceutically acceptable salt or stereoisomer thereof, wherein $X^1$ is —O— or —$NR^3$—;

$R^1$ is H or F;

$R^2$ is hydrogen or $C_{1-4}$ alkyl, preferably methyl or is —$(CH_2)_q$— which forms a ring with $R^3$;

$R^3$ is hydrogen or $C_{1-4}$ alkyl, preferably hydrogen or methyl, or is —$(CH_2)_p$— which forms a ring with $R^2$;

m is 1, 2 or 3;

n is 0, 1 or 2;

p is 1 or 2;

q is 0, 1 or 2;

r is 0 or 1;

s is 1 or 2; and $Ar^1$ is a 6-membered aryl, which is unsubstituted or substituted with one or more of a group selected from halogen, —$CF_3$, $C_{1-6}$ alkyl, $C_{1-6}$ alkoxy, $C_{3-7}$ cycloalkyl, hydroxy $C_{1-5}$ alkyl, $C_{1-6}$ alkoxy-$C_{1-6}$ alkyl, $C_{1-6}$ alkoxy-$C_6$ aryl, $C_{1-6}$ alkoxy-$C_{5*6}$ heteroaryl, amino, amino $C_{1-4}$ alkyl, $C_{1-6}$ alkylamino, $C_{1-6}$ aminoalkyl-$C_6$ aryl, $C_{1-6}$ aminoalkyl-$C_{5-6}$ heteroaryl, $C_{1-6}$ alkoxycarbonyl, $C_{1-6}$ alkoxyaminocarbonyl, aryl $C_{1-6}$ alkoxy, or $C_6$ aryl.

Embodiment No. 145

The compound of any one of the preceding Embodiments, wherein $R^1$ is hydrogen.

Embodiment No. 146

The compound of any one of the preceding Embodiments, wherein $R^2$ is methyl or wherein $R^2$ is —$(CH_2)$— or —$(CH_2)_2$— which forms a ring with $R^3$.

Embodiment No. 147

The compound of any one of the preceding Embodiments, being of formula III

III

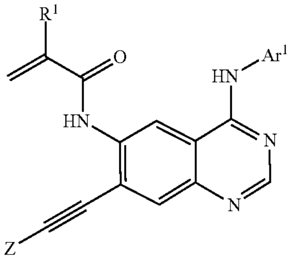

or a pharmaceutically acceptable salt or stereoisomer thereof, wherein $R^1$ is H or F;

$Ar^1$ is a 6-membered aryl, which is unsubstituted or substituted with one or more of a group selected from halogen, —$CF_3$, $C_{1-6}$ alkyl, $C_{1-6}$ alkoxy, $C_{3-7}$ cycloalkyl, hydroxy $C_{1-5}$ alkyl, $C_{1-6}$ alkoxy-$C_{1-6}$ alkyl, $C_{1-6}$ alkoxy-$C_6$ aryl, $C_{1-6}$ alkoxy-$C_{5*6}$ heteroaryl, amino, amino $C_{1-4}$ alkyl, $C_{1-6}$ alkylamino, $C_{1-6}$ aminoalkyl-$C_6$ aryl, $C_{1-6}$ aminoalkyl-$C_{5-6}$ heteroaryl, $C_{1-6}$ alkoxycarbonyl, $C_{1-6}$ alkoxyaminocarbonyl, or $C_6$ aryl;

Z is selected from

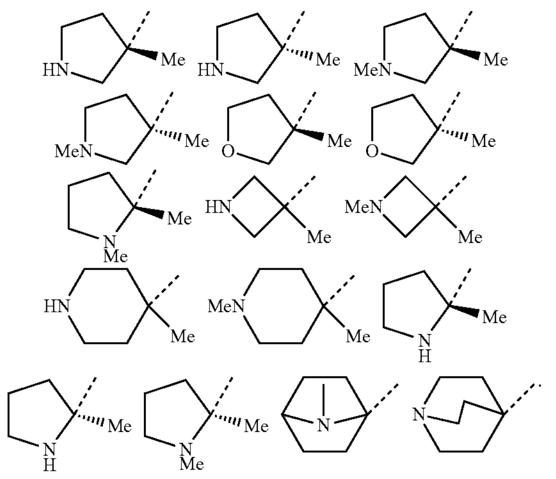

Embodiment No. 148

The compound of any one of the preceding Embodiments, wherein $R^1$ is hydrogen.

Embodiment No. 149

The compound of any one of the preceding Embodiments, being of formula IV

IV

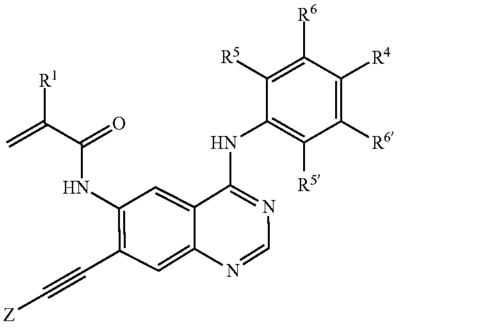

or a pharmaceutically acceptable salt or stereoisomer thereof, wherein $R^1$ is H or F;

$R^4$ is hydrogen, halogen, $C_{1-6}$ alkyl, $C_{1-6}$ alkoxy, $C_{3-7}$ cycloalkyl, hydroxy $C_{1-5}$ alkyl, $C_{1-6}$ alkoxy-$C_{1-6}$ alkyl, $C_{1-6}$ alkoxy-$C_6$ aryl, $C_{1-6}$ alkoxy-$C_{5*6}$ heteroaryl, amino $C_{1-4}$ alkyl, $C_{1-6}$ alkylamino, $C_{1-6}$ aminoalkyl-$C_6$ aryl, $C_{1-6}$ aminoalkyl-$C_{5-6}$ heteroaryl, $C_{1-6}$ alkoxycarbonyl, $C_{1-6}$ alkoxyaminocarbonyl or $C_6$ aryl;

$R^5$, $R^{5'}$, $R^6$, $R^{6'}$ are independently of each other hydrogen, —$CF_3$ or halogen, preferably F or Cl;

Z is selected from

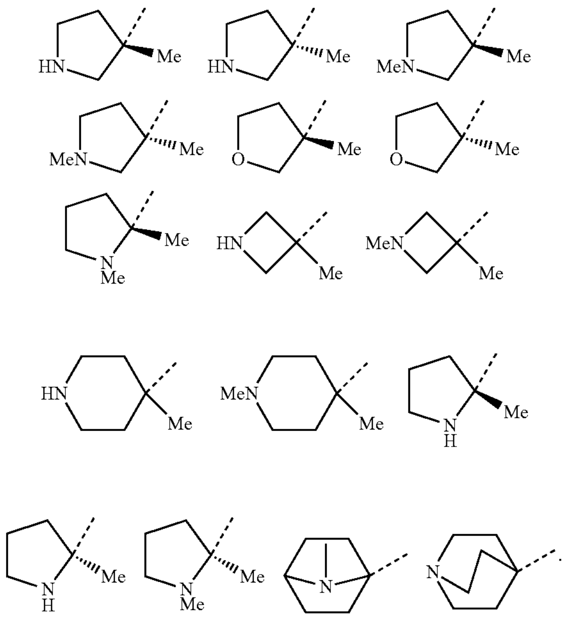

Embodiment No. 150

The compound of any one of the preceding Embodiments, wherein $R^5$ is F and/or wherein $R^6$ is F or Cl.

Embodiment No. 151

The compound of any one of the preceding Embodiments, wherein $R^1$ is hydrogen.

Embodiment No. 152

The compound of any one of the preceding Embodiments, being of formula V-1, V-2, V-3 or V-4

V-1

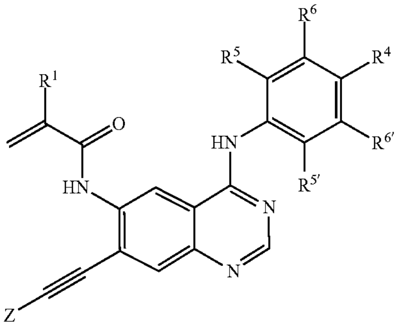

-continued

V-2

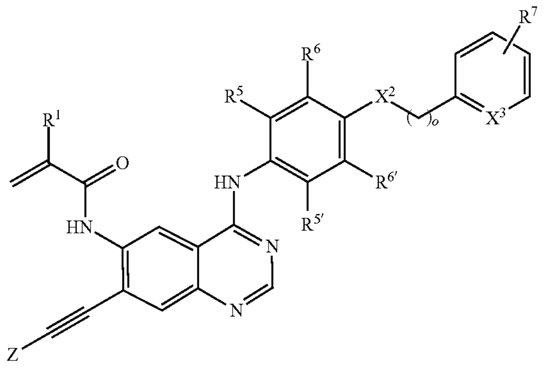

V-3

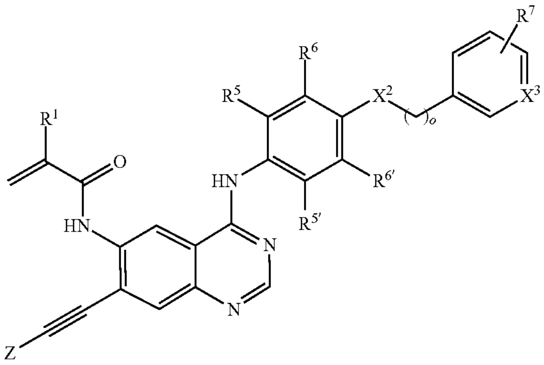

V-4

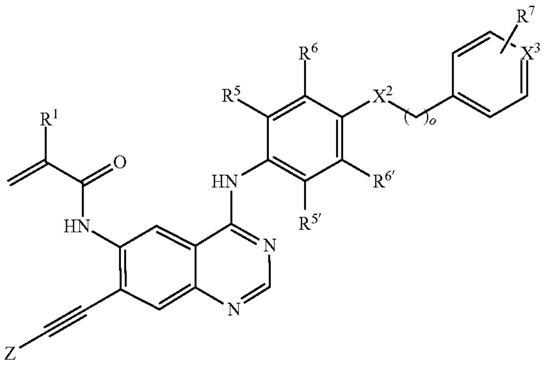

or a pharmaceutically acceptable salt or stereoisomer thereof, wherein $R^1$ is H or F;

$X^2$ is O, NH or NMe;

$X^3$ is C or N;

is 0 or 1;

$R^4$ is hydrogen or halogen, preferably F or Cl;

$R^5$, $R^{5'}$, $R^6$, $R^{6'}$ are independently of each other hydrogen, —$CF_3$ or halogen, preferably F or Cl;

$R^7$ is hydrogen or halogen, preferably F;

Z is selected from

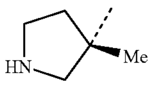
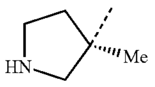
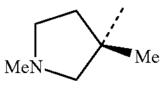

-continued

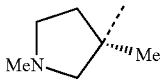
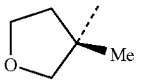
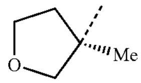
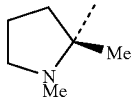
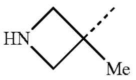
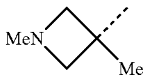
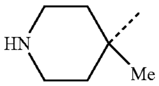
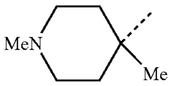
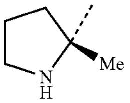
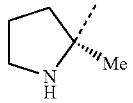
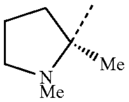
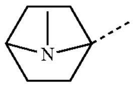
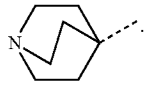

Embodiment No. 153

The compound of any one of the preceding Embodiments, wherein $R^5$ is F and/or wherein $R^6$ is F or Cl.

Embodiment No. 154

The compound of any one of the preceding Embodiments, wherein $R^1$ is hydrogen.

Embodiment No. 155

The compound of any one of the preceding Embodiments, being of formula VI-1, VI-2, VI-3 or VI-4

VI-1

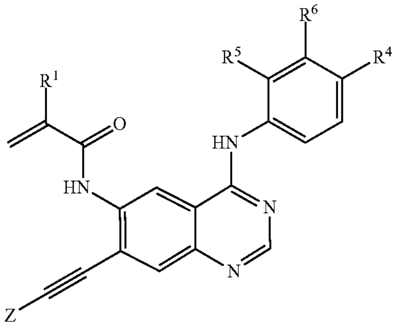

VI-2

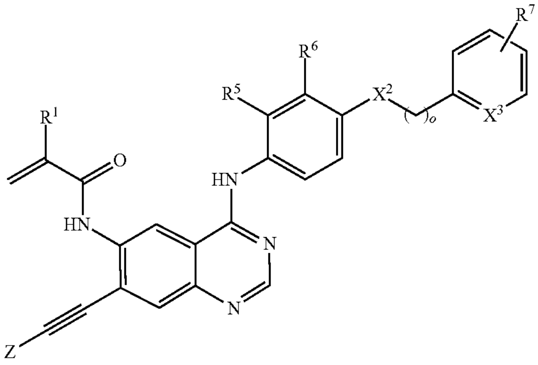

-continued

VI-3

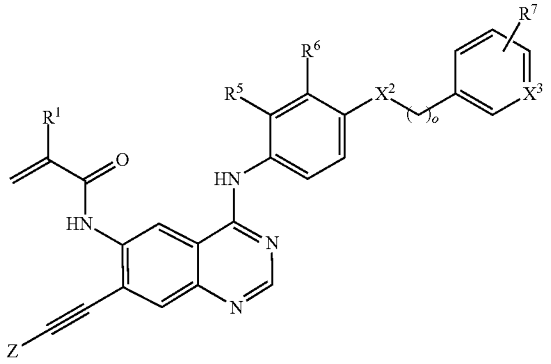

VI-4

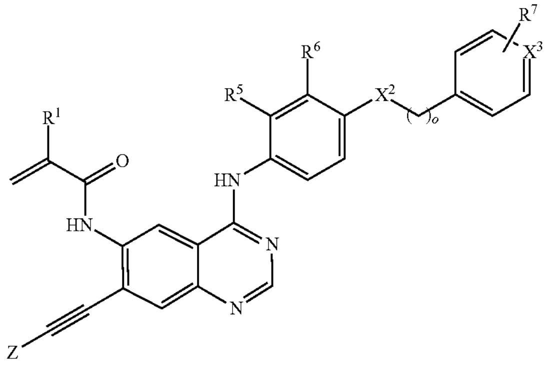

or a pharmaceutically acceptable salt or stereoisomer thereof, wherein $R^1$ is H or F;

$X^2$ is O, NH or NMe;

$X^3$ is C or N;

is 0 or 1;

$R^4$ is hydrogen or halogen, preferably F or Cl;

$R^5$, $R^6$ are independently of each other hydrogen, —$CF_3$ or halogen, preferably F or Cl;

$R^7$ is hydrogen or halogen, preferably F:

Z is selected from

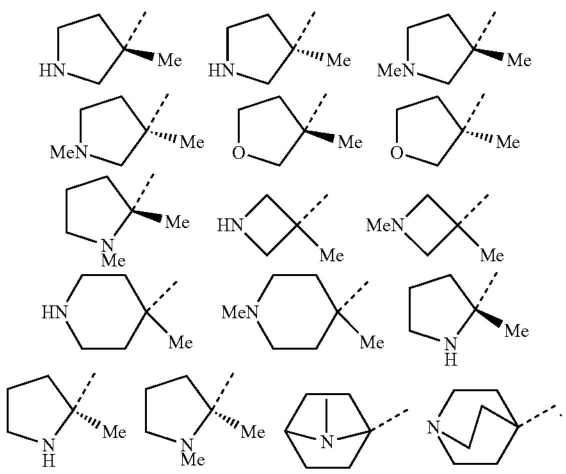

Embodiment No. 156

The compound of any one of the preceding Embodiments, wherein $R^5$ is F and/or wherein $R^6$ is F or Cl.

Embodiment No. 157

The compound of any one of the preceding Embodiments, wherein $R^1$ is hydrogen.

Embodiment No. 158

The compound of any one of the preceding Embodiments, being of formula VII-1, VII-2, VII-3 or VII-4, VII-5, VII-6 VII-7, VII-8 or VII-9

VII-1

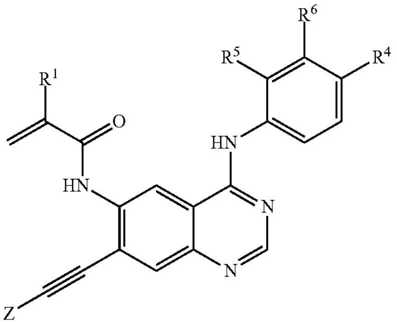

VII-2

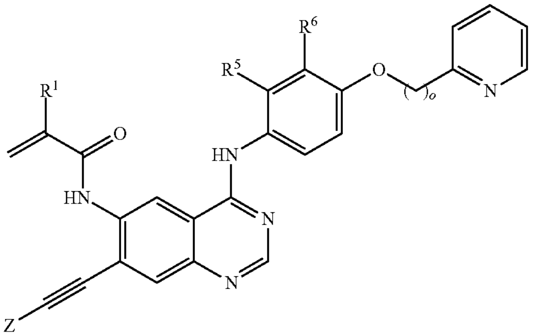

VII-3

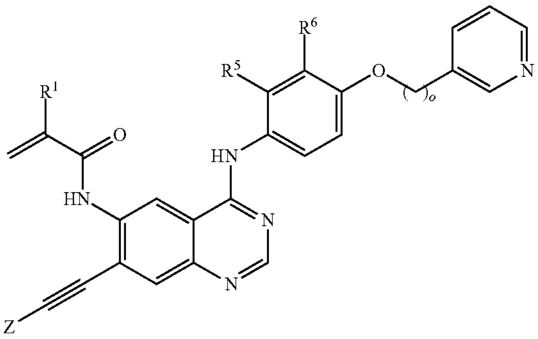

-continued

VII-4

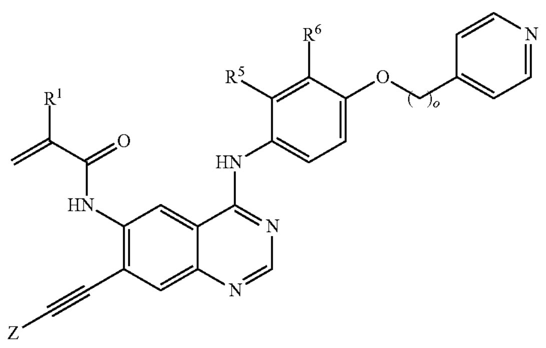

VII-5

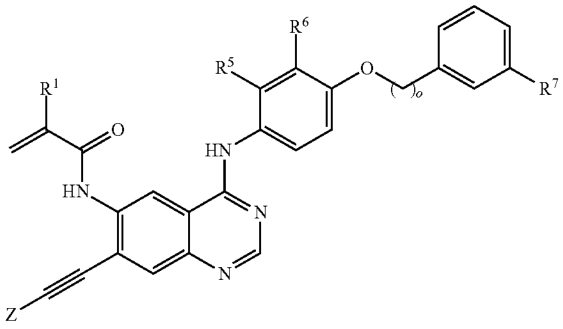

VII-6

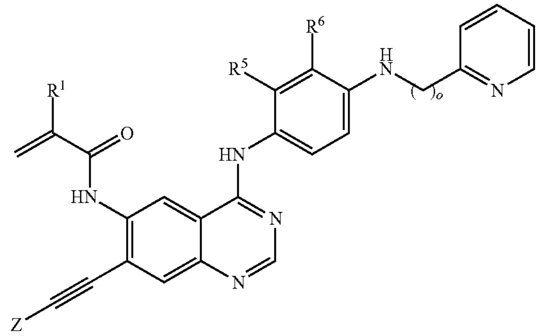

VII-7

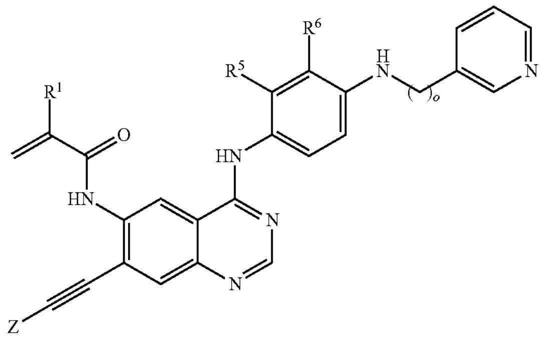

-continued

VII-8

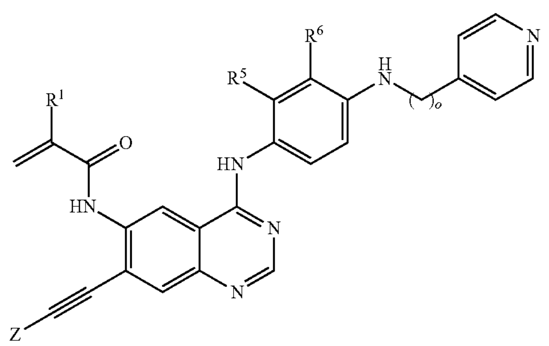

VII-9

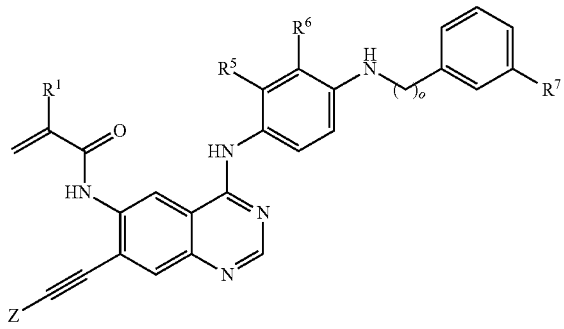

or a pharmaceutically acceptable salt or stereoisomer thereof, wherein $R^1$ is H or F;

is 0 or 1;

$R^4$ is hydrogen or halogen, preferably F or Cl;

$R^5$, $R^6$ are independently of each other hydrogen, —$CF_3$ or halogen, preferably F or Cl;

$R^7$ is hydrogen or halogen, preferably F;

Z is selected from

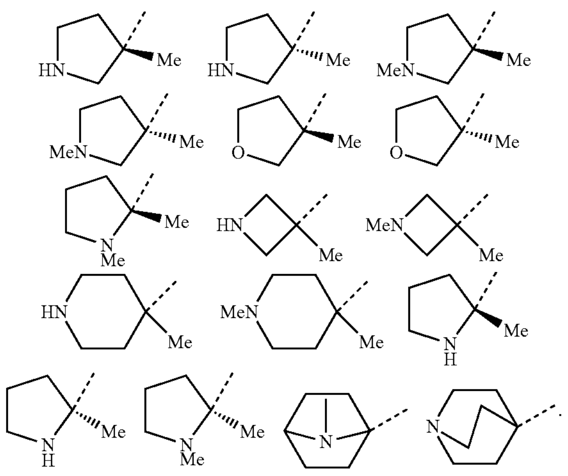

Embodiment No. 159

The compound of any one of the preceding Embodiments, wherein $R^5$ is F and/or wherein $R^6$ is F or Cl.

Embodiment No. 160

The compound of any one of the preceding Embodiments, wherein $R^1$ is hydrogen.

Embodiment No. 161

The compound of any one of the preceding Embodiments, being selected from the compounds described in Tables 1 and 2, pharmaceutically acceptable salts thereof, and stereoisomers thereof.

Embodiment No. 162

The compound of any one of the preceding Embodiments, being selected from the compounds described in Tables 1 and 2 and pharmaceutically acceptable salts thereof.

Embodiment No. 163

The compound of any one of the preceding Embodiments, being selected from the compounds described in Tables 1 and 2.

Embodiment No. 164

A composition comprising to the compound of any one of the preceding Embodiments, and a pharmaceutically acceptable carrier.

Embodiment No. 165

The composition of any one of the preceding Embodiments, further comprising a second therapeutically active agent.

Embodiment No. 166

A method of inhibiting an oncogenic variant of an ErbB receptor, comprising administering the subject in need thereof a therapeutically effective amount of the compound of any one of the preceding Embodiments.

Embodiment No. 167

A method of inhibiting an oncogenic variant of an ErbB receptor, comprising administering the subject in need thereof the composition of any one of the preceding Embodiments.

Embodiment No. 168

A method of preventing or treating cancer, comprising administering the subject in need thereof a therapeutically effective amount of the compound of any one of the preceding Embodiments.

Embodiment No. 169

A method of preventing or treating cancer, comprising administering the subject in need thereof the composition of any one of the preceding Embodiments.

Embodiment No. 170

The compound of any one of the preceding Embodiments for use in the prevention or treatment of cancer.

Embodiment No. 171

The compound of any one of the preceding Embodiments for use in the inhibition of an oncogenic variant of an ErbB receptor.

Embodiment No. 172

The composition of any one of the preceding Embodiments for use in the inhibition of an oncogenic variant of an ErbB receptor.

Embodiment No. 173

The composition of any one of the preceding Embodiments for use in the prevention or treatment of cancer.

Embodiment No. 174

The method, the compound for use, or the composition for use of any one of the preceding Embodiments, wherein the cancer is a solid tumor.

Embodiment No. 175

The method, the compound for use, or the composition for use of any one of the preceding Embodiments, wherein the cancer is a bladder cancer, a breast cancer, a cervical cancer, a colorectal cancer, an endometrial cancer, a gastric cancer, a glioblastoma (GBM), a head and neck cancer, a lung cancer, a non-small cell lung cancer (NSCLC), or any subtype thereof.

Embodiment No. 176

The method, the compound for use, or the composition for use of any one of the preceding Embodiments, wherein the cancer is glioblastoma (GBM) or any subtype thereof.

Embodiment No. 177

The method, the compound for use, or the composition for use of any one of the preceding Embodiments, wherein the cancer is glioblastoma.

Embodiment No. 178

The method, the compound for use, or the composition for use of any one of the preceding Embodiments, wherein the cancer, or a tumor or a cell thereof, expresses an oncogenic variant of an ErbB receptor.

Embodiment No. 179

The method, the compound for use, or the composition for use of any one of the preceding Embodiments, wherein the oncogenic variant of the ErbB receptor comprises an allosteric mutation.

Embodiment No. 180

The method, the compound for use, or the composition for use of any one of the preceding Embodiments, wherein the oncogenic variant of an ErbB receptor is is an allosteric variant of the ErbB receptor.

Embodiment No. 181

The method, the compound for use, or the composition for use of any one of the preceding Embodiments, wherein the cancer, or a tumor or a cell thereof, expresses an oncogenic variant of an epidermal growth factor receptor (EGFR).

Embodiment No. 182

The method, the compound for use, or the composition for use of any one of the preceding Embodiments, wherein the oncogenic variant of EGFR is an allosteric variant of EGFR.

Embodiment No. 183

The method, the compound for use, or the composition for use of any one of the preceding Embodiments, wherein the oncogenic variant of EGFR comprises an allosteric mutation.

Embodiment No. 184

The method, the compound for use, or the composition for use of any one of the preceding Embodiments, wherein the cancer, or a tumor or a cell thereof, expresses an oncogenic variant of a human epidermal growth factor receptor 2 (HER2) receptor.

Embodiment No. 185

The method, the compound for use, or the composition for use of any one of the preceding Embodiments, wherein the oncogenic variant of the HER2 receptor is an allosteric variant of the HER2 receptor.

Embodiment No. 186

The method, the compound for use, or the composition for use of any one of the preceding Embodiments, wherein the oncogenic variant of the HER2 receptor comprises an allosteric mutation.

Embodiment No. 187

The method, the compound for use, or the composition for use of any one of the preceding Embodiments, wherein the oncogenic variant or the oncogenic mutation is detected by a Food and Drug Administration (FDA)-approved diagnosis.

Embodiment No. 188

The method, the compound for use, or the composition for use of any one of the preceding Embodiments, wherein prior to the treatment with the compound of the present disclosure, the subject is treated with a therapeutic agent different from the compound of any one of the preceding Embodiments.

Embodiment No. 189

The method, the compound for use, or the composition for use of any one of the preceding Embodiments, wherein the cancer, or a tumor or a cell thereof, is insensitive or resistant to treatment with the therapeutic agent different from the compound of any one of the preceding Embodiments.

Embodiment No. 190

The method, the compound for use, or the composition for use of any one of the preceding Embodiments, wherein the subject has an adverse reaction to treatment with a therapeutic agent different from the compound of any one of the preceding Embodiments.

Embodiment No. 191

The method, the compound for use, or the composition for use of any one of the preceding Embodiments, wherein the therapeutically effective amount reduces a severity of a sign or symptom of the cancer.

Embodiment No. 192

The method, the compound for use, or the composition for use of any one of the preceding Embodiments, wherein the sign of the cancer comprises a tumor grade and wherein a reduction of the severity of the sign comprises a decrease of the tumor grade.

Embodiment No. 193

The method, the compound for use, or the composition for use of any one of the preceding Embodiments, wherein the sign of the cancer comprises a tumor metastasis and wherein a reduction of the severity of the sign comprises an elimination of the metastasis or a reduction in the rate or extent the metastasis.

Embodiment No. 194

The method, the compound for use, or the composition for use of any one of the preceding Embodiments, wherein the sign of the cancer comprises a tumor volume and wherein a reduction of the severity of the sign comprises an elimination of the tumor or a reduction in the volume.

Embodiment No. 195

The method, the compound for use, or the composition for use of any one of the preceding Embodiments, wherein the symptom of the cancer comprises pain and wherein a reduction of the severity of the sign comprises an elimination or a reduction in the pain.

Embodiment No. 196

The method, the compound for use, or the composition for use of any one of the preceding Embodiments, wherein the therapeutically effective amount induces a period of remission.

Embodiment No. 197

The method, the compound for use, or the composition for use of any one of the preceding Embodiments, wherein the therapeutically effective amount improves a prognosis of the subject.

Embodiment No. 198

A method of preventing or treating glioblastoma, comprising administering the subject in need thereof a therapeutically effective amount of the compound of any one of the preceding Embodiments.

Embodiment No. 199

A method of preventing or treating glioblastoma, comprising administering the subject in need thereof the composition of any one of the preceding Embodiments.

Embodiment No. 200

The compound of any one of the preceding Embodiments for use in the prevention or treatment of glioblastoma.

Embodiment No. 201

The composition of any one of the preceding Embodiments for use in the prevention or treatment of glioblastoma.

Embodiment No. 202

The method, the compound for use, or the composition for use of any one of the preceding Embodiments, wherein the compound is selected from the compounds described in Tables 1 and 2, pharmaceutically acceptable salts thereof, and stereoisomers thereof.

Embodiment No. 203

The method, the compound for use, or the composition for use of any one of the preceding Embodiments, wherein the compound is selected from the compounds described in Tables 1 and 2 and pharmaceutically acceptable salts thereof.

Embodiment No. 204

The method, the compound for use, or the composition for use of any one of the preceding Embodiments, wherein the compound is selected from the compounds described in Table 1 and 2.

EXAMPLES

Preparation of (R)-tert-butyl 2-ethynyl-2-methylpyrrolidine-1-carboxylate (S5)

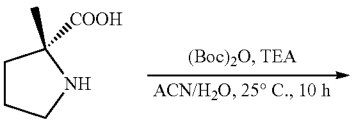

S1

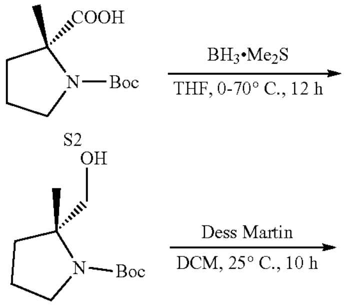

S2

S3

-continued

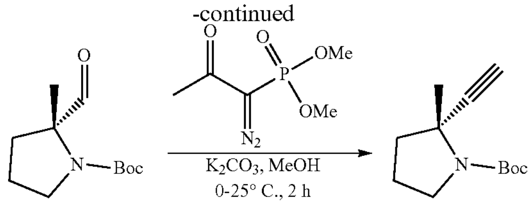

S4 S5

S2: To a solution of (R)-2-methylpyrrolidine-2-carboxylic acid S1 (3.00 g, 23.3 mmol, 1.00 eq) and triethylamine (7.05 g, 69.7 mmol, 9.70 mL, 3.00 eq) in a mixture solvent of water (20.0 mL) and acetonitrile (20.0 mL) was added di-tert-butyl dicarbonate (5.58 g, 25.6 mmol, 5.87 mL, 1.10 eq). The mixture was stirred at 25° C. for 10 h. The pH of the reaction mixture was adjusted to around 2.00 by progressively adding aqueous solution of hydrochloric acid (2.00 M, 15.0 ml). The mixture was filtered and concentrated to give (R)-1-(tert-butoxycarbonyl)-2-methylpyrrolidine-2-carboxylic acid S2 (4.20 g, crude) as a white solid. $^1H$ NMR (400 MHz, CDC13) δ=3.65-3.46 (m, 4H), 2.59 (br d, J=5.1 Hz, 1H), 2.34-2.25 (m, 1H), 2.03-1.92 (m, 2H), 1.91-1.79 (m, 4H), 1.63 (s, 3H), 1.55-1.53 (m, 3H), 1.49 (s, 9H).

S3: To a solution of (R)-1-(tert-butoxycarbonyl)-2-methylpyrrolidine-2-carboxylic acid S2 (5.30 g, 23.1 mmol, 1.00 eq) in tetrahydrofuran (50.0 mL) was added borane dimethyl sulfide complex (10.0 M, 4.62 mL, 2.00 eq) dropwise at 0° C. Then the mixture was stirred at 70° C. for 12 h. The reaction mixture was quenched by methanol (15.0 ml) and concentrated to give a residue. The residue was purified by silica gel column chromatography (petroleum ether/ethyl acetate=3/1) to afford (R)-tert-butyl 2-(hydroxymethyl)-2-methylpyrrolidine-1-carboxylate S3 (1.10 g, 5.11 mmol, 22% yield) as yellow oil. $^1H$ NMR (400 MHz, $CDCl_3$) δ=3.72-3.64 (m, 1H), 3.63-3.50 (m, 2H), 3.38-3.27 (m, 1H), 2.03-1.70 (m, 4H), 1.47 (s, 9H), 1.38 (s, 3H).

S4: To a solution of (R)-tert-butyl 2-(hydroxymethyl)-2-methylpyrrolidine-1-carboxylate S3 (1.10 g, 5.11 mmol, 1.00 eq) in dichloromethane (15.0 mL) was added (1,1-diacetoxy-3-oxo-1,2-benziodoxol-1-yl) acetate (2.60 g, 6.13 mmol, 1.90 mL, 1.20 eq). The mixture was stirred at 25° C. for 10 h. The reaction mixture was filtered and the filtrate was poured into saturated aqueous solution of sodium carbonate (60.0 mL). The aqueous phase was extracted with ethyl acetate (3×40.0 mL). The combined organic phase was washed with brine (2×30.0 mL), dried over anhydrous sodium sulfate, filtered and concentrated in vacuum to afford (R)-tert-butyl 2-formyl-2-methylpyrrolidine-1-carboxylate S4 (0.900 g, 4.22 mmol, 83% yield) as a yellow oil. It was used for the next step directly. $^1H$ NMR (400 MHz, $CDCl_3$) δ=9.26 (s, 1H), 3.50-3.36 (m, 2H), 1.89 (dd, J=1.3, 5.8 Hz, 2H), 1.66-1.49 (m, 2H), 1.34 (s, 9H), 1.31 (s, 3H).

S5: To a solution of (R)-tert-butyl 2-formyl-2-methylpyrrolidine-1-carboxylate S4 (0.900 g, 4.22 mmol, 1.00 eq) in methanol (8.00 mL) was added potassium carbonate (1.17 g, 8.44 mmol, 2.00 eq) and dimethyl (1-diazo-2-oxopropyl) phosphonate (1.22 g, 6.33 mmol, 1.50 eq) dropwise at 0° C. Then the mixture was stirred at 25° C. for 2 h. The reaction mixture was concentrated in vacuum to give a residue. The residue was purified by silica gel column chromatography (petroleum ether/ethyl acetate=10/1) to afford (R)-tert-butyl 2-ethynyl-2-methylpyrrolidine-1-carboxylate S5 (0.620 g, 2.96 mmol, 70% yield) as a colorless oil. $^1H$ NMR (400

MHz, $CDCl_3$) δ=3.56-3.40 (m, 1H), 3.36-3.25 (m, 1H), 2.21 (br s, 2H), 1.94-1.81 (m, 2H), 1.78-1.67 (m, 1H), 1.55 (br s, 3H), 1.42 (s, 9H).

Example 1. Synthesis of Compound 1

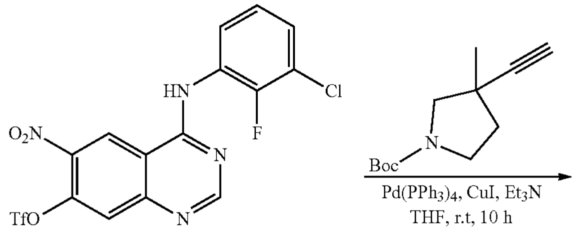

S6

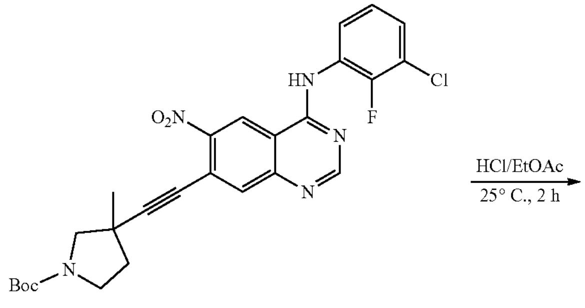

S7

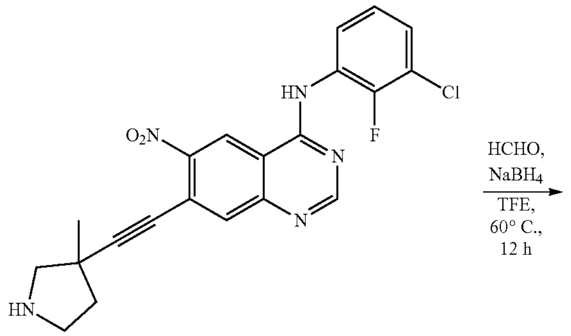

S8

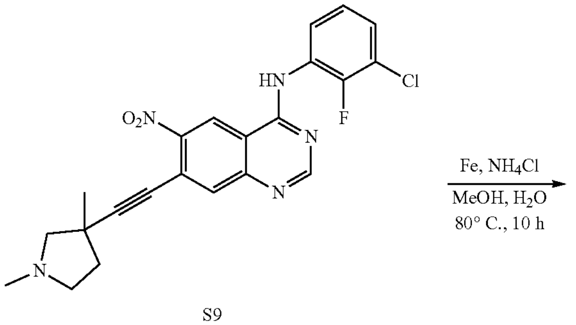

S9

-continued

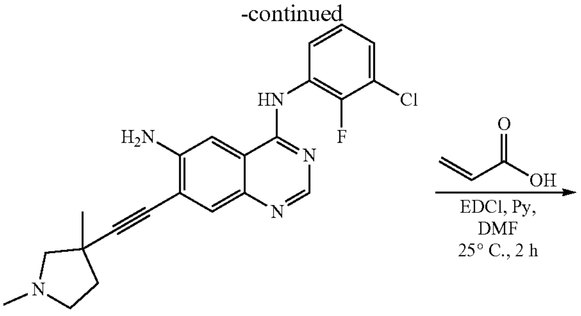

S10

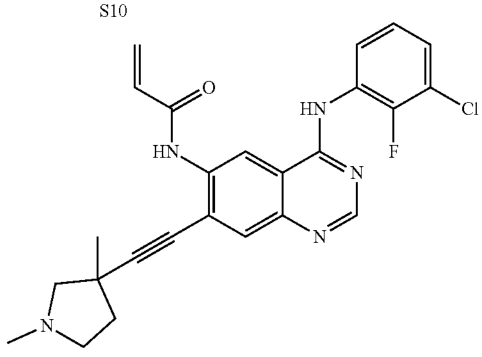

1

Synthesis of S6: To a solution of 7-fluoro-6-nitro-quinazolin-4-ol (5.00 g, 23.9 mmol, 1.00 eq) in thionyl chloride (82.0 g, 689 mmol, 50.0 mL, 28.8 eq) was added dropwise dimethylformamide (175 mg, 2.39 mmol, 184 uL, 0.100 eq) as catalyst. The mixture was heated to 80° C. and stirred for 12 h. The reaction mixture was concentrated to afford 4-chloro-7-fluoro-6-nitro-quinazoline (5.44 g, 23.9 mmol, 100% yield) as a white solid. The product was used in next step directly.

To a solution of 4-chloro-7-fluoro-6-nitro-quinazoline (5.44 g, 23.9 mmol, 1.00 eq) in iso-propanol (100 mL) was added 3-chloro-2-fluoro-aniline (3.83 g, 26.3 mmol, 1.10 eq). The mixture was stirred at 90° C. for 2 hr. The mixture was concentrated to afford a yellow solid which was triturated with ethyl acetate (50.0 mL). After filtration, the filter cake was washed with ethyl acetate (20.0 mL), dried in vacuum to afford N-(3-chloro-2-fluoro-phenyl)-7-fluoro-6-nitro-quinazolin-4-amine (8.40 g, crude) as a yellow solid. $^1H$ NMR (400 MHz, DMSO-$d_6$) δ=12.5 (br s, 1H), 9.7-10.0 (m, 1H), 8.8-8.9 (m, 1H), 7.9-8.1 (m, 1H), 7.6 (td, J=7.46, 1.47 Hz, 1H), 7.5 (br t, J=7.34 Hz, 1H), 7.3-7.4 (m, 1H). MS (ESI) m/z 336.9 $[M+H]^+$ To a solution of N-(3-chloro-2-fluorophenyl)-7-fluoro-6-nitroquinazolin-4-amine (8.40 g, 25.0 mmol, 1.00 eq) in dimethylformamide (100 mL) was added potassium acetate (12.2 g, 125 mmol, 5.00 eq) at 15° C. The mixture was stirred at 100° C. for 1 h. The mixture was concentrated to afford a residue. The residue was diluted with water (100 mL). After filtration, the filter cake was washed with water (30.0 mL), dried in vacuum to afford 4-((3-chloro-2-fluorophenyl)amino)-6-nitroquinazolin-7-ol S93 (9.00 g, crude) as a brown solid. $^1H$ NMR (400 MHz, DMSO-$d_6$) δ=9.0 (s, 1H), 8.3 (s, 1H), 7.4-7.5 (m, 2H), 7.2-7.3 (m, 1H), 7.0-7.1 (m, 1H). MS (ESI) m/z 335.2 $[M+H]^+$ To a solution of 4-((3-chloro-2-fluorophenyl)amino)-6-nitroquinazolin-7-ol S93 (9.00 g, 26.9 mmol, 1.00 eq) and pyridine (10.6 g, 134 mmol, 10.9 mL, 5.00 eq) in dichloromethane (200 mL) was added trifluoromethanesulfonic anhydride (15.2 g, 53.8 mmol, 8.87 mL, 2.00 eq) at 0° C. The mixture was stirred at 20° C. for 12 h. The mixture was concentrated to afford a residue. The residue was purified by silica gel chromatography (petroleum ether/ethyl acetate=1: 1-0:1) to afford 4-((3-chloro-2-fluorophenyl)amino)-6-nitro-quinazolin-7-yl trifluoromethanesulfonate S6 (4.00 g, 7.97 mmol, 30% yield, 93% purity) as a yellow solid. $^1$H NMR (400 MHz, DMSO-$d_6$) δ=10.9 (br s, 1H), 9.7 (br s, 1H), 8.7 (br d, J=9.41 Hz, 1H), 8.1 (br s, 1H), 7.5-7.6 (m, 2H), 7.3-7.4 (m, 1H). MS (ESI) m/z 467.2 $[M+H]^+$ S7: A mixture of 4-((3-chloro-2-fluorophenyl)amino)-6-nitroquinazolin-7-yl trifluoromethanesulfonate S6 (0.500 g, 1.07 mmol, 1.00 eq), tert-butyl 3-ethynyl-3-methylpyrrolidine-1-carboxylate (291 mg, 1.39 mmol, 1.30 eq), tetrakis (triphenylphosphine) palladium(0) (124 mg, 107 umol, 0.100 eq), cuprous iodide (40.8 mg, 214 umol, 0.200 eq) and triethylamine (325 mg, 3.21 mmol, 447 uL, 3.00 eq) in tetrahydrofuran (10.0 mL) was stirred at 25° C. in nitrogen atmosphere for 10 h. The reaction mixture was filtered and concentrated under reduced pressure to give a residue. The residue was purified by column chromatography (petroleum ether/ethyl acetate=1/1) to give tert-butyl 3-((4-((3-chloro-2-fluorophenyl)amino)-6-nitroquinazolin-7-yl) ethynyl)-3-methyl pyrrolidine-1-carboxylate S7 (525 mg, 998 umol, 93% yield) as a yellow solid. $^1$H NMR (400 MHz, $CDCl_3$) δ=8.88 (s, 1H), 8.79 (d, J=3.4 Hz, 1H), 8.31 (t, J=7.4 Hz, 1H), 8.11 (s, 1H), 8.02-7.94 (m, 1H), 7.44-7.34 (m, 1H), 7.25-7.19 (m, 1H), 3.83-3.70 (m, 1H), 3.68-3.49 (m, 2H), 3.38-3.30 (m, 1H), 2.36-2.27 (m, 1H), 2.02-1.92 (m, 1H), 1.55-1.47 (m, 12H).

S8: A mixture of N-(3-chloro-2-fluorophenyl)-7-((3-methylpyrrolidin-3-yl)ethynyl)-6-nitroquinazolin-4-amine S7 (0.520 g, 998 umol, 1.00 eq) in hydrochloric acid/ethyl acetate (5.00 mL) was stirred at 25° C. for 2 h. The reaction mixture was concentrated under reduced pressure to afford N-(3-chloro-2-fluorophenyl)-7-((3-methylpyrrolidin-3-yl) ethynyl)-6-nitroquinazolin-4-amine S8 (0.500 g, crude, hydrochloric acid) as a yellow solid.

S9: To a solution of N-(3-chloro-2-fluorophenyl)-7-((3-methylpyrrolidin-3-yl)ethynyl)-6-nitroquinazolin-4-amine S8 (0.500 g, 1.17 mmol, 1.00 eq) and paraformaldehyde (176 mg, 5.87 mmol, 162 uL, 5.00 eq) in trifluoroethanol (8.00 mL) was added sodium borohydride (88.8 mg, 2.35 mmol, 2.00 eq). Then the mixture was stirred at 60° C. for 12 h. The reaction mixture was quenched by addition methanol (10.0 mL), and concentrated to obtain a residue. Then the mixture diluted with water (10.0 mL) and extracted with ethyl acetate (3×25.0 mL). The combined organic layers were washed with brine (15.0 mL), dried over sodium sulfate, filtered and concentrated under reduced pressure to give N-(3-chloro-2-fluorophenyl)-7-((1,3-dimethylpyrrolidin-3-yl)ethynyl)-6-nitroquinazolin-4-amine S9 (0.500 g, crude) as a yellow solid. $^1$H NMR (400 MHz, $CDCl_3$) δ=8.91-8.78 (m, 1H), 8.16-8.05 (m, 1H), 7.63 (br dd, J=8.0, 12.0 Hz, 1H), 7.59-7.53 (m, 1H), 7.49-7.44 (m, 1H), 7.17 (br t, J=7.8 Hz, 1H), 4.02-3.87 (m, 1H), 2.95 (d, J=9.2 Hz, 1H), 2.77-2.69 (m, 1H), 2.67-2.59 (m, 1H), 2.46-2.30 (m, 4H), 1.99-1.91 (m, 1H), 1.53 (s, 3H).

S10: A mixture of N-(3-chloro-2-fluorophenyl)-7-((1,3-dimethylpyrrolidin-3-yl)ethynyl)-6-nitroquinazolin-4-amine S9 (0.500 g, 1.14 mmol, 1.00 eq), ammonium chloride (182 mg, 3.41 mmol, 3.00 eq) and iron powder (190 mg, 3.41 mmol, 3.00 eq) in water (8.00 mL) and methanol (8.00 mL) was stirred at 80° C. for 10 h. The reaction mixture was filtered and the filtration was concentrated under reduced pressure to give a residue. The residue was purified by reverse phase chromatography (column: $C_{18}$, condition: H2O-0.1% FA-acetonitrile) and lyophilized to give $N^4$-(3-chloro-2-fluorophenyl)-7-((1,3-dimethylpyrrolidin-3-yl) ethynyl)quinazoline-4,6-diamine S10 (over two steps 0.220 g, 444 umol, 85% purity) as a yellow solid. $^1$H NMR (400 MHz, $CD_3OD$) δ=8.27 (s, 1H), 7.98 (s, 1H), 7.74 (s, 1H), 7.64-7.58 (m, 1H), 7.45-7.38 (m, 2H), 7.24 (br dd, J=1.2, 8.2 Hz, 1H), 3.87 (br d, J=11.8 Hz, 1H), 3.82-3.72 (m, 1H), 3.66-3.54 (m, 1H), 3.38 (br d, J=12.6 Hz, 1H), 2.86 (s, 3H), 2.66-2.56 (m, 1H), 2.39-2.27 (m, 1H), 1.71-1.62 (m, 3H).

1: A mixture of $N^4$-(3-chloro-2-fluorophenyl)-7-((1,3-dimethylpyrrolidin-3-yl)ethynyl)quinazoline-4,6-diamine 510 (0.250 g, 609 umol, 1.00 eq), acrylic acid (57.1 mg, 792 umol, 54.4 uL, 1.30 eq), pyridine (144 mg, 1.83 mmol, 147 uL, 3.00 eq) and 1-ethyl-3-(3-dimethylamino-propyl)-carbodiimide hydrochloride (350 mg, 1.83 mmol, 3.00 eq) in dimethyl formamide (2.00 ml) was stirred at 25° C. for 2 hr. The reaction mixture was filtered and the filtration was purified by prep-HPLC (column: Xtimate C18 150×25 mm×5 um; mobile phase: [water (0.05% ammonia hydroxide v/v)-ACN]; B %: 48%-78%, 10 min) and lyophilized to give N-(4-((3-chloro-2-fluorophenyl)amino)-7-((1,3-dimethylpyrrolidin-3-yl)ethynyl)quinazolin-6-yl)acrylamide 1 (35.3 mg, 74.5 umol, 12% yield, 98% purity) as a yellow solid. $^1$H NMR (400 MHz, $CDCl_3$) δ=9.13 (s, 1H), 8.69-8.63 (m, 1H), 8.60-8.54 (m, 1H), 8.28 (dt, J=2.2, 7.4 Hz, 1H), 7.87 (s, 1H), 7.73 (br s, 1H), 7.16-7.05 (m, 2H), 6.52-6.43 (m, 1H), 6.40-6.29 (m, 1H), 5.80 (dd, J=1.2, 10.0 Hz, 1H), 3.01 (d, J=8.8 Hz, 1H), 2.92 (dt, J=5.8, 8.8 Hz, 1H), 2.55-2.46 (m, 1H), 2.41-2.35 (m, 4H), 2.34-2.26 (m, 1H), 1.91 (ddd, J=5.8, 8.8, 12.8 Hz, 1H), 1.47 (s, 3H). MS (ESI) m/z 464.2 $[M+H]^+$.

Example 2. Synthesis of Compound 2

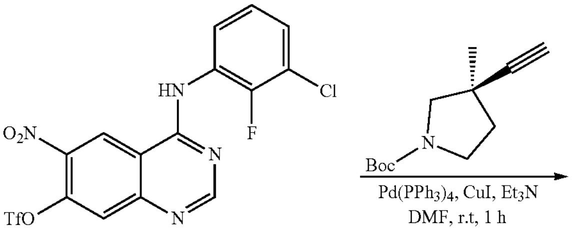

S6

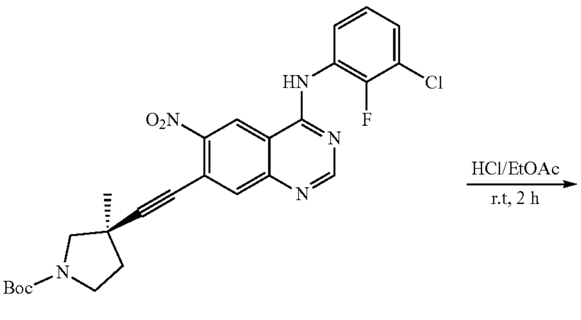

S11

-continued

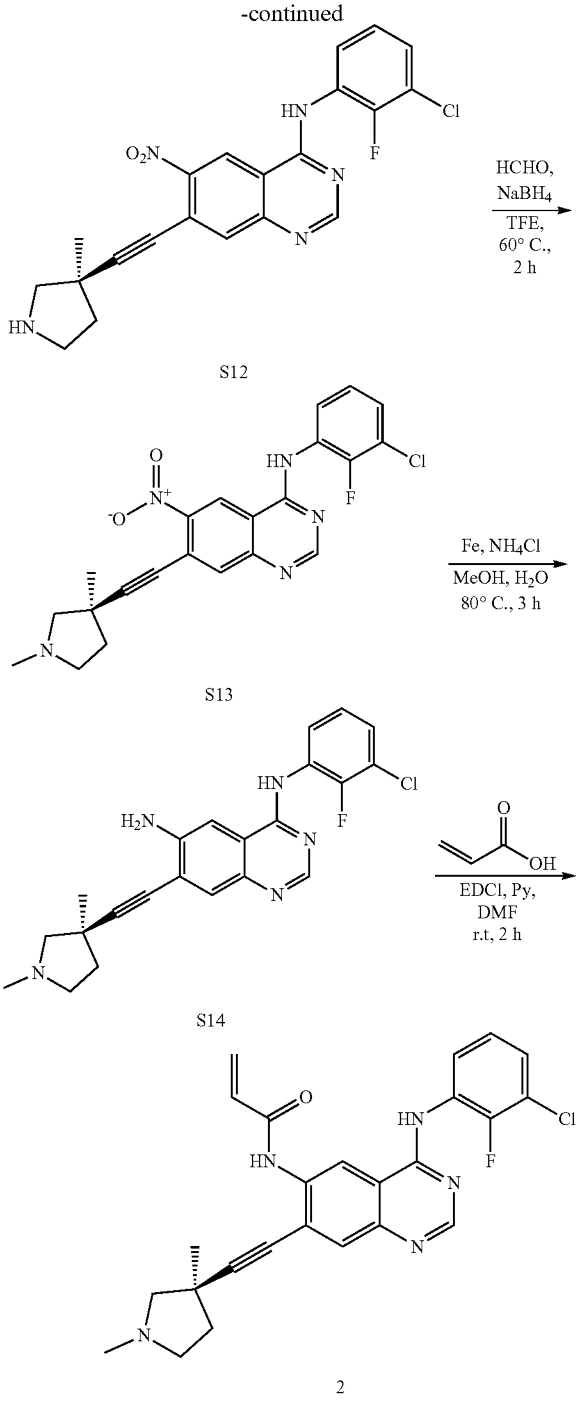

S11: To a mixture of 4-((3-chloro-2-fluorophenyl)amino)-6-nitroquinazolin-7-yl trifluoromethanesulfonate S6 (710 mg, 1.52 mmol, 1.00 eq), (R)-tert-butyl 3-ethynyl-3-methylpyrrolidine-1-carboxylate (350 mg, 1.67 mmol, 1.10 eq) and cuprous iodide (57.9 mg, 304 umol, 0.200 eq) in dimethyl formamide (2.00 mL) and triethylamine (2.00 mL) was added tetrakis(triphenylphosphine) palladium (0) (176 mg, 152 umol, 0.100 eq) under nitrogen atmosphere. The mixture was stirred at 15° C. for 1 h. The mixture was concentrated to give a residue. The residue was purified by silica gel chromatography (Petroleum ether/Ethyl acetate=5/1-2/1) to give (R)-tert-butyl 3-((4-((3-chloro-2-fluorophenyl)amino)-6-nitroquinazolin-7-yl)ethynyl)-3-methylpyrrolidine-1-carboxylate S11 (800 mg, 1.52 mmol, 99% yield) as a yellow solid. $^1$H NMR (400 MHz, DMSO-d6) δ=10.62 (br s, 1H), 9.41 (br s, 1H), 8.67 (br s, 1H), 7.99 (br s, 1H), 7.43 (br s, 1H), 7.39-7.26 (m, 2H), 3.61 (d, J=10.4 Hz, 1H), 3.56-3.41 (m, 2H), 3.30-3.21 (m, 1H), 2.24-2.15 (m, 1H), 1.98-1.90 (m, 1H), 1.45 (s, 3H), 1.42 (s, 9H). MS (ESI) m/z 526.0 $[M+H]^+$.

S12: To a mixture of (R)-tert-butyl 3-((4-((3-chloro-2-fluorophenyl)amino)-6-nitroquinazolin-7-yl)ethynyl)-3-methylpyrrolidine-1-carboxylate S11 (700 mg, 1.33 mmol, 1.00 eq) in ethyl acetate (10.0 mL) was added hydrochloric acid/ethyl acetate (4.00 M, 12.0 mL), the mixture was stirred at 15° C. for 2 h. The mixture was concentrated to dryness to give a residue. The residue was triturated with ethyl acetate (10.0 mL). After filtration, the filter cake was washed with ethyl acetate (5.00 mL), dried in vacuum to give (R)—N-(3-chloro-2-fluorophenyl)-7-((3-methylpyrrolidin-3-yl)ethynyl)-6-nitroquinazolin-4-amine 512 (600 mg, 1.30 mmol, 97% yield, hydrochloric acid) as a yellow solid. MS (ESI) m/z 426.0 $[M+H]^+$.

S13: A mixture of (R)—N-(3-chloro-2-fluorophenyl)-7-((3-methylpyrrolidin-3-yl)ethynyl)-6-nitroquinazolin-4-amine S12 (500 mg, 1.17 mmol, 1.00 eq), paraformaldehyde (176 mg, 5.87 mmol, 5.00 eq) in trifluoroethanol (8.00 mL) was added sodium borohydride (88.8 mg, 2.35 mmol, 2.00 eq) at 15° C. The mixture was stirred at 60° C. for 2 h. The mixture was quenched by methanol (5.00 mL) and concentrated to dryness to give a residue. The residue was diluted with ethyl acetate (20.0 mL) and washed with water (20.0 mL), dried over anhydrous sodium sulfate, filtered and concentrated in vacuum to give (R)—N-(3-chloro-2-fluorophenyl)-7-((1,3-dimethylpyrrolidin-3-yl)ethynyl)-6-nitroquinazolin-4-amine S13 (500 mg, 1.14 mmol, 97% yield) as a yellow solid. $^1$H NMR (400 MHz, $CDCl_3$) δ=8.87 (br s, 1H), 8.73 (s, 1H), 8.32 (br s, 1H), 8.10 (s, 1H), 7.71-7.59 (m, 1H), 7.46 (dt, J=3.2, 7.4 Hz, 1H), 7.22-7.15 (m, 1H), 2.96 (d, J=9.2 Hz, 1H), 2.80-2.70 (m, 2H), 2.65 (d, J=9.2 Hz, 1H), 2.46-2.38 (m, 4H), 1.96 (td, J=7.2, 12.6 Hz, 1H), 1.54 (s, 3H). MS (ESI) m/z 439.8 $[M+H]^+$.

S14: A mixture of (R)—N-(3-chloro-2-fluorophenyl)-7-((1,3-dimethylpyrrolidin-3-yl)ethynyl)-6-nitroquinazolin-4-amine S13 (450 mg, 1.02 mmol, 1.00 eq), iron powder (286 mg, 5.12 mmol, 5.00 eq) and ammonium chloride (274 mg, 5.12 mmol, 5.00 eq) in methanol (10.0 mL) and water (3.00 mL) was stirred at 80° C. for 3 h. The mixture was filtered and the filtrate was concentrated to dryness to give a residue. The residue was diluted with ethyl acetate (20.0 mL) and washed with saturated sodium bicarbonate solution (20.0 mL), brine (15.0 mL), dried over anhydrous sodium sulfate, filtered and concentrated in vacuum to give (R)—$N^4$-(3-chloro-2-fluorophenyl)-7-((1,3-dimethylpyrrolidin-3-yl)ethynyl)quinazoline-4,6-diamine S14 (260 mg, 634 umol, 62% yield) as a yellow solid. MS (ESI) m/z 410.1 $[M+H]^+$.

2: To a mixture of (R)—$N^4$-(3-chloro-2-fluorophenyl)-7-((1,3-dimethylpyrrolidin-3-yl)ethynyl)quinazoline-4,6-diamine S14 (200 mg, 488 umol, 1.00 eq), acrylic acid (45.7 mg, 634 umol, 1.30 eq) and pyridine (154 mg, 1.95 mmol, 4.00 eq) in dimethyl formamide (3.00 mL) was added 1-ethyl-3-(3-dimethylamino-propyl)-carbodiimide hydrochloride (374 mg, 1.95 mmol, 4.00 eq) at 15° C. The mixture was stirred at 15° C. for 2 h and then filtered. The filtrate was purified by prep-HPLC (column: Xtimate C18 10 u 250 mm*80 mm; mobile phase: [water (0.05% ammonia hydroxide v/v)-ACN]; B %: 47%-67%, 10 min) and (column: Phenomenex Synergi C18 150*25*10 um; mobile phase: [water (0.225% FA)-ACN]; B %: 20%-50%, 9 min) to give (R)—N-(4-((3-chloro-2-fluorophenyl)amino)-7-((1,3-dimethylpyrrolidin-3-yl)ethynyl)quinazol in-6-yl)acrylamide 2 (60.0 mg, 129 umol, 27% yield) as a yellow solid. $^1$H NMR (400 MHz, $CDCl_3$) δ=9.28 (br s, 1H), 9.12 (s, 1H), 8.75 (s, 1H), 8.44 (br s, 1H), 8.37-8.31 (m, 1H), 7.97 (s, 1H), 7.78 (br s, 1H), 7.25-7.14 (m, 2H), 6.67-6.56 (m, 2H), 5.87 (dd, J=2.4, 9.2 Hz, 1H), 3.52 (d, J=10.0 Hz, 1H), 3.50-3.41 (m, 1H), 2.94-2.84 (m, 1H), 2.73-2.67 (m, 4H), 2.50 (ddd, J=5.6, 7.8, 13.2 Hz, 1H), 2.12 (ddd, J=7.0, 8.6, 13.1 Hz, 1H), 1.62 (s, 3H). MS (ESI) m/z 464.0[M+H]$^+$.

Example 3. Synthesis of Compound 3

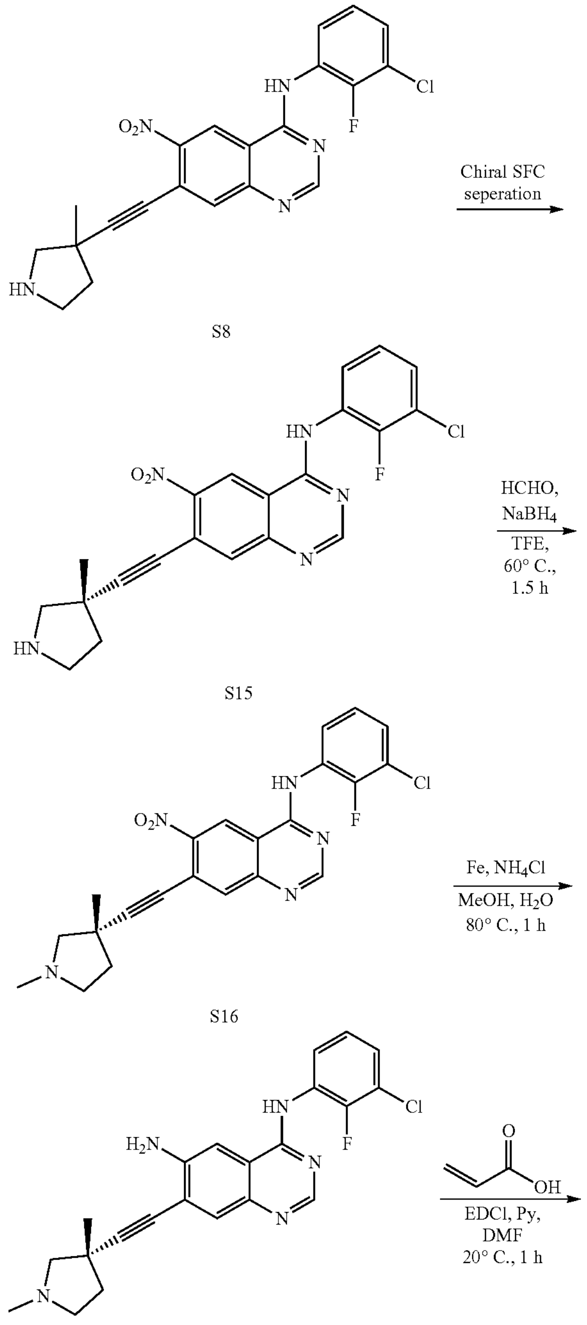

S8

S15

S16

S17

-continued

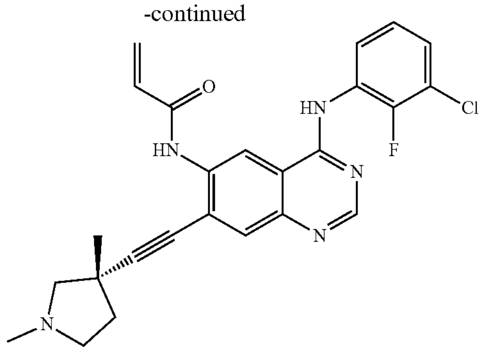

3

S15: N-(3-chloro-2-fluorophenyl)-7-((3-methylpyrrolidin-3-yl) ethynyl)-6-nitro-quinazolin-4-amine S8 (23.0 g, 54.0 mmol, 1.00 eq) was separated by chiral resolution (column: Phenomenex-Cellulose-2 (250 mm*30 mm, 10 um); mobile phase: [0.1% NH3H2O MEOH]; 13%: 70%-70%, 8.9 min; 1900 min) to give (S)—N-(3-chloro-2-fluorophenyl)-7-((3-methylpyrrolidin-3-yl)ethynyl)-6-nitroquinazolin-4-amine S15 (8.40 g, 18.2 mmol, 34% yield, 92% purity, 99% ee) and (R)—N-(3-chloro-2-fluorophenyl)-7-methylpyrrolidin-3-yl)ethynyl)-6-nitroquinazolin-4-amine S12 (8.30 g, 16.6 mmol, 31% yield, 85% purity, 95% ee) as a yellow solid. S15: MS (ESI) m/z 426.1 [M+H]$^+$; $^1$H NMR (400 MHz, DMSO-$d_6$) δ=11.02-10.60 (m, 1H), 9.50 (br d, J=1.4 Hz, 1H), 8.80-8.59 (m, 1H), 8.25-8.04 (m, 1H), 7.63-7.47 (m, 2H), 7.32 (br t, J=7.4 Hz, 1H), 4.12 (q, J=5.3 Hz, 1H), 3.53-3.43 (m, 2H), 3.17 (d, J=4.9 Hz, 2H), 2.34-2.25 (m, 1H), 2.14-2.00 (m, 1H), 1.53 (s, 3H); S12: MS (ESI) m/z 426.1 [M+H]$^+$; $^1$H NMR (400 MHz, DMSO-d6) δ=9.40 (s, 1H), 8.61 (s, 1H), 8.05 (s, 1H), 7.51 (td, J=6.8, 13.8 Hz, 2H), 7.36-7.27 (m, 1H), 3.69-3.59 (m, 2H), 3.17 (s, 2H), 2.30-2.17 (m, 1H), 2.02-1.87 (m, 1H), 1.49 (s, 3H).

S16: To a solution of (S)—N-(3-chloro-2-fluorophenyl)-7-((3-methylpyrrolidin-3-yl)ethynyl)-6-nitroquinazolin-4-amine S15 (8.40 g, 19.7 mmol, 1.00 eq) in 2,2,2-trifluoroethanol (80.0 mL) was added paraformaldehyde (2.96 g, 98.6 mmol, 2.72 mL, 5.00 eq) in portions. The mixture was stirred at 60° C. for 0.5 h. Then the mixture was added sodium borohydride (1.49 g, 39.5 mmol, 2.00 eq) in portions at 60° C. The mixture was stirred at 60° C. for 1 h. The mixture was added methanol (50.0 mL) and concentrated to give crude product. The crude product was diluted with water (100 mL) and extracted with ethyl acetate (3×70.0 mL). The combined organic layer was washed with brine (50.0 mL) and dried over sodium sulfate, filtered and concentrated to give (S)—N-(3-chloro-2-fluorophenyl)-7-((1,3-dimethylpyrrolidin-3-yl)ethynyl)-6-nitroquinazolin-4-amine S16 (7.50 g, crude) as a yellow solid. MS (ESI) m/z 440.1 [M+H]$^+$.

S17: To a solution of (S)—N-(3-chloro-2-fluorophenyl)-7-((1,3-dimethylpyrrolidin-3-yl)ethynyl)-6-nitroquinazolin-4-amine S16 (7.50 g, 17.1 mmol, 1.00 eq) and ammonium chloride (4.56 g, 85.5 mmol, 5.00 eq) in methanol (80.0 mL) and water (20.0 mL) was added iron powder (4.76 g, 85.3 mmol, 5.00 eq) in portions. The mixture was stirred at 80° C. for 1 h. The mixture was added methanol (200 mL) and filtered. The filtrate was concentrated to give the residue. The residue was diluted with saturated sodium hydrogencarbonate solution (200 mL) and extracted with ethyl acetate (3×100 mL). The combined organic layer was washed with brine (50.0 mL) and dried over sodium sulfate, filtered and concentrated to give (S)—$N^4$-(3-chloro-2-fluorophenyl)-7-((1,3-dimethylpyrrolidin-3-yl)ethynyl)quinazoline-4,6-diamine S17 (6.10 g, crude) as a yellow solid. MS (ESI) m/z 410.1 $[M+H]^+$.

3: To a solution of (S)—$N^4$-(3-chloro-2-fluorophenyl)-7-((1,3-dimethylpyrrolidin-3-yl)ethynyl)quinazoline-4,6-diamine S17 (5.60 g, 13.7 mmol, 1.00 eq), acrylic acid (1.18 g, 16.4 mmol, 1.13 mL, 1.20 eq) and pyridine (4.32 g, 54.7 mmol, 4.41 mL, 4.00 eq) in dimethyl formamide (40.0 mL) was added 1-(3-dimethylaminopropyl)-3-ethylcarbodiimide hydrochloride (10.5 g, 54.7 mmol, 4.00 eq) in portions. The mixture was stirred at 20° C. for 1 h. The mixture was diluted with water (200 mL) and extracted with ethyl acetate (3×100 mL). The combined organic layer was washed with brine (50.0 mL) and dried over sodium sulfate, filtered and concentrated to give crude product. The crude product was purified by silica gel chromatography (ethyl acetate/methanol=1/0 to 10/1) and further purified by prep-HPLC (column: Waters Xbridge C18 150*50 mm*10 um; mobile phase: [water (10 mM NH4HCO3)-ACN]; B %: 38%-68%, 11.5 min) and lyophilized to give (S)—N-(4-((3-chloro-2-fluorophenyl)amino)-7-((1,3-dimethylpyrrolidin-3-yl)ethynyl)quinazolin-6-yl)acrylamide 3 (1.76 g, 3.71 mmol, 27% yield, 98% purity) as a yellow solid. $^1H$ NMR (400 MHz, $CDCl_3$) δ=9.21 (s, 1H), 8.73 (s, 1H), 8.68 (s, 1H), 8.32 (dt, J=1.9, 7.4 Hz, 1H), 7.95 (s, 1H), 7.91 (br s, 1H), 7.24-7.12 (m, 2H), 6.59-6.51 (m, 1H), 6.49-6.37 (m, 1H), 5.89 (dd, J=1.2, 10.1 Hz, 1H), 3.09 (d, J=9.0 Hz, 1H), 3.01 (dt, J=5.6, 8.8 Hz, 1H), 2.58 (dt, J=6.1, 9.1 Hz, 1H), 2.48 (s, 1H), 2.45 (s, 3H), 2.43-2.34 (m, 1H), 2.00 (ddd, J=5.6, 8.8, 12.9 Hz, 1H), 1.56 (s, 3H). MS (ESI) m/z 464.2 $[M+H]^+$.

Example 4. Synthesis of Compound 4

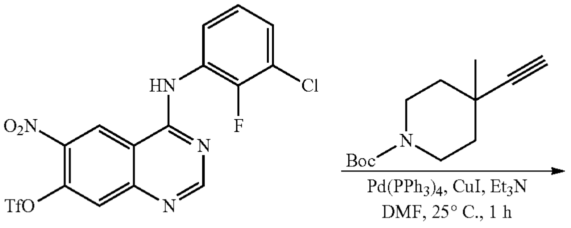

S8

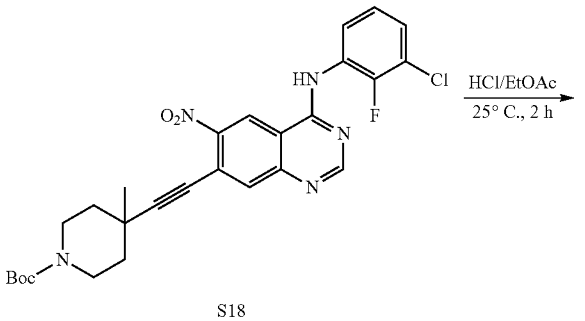

S18

-continued

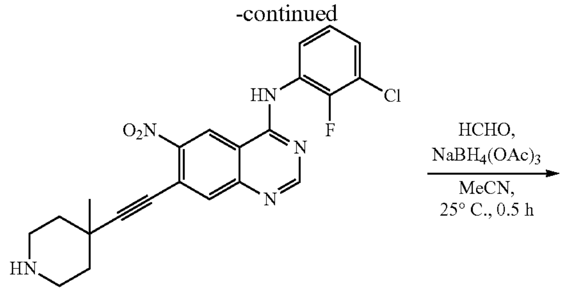

S19

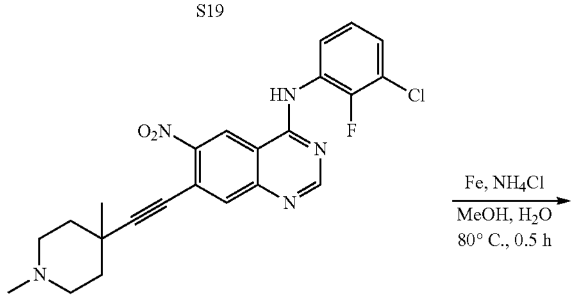

S20

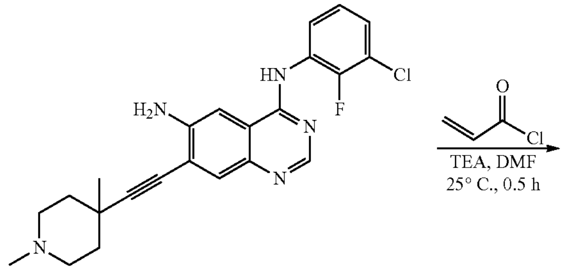

S21

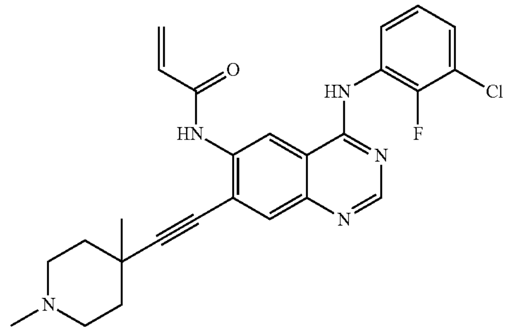

4

S18: To a solution of 4-((3-chloro-2-fluorophenyl)amino)-6-nitroquinazolin-7-yl trifluoromethanesulfonate S6 (600 mg, 1.29 mmol, 1.00 eq), tert-butyl 4-ethynyl-4-methylpiperidine-1-carboxylate (315 mg, 1.41 mmol, 1.10 eq), triethylamine (390 mg, 3.86 mmol, 536 uL, 3.00 eq) and copper(I) iodide (48.9 mg, 257 umol, 0.200 eq) in dimethyl formamide (1.00 mL) was added tetrakis[triphenylphosphine]palladium(0) (148 mg, 128 umol, 0.100 eq) at 25° C. The mixture was stirred at 25° C. for 1 h. The reaction mixture was concentrated to remove dimethyl formamide. The residue was purified by column chromatography (SiO2, Petroleum ether/Ethyl acetate=10/1 to 1/1) to give tert-butyl4-((4-((3-chloro-2-fluorophenyl) amino)-6-nitroquinazolin-7-yl)ethynyl)-4-methylpiperidine-1-carboxylate S18 (700 mg, crude) as a yellow solid. MS (ESI) m/z 540.2 $[M+H]^+$.

S19: A mixture of tert-butyl-4-((4-((3-chloro-2-fluorophenyl)amino)-6-nitroquinazolin-7-yl)ethynyl)-4-methylpiperidine-1-carboxylate S18 (700 mg, 1.30 mmol, 1.00 eq) in hydrogen chloride/ethyl acetate (4 M, 3.00 mL, 9.26 eq) was stirred at 25° C. for 2 h. The reaction mixture was concentrated to give a residue. The residue was triturated with ethyl acetate (10.0 mL) to give N-(3-chloro-2-fluorophenyl)-7-((4-methylpiperidin-4-yl)ethynyl)-6-nitroquinazolin-4-amine S19 (550 mg, 1.25 mmol, 96% yield) as a yellow solid. MS (ESI) m/z 440.2 $[M+H]^+$.

S20: To a solution of N-(3-chloro-2-fluorophenyl)-7-((4-methylpiperidin-4-yl)ethynyl)-6-nitroquinazolin-4-amine S19 (450 mg, 1.02 mmol, 1.00 eq) and formaldehyde (415 mg, 5.12 mmol, 5.00 eq) in acetonitrile (5.00 mL) was added sodium triacetoxyborohydride (650 mg, 3.07 mmol, 3.00 eq). The mixture was stirred at 25° C. for 0.5 h. The reaction mixture was diluted with water (50.0 mL) and extracted with ethyl acetate (3×100 mL). The combined organic layers were washed with brine (3×50.0 mL), dried over sodium sulfate, filtered and concentrated under reduced pressure to give N-(3-chloro-2-fluorophenyl)-7-((1,4-dimethylpiperidin-4-yl)ethynyl)-6-nitroquinazolin-4-amine S20 (500 mg, crude) as a yellow solid. MS (ESI) m/z 454.4 $[M+H]^+$.

S21: A mixture of N-(3-chloro-2-fluorophenyl)-7-((1,4-dimethylpiperidin-4-yl)ethynyl)-6-nitroquinazolin-4-amine S20 (400 mg, 881 umol, 1.00 eq), iron powder (492 mg, 8.81 mmol, 10.0 eq) and ammonium chloride (471 mg, 8.81 mmol, 10.0 eq) in methanol (2.00 mL) and water (1.00 mL) was stirred at 80° C. for 0.5 h. The reaction mixture was concentrated to give a residue. The crude product was purified by reversed-phase HPLC (0.1% NH3·H2O) and lyophilized to give $N^4$-(3-chloro-2-fluorophenyl)-7-((1,4-dimethylpiperidin-4-yl)ethynyl)quinazoline-4,6-diamine S21 (200 mg, crude) as a yellow solid. MS (ESI) m/z 424.2 $[M+H]^+$.

4: To a solution of $N^4$-(3-chloro-2-fluorophenyl)-7-((1,4-dimethylpiperidin-4-yl)ethynyl)quinazoline-4,6-diamine S21 (100 mg, 235 umol, 1.00 eq) and triethylamine (47.7 mg, 471 umol, 2.00 eq) in dimethyl formamide (1.00 mL) was added prop-2-enoyl chloride (23.5 mg, 259 umol, 1.10 eq) at 25° C. The mixture was stirred at 25° C. for 0.5 h. The reaction mixture was filtered. The filtrate was purified by prep-HPLC (column: Waters Xbridge 150*25 5 u; mobile phase: [water (10 mM NH4HCO3)-ACN]; B %: 27%-57%, 10 min) and further purified by prep-HPLC (column: Phenomenex Synergi C18 150*30 mm*4 um; mobile phase: [water (0.225% FA)-ACN]; B %: 10%-40%, 10 min) and lyophilized to give N-(4-((3-chloro-2-fluorophenyl)amino)-7-((1,4-dimethylpiperidin-4-yl)ethynyl)quinazolin-6-yl) acrylamide 4 (3.51 mg, 7.27 umol, 3% yield, 99% purity) as a yellow solid. $^1$H NMR (400 MHz, DMSO-d6) δ=10.10 (br s, 1H), 9.82 (br s, 1H), 8.65 (s, 1H), 8.50 (br s, 1H), 8.25 (s, 1H), 7.84 (br s, 1H), 7.51 (br s, 2H), 7.30 (br d, J=8.2 Hz, 1H), 6.56 (dd, J=10.3, 17.2 Hz, 1H), 6.34 (br d, J=17.0 Hz, 1H), 5.85 (br d, J=10.0 Hz, 1H), 2.64 (br d, J=11.4 Hz, 2H), 2.32-2.25 (m, 2H), 2.19 (s, 3H), 1.79 (br d, J=12.5 Hz, 2H), 1.54 (dt, J=3.7, 12.4 Hz, 2H), 1.34 (s, 3H). MS (ESI) m/z 478.3 $[M+H]^+$.

Example 5. Synthesis of Compound 5

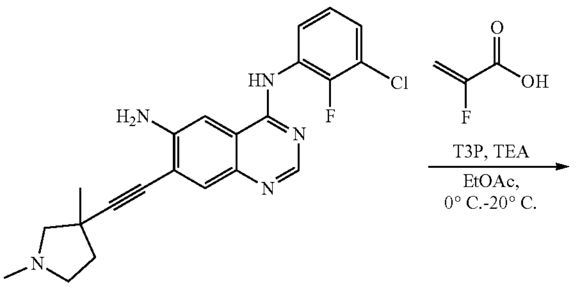

S10

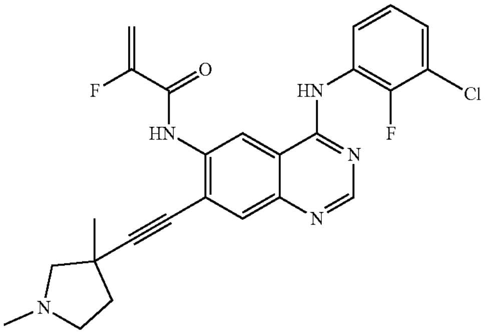

5

5: To a solution of $N^4$-(3-chloro-2-fluorophenyl)-7-((1,3-dimethylpyrrolidin-3-yl)ethynyl)quinazoline-4,6-diamine S10 (250 mg, 610 umol, 1.00 eq), 2-fluoroacrylic acid (82.4 mg, 915 umol, 1.50 eq) and triethylamine (494 mg, 4.88 mmol, 679 uL, 8.00 eq) in ethyl acetate (3.00 mL) was added propylphosphonic anhydride (1.55 g, 2.44 mmol, 1.45 mL, 50% purity, 4.00 eq) dropwise at 0° C. The mixture was stirred at 20° C. for 1 h. The mixture was diluted with water (30.0 mL) and extracted with ethyl acetate (3×30.0 mL). The combined organic layer was washed with brine (20.0 mL) and dried over sodium sulfate, filtered and concentrated to give crude product. The crude product was purified by prep-HPLC (column: Waters Xbridge 150*25 mm*5 um; mobile phase: [water (10 mM $NH_4HCO_3$)-ACN (═MeCN)]; B %: 32%-62%, 10 min) and lyophilized to give N-(4-((3-chloro-2-fluorophenyl)amino)-7-((1,3-dimethylpyrrolidin-3-yl)ethynyl) quinazolin-6-yl)-2-fluoroacrylamide 5 (35.22 mg, 67.9 umol, 11% yield, 93% purity) as a yellow solid. $^1$H NMR (400 MHz, DMSO-d6) δ=10.12 (br s, 1H), 10.04 (br s, 1H), 8.70 (s, 1H), 8.52 (s, 1H), 7.84 (s, 1H), 7.52 (br t, J=7.3 Hz, 2H), 7.30 (br t, J=8.0 Hz, 1H), 5.89-5.69 (m, 1H), 5.55 (dd, J=3.7, 15.7 Hz, 1H), 2.73 (d, J=8.8 Hz, 1H), 2.65-2.62 (m, 1H), 2.57 (br s, 2H), 2.27 (s, 3H), 2.24-2.16 (m, 1H), 1.86 (td, J=7.3, 12.5 Hz, 1H), 1.43 (s, 3H). LC-MS (ESI) m/z 482.1 $[M+H]^+$.

Example 6. Synthesis of Compound 6

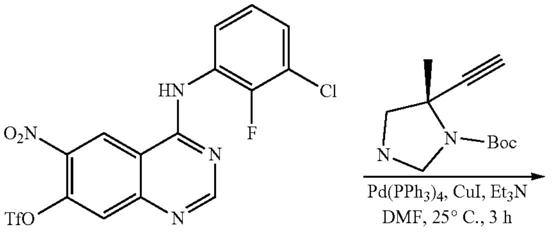

S6

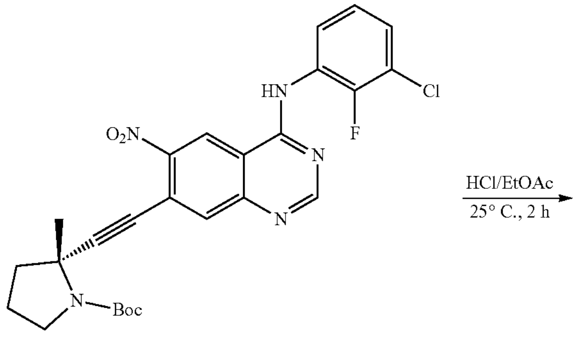

S22

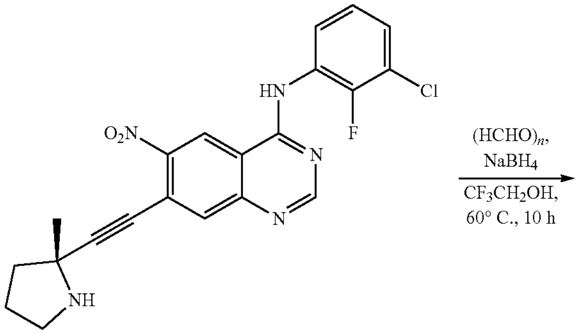

S23

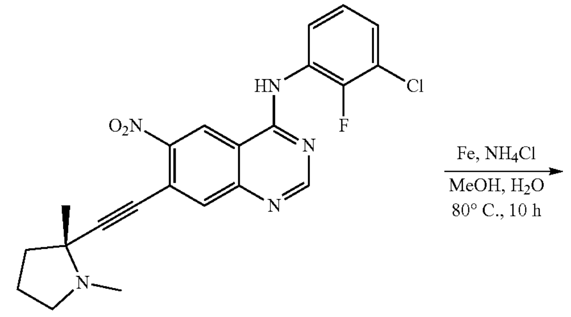

S24

-continued

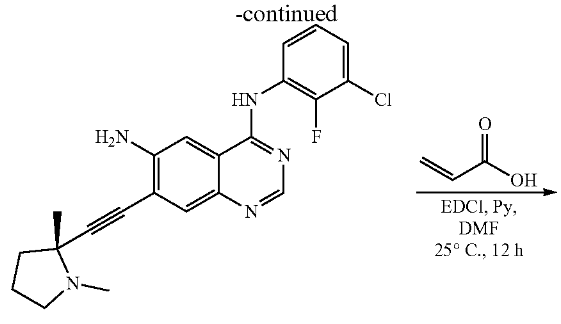

S25

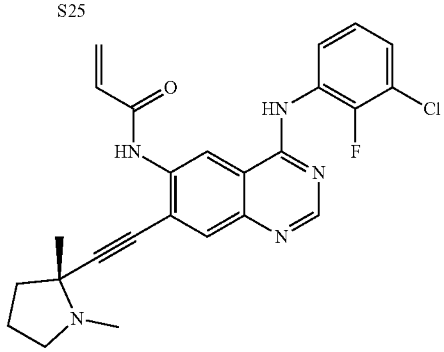

6

S22: A mixture of 4-((3-chloro-2-fluorophenyl)amino)-6-nitroquinazolin-7-yl trifluoromethanesulfonate S6 (1.20 g, 2.57 mmol, 1.00 eq), (R)-tert-butyl 2-ethynyl-2-methylpyrrolidine-1-carboxylate S5 (591 mg, 2.83 mmol, 1.10 eq), tetrakis(triphenylphosphine) palladium(0) (297 mg, 257 umol, 0.100 eq), cuprous iodide (97.9 mg, 514 umol, 0.200 eq) and triethylamine (780 mg, 7.71 mmol, 1.07 mL, 3.00 eq) in tetrahydrofuran (10.0 mL) was degassed and purged with nitrogen for three times. Then the mixture was stirred at 25° C. for 3 h under nitrogen atmosphere. The reaction mixture was filtered and concentrated in vacuo to give a residue. The residue was purified by silica gel column chromatography (petroleum ether/ethyl acetate=3/1) to afford (R)-tert-butyl 2-((4-((3-chloro-2-fluorophenyl)amino)-6-nitroquinazolin-7-yl)ethynyl)-2-methylpyrrolidine-1-carboxylate S22 (1.43 g, crude) as a yellow oil. $^1$H NMR (400 MHz, $CDCl_3$) δ=8.92-8.69 (m, 2H), 8.14-7.99 (m, 1H), 7.67-7.41 (m, 1H), 7.40-7.33 (m, 1H), 7.22-7.16 (m, 1H), 3.72-3.64 (m, 1H), 3.45 (br d, J=8.6 Hz, 1H), 2.54-2.42 (m, 1H), 2.20-2.05 (m, 2H), 1.95-1.84 (m, 1H), 1.74 (br s, 3H), 1.49 (br s, 9H).

S23: To a solution of (R)-tert-butyl 2-((4-((3-chloro-2-fluorophenyl)amino)-6-nitroquinazolin-7-yl)ethynyl)-2-methylpyrrolidine-1-carboxylate S22 (1.90 g, 3.61 mmol, 1.00 eq) in hydrochloric/ethyl acetate (4M, 18.0 mL). The mixture was stirred at 25° C. for 2 h. The reaction mixture was concentrated under reduced pressure to give (R)—N-(3-chloro-2-fluorophenyl)-7-((2-methylpyrrolidin-2-yl)ethynyl)-6-nitroquinazolin-4-amine S23 (1.60 g, 3.46 mmol, 96% yield, hydrochloride) as a brown solid. It was used for the next step without purification. $^1$H NMR (400 MHz, DMSO-d6) δ=10.28-10.05 (m, 2H), 9.70 (s, 1H), 8.80 (s, 1H), 8.26 (s, 1H), 7.66-7.59 (m, 2H), 7.59-7.49 (m, 2H), 7.35 (dt, J=1.1, 8.1 Hz, 1H), 3.47-3.37 (m, 2H), 2.41-2.32 (m, 1H), 2.26-2.08 (m, 3H), 1.91 (s, 4H), 1.83 (s, 3H).

S24: To a solution of (R)—N-(3-chloro-2-fluorophenyl)-7-((2-methylpyrrolidin-2-yl)ethynyl)-6-nitroquinazolin-4-amine S23 (1.60 g, 3.46 mmol, 1.00 eq, hydrochloride) and paraformaldehyde (519 mg, 17.3 mmol, 476 uL, 5.00 eq) in trifluoroethanol (16.0 mL) was added sodium borohydride (654 mg, 17.3 mmol, 5.00 eq) slowly. The mixture was stirred at 60° C. for 10 h. The reaction mixture was concentrated under reduced pressure to give a residue. The residue was purified was by reversed phase chromatography (column: C18, 330 g; condition: $CH_3CN$ –0.1% $NH_3$·H2O) to afford (R)—N-(3-chloro-2-fluorophenyl)-7-((1,2-dimethylpyrrolidin-2-yl)ethynyl)-6-nitroquinazolin-4-amine S24 (0.360 g, 0.818 mmol, 23% yield) as a brown solid. $^1H$ NMR (400 MHz, $CDCl_3$) δ=8.89 (s, 1H), 8.74 (s, 1H), 8.35 (br t, J=7.30 Hz, 1H), 8.15 (s, 1H), 7.32-7.26 (m, 2H), 7.25-7.18 (m, 1H), 3.19-3.06 (m, 1H), 2.77-2.61 (m, 1H), 2.45 (s, 3H), 2.36-2.26 (m, 1H), 1.96-1.89 (m, 3H), 1.54 (s, 3H).

S25: To a solution of (R)—N-(3-chloro-2-fluorophenyl)-7-((1,2-dimethylpyrrolidin-2-yl)ethynyl)-6-nitroquinazolin-4-amine S24 (0.358 g, 813 umol, 1.00 eq) in methanol (8.00 mL) and water (5.00 mL) was added ammonium chloride (348 mg, 6.51 mmol, 8.00 eq) and iron powder (363 mg, 6.51 mmol, 8.00 eq). Then the mixture was stirred at 80° C. for 10 h. The reaction mixture was filtered and concentrated in vacuum to give a residue. The residue was poured into water (20.0 mL). The aqueous phase was extracted with ethyl acetate (3×30.0 mL). The combined organic phase was washed with brine (3×30.0 mL), dried over anhydrous sodium sulfate, filtered and concentrated in vacuum to give a residue. The residue was purified by reversed phase chromatography (column: C18, 80 g; condition: $CH_3CN$-0.1% $NH_3H_2O$) to afford (R)—$N^4$-(3-chloro-2-fluorophenyl)-7-((1,2-dimethylpyrrolidin-2-yl)ethynyl)quinazoline-4,6-diamine S25 (0.160 g, 390 umol, 48% yield) as a brown solid. $^1H$ NMR (400 MHz, $CDCl_3$) δ=8.59-8.52 (m, 2H), 7.83 (s, 1H), 7.29 (br s, 1H), 7.10-7.03 (m, 2H), 6.88 (s, 1H), 4.50 (br s, 2H), 3.08-2.98 (m, 1H), 2.57-2.48 (m, 1H), 2.34 (s, 3H), 2.22-2.16 (m, 1H), 1.86-1.79 (m, 3H), 1.45 (s, 3H).

6: To a solution of (R)—$N^4$-(3-chloro-2-fluorophenyl)-7-((1,2-dimethylpyrrolidin-2-yl)ethynyl)quinazoline-4,6-diamine S25 (0.076 g, 185 umol, 1.00 eq) and acrylic acid (26.7 mg, 370 umol, 25.5 uL, 2.00 eq) in dimethylformamide (3.00 mL) was added pyridine (44.0 mg, 556 umol, 44.9 uL, 3.00 eq) and 1-ethyl-3-(3-dimethylamino-propyl)-carbodiimide hydrochloride (88.9 mg, 463 umol, 2.50 eq). The mixture was stirred at 25° C. for 2 h. The reaction mixture was filtered and concentrated in vacuum to give a residue. The residue was purified by Prep-HPLC (column: Xtimate C18 150×25 mm×5 um; mobile phase: [water (0.05% ammonia hydroxide v/v)-ACN]; B %: 38%-68%, 10 min) and lyophilized to afford (R)—N-(4-((3-chloro-2-fluorophenyl)amino)-7-((1,2-dimethylpyrrolidin-2-yl)-ethynyl) quinazolin-6-yl)acrylamide 6 (18.09 mg, 38.60 umol, 21% yield, 99% purity) as a yellow solid. $^1H$ NMR (400 MHz, $CDCl_3$) δ=9.23 (s, 1H), 8.76 (s, 1H), 8.45-8.28 (m, 2H), 8.03 (s, 1H), 7.82 (br s, 1H), 7.26-7.15 (m, 2H), 6.56 (dd, J=0.7, 16.8 Hz, 1H), 6.32 (dd, J=10.3, 16.8 Hz, 1H), 5.94 (d, J=10.1 Hz, 1H), 3.21-3.13 (m, 1H), 2.67-2.59 (m, 1H), 2.46 (s, 3H), 2.36-2.27 (m, 1H), 2.07-1.89 (m, 3H), 1.58 (s, 3H), MS (ESI) m/z 464.2 $[M+H]^+$.

Example 7. Synthesis of Compound 7

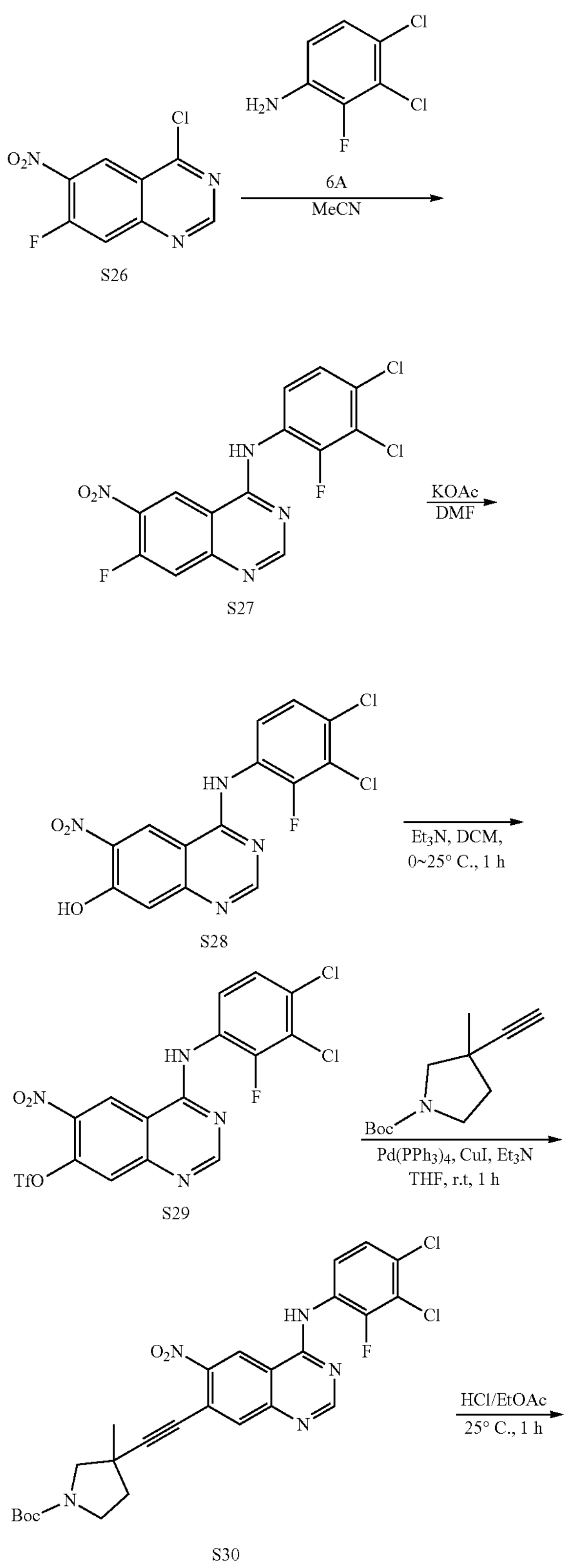

-continued

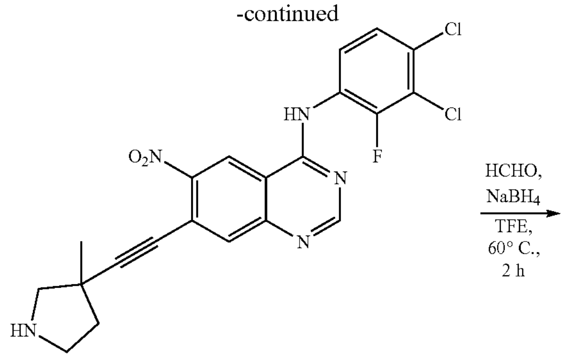

S31

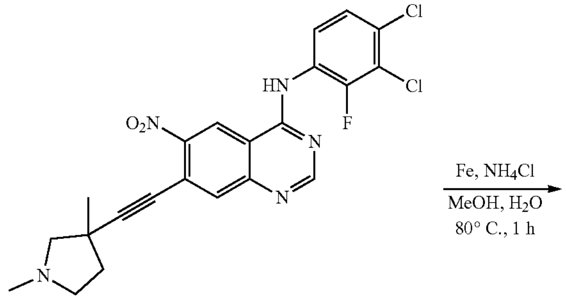

S32

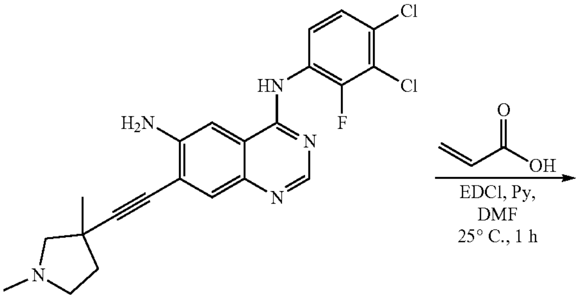

S33

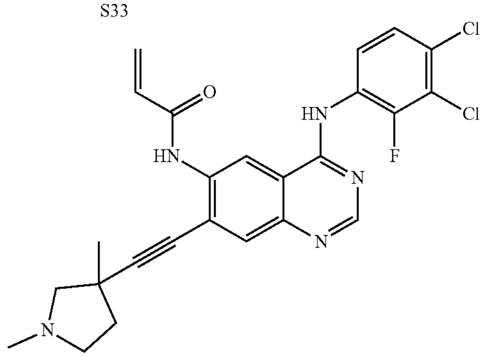

&007

S27: A mixture of 4-chloro-7-fluoro-6-nitro-quinazoline S26 (3.00 g, 13.2 mmol, 1.00 eq) and 3,4-dichloro-2-fluoro-aniline (2.37 g, 13.2 mmol, 1.00 eq) in acetonitrile (30.0 mL) was stirred at 25° C. for 12 h. The mixture was concentrated to dryness to give a residue. The residue was triturated with ethyl acetate (20.0 mL) and filtered, the filter cake was washed with ethyl acetate (10.0 mL) and concentrated to dryness to give N-(3,4-dichloro-2-fluorophenyl)-7-fluoro-6-nitroquinazolin-4-amine S27 (4.00 g, 10.8 mmol, 82% yield) as an off-white solid. 41 NMR (400 MHz, DMSO-d6) δ=9.87-9.72 (m, 1H), 8.90-8.79 (m, 1H), 8.35 (s, 1H), 8.05-7.96 (m, 1H), 7.81 (d, J=12.2 Hz, 1H), 7.69-7.64 (m, 1H), 7.62-7.55 (m, 1H). MS (ESI) m/z 370.8 $[M+H]^+$.

S28: To a solution of N-(3,4-dichloro-2-fluorophenyl)-7-fluoro-6-nitroquinazolin-4-amine S27 (4.00 g, 10.8 mmol, 1.00 eq) in dimethyl formamide (40.0 mL) was added potassium acetate (5.29 g, 53.9 mmol, 5.00 eq) at 25° C. The mixture was stirred at 100° C. for 5 h. The mixture was concentrated to afford a residue. The residue was triturated with water (50.0 mL). After filtration, the filter cake was washed with water (30.0 mL), dried in vacuum to give 4-((3,4-dichloro-2-fluorophenyl)amino)-6-nitroquinazolin-7-ol S28 (3.50 g, 9.48 mmol, 88% yield) as a brown solid. MS (ESI) m/z 368.9 $[M+H]^+$.

S29: To a solution of 4-(3,4-dichloro-2-fluoro-anilino)-6-nitro-quinazolin-7-ol S28 (3.50 g, 9.48 mmol, 1.00 eq) and pyridine (3.75 g, 47.4 mmol, 3.83 mL, 5.00 eq) in dichloromethane (40.0 mL) was added trifluoromethanesulfonic peroxyanhydride (5.35 g, 18.9 mmol, 3.13 mL, 2.00 eq) dropwise at 0° C., the mixture was stirred at 25° C. for 1 h. The reaction mixture was poured into water (300 mL) and the aqueous phase was extracted with ethyl acetate (3×100 mL). The combined organic phase was washed with brine (150 mL), dried over anhydrous sodium sulfate, filtered and concentrated in vacuum to give a residue. The residue was purified by silica gel chromatography (Petroleum ether/Ethyl acetate=8/1) to afford 4-((3,4-dichloro-2-fluorophenyl)amino)-6-nitroquinazolin-7-yl trifluoromethanesulfonate S29 (700 mg, 1.40 mmol, 14% yield) as a yellow oil. MS (ESI) m/z 500.9 $[M+H]^+$.

S30: To a solution of 4-((3,4-dichloro-2-fluorophenyl)amino)-6-nitroquinazolin-7-yl trifluoromethanesulfonate S29 (600 mg, 1.20 mmol, 1.00 eq), tert-butyl 3-ethynyl-3-methyl-pyrrolidine-1-carboxylate (250 mg, 1.20 mmol, 1.00 eq) and triethylamine (4.36 g, 43.1 mmol, 6.00 mL, 36.0 eq) in dimethyl formamide (6.00 mL) was added cuprous iodid (45.6 mg, 239 umol, 0.200 eq) and tetrakis(triphenylphosphine) palladium(0) (138 mg, 119 umol, 0.100 eq) at 25° C. under nitrogen, the mixture was stirred at 25° C. for 1 h. The reaction mixture was poured into water (120 mL) and stirred for 10 min. The aqueous phase was extracted with ethyl acetate (3×60.0 mL). The combined organic phase was washed with brine (100 mL), dried over anhydrous sodium sulfate, filtered and concentrated in vacuum to give a residue. The residue was purified by silica gel chromatography (Petroleum ether/Ethyl acetate=6/1 to 3/1) to afford tert-butyl 3-((4-((3,4-dichloro-2-fluorophenyl)amino)-6-nitroquinazolin-7-yl)ethynyl)-3-methylpyrrolidine-1-carboxylate S30 (600 mg, 1.07 mmol, 89% yield) as a yellow oil. $^1H$ NMR (400 MHz, DMSO-d6) δ=10.84-10.57 (m, 1H), 9.57-9.22 (m, 1H), 8.66 (br s, 1H), 8.03-7.86 (m, 2H), 7.49-7.36 (m, 1H), 3.61 (d, J=10.2 Hz, 1H), 3.56-3.44 (m, 2H), 3.30-3.22 (m, 1H), 2.26-2.13 (m, 1H), 2.05-1.93 (m, 1H), 1.47-1.44 (m, 3H), 1.42 (s, 9H). MS (ESI) m/z 504.1 $[M+H-56]^+$.

S31: To a solution of tert-butyl 3-((4-((3,4-dichloro-2-fluorophenyl)amino)-6-nitroquinazolin-7-yl)ethynyl)-3-methylpyrrolidine-1-carboxylate S30 (500 mg, 892 umol, 1.00 eq) in dichloromethane (5.00 mL) was added trifluoroacetic acid (1.54 g, 13.5 mmol, 1.00 mL, 15.1 eq) at 25° C., the mixture was stirred at 25° C. for 1 h. The reaction mixture was concentrated to give N-(3,4-dichloro-2-fluorophenyl)-7-((3-methylpyrrolidin-3-yl) ethynyl)-6-nitroquinazolin-4-amine (400 mg, 869 umol, 97% yield) S31 as a yellow oil. MS (ESI) m/z 460.1 $[M+H]^+$.

S32: To a solution of N-(3,4-dichloro-2-fluorophenyl)-7-((3-methylpyrrolidin-3-yl)ethynyl)-6-nitroquinazolin-4-amine S31 (400 mg, 869 umol, 1.00 eq) and paraformaldehyde (130 mg, 4.35 mmol, 119 uL, 5.00 eq) in trifluoroethanol (4.00 mL) was added sodium borohydride (65.7 mg, 1.74 mmol, 2.00 eq) at 25° C., the mixture was stirred at 60° C. for 2 h. The reaction was quenched with methanol slowly and then concentrated to give a residue which was poured into water (80.0 mL) and stirred for 10 min. The aqueous phase was extracted with ethyl acetate (3×60.0 mL). The combined organic phase was washed with brine (50.0 mL), dried over anhydrous sodium sulfate, filtered and concentrated in vacuum to give N-(3,4-dichloro-2-fluorophenyl)-7-((1,3-dimethylpyrrolidin-3-yl)ethynyl)-6-nitroquinazolin-4-amine S32 (400 mg, crude) as a yellow solid. MS (ESI) m/z 474.4 $[M+H]^+$.

S33: A mixture of N-(3,4-dichloro-2-fluorophenyl)-7-((1,3-dimethylpyrrolidin-3-yl)ethynyl)-6-nitroquinazolin-4-amine S32 (400 mg, 843 umol, 1.00 eq), iron powder (141 mg, 2.53 mmol, 3.00 eq) and ammonium chloride (225 mg, 4.22 mmol, 5.00 eq) in methanol (4.00 mL) and water (2.00 mL) was stirred at 80° C. for 1 h. The reaction mixture was filtered and the filtrate was concentrated to give a residue, the residue was poured into water (80.0 mL), the aqueous phase was extracted with ethyl acetate (3×40.0 mL). The combined organic phase was washed with brine (100 mL), dried over anhydrous sodium sulfate, filtered and concentrated in vacuum to give a residue. The residue was purified by reversed-phase HPLC (0.1% ammonium hydroxide) to afford $N^4$-(3,4-dichloro-2-fluorophenyl)-7-((1,3-dimethylpyrrolidin-3-yl)ethynyl) quinazoline-4,6-diamine S33 (140 mg, 315 umol, 37% yield) as a yellow solid. MS (ESI) m/z 444.1 $[M+H]^+$.

7: To a solution of $N^4$-(3,4-dichloro-2-fluorophenyl)-7-((1,3-dimethylpyrrolidin-3-yl)ethynyl)quinazoline-4,6-diamine S33 (100 mg, 225 umol, 1.00 eq), acrylic acid (16.2 mg, 225 umol, 15.4 uL, 1.00 eq) and pyridine (89.0 mg, 1.13 mmol, 90.8 uL, 5.00 eq) in dimethyl formamide (1.00 mL) was added 1-ethyl-3-(3-dimethylamino-propyl)-carbodiimide hydrochloride (172 mg, 900 umol, 4.00 eq), the mixture was stirred at 25° C. for 2 h. The reaction mixture was filtered to give a filtrate. The filtrate was purified by prep-HPLC (column: Waters Xbridge 150*25 mm*5 um; mobile phase: [water (0.05% ammonia hydroxide v/v)-ACN]; B %: 51%-70%, 10 min) and prep-HPLC (column: UniSil 3-100 C18 Ultra (150*25 mm*3 um); mobile phase: [water (0.225% FA)-ACN]; B %: 14%-44%, 10 min) to afford N-(4-((3,4-dichloro-2-fluorophenyl)amino)-7-((1,3-dimethylpyrrolidin-3-yl)ethynyl)quinazolin-6-yl)acrylamide 7 (29.0 mg, 53.2 umol, 23% yield, FA) as a yellow solid. 41 NMR (400 MHz, $CDCl_3$) δ=9.07 (s, 1H), 8.82 (br s, 1H), 8.64 (s, 1H), 8.37 (s, 1H), 8.22 (t, J=8.4 Hz, 1H), 7.86 (s, 1H), 7.77 (br s, 1H), 7.24 (dd, J=2.0, 9.0 Hz, 1H), 6.51-6.35 (m, 2H), 5.83-5.76 (m, 1H), 3.17 (br d, J=9.2 Hz, 1H), 3.14-3.05 (m, 1H), 2.60 (dt, J=6.0, 9.4 Hz, 1H), 2.46 (s, 3H), 2.40-2.30 (m, 2H), 1.96 (ddd, J=6.2, 8.8, 13.0 Hz, 1H), 1.50 (s, 3H). MS (ESI) m/z 498.1 $[M+H]^+$.

Example 8. Synthesis of Compound 8

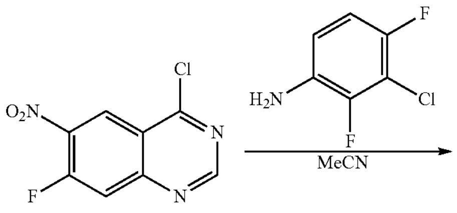

S26

-continued

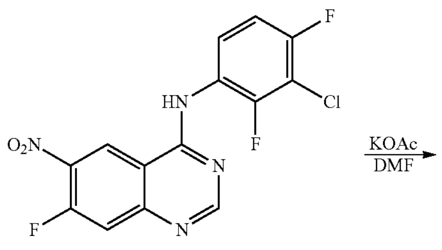

S34

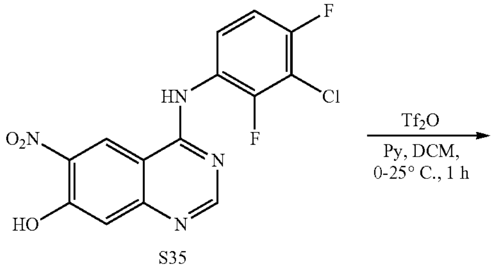

S35

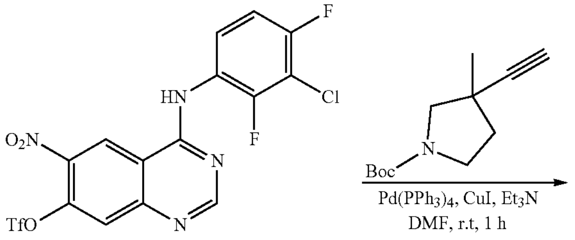

S36

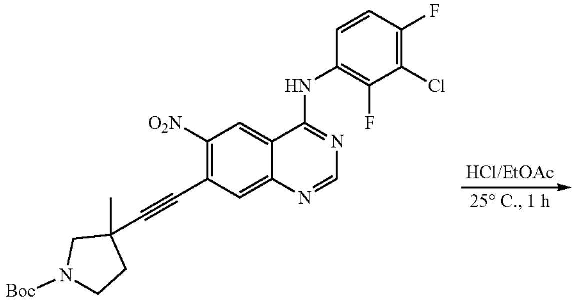

S37

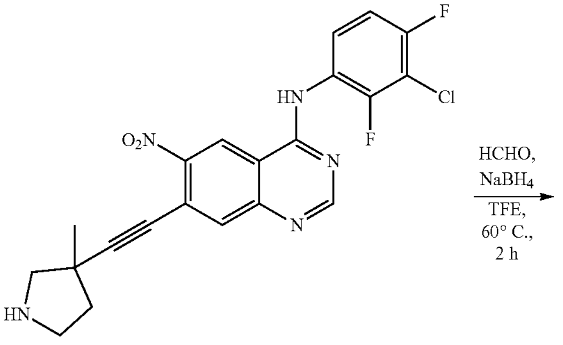

S38

-continued

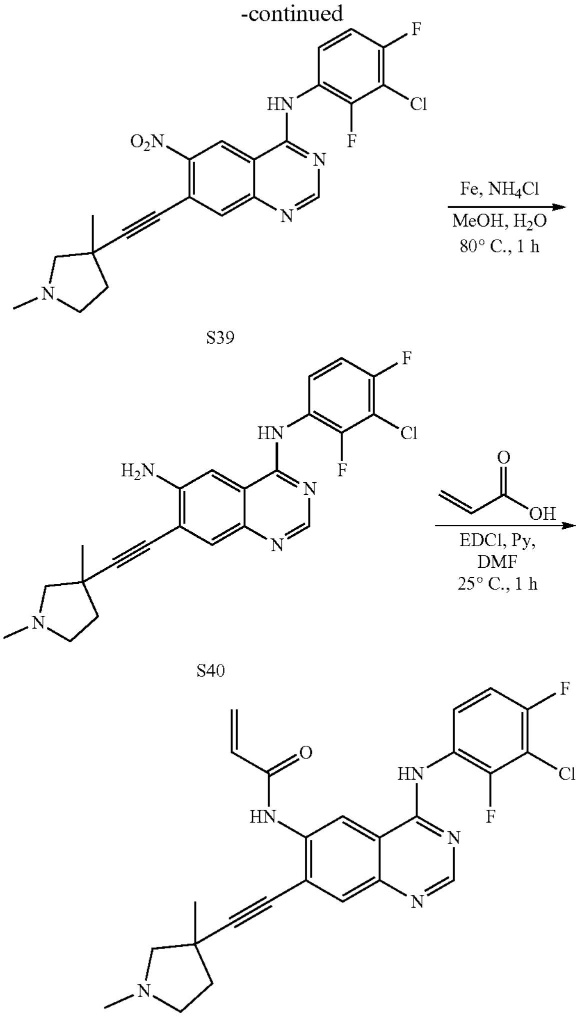

S39

S40

8

S34: A mixture of 4-chloro-7-fluoro-6-nitro-quinazoline S26 (3.50 g, 15.4 mmol, 1.00 eq) and 3-chloro-2,4-difluoroaniline (2.52 g, 15.4 mmol, 1.00 eq) in acetonitrile (30.0 mL) was stirred at 25° C. for 12 h. The mixture was concentrated to dryness to give a residue. The residue was triturated with ethyl acetate (20.0 mL) and filtered, the filter cake was washed with ethyl acetate (10.0 mL) and concentrated to dryness to give N-(3-chloro-2,4-difluorophenyl)-7-fluoro-6-nitroquinazolin-4-amine S34 (4.20 g, 11.8 mmol, 77% yield) as an off-white solid. MS (ESI) m/z 354.9 $[M+H]^+$.

S35: To a solution of N-(3-chloro-2,4-difluorophenyl)-7-fluoro-6-nitroquinazolin-4-amine S34 (4.05 g, 11.4 mmol, 1.00 eq) in dimethyl formamide (40.0 mL) was added potassium acetate (5.60 g, 57.1 mmol, 5.00 eq) at 25° C. The mixture was stirred at 100° C. for 5 h. The mixture was concentrated to afford a residue. The residue was triturated with water (50.0 mL). After filtration, the filter cake was washed with water (30.0 mL), dried in vacuum to give 4-((3-chloro-2,4-difluorophenyl)amino)-6-nitroquinazolin-7-ol S35 (3.50 g, 9.92 mmol, 87% yield) as a brown solid. MS (ESI) m/z 353.0 $[M+H]^+$.

S36: To a solution of 4-((3-chloro-2,4-difluorophenyl) amino)-6-nitroquinazolin-7-ol S35 (3.00 g, 8.51 mmol, 1.00 eq) and pyridine (3.36 g, 42.5 mmol, 3.43 mL, 5.00 eq) in dichloromethane (40.0 mL) was added trifluoromethanesulfonic peroxyanhydride (4.80 g, 17.0 mmol, 2.81 mL, 2.00 eq) dropwise at 0° C., the mixture was stirred at 25° C. for 1 h. The reaction mixture was poured into water (150 mL) and the aqueous phase was extracted with ethyl acetate (3×50.0 mL). The combined organic phase was washed with brine (50.0 mL), dried over anhydrous sodium sulfate, filtered and concentrated in vacuum to give a residue. The residue was purified by silica gel chromatography (Petroleum ether/Ethyl acetate=8/1) to afford 4-((3-chloro-2,4-difluorophenyl)amino)-6-nitroquinazolin-7-yl trifluoromethanesulfonate S36 (1.20 g, 2.48 mmol, 29% yield) as a yellow oil. $^1H$ NMR (400 MHz, $CDCl_3$) δ=9.02-8.96 (m, 1H), 8.90 (s, 1H), 8.07 (dt, J=5.4, 8.8 Hz, 1H), 8.01-7.89 (m, 2H), 7.18-7.11 (m, 1H). MS (ESI) m/z 484.9 $[M+H]^+$.

S37: To a solution of 4-((3-chloro-2,4-difluorophenyl) amino)-6-nitroquinazolin-7-yl trifluoromethanesulfonate S36 (1.00 g, 2.06 mmol, 1.00 eq), tert-butyl 3-ethynyl-3-methyl-pyrrolidine-1-carboxylate (518 mg, 2.48 mmol, 1.20 eq) and triethylamine (2.18 g, 21.6 mmol, 3.00 mL, 10.5 eq) in dimethyl formamide (6.00 mL) was added cuprous iodid (78.6 mg, 413 umol, 0.200 eq) and tetrakis(triphenylphosphine) palladium(0) (238 mg, 206 umol, 0.100 eq) at 25° C. under nitrogen, the mixture was stirred at 25° C. for 1 h. The reaction mixture was poured into water (120 mL) and stirred for 10 min. The aqueous phase was extracted with ethyl acetate (3×60.0 mL). The combined organic phase was washed with brine (100 mL), dried over anhydrous sodium sulfate, filtered and concentrated in vacuum to give a residue. The residue was purified by silica gel chromatography (Petroleum ether/Ethyl acetate=6/1 to 3/1) to afford tert-butyl 3-((4-((3-chloro-2,4-difluorophenyl)amino)-6-nitroquinazolin-7-yl)ethynyl)-3-methylpyrrolidine-1-carboxylate S37 (1.20 g, crude) as a yellow oil. $^1H$ NMR (400 MHz, DMSO-d6) δ=10.63 (s, 1H), 9.39 (s, 1H), 8.67 (br s, 1H), 8.01 (br s, 1H), 7.41 (br s, 2H), 3.61 (d, J=10.4 Hz, 1H), 3.54-3.42 (m, 2H), 3.29-3.22 (m, 1H), 2.24-2.15 (m, 1H), 1.99-1.92 (m, 1H), 1.45 (s, 3H), 1.42 (s, 9H). MS (ESI) m/z 487.9 $[M+H-56]^+$.

S38: To a solution of tert-butyl 3-((4-((3-chloro-2,4-difluorophenyl)amino)-6-nitroquinazolin-7-yl) ethynyl)-3-methylpyrrolidine-1-carboxylate S37 (900 mg, 1.65 mmol, 1.00 eq) in ethyl acetate (4.00 mL) was added 4 M hydrochloride/ethyl acetate (4.00 mL) at 25° C., the mixture was stirred at 25° C. for 1 h. The mixture was concentrated to give a residue. The residue was triturated with ethyl acetate (5.00 mL). After filtration, the filter cake was washed with ethyl acetate (2.00 mL), dried in vacuum to afford N-(3-chloro-2,4-difluorophenyl)-7-((3-methylpyrrolidin-3-yl) ethynyl)-6-nitroquinazolin-4-amine S38 (1.00 g, crude, hydrochloride) as a yellow solid. $^1H$ NMR (400 MHz, DMSO-d6) δ=9.74 (br s, 1H), 9.61 (s, 2H), 8.80 (br s, 1H), 8.21 (br s, 1H), 7.46 (dt, J=1.6, 8.8 Hz, 1H), 3.51-3.42 (m, 3H), 3.25-3.18 (m, 1H), 2.33 (td, J=6.2, 12.6 Hz, 1H), 2.12-2.07 (m, 1H), 1.53 (s, 3H). MS (ESI) m/z 444.0 $[M+H]^+$.

S39: To a solution of N-(3,4-dichloro-2-fluorophenyl)-7-((3-methylpyrrolidin-3-yl)ethynyl)-6-nitroquinazolin-4-amine S38 (600 mg, 1.35 mmol, 1.00 eq) and paraformaldehyde (203 mg, 6.76 mmol, 5.00 eq) in trifluoroethanol (4.00 mL) was added sodium borohydride (102 mg, 2.70 mmol, 2.00 eq) at 25° C., the mixture was stirred at 60° C. for 2 h. The reaction was quenched with methanol slowly and then concentrated to give a residue which was poured into water (50.0 mL) and stirred for 10 min. The aqueous phase was extracted with ethyl acetate (3×50.0 mL). The combined organic phase was washed with brine (50.0 mL), dried over anhydrous sodium sulfate, filtered and concentrated in vacuum to give N-(3-chloro-2,4-difluorophenyl)-7-((1,3-dimethylpyrrolidin-3-yl)ethynyl)-6-nitroquinazolin-4-amine S39 (550 mg, crude) as a yellow solid. MS (ESI) m/z 458.1 $[M+H]^+$.

S40: A mixture of N-(3-chloro-2,4-difluorophenyl)-7-((1,3-dimethylpyrrolidin-3-yl)ethynyl)-6-nitroquinazolin-4-amine S39 (700 mg, 1.53 mmol, 1.00 eq), iron powder (256 mg, 4.59 mmol, 3.00 eq) and ammonium chloride (409 mg, 4.64 mmol, 5.00 eq) in methanol (7.00 mL) and water (3.00 mL) was stirred at 80° C. for 1 h. The reaction mixture was filtered and the filtrate was concentrated to give a residue, the residue was poured into water (80.0 mL), the aqueous phase was extracted with ethyl acetate (3×40.0 mL). The combined organic phase was washed with brine (100 mL), dried over anhydrous sodium sulfate, filtered and concentrated in vacuum to give N4-(3-chloro-2,4-difluorophenyl)-7-((1,3-dimethylpyrrolidin-3-yl)ethynyl)quinazoline-4,6-diamine S40 (500 mg, 1.17 mmol, 76% yield) as a yellow solid. MS (ESI) m/z 428.2 $[M+H]^+$.

8: To a solution of $N^4$-(3-chloro-2,4-difluorophenyl)-7-((1,3-dimethylpyrrolidin-3-yl)ethynyl)quinazoline-4,6-diamine S40 (200 mg, 467 umol, 1.00 eq), acrylic acid (34.0 mg, 468 umol, 32.0 uL, 1.00 eq) and pyridine (185.0 mg, 2.34 mmol, 189 uL, 5.00 eq) in dimethyl formamide (1.00 mL) was added 1-ethyl-3-(3-dimethylamino-propyl)-carbodiimide hydrochloride (358 mg, 1.87 mmol, 4.00 eq), the mixture was stirred at 25° C. for 2 h. The reaction mixture was filtered to give a filtrate. The filtrate was purified by prep-HPLC (column: Waters Xbridge 150*25 mm*5 um; mobile phase: [water (10 mM $NH_4HCO_3$)-ACN]; B %: 37%-65%, 10 min) to afford N-(4-((3-chloro-2,4-difluorophenyl)amino)-7-((1,3-dimethylpyrrolidin-3-yl)ethynyl)-quinazolin-6-yl)acrylamide 8 (40.6 mg, 1.84 mmol, 18% yield, FA) as a yellow solid. 1H NMR (400 MHz, $CDCl_3$) δ=9.10 (s, 1H), 8.60 (s, 2H), 8.04 (dt, J=5.6, 8.8 Hz, 1H), 7.85 (s, 1H), 7.71 (br s, 1H), 7.02-6.93 (m, 1H), 6.52-6.42 (m, 1H), 6.39-6.29 (m, 1H), 5.80 (dd, J=1.2, 10.0 Hz, 1H), 3.01 (d, J=8.8 Hz, 1H), 2.97-2.87 (m, 1H), 2.55-2.45 (m, 1H), 2.40-2.34 (m, 4H), 2.34-2.27 (m, 1H). MS (ESI) m/z 482.2 $[M+H]^+$.

-continued

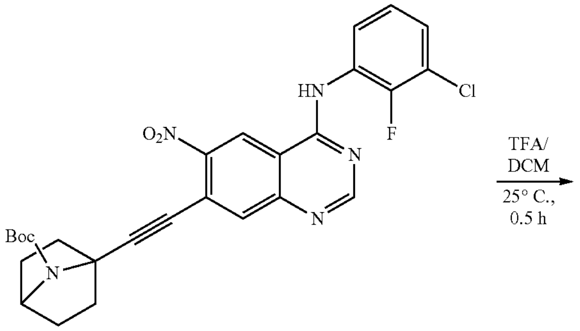

S51

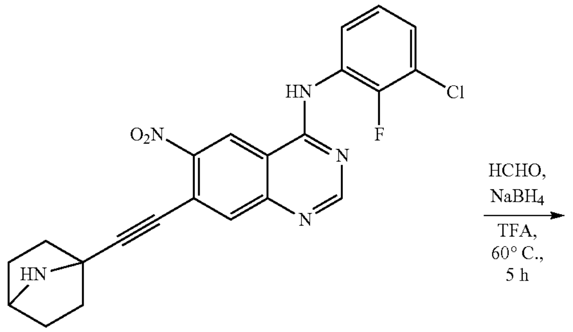

S52

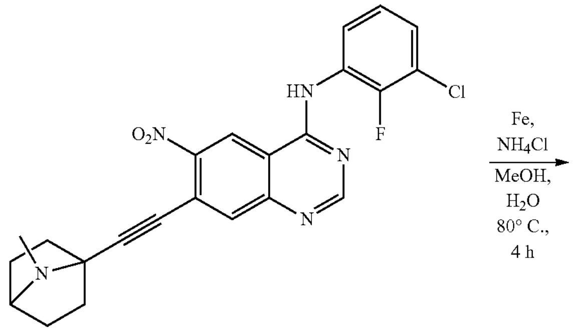

S53

Example 9. Synthesis of Compound 10

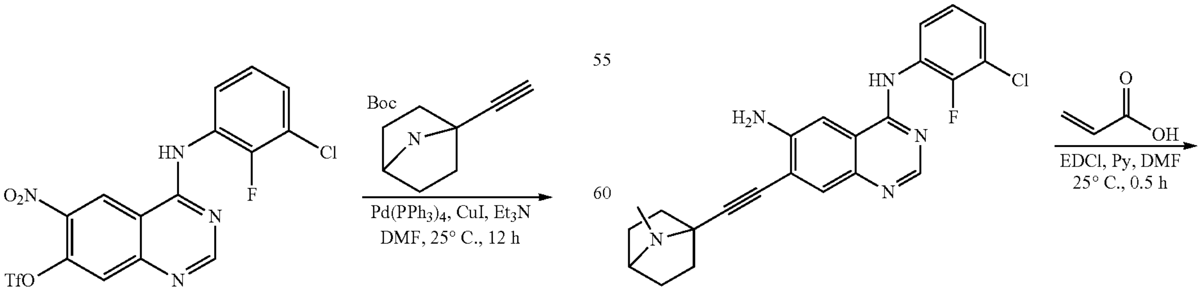

S6 S54

-continued

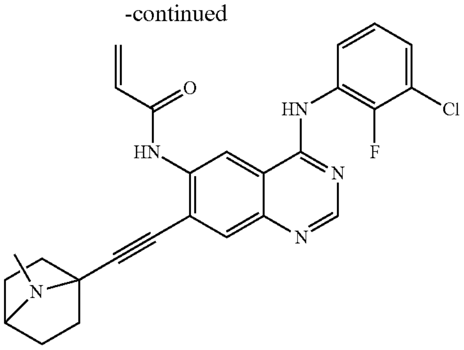

10

S51: To a solution of 4-((3-chloro-2-fluorophenyl) amino)-6-nitroquinazolin-7-yl trifluoromethanesulfonate S6 (1.00 g, 2.14 mmol, 1.00 eq), tert-butyl 1-ethynyl-7-azabicyclo[2.2.1]heptane-7-carboxylate S45 (616 mg, 2.79 mmol, 1.30 eq), triethylamine (2.17 g, 21.42 mmol, 2.98 mL, 10.0 eq) and copper iodide (81.6 mg, 428 umol, 0.200 eq) in dimethyl formamide (25.0 mL) was added tetrakis [triphenylphosphine]palladium(0) (128 mg, 107 umol, 0.0500 eq) at 25° C. The mixture was stirred at 25° C. for 12 h. The reaction mixture was diluted with water (50 mL) and extracted with ethyl acetate (3×20 mL). The combined organic layers were washed with brine (3×20 mL), dried over sodium sulfate, filtered and concentrated under reduced pressure to give a residue. The residue was purified by column chromatography ($SiO_2$, Petroleum ether/Ethyl acetate=1/0 to 1/1) to give tert-butyl 1-((4-((3-chloro-2-fluorophenyl)amino)-6-nitroquinazolin-7-yl) ethynyl)-7-azabicyclo[2.2.1]heptane-7-carboxylate S51 (700 mg, 1.30 mmol, 60% yield) as a yellow solid. $^1H$ NMR (400 MHz, DMSO-$d_6$) δ=10.66 (s, 1H), 9.45 (s, 1H), 8.68 (s, 1H), 8.01 (s, 1H), 7.61-7.55 (m, 2H), 7.33 (dt, J=1.0, 8.0 Hz, 1H), 4.22 (t, J=5.0 Hz, 1H), 2.10-1.94 (m, 4H), 1.81 (td, J=5.6, 10.8 Hz, 2H), 1.62-1.47 (m, 2H), 1.38 (s, 9H). MS (ESI) m/z 538.2 $[M+H]^+$ S52: To a solution of tert-butyl 1-((4-((3-chloro-2-fluorophenyl)amino)-6-nitroquinazolin-7-yl)ethynyl)-7-azabicyclo[2.2.1]heptane-7-carboxylate S51 (650 mg, 1.21 mmol, 1.00 eq) in dichloromethane (25.0 mL) was added trifluoracetic acid (5.51 g, 48.3 mmol, 3.58 mL, 40.0 eq) dropwise and the mixture was stirred at 25° C. for 0.5 h. The reaction mixture was concentrated under reduced pressure to remove solvent. To the residue was added saturated sodium dicarbonate solution till pH=8. Then the mixture was filtered and the filter cake was dried to give 7-(7-azabicyclo[2.2.1] heptan-1-ylethynyl)-N-(3-chloro-2-fluorophenyl)-6-nitro quinazolin-4-amine S52 (500 mg, crude) as a yellow solid. MS (ESI) m/z 438.2 $[M+H]^+$ S53: A mixture of 7-(7-azabicyclo[2.2.1]heptan-1-ylethynyl)-N-(3-chloro-2-fluorophenyl)-6-nitroquinazolin-4-amine S52 (450 mg, 1.03 mmol, 1.00 eq) and paraformaldehyde (154 mg, 5.14 mmol, 5.00 eq) in trifluoethanol (25.0 mL) was stirred at 60° C. for 0.5 h under nitrogen atmosphere. Then to the mixture was added sodium borohydride (77.7 mg, 2.06 mmol, 2.00 eq) in portions at 60° C. and the mixture was refluxed for 4.5 h at 60° C. The reaction mixture was concentrated under reduced pressure to remove solvent and diluted with water (20 mL), extracted with ethyl acetate (3×20 mL). The combined organic layers were washed with brine (3×20 mL), dried over sodium sulfate, filtered and concentrated under reduced pressure to give a residue. The residue was purified by column chromatography ($SiO_2$, Ethyl acetate) to give N-(3-chloro-2-fluorophenyl)-7-((7-methyl-7-azabicyclo[2.2.1]heptan-1-yl)ethynyl)-6-nitroquinazolin-4-amine S53 (300 mg, 664 umol, 64% yield) as a yellow solid. $^1H$ NMR (400 MHz, $CDCl_3$) δ=8.88 (br s, 1H), 8.79 (s, 1H), 8.30 (br s, 1H), 8.15 (s, 1H), 8.06-7.90 (m, 1H), 7.32-7.29 (m, 1H), 7.25-7.17 (m, 1H), 3.48-3.38 (m, 1H), 2.49 (s, 3H), 2.14 (br d, J=1.8 Hz, 2H), 2.02 (br d, J=8.8 Hz, 2H), 1.92-1.84 (m, 2H), 1.49 (br s, 2H). MS (ESI) m/z 452.3 $[M+H]^+$ S54: A mixture of N-(3-chloro-2-fluorophenyl)-7-((7-methyl-7-azabicyclo[2.2.1]heptan-1-yl)ethynyl)-6-nitroquinazolin-4-amine S53 (300 mg, 664 umol, 1.00 eq), iron powder (185 mg, 3.32 mmol, 5.00 eq), ammonium chloride (177 mg, 3.32 mmol, 5.00 eq) in water (10.0 mL) and methanol (15.0 mL) was degassed and purged with nitrogen for 3 times, and then the mixture was stirred at 80° C. for 4 h under nitrogen atmosphere. The reaction mixture was filtered and the filtrate was concentrated under reduced pressure to give a residue. The residue was purified by column chromatography ($SiO_2$, Methanol/Ethyl acetate=0/1 to 1/5) to give $N^4$-(3-chloro-2-fluorophenyl)-7-((7-methyl-7-azabicyclo[2.2.1]heptan-1-yl)ethynyl)quinazoline-4,6-diamine S54 (90.0 mg, 213 umol, 32% yield) as a yellow solid. MS (ESI) m/z 422.3 $[M+H]^+$ 10: To a stirring solution of $N^4$-(3-chloro-2-fluorophenyl)-7-((7-methyl-7-azabicyclo[2.2.1]heptan-1-yl)ethynyl) quinazoline-4,6-diamine S54 (45.0 mg, 107 umol, 1.00 eq), pyridine (16.8 mg, 213 umol, 17.2 uL, 2.00 eq) and acrylic acid (15.4 mg, 213 umol, 14.6 uL, 2.00 eq) in dimethyl formamide (1.50 mL) was added 1-(3-dimethylaminopropyl)-3-ethylcarbodiimide hydrochloride (81.8 mg, 427 umol, 4.00 eq) in portions at 25° C. The mixture was stirred at 25° C. for 0.5 h. The reaction mixture was filtered and the filtrate was purified by prep-HPLC (column: Xtimate $C_{18}$ 150*25 mm*5 um; mobile phase: [water (0.05% ammonia hydroxide v/v)-ACN]; B %: 43%-73%, 10 min) to give N-(4-((3-chloro-2-fluorophenyl)amino)-7-((7-methyl-7-azabicyclo[2.2.1]heptan-1-yl)ethynyl)quinazol in-6-yl)acrylamide 10 (15.79 mg, 32.8 umol, 30% yield, 99% purity) as a yellow solid. $^1H$ NMR (400 MHz, $CDCl_3$) δ=9.22 (s, 1H), 8.76 (s, 1H), 8.51 (br s, 1H), 8.35 (br t, J=7.4 Hz, 1H), 8.05 (s, 1H), 7.87 (br s, 1H), 7.26-7.15 (m, 2H), 6.62-6.42 (m, 2H), 5.91 (br d, J=8.8 Hz, 1H), 3.49 (br s, 1H), 2.50 (s, 3H), 2.17 (br d, J=11.5 Hz, 2H), 2.11-2.02 (m, 2H), 1.94 (br d, J=10.4 Hz, 2H), 1.57 (br s, 2H). MS (ESI) m/z 476.3 $[M+H]^+$

Example 10. Synthesis of Compound 11

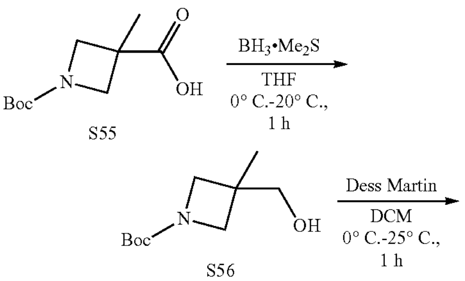

S55
S56

-continued

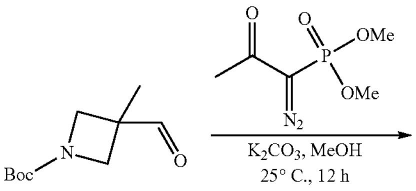

S57

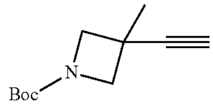

S58

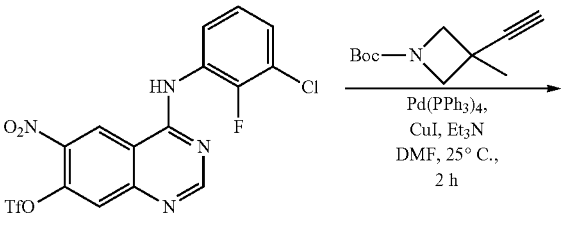

S6

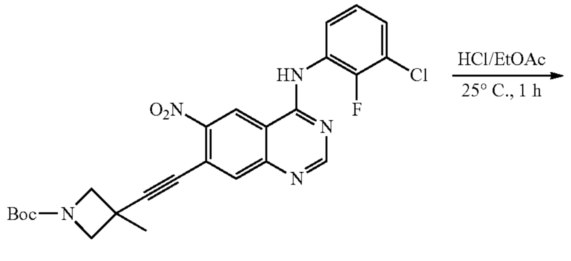

S59

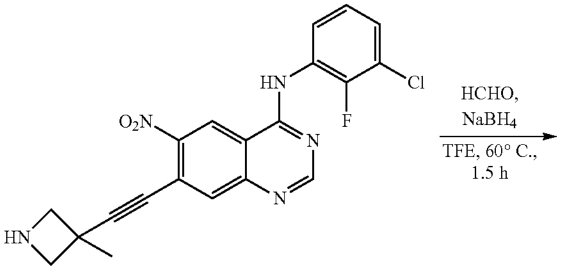

S60

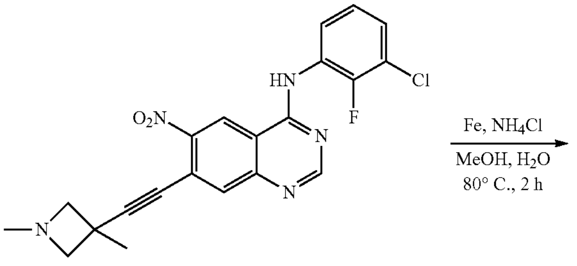

S61

-continued

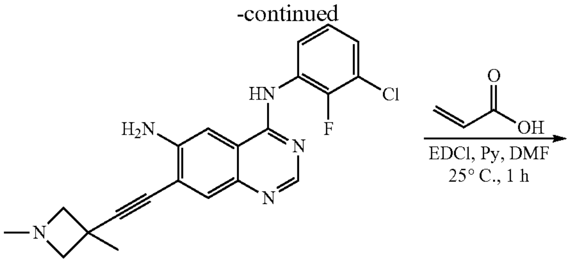

S62

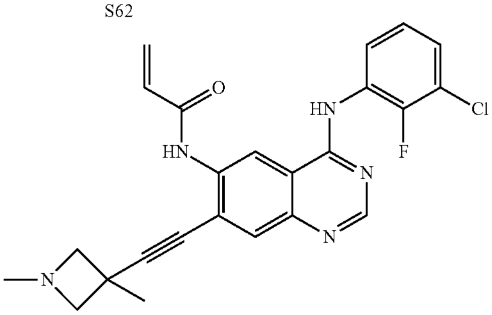

11

S56: To a solution of 1-(tert-butoxycarbonyl)-3-methylazetidine-3-carboxylic acid S55 (800 mg, 3.72 mmol, 1.00 eq) in tetrahydrofuran (10.0 mL) was added borane dimethyl sulfide complex (10.0 M, 558 uL, 1.50 eq) dropwise at 0° C. The mixture was stirred at 20° C. for 1 h. The mixture was quenched with methanol (50.0 mL) and concentrated to give tert-butyl 3-(hydroxymethyl)-3-methylazetidine-1-carboxylate S56 (750 mg, crude) as colorless oil. $^1$H NMR (400 MHz, $CDCl_3$) δ=3.70 (d, J=8.4 Hz, 2H), 3.63 (br t, J=5.8 Hz, 1H), 3.54 (s, 2H), 3.48 (d, J=8.4 Hz, 2H), 1.37 (s, 9H), 1.20 (s, 3H).

S57: To a solution of tert-butyl 3-(hydroxymethyl)-3-methylazetidine-1-carboxylate S56 (750 mg, 3.73 mmol, 1.00 eq) in dichloromethane (10.0 mL) was added Dess-Martin Periodinane (3.16 g, 7.45 mmol, 2.31 mL, 2.00 eq) in portions at 0° C. The mixture was stirred at 25° C. for 1 h. The mixture was concentrated to give crude product. The crude product was purified by silica gel chromatography (petroleum ether/ethyl acetate=10/1 to 3/1) to give tert-butyl 3-formyl-3-methylazetidine-1-carboxylate S57 (740 mg, crude) as colorless oil.

S58: To a solution of tert-butyl 3-formyl-3-methylazetidine-1-carboxylate S57 (740 mg, 3.71 mmol, 1.00 eq) and potassium carbonate (1.03 g, 7.43 mmol, 2.00 eq) in methanol (8.00 mL) was added dimethyl (1-diazo-2-oxopropyl) phosphonate (928 mg, 4.83 mmol, 1.30 eq) dropwise. The mixture was stirred at 25° C. for 12 h. The mixture was concentrated to give crude product. The crude product was purified by silica gel chromatography (petroleum ether/ethyl acetate=20/1 to 10/1) to give tert-butyl 3-ethynyl-3-methylazetidine-1-carboxylate S58 (700 mg, 3.59 mmol, 97% yield) as colorless oil. $^1$H NMR (400 MHz, $CDCl_3$) δ=4.00 (d, J=8.1 Hz, 2H), 3.66 (d, J=8.2 Hz, 2H), 2.25 (s, 1H), 1.47 (s, 3H), 1.37 (s, 9H).

S59: To a solution of 4-((3-chloro-2-fluorophenyl)amino)-6-nitroquinazolin-7-yl trifluoromethanesulfonate S6 (900 mg, 1.93 mmol, 1.00 eq), tert-butyl 3-ethynyl-3-methylazetidine-1-carboxylate (414 mg, 2.12 mmol, 1.10 eq) and copper(I) iodide (73.5 mg, 386 umol, 0.200 eq) in dimethyl formamide (5.00 mL) and triethylamine (5.00 mL) was added tetrakis[triphenylphosphine]palladium(0) (223 mg, 193 umol, 0.100 eq) in one portion under nitrogen. The mixture was stirred at 25° C. for 2 h. The mixture was diluted with water (50.0 mL) and extracted with ethyl acetate (2×40.0 mL). The combined organic layer was washed with brine (20.0 mL) and dried over sodium sulfate, filtered and concentrated to give crude product. The crude product was purified by silica gel chromatography (petroleum ether/ethyl acetate=10/1 to 3/1) to give tert-butyl 3-((4-((3-chloro-2-fluorophenyl)amino)-6-nitroquinazolin-7-yl)ethynyl)-3-methylazetidine-1-carboxylate S59 (650 mg, 1.27 mmol, 66% yield) as yellow oil. $^1$H NMR (400 MHz, DMSO-$d_6$) δ=10.88-10.52 (m, 1H), 9.43 (br s, 1H), 8.67 (br s, 1H), 8.06 (br s, 1H), 7.67-7.45 (m, 2H), 7.37-7.28 (m, 1H), 4.11 (br d, J=7.7 Hz, 2H), 3.88 (br d, J=7.7 Hz, 2H), 1.62 (s, 3H), 1.41 (s, 9H). MS (ESI) m/z 512.0 $[M+H]^+$ S60: To a solution of tert-butyl 3-((4-((3-chloro-2-fluorophenyl)amino)-6-nitroquinazolin-7-yl)ethynyl)-3-methylazetidine-1-carboxylate S59 (600 mg, 1.17 mmol, 1.00 eq) in methanol (5.00 mL) was added hydrochloric acid/ethyl acetate (4 M, 5.00 mL, 17.1 eq) dropwise. The mixture was stirred at 25° C. for 1 h. The mixture was concentrated to give N-(3-chloro-2-fluorophenyl)-7-((3-methylazetidin-3-yl)ethynyl)-6-nitroquinazolin-4-amine S60 (480 mg, 1.17 mmol, 99% yield) as a yellow solid. MS (ESI) m/z 411.9 $[M+H]^+$ S61: To a solution of N-(3-chloro-2-fluorophenyl)-7-((3-methylazetidin-3-yl)ethynyl)-6-nitroquinazolin-4-amine S60 (480 mg, 1.17 mmol, 1.00 eq) in 2,2,2-trifluoroethanol (10.0 mL) was added paraformaldehyde (175 mg, 5.83 mmol, 161 uL, 5.00 eq) in portions at 60° C. The mixture was stirred at 60° C. for 0.5 h. Then the mixture was added sodium borohydride (88.2 mg, 2.33 mmol, 2.00 eq) in portions. The mixture was stirred at 60° C. for 1 h. The mixture was concentrated to give crude product. The residue was diluted with water (50.0 mL) and extracted with ethyl acetate (3x30.0 mL). The combined organic layer was washed with brine (20.0 mL) and dried over sodium sulfate, filtered and concentrated to give N-(3-chloro-2-fluorophenyl)-7-((1,3-dimethylazetidin-3-yl)ethynyl)-6-nitroquinazolin-4-amine S61 (500 mg, crude) as a yellow solid.

$^1$H NMR (400 MHz, DMSO-$d_6$) δ=9.36 (s, 1H), 8.60 (br s, 1H), 7.95 (s, 1H), 7.71-7.42 (m, 3H), 7.31 (t, J=7.7 Hz, 1H), 3.32-3.30 (m, 2H), 3.28-3.24 (m, 2H), 2.27 (s, 3H), 1.60 (s, 3H).

S62: To a solution of N-(3-chloro-2-fluorophenyl)-7-((1,3-dimethylazetidin-3-yl)ethynyl)-6-nitroquinazolin-4-amine S61 (500 mg, 1.17 mmol, 1.00 eq) and ammonium chloride (314 mg, 5.87 mmol, 5.00 eq) in methanol (20.0 mL) and water (5.00 mL) was added iron powder (328 mg, 5.87 mmol, 5.00 eq) in portions. The mixture was stirred at 80° C. for 2 h. The mixture was added methanol (200 mL) and filtered. The filtrate was concentrated to give crude product. The residue was diluted with saturated sodium hydrogencarbonate solution (50.0 mL) and extracted with ethyl acetate (3x40.0 mL). The combined organic layer was washed with brine (20.0 mL) and dried over sodium sulfate, filtered and concentrated to give $N^4$-(3-chloro-2-fluorophenyl)-7-((1,3-dimethylazetidin-3-yl)ethynyl)quinazoline-4,6-diamine S62 (450 mg, 1.14 mmol, 97% yield) as a yellow solid. MS (ESI) m/z 396.0 $[M+H]^+$ 11: To a solution of $N^4$-(3-chloro-2-fluorophenyl)-7-((1,3-dimethylazetidin-3-yl)ethynyl)quinazoline-4,6-diamine S62 (400 mg, 1.01 mmol, 1.00 eq), acrylic acid (87.4 mg, 1.21 mmol, 83.2 uL, 1.20 eq) and pyridine (320 mg, 4.04 mmol, 326 uL, 4.00 eq) in dimethyl formamide (6.00 mL) was added 1-(3-dimethyl aminopropyl)-3-ethylcarbodiimide hydrochloride (775 mg, 4.04 mmol, 4.00 eq) in portions. The mixture was stirred at 25° C. for 1 h. The mixture was filtered and the filtrate was purified by prep-HPLC (column: Waters Xbridge 150*25 mm*5 um; mobile phase: [water (10 mM $NH_4HCO_3$)-ACN]; B %: 37%-67%, 10 min) and lyophilized to give N-(4-((3-chloro-2-fluorophenyl)amino)-7-((1,3-dimethylazetidin-3-yl)ethynyl) quinazolin-6-yl) acrylamide 11 (14.08 mg, 30.7 umol, 3% yield, 98% purity) as a yellow solid.

$^1$H NMR (400 MHz, $CDCl_3$) δ=9.20 (s, 1H), 8.75 (s, 1H), 8.69 (br s, 1H), 8.35 (dt, J=1.9, 7.4 Hz, 1H), 7.99 (s, 1H), 7.87 (br s, 1H), 7.24-7.15 (m, 2H), 6.60-6.44 (m, 2H), 5.94-5.88 (m, 1H), 3.66 (br d, J=3.2 Hz, 2H), 3.36 (br d, J=6.7 Hz, 2H), 2.48 (s, 3H), 1.70 (s, 3H). MS (ESI) m/z 449.9 $[M+H]^+$

Example 11. Synthesis of Compound 12

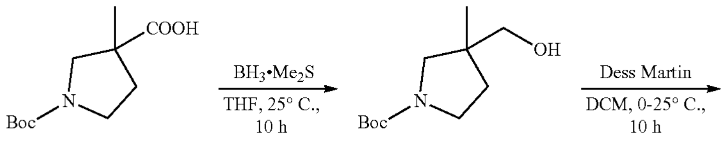

S63 S64

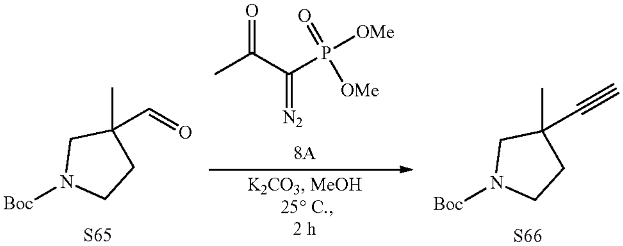

S65 S66

-continued
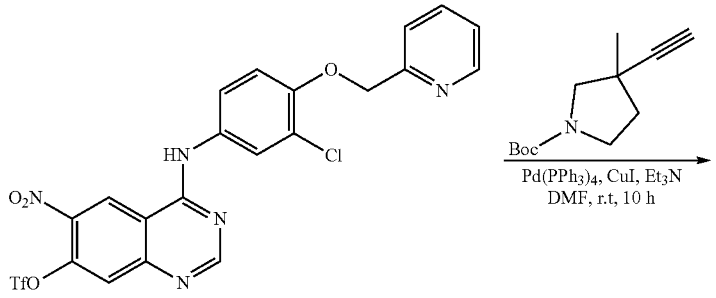
S46
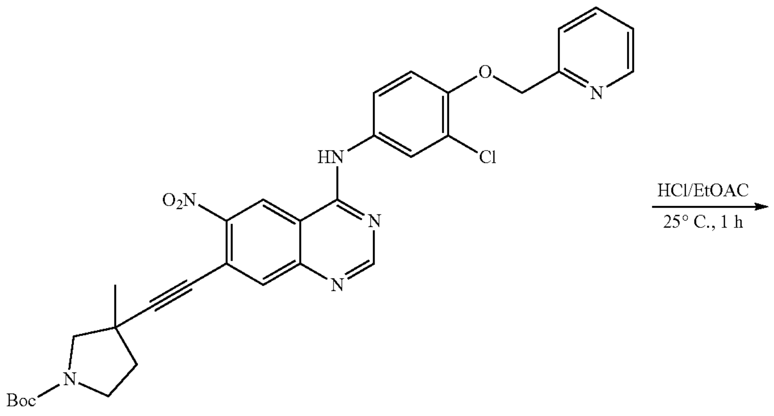
S67
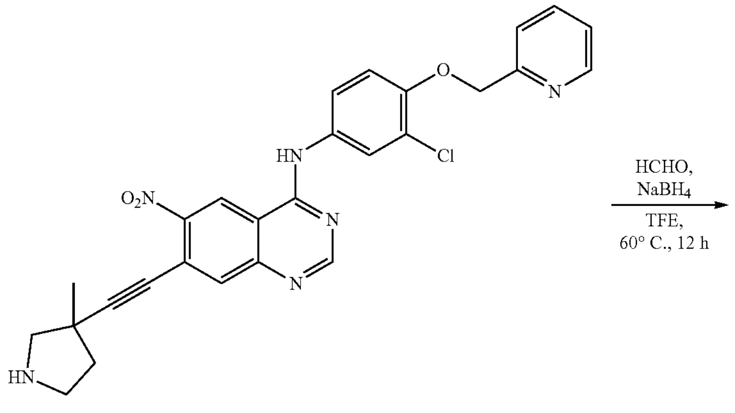
S68
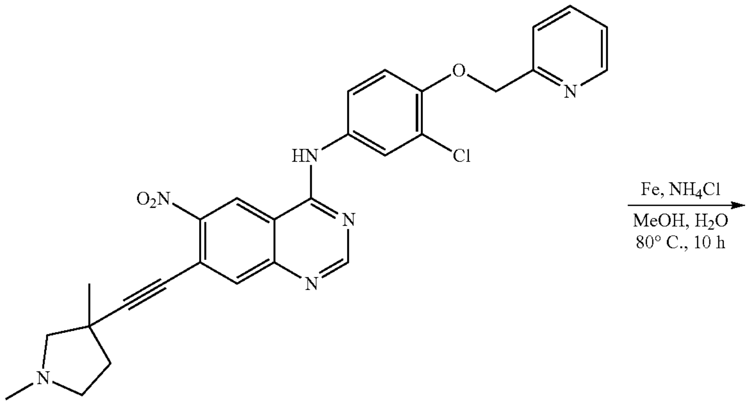
S69

-continued

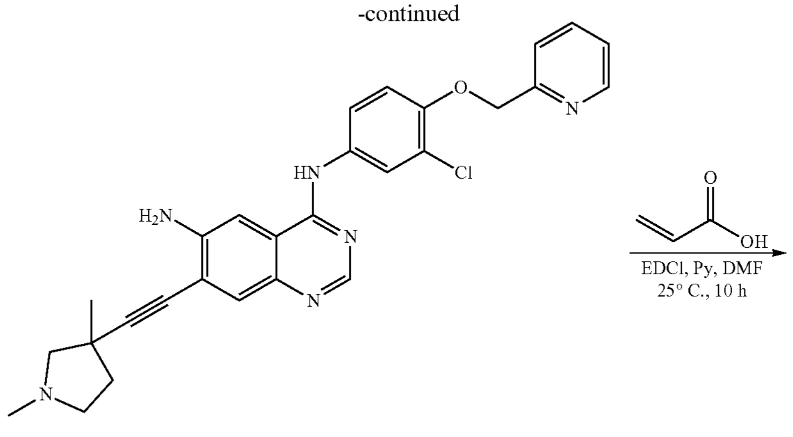

S70

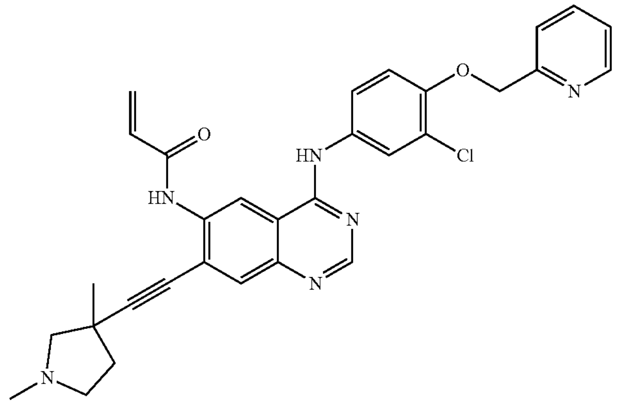

12

S64: To a solution of 1-(tert-butoxycarbonyl)-3-methylpyrrolidine-3-carboxylic acid S63 (1.50 g, 6.54 mmol, 1.00 eq) in THF (10.0 mL) was added borane dimethyl sulfide complex (10.0 M, 654 uL, 1.00 eq) dropwise at 0° C. Then the mixture was stirred at 25° C. for 10 h. The reaction mixture was quenched by addition methanol (15.0 mL), and then diluted with water (30.0 mL) and extracted with ethyl acetate (3×60.0 mL). The combined organic layers were washed with brine (20.0 mL), dried over sodium sulfate, filtered and concentrated under reduced pressure to give tert-butyl 3-(hydroxymethyl)-3-methylpyrrolidine-1-carboxylate S64 (1.65 g, crude) as yellow oil. $^1$H NMR (400 MHz, Chloroform-d) δ=3.48-3.27 (m, 4H), 3.27-3.14 (m, 1H), 3.05-2.90 (m, 1H), 1.86-1.70 (m, 1H), 1.56-1.46 (m, 1H), 1.46-1.34 (m, 9H), 1.03 (s, 3H).

S65: To a solution of tert-butyl 3-(hydroxymethyl)-3-methylpyrrolidine-1-carboxylate S64 (1.83 g, 8.50 mmol, 1.00 eq) in dichloromethane (20.0 mL) was added (1,1-diacetoxy-3-oxo-1,2-benziodoxol-1-yl) acetate (3.61 g, 8.50 mmol, 2.63 mL, 1.00 eq). Then the mixture was stirred at 25° C. for 10 h. The reaction mixture was concentrated under reduced pressure to remove dichloromethane. The residue was diluted with saturated sodium bicarbonate (40.0 mL) and extracted with ethyl acetate (3×80.0 mL). The combined organic layers were washed with brine (45.0 mL), dried over sodium sulfate, filtered and concentrated under reduced pressure to give tert-butyl 3-formyl-3-methylpyrrolidine-1-carboxylate S65 (1.90 g, crude) as yellow oil. $^1$H NMR (400 MHz, Chloroform-d) δ=9.48 (s, 1H), 3.76-3.61 (m, 1H), 3.38-3.25 (m, 2H), 3.12-2.97 (m, 1H), 2.25-2.12 (m, 1H), 1.64 (br dd, J=7.6, 12.9 Hz, 1H), 1.39 (s, 9H), 1.17 (s, 3H).

S66: To a solution of tert-butyl 3-formyl-3-methylpyrrolidine-1-carboxylate S65 (1.90 g, 8.91 mmol, 1.00 eq) and potassium carbonate (2.46 g, 17.8 mmol, 2.00 eq) in methanol (20.0 mL) was added dimethyl (1-diazo-2-oxopropyl) phosphonate (2.05 g, 10.7 mmol, 1.20 eq) dropwise at 0° C. Then the mixture was stirred at 25° C. for 2 h. The reaction mixture was concentrated under reduced pressure to give a residue. The residue was purified by column chromatography (petroleum ether/ethyl acetate=10/1) to afford tert-butyl 3-ethynyl-3-methylpyrrolidine-1-carboxylate S66 (1.40 g, 6.69 mmol, 75% yield) as yellow oil. $^1$H NMR (400 MHz, Chloroform-d) δ=3.55-3.29 (m, 3H), 3.19-3.06 (m, 1H), 2.09 (s, 1H), 2.07-1.99 (m, 1H), 1.78-1.68 (m, 1H), 1.39 (s, 9H), 1.28 (s, 3H).

S67: A mixture of 4-((3-chloro-4-(pyridin-2-ylmethoxy) phenyl)amino)-6-nitroquinazolin-7-yltrifluoromethane sulfonate S46 (1.00 g, 1.80 mmol, 1.00 eq), tert-butyl 3-ethynyl-3-methylpyrrolidine-1-carboxylate S66 (489 mg, 2.34 mmol, 1.30 eq), tetrakis(triphenylphosphine) palladium (0) (208 mg, 180 umol, 0.100 eq), cuprous iodide (68.5 mg, 360 umol, 0.200 eq) and triethylamine (546 mg, 5.40 mmol, 751 uL, 3.00 eq) in tetrahydrofuran (10.0 mL) was stirred at 25° C. in nitrogen atmosphere for 10 h. The reaction mixture was filtered and concentrated under reduced pressure to give a residue. The residue was purified by column chromatography (petroleum ether/ethyl acetate=1/1) to afford tert-butyl 3-((4-((3-chloro-4-(pyridin-2-ylmethoxy)phenyl)amino)-6-nitroquinazolin-7-yl)ethynyl)-3-methylpyrrolidine-1-carb oxy late S67 (0.862 g, 1.40 mmol, 78% yield) as a yellow solid. $^1$H NMR (400 MHz, Chloroform-d) 6=9.03 (d, J=14.2

Hz, 1H), 8.80 (s, 1H), 8.62 (d, J=4.6 Hz, 1H), 8.02 (d, J=4.2 Hz, 1H), 7.93 (s, 1H), 7.82-7.76 (m, 1H), 7.70-7.65 (m, 2H), 7.48 (dd, J=3.2, 7.7 Hz, 1H), 7.03 (d, J=9.0 Hz, 1H), 5.32 (s, 2H), 3.83-3.74 (m, 1H), 3.71-3.62 (m, 1H), 3.61-3.52 (m, 1H), 3.31 (br d, J=10.4 Hz, 1H), 2.36-2.22 (m, 1H), 1.99-1.88 (m, 1H), 1.53-1.48 (m, 12H).

S68: A mixture of tert-butyl 3-((4-((3-chloro-4-(pyridin-2-ylmethoxy)phenyl)amino)-6-nitroquinazolin-7-yl) ethynyl)-3-methylpyrrolidine-1-carboxylate S67 (0.862 g, 1.40 mmol, 1.00 eq) in hydrochloric acid/ethyl acetate (2.00 mL) was stirred at 25° C. for 1 h. The reaction mixture was concentrated under reduced pressure to give N-(3-chloro-4-(pyridin-2-ylmethoxy)phenyl)-7-((3-methylpyrrolidin-3-yl) ethynyl)-6-nitroquinazolin-4-amine S68 (0.800 g, crude, hydrochloric acid) as a yellow solid. $^1$H NMR (400 MHz, DMSO-$d_6$) δ=9.61 (s, 1H), 9.57-9.42 (m, 2H), 8.85-8.81 (m, 1H), 8.67 (d, J=5.0 Hz, 1H), 8.14 (s, 1H), 8.05-7.98 (m, 2H), 7.59-7.55 (m, 1H), 7.49 (dd, J=5.0, 7.8 Hz, 1H), 7.35 (d, J=9.0 Hz, 1H), 5.38 (s, 2H), 3.46-3.39 (m, 3H), 3.24-3.16 (m, 1H), 2.12-2.01 (m, 2H), 1.53 (s, 3H).

S69: A mixture of N-(3-chloro-4-(pyridin-2-ylmethoxy) phenyl)-7-((3-methylpyrrolidin-3-yl)ethynyl)-6-nitroquinazolin-4-amine S68 (0.800 g, 1.45 mmol, 1.00 eq, hydrochloric acid), paraformaldehyde (218 mg, 7.25 mmol, 200 uL, 5.00 eq) and sodium borohydride (110 mg, 2.90 mmol, 2.00 eq) in trifluoroethanol (10.0 mL) was stirred at 60° C. for 12 h. The reaction mixture was quenched by addition methanol (15.0 mL), and concentrated to obtained a residue. Then the mixture diluted with water (15.0 mL) and extracted with ethyl acetate (3×35.0 mL). The combined organic layers were washed with brine (20.0 mL), dried over sodium sulfate, filtered and concentrated under reduced pressure to give N-(3-chloro-4-(pyridin-2-ylmethoxy) phenyl)-7-((1,3-dimethylpyrrolidin-3-yl)ethynyl)-6-nitroquinazolin-4-amine S69 (0.800 g, crude) as a yellow solid. $^1$H NMR (400 MHz, Chloroform-d) δ=8.81 (s, 1H), 8.73 (s, 1H), 8.65-8.59 (m, 1H), 8.06 (s, 1H), 7.92-7.89 (m, 1H), 7.80-7.77 (m, 1H), 7.68 (s, 1H), 7.58-7.54 (m, 1H), 7.50 (d, J=2.8 Hz, 1H), 7.09-7.04 (m, 1H), 5.36-5.29 (m, 2H), 4.02-3.94 (m, 1H), 2.99-2.88 (m, 1H), 2.78-2.71 (m, 1H), 2.68-2.63 (m, 1H), 2.50-2.33 (m, 4H), 2.00-1.92 (m, 1H), 1.55-1.52 (m, 3H).

S70: A mixture of N-(3-chloro-4-(pyridin-2-ylmethoxy) phenyl)-7-((1,3-dimethylpyrrolidin-3-yl)ethynyl)-6-nitroquinazolin-4-amine S69 (0.800 g, 1.51 mmol, 1.00 eq), ammonium chloride (243 mg, 4.54 mmol, 3.00 eq) and ferrous powder (253 mg, 4.54 mmol, 3.00 eq) in methanol (8.00 mL) and water (8.00 mL) was stirred at 80° C. for 10 h. The reaction mixture was filtered and concentrated under reduced pressure to give a residue. The residue was purified was by reverse phase chromatography (column: C18, 80 g; condition: water-0.1% formic acid-acetonitrile) and lyophilized to afford N$^4$-(3-chloro-4-(pyridin-2-ylmethoxy) phenyl)-7-((1,3-dimethylpyrrolidin-3-yl)ethynyl)quinazoline-4,6-diamine S70 (160 mg, 317 umol, 21% yield, 99% purity) as a yellow solid. $^1$H NMR (400 MHz, Chloroform-d) δ=8.56-8.48 (m, 1H), 8.44 (s, 1H), 7.78 (d, J=2.4 Hz, 1H), 7.73-7.65 (m, 2H), 7.58 (br d, J=7.8 Hz, 1H), 7.47-7.39 (m, 1H), 7.17 (br d, J=6.5 Hz, 1H), 6.98-6.87 (m, 2H), 5.25-5.14 (m, 2H), 3.19 (br d, J=10.0 Hz, 1H), 3.13-3.02 (m, 1H), 2.92-2.84 (m, 1H), 2.72 (br d, J=10.0 Hz, 1H), 2.51 (s, 3H), 2.34 (br d, J=5.4 Hz, 1H), 1.97 (td, J=7.7, 12.9 Hz, 1H), 1.48 (s, 3H).

12: A mixture of N$^4$-(3-chloro-4-(pyridin-2-ylmethoxy) phenyl)-7-((1,3-dimethylpyrrolidin-3-yl)ethynyl) quinazoline-4,6-diamine S70 (80.0 mg, 160 umol, 1.00 eq), acrylic acid (15.0 mg, 208 umol, 14.3 uL, 1.30 eq), 1-ethyl-3-(3-dimethylamino-propyl)-carbodiimide hydrochloride (92.2 mg, 481 umol, 3.00 eq) and pyridine (38.0 mg, 481 umol, 38.8 uL, 3.00 eq) in dimethyl formamide (2.00 mL) was stirred at 25° C. for 10 h. The reaction mixture was concentrated under reduced pressure to give a residue. The residue was purified by prep-HPLC (column: Phenomenex Gemini 150×25 mm×10 um; mobile phase: [water (10 mM $NH_4HCO_3$)-ACN]; B %: 45%-69%, 10 min) and lyophilized to afford N-(4-((3-chloro-4-(pyridin-2-ylmethoxy)phenyl) amino)-7-((1,3-dimethylpyrrolidin-3-yl)ethynyl)quinazolin-6-yl)acrylamide 12 (27.35 mg, 49.0 umol, 30% yield, 99% purity) as a yellow solid. $^1$H NMR (400 MHz, Chloroform-d) δ=9.02 (s, 1H), 8.59 (s, 2H), 8.54-8.50 (m, 1H), 7.86-7.80 (m, 2H), 7.74 (s, 1H), 7.71-7.66 (m, 1H), 7.62-7.57 (m, 1H), 7.47 (dd, J=2.8, 8.8 Hz, 1H), 7.18-7.15 (m, 1H), 6.94 (d, J=8.8 Hz, 1H), 6.50-6.41 (m, 1H), 6.39-6.29 (m, 1H), 5.83-5.76 (m, 1H), 5.23 (s, 2H), 3.00 (d, J=9.0 Hz, 1H), 2.91 (dt, J=5.6, 8.8 Hz, 1H), 2.49 (dt, J=6.0, 9.2 Hz, 1H), 2.40-2.35 (m, 4H), 2.34-2.25 (m, 1H), 1.90 (ddd, J=5.6, 8.8, 13.0 Hz, 1H), 1.46 (s, 3H). MS (ESI) m/z 553.4 [M+H]$^+$ Example 12. Synthesis of Compound 13

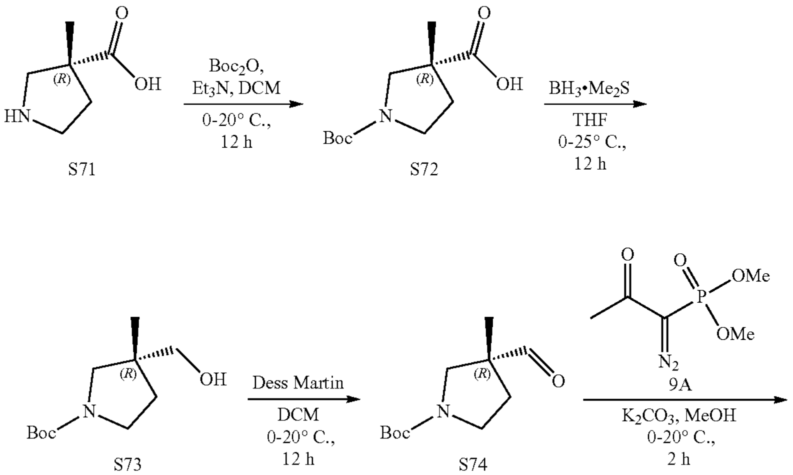

S71 S72 S73 S74 9A

-continued
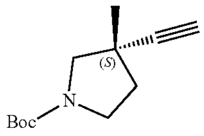
S75
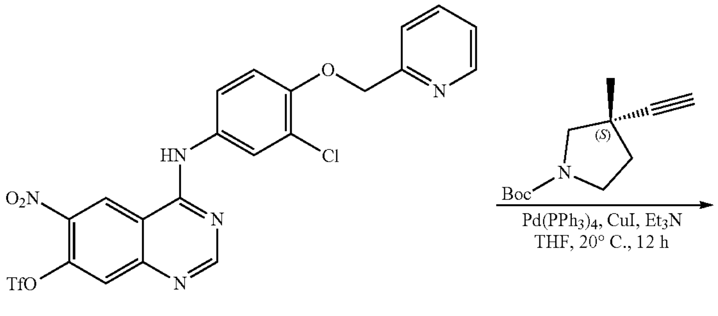
S46
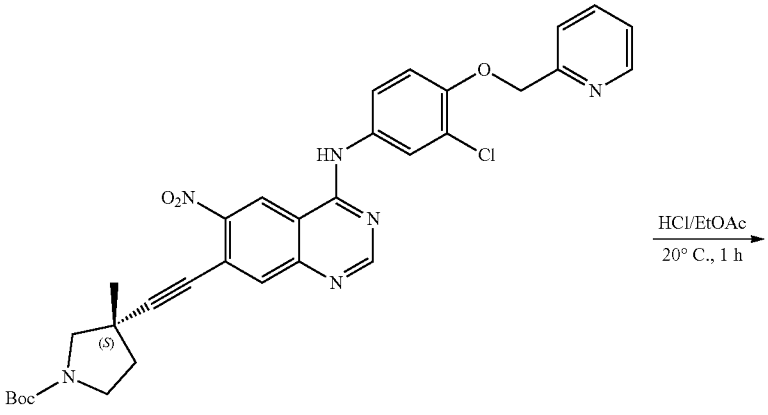
S76
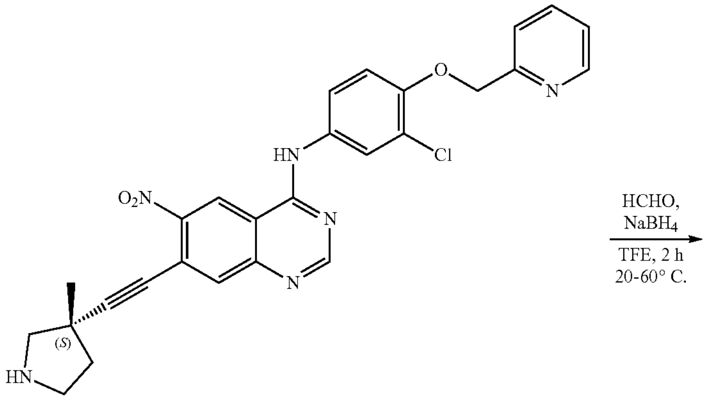
S77

-continued

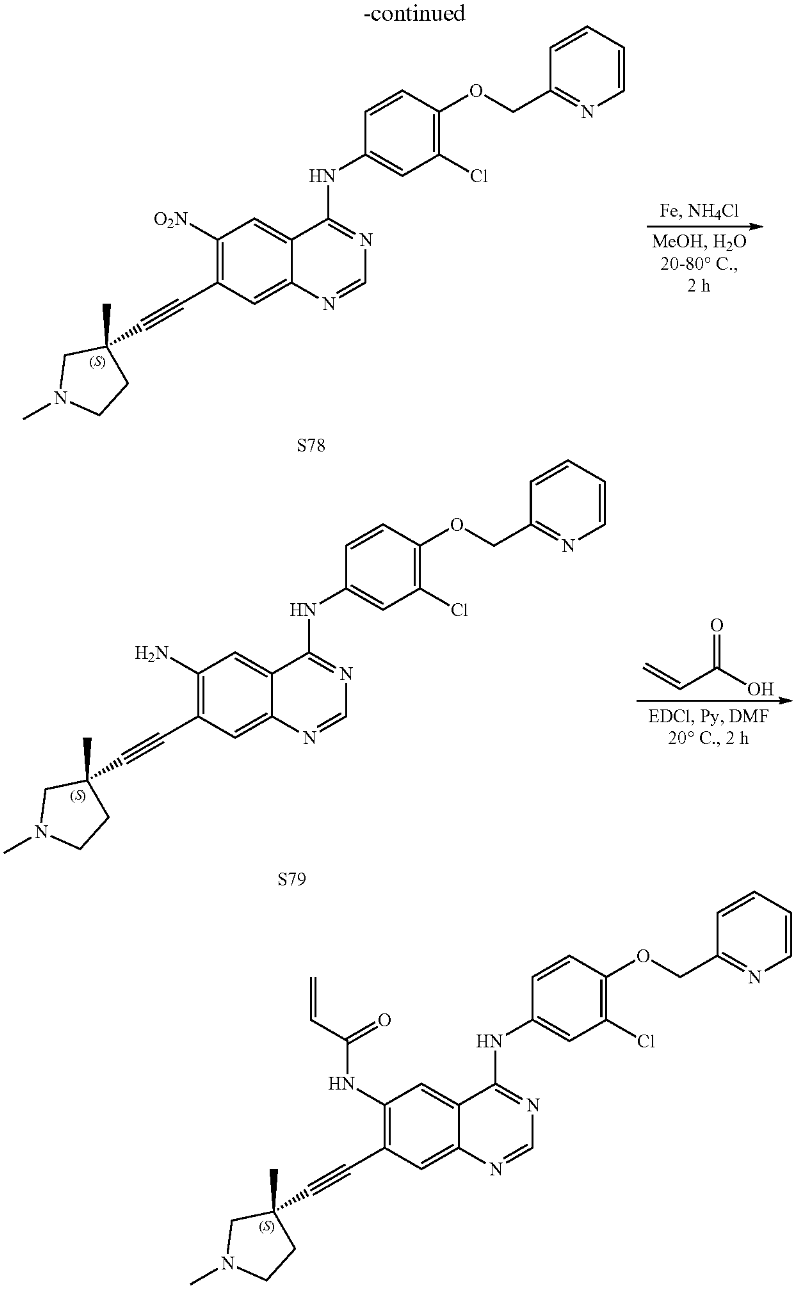

S78

S79

13

S72: To a solution of (R)-3-methylpyrrolidine-3-carboxylic acid S71 (1.20 g, 9.29 mmol) in dichloromethane (40.0 mL) was added di-tert butyl dicarbonate (2.43 g, 11.2 mmol) and triethylamine (1.88 g, 18.6 mmol) at 0° C. The mixture was stirred at 20° C. for 12 h. The mixture was concentrated under vacuum to give a residue. The residue was purified by column chromatography on silica gel (petroleum ether/ethyl acetate=10/1, dichloromethane/methanol/formic acid=10/0/0.001) to give (R)-1-(tert-butoxycarbonyl)-3-methylpyrrolidine-3-carboxylic acid S72 (2.20 g, crude) as brown oil. $^1H$ NMR (400 MHz, $CDCl_3$) δ=3.88-3.75 (m, 1H), 3.46 (br s, 2H), 3.29-3.17 (m, 1H), 2.45-2.23 (m, 1H), 1.90-1.67 (m, 1H), 1.47 (br s, 9H), 1.39 (br s, 3H).

S73: To a solution of (R)-1-(tert-butoxycarbonyl)-3-methylpyrrolidine-3-carboxylic acid S72 (2.20 g, 9.60 mmol) in tetrahydrofuran (30.0 mL) was added borane dimethyl sulfide complex (10.0 M, 0.960 mL) drop-wise at 0° C. The mixture was stirred at 25° C. for 12 h. The reaction mixture was quenched by addition methanol (15.0 mL) and then concentrated under vacuum. The residue was diluted with ethyl acetate (60.0 mL), washed with brine (2×20.0 mL). The combined organic layer was dried over anhydrous sodium sulfate to give (R)-tert-butyl 3-(hydroxymethyl)-3-methylpyrrolidine-1-carboxylate S73 (1.90 g, crude) as colorless oil. $^1H$ NMR (400 MHz, $CDCl_3$) δ=3.49 (br d, J=4.2 Hz, 2H), 3.45-3.35 (m, 2H), 3.33-3.23 (m, 1H), 3.11-2.98 (m, 1H), 1.91-1.81 (m, 1H), 1.53-1.49 (m, 1H), 1.47 (s, 9H), 1.11 (s, 3H).

S74: To a solution (R)-tert-butyl 3-(hydroxymethyl)-3-methylpyrrolidine-1-carboxylate S73 (1.90 g, 8.83 mmol) in dichloromethane (100 mL) was added (1,1-diacetoxy-3-oxo-1,2-benziodoxol-1-yl) acetate (3.74 g, 8.83 mmol) at 0° C. The mixture was stirred at 20° C. for 12 h. The reaction mixture was concentrated under reduced pressure to remove dichloromethane to give a residue. The residue was diluted with saturated sodium bicarbonate (40.0 mL) and ethyl acetate (100 mL). The mixture was filtered and the filtrate was extracted with ethyl acetate (2×100 mL). The combined organic layers were washed with brine (45.0 mL), dried over sodium sulfate, filtered and concentrated under reduced pressure to give (R)-tert-butyl 3-formyl-3-methylpyrrolidine-1-carboxylate S74 (1.70 g, crude) as colorless oil. $^1$H NMR (400 MHz, $CDCl_3$) δ=9.55 (s, 1H), 3.84-3.73 (m, 1H), 3.46-3.35 (m, 2H), 3.16-3.07 (m, 1H), 2.27-2.20 (m, 1H), 1.76-1.69 (m, 1H), 1.47 (s, 9H), 1.24 (s, 3H).

S75: To a suspension of (R)-tert-butyl 3-formyl-3-methylpyrrolidine-1-carboxylate S74 (1.70 g, 7.97 mmol), dimethyl (1-diazo-2-oxopropyl)phosphonate (1.84 g, 9.57 mmol) in methanol (10.0 mL) was added potassium carbonate (2.20 g, 15.9 mmol) at 0° C. The mixture was stirred at 20° C. for 2 h. The reaction mixture was filtered, and filtrate was concentrated under reduced pressure to give a residue. The residue was purified by column chromatography (petroleum ether/ethyl acetate=10/1) to give (S)-tert-butyl 3-ethynyl-3-methylpyrrolidine-1-carboxylate S75 (1.10 g, 5.26 mmol, 65% yield) as colorless oil. $^1$H NMR (400 MHz, $CDCl_3$) δ=3.62-3.40 (m, 3H), 3.26-3.15 (m, 1H), 2.16 (d, J=3.0 Hz, 1H), 2.14-2.08 (m, 1H), 2.14-2.07 (m, 1H), 1.87-1.77 (m, 1H), 1.47 (s, 9H), 1.36 (s, 3H).

S76: To a suspension of 4-((3-chloro-4-(pyridin-2-ylmethoxy)phenyl)amino)-6-nitroquinazolin-7-yltrifluoromethanesulfonate S46 (2.78 g, 5.01 mmol), (S)-tert-butyl 3-ethynyl-3-methylpyrrolidine-1-carboxylate S75 (1.10 g, 5.26 mmol), cuprous iodide (0.191 g, 1.00 mmol), triethylamine (1.52 g, 15.0 mmol) in tetrahydrofuran (30.0 mL) was added tetrakis(triphenylphosphine) palladium (0) (0.578 g, 0.501 mmol) at 20° C. The mixture was degassed with nitrogen for 0.1 h, and stirred at 20° C. under nitrogen atmosphere for 12 h. The reaction mixture was filtered and concentrated under reduced pressure to give a residue. The residue was purified by column chromatography on silica gel (petroleum ether/ethyl acetate=5/1 to 0/1) to afford (S)-tert-butyl 3-((4-(((3-chloro-4-(pyridin-2-ylmethoxy) phenyl)amino)-6-nitroquinazolin-7-yl) ethynyl)-3-methylpyrrolidine-1-carboxylate S76 (2.50 g, 4.06 mmol, 81% yield) as a yellow solid. $^1$H NMR (400 MHz, $CDCl_3$) δ=8.92 (s, 1H), 8.80 (s, 1H), 8.61 (td, J=0.8, 4.1 Hz, 1H), 8.43-8.33 (m, 1H), 8.11-8.00 (m, 1H), 7.96-7.90 (m, 1H), 7.82-7.73 (m, 1H), 7.70-7.63 (m, 1H), 7.55 (dt, J=2.8, 5.8 Hz, 1H), 7.07-6.98 (m, 1H), 5.32 (s, 2H), 3.77 (s, 1H), 3.69-3.61 (m, 1H), 3.59-3.48 (m, 1H), 3.19 (br dd, J=3.6, 7.2 Hz, 1H), 2.35-2.23 (m, 1H), 1.99-1.88 (m, 1H), 1.50 (br s, 3H), 1.49 (s, 9H).

S77: A solution of (S)-tert-butyl 3-((4-((3-chloro-4-(pyridin-2-ylmethoxy)phenyl)amino)-6-nitroquinazolin-7-yl) ethynyl)-3-methylpyrrolidine-1-carboxylate S76 (1.50 g, 2.44 mmol) in hydrochloric acid/ethyl acetate (4.00 M, 10.0 mL) was stirred at 20° C. for 1 h. The mixture was concentrated under vacuum to give a residue. The residue was triturated with ethyl acetate (20.0 mL) to give (S)—N-(3-chloro-4-(pyridin-2-ylmethoxy) phenyl)-7-((3-methylpyrrolidin-3-yl)ethynyl)-6-nitroquinazolin-4-amine S77 (hydrochloride, 1.30 g, 2.36 mmol, 96% yield) as a yellow solid. $^1$H NMR (400 MHz, DMSO-$d_6$) δ=11.74-11.47 (m, 1H), 9.74 (s, 2H), 9.69-9.58 (m, 1H), 8.90 (s, 1H), 8.72 (br d, J=4.5 Hz, 1H), 8.21-8.17 (m, 1H), 8.15-8.09 (m, 1H), 8.01-7.98 (m, 1H), 7.80-7.74 (m, 1H), 7.72 (dd, J=2.5, 8.9 Hz, 1H), 7.62-7.56 (m, 1H), 7.37 (d, J=9.0 Hz, 1H), 5.43 (s, 2H), 3.51-3.37 (m, 3H), 3.26-3.16 (m, 1H), 2.36-2.25 (m, 1H), 2.07 (td, J=8.2, 12.9 Hz, 1H), 1.52 (s, 3H). MS (ESI) m/z 515.3 $[M+H]^+$ S78: To a solution of (S)—N-(3-chloro-4-(pyridin-2-ylmethoxy)phenyl)-7-((3-methylpyrrolidin-3-yl)ethynyl)-6-nitroquinazolin-4-amine S77 (1.40 g, 2.54 mmol, hydrochloride) and paraformaldehyde (0.762 g, 25.4 mmol) in trifluoroethanol (60.0 mL) was added sodium borohydride (0.192 g, 5.08 mmol) at 20° C. The mixture was stirred at 60° C. for 2 h. The reaction mixture was quenched by addition methanol (15.0 mL), and concentrated to give a residue. Then the residue was diluted with water (15.0 mL) and extracted with ethyl acetate (3×35.0 mL). The combined organic layers were washed with brine (20.0 mL), dried over sodium sulfate, filtered and concentrated under reduced pressure to give a residue. The residue was triturated with petroleum ether (5.00 mL) and ethyl acetate (1.00 mL) to give (S)—N-(3-chloro-4-(pyridin-2-ylmethoxy)phenyl)-7-((1,3-dimethylpyrrolidin-3-yl)ethynyl)-6-nitroquinazolin-4-amine S78 (1.10 g, 2.08 mmol, 81% yield) as a yellow solid. 41 NMR (400 MHz, $CDCl_3$) δ=8.90 (s, 1H), 8.76 (s, 1H), 8.61 (d, J=4.5 Hz, 1H), 8.31 (br s, 1H), 8.00 (s, 1H), 7.89 (d, J=2.4 Hz, 1H), 7.78 (br d, J=1.6 Hz, 1H), 7.66 (d, J=7.8 Hz, 1H), 7.52 (dd, J=2.4, 8.7 Hz, 1H), 7.00 (d, J=8.9 Hz, 1H), 5.30 (s, 2H), 3.08 (br d, J=9.8 Hz, 1H), 2.95 (br s, 2H), 2.83 (br d, J=9.4 Hz, 1H), 2.55 (s, 3H), 2.44-2.39 (m, 1H), 2.03-1.98 (m, 1H), 1.54 (s, 3H). MS (ESI) m/z 529.3 $[M+H]^+$ S79: To a suspension of (S)—N-(3-chloro-4-(pyridin-2-ylmethoxy)phenyl)-7-((1,3-dimethylpyrrolidin-3-yl)ethynyl)-6-nitroquinazolin-4-amine S78 (1.10 g, 2.08 mmol) in methanol (100 mL) and water (20.0 mL) was added iron powder (0.813 g, 14.6 mmol), ammonium chloride (0.779 mg, 14.6 mmol) at 20° C. The mixture was stirred at 80° C. for 2 h. The mixture was added methanol (100 mL) and filter. The filtration was concentrated under vacuum. The residue was purified by reverse phase chromatography (column: C18, 80 g; condition: water-0.1% ammonium hydroxide-acetonitrile) and concentrated to give (S)—$N^4$-(3-chloro-4-(pyridin-2-ylmethoxy)phenyl)-7-((1,3-dimethylpyrrolidin-3-yl)ethynyl)quinazoline-4,6-diamine S79 (0.900 g, 1.80 mmol, 87% yield) as a yellow solid. $^1$H NMR (400 MHz, $CDCl_3$) δ=8.60 (d, J=4.6 Hz, 1H), 8.57 (s, 1H), 7.86 (d, J=2.6 Hz, 1H), 7.82 (s, 1H), 7.79-7.74 (m, 1H), 7.67 (d, J=8.0 Hz, 1H), 7.49 (dd, J=2.6, 8.9 Hz, 1H), 7.26-7.22 (m, 1H), 7.01 (d, J=8.8 Hz, 2H), 6.91 (s, 1H), 5.30 (s, 2H), 4.57 (br s, 2H), 2.94 (d, J=9.1 Hz, 1H), 2.85-2.75 (m, 1H), 2.74-2.66 (m, 1H), 2.65-2.57 (m, 1H), 2.42 (s, 3H), 2.39-2.31 (m, 1H), 2.01-1.91 (m, 1H), 1.53 (s, 3H). MS (ESI) m/z 499.2 $[M+H]^+$ 13: To a solution of (S)—$N^4$-(3-chloro-4-(pyridin-2-ylmethoxy)phenyl)-7-((1,3-dimethylpyrrolidin-3-yl)ethynyl) quinazoline-4,6-diamine S79 (0.700 g, 1.40 mmol), 1-ethyl-3-(3-dimethylamino-propyl)-carbodiimide hydrochloride (0.807 g, 4.21 mmol), pyridine (0.333 g, 4.21 mmol) in dimethyl formamide (5.00 mL) was added acrylic acid (0.131 g, 1.82 mmol) at 20° C. The mixture was stirred at 20° C. for 2 h. The mixture was filtered, filtrate was purified by prep-HPLC (column: Phenomenex Gemini 150*25 mm*10 um; mobile phase: [water (10 mM $NH_4HCO_3$)-ACN]; B %: 38%-68%, min) and lyophilized to afford (S)—N-(4-((3-chloro-4-(pyridin-2-ylmethoxy)phenyl) amino)-7-((1,3-dimethylpyrrolidin-3-yl)ethynyl)quinazolin-6-yl)acrylamide 13 (345.9 mg, 619.18 umol, 44% yield, 99% purity) as a yellow solid. $^1$H NMR (400 MHz, $CDCl_3$) δ=9.13 (s, 1H), 8.68 (s, 1H), 8.65-8.58 (m, 2H), 7.90 (s, 2H), 7.81-7.73 (m, 1H), 7.67 (d, J=8.1 Hz, 1H), 7.60 (s, 1H), 7.53 (dd, J=2.6, 8.8 Hz, 1H), 7.24 (br d, J=7.2 Hz, 1H), 7.03 (d, J=8.9 Hz, 1H), 6.56-6.49 (m, 1H), 6.45-6.36 (m, 1H), 5.88 (d, J=10.4 Hz, 1H), 5.31 (s, 2H), 3.07 (d, J=8.9 Hz, 1H), 2.98 (dt, J=5.6, 8.7 Hz, 1H), 2.57 (dt, J=6.0, 9.0 Hz, 1H), 2.46 (d, J=9.0 Hz, 1H), 2.44 (s, 3H), 2.41-2.33 (m, 1H), 2.03-1.94 (m, 1H), 1.54 (s, 3H). MS (ESI) m/z 553.3 $[M+H]^+$
Example 13. Synthesis of Compound 14
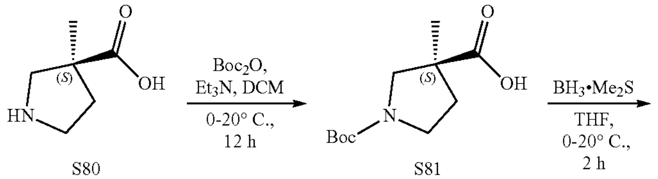
S80 S81
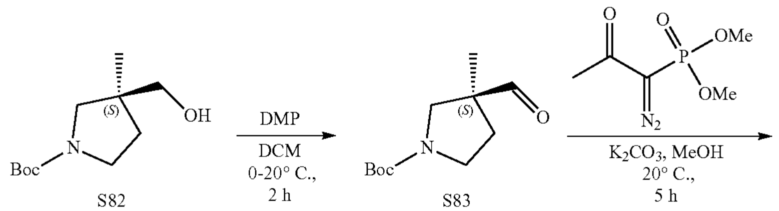
S82 S83
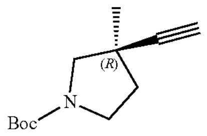
S84
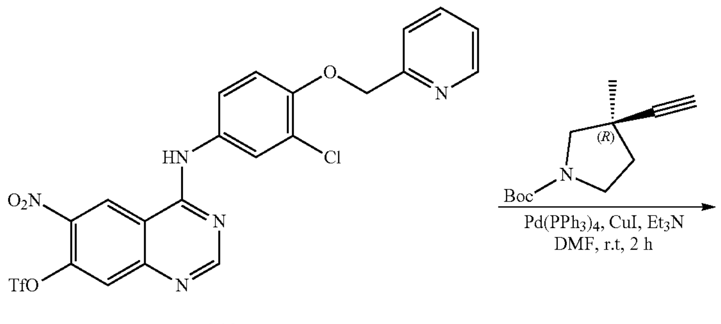
S46
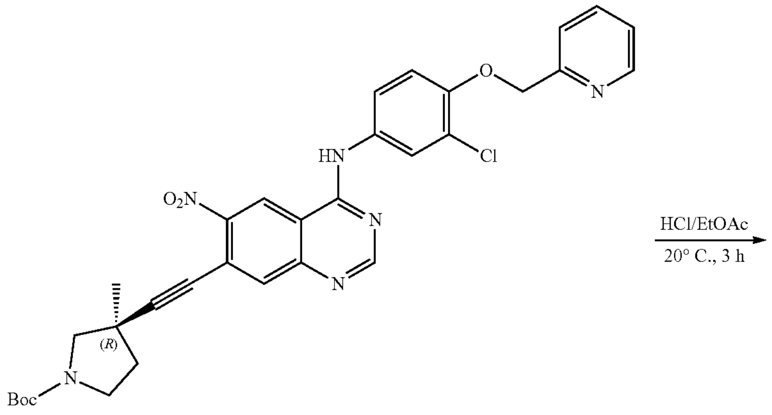
S85

-continued
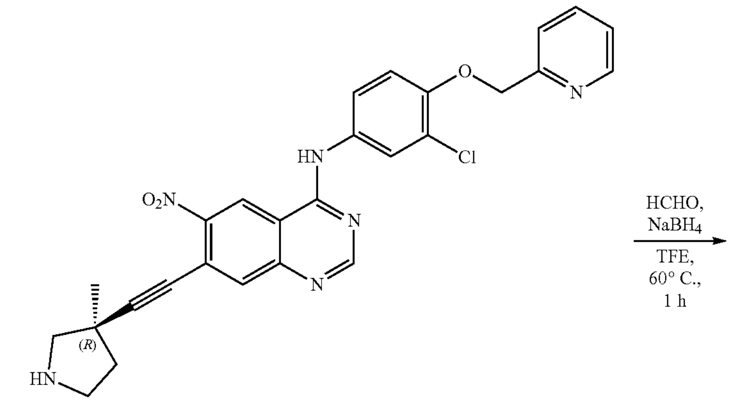
S86
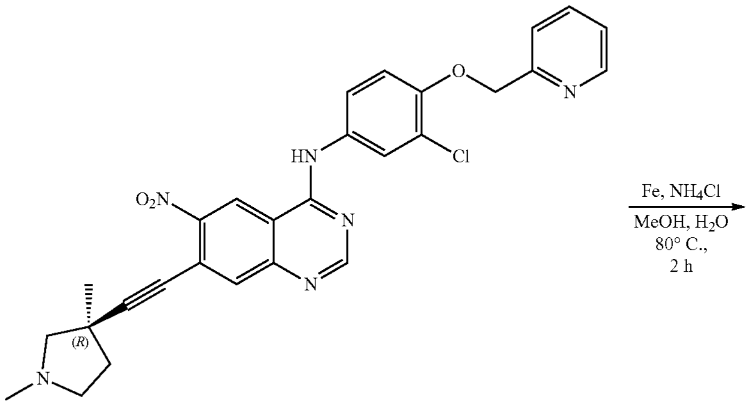
S87
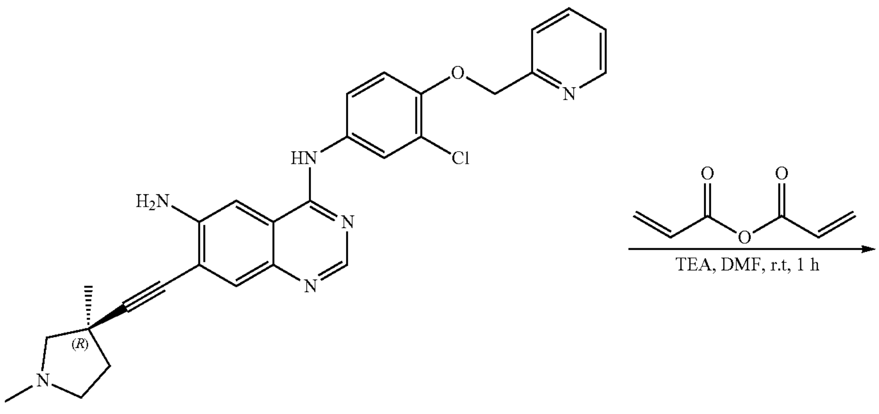
S88

-continued

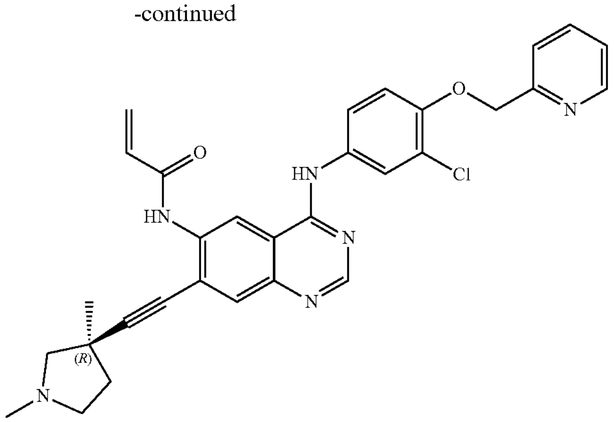

14

S81: To a mixture of (S)-3-methylpyrrolidine-3-carboxylic acid S80 (1.70 g, 13.2 mmol, 1.00 eq) and triethylamine (2.66 g, 26.3 mmol, 3.66 mL, 2.00 eq) in dichloromethane (30.0 mL) was added di-tert butyl dicarbonate (4.31 g, 19.7 mmol, 4.54 mL, 1.50 eq) at 0° C. The mixture was stirred at 20° C. for 12 h. The mixture was concentrated to dryness to give a residue. The residue was purified by silica gel chromatography (dichloromethane/methanol/formic acid=10/1/0.001) to give (S)-1-(tert-butoxycarbonyl)-3-methylpyrrolidine-3-carboxylic acid S81 (2.83 g, 12.3 mmol, 94% yield) as a brown oil. $^1$H NMR (400 MHz, $CDCl_3$) δ=8.91 (br s, 1H), 3.81-3.71 (m, 1H), 3.46-3.34 (m, 2H), 3.23-3.12 (m, 1H), 2.39-2.25 (m, 1H), 1.71 (td, J=6.4, 12.8 Hz, 1H), 1.45 (s, 9H), 1.31 (s, 3H).

S82: To a solution of (S)-1-(tert-butoxycarbonyl)-3-methylpyrrolidine-3-carboxylic acid S81 (2.80 g, 12.2 mmol, 1.00 eq) in tetrahydrofuran (20.0 mL) was added borane dimethyl sulfide complex (10.0 M, 2.50 mL, 2.00 eq) at 0° C. The mixture was stirred at 20° C. for 2 h. The reaction mixture was quenched by addition of methanol (20.0 mL) and concentrated to dryness to give a residue. The residue was diluted with ethyl acetate (60.0 mL) and washed with water (50.0 mL), the organic layer was dried over anhydrous sodium sulfate, filtered and concentrated to afford (5)-tert-butyl 3-(hydroxymethyl)-3-methylpyrrolidine-1-carboxylate S82 (2.10 g, crude) as a colorless oil. $^1$H NMR (400 MHz, $CDCl_3$) δ=3.42-3.30 (m, 4H), 3.21 (br dd, J=10.8, 18.8 Hz, 1H), 3.01-2.92 (m, 1H), 2.37 (br s, 1H), 1.83-1.72 (m, 1H), 1.51 (td, J=6.0, 12.0 Hz, 1H), 1.38 (s, 9H), 1.03 (s, 3H).

S83: To a solution of (S)-tert-butyl 3-(hydroxymethyl)-3-methylpyrrolidine-1-carboxylate S82 (2.10 g, 9.75 mmol, 1.00 eq) in dichloromethane (10.0 mL) was added (1,1-diacetoxy-3-oxo-1,2-benziodoxol-1-yl) acetate (6.20 g, 14.6 mmol, 1.50 eq) at 0° C. The mixture was stirred at 20° C. for 2 h. The mixture was diluted with water (5.00 mL) and saturated sodium carbonate (5.00 mL), extracted with dichloromethane (2×20.0 mL). The combined organic layers were washed with water (20.0 mL), dried over anhydrous sodium sulfate, filtered. The filtrate was concentrated to afford a residue. The residue was purified by silica gel chromatography (Petroleum ether/Ethyl acetate=5/1) to give (9-ten-butyl 3-formyl-3-methylpyrrolidine-1-carboxylate S83 (1.60 g, 7.50 mmol, 77% yield) as a colorless oil. $^1$H NMR (400 MHz, $CDCl_3$) δ=9.48 (s, 1H), 3.74-3.62 (m, 1H), 3.41-3.24 (m, 2H), 3.11-2.98 (m, 1H), 2.23-2.11 (m, 1H), 1.68-1.59 (m, 1H), 1.39 (s, 9H), 1.17 (s, 3H).

S84: To a mixture of (9-ten-butyl 3-formyl-3-methylpyrrolidine-1-carboxylate S83 (1.50 g, 7.03 mmol, 1.00 eq) and potassium carbonate (1.94 g, 14.1 mmol, 2.00 eq) in methanol (20.0 mL) was added dimethyl (1-diazo-2-oxopropyl) phosphonate (1.76 g, 9.14 mmol, 1.30 eq) at 20° C. The mixture was stirred at 20° C. for 5 h. The mixture was concentrated to dryness to give a residue. The residue was purified by silica gel chromatography (Petroleum ether/Ethyl acetate=10/1) to give (R)-tert-butyl 3-ethynyl-3-methylpyrrolidine-1-carboxylate S84 (1.10 g, 5.26 mmol, 75% yield) as a colorless oil. $^1$H NMR (400 MHz, $CDCl_3$) δ=3.54-3.31 (m, 3H), 3.18-3.07 (m, 1H), 2.09 (s, 1H), 2.06-1.99 (m, 1H), 1.77-1.68 (m, 1H), 1.39 (s, 9H), 1.28 (s, 3H).

S85: To a mixture of 4-((3-chloro-4-(pyridin-2-ylmethoxy)phenyl)amino)-6-nitroquinazolin-7-yltrifluoromethanesulfonate S46 (2.00 g, 3.60 mmol, 1.00 eq), (R)-tert-butyl 3-ethynyl-3-methylpyrrolidine-1-carboxylate S84 (753 mg, 3.60 mmol, 1.00 eq) and triethylamine (3.64 g, 35.9 mmol, 5.00 mL, 10.0 eq) in dimethyl formamide (5.00 mL) was added tetrakis(triphenylphosphine) palladium (0) (416 mg, 360 umol, 0.10 eq) and cuprous iodide (140 mg, 735.10 umol, 0.20 eq) at 25° C. The mixture was stirred under nitrogen atmosphere at 20° C. for 2 h. The mixture was concentrated to give a residue. The residue was purified by silica gel chromatography (Petroleum ether/Ethyl acetate=2/1-1/2) to afford (R)-tert-butyl 3-((4-((3-chloro-4-(pyridin-2-ylmethoxy)phenyl)amino)-6-nitroquinazolin-7-yl)ethynyl)-3-methylpyrrolidine-1-carboxylate S85 (2.00 g, 3.25 mmol, 90% yield) as a yellow solid. $^1$H NMR (400 MHz, DMSO-$d_6$) δ=10.36 (s, 1H), 9.44 (s, 1H), 8.71 (s, 1H), 8.61 (d, J=4.6 Hz, 1H), 8.02 (d, J=2.6 Hz, 1H), 7.94 (s, 1H), 7.89 (dt, J=1.8, 7.8 Hz, 1H), 7.72 (dd, J=2.6, 8.8 Hz, 1H), 7.38 (dd, J=5.2, 7.2 Hz, 1H), 7.31 (d, J=9.0 Hz, 1H), 5.31 (s, 2H), 3.61 (d, J=10.4 Hz, 1H), 3.55-3.41 (m, 2H), 3.28-3.22 (m, 1H), 2.19 (br d, J=4.8 Hz, 1H), 1.99-1.91 (m, 1H), 1.44 (s, 3H), 1.42 (s, 9H). MS (ESI) m/z 615.1 $[M+H]^+$ S86: To a mixture of (R)-tert-butyl 3-((4-((3-chloro-4-(pyridin-2-ylmethoxy)phenyl)amino)-6-nitroquinazolin-7-yl)ethynyl)-3-methylpyrrolidine-1-carboxylate S85 (2.00 g, 3.25 mmol, 1.00 eq) in ethyl acetate (20.0 mL) was added hydrochloric acid/ethyl acetate (4.00 M, 12.00 mL), the mixture was stirred at 20° C. for 3 h. The mixture was concentrated to dryness to give a residue. The residue was triturated with ethyl acetate (20.0 mL). After filtration, the filter cake was washed with ethyl acetate (10.0 mL) dried in vacuum to give (R)—N-(3-chloro-4-(pyridin-2-ylmethoxy)phenyl)-7-((3-methylpyrrolidin-3-yl)ethynyl)-6-nitroquinazolin-4-amine S86 (2.00 g, crude, HCl) as a yellow solid. 41 NMR (400 MHz, DMSO-$d_6$) δ=9.83 (br s, 2H), 9.77-9.65 (m, 1H), 8.94 (s, 1H), 8.76 (br d, J=4.4 Hz, 1H), 8.26-8.16 (m, 2H), 7.99 (d, J=2.6 Hz, 1H), 7.83 (br d, J=7.4 Hz, 1H), 7.73 (dd, J=2.4, 8.8 Hz, 1H), 7.69-7.62 (m, 1H), 7.39 (d, J=9.0 Hz, 1H), 5.48 (s, 2H), 3.52-3.35 (m, 3H), 3.26-3.17 (m, 1H), 2.37-2.27 (m, 1H), 2.13-2.06 (m, 1H), 1.53 (s, 3H). MS (ESI) m/z 515.0 $[M+H]^+$ S87: A mixture of (R)—N-(3-chloro-4-(pyridin-2-ylmethoxy)phenyl)-7-((3-methylpyrrolidin-3-yl)ethynyl)-6-nitroquinazolin-4-amine S86 (1.00 g, 1.94 mmol, 1.00 eq), paraformaldehyde (195 mg, 9.70 mmol, 5.00 eq) in trifluoroethanol (15.0 mL) was added sodium borohydride (148 mg, 3.91 mmol, 2.00 eq) at 20° C. The mixture was stirred at 60° C. for 1 h. The mixture was quenched with methanol (5.00 mL) and concentrated to dryness to give a residue. The residue was purified by prep-HPLC (column: Phenomenex luna C18 150*25 10 u; mobile phase: [water (0.1% TFA)-ACN]; B %: 13%-43%, 10 min) to give (R)—N-(3-chloro-4-(pyridin-2-ylmethoxy)phenyl)-7-((1,3-dimethylpyrrolidin-3-yl)ethynyl)-6-nitroquinazolin-4-amine S87 (1.40 g, crude) as a yellow solid. 41 NMR (400 MHz, DMSO-$d_6$) δ=10.31 (br s, 1H), 9.39 (s, 1H), 8.69 (s, 1H), 8.61 (br d, J=4.4 Hz, 1H), 8.01 (d, J=2.4 Hz, 1H), 7.93-7.85 (m, 2H), 7.71 (br dd, J=2.4, 8.8 Hz, 1H), 7.59 (d, J=7.8 Hz, 1H), 7.38 (dd, J=5.2, 6.8 Hz, 1H), 7.29 (d, J=9.2 Hz, 1H), 5.31 (s, 2H), 2.76 (d, J=9.0 Hz, 1H), 2.65 (dt, J=5.4, 8.4 Hz, 1H), 2.56 (br d, J=8.8 Hz, 2H), 2.28 (s, 3H), 2.25-2.17 (m, 1H), 1.94-1.82 (m, 1H), 1.43 (s, 3H). MS (ESI) m/z 529.0 $[M+H]^+$ S88: A mixture of (R)—N-(3-chloro-4-(pyridin-2-ylmethoxy)phenyl)-7-((1,3-dimethylpyrrolidin-3-yl)ethynyl)-6-nitroquinazolin-4-amine S87 (900 mg, 1.70 mmol, 1.00 eq), iron powder (383 mg, 6.86 mmol, 4.00 eq) and ammonium chloride (460 mg, 8.50 mmol, 5.00 eq) in methanol (15.0 mL) and water (7.00 mL) was stirred at 80° C. for 2 h. The mixture was filtered and the filtrated was concentrated to dryness to give a residue. The residue was diluted with ethyl acetate (20.0 mL) and washed with saturated sodium bicarbonate solution (20.0 mL), brine (20.0 mL), dried under vacuum to afford (R)—$N^4$-(3-chloro-4-(pyridin-2-ylmethoxy)phenyl)-7-((1,3-dimethylpyrrolidin-3-yl)ethynyl)quinazoline-4,6-diamine S88 (750 mg, 1.50 mmol, 88% yield) as a yellow solid. MS (ESI) m/z 499.4 $[M+H]^+$ 14: To a mixture of (R)—$N^4$-(3-chloro-4-(pyridin-2-ylmethoxy)phenyl)-7-((1,3-dimethylpyrrolidin-3-yl)ethynyl) quinazoline-4,6-diamine S88 (600 mg, 1.20 mmol, 1.00 eq) and triethylamine (254 mg, 2.51 mmol, 350 uL, 2.00 eq) in dimethyl formamide (6.00 mL) was added acrylic anhydride (200 mg, 1.59 mmol, 1.30 eq) at 20° C. The mixture was stirred at 20° C. for 1 h and then filtered. The filtrate was purified by prep-HPLC (column: Phenomenex Gemini 150*25 mm*10 um; mobile phase: [water (10 mM NH4HCO3)-ACN]; B %: 39%-69%, min) to give (R)—N-(4-((3-chloro-4-(pyridin-2-ylmethoxy)phenyl)amino)-7-((1,3-dimethylpyrrolidin-3-yl)ethynyl) quinazolin-6-yl)acrylamide 14 (130 mg, 235.06 umol, 19.55% yield) as a yellow solid. $^1H$ NMR (400 MHz, $CDCl_3$) δ=9.11 (s, 1H), 8.71-8.59 (m, 3H), 7.93-7.88 (m, 2H), 7.84 (s, 1H), 7.81-7.74 (m, 1H), 7.68 (br d, J=7.8 Hz, 1H), 7.55 (dd, J=2.4, 8.8 Hz, 1H), 7.26 (br d, J=6.6 Hz, 1H), 7.02 (d, J=8.8 Hz, 1H), 6.56-6.38 (m, 2H), 5.88 (d, J=9.8 Hz, 1H), 5.32 (s, 2H), 3.08 (d, J=8.8 Hz, 1H), 3.03-2.96 (m, 1H), 2.61-2.53 (m, 1H), 2.49-2.42 (m, 4H), 2.42-2.36 (m, 1H), 2.03-1.95 (m, 1H), 1.55 (s, 3H). MS (ESI) m/z 553.6 $[M+H]^+$ Example 14. Synthesis of Compound 16

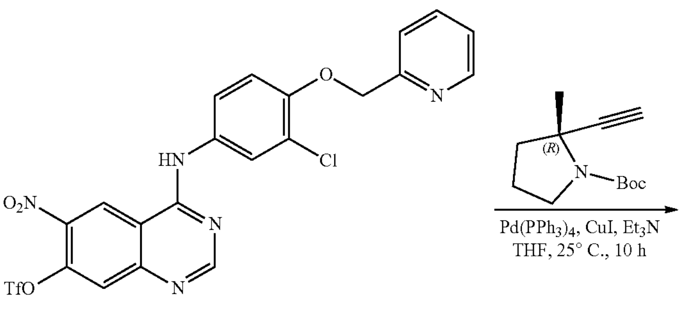

S46

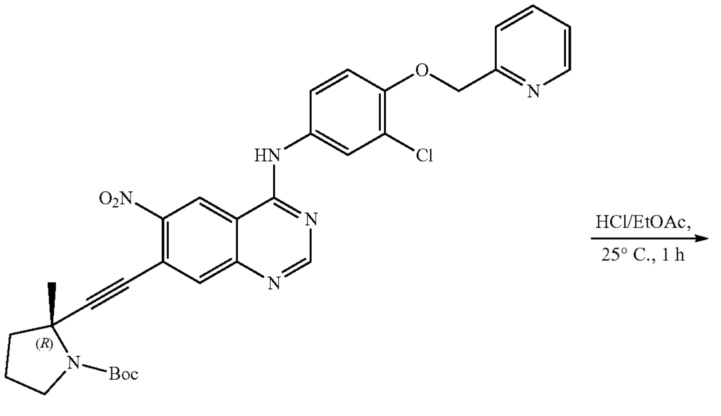

S89

-continued
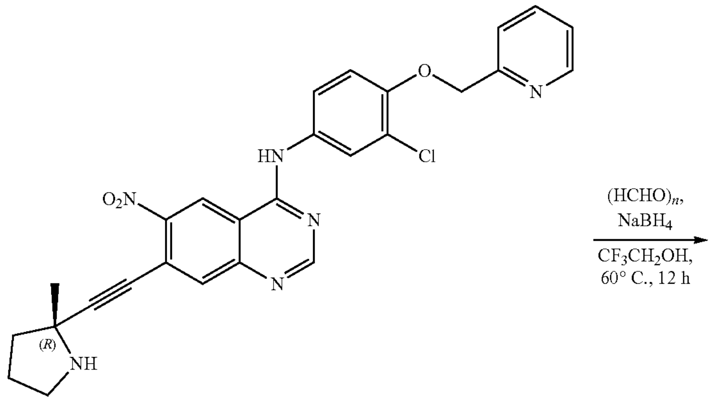
S90
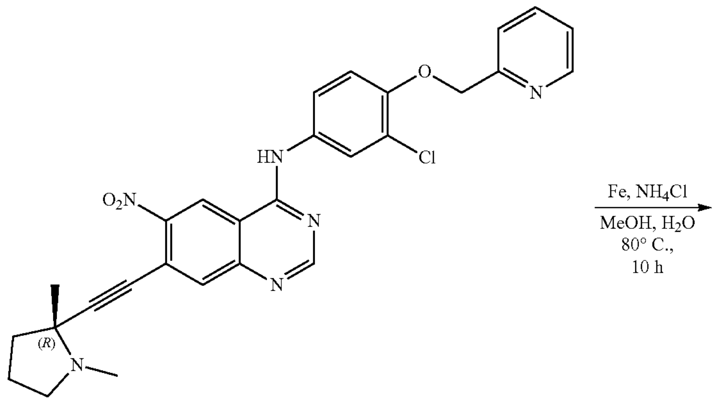
S91
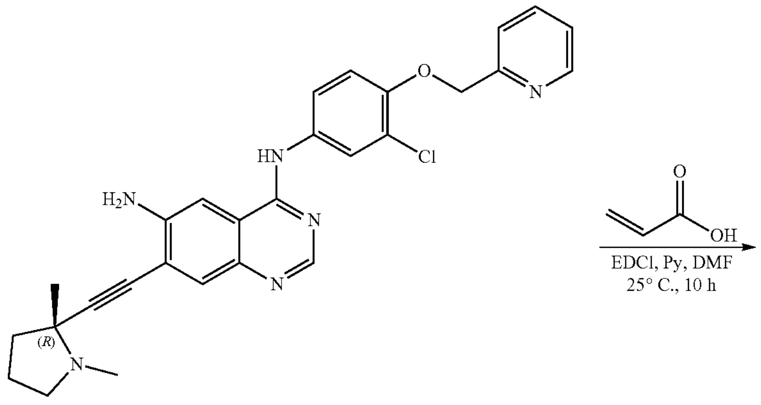
S92

-continued

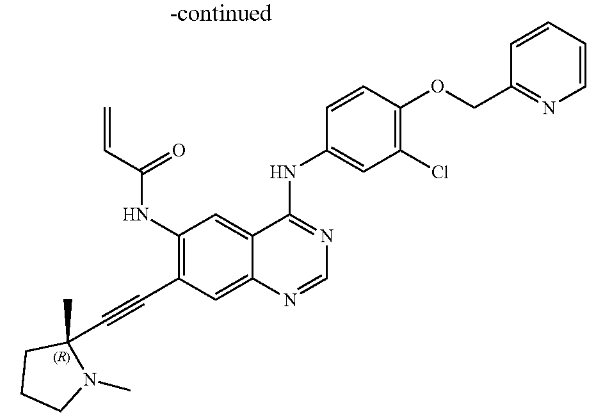

16

S89: A mixture of 4-((3-chloro-4-(pyridin-2-ylmethoxy) phenyl)amino)-6-nitroquinazolin-7-yl trifluorometh anesulfonate S46 (0.540 g, 971 umol, 1.00 eq), (R)-tert-butyl 2-ethynyl-2-methylpyrrolidine-1-carboxylate (203 mg, 971 umol, 1.00 eq), tetrakis(triphenylphosphine) palladium(0) (112 mg, 97.1 umol, 0.10 eq), cuprous iodide (37.0 mg, 194 umol, 0.20 eq) and triethylamine (197 mg, 1.94 mmol, 270 uL, 2.00 eq) in tetrahydrofuran (10.0 mL) was stirred at 25° C. for 10 h. The reaction mixture was filtered and concentrated under reduced pressure to give a residue. The residue was purified by silica gel column chromatography (petroleum ether/ethyl acetate=1/1) to afford (R)-tert-butyl 2-((4-((3-chloro-4-(pyridin-2-ylmethoxy)phenyl)amino)-6-nitroquinazolin-7-yl)ethynyl)-2-methylpyrrolidine-1-carboxylate S89 (0.6 g, crude) as a yellow solid. $^1$H NMR (400 MHz, $CDCl_3$) δ=8.89 (s, 1H), 8.73-8.58 (m, 1H), 8.53 (br d, J=4.4 Hz, 1H), 8.01-7.87 (m, 1H), 7.69 (dd, J=1.7, 7.6 Hz, 1H), 7.62-7.54 (m, 3H), 7.46 (qd, J=1.7, 7.6 Hz, 1H), 7.41-7.36 (m, 2H), 5.30-5.15 (m, 2H), 3.75-3.55 (m, 1H), 3.45-3.35 (m, 1H), 2.48-2.33 (m, 1H), 2.16-1.98 (m, 2H), 1.89-1.77 (m, 1H), 1.67 (s, 3H), 1.58 (s, 9H).

S90: A mixture of (R)-tert-butyl 2-((4-((3-chloro-4-(pyridin-2-ylmethoxy)phenyl)amino)-6-nitroquinazolin-7-yl) ethynyl)-2-methylpyrrolidine-1-carboxylate S89 (0.600 g, 976 umol, 1.00 eq) in hydrochloric acid/ethyl acetate (2.00 mL) was stirred at 25° C. for 1 h. The reaction mixture was concentrated under reduced pressure to afford (R)—N-(3-chloro-4-(pyridin-2-ylmethoxy)phenyl)-7-((2-methylpyrrolidin-2-yl)ethynyl)-6-nitroquinazolin-4-amine S90 (0.55 g, crude, hydrochloride) as a yellow solid. $^1$H NMR (400 MHz, DMSO-$d_6$) δ=11.52-11.28 (m, 1H), 10.07 (br s, 2H), 9.79-9.71 (m, 1H), 8.89 (s, 1H), 8.72 (d, J=4.5 Hz, 1H), 8.24 (s, 1H), 8.10 (dt, J=1.6, 7.7 Hz, 1H), 8.01 (d, J=2.6 Hz, 1H), 7.78-7.71 (m, 2H), 7.62-7.61 (m, 1H), 7.56 (d, J=1.0 Hz, 1H), 7.37 (d, J=9.0 Hz, 1H), 5.43 (s, 2H), 3.47-3.36 (m, 2H), 2.27-2.07 (m, 4H), 1.82 (s, 3H).

S91: To a solution of (R)—N-(3-chloro-4-(pyridin-2-ylmethoxy)phenyl)-7-((2-methylpyrrolidin-2-yl)ethynyl)-6-nitroquinazolin-4-amine S90 (0.55 g, 1.07 mmol, 1.00 eq) and paraformaldehyde (160 mg, 5.34 mmol, 147 uL, 5.00 eq) in trifluoroethanol (10.0 mL) was added sodium borohydride (80.8 mg, 2.14 mmol, 2.00 eq) slowly. The mixture was stirred at 60° C. for 12 h. The mixture was concentrated under reduced pressure to give a residue. The residue was purified by silica gel column chromatography (petroleum ether/ethyl acetate=0/1) to afford (R)—N-(3-chloro-4-(pyridin-2-ylmethoxy)phenyl)-7-((1,2-dimethylpyrrolidin-2-yl) ethynyl)-6-nitroquinazolin-4-amine S91 (130 mg, 246 umol, 23% yield) as a yellow solid. $^1$H NMR (400 MHz, $CDCl_3$) δ=8.82 (s, 1H), 8.77 (s, 1H), 8.62 (d, J=4.2 Hz, 1H), 8.10 (s, 1H), 7.92-7.86 (m, 2H), 7.83-7.77 (m, 1H), 7.68 (d, J=7.8 Hz, 1H), 7.51 (dd, J=2.7, 8.8 Hz, 1H), 7.30 (s, 1H), 7.27 (br s, 1H), 7.05 (d, J=8.8 Hz, 1H), 5.34 (s, 2H), 3.19-3.07 (m, 1H), 2.75-2.63 (m, 1H), 2.46 (s, 3H), 2.36-2.26 (m, 1H), 1.99-1.87 (m, 3H), 1.57-1.50 (m, 3H).

S92: A mixture of (R)—N-(3-chloro-4-(pyridin-2-ylmethoxy)phenyl)-7-((1,2-dimethylpyrrolidin-2-yl)ethynyl)-6-nitroquinazolin-4-amine S91 (130 mg, 246 umol, 1.00 eq), ammonium chloride (39.4 mg, 737 umol, 3.00 eq) and ferrous powder (41.2 mg, 737 umol, 3.00 eq) in a mixture solvent of methanol (3.00 mL) and water (3.00 mL) was stirred at 80° C. for 10 h. The reaction mixture was filtered and concentrated under reduced pressure to give a residue. The residue was purified was by reversed phase chromatography (column: C18, 80 g; condition: $H_2O$-0.1% $NH_3$·$H_2O$—$CH_3CN$) and lyophilized to afford (R)—$N^4$-(3-chloro-4-(pyridin-2-ylmethoxy)phenyl)-7-((1,2-dimethylpyrrolidin-2-yl)ethynyl)quinazoline-4,6-diamine S92 (60.0 mg, 120 umol, 49% yield) as a yellow solid. $^1$H NMR (400 MHz, $CDCl_3$) δ=8.62 (d, J=4.6 Hz, 1H), 8.59 (s, 1H), 7.90-7.87 (m, 2H), 7.78 (dt, J=1.7, 7.7 Hz, 1H), 7.68 (d, J=7.5 Hz, 1H), 7.55-7.49 (m, 1H), 7.26 (br s, 1H), 7.06-7.02 (m, 1H), 7.00 (s, 1H), 6.95 (s, 1H), 5.35-5.30 (m, 2H), 3.18-3.07 (m, 1H), 2.66-2.56 (m, 1H), 2.43 (s, 3H), 2.33-2.24 (m, 1H), 1.98-1.85 (m, 3H), 1.54 (s, 3H).

16: A mixture of (R)—$N^4$-(3-chloro-4-(pyridin-2-ylmethoxy)phenyl)-7-((1,2-dimethylpyrrolidin-2-yl)ethynyl) quinazoline-4,6-diamine S92 (50.0 mg, 100 umol, 1.00 eq), acrylic acid (10.8 mg, 150 umol, 10.3 uL, 1.50 eq), 1-ethyl-3-(3-dimethylamino-propyl)-carbodiimide hydrochloride (57.6 mg, 300 umol, 3.00 eq) and pyridine (23.8 mg, 300 umol, 24.3 uL, 3.00 eq) in dimethylformamide (1.00 mL) was stirred at 25° C. for 10 h. The reaction mixture was filtered and the filtrate was purified by prep-HPLC (column: Waters Xbridge 150×25 5 u; mobile phase: [water (10 mM $NH_4HCO_3$)-ACN]; B %: 35%-65%, 10 min) to afford (R)—N-(4-((3-chloro-4-(pyridin-2-ylmethoxy)phenyl)amino)-7-((1,2-dimethylpyrrolidin-2-yl)ethynyl)quinazolin-6-yl)acrylamide 16 (28.33 mg, 50.7 umol, 51% yield, 99% purity, >99% ee) as a yellow solid. 41 NMR (400 MHz, $CDCl_3$) δ=9.04 (s, 1H), 8.61 (s, 1H), 8.53 (d, J=4.2 Hz, 1H), 8.25 (s, 1H), 7.89 (s, 1H), 7.83 (d, J=2.7 Hz, 1H), 7.72-7.66 (m, 1H), 7.63-7.57 (m, 2H), 7.46 (dd, J=2.6, 8.8 Hz, 1H), 7.18-7.15 (m, 1H), 6.95 (d, J=8.9 Hz, 1H), 6.45 (dd, J=0.7, 16.9 Hz, 1H), 6.28-6.16 (m, 1H), 5.89-5.78 (m, 1H), 5.23 (s, 2H), 3.08 (ddd, J=3.7, 7.7, 9.5 Hz, 1H), 2.59-2.48 (m, 1H), 2.36 (s, 3H), 2.26-2.18 (m, 1H), 1.97-1.78 (m, 3H), 1.48 (s, 3H). MS (ESI) m/z 553.4 $[M+H]^+$ Example 15. Synthesis of Compound 17

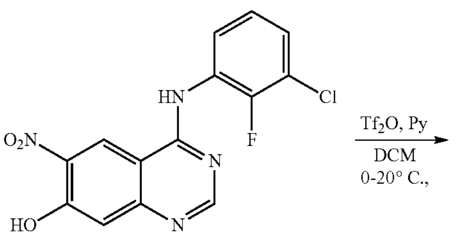

S93

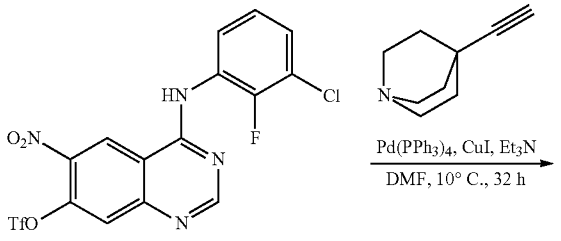

S6

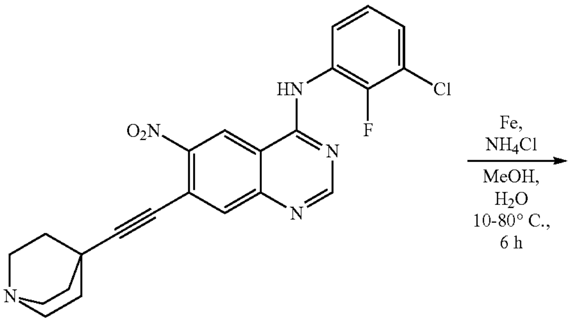

S94

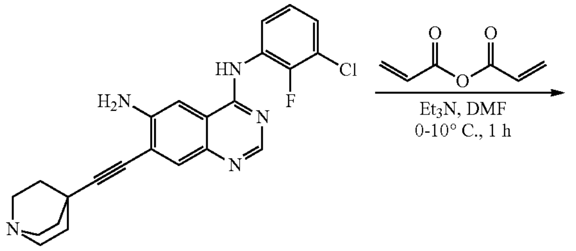

S95

-continued

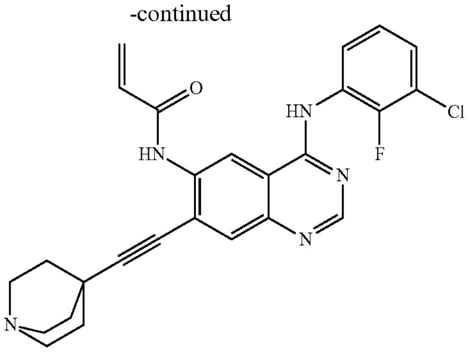

17

Synthesis of 4-ethynylquinuclidine: To a solution of quinuclidine-4-carbonitrile (900 mg, 6.61 mmol, 1.00 eq) in toluene (10.0 mL) was added diisobutylaluminium Hydride (1 M in toluene, 13.2 mL, 2.00 eq) at −78° C. Then the mixture was stirred at −78° C. for 1 h. The reaction mixture was quenched by addition sodium sulfate decahydrate (15.0 g), and then filtered and the filtrate was concentrated under reduced pressure to give quinuclidine-4-carbaldehyde (1 g, crude) as a white solid. $^1H$ NMR (400 MHz, DMSO-$d_6$) δ=9.34 (s, 1H), 2.77-2.75 (m, 6H), 1.48 (br d, J=2.4 Hz, 6H).

To a solution of quinuclidine-4-carbaldehyde (540 mg, 3.88 mmol, 1.00 eq) and potassium carbonate (1.07 g, 7.76 mmol, 2.00 eq) in methanol (10.0 mL) was added dimethyl (1-diazo-2-oxopropyl)phosphonate (894 mg, 4.66 mmol, 1.20 eq) at 0° C. Then the mixture was stirred at 25° C. for 2 h. The reaction mixture was concentrated under reduced pressure to give a residue. The residue was purified by column chromatography (Silica, dichloromethane/methanol=10/1) to afford 4-ethynylquinuclidine (600 mg, crude) as colorless oil. $^1H$ NMR (400 MHz, DMSO-$d_6$) δ=2.98 (s, 1H), 2.87-2.81 (m, 6H), 1.69-1.64 (m, 6H).

S6: To a mixture of 4-((3-chloro-2-fluorophenyl)amino)-6-nitroquinazolin-7-ol S93 (2.00 g, 5.98 mmol, 1.00 eq) in dichloromethane (20.0 mL) was added pyridine (2.36 g, 29.9 mmol, 2.41 mL, 5.00 eq) at 20° C. After cooling to 0° C., trifluoromethanesulfonic anhydride (2.53 g, 8.96 mmol, 1.48 mL, 1.50 eq) was added dropwise and the mixture was stirred at 20° C. for 1 h. The mixture was concentrated under vacuum at 20° C. to give a residue. The residue was poured into water (50.0 mL) and the aqueous solution was extracted with ethyl acetate (2×50.0 mL). All organic phases were combined, dried over anhydrous sodium sulfate, filtered and concentrated to give a crude product. The crude product was purified by column chromatography on silica gel (petroleum ether/ethyl acetate=10/1 to 1/1) to give 4-((3-chloro-2-fluorophenyl)amino)-6-nitroquinazolin-7-yltrifluoromethanesulfonate S6 (1.40 g, 2.95 mmol, 49% yield, 98% purity) as a yellow solid. MS (ESI) m/z 467.0 $[M+H]^+$ S94: To a solution of 4-((3-chloro-2-fluorophenyl)amino)-6-nitroquinazolin-7-yltrifluoromethanesulfonate S6 (600 mg, 1.29 mmol, 1.00 eq) and 4-ethynylquinuclidine (220 mg, 1.63 mmol, 1.27 eq) in dimethyl formamide (2.00 mL) was added copper(I) iodide (49.0 mg, 257 umol, 0.200 eq), Tetrakis(triphenylphosphine) palladium(0) (149 mg, 129 umol, 0.100 eq) and triethylamine (1.30 g, 12.9 mmol, 1.79 mL, 10.0 eq) at 10° C. under nitrogen atmosphere. Then the mixture was stirred at 10° C. for 32 h. The mixture was poured into ammonium hydroxide aqueous solution (100 mL) and extracted with ethyl acetate (3×100 mL). All organic phases were combined, washed with brine (100 mL), dried over anhydrous sodium sulfate, filtered and concentrated under vacuum to give a residue. The residue was purified by column chromatography on silica gel (ethyl acetate/methanol=1/0 to 1/1) to give N-(3-chloro-2-fluorophenyl)-6-nitro-7-(quinuclidin-4-ylethynyl)quinazolin-4-amine S94 (150 mg, 279 umol, 21% yield, 84% purity) as a brown solid. MS (ESI) m/z 452.3 $[M+H]^+$ S95: To a solution of N-(3-chloro-2-fluorophenyl)-6-nitro-7-(quinuclidin-4-ylethynyl)quinazolin-4-amine S94 (150 mg, 332 umol, 1.00 eq) in methanol (4.00 mL) was added a solution of ammonium chloride (88.8 mg, 1.66 mmol, 5.00 eq) in water (1.00 mL) and iron powder (92.7 mg, 1.66 mmol, 5.00 eq) at 10° C. The mixture was stirred at 80° C. for 6 h. The mixture was filtered and the filtrate was concentrated to give a residue. The residue was diluted with water (2.00 mL) and extracted with ethyl acetate (5×10.0 mL). All organic phases were combined, dried over anhydrous sodium sulfate, filtered and concentrated under vacuum to give $N^4$-(3-chloro-2-fluorophenyl)-7-(quinuclidin-4-ylethynyl)quinazoline-4,6-diamine S95 (100 mg, 171 umol, 51% yield, 72% purity) as a yellow solid was used into next step without further purification. MS (ESI) m/z 422.3 $[M+H]^+$ 17: To a solution of $N^4$-(3-chloro-2-fluorophenyl)-7-(quinuclidin-4-ylethynyl)quinazoline-4,6-diamine S95 (50.0 mg, 119 umol, 1.00 eq) in dimethyl formamide (1.00 mL) was added a solution of triethylamine (36.0 mg, 356 umol, 49.5 uL, 3.00 eq) in dimethyl formamide (0.100 mL), followed by a solution of acrylic anhydride (15.0 mg, 119 umol, 1.00 eq) in dimethyl formamide (0.100 mL) at 0° C. and the mixture was stirred at 0° C. for 30 min. Then a solution of acrylic anhydride (4.48 mg, 35.6 umol, 0.300 eq) in dimethyl formamide (30.0 uL) was added and the mixture was stirred at 10° C. for 30 min. The mixture was diluted with dimethyl formamide (1.00 mL) to give a solution. The solution was purified by prep-HPLC (column: Waters Xbridge 150*25 5 u; mobile phase: [water (0.05% ammonia hydroxide v/v)-ACN]; B %: 30%-60%, 10 min) and further purified by prep-HPLC (column: Phenomenex Synergi C18 150*30 mm*4 um; mobile phase: [water (0.225% FA)-ACN]; B %: 8%-38%, 10 min). The desired fraction was collected and lyophilized to give N-(4-((3-chloro-2-fluorophenyl)amino)-7-(quinuclidin-4-ylethynyl)-quinazolin-6-yl)acrylamide 17 (1.75 mg, 3.35 umol, 2% yield, 100% purity, formic acid) as a yellow solid. $^1H$ NMR (400 MHz, DMSO-$d_6$) δ=10.09 (br s, 1H), 9.74 (br s, 1H), 8.68 (s, 1H), 8.57-8.41 (m, 1H), 8.34 (br s, 1H), 7.95-7.65 (m, 1H), 7.48 (br s, 2H), 7.33-7.19 (m, 1H), 6.57 (br dd, J=10.4, 17.0 Hz, 1H), 6.33 (dd, J=1.5, 16.9 Hz, 1H), 5.85 (dd, J=1.5, 10.3 Hz, 1H), 2.82 (br s, 6H), 1.75 (br s, 6H). MS (ESI) m/z 476.2 $[M+H]^+$.

Example 16. Synthesis of Compound No. 18 (N-(4-((3-chloro-2-fluorophenyl)amino)-7-(((1R,5S)-3-methyl-3-azabicyclo[3.1.0]hexan-1-yl)ethynyl)quinazolin-6-yl)-4-morpholinobut-2-ynamide)

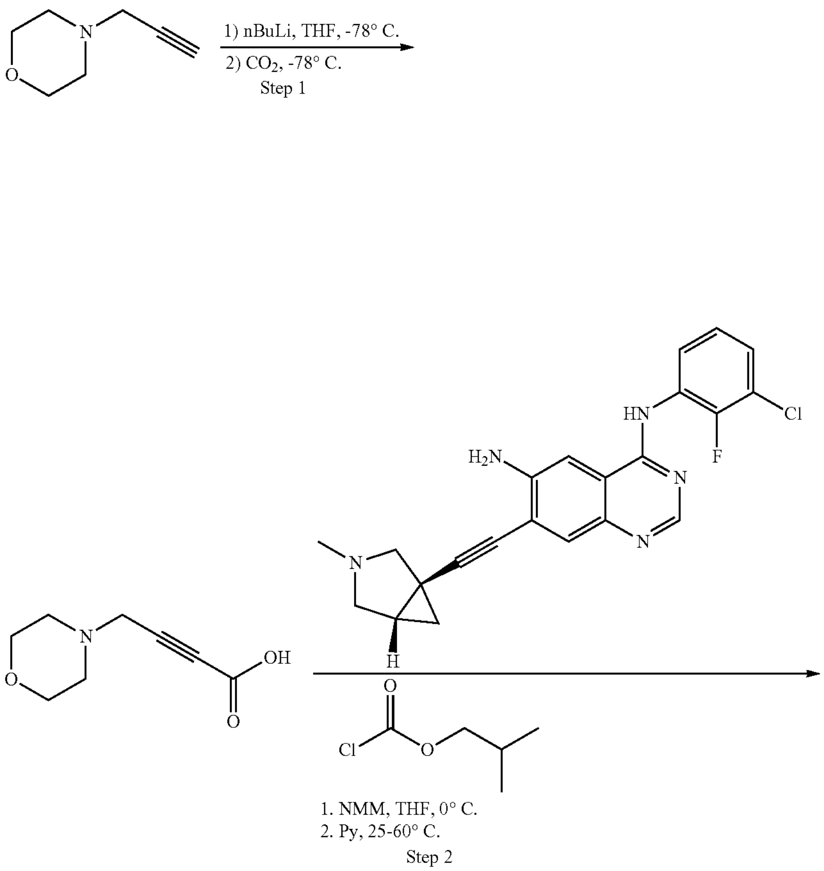

-continued

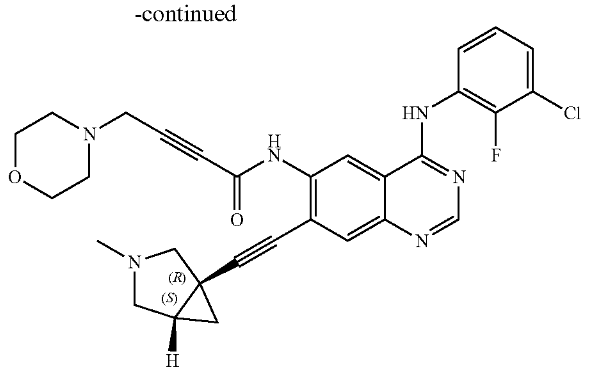

Step 1. To a solution of 4-prop-2-ynylmorpholine (500 mg, 3.99 mmol) in tetrahydrofuran (2.0 mL) was added n-BuLi (2.5 M, 1.60 mL) dropwise at −78° C. The mixture was stirred at −78° C. for 1 h. Then dry ice (175 mg, 3.99 mmol) was added. The mixture was stirred at 25° C. for 16 h. Upon completion, the resulting solution was poured into saturated aqueous $NH_4C_1$ solution (50 mL) and washed with ethyl acetate (50 mL). The aqueous layer was evaporated under reduced pressure to give the crude product. The crude product was dissolved in methanol (20 mL) and then filtered to remove any insoluble salt. The filtrate was collected and dried in vacuo to give 4-morpholinobut-2-ynoic acid (500 mg, 90% purity) as a yellow solid. $^1$H NMR (400 MHz, DMSO-$d_6$) δ=3.63-3.59 (m, 4H), 3.56 (s, 2H), 2.52 (s, 4H).

Step 2. To a solution of 4-morpholinobut-2-ynoic acid (31.1 mg, 183 umol) in tetrahydrofuran (3.0 mL) was added 4-methylmorpholine (18.6 mg, 183 umol) and isobutyl carbonochloridate (25.1 mg, 183 umol) at 0° C. The mixture was stirred at 0° C. for 30 min, then mixture of N4-(3-chloro-2-fluoro-phenyl)-7-[2-[(1R,5S)-3-methyl-3-azabicyclo[3.1.0]hexan-1-yl]ethynyl]quinazoline-4,6-diamine (25.0 mg, 61.2 umol) in pyridine (0.6 mL) was added. The mixture was stirred at 0° C. for 2 h. Upon completion, the mixture was concentrated in vacuo. The residue was purified by prep-HPLC (column: Phenomenex Gemini-NX C18 75*30 mm*3 um; mobile phase: [water (0.225% formic acid)-acetonitrile]; B %: 1%-30%, 7 min) to give N-[4-(3-chloro-2-fluoro-anilino)-7-[2-[(1R,5S)-3-methyl-3-azabicyclo[3.1.0]hexan-1-yl]ethynyl]quinazolin-6-yl]-4-morpholino-but-2-ynamide (6.0 mg, 16.6% yield) as a yellow solid.

m/z ES+ [M+H]+ 559.4; $^1$H NMR (400 MHz, DMSO-$d_6$) δ=10.47 (d, J=3.2 Hz, 1H), 10.06 (s, 1H), 8.50 (s, 2H), 8.30-8.18 (m, 1H), 7.80 (s, 1H), 7.55-7.50 (m, 2H), 7.29 (t, J=7.2 Hz, 1H), 3.67-3.61 (m, 4H), 3.58 (s, 2H), 3.12 (d, J=8.4 Hz, 2H), 2.94 (d, J=9.2 Hz, 1H), 2.57 (d, J=1.6 Hz, 2H), 2.41 (dd, J=4.0, 9.2 Hz, 2H), 2.26 (s, 3H), 2.00-1.90 (m, 2H), 1.39 (t, J=4.4 Hz, 1H), 1.07-1.02 (m, 1H).

Example 17. Synthesis of Compound No. 19 (1-((E)-4-((4-((3-chloro-2-fluorophenyl)amino)-7-0(1R,5S)-3-methyl-3-azabicyclo[3.1.0]hexan-1-yl)ethynyl)quinazolin-6-yl)amino)-4-oxobut-2-en-1-yl)piperidine-3-carboxylic Acid)

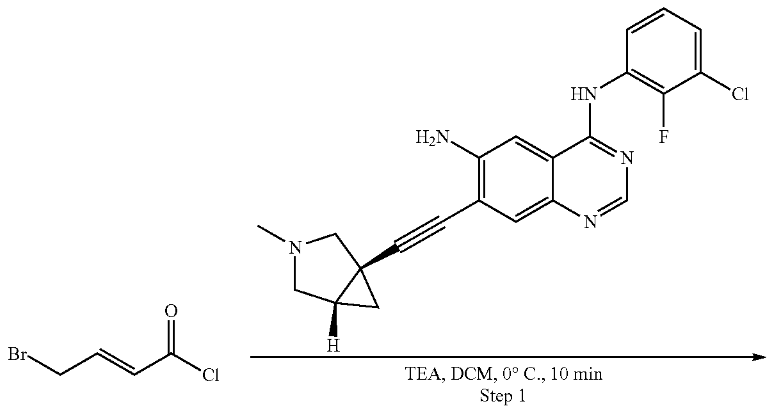

-continued

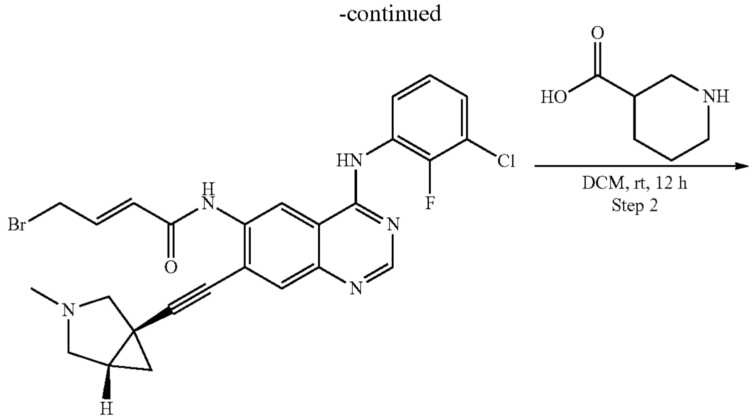

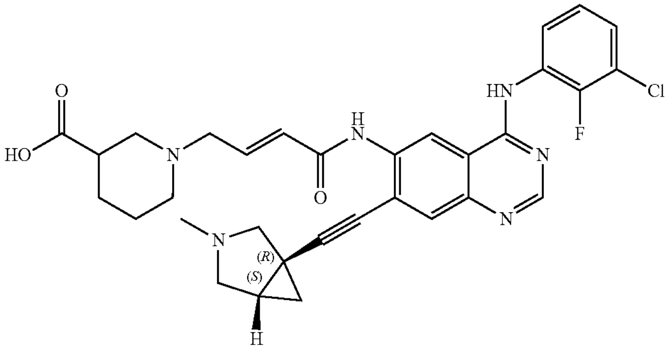

Step 1. To a solution of N4-(3-chloro-2-fluoro-phenyl)-7-[2-[(1S,5R)-3-methyl-3-azabicyclo[3.1.0]hexan-1-yl] ethynyl]quinazoline-4,6-diamine (100 mg, 245 umol) and triethylamine (74.4 mg, 735 umol) in dichloromethane (2 mL) was added a solution of (E)-4-bromobut-2-enoyl chloride (89.9 mg, crude) in dichloromethane (0.5 mL) dropwise at 0° C. and the mixture was stirred at 0° C. for 10 min. On completion, the reaction mixture was concentrated under vacuum to give (E)-4-bromo-N-(4-((3-chloro-2-fluorophenyl)amino)-7-4(1R,5S)-3-methyl-3-azabicyclo[3.1.0] hexan-1-yl)ethynyl)quinazolin-6-yl)but-2-enamide (140 mg, crude) as a yellow solid, which was used in the next step directly. m/z ES+ $[M+H]^+$ 556.0.

Step 2. A mixture of (E)-4-bromo-N-[4-(3-chloro-2-fluoro-anilino)-7-[2-[(1R,5S)-3-methyl-3-azabicyclo[3.1.0] hexan-1-yl]ethynyl]quinazolin-6-yl]but-2-enamide (134 mg, 242 umol), piperidine-3-carboxylic acid (46.8 mg, 362 umol) and triethylamine (48.9 mg, 483 umol) in dichloromethane (3.0 mL) was stirred at 25° C. for 12 h. On completion, the reaction mixture was concentrated in vacuo to give a residue. The residue was purified by reverse-phase flash chromatography [acetonitrile/(0.1% $NH_3 \cdot H_2O$ in water), 0% to 90%] and further purified by Prep-HPLC [column: Phenomenex luna C18 150*25 mm*10 um; mobile phase: [water (0.225% formic acid)-acetonitrile]; B %: 3%-33%, 10 min] to give 1-[(E)-4-[[4-(3-chloro-2-fluoro-anilino)-7-[2-[(1R,5S)-3-methyl-3-azabicyclo[3.1.0]hexan-1-yl]ethynyl]quinazolin-6-yl]amino]-4-oxo-but-2-enyl]piperidine-3-carboxylic acid (8.01 mg, 5.5% yield) as a brown solid. m/z ES+ $[M+H]^+$ 603.4; $^1H$ NMR (400 MHz, DMSO-$d_6$) δ 10.29-9.87 (m, 1H), 9.79 (s, 1H), 8.66 (s, 1H), 8.51-8.39 (m, 1H), 8.33-8.22 (m, 2H), 7.78 (s, 1H), 7.48 (d, J=6.8 Hz, 2H), 7.34-7.20 (m, 1H), 6.81 (td, J=6.0, 15.6 Hz, 1H), 6.42 (d, J=15.6 Hz, 1H), 3.18 (d, J=3.2 Hz, 1H), 3.11 (d, J=8.8 Hz, 1H), 2.95-2.88 (m, 2H), 2.74-2.67 (m, 1H), 2.45 (d, J=8.6 Hz, 1H), 2.40 (dd, J=3.6, 8.8 Hz, 1H), 2.25 (s, 3H), 2.17-2.01 (m, 2H), 1.93 (td, J=3.9, 8.0 Hz, 1H), 1.84 (dd, J=3.6, 12.4 Hz, 1H), 1.71-1.61 (m, 2H), 1.53-1.43 (m, 1H), 1.40-1.31 (m, 2H), 1.25-1.15 (m, 1H), 1.02 (dd, J=4.0, 8.0 Hz, 1H).

Example 18. Synthesis of Compound No. 20 ((E)-4-(3-oxa-6-azabicyclo[3.1.1]heptan-6-yl)-N-(4-((3-chloro-2-fluorophenyl)amino)-7-(((1R,5S)-3-methyl-3-azabicyclo[3.1.0]hexan-1-yl)ethynyl)quinazolin-6-yl)but-2-enamide)

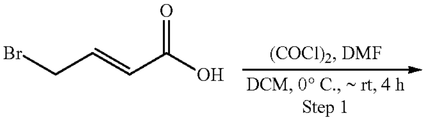

-continued

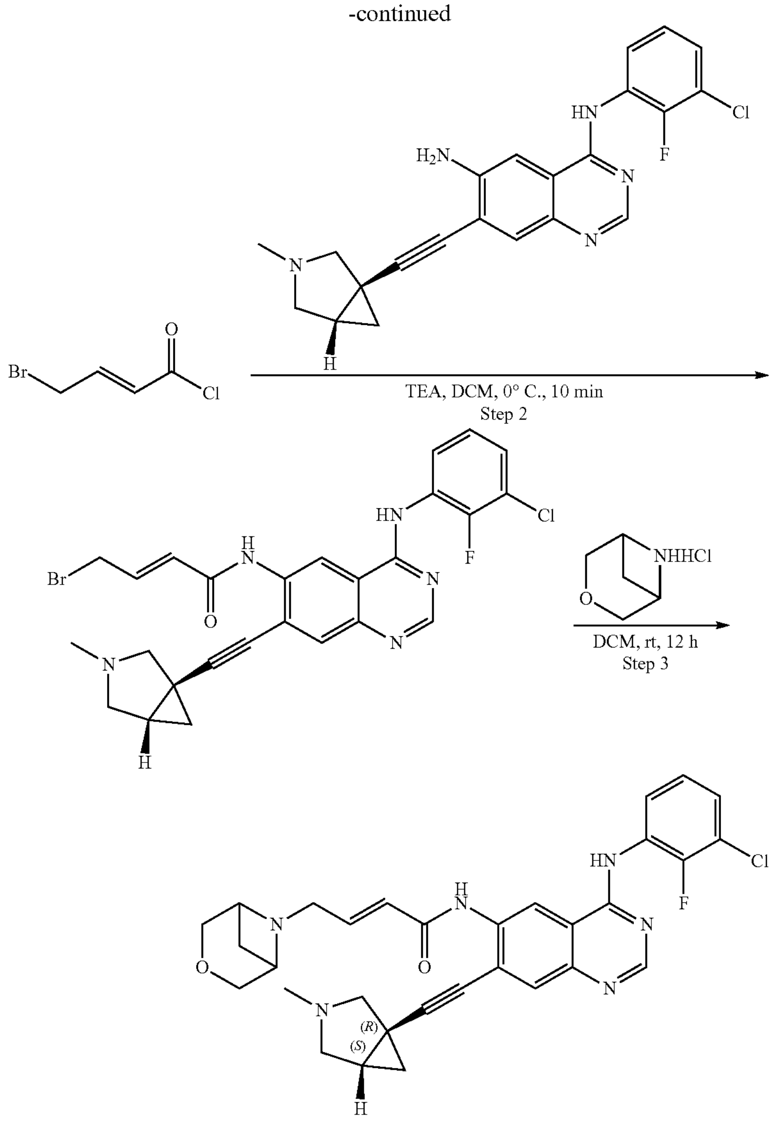

Step 1. To a solution of (E)-4-bromobut-2-enoic acid (500 mg, 3.03 mmol) in dichloromethane (5 mL) was added $(COCl)_2$ (385 mg, 3.03 mmol) and one drop of dimethylformamide at 0° C. under $N_2$. The mixture was slowly warmed to 25° C. then stirred at 25° C. for 4 h. On completion, the reaction mixture was concentrated in vacuo to give (E)-4-bromobut-2-enoyl chloride (560 mg, crude) as a yellow oil.

Step 2. To a solution of N4-(3-chloro-2-fluoro-phenyl)-7-[2-[(1S,5R)-3-methyl-3-azabicyclo[3.1.0]hexan-1-yl]ethynyl]quinazoline-4,6-diamine (100 mg, 245 umol) and triethylamine (74.4 mg, 736) in dichloromethane (2.0 mL) was added a solution of (E)-4-bromobut-2-enoyl chloride (89.9 mg, 490) in dichloromethane (0.5 mL) dropwise at 0° C. and the mixture was stirred at 0° C. for 10 min. On completion, the reaction mixture was concentrated under vacuum to give (E)-4-bromo-N-(4-((3-chloro-2-fluorophenyl)amino)-7-4(1R,5S)-3-methyl-3-azabicyclo[3.1.0]hexan-1-yl)ethynyl)quinazolin-6-yl)but-2-enamide (140 mg, crude) as a yellow solid, which was used in the next step directly. m/z ES+ $[M+H]^+$ 556.1

Step 3. A mixture of (E)-4-bromo-N-[4-(3-chloro-2-fluoro-anilino)-7-[2-[(1R,5S)-3-methyl-3-azabicyclo[3.1.0]hexan-1-yl]ethynyl]quinazolin-6-yl]but-2-enamide (100 mg, 180 umol), 3-oxa-6-azabicyclo[3.1.1]heptane (48.9 mg, 360 umol, HCl salt), triethylamine (36.5 mg, 360 umol) in dichloromethane (2.0 mL) was stirred at 25° C. for 12 h. On completion, the reaction mixture was concentrated in vacuo to give a residue. The residue was purified by reverse-phase flash [acetonitrile/(0.1% $NH_{3l}$-120 in water), 0% to 90%] and further purified by prep-HPLC [column: Phenomenex Gemini-NX C18 75*30 mm*3 um; mobile phase: [water (0.05% ammonium hydroxide v/v)-acetonitrile]; B %: 27%-57%, 11.5 min] to give 30 mg crude product. The crude product was then purified by prep-HPLC [column: Phenomenex luna C18 150*25 mm*10 um; mobile phase: [water (0.225% formic acid)-acetonitrile]; B %: 2%-32%, 10 min] to give (E)-N-[4-(3-chloro-2-fluoro-anilino)-7-[2-[(1R,5S)-3-methyl-3-azabicyclo[3.1.0]hexan-1-yl]-ethynyl]quinazolin-6-yl]-4-(3-oxa-6-azabicyclo[3.1.1]heptan-6-yl)but-2-enamide (3.6 mg, 3% yield) as a white solid. m/z ES+ $[M+H]^+$ 573.4; $^1H$ NMR (400 MHz, DMSO-$d_6$) δ 10.31-9.97 (m, 1H), 9.74 (s, 1H), 8.66 (s, 1H), 8.46 (s, 1H), 8.36 (s, 1H), 7.86-7.69 (m, 1H), 7.49 (d, J=1.2 Hz, 2H), 7.28 (t, J=8.4 Hz, 1H), 6.83 (td, J=5.2, 15.6 Hz, 1H), 6.47 (d, J=15.6 Hz, 1H), 4.10 (d, J=10.8 Hz, 2H), 3.65 (d, J=10.8 Hz, 2H), 3.52-3.47 (m, 4H), 3.10 (d, J=8.4 Hz, 1H), 2.93 (d, J=9.2 Hz, 1H), 2.56 (d, J=6.4 Hz, 1H), 2.46-2.39 (m, 2H), 2.25 (s, 3H), 1.98-1.90 (m, 1H), 1.77 (d, J=8.0 Hz, 1H), 1.37 (t, J=4.4 Hz, 1H), 1.02 (dd, J=3.6, 8.0 Hz, 1H).

Example 19. Synthesis of Compound No. 21 ((E)-N-(4-((3-chloro-2-fluorophenyl)amino)-7-(((1R,5S)-3-methyl-3-azabicyclo[3.1.0]hexan-1-yl)ethynyl)quinazolin-6-yl)-4-methoxybut-2-enamide)

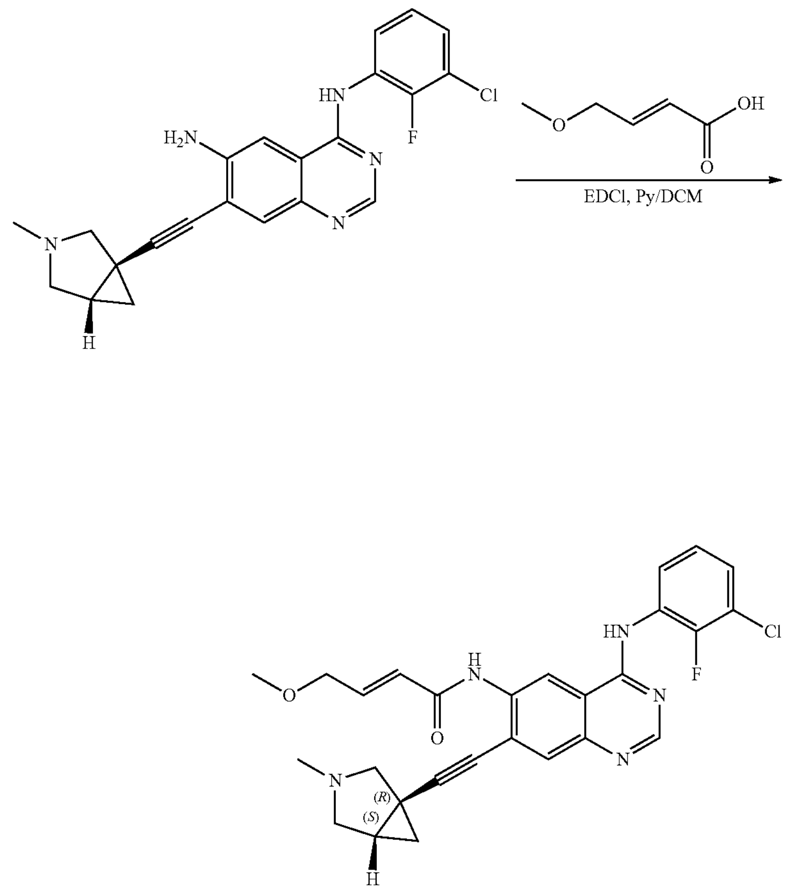

To a solution of N4-(3-chloro-2-fluoro-phenyl)-7-[2-[(1R,5S)-3-methyl-3-azabicyclo[3.1.0]hexan-1-yl]ethynyl]quinazoline-4,6-diamine (100 mg, 245 umol), (E)-4-methoxybut-2-enoic acid (42.7 mg, 367 umol) in pyridine (1.5 mL) and dichloromethane (1.5 mL) was added 1-ethyl-3-(3-dimethylaminopropyl)carbodiimide (141 mg, 735 umol) at 0° C. The mixture was stirred at 25° C. for 16 h. Upon completion, the reaction mixture was concentrated under reduced pressure to give a crude product. The residue was purified by prep-HPLC (column: Phenomenex Gemini-NX C18 75*30 mm*3 um; mobile phase: [water (10 mM NH4HCO3)-acetonitrile]; B %: 36%-66%, 8 min) to give (E)-N-[4-(3-chloro-2-fluoro-anilino)-7-[2-[(1R,5S)-3-methyl-3-azabicyclo[3.1.0]hexan-1-yl]ethynyl]quinazolin-6-yl]-4-methoxy-but-2-enamide (10.0 mg, 8% yield) as a yellow solid. m/z ES+ $[M+H]^+$ 506.1; $^1H$ NMR (400 MHz, DMSO-$d_6$) δ=10.22-9.93 (m, 1H), 9.78 (s, 1H), 8.64 (s, 1H), 8.52-8.35 (m, 1H), 7.83-7.70 (m, 1H), 7.47 (d, J=2.0 Hz, 2H), 7.33-7.18 (m, 1H), 6.87 (td, J=4.4, 15.6 Hz, 1H), 6.46 (d, J=15.6 Hz, 1H), 4.14 (dd, J=2.0, 4.4 Hz, 2H), 3.28 (s, 3H), 3.10 (d, J=8.4 Hz, 1H), 2.92 (d, J=8.8 Hz, 1H), 2.43 (d, J=8.4 Hz, 1H), 2.39 (dd, J=3.6, 9.2 Hz, 1H), 2.25 (s, 3H), 1.93 (td, J=4.4, 8.0 Hz, 1H), 1.37 (t, J=4.4 Hz, 1H), 1.02 (dd, J=3.6, 8.0 Hz, 1H).

Example 20. Synthesis of Compound No. 22 ((R)—N-(4-((3-chloro-2-fluorophenyl)amino)-7-((1,3-dimethylpyrrolidin-3-yl)ethynyl)quinazolin-6-yl)propionamide)

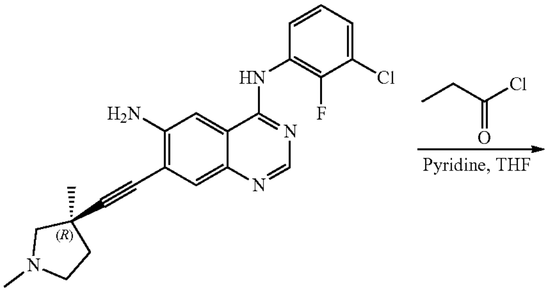

-continued

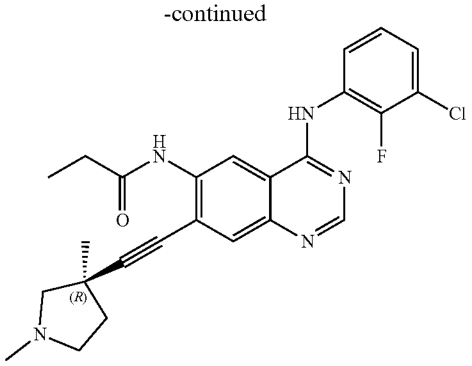

To a mixture of $N^4$-(3-chloro-2-fluoro-phenyl)-7-[2-[(3R)-1,3-dimethylpyrrolidin-3-yl]ethynyl]quinazoline-4,6-diamine (0.05 g, 122 umol) and pyridine (482.45 mg, 6.10 mmol) in tetrahydrofuran (1 mL) was added propanoyl chloride (33.86 mg, 365.96 umol) dropwise at 25° C. under $N_2$. The mixture was stirred at 25° C. for 1 h. On completion, the reaction mixture was concentrated under reduced pressure to give a residue. The residue was purified by prep-HPLC (column: Phenomenex Gemini-NX C18 75*30 mm*3 um; mobile phase: [water (10 mM $NH_4HCO_3$)-acetonitrile]; B %: 45%-75%, 8 min) to give (R)—N-(4-((3-chloro-2-fluorophenyl)amino)-7-((1,3-dimethylpyrrolidin-3-yl)ethynyl)quinazolin-6-yl)propionamide (3.4 mg, 6% yield) as a white solid.

m/z ES+ $[M+H]^+$ 466.1; $^1H$ NMR (400 MHz, DMSO-$d_6$) δ 10.06 (s, 1H), 9.37 (s, 1H), 8.66 (s, 1H), 8.45 (s, 1H), 7.76 (s, 1H), 7.49 (d, J=8.8 Hz, 2H), 7.27 (t, J=8.4 Hz, 1H), 2.82 (d, J=8.4 Hz, 1H), 2.62 (dd, J=7.2, 2.0 Hz, 2H), 2.55-2.50 (m, 1H), 2.46-2.40 (m, 2H), 2.28 (s, 3H), 2.26-2.20 (m, 1H), 1.90-1.85 (m, 1H), 1.45 (s, 3H), 1.15-1.18 (t, J=7.6 Hz, 3H).

Example 21. Synthesis of Compound No. 23 (2-chloro-N-(4-((3-chloro-2-fluorophenyl)-amino)-7-(((1R,5S)-3-methyl-3-azabicyclo[3.1.0]hexan-1-yl) ethynyl)quinazolin-6-yl)-2-fluoroacetamide)

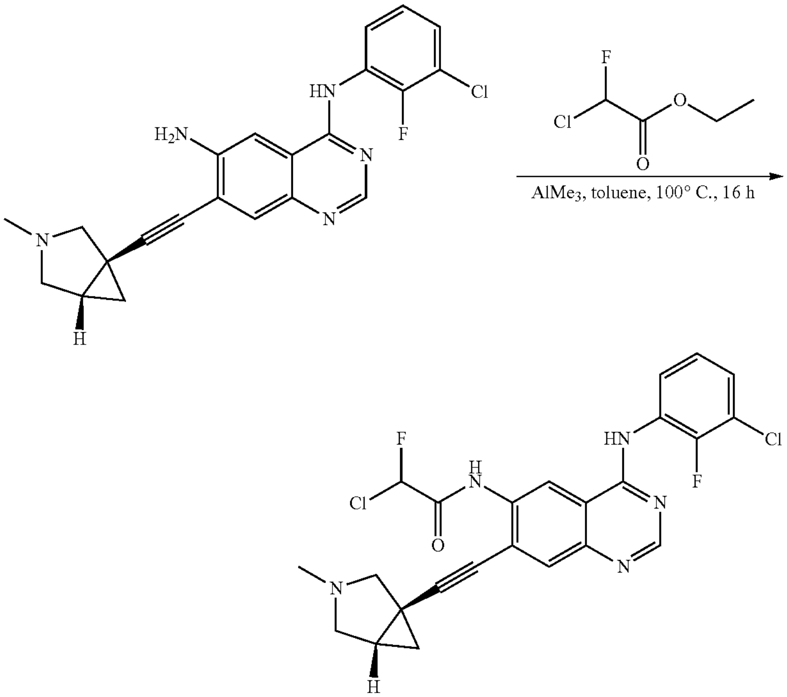

To a mixture of N4-(3-chloro-2-fluoro-phenyl)-7-[2-[(1R, 5S)-3-methyl-3-azabicyclo[3.1.0]hexan-1-yl]ethynyl]quinazoline-4,6-diamine (100 mg, 245 umol), ethyl 2-chloro-2-fluoro-acetate (68.9 mg, 490 umol) in toluene (1.0 mL) was added trimethylaluminium (2 M in toluene, 245 uL) and the mixture was stirred at 100° C. for 16 h. On completion, the mixture was quenched by 0.2 mL MeOH and filtered. The filtrate was concentrated under vacuum. The obtained residue was purified by prep-HPLC (column: Phenomenex Gemini-NX C18 75*30 mm*3 um; mobile phase: [water (10 mM $NH_4HCO_3$)-acetonitrile]; B %: 42%-72%, 8 min) to give 2-chloro-N-[4-(3-chloro-2-fluoro-anilino)-7-[2-[(1R, 5S)-3-methyl-3-azabicyclo[3.1.0]hexan-1-yl]ethynyl]-quinazolin-6-yl]-2-fluoro-acetamide (20.2 mg, 16% yield) as a yellow solid. m/z ES+ $[M+H]^+$ 502.1; $^1H$ NMR (400 MHz, DMSO-$d_6$) δ 10.58 (s, 1H), 10.16 (s, 1H), 8.65-8.45 (m, 2H), 7.85 (s, 1H), 7.58-7.45 (m, 2H), 7.30 (t, J=7.6 Hz, 1H), 7.08 (d, J=49.6 Hz, 1H), 3.12 (d, J=8.8 Hz, 1H), 2.94 (d, J=9.2 Hz, 1H), 2.47-2.36 (m, 2H), 2.26 (s, 3H), 2.00-1.92 (m, 1H), 1.39 (t, J=4.4 Hz, 1H), 1.04 (td, J=4.4, 8.0 Hz, 1H).

Example 22. Synthesis of Compound No. 24 ((R, E)-N-(4-((3-chloro-2-fluorophenyl)amino)-7-((1,3-dimethylpyrrolidin-3-yl)ethynyl)quinazolin-6-yl)-4-(dimethylamino)but-2-enamide)

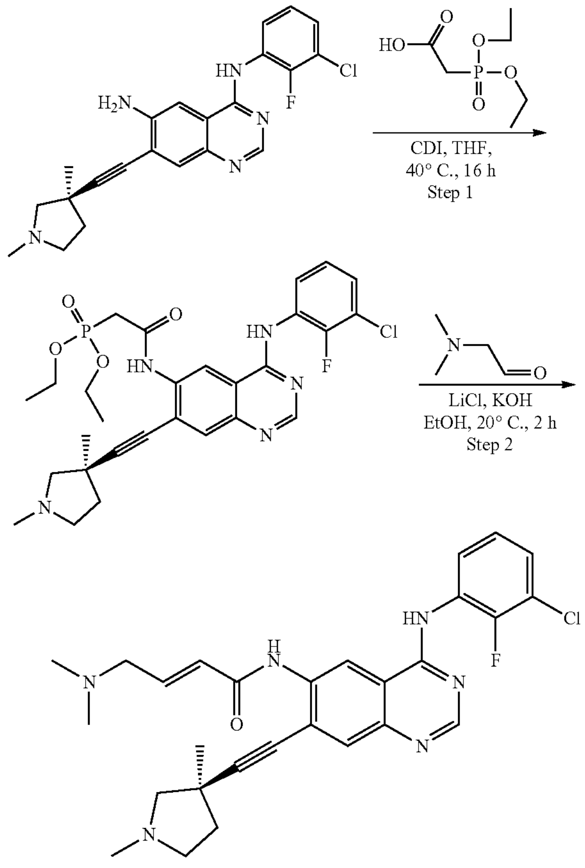

Step 1. To a solution of 2-diethoxyphosphorylacetic acid (143 mg, 731 umol) in tetrahydrofuran (2 mL) was added 1,1'-carbonyldiimidazole (122 mg, 756 umol) at 20° C. The mixture was stirred at 40° C. for 0.5 h. Then (R)—N4-(3-chloro-2-fluorophenyl)-7-((1,3-dimethylpyrrolidin-3-yl)ethynyl)quinazoline-4,6-diamine (100 mg, 243 umol) was added and the mixture was stirred at 40° C. for 16 h. On completion, the reaction mixture was diluted with ethyl acetate (10 mL), washed with saturated aqueous $NaHCO_3$ (5 mL), $H_2O$ (5 mL) and brine (5 mL×3). The organic layer was dried over $Na_2SO_4$ and concentrated to give N-[4-(3-chloro-2-fluoro-anilino)-7-[2-[(3R)-1,3-dimethylpyrrolidin-3-yl]ethynyl]quinazolin-6-yl]-2-diethoxyphosphoryl-acetamide (143 mg, crude) as a brown oil, which was used in the next step directly. m/z ES+ $[M+H]^+$ 588.1.

Step 2. To a mixture of N-[4-(3-chloro-2-fluoro-anilino)-7-[2-[(3R)-1,3-dimethylpyrrolidin-3-yl]ethynyl]quinazolin-6-yl]-2-diethoxyphosphoryl-acetamide (143 mg, 243 umol) in ethanol (1.2 mL) was added LiCl (41.2 mg, 972 umol) in one portion at 20° C. under $N_2$. Then KOH (181 mg, 1.46 mmol, 45% aqueous solution) was added and the mixture was stirred at 20° C. for 5 min. Then 2-(dimethylamino)acetaldehyde (82.3 mg, 486 umol, $H_2SO_3$ salt) in $H_2O$ (0.7 mL) was added and the mixture was stirred at 20° C. for 0.5 h. On completion, the mixture was quenched by $H_2O$ (5 mL) and then filtered to give a solid. The solid was purified by prep-HPLC (column: Phenomenex Gemini-NX C18 75*30 mm*3 um; mobile phase: [water (10 mM $NH_4HCO_3$)-acetonitrile]; B %: 30%-50%, 6 min) to give (E)-N-[4-(3-chloro-2-fluoro-anilino)-7-[2-[(3R)-1,3-dimethylpyrrolidin-3-yl]ethynyl]quinazolin-6-yl]-4-(dimethylamino)but-2-enamide (16.9 mg, 13% yield) as a white solid. m/z ES+ $[M+H]^+$ 521.1; $^1$H NMR (400 MHz, DMSO-$d_6$) δ 10.08 (br s, 1H), 9.68 (s, 1H), 8.69 (s, 1H), 8.47 (s, 1H), 7.79 (s, 1H), 7.55-7.45 (m, 2H), 7.28 (t, J=8.0 Hz, 1H), 6.85-6.75 (m, 1H), 6.39 (d, J=15.6 Hz, 1H), 3.08 (br d, J=5.6 Hz, 2H), 2.79 (d, J=8.8 Hz, 1H), 2.59 (t, J=7.2 Hz, 2H), 2.53-2.52 (m, 1H), 2.27 (s, 3H), 2.23 (dd, J=6.4, 12.8 Hz, 1H), 2.18 (s, 6H), 1.84 (td, J=7.2, 12.8 Hz, 1H), 1.42 (s, 3H).

Example 23. Synthesis of Compound No. 25 ((R)—N-(4-((3-chloro-2-fluorophenyl)amino)-7-((1,3-dimethylpyrrolidin-3-yl)ethynyl)quinazolin-6-yl)methacrylamide)

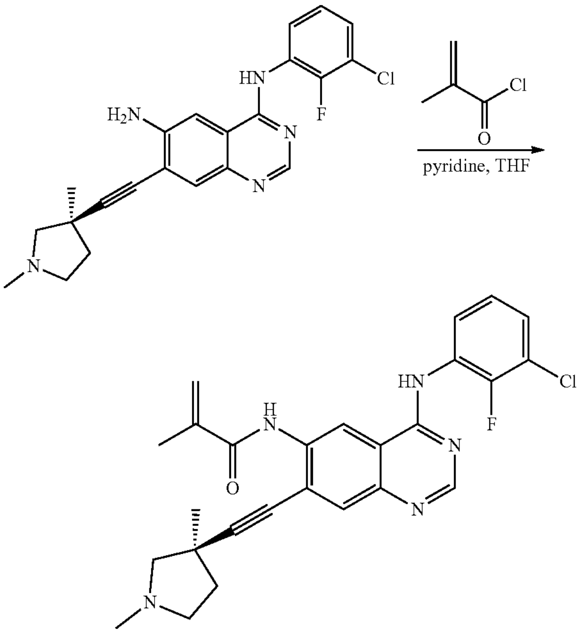

To a mixture of (R)—N4-(3-chloro-2-fluorophenyl)-7-((1,3-dimethylpyrrolidin-3-yl)ethynyl)quinazoline-4,6-diamine (20.0 mg, 49 umol) in pyridine (1.5 mL) was added 2-methylprop-2-enoyl chloride (6.1 mg, 58.6 umol) dropwise at 0° C. under $N_2$. The mixture was stirred at 0° C. for 0.5 hour. Then the reaction mixture was warmed to 50° C. and stirred for 1.5 hour. On completion, the reaction mixture was concentrated under reduced pressure to give a residue. The residue was purified by prep-HPLC (column: 3 Phenomenex Luna C18 75*30 mm*3 um; mobile phase: [water (0.2% formic acid)-acetonitrile]; B %: 15%-50%, 8 min) to give N-[4-(3-chloro-2-fluoro-anilino)-7-[2-[(3R)-1,3-dimethylpyrrolidin-3-yl]ethynyl]-quinazolin-6-yl]-2-methyl-prop-2-enamide (5.4 mg, 23% yield, formic acid salt) as a brown solid. m/z ES+ $[M+H]^+$ 478.1; $^1$H NMR (400 MHz, $CDCl_3$) δ 10.08 (s, 1H), 9.45 (s, 1H), 8.73 (s, 1H), 8.48 (s, 1H), 7.81 (s, 1H), 7.50 (t, J=6.8 Hz, 2H), 7.30-7.25 (m, 1H), 6.01 (s, 1H), 5.62 (s, 1H), 2.77 (d, J=8.8 Hz, 1H), 2.62-2.55 (m, 2H), 2.55-2.50 (m, 1H), 2.24 (s, 3H), 2.22-2.15 (m, 1H), 2.04 (s, 3H), 1.87-1.80 (m, 1H), 1.43 (s, 3H).

Example 24. Synthesis of Compound No. 26 (N-(4-((3-chloro-2-fluorophenyl)amino)-7-(((1R,5S)-3-methyl-3-azabicyclo[3.1.0]hexan-1-yl)ethynyl)quinazolin-6-yl)-2-(hydroxyl-methyl)acrylamide)

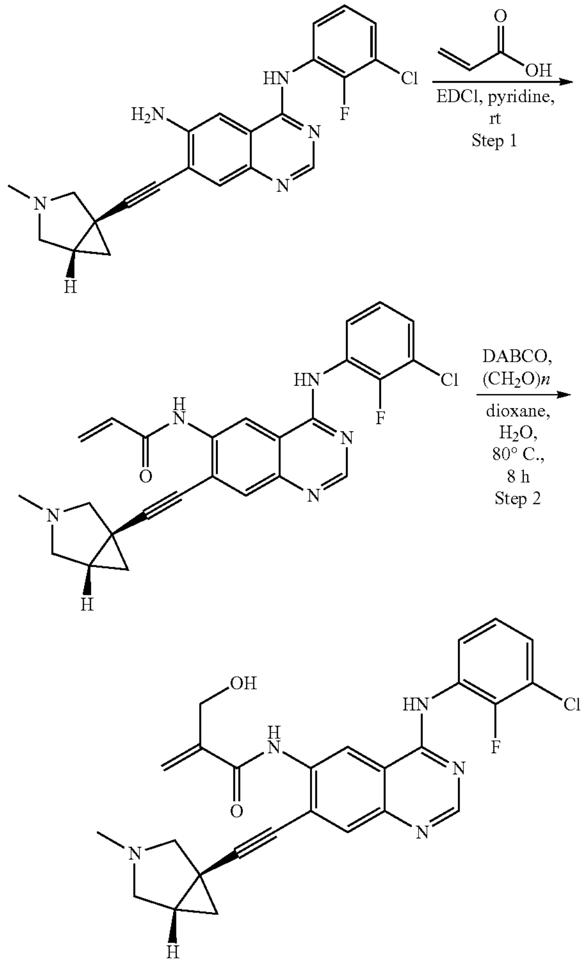

Step 1. To a mixture of N4-(3-chloro-2-fluoro-phenyl)-7-[2-[(1S,5R)-3-methyl-3-azabicyclo[3.1.0]hexan-1-yl]ethynyl]quinazoline-4,6-diamine (150 mg, 367 umol) and acrylic acid (31.8 mg, 441 umol) in pyridine (3.0 mL) and dichloromethane (3.0 mL) was added 1-ethyl-3-(3-dimethylaminopropyl)carbodiimide (211 mg, 1.10 mmol) in portions at 0° C. The mixture was stirred at 0-20° C. for 1 h. On completion, the mixture was quenched by 0.1 mL water and concentrated. The obtained residue was purified by prep-HPLC (column: Waters Xbridge 150*25 mm*5 um; mobile phase: [water (10 mM $NH_4HCO_3$)-acetonitrile]; B %: 32%-62%, 9 min) to give N-[4-(3-chloro-2-fluoro-anilino)-7-[2-[(1S,5R)-3-methyl-3-azabicyclo[3.1.0]hexan-1-yl]ethynyl] quinazolin-6-yl]prop-2-enamide (40.0 mg, 23% yield) as an off white solid. $^1H$ NMR (400 MHz, DMSO-$d_6$) δ 10.16-10.00 (m, 1H), 9.86 (s, 1H), 8.68 (s, 1H), 8.46 (d, J=2.4 Hz, 1H), 7.79 (s, 1H), 7.50 (d, J=7.2 Hz, 2H), 7.34-7.23 (m, 1H), 6.61 (dd, J=10.4, 17.2 Hz, 1H), 6.34 (dd, J=2.0, 17.2 Hz, 1H), 5.89-5.81 (m, 1H), 3.11 (d, J=8.4 Hz, 1H), 2.93 (d, J=9.2 Hz, 1H), 2.46-2.37 (m, 2H), 2.26 (s, 3H), 1.98-1.91 (m, 1H), 1.38 (t, J=4.4 Hz, 1H), 1.03 (dd, J=3.6, 8.0 Hz, 1H).

Step 2. To a solution of N-[4-(3-chloro-2-fluoro-anilino)-7-[2-[(1R,5S)-3-methyl-3-azabicyclo[3.1.0]hexan-1-yl] ethynyl]quinazolin-6-yl]prop-2-enamide (40.0 mg, 86.6 umol) in dioxane (2.0 mL) and $H_2O$ (1.0 mL) was added paraformaldehyde (20.0 mg, 432 umol) and DABCO (29.1 mg, 259 umol). The mixture was heated to 80° C. for 8 hours. On completion, the mixture was concentrated. The residue was purified by prep-HPLC (column: Phenomenex Gemini-NX C18 75*30 mm*3 um; mobile phase: [water (0.05% ammonium hydroxide v/v)-acetonitrile]; B %: 30%-60%, 7 min) to give N-[4-(3-chloro-2-fluoro-anilino)-7-[2-[(1R,5S)-3-methyl-3-azabicyclo[3.1.0]hexan-1-yl]ethynyl] quinazolin-6-yl]-2-(hydroxymethyl)prop-2-enamide (30.0 mg, 70% yield) as white solid. m/z ES+ $[M+H]^+$ 492.1; $^1H$ NMR (400 MHz, DMSO-$d_6$) δ 10.10 (s, 1H), 10.02 (s, 1H), 8.96 (s, 1H), 8.47 (s, 1H), 7.83 (s, 1H), 7.50 (dt, J=2.0, 7.6 Hz, 2H), 7.32-7.24 (m, 1H), 6.14 (s, 1H), 5.76 (s, 1H), 5.70 (t, J=5.6 Hz, 1H), 4.35 (d, J=5.2 Hz, 2H), 3.13 (d, J=8.0 Hz, 1H), 2.93 (d, J=8.8 Hz, 1H), 2.48-2.37 (m, 2H), 2.27 (s, 3H), 1.98 (td, J=4.0, 7.6 Hz, 1H), 1.37 (t, J=4.4 Hz, 1H), 1.07 (dd, J=3.6, 7.6 Hz, 1H).

Example 25. Synthesis of Compound No. 27 ((R,E)-N-(4-((3-chloro-2-fluorophenyl)amino)-7-((1,3-dimethylpyrrolidin-3-yl)ethynyl)quinazolin-6-yl)but-2-enamide)

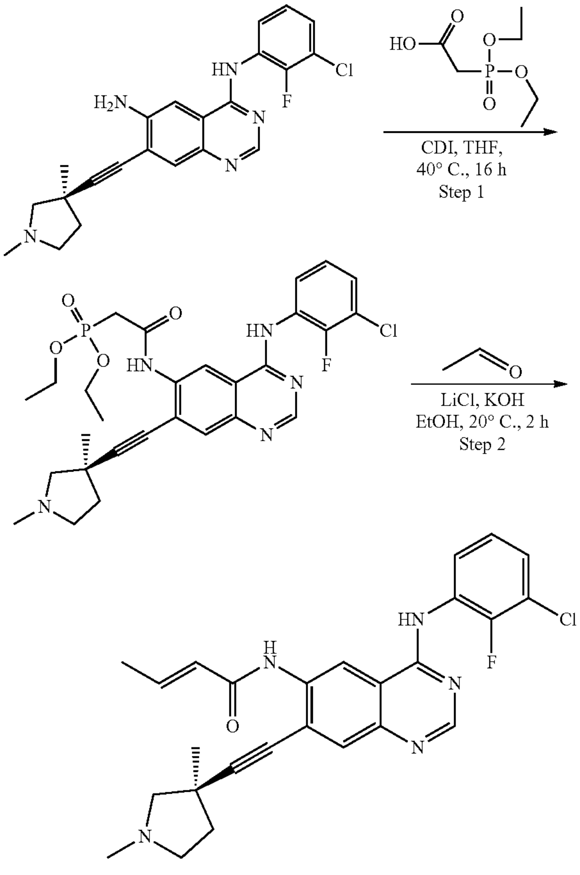

Step 1. To a solution of 2-diethoxyphosphorylacetic acid (143 mg, 731 umol) in tetrahydrofuran (2 mL) was added 1,1'-carbonyldiimidazole (122 mg, 756 umol) at 20° C. The mixture was stirred at 40° C. for 0.5 h. Then N4-(3-chloro-2-fluoro-phenyl)-7-[2-[(3R)-1,3-dimethylpyrrolidin-3-yl] ethynyl]quinazoline-4,6-diamine (100 mg, 243 umol) was added and the mixture was stirred at 45° C. for 16 h. On completion, the reaction mixture was diluted in ethyl acetate (10 mL), washed with saturated aqueous $NaHCO_3$ (5 mL), $H_2O$ (5 mL), and brine (5 mL×3), then dried with $Na_2SO_4$ and concentrated to give N-[4-(3-chloro-2-fluoro-anilino)-7-[2-[(3R)-1,3-dimethylpyrrolidin-3-yl]ethynyl]quinazolin-6-yl]-2-diethoxyphosphoryl-acetamide (143 mg, crude) as a brown oil which was used for next step directly. m/z ES+ $[M+H]^+$ 588.3.

Step 2. To a mixture of N-[4-(3-chloro-2-fluoro-anilino)-7-[2-[(3R)-1,3-dimethylpyrrolidin-3-yl]ethynyl]quinazolin-6-yl]-2-diethoxyphosphoryl-acetamide (143 mg, 243 umol) in ethanol (1.2 mL) was added LiCl (41.2 mg, 972 umol) in one portion at 20° C. under $N_2$. Then aqueous KOH (181 mg, 1.46 mmol, 45 wt %) was added and the mixture was stirred at 20° C. for 5 min. Then acetaldehyde (53.5 mg, 486 umol, 40% in water) in $H_2O$ (0.7 mL) was added and the mixture was stirred at 20° C. for 1 h. On completion, the mixture was quenched by 5 mL $H_2O$ and then filtered. The resulting precipitate was purified by prep-HPLC (column: Waters Xbridge BEH C18 100*25 mm*5 um; mobile phase: [water (10 mM $NH_4HCO_3$)-acetonitrile]; B %: 35%-65%, 10 min) to give (E)-N-[4-(3-chloro-2-fluoro-anilino)-7-[2-[(3R)-1,3-dimethylpyrrolidin-3-yl]ethynyl]quinazolin-6-yl] but-2-enamide (20.5 mg, 17% yield) as a white solid. m/z ES+ $[M+H]^+$ 478.2; $^1H$ NMR (400 MHz, DMSO-$d_6$) δ 10.07 (br s, 1H), 9.48 (s, 1H), 8.72 (s, 1H), 8.47 (s, 1H), 7.78 (s, 1H), 7.55-7.40 (m, 2H), 7.28 (t, J=7.6 Hz, 1H), 6.97-6.81 (m, 1H), 6.26 (d, J=14.4 Hz, 1H), 2.81 (d, J=8.8 Hz, 1H), 2.61 (t, J=6.8 Hz, 2H), 2.55-2.50 (m, 1H), 2.28 (s, 3H), 2.27-2.20 (m, 1H), 1.91 (d, J=6.8 Hz, 3H), 1.88-1.79 (m, 1H), 1.44 (s, 3H). SFC retention time: 1.31 min Example 26. Synthesis of Compound No. 28 (N-(4-((4-([1,2,4]triazolo[1,5-a]pyridin-7-yloxy)-3-methylphenyl)amino)-7-((3-methyl-3-azabicyclo[3.1.0]hexan-1-yl)ethynyl)quinazolin-6-yl)acrylamide)

Step 1. To a solution of 2-methyl-4-nitrophenol (9.00 g, 58.8 mmol) in N-methyl pyrrolidone (65 mL) was added diisopropylethylamine (22.8 g, 176 mmol) and 4-chloropyridin-2-amine (7.56 g, 58.8 mmol). The mixture was stirred at 135° C. for 48 hours. On completion, the reaction mixture was diluted with water (300 mL) and extracted with ethyl acetate (300 mL×4). The combined organic layers were dried over anhydrous sodium sulfate, filtered and concentrated under reduced pressure to give a residue. The residue was purified by column chromatography [petroleum ether/ethyl acetate=20/1 to 0/1] to give 4-(2-methyl-4-nitrophenoxy)pyridin-2-amine (1.14 g, 8% yield) as a brown oil. $^1H$ NMR (400 MHz, DMSO-$d_6$) δ=8.29 (d, J=2.4 Hz, 1H), 8.13 (dd, J=2.8, 8.8 Hz, 1H), 7.87 (d, J=5.6 Hz, 1H), 7.22 (d, J=8.8 Hz, 1H), 6.19 (dd, J=2.4, 5.6 Hz, 1H), 6.06 (s, 2H), 5.89 (d, J=2.4 Hz, 1H), 2.28 (s, 3H).

Step 2. To a mixture of 4-(2-methyl-4-nitrophenoxy) pyridin-2-amine (1.14 g, 4.65 mmol) in ethyl alcohol (12 mL) was added dimethyl formamide dimethyl acetal (665 mg, 5.58 mmol), and the mixture was stirred at 75° C. for 16 h. On completion, the mixture was concentrated under vacuum to give (E)-N,N-dimethyl-N'-(4-(2-methyl-4-nitrophenoxy)pyridin-2-yl)formimidamide (1.40 g, crude) as a brown oil, which was used for next step directly.

Step 3. To a mixture of (E)-N,N-dimethyl-N'-(4-(2-methyl-4-nitrophenoxy)pyridin-2-yl)formimidamide (1.40 g, 4.66 mmol) in ethyl alcohol (12 mL) was added hydroxylamine hydrochloride (389 mg, 5.59 mmol). The mixture was stirred at 50° C. for 3 h under nitrogen atmosphere. On completion, the mixture was cooled to 20° C. and the resulting precipitate was filtered. The filter cake was dried under reduced pressure to give (E)-N-hydroxy-N'-(4-(2-methyl-4-nitrophenoxy) pyridin-2-yl) formimidamide (800 mg, 60% yield) as a yellow solid. 41 NMR (400 MHz, DMSO-$d_6$) δ=10.07 (s, 1H), 9.36 (d, J=10.0 Hz, 1H), 8.32 (d, J=2.4 Hz, 1H), 8.16 (dd, J=2.8, 9.2 Hz, 1H), 8.09 (d, J=5.6 Hz, 1H), 7.82 (d, J=10.2 Hz, 1H), 7.30 (d, J=8.8 Hz, 1H), 6.60 (d, J=2.0 Hz, 1H), 6.54 (dd, J=2.4, 5.6 Hz, 1H), 2.27 (s, 3H).

Step 4. A mixture of 7-(2-methyl-4-nitro-phenoxy)-[1,2,4]triazolo[1,5-a]pyridine (420 mg, 1.55 mmol) and palladium on carbon (200 mg, 1.55 mmol, 10% loading) in tetrahydrofuran (10 mL) was degassed and purged with hydrogen for 3 times, and then the mixture was stirred at 40° C. for 16 h under hydrogen atmosphere. On completion, the mixture was filtered and concentrated under reduced pressure to give 4-([1,2,4]triazolo[1,5-a]pyridin-7-yloxy)-3-methylaniline (420 mg, crude) as a yellow solid. m/z ES+ $[M+H]^+$ 241.4; $^1H$ NMR (400 MHz, DMSO-$d_6$) δ=8.88 (d, J=7.6 Hz, 1H), 8.35 (s, 1H), 6.96 (dd, J=2.8, 7.6 Hz, 1H), 6.86 (d, J=8.4 Hz, 1H), 6.62 (dd, J=2.4, 9.6 Hz, 2H), 6.56 (dd, J=2.8, 8.4 Hz, 1H), 2.00 (s, 3H).

Step 5. To a solution of 3-methyl-4-([1,2,4]triazolo[1,5-a]pyridin-7-yloxy)aniline (485 mg, 2.02 mmol) in $CH_3CN$ (10 mL) was added 4-chloro-7-fluoro-6-nitro-quinazoline (505 mg, 2.22 mmol). The mixture was stirred at 60° C. for 2 h. On completion, the mixture was concentrated. The residue was washed with $CH_3CN$ (5 mL) and then dried in vacuum to give 7-fluoro-N-[3-methyl-4-([1,2,4]triazolo[1,5-a]pyridin-7-yloxy)phenyl]-6-nitro-quinazolin-4-amine (1.00 g, 93% yield) as a yellow solid. m/z ES+ $[M+H]^+$ 432.0

Step 6. To a solution of 7-fluoro-N-[3-methyl-4-([1,2,4]triazolo[1,5-a]pyridin-7-yloxy)phenyl]-6-nitro-quinazolin-4-amine (1.00 mg, 2.32 mmol) in dimethylformamide (8 mL) was added KOAc (1.14 g, 11.6 mmol) at 15° C. The mixture was stirred at 100° C. for 2 h. On completion, the mixture was concentrated to afford a yellow solid, which was triturated with $H_2O$ (50 mL). After filtration, the filter cake was washed with $H_2O$ (20 mL) and dried in vacuum to give compound 4-[3-methyl-4-([1,2,4]triazolo[1,5-a]pyridin-7-yloxy)anilino]-6-nitro-quinazolin-7-ol (400 mg, 38% yield) as a yellow solid. m/z ES+ $[M+H]^+$ 430.0

Step 7. To a mixture of 4-[3-methyl-4-([1,2,4]triazolo[1,5-a]pyridin-7-yloxy)anilino]-6-nitro-quinazolin-7-ol (400 mg, 931 umol) and pyridine (368 mg, 4.66 mmol) in $CH_2Cl_2$ (5 mL) was added $Tf_2O$ (394 mg, 1.40 mmol) at 0° C. The mixture was stirred at 20° C. for 3 h. On completion, the mixture was concentrated under vacuum to give a residue. The residue was purified by column chromatography [petroleum ether/ethyl acetate=1/1 to 0/1] to give [4-[3-methyl-4-([1,2,4]triazolo[1,5-a]pyridin-7-yloxy)anilino]-6-nitro-quinazolin-7-yl]trifluoromethanesulfonate (400 mg, 74% yield) as a yellow solid. m/z ES+ $[M+H]^+$ 562.0

Step 8. To a solution of tert-butyl 1-ethynyl-3-azabicyclo[3.1.0]hexane-3-carboxylate (310 mg, 1.50 mmol), [4-[3-methyl-4-([1,2,4]triazolo[1,5-a]pyridin-7-yloxy)anilino]-6-nitro-quinazolin-7-yl]trifluoromethanesulfonate (700 mg, 1.25 mmol), CuI (47.5 mg, 249 umol) and triethylamine (4.16 g, 41.1 mmol) in dimethylformamide (7 mL) was added $Pd(PPh_3)_4$ (144 mg, 125 umol) at 20° C. The mixture was stirred at 20° C. for 12 h under $N_2$. On completion, the mixture was concentrated to give a residue. The residue was purified by column chromatography [petroleum ether/ethyl acetate=1/1 to 0/1] to give tert-butyl 1-[2-[4-[3-methyl-4-([1,2,4]triazolo[1,5-a]pyridin-7-yloxy)anilino]-6-nitro-quinazolin-7-yl]ethynyl]-3-azabicyclo[3.1.0]hexane-3-carboxylate (400 mg, 38% yield) as a yellow gum. m/z ES+ $[M+H]^+$ 619.2

Step 9. To a solution of tert-butyl 1-[2-[4-[3-methyl-4-([1,2,4]triazolo[1,5-a]pyridin-7-yloxy)anilino]-6-nitro-quinazolin-7-yl]ethynyl]-3-azabicyclo[3.1.0]hexane-3-carb oxy late (400 mg, 647 umol) in $CH_2Cl_2$ (5 mL) was added HCl/ethyl acetate (4 M, 3.23 mL) and the mixture was stirred at 20° C. for 1 h. On completion, the mixture was concentrated to give a residue. The residue was neutralized with saturated sodium carbonate (15.0 mL) and extracted with ethyl acetate (30 mL×2). The combined organic layers were washed with water (20 mL), dried over anhydrous sodium sulfate, filtered and concentrated in vacuum to give compound 7-[2-(3-azabicyclo[3.1.0]hexan-1-yl)ethynyl]-N-[3-methyl-4-([1,2,4]triazolo[1,5-a]pyridin-7-yloxy)-phenyl]-6-nitro-quinazolin-4-amine (270 mg, 69% yield) as a brown solid. m/z ES+ $[M+H]^+$ 519.1; $^1H$ NMR (400 MHz, DMSO-$d_6$) δ 9.87 (br s, 1H), 9.72 (s, 1H), 9.48 (br s, 1H), 8.99 (d, J=7.6 Hz, 1H), 8.90 (s, 1H), 8.48 (s, 1H), 8.11 (s, 1H), 7.85-7.70 (m, 2H), 7.30 (d, J=8.8 Hz, 1H), 7.09 (dd, J=2.0, 7.6 Hz, 1H), 6.88 (s, 1H), 3.60-3.35 (m, 4H), 2.23 (s, 3H), 1.55 (t, J=6.0 Hz, 1H), 1.41 (t, J=7.6 Hz, 1H), 1.17 (t, J=7.2 Hz, 1H).

Step 10. To a solution of 7-[2-(3-azabicyclo[3.1.0]hexan-1-yl)ethynyl]-N-[3-methyl-4-([1,2,4]triazolo[1,5-a]pyridin-7-yloxy)phenyl]-6-nitro-quinazolin-4-amine (125 mg, 241 umol) in dimethylformamide (3 mL) was added formic acid (222 mg, 4.82 mmol) and $(HCHO)_n$ (145 mg, 4.82 mmol). The mixture was stirred at 60° C. for 2 h. On completion, the reaction was quenched by 10% NaOH solution (10 mL), then extracted with ethyl acetate (15 mL×2). The combined organic phases were washed with brine (10 mL), dried with anhydrous $Na_2SO_4$, filtered and concentrated under reduced pressure to give 7-[2-(3-methyl-3-azabicyclo[3.1.0]hexan-1-yl)ethynyl]-N-[3-methyl-4-([1,2,4]triazolo[1,5-a]pyridin-7-yloxy)phenyl]-6-nitro-quinazolin-4-amine (120 mg, 79% yield) as a brown solid. m/z ES+ $[M+H]^+$ 533.2

Step 11. To a solution of 7-[2-(3-methyl-3-azabicyclo[3.1.0]hexan-1-yl)ethynyl]-N-[3-methyl-4-([1,2,4]triazolo[1,5-a]pyridin-7-yl oxy)phenyl]-6-nitro-quinazolin-4-amine (110 mg, 207 umol) and $NH_4C_1$ (122 mg, 2.27 mmol) in MeOH (2 mL) and $H_2O$ (2 mL) was added iron powder (101 mg, 1.81 mmol) at 20° C. The mixture was stirred at 80° C. for 1 h. On completion, the reaction mixture was filtered and concentrated under vacuum to afford a residue. The residue was diluted with water (10 mL) and stirred for 30 min. After filtration, the filter cake was washed with water (15 mL) and collected. The filtrate was extracted with ethyl acetate (20 mL×2) to recover additional product. The combined organic layers were dried over anhydrous sodium sulfate, filtered and concentrated in vacuum to give compound 7-[2-(3-methyl-3-azabicyclo[3.1.0]hexan-1-yl)ethynyl]-N4-[3-methyl-4-([1,2,4]triazolo[1,5-a]pyridin-7-yloxy)-phenyl] quinazoline-4,6-diamine (100 mg, 76% yield) as a brown solid. m/z ES+ $[M+H]^+$ 503.1

Step 12. To a mixture of 7-[2-(3-methyl-3-azabicyclo[3.1.0]hexan-1-yl)ethynyl]-N4-[3-methyl-4-([1,2,4]triazolo[1,5-a]pyridin-7-yloxy)phenyl]quinazoline-4,6-diamine (90.0 mg, 179 umol), 1-ethyl-3-(3-dimethylaminopropyl) carbodiimide (137 mg, 716 umol) and pyridine (42.5 mg, 537 umol) in dimethylformamide (2 mL) was added a solution of acrylic acid (15.5 mg, 215 umol) in dimethylformamide (2 mL) dropwise at 20° C. The mixture was stirred at 20° C. for 2 h. On completion, the reaction mixture was quenched by $H_2O$ (5 mL). The aqueous layer was extracted with ethyl acetate (10 mL×2). The organic layers were combined, dried over anhydrous $Na_2SO_4$, filtered and concentrated under reduced pressure to give a residue. The residue was purified by prep-HPLC (column: Waters Xbridge 150*25 mm*5 um; mobile phase: [water (10 mM NH4HCO3)-acetonitrile]; B %: 26%-56%, 9 min) and prep-HPLC (formic acid condition; column: Unisil 3-100 C18 Ultra 150*50 mm*3 um; mobile phase: [water (0.225% formic acid)-acetonitrile]; B %: 10%-30%, 10 min) to give N-[7-[2-(3-methyl-3-azabicyclo[3.1.0]hexan-1-yl)ethynyl]-4-[3-methyl-4-([1,2,4]triazolo[1,5-a]pyridin-7-yloxy)anilino]quinazolin-6-yl]prop-2-enamide (15.0 mg, 15% yield, formic acid salt) as a yellow solid. m/z ES+ $[M+H]^+$ 557.3; $^1H$ NMR (400 MHz, DMSO-$d_6$) δ 9.92 (s, 2H), 8.93 (d, J=7.6 Hz, 1H), 8.74 (s, 1H), 8.58 (s, 1H), 8.38 (s, 1H), 8.35 (s, 1H), 7.88-8.80 (m, 2H), 7.79 (s, 1H), 7.21 (d, J=8.8 Hz, 1H), 7.03 (dd, J=2.4, 7.2 Hz, 1H), 6.81 (d, J=2.4 Hz, 1H), 6.60 (dd, J=10.4, 17.6 Hz, 1H), 6.34 (dd, J=1.6, 16.8 Hz, 1H), 5.89-5.83 (m, 1H), 3.10 (d, J=8.8 Hz, 1H), 2.92 (d, J=9.2 Hz, 1H), 2.43 (d, J=8.4 Hz, 1H), 2.39 (dd, J=3.6, 9.2 Hz, 1H), 2.25 (s, 3H), 2.19 (s, 3H), 1.95-1.88 (m, 1H), 1.37 (t, J=4.8 Hz, 1H), 1.01 (dd, J=4.0, 8.0 Hz, 1H).

Example 27. Synthesis of Compound No. 29 (N-(4-((5-chloro-2-fluorophenyl)amino)-7-((3-methyloxetan-3-yl)ethynyl)quinazolin-6-yl)acrylamide)

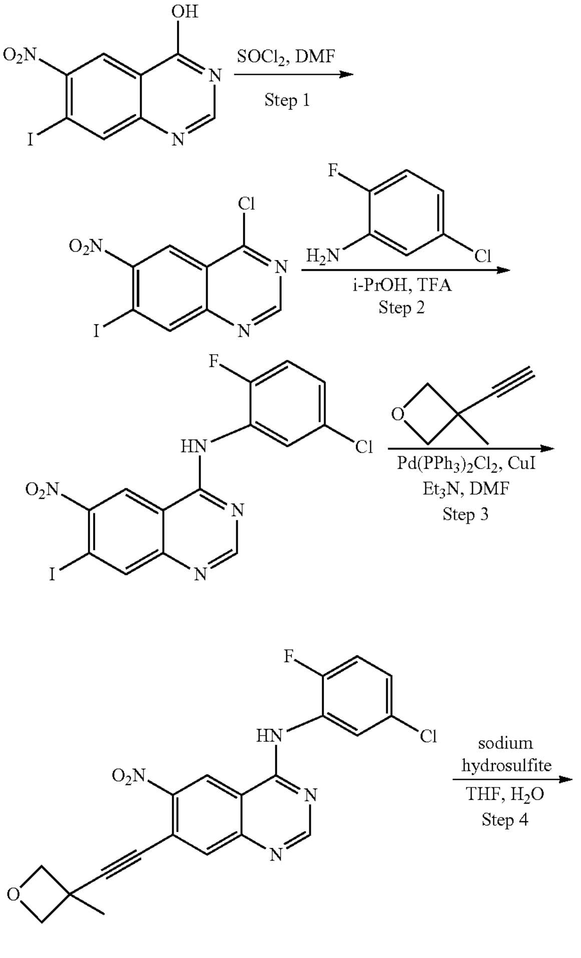

-continued

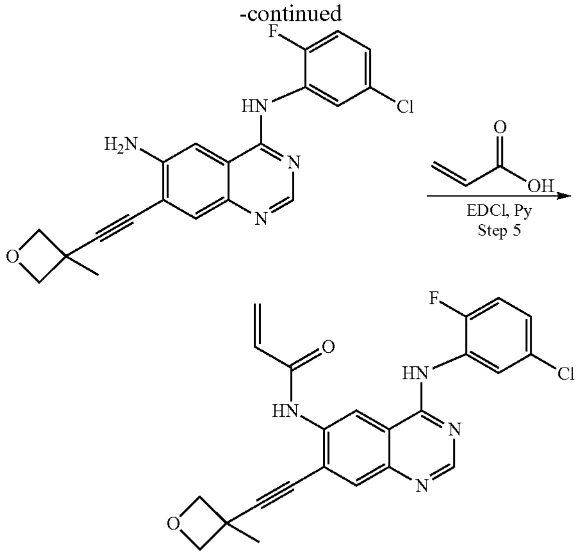

Step 1. To a solution of 7-iodo-6-nitro-quinazolin-4-ol (300 mg, 946 umol) in $SOCl_2$ (3.0 mL) was added dimethylformamide (69.1 mg, 946 umol) at 20° C. Then the mixture was stirred at 90° C. for 4 hours. The reaction mixture was concentrated under reduced pressure to give a residue. Then it was dissolved in dichloromethane (10 mL) and washed with saturated sodium bicarbonate (5 mL) at 0° C. The organic phase was washed with brine (3 mL), dried over anhydrous sodium sulfate, filtered and concentrated under reduced pressure to give 4-chloro-7-iodo-6-nitro-quinazoline (240 mg, 75% yield) as a brown solid. $^1$H NMR (400 MHz, DMSO-$d_6$) δ 8.59 (s, 1H), 8.44 (s, 1H), 8.35 (s, 1H).

Step 2. To a solution of 4-chloro-7-iodo-6-nitro-quinazoline (240 mg, 715 umol) in i-PrOH (2.0 mL) and dichloromethane (2 mL) was added 5-chloro-2-fluoro-aniline (124 mg, 858 umol) and Tformic acid (120 mg, 1.05 mmol) at 0° C. Then the mixture was stirred at 20° C. for 0.5 hour. The reaction mixture was poured into water (5 mL) and extracted with ethyl acetate (10 mL×3). The combined organic phase was washed with brine (10 mL), dried over anhydrous sodium sulfate, filtered and concentrated under reduced pressure to give a residue. The residue was purified by column chromatography (petroleum ether/ethyl acetate=15/1 to 3/1) to give N-(5-chloro-2-fluoro-phenyl)-7-iodo-6-nitro-quinazolin-4-amine (120 mg, 37% yield) as a yellow solid. $^1$H NMR (400 MHz, DMSO-$d_6$) δ 10.45 (s, 1H), 9.22 (s, 1H), 8.66 (s, 1H), 8.52 (s, 1H), 7.72 (d, J=6.8 Hz, 1H), 7.43 (d, J=8.4 Hz, 2H).

Step 3. A mixture of N-(5-chloro-2-fluoro-phenyl)-7-iodo-6-nitro-quinazolin-4-amine (120 mg, 269 umol), 3-ethynyl-3-methyl-oxetane (31.1 mg, 323 umol), CuI (10.2 mg, 53.9 umol), $Et_3N$ (872 mg, 8.62 mmol) and $Pd(PPh_3)_2Cl_2$ (18.9 mg, 26.9 umol) in dimethylformamide (1.2 mL) was degassed and purged with $N_2$ for 3 times, and then the mixture was stirred at 20° C. for 1 hour under $N_2$. The reaction mixture was poured into water (5 mL) and extracted with ethyl acetate (10 mL, ×3). The combined organic phase was washed with brine (5 mL), dried over anhydrous sodium sulfate, filtered and concentrated under reduced pressure to give a residue. The residue was purified by column chromatography (petroleum ether/ethyl acetate=15/1 to 2/1) to give N-(5-chloro-2-fluoro-phenyl)-7-[2-(3-methyloxetan-3-yl)ethynyl]-6-nitro-quinazolin-4-amine (100 mg 89% yield) as a yellow solid. $^1$H NMR (400 MHz, DMSO-$d_6$) δ 10.57 (s, 1H), 9.44 (s, 1H), 8.69 (s, 1H), 8.07 (s, 1H), 7.73 (d, J=6.0 Hz, 1H), 7.44 (d, J=8.4 Hz, 2H), 4.83 (d, J=5.6 Hz, 2H), 4.51 (d, J=5.6 Hz, 2H), 1.70 (s, 3H).

Step 4. To a mixture of N-(5-chloro-2-fluoro-phenyl)-7-[2-(3-methyloxetan-3-yl)ethynyl]-6-nitro-quinazolin-4-amine (90.0 mg, 218 umol) in tetrahydrofuran (1.0 mL) and $H_2O$ (1.0 mL) was added sodium hydrosulfite (303.67 mg, 1.74 mmol) at 20° C. The mixture was stirred at 60° C. for 16 hours. The reaction mixture was poured into water (5 mL) and extracted with dichloromethane (10 mL×3). The combined organic phase was washed with brine (5 mL), dried with anhydrous sodium sulfate, filtered and concentrated in vacuum. The residue was purified by column chromatography (petroleum ether/ethyl acetate=10/1 to 1/1) to give N4-(5-chloro-2-fluoro-phenyl)-7-[2-(3-methyl oxetan-3-yl)ethynyl]quinazoline-4,6-diamine (50.0 mg, 60% yield) as a yellow solid. $^1$H NMR (400 MHz, DMSO-$d_6$) δ 9.44 (s, 1H), 8.28 (s, 1H), 7.77 (d, J=5.6 Hz, 1H), 7.68-7.61 (m, 1H), 7.39 (s, 1H), 7.34 (br s, 1H), 5.76 (s, 2H), 4.87 (d, J=5.2 Hz, 2H), 4.46 (d, J=5.2 Hz, 2H), 1.71 (s, 3H).

Step 5. To a mixture of N4-(5-chloro-2-fluoro-phenyl)-7-[2-(3-methyloxetan-3-yl)ethynyl]quinazoline-4,6-diamine (45.0 mg, 117 umol) and acrylic acid (8.47 mg, 118 umol) in pyridine (1.0 mL) was added 1-ethyl-3-(3-dimethylaminopropyl)carbodiimide (22.5 mg, 118 umol) at 20° C. The mixture was stirred at 20° C. for 16 hours. The organic solvent was removed by nitrogen purge. The residue was purified by prep-HPLC (column: Phenomenex Gemini-NX C18 75*30 mm*3 um; mobile phase: [water (10 mM $NH_4HCO_3$)-acetonitrile]; B %: 36%-56%, 6 min) to give N4-(5-chloro-2-fluoro-phenyl)-7-[2-(3-methyloxetan-3-yl)ethynyl]quinazoline-4,6-diamine (20.4 mg, 45% yield) as a yellow solid. m/z ES+ $[M+H]^+$ 437.1; $^1$H NMR (400 MHz, DMSO-$d_6$) δ 9.93 (br s, 1H), 8.70 (s, 1H), 8.44 (br s, 1H), 7.83 (s, 1H), 7.63 (br d, J=5.6 Hz, 1H), 7.41-7.29 (m, 2H), 6.62 (dd, J=10.4, 16.8 Hz, 1H), 6.34 (dd, J=2.0, 16.8 Hz, 1H), 5.86 (dd, J=1.6, 10.2 Hz, 1H), 4.83 (d, J=5.2 Hz, 2H), 4.45 (d, J=5.6 Hz, 2H), 1.68 (s, 3H).

Example 28. Synthesis of Compound No. 30 (N-(4-((3-chloro-2-fluorophenyl)amino)-7-((3-methyloxetan-3-yl)ethynyl)quinazolin-6-yl)acrylamide)

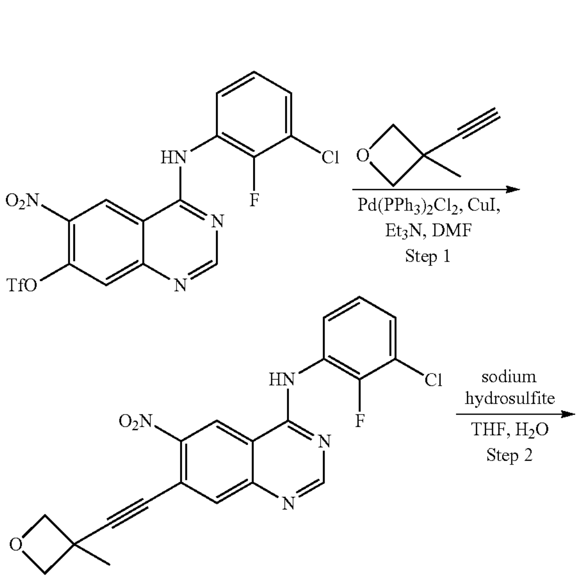

-continued

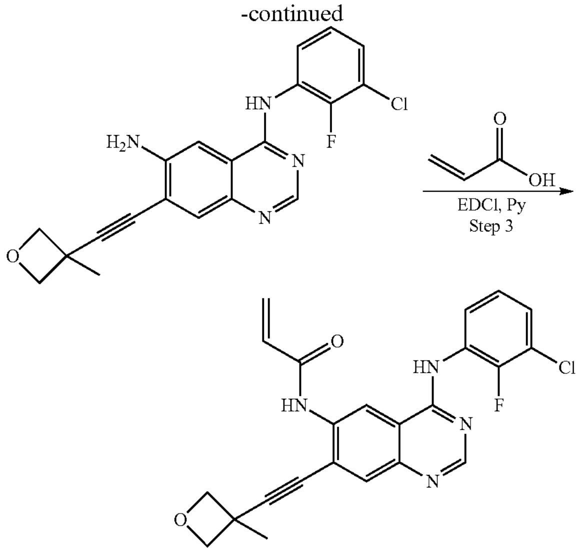

Step 1. To a solution of [4-(3-chloro-2-fluoro-anilino)-6-nitro-quinazolin-7-yl]trifluoromethanesulfonate (200 mg, 428 umol) in dimethylformamide (2.0 mL) was added CuI (16.3 mg, 85.7 umol), $Et_3N$ (1.45 g, 14.3 mmol), 3-ethynyl-3-methyl-oxetane (45.3 mg, 471 umol) and $Pd(PPh_3)_2Cl_2$ (30.0 mg, 42.8 umol). The mixture was stirred at 20° C. for 1 h under $N_2$. On completion, the reaction mixture was quenched by water (10 mL), and extracted with ethyl acetate (5 mL×3). The combined organic phase was washed with saturated $NH_4C_1$ solution (15 mL), dried over anhydrous sodium sulfate, filtered and concentrated under reduced pressure to give a residue. The residue was purified by column chromatography (petroleum ether/ethyl acetate=10/1 to 1/1) to give N-(3-chloro-2-fluoro-phenyl)-7-[2-(3-methyl oxetan-3-yl)ethynyl]-6-nitro-quinazolin-4-amine (150 mg, 84% yield) as an orange solid. $^1H$ NMR (400 MHz, DMSO-$d_6$) δ 10.66 (s, 1H), 9.43 (s, 1H), 8.67 (s, 1H), 8.06 (s, 1H), 7.67-7.49 (m, 2H), 7.32 (t, J=8.4 Hz, 1H), 4.82 (d, J=5.6 Hz, 2H), 4.50 (d, J=5.6 Hz, 2H), 1.69 (s, 3H).

Step 2. To a mixture of N-(3-chloro-2-fluoro-phenyl)-7-[2-(3-methyloxetan-3-yl)ethynyl]-6-nitro-quinazolin-4-amine (80.0 mg, 194 umol) in tetrahydrofuran (1.0 mL) and $H_2O$ (1.0 mL) was added sodium hydrosulfite (270 mg, 1.55 mmol) at 20° C. The mixture was stirred at 60° C. for 16 h. On completion, the reaction mixture was poured into water (5 mL) and extracted with dichloromethane (10 mL×3). The combined organic phase was washed with brine (5 mL), dried with anhydrous sodium sulfate, filtered and concentrated in vacuum. The residue was purified by column chromatography (petroleum ether/ethyl acetate=10/1 to 1/1) to give N-(4-((3-chloro-2-fluorophenyl)amino)-7-((3-methyloxetan-3-yl)ethynyl)quinazoline-4,6-diamine (50.0 mg, 67% yield) as a yellow solid. $^1H$ NMR (400 MHz, DMSO-$d_6$) δ 9.57 (s, 1H), 8.25 (s, 1H), 7.67-7.62 (m, 1H), 7.58-7.51 (m, 1H), 7.45 (t, J=6.8 Hz, 1H), 7.39 (s, 1H), 7.26 (t, J=8.0 Hz, 1H), 5.76-5.71 (m, 2H), 4.87 (d, J=5.2 Hz, 2H), 4.45 (d, J=5.2 Hz, 2H), 1.71 (s, 3H).

Step 3. To a mixture of N-(4-((3-chloro-2-fluorophenyl) amino)-7-((3-methyloxetan-3-yl)ethynyl)quinazoline-4,6-diamine (30.0 mg, 78.4 mol) in pyridine (1.0 mL) was added 1-ethyl-3-(3-dimethylaminopropyl)carbodiimide (18.0 mg, 94.0 umol) and acrylic acid (6.78 mg, 94.0 umol) at 20° C. The mixture was stirred at 20° C. for 16 h. On completion, the organic solvent was removed by nitrogen purge. The residue was purified by prep-HPLC (column: Phenomenex Gemini-NX C18 75*30 mm*3 um; mobile phase: [water (10 mM $NH_4HCO_3$)-acetonitrile]; B %: 34%-54%, 6 min) to give N-(4-((3-chloro-2-fluorophenyl) amino)-7-((3-methyloxetan-3-yl)ethynyl)quinazolin-6-yl)acrylamide (12.8 mg, 37% yield) as a yellow solid. m/z ES+ $[M+H]^+$ 437.1; $^1H$ NMR (400 MHz, DMSO-$d_6$) δ 10.13 (s, 1H), 9.96 (s, 1H), 8.73 (s, 1H), 8.50 (s, 1H), 7.88 (s, 1H), 7.51 (q, J=7.2 Hz, 2H), 7.29 (t, J=8.0 Hz, 1H), 6.63 (dd, J=10.0, 16.8 Hz, 1H), 6.35 (br d, J=17.2 Hz, 1H), 5.86 (br d, J=10.4 Hz, 1H), 4.83 (d, J=5.6 Hz, 2H), 4.46 (d, J=5.6 Hz, 2H), 1.68 (s, 3H).

Example 29. Synthesis of Compound No. 31 ((R)—N-(4-((3-chloro-2-fluorophenyl)amino)-7-((1,3-dimethylpyrrolidin-3-yl)ethynyl)quinazolin-6-yl)-2-(hydroxymethyl)acrylamide)

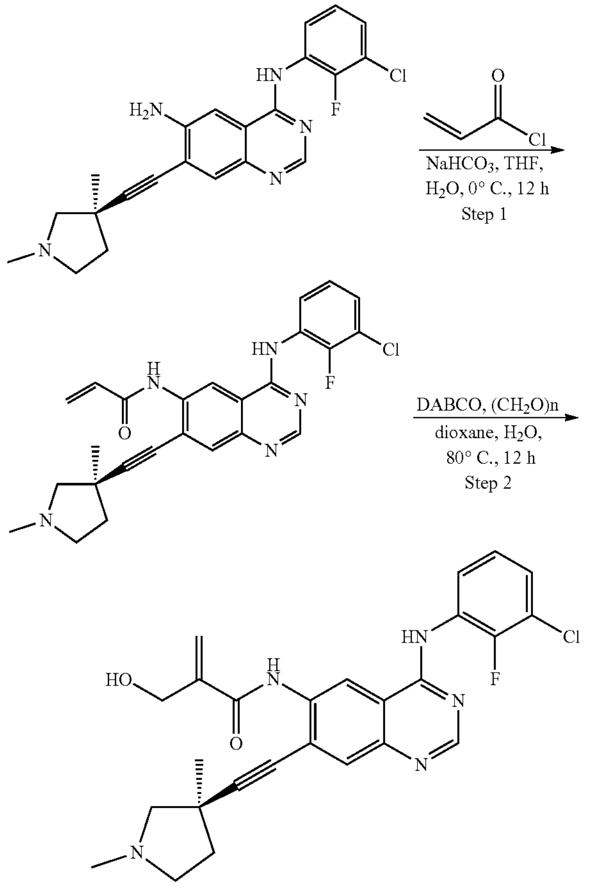

Step 1. To a mixture of N4-(3-chloro-2-fluoro-phenyl)-7-[2-[(3R)-1,3-dimethylpyrrolidin-3-yl]ethynyl]quinazoline-4,6-diamine (100 mg, 243.97 umol) in tetrahydrofuran (1 mL) and $H_2O$ (0.25 mL) was added $NaHCO_3$ (102.48 mg, 1.22 mmol) and prop-2-enoyl chloride (66.1 mg, 730 umol) in tetrahydrofuran (1.5 mL) dropwise at 0° C. Then the mixture was stirred at 20° C. for 12 h. On completion, the reaction was concentrated in vacuo. The residue was diluted with $H_2O$ (2 mL) and extracted with ethyl acetate (3 mL×3). The combined organic layers were dried over $Na_2SO_4$, filtered and concentrated under vacuum to give N-[4-(3-chloro-2-fluoro-anilino)-7-[2-[(3R)-1,3-dimethylpyrrolidin-3-yl]ethynyl]quinazolin-6-yl]prop-2-enamide (80 mg, 70.68% yield) as a yellow solid. m/z ES+ $[M+H]^+$ 464.1

Step 2. To a mixture of N-[4-(3-chloro-2-fluoro-anilino)-7-[2-[(3R)-1,3-dimethylpyrrolidin-3-yl]ethynyl]quinazolin-6-yl]prop-2-enamide (60 mg, 129.33 umol) in dioxane (4 mL) and $H_2O$ (1 mL) was added 1,4-diazabicyclo[2.2.2]octane (43.52 mg, 387.99 umol) and $(CH_2O)_n$ (18.11 mg, 646.64 umol) at 20° C. Then the mixture was stirred at 80° C. for 12 h. On completion, the reaction was diluted in DMSO (1 mL). The mixture was purified by prep-HPLC (column: Waters Xbridge BEH C18 100*30 mm*10 um; mobile phase: [water (10 mM $NH_4HCO_3$)-acetonitrile]; B %: 33%-53%, 8 min) to give N-[4-(3-chloro-2-fluoro-anilino)-7-[2-[(3R)-1,3-dimethylpyrrolidin-3-yl]ethynyl]quinazolin-6-yl]-2-(hydroxymethyl)prop-2-enamide (5 mg, 7.83% yield) as a yellow solid. m/z ES+ $[M+H]^+$ 494.0; 41 NMR (400 MHz, $CDCl_3$) δ 11.01 (br s, 1H), 9.36 (s, 1H), 8.73 (s, 1H), 8.45-8.31 (m, 1H), 7.95 (s, 1H), 7.73 (br s, 1H), 7.23-7.11 (m, 2H), 6.44 (s, 1H), 5.69 (s, 1H), 4.62 (d, J=11.2 Hz, 1H), 4.54 (d, J=10.8 Hz, 1H), 3.44 (d, J=10.0 Hz, 1H), 3.26 (br t, J=8.4 Hz, 1H), 2.55-2.42 (m, 4H), 2.34 (q, J=9.2 Hz, 1H), 2.26-2.16 (m, 1H), 2.08-1.93 (m, 1H), 1.61 (s, 4H).

Example 30. Synthesis of Compound No. 32 (N-(4-((3-chloro-2-fluorophenyl)amino)-7-((2,4-dimethylmorpholin-2-yl)ethynyl)quinazolin-6-yl)acrylamide)

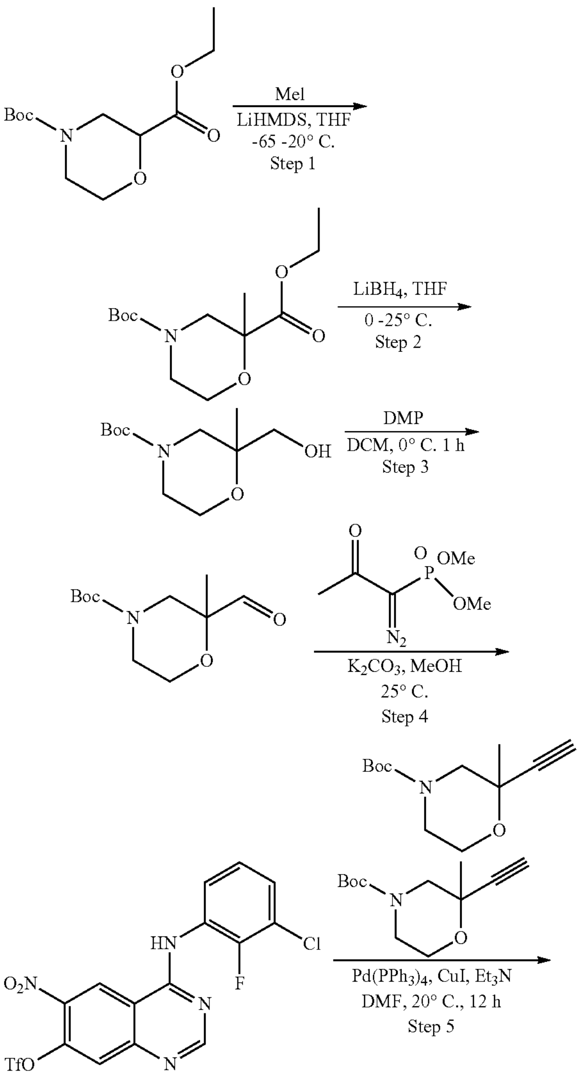

-continued

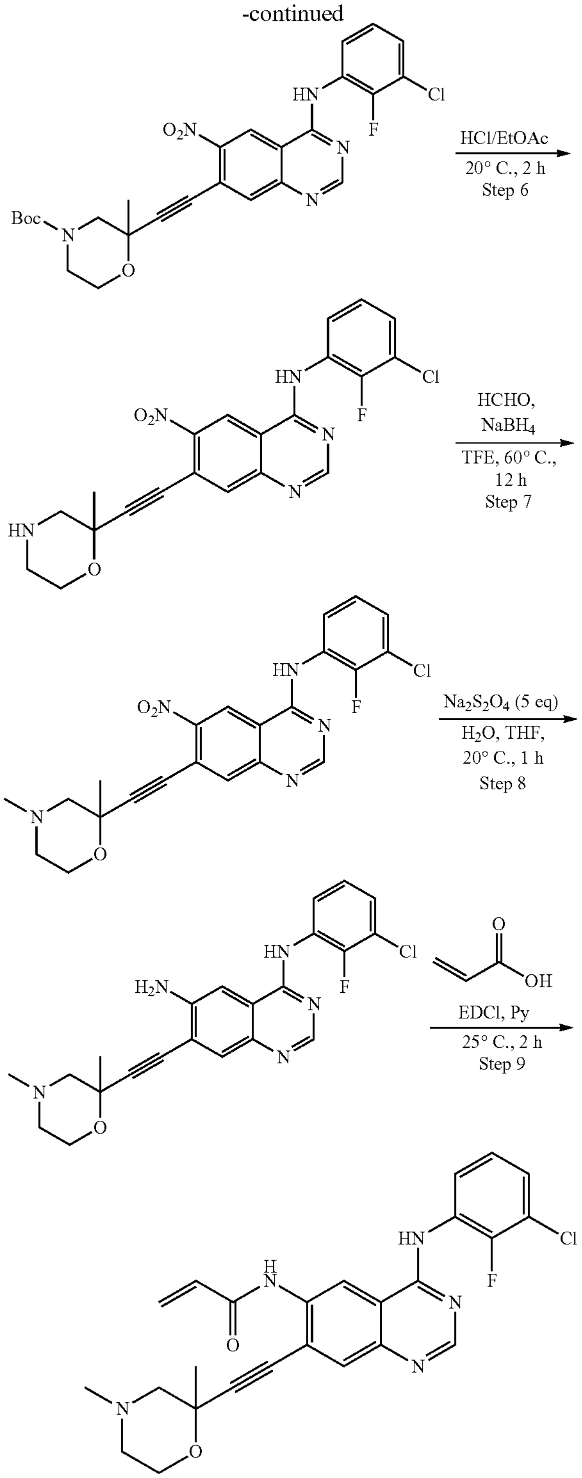

Step 1. To a solution of 4-(tert-butyl) 2-ethyl morpholine-2,4-dicarboxylate (5 g, 19.3 mmol) in tetrahydrofuran (38 mL) was added LiHMDS (1 M, 38.6 mL) dropwise under $N_2$ at −65° C. over 1 h. Then the mixture was stirred at −65° C. for 1.5 h. And MeI (11.0 g, 77.1 mmol, 4.80 mL) was added dropwise at −65° C. The mixture was slowly warmed to 20° C. and stirred at 20° C. for 12 h. On completion, the reaction mixture was quenched by saturated $NH_4C_1$ solution (50 mL) at 15° C., and extracted with ethyl acetate (50 mL×2). The combined organic layers were washed with brine (100 mL), dried over $Na_2SO_4$, filtered and the filtrate was concentrated under reduced pressure to give a residue. The residue was purified by column chromatography [$SiO_2$, petroleum ether/ethyl acetate=50/1 to 3/1] to give 4-tert-butyl 2-ethyl morpholine-2,4-dicarboxylate (3.03 g, 57.49% yield) as a yellow oil. $^1H$ NMR (400 MHz, $CDCl_3$) δ 4.37 (d, J=13.2 Hz, 1H), 4.23 (s, 2H), 3.89-3.75 (m, 3H), 3.02 (br s, 1H), 2.87 (d, J=13.2 Hz, 1H), 1.47 (s, 9H), 1.39 (s, 3H), 1.30 (t, J=7.2 Hz, 3H).

Step 2. To a mixture of 4-tert-butyl 2-ethyl morpholine-2,4-dicarboxylate (3 g, 11.0 mmol) in tetrahydrofuran (30 mL) was added $LiBH_4$ (960 mg, 44.1 mmol) at 0° C. under $N_2$. The mixture was stirred at 25° C. for 6 hours. On completion, the mixture was quenched by MeOH (30 mL) carefully and then concentrated in vacuum to give a residue. The residue was partitioned between HCl (0.5 N, 20 mL) and ethyl acetate (10 mL). The aqueous phase was extracted with ethyl acetate (20 mL, ×2). The combined organic phase was washed with brine (50 mL×2), dried with anhydrous $Na_2SO_4$, filtered and concentrated in vacuum to give a residue. The residue was purified by column chromatography [$SiO_2$, petroleum ether/ethyl acetate=1/0 to 0/1] to give tert-butyl 2-(hydroxymethyl)-2-methylmorpholine-4-carboxylate (1.8 g, 70.65% yield) as a yellow oil. m/z ES+ $[M+H]^+$ 176.2

Step 3. To a mixture of tert-butyl 2-(hydroxymethyl)-2-methylmorpholine-4-carboxylate (1.4 g, 6.05 mmol) in dichloromethane (15 mL) was added DMI) (3.34 g, 7.87 mmol) in one portion at 0° C. under $N_2$. The mixture was stirred at 0° C. for 1 hour. On completion, the mixture was poured into saturated aqueous $Na_2CO_3$ (20 mL) and dichloromethane (10 mL). The aqueous phase was extracted with dichloromethane (5 mL×3). The combined organic phase was washed with brine (10 mL×2), dried with anhydrous $Na_2SO_4$, filtered and concentrated in vacuum to give tert-butyl 2-formyl-2-methylmorpholine-4-carboxylate (2.2 g, crude) as a white solid.

Step 4. To a mixture of tert-butyl 2-formyl-2-methylmorpholine-4-carboxylate (2.2 g, 9.60 mmol) and 1-diazo-1-dimethoxyphosphoryl-propan-2-one (2.77 g, 14.4 mmol) in MeOH (30 mL) was added $K_2CO_3$ (2.65 g, 19.2 mmol) in one portion at 0° C. under $N_2$. The mixture was stirred at 25° C. for 2 hours. On completion, the mixture was filtered and the filter cake was washed with MeOH (4 mL×2). Then the filtrate was concentrated in vacuum to give a residue. The residue was purified by column chromatography [$SiO_2$, petroleum ether/ethyl acetate=1/0 to 0/1] to give tert-butyl 2-ethynyl-2-methylmorpholine-4-carboxylate (1.2 g, 55.51% yield) as a yellow solid. 41 NMR (400 MHz, DMSO-$d_6$) δ 3.95-3.83 (m, 1H), 3.83-3.73 (m, 2H), 3.62 (dd, J=11.2, 2.8 Hz, 1H), 3.47 (s, 1H), 2.83 (s, 1H), 2.90-2.70 (m, 2H), 1.40 (s, 9H), 1.35 (s, 3H).

Step 5. To a mixture of tert-butyl 2-ethynyl-2-methylmorpholine-4-carboxylate (265 mg, 1.18 mmol), CuI (40.8 mg, 214 umol), $Et_3N$ (3.63 g, 35.9 mmol, 4.99 mL) and [4-(3-chloro-2-fluoro-anilino)-6-nitro-quinazolin-7-yl]trifluoromethanesulfonate (500 mg, 1.07 mmol) in dimethylformamide (5 mL) was added $Pd(PPh_3)_4$ (124 mg, 107 umol) in one portion at 20° C. The mixture was degassed and purged with $N_2$ for 3 times, and then stirred at 20° C. for 12 hours. On completion, the mixture was poured into $H_2O$ (10 mL) and ethyl acetate (5 mL). The aqueous phase was extracted with ethyl acetate (5 mL×2). The combined organic phase was washed with brine (5 mL×2), dried with anhydrous $Na_2SO_4$, filtered and concentrated in vacuum to give a residue. The residue was purified by column chromatography [$SiO_2$, petroleum ether/ethyl acetate=1/0 to 0/1] to give tert-butyl2-((4-((3-chloro-2-fluorophenyl) amino)-6-nitroquinazolin-7-yl)ethynyl)-2-methylmorpholine-4-carboxylate (0.65 g, crude) as a brown solid. $^1H$ NMR (400 MHz, DMSO-$d_6$) δ 9.46 (s, 1H), 8.68 (s, 1H), 8.02 (s, 1H), 7.95 (s, 1H), 7.60-7.45 (m, 2H), 7.37-7.27 (m, 1H), 4.15-4.05 (m, 1H), 4.05-3.95 (m, 1H), 3.95-3.80 (m, 1H), 3.80-3.70 (m, 1H), 3.10-2.93 (m, 1H), 2.89-2.80 (m, 1H), 1.52 (s, 3H), 1.32 (s, 9H).

Step 6. A mixture of tert-butyl2-((4-((3-chloro-2-fluorophenyl)amino)-6-nitroquinazolin-7-yl)ethynyl)-2-methylmorpholine-4-carboxylate (500 mg, 923 umol) in HCl/ethyl acetate (6 mL) was stirred at 20° C. for 2 hours. On completion, the mixture was concentrated in vacuum to give a residue. The residue was poured into saturated aqueous $NaHCO_3$ solution (15 mL) and ethyl acetate (10 mL). The aqueous phase was extracted with ethyl acetate (8 mL×3). The combined organic phase was washed with brine (10 mL×2), dried with anhydrous $Na_2SO_4$, filtered and concentrated in vacuum to give N-(3-chloro-2-fluorophenyl)-7-((2-methylmorpholin-2-yl)ethynyl)-6-nitroquinazolin-4-amine (500 mg, crude) as a yellow solid. m/z ES+ $[M+H]^+$ 442.2

Step 7. To a solution of N-(3-chloro-2-fluorophenyl)-7-((2-methylmorpholin-2-yl)ethynyl)-6-nitroquinazolin-4-amine (500 mg, 1.13 mmol) in trifluoroethanol (5 mL) was added $(CH_2O)_n$ (170 mg, 5.66 mmol) at 60° C. The mixture was stirred at 60° C. for 10 min. Then $NaBH_4$ (85.6 mg, 2.26 mmol) was added. The mixture was stirred at 60° C. for 12 hours. On completion, the mixture was quenched by saturated aqueous $NH_4C_1$ (10 mL). The aqueous phase was extracted with ethyl acetate (5 mL×3). The combined organic phase was washed with brine (5 mL×2), dried with anhydrous $Na_2SO_4$, filtered and concentrated in vacuum to give a residue. The residue was purified by prep-TLC [$SiO_2$, dichloromethane/MeOH=10/1, $R_f$=0.21] to give N-(3-chloro-2-fluorophenyl)-7-((2,4-dimethylmorpholin-2-yl)ethynyl)-6-nitroquinazolin-4-amine (0.2 g, 38.77% yield) as a white solid.

Step 8. To a mixture of N-(3-chloro-2-fluorophenyl)-7-((2,4-dimethylmorpholin-2-yl) ethynyl)-6-nitroquinazolin-4-amine (200 mg, 439 umol) in tetrahydrofuran (1 mL) and $H_2O$ (1 mL) was added sodium hydrosulfite (382 mg, 2.19 mmol) in one portion at 20° C. under $N_2$. The mixture was stirred at 20° C. for 2 hours. On completion, the mixture was poured into $H_2O$ (5 mL) and dichloromethane (3 mL). The aqueous phase was extracted with dichloromethane (3 mL×3). The combined organic phase was washed with brine (3 mL×3), dried with anhydrous $Na_2SO_4$, filtered and concentrated in vacuum to give a residue. The residue was purified by prep-TLC [dichloromethane/MeOH=10/1, $R_f$=0.24] to give N4-(3-chloro-2-fluorophenyl)-7-((2,4-dimethylmorpholin-2-yl)ethynyl)quinazoline-4,6-diamine (0.1 g, 53.52% yield) as a white solid. m/z ES+ $[M+H]^+$ 399.1

Step 9. To a mixture of N4-(3-chloro-2-fluorophenyl)-7-((2,4-dimethylmorpholin-2-yl)ethynyl)quinazoline-4,6-diamine (0.06 g, 140 umol) and acrylic acid (15.2 mg, 112 umol) in dimethylformamide (1 mL) was added 1-ethyl-3-(3-dimethylaminopropyl)carbodiimide (108 mg, 564 umol) and pyridine (89.16 mg, 1.13 mmol) in one portion at 25° C. under $N_2$. The mixture was stirred at 25° C. for 2 hours. On completion, the mixture was concentrated in vacuum to give a residue. The residue was purified by prep-HPLC (column: Waters Xbridge BEH C18 100*30 mm*10 um; mobile phase: [water (10 mM $NH_4HCO_3$)-acetonitrile]; B %: 35%-60%, 8 min) to give N-(4-((3-chloro-2-fluorophenyl) amino)-7-((2,4-dimethylmorpholin-2-yl)ethynyl)quinazolin-6-yl)acrylamide (2 mg, 2.79% yield) as a white solicd. m/z ES+ $[M+H]^+$ 480.0; $^1H$ NMR (400 MHz, DMSO-$d_6$) δ

10.14 (br s, 1H), 9.68 (br s, 1H), 8.83 (s, 1H), 8.50 (s, 1H), 7.88 (s, 1H), 7.55-7.45 (m, 2H), 7.29 (t, J=7.6 Hz, 1H), 6.63-6.47 (m, 1H), 6.41-6.28 (m, 1H), 5.88 (d, J=10.4 Hz, 1H), 4.00 (t, J=10.4 Hz, 1H), 3.70 (d, J=11.2 Hz, 1H), 2.98 (d, J=11.2 Hz, 1H), 2.67 (d, J=10.4 Hz, 1H), 2.21 (s, 3H), 2.05-1.93 (m, 2H), 1.49 (s, 3H).
Example 31. Synthesis of Compound No. 33 (N-(4-((3,4-dichloro-2-fluorophenyl)amino)-7-(((1S,5R)-3-methyl-3-azabicyclo[3.1.0]hexan-1-yl)ethynyl)quinazolin-6-yl)acrylamide) and Compound No. 34 (N-(4-((3,4-dichloro-2-fluorophenyl)amino)-7-0(1R, 5S)-3-methyl-3-azabicyclo[3.1.0]hexan-1-yl) ethynyl)quinazolin-6-yl)acrylamide)
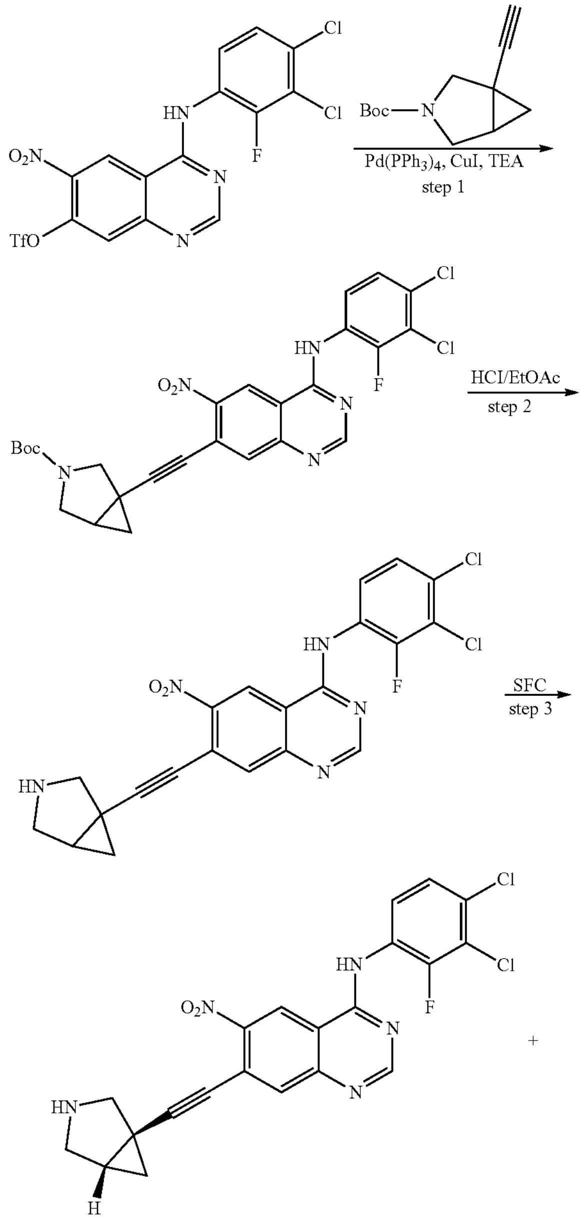
-continued
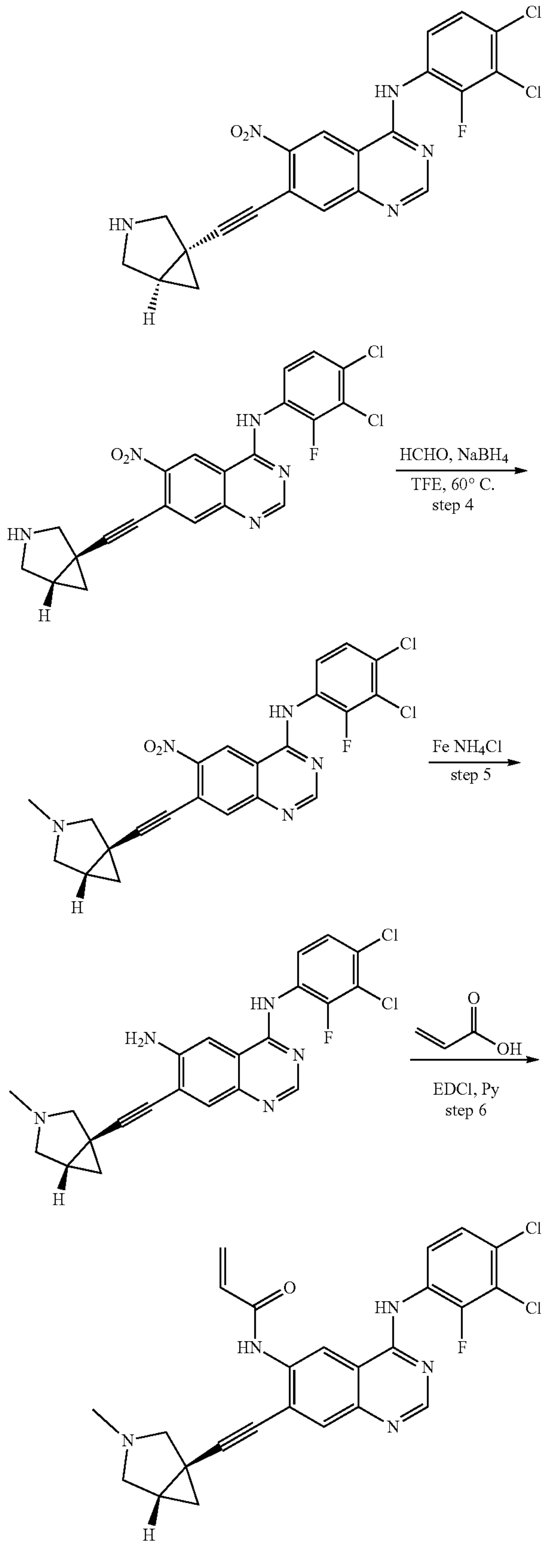

-continued

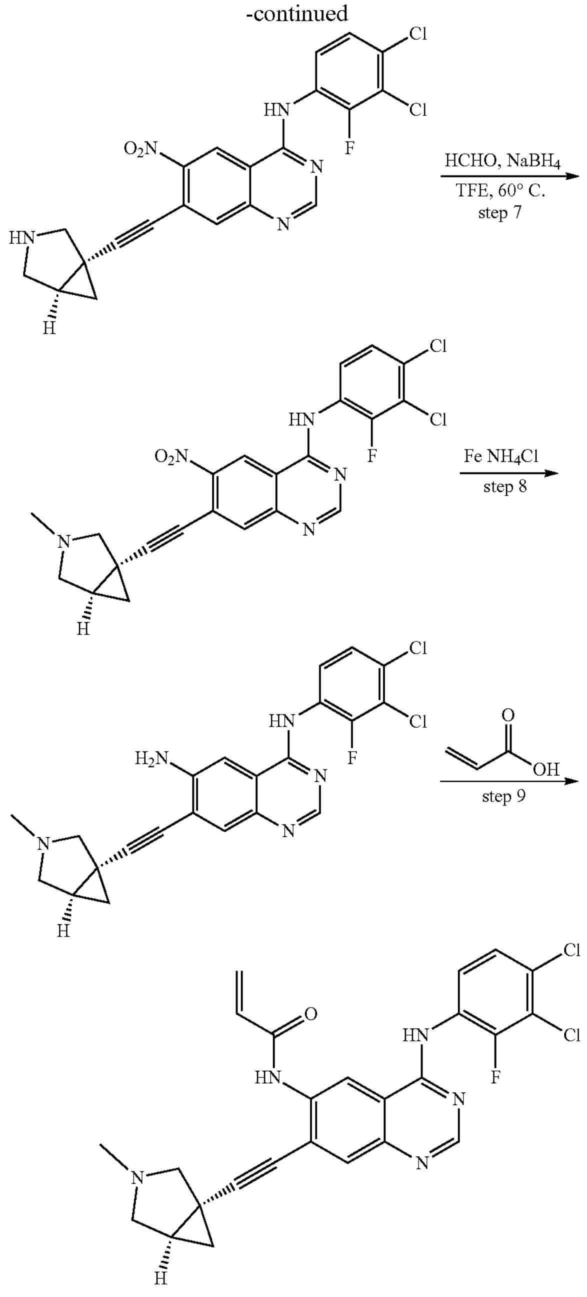

Step 1. To a solution of [4-(3,4-dichloro-2-fluoro-anilino)-6-nitro-quinazolin-7-yl]trifluoromethanesulfonate (2.4 g, 4.79 mmol) and tert-butyl 1-ethynyl-3-azabicyclo[3.1.0]hexane-3-carboxylate (1.09 g, 5.27 mmol) in dimethylformamide (20 mL) and triethylamine (14.5 g, 144 mmol, 20 mL) was added CuI (182 mg, 958 umol) and $Pd(PPh_3)_4$ (277 mg, 239 umol) in one portion under nitrogen. The mixture was stirred at 25° C. for 2 h. On completion, the reaction mixture was diluted with $H_2O$ (100 mL) and extracted with ethyl acetate (100 mL×3). The combined organic layers were washed with brine (100 mL×2), dried over $Na_2SO_4$, filtered and concentrated under reduced pressure to give a residue. The residue was purified by column chromatography (Petroleum ether/Ethyl acetate=5/1 to 1/1) to give tert-butyl 1-((4-((3,4-dichloro-2-fluorophenyl)amino)-6-nitroquinazolin-7-yl) ethynyl)-3-azabicyclo[3.1.0]hexane-3-carboxylate (2.60 g, 88% yield) as a yellow solid. m/z ES+ $[M+H]^+$ 558.2; $^1H$ NMR (400 MHz, $CDCl_3$) δ 8.93-8.78 (m, 2H), 8.62-8.36 (m, 1H), 8.05 (s, 2H), 7.57 (dd, J=7.2, 11.6 Hz, 1H), 3.83 (d, J=10.8 Hz, 1H), 3.63-3.48 (m, 2H), 2.99 (s, 1H), 2.89 (s, 1H), 1.45 (s, 9H)

Step 2. To a solution of tert-butyl 1-[2-[4-(3,4-dichloro-2-fluoro-anilino)-6-nitro-quinazolin-7-yl]ethynyl]-3-azabicyclo[3.1.0]hexane-3-carboxylate (2.40 g, 4.30 mmol) in ethyl acetate (20 mL) was added HCl/ethyl acetate (4 M, 7.68 mL), it was stirred at 20° C. for 2 hs. On completion, the reaction mixture was concentrated under reduced pressure to give a residue. The residue was purified by prep-HPLC (column: Phenomenex Luna C8 250*50 mm*10 um; mobile phase: [water (0.225% formic acid)-acetonitrile]; B %: 5%-40%, 14.5 min) to give 7-(3-azabicyclo[3.1.0]hexan-1-yl ethynyl)-N-(3,4-dichloro-2-fluorophenyl)-6-nitroquinazolin-4-amine (780 mg, 36% yield) as a yellow solid. m/z ES+ $[M+H]^+$ 458.1; $^1H$ NMR (400 MHz, DMSO-$d_6$) δ 9.90 (s, 1H), 8.74 (s, 1H), 8.08 (s, 1H), 7.67-7.63 (m, 1H), 7.57 (d, J=7.6 Hz, 1H), 3.71-3.57 (m, 1H), 3.56-3.41 (m, 2H), 3.37 (dd, J=6.0, 11.6 Hz, 1H), 2.42-2.33 (m, 1H), 1.56 (t, J=5.6 Hz, 1H), 1.40 (t, J=7.2 Hz, 1H).

Step 3. 7-[2-(3-azabicyclo[3.1.0]hexan-1-yl) ethynyl]-N-(3,4-dichloro-2-fluoro-phenyl)-6-nitro-quinazolin-4-amine (780 mg, 1.53 mmol, 90% purity) was purified by SFC (column: Phenomenex-Cellulose-2 (250 mm*30 mm, 10 um); mobile phase: [0.1% ammonium hydroxide methanol]; B %: 60%-60%, min) to give 7-((1R,5S)-3-azabicyclo[3.1.0]hexan-1-ylethynyl)-N-(3,4-dichloro-2-fluorophenyl)-6-nitroquinazolin-4-amine (300 mg, 40% yield) as a yellow solid and 7-((1S,5R)-3-azabicyclo[3.1.0]hexan-1-ylethynyl)-N-(3,4-dichloro-2-fluorophenyl)-6-nitroquinazolin-4-amine (300 mg, 40% yield) as a yellow solid. m/z ES+ $[M+H]^+$ 458.1; $^1H$ NMR (400 MHz, DMSO-$d_6$) δ 9.27 (s, 1H), 8.53 (s, 1H), 7.87 (s, 1H), 7.64-7.44 (m, 2H), 3.08 (d, J=11.2 Hz, 1H), 2.91-2.80 (m, 3H), 1.93 (dd, J=6.0, 7.2 Hz, 1H), 1.11 (t, J=4.8 Hz, 1H), 1.07-1.03 (m, 1H). m/z ES+ $[M+H]^+$ 458.1; $^1H$ NMR (400 MHz, DMSO-$d_6$) δ 9.30 (s, 1H), 8.55 (s, 1H), 8.18 (s, 1H), 7.90 (s, 1H), 7.58 (d, J=1.2 Hz, 2H), 3.12 (d, J=11.2 Hz, 1H), 2.93-2.87 (m, 3H), 1.97 (dd, J=5.2, 7.6 Hz, 1H), 1.14 (t, J=4.8 Hz, 1H), 1.11-1.05 (m, 1H).

Step 4. To a solution of 7-[2-[(1R,5S)-3-azabicyclo[3.1.0]hexan-1-yl]ethynyl]-N-(3,4-dichloro-2-fluoro-phenyl)-6-nitro-quinazolin-4-amine (150 mg, 327 umol) in trifluoroethanol (3 mL) was added HCHO (49.1 mg, 1.64 mmol) and the mixture was stirred at 25° C. for 0.5 h. Then $NaBH_4$ (37.2 mg, 982 umol) was added, it was stirred at 60° C. for 3 hs. On completion, the mixture was quenched with methanol (8.0 mL) and concentrated to dryness to give a residue. The reaction mixture was diluted with $H_2O$ (20 mL) and extracted with ethyl acetate (30 mL×3). The combined organic layers were washed with brine (25 mL×2), dried over $Na_2SO_4$, filtered and concentrated under reduced pressure to give N-(3,4-dichloro-2-fluorophenyl)-7-(((1R,5S)-3-methyl-3-azabicyclo[3.1.0]hexan-1-yl)ethynyl)-6-nitroquinazolin-4-amine (200 mg, crude) as a yellow solid. m/z ES+ $[M+H]^+$ 472.2

Step 5. To a solution of N-(3,4-dichloro-2-fluoro-phenyl)-7-[2-[(1R,5S)-3-methyl-3-azabicyclo[3.1.0]hexan-1-yl]ethynyl]-6-nitro-quinazolin-4-amine (150 mg, 318 umol) in ethanol (3 mL) was added Fe (177 mg, 3.18 mmol) and HOAc (1.05 g, 17.48 mmol, 1.00 mL), it was stirred at 80° C. for 2 h. On completion, the reaction mixture was filtered and concentrated under reduced pressure to give a residue. The residue was diluted with $H_2O$ (50 mL) and extracted with ethyl acetate (50 mL×3). The combined organic layers were dried over $Na_2SO_4$, filtered and concentrated under reduced pressure to give N4-(3-chloro-2-fluorophenyl)-7-(6-methyl-2,6-diazaspiro[3.4]octan-2-yl) quinazoline-4,6-diamine (150 mg, crude) as a yellow solid. m/z ES+ $[M+H]^+$ 442.1

Step 6. To a solution of N4-(3,4-dichloro-2-fluoro-phenyl)-7-[2-[(1R,5S)-3-methyl-3-azabicyclo[3.1.0]hexan-1-yl]ethynyl]quinazoline-4,6-diamine (65.6 mg, 148 umol) in pyridine (1 mL) was added 1-ethyl-3-(3-dimethylaminopropyl)carbodiimide (142 mg, 741 umol) and acrylic acid (10.7 mg, 148 umol), it was stirred at 20° C. for 1 h. On completion, the reaction mixture was diluted with $H_2O$ (10 mL) and extracted with ethyl acetate (10 mL×3). The combined organic layers were dried over $Na_2SO_4$, filtered and concentrated under reduced pressure to give a residue. The residue was purified by prep-HPLC (column: Waters Xbridge 150*25 mm*5 um; mobile phase: [water (10 mM $NH_4HCO_3$)-acetonitrile]; B %: 46%-76%, 10 min) to give N-(4-((3,4-dichloro-2-fluorophenyl) amino)-7-(((1R,5S)-3-methyl-3-azabicyclo[3.1.0]hexan-1-yl)ethynyl)quinazolin-6-yl)acrylamide (16.3 mg, 21% yield) as a yellow solid. m/z ES+ $[M+H]^+$ 496.1; $^1$H NMR (400 MHz, DMSO-$d_6$) δ 10.35-9.97 (m, 1H), 9.84 (s, 1H), 8.67 (s, 1H), 8.52-8.30 (m, 1H), 7.76 (s, 1H), 7.64-7.37 (m, 2H), 6.60 (dd, J=10.4, 17.2 Hz, 1H), 6.33 (dd, J=1.6, 17.2 Hz, 1H), 5.94-5.71 (m, 1H), 3.11 (d, J=8.4 Hz, 1H), 2.92 (d, J=9.2 Hz, 1H), 2.47-2.38 (m, 2H), 2.25 (s, 3H), 1.99-1.87 (m, 1H), 1.37 (t, J=4.4 Hz, 1H), 1.03 (s, 1H).

Step 7. To a solution of 7-[2-[(1S,5R)-3-azabicyclo[3.1.0]hexan-1-yl]ethynyl]-N-(3,4-dichloro-2-fluoro-phenyl)-6-nitro-quinazolin-4-amine (150 mg, 327 umol) in trifluoroethanol (5 mL) was added HCHO (49.1 mg, 1.64 mmol) and the mixture was stirred at 25° C. for 0.5 h. Then $NaBH_4$ (37.2 mg, 982 umol) was added and the mixture was stirred at 60° C. for 3 h. On completion, the mixture was quenched with methanol (8 mL) and concentrated to dryness to give a residue. The reaction mixture was diluted with $H_2O$ 20 mL and extracted with ethyl acetate (30 mL×3). The combined organic layers were washed with brine (25 mL*2), dried over $Na_2SO_4$, filtered and concentrated under reduced pressure to give N-(3,4-dichloro-2-fluorophenyl)-7-(((1S,5R)-3-methyl-3-azabicyclo[3.1.0]hexan-1-yl)ethynyl)-6-nitroquinazolin-4-amine (130 mg, crude) as a yellow solid. m/z ES+ $[M+H]^+$ 472.1

Step 8. To a solution of N-(3,4-dichloro-2-fluoro-phenyl)-7-[2-[(1S,5R)-3-methyl-3-azabicyclo[3.1.0]hexan-1-yl] ethynyl]-6-nitro-quinazolin-4-amine (65.0 mg, 138 umol) in MeOH (1 mL) and $H_2O$ (1 mL) was added Fe (38.4 mg, 688 umol) and $NH_4C_1$ (73.6 mg, 1.38 mmol), it was stirred at 80° C. for 2 h. On completion, the reaction mixture was filtered and concentrated under reduced pressure to give a residue. The residue was diluted with $H_2O$ (50 mL) and extracted with ethyl acetate (50 mL×3). The combined organic layers were dried over $Na_2SO_4$, filtered and concentrated under reduced pressure to give N4-(3,4-dichloro-2-fluorophenyl)-7-(((1S,5R)-3-methyl-3-azabicyclo[3.1.0]hexan-1-yl) ethynyl)quinazoline-4,6-diamine (60 mg, crude) as a yellow solid. m/z ES+ $[M+H]^+$ 442.2

Step 9. To a solution of N4-(3,4-dichloro-2-fluoro-phenyl)-7-[2-[(1S,5R)-3-methyl-3-azabicyclo[3.1.0]hexan-1-yl]ethynyl]quinazoline-4,6-diamine (55.0 mg, 124 umol) in pyridine (1 mL) was added 1-ethyl-3-(3-dimethylaminopropyl)carbodiimide (119 mg, 622 umol) and acrylic acid (9.86 mg, 137 umol), it was stirred at 20° C. for 1 h. On completion, the reaction mixture was diluted with $H_2O$ (30 mL) and extracted with ethyl acetate (20 mL×3). The combined organic layers were washed with brine (20 mL×2), dried over $Na_2SO_4$, filtered and concentrated under reduced pressure to give a residue. It was purified by prep-HPLC (column: Phenomenex Gemini-NX C18 75*30 mm*3 um; mobile phase: [water (0.225% formic acid)-acetonitrile]; B %: 15%-45%, 9 min) to give N-(4-((3,4-dichloro-2-fluorophenyl) amino)-7-(((1S,5R)-3-methyl-3-azabicyclo[3.1.0]hexan-1-yl) ethynyl) quinazolin-6-yl) acrylamide (14.4 mg, 21% yield, formic acid) as a yellow solid. m/z ES+ $[M+H]^+$ 496.1; $^1$H NMR (400 MHz, DMSO-$d_6$) δ 10.22-10.02 (m, 1H), 9.86 (s, 1H), 8.68 (s, 1H), 8.55-8.35 (m, 1H), 8.33-8.26 (m, 1H), 7.79 (d, J=1.6 Hz, 1H), 7.55 (s, 2H), 6.60 (dd, J=10.0, 16.8 Hz, 1H), 6.33 (dd, J=1.6, 17.2 Hz, 1H), 5.85 (dd, J=1.6, 10.2 Hz, 1H), 3.10 (d, J=8.4 Hz, 1H), 2.92 (d, J=9.2 Hz, 1H), 2.39 (dd, J=3.6, 9.2 Hz, 2H), 2.25 (s, 3H), 1.94 (td, J=4.4, 8.0 Hz, 1H), 1.37 (t, J=4.4 Hz, 1H), 1.03 (dd, J=3.6, 8.0 Hz, 1H).

Example 32. Synthesis of Compound No. 35 ((S)—N-(4-((3-chloro-2-fluorophenyl)amino)-7-((3-methoxy-1-methylpyrrolidin-3-yl)ethynyl)quinazolin-6-yl)acrylamide) and Compound No. 36 ((R)—N-(4-((3-chloro-2-fluorophenyl)amino)-7-((3-methoxy-1-methylpyrrolidin-3-yl)ethynyl) quinazolin-6-yl)acrylamide)

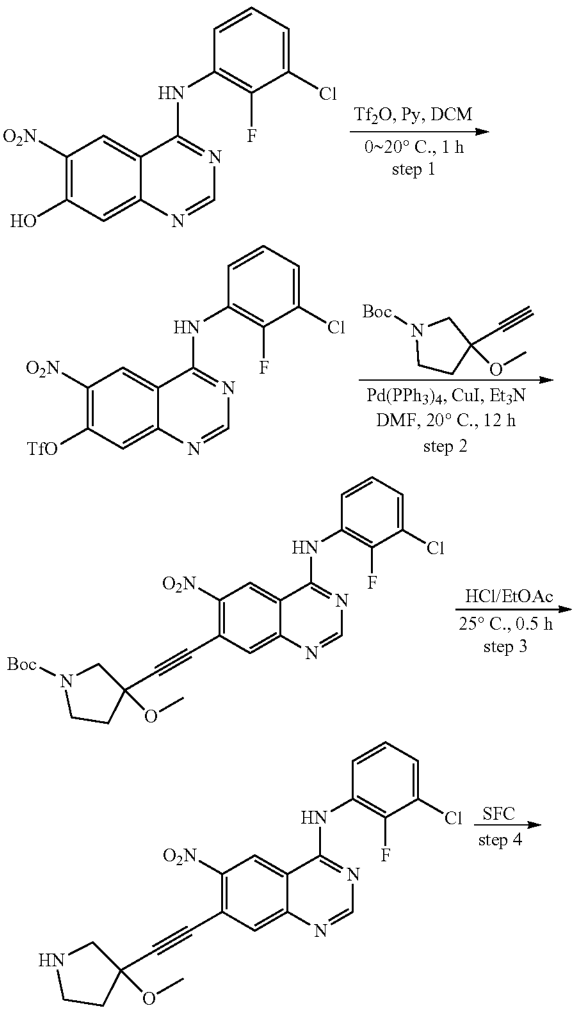

-continued

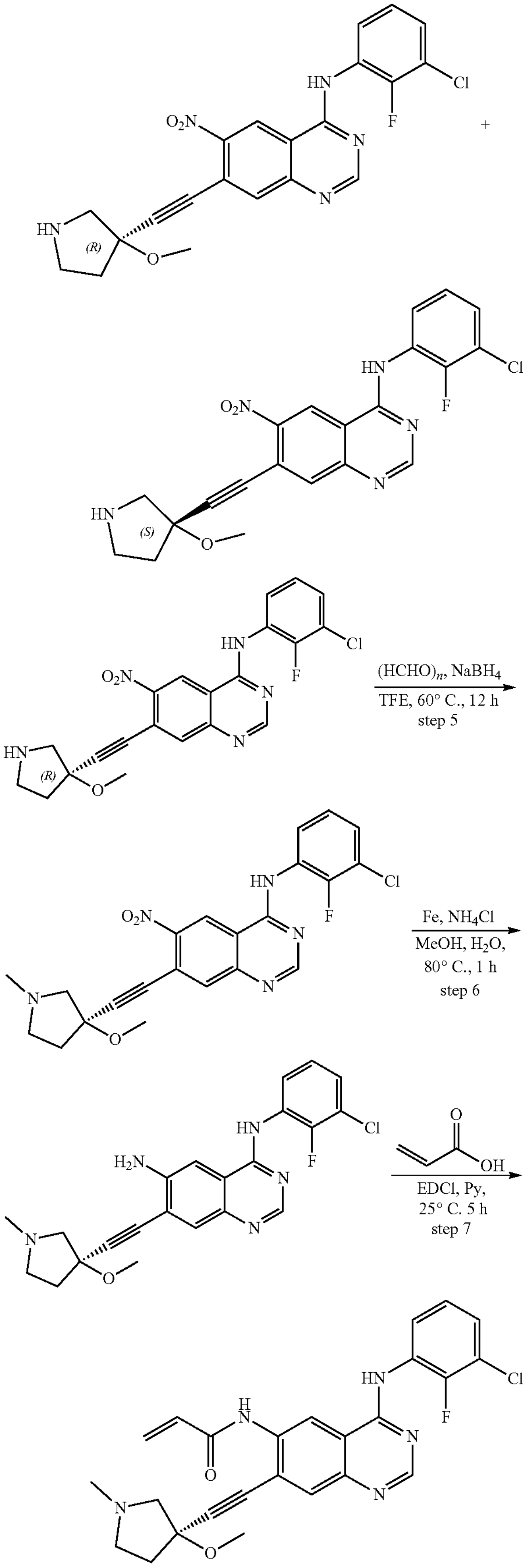

-continued

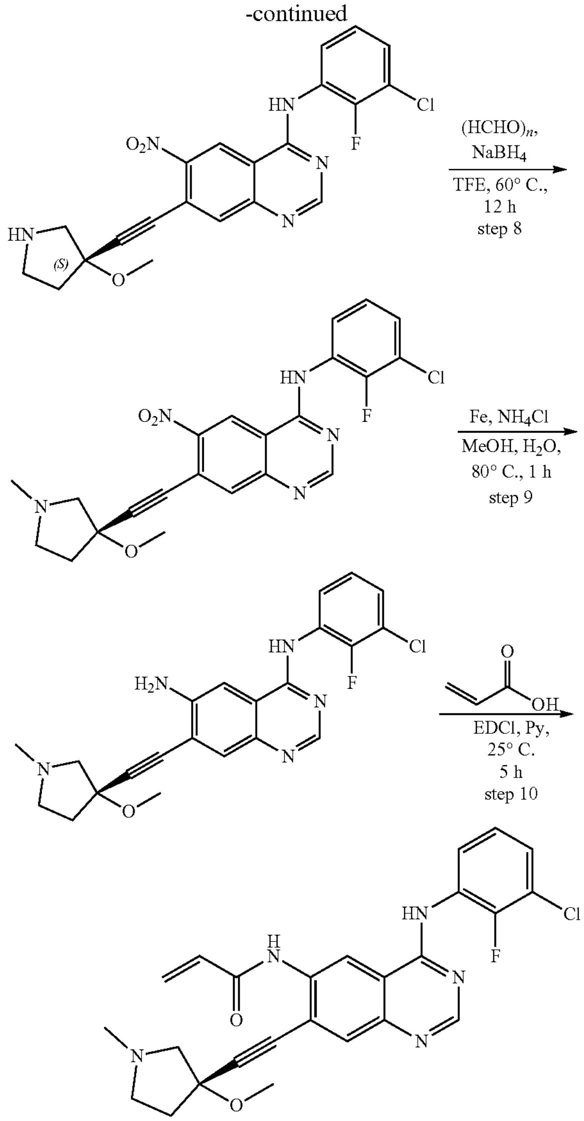

Step 1. To a solution of 4-(3-chloro-2-fluoro-anilino)-6-nitro-quinazolin-7-ol (8.00 g, 23.9 mmol) in dichloromethane (120 mL) was added $Tf_2O$ (20.2 g, 71.7 mmol) and pyridine (7.56 g, 95.6 mmol) at 0° C. The mixture was stirred at 20° C. for 2 h. On completion, the organic solvent was removed under vacuum, the residue was diluted with ethyl acetate (150 mL), washed with water (50 mL×3) and brine (50 mL), dried over $Na_2SO_4$, filtered and concentrated under vacuum to give [4-(3-chloro-2-fluoro-anilino)-6-nitro-quinazolin-7-yl]trifluoromethanesulfonate (4.10 g, crude) as an orange solid. m/z ES+ $[M+H]^+$ 466.9

Step 2. To a solution of [4-(3-chloro-2-fluoro-anilino)-6-nitro-quinazolin-7-yl]trifluoromethanesulfonate (2.00 g, 4.28 mmol) and tert-butyl 3-ethynyl-3-methoxy-pyrrolidine-1-carboxylate (965 mg, 4.28 mmol) in dimethylformamide (20 mL) was added CuI (163 mg, 857 umol), $Et_3N$ (14.5 g, 144 mmol) and $Pd(PPh_3)_4$ (495 mg, 428 umol). The mixture was degassed and purged with $N_2$ for 3 times and then it was stirred at 20° C. for 12 h. On completion, the reaction was filtered and the filtered cake was washed with ethyl acetate (50 mL) to give tert-butyl3-[2-[4-(3-chloro-2-fluoro-anilino)-6-nitro-quinazolin-7-yl]ethynyl]-3-methoxy-pyrrolidine-1-carboxylate (2 g, crude) as a brown solid. m/z ES+ $[M+H]^+$ 542.1

Step 3. To a solution of tert-butyl 3-[2-[4-(3-chloro-2-fluoro-anilino)-6-nitro-quinazolin-7-yl]ethynyl]-3-methoxy-pyrrolidine-1-carboxylate (2.50 g, 4.61 mmol) in dichloromethane (20 mL) was added HCl/ethyl acetate (4 M, 5 mL). The mixture was stirred at 20° C. for 1 h. On completion, the organic solvent was removed under vacuum to afford N-(3-chloro-2-fluoro-phenyl)-7-[2-(3-methoxypyrrolidin-3-yl)ethynyl]-6-nitro-quinazolin-4-amine (2.00 g, crude) as a brown solid. m/z ES+ $[M+H]^+$ 442.0

Step 4. The N-(3-chloro-2-fluoro-phenyl)-7-[2-(3-methoxypyrrolidin-3-yl)ethynyl]-6-nitro-quinazolin-4-amine (1.50 g, 3.39 mmol) was purified by SFC (column: DAICEL CHIRALPAK AD-H (250 mm*30 mm, 5 um); mobile phase: [Neu-ETOH]; B %: 0%-0%, 0 min; 0 min) to afford N-(3-chloro-2-fluoro-phenyl)-7-[2-[(3R)-3-methoxy-pyrrolidin-3-yl]ethynyl]-6-nitro-quinazolin-4-amine (0.32 g, 724 umol, 21% yield, 100% purity) and N-(3-chloro-2-fluoro-phenyl)-7-[2-[(3 S)-3-methoxypyrrolidin-3-yl]ethynyl]-6-nitro-quinazol in-4-amine (0.30 g, 659 umol, 19% yield, 97% purity) as red solids. SFC Retention time: 1.625 min, 2.566 min Step 5. To a solution of N-(3-chloro-2-fluoro-phenyl)-7-[2-[(3R)-3-methoxypyrrolidin-3-yl]ethynyl]-6-nitro-quinazolin-4-amine (0.30 g, 679 umol) in trifluoroethanol (6 mL) was added HCHO (102 mg, 3.4 mmol) and $NaBH_4$ (51.4 mg, 1.36 mmol). The mixture was stirred at 60° C. for 4 h. On completion, the reaction was diluted with water (100 mL), extracted with EA (30 mL×3), washed with brine (40 mL), dried over $Na_2SO_4$, filtered and concentrated under vacuum to afford N-(3-chloro-2-fluoro-phenyl)-7-[2-[(3R)-3-methoxy-1-methyl-pyrrolidin-3-yl]ethynyl]-6-nitro-quinazolin-4-amine (0.30 g, crude) as a brown solid. m/z ES+ $[M+H]^+$ 456.0

Step 6. To a solution of N-(3-chloro-2-fluoro-phenyl)-7-[2-[(3R)-3-methoxy-1-methyl-pyrrolidin-3-yl]ethynyl]-6-nitro-quinazolin-4-amine (0.30 g, 658 umol) in MeOH (3.0 mL) and $H_2O$ (3.0 mL) was added $NH_4C_1$ (422 mg, 7.9 mmol) and Fe (331 mg, 5.9 mmol). The mixture was stirred at 80° C. for 1 h. On completion, the reaction was filtered through a pad of celite while it was still hot, the filtered cake was washed with MeOH (10 mL), and the combined organic solvent was concentrated in vacuo to afford N4-(3-chloro-2-fluoro-phenyl)-7-[2-[(3R)-3-methoxy-1-methyl-pyrrolidin-3-yl]ethynyl]quinazoline-4,6-diamine (0.22 g, crude) as a brown solid.

Step 7. To a solution of N4-(3-chloro-2-fluoro-phenyl)-7-[2-[(3R)-3-methoxy-1-methyl-pyrrolidin-3-yl]ethynyl] quinazoline-4,6-diamine (200 mg, 470 umol) in pyridine (4.00 mL) was added 1-ethyl-3-(3-dimethylaminopropyl) carbodiimide (360 mg, 1.88 mmol) and acrylic acid (50.8 mg, 704.4 umol). The mixture was stirred at 0° C. for 2 h. On completion, the organic solvent was removed under vacuum and the crude was purified by prep-HPLC (column: Waters Xbridge 150*25 mm*5 um; mobile phase: [water (10 mM $NH_4HCO_3$)-acetonitrile]; B %: 26%-56%, 8 min) and repurified by prep-HPLC (column: Phenomenex Gemini-NX C18 75*30 mm*3 um; mobile phase: [water (0.225% formic acid)-acetonitrile]; B %: 15%-25%, 9 min) to afford N-[4-(3-chloro-2-fluoro-anilino)-7-[2-[(3R)-3-methoxy-1-methyl-pyrrolidin-3-yl]ethynyl]quinazolin-6-yl]prop-2-enamide (24 mg, 50 umol, 10.7% yield) as a yellow solid. m/z ES+ $[M+H]^+$ 480.2; $^1H$ NMR (400 MHz, DMSO-$d_6$) δ 10.36-9.90 (m, 2H), 8.64 (s, 1H), 8.55-8.42 (m, 1H), 8.26 (s, 2H), 7.91 (br s, 1H), 7.49 (br d, J=6.4 Hz, 2H), 7.33-7.26 (m, 1H), 6.56 (dd, J=10.2, 17.2 Hz, 1H), 6.33 (dd, J=1.6, 17.2 Hz, 1H), 5.85 (dd, J=1.6, 10.4 Hz, 1H), 3.34 (s, 3H), 2.94-2.83 (m, 2H), 2.68-2.57 (m, 2H), 2.34-2.27 (m, 4H), 2.21-2.13 (m, 1H).

Step 8. To a solution of N-(3-chloro-2-fluoro-phenyl)-7-[2-[(3S)-3-methoxypyrrolidin-3-yl]ethynyl]-6-nitro-quinazolin-4-amine (0.30 g, 679 umol) in trifluoroethanol (6.0 mL) was added HCHO (102 mg, 3.40 mmol) and $NaBH_4$ (51.4 mg, 1.36 mmol). The mixture was stirred at 60° C. for 4 h. On completion, the reaction was diluted with water (100 mL), extracted with ethyl acetate (30 mL×3), washed with brine (40 mL), dried over $Na_2SO_4$, filtered and concentrated under vacuum to afford N-(3-chloro-2-fluoro-phenyl)-7-[2-[(3 S)-3-methoxy-1-methyl-pyrrolidin-3-yl]ethynyl]-6-nitro-quinazolin-4-amine (0.30 g, crude) as a brown solid. m/z ES+ $[M+H]^+$ 456.0

Step 9. To a solution of N-(3-chloro-2-fluoro-phenyl)-7-[2-[(3S)-3-methoxy-1-methyl-pyrrolidin-3-yl]ethynyl]-6-nitro-quinazolin-4-amine (0.30 g, 658 umol) in MeOH (3.0 mL) and $H_2O$ (3.0 mL) was added $NH_4C_1$ (422 mg, 7.90 mmol) and Fe (331 mg, 5.90 mmol). The mixture was stirred at 80° C. for 1 h. On completion, the reaction was filtered through a pad of celite while it was still hot and the filtered cake was washed with MeOH (10 mL), the combined organic solvent was concentrated in vacuo to afford N4-(3-chloro-2-fluoro-phenyl)-7-[2-[(3S)-3-methoxy-1-methyl-pyrrolidin-3-yl]ethynyl]quinazoline-4,6-diamine (0.24 g, crude) as a brown solid. m/z ES+$[M+H]^+$ 426.1

Step 10. To a solution of N4-(3-chloro-2-fluoro-phenyl)-7-[2-[(3S)-3-methoxy-1-methyl-pyrrolidin-3-yl]ethynyl] quinazoline-4,6-diamine (0.20 g, 470 umol) in pyridine (4.0 mL) was added 1-ethyl-3-(3-dimethylaminopropyl)carbodiimide (360 mg, 1.88 mmol) and acrylic acid (33.8 mg, 470 umol). The mixture was stirred at 0° C. for 2 h. On completion, the reaction was concentrated in vacuo and the crude was purified by prep-HPLC (column: Waters Xbridge 150*25 mm*5 um; mobile phase: [water (10 mM $NH_4HCO_3$)-acetonitrile]; B %: 26%-56%, 8 min) and repurified by prep-HPLC (column: Phenomenex Gemini-NX C18 75*30 mm*3 um; mobile phase: [water (0.225% formic acid)-acetonitrile]; B %: 15%-25%, 9 min) to afford N-[4-(3-chloro-2-fluoro-anilino)-7-[2-[(3S)-3-methoxy-1-methyl-pyrrolidin-3-yl]ethynyl]quinazolin-6-yl]prop-2-enamide (26.0 mg, 54.2 umol, 11.5% yield) as a yellow solid. m/z ES+ $[M+H]^+$ 480.2; $^1H$ NMR (400 MHz, DMSO-$d_6$) δ 10.33-9.88 (m, 2H), 8.64 (s, 1H), 8.50 (br d, J=1.2 Hz, 1H), 8.23 (s, 1H), 7.91 (br s, 1H), 7.55-7.41 (m, 2H), 7.33-7.25 (m, 1H), 6.56 (dd, J=10.2, 16.8 Hz, 1H), 6.33 (dd, J=1.6, 17.2 Hz, 1H), 5.90-5.81 (m, 1H), 3.34 (s, 3H), 2.94-2.82 (m, 2H), 2.70-2.57 (m, 2H), 2.34-2.27 (m, 4H), 2.22-2.12 (m, 1H).

Example 33. Synthesis of Compound No. 37 ((E)-N-(4-((3-chloro-2-fluorophenyl)amino)-7-(((1R,5S)-3-methyl-3-azabicyclo[3.1.0]hexan-1-yl)ethynyl)quinazolin-6-yl)-4-morpholinobut-2-enamide)

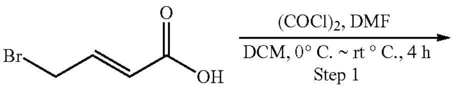

-continued

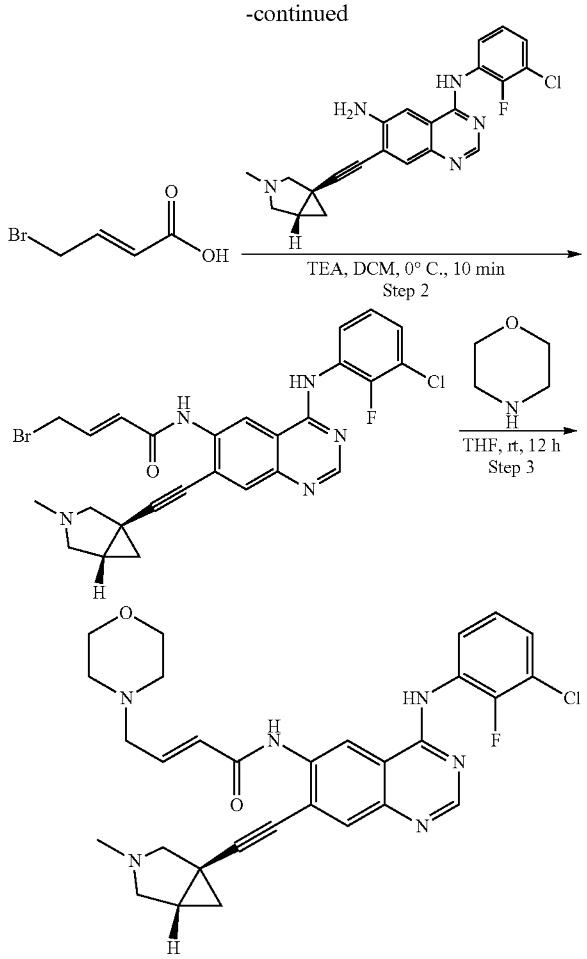

Step 1. To a solution of (E)-4-bromobut-2-enoic acid (5.00 g, 30.3 mmol) and dimethylformamide (22.2 mg, 303 umol) in dichloromethane (20 mL) was added $(COCl)_2$ (3.85 g, 30.3 mmol) dropwise at 0° C. under $N_2$. The mixture was stirred at 0-25° C. for 4 h. On completion, the reaction mixture was concentrated in vacuo to give (E)-4-bromobut-2-enoyl chloride (5.8 g, crude) as a yellow oil.

Step 2. To a solution of N4-(3-chloro-2-fluoro-phenyl)-7-[2-[(1S,5R)-3-methyl-3-azabicyclo[3.1.0]hexan-1-yl] ethynyl]quinazoline-4,6-diamine (4.00 g, 9.81 mmol) and triethylamine (2.98 g, 29.4 mmol) in dichloromethane (70 mL) was added a solution of (E)-4-bromobut-2-enoyl chloride (3.60 g, 19.6 mmol) in dichloromethane (15 mL) dropwise at 0° C. and the mixture was stirred at 0° C. for 10 min. On completion, the reaction mixture was concentrated under vacuum to give (E)-4-bromo-N-(4-((3-chloro-2-fluorophenyl)amino)-7-4(1R,5S)-3-methyl-3-azabicyclo[3.1.0] hexan-1-yl)ethynyl)quinazolin-6-yl)but-2-enamide (5.44 g, crude) as a yellow solid, which was used for next step directly. m/z ES+ $[M+H]^+$ 556.0

Step 3. A mixture of (E)-4-bromo-N-[4-(3-chloro-2-fluoro-anilino)-7-[2-[(1S,5R)-3-methyl-3-azabicyclo[3.1.0] hexan-1-yl]ethynyl]quinazolin-6-yl]but-2-enamide (5.44 g, 9.80 mmol), morpholine (1.71 g, 19.6 mmol), triethylamine (992 mg, 9.80 mmol) in dichloromethane (1.5 mL) was degassed and purged with $N_2$ for 3 times, and then the mixture was stirred at 25° C. for 12 hrs under $N_2$ atmosphere. On completion, the reaction mixture was concentrated in vacuo to give a residue. The residue was purified by reverse phase flash [acetonitrile/(0.1% formic acid in water), 0% to 90%] to give 2.8 g crude product. Then it was purified by Prep-HPLC [column: Waters Xbridge BEH C18 250*50 mm*10 um; mobile phase: [water (0.05% ammonium hydroxide v/v)-acetonitrile]; B %: 35%-55%, 22 min] to give 2.2 g crude product. Then the crude product was triturated with EA/petroleum ether=5/1 (200 mL) twice to give (E)-N-[4-(3-chloro-2-fluoro-anilino)-7-[2-[(1S,5R)-3-methyl-3-azabicyclo[3.1.0]hexan-1-yl]ethynyl]quinazolin-6-yl]-4-morpholino-but-2-enamide (1.84 g, 33% yield) as a yellow solid. m/z ES+ $[M+H]^+$ 561.3; $^1$H NMR (400 MHz, DMSO-$d_6$) δ 10.06 (s, 1H), 9.78 (s, 1H), 8.67 (s, 1H), 8.48 (s, 1H), 7.80 (s, 1H), 7.50 (s, 2H), 7.29 (t, J=7.6 Hz, 1H), 6.81 (td, J=5.6, 15.6 Hz, 1H), 6.45 (d, J=15.6 Hz, 1H), 3.65-3.60 (m, 4H), 3.17 (d, J=5.2 Hz, 2H), 3.11 (d, J=8.4 Hz, 1H), 2.93 (d, J=9.0 Hz, 1H), 2.46-2.38 (m, 6H), 2.26 (s, 3H), 1.98-1.90 (m, 1H), 1.38 (t, J=4.4 Hz, 1H), 1.03 (dd, J=4.0, 8.0 Hz, 1H).

Example 34. Synthesis of Compound No. 38 (N-(4-((3-chloro-2-fluorophenyl)amino)-7-(((1R,5S)-3-methyl-3-azabicyclo[3.1.0]hexan-1-yl)ethynyl)quinazolin-6-yl)but-2-ynamide)

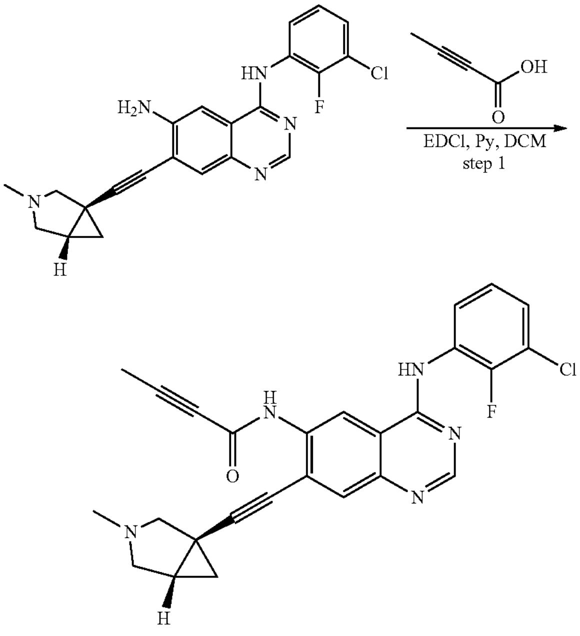

Step 1. To a solution of N4-(3-chloro-2-fluoro-phenyl)-7-[2-[(1R,5S)-3-methyl-3-azabicyclo[3.1.0]hexan-1-yl] ethynyl]quinazoline-4,6-diamine (100 mg, 245 umol), but-2-ynoic acid (41.2 mg, 490 umol) in pyridine (1.0 mL) and dichloromethane (1.0 mL) was added 1-ethyl-3-(3-dimethylaminopropyl)carbodiimide (188 mg, 980 umol) at 0° C. The mixture was stirred at 0-25° C. for 1 h. Upon completion, the mixture was concentrated in vacuo to give a residue. The residue was purified by prep-HPLC (column: Waters Xbridge C18 150*50 mm*10 um; mobile phase: [water (0.05% ammonium hydroxide v/v)-acetonitrile]; B %: 42%-72%, 11 min) to give N-[4-(3-chloro-2-fluoro-anilino)-7-[2-[(1S,5R)-3-methyl-3-azabicyclo[3.1.0]hexan-1-yl]ethynyl]-quinazolin-6-yl]but-2-ynamide (38.0 mg, 31% yield) as a yellow solid. m/z ES+ $[M+H]^+$ 474.2; $^1$H NMR (400 MHz, DMSO-$d_6$) δ=10.25 (s, 1H), 10.04 (s, 1H), 8.48 (s, 2H), 7.78 (s, 1H), 7.53-7.48 (m, 2H), 7.31-7.25 (m, 1H), 3.12 (d, J=8.8 Hz, 1H), 2.93 (d, J=9.2 Hz, 1H), 2.40 (dd, J=3.6, 9.2 Hz, 1H), 2.26 (s, 3H), 2.07 (s, 3H), 1.96-1.93 (m, 1H), 1.39 (t, J=4.4 Hz, 1H), 1.23 (s, 1H), 1.03 (dd, J=4.0, 8.0 Hz, 1H).

Example 35. Synthesis of Compound No. 39 ((E)-N-[4-(3-chloro-2-fluoro-anilino)-7-[2-[(3R)-1,3-dimethylpyrrolidin-3-yl]ethynyl]quinazolin-6-yl]-4-methyl-pent-2-enamide)

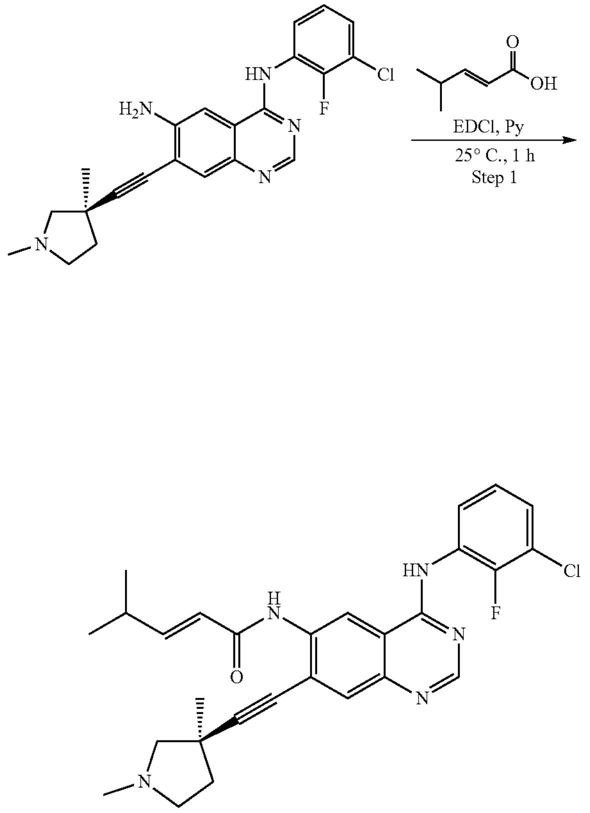

Step 1. A solution of N4-(3-chloro-2-fluoro-phenyl)-7-[2-[(3R)-1,3-dimethylpyrrolidin-3-yl]ethynyl]quinazoline-4,6-diamine (60.0 mg, 146 umol), (E)-4-methylpent-2-enoic acid (21.7 mg, 190 umol) and 1-ethyl-3-(3-dimethylamino-propyl)carbodiimide (112 mg, 586 umol) in pyridine (0.6 mL) was stirred at 25° C. for 1 h. On completion, the reaction mixture was evaporated. The residue was purified by prep-HPLC (column: Waters Xbridge 150*25 mm*5 um; mobile phase: [water (10 mM NH4HCO3)-acetonitrile]; B %: 56%-86%, 10 min) to afford (E)-N-[4-(3-chloro-2-fluoro-anilino)-7-[2-[(3R)-1,3-dimethylpyrrolidin-3-yl] ethynyl]quinazolin-6-yl]-4-methyl-pent-2-enamide (20.0 mg, 27% yield, 100% purity) as a yellow solid. m/z ES+ $[M+H]^+$ 506.3; $^1$H NMR (400 MHz, DMSO-$d_6$) δ=10.04 (br s, 1H), 9.56 (s, 1H), 8.67 (s, 1H), 8.47 (s, 1H), 7.78 (s, 1H), 7.50 (s, 2H), 7.31-7.23 (m, 1H), 6.87 (dd, J=6.8, 15.6 Hz, 1H), 6.20 (d, J=16.0 Hz, 1H), 2.78 (d, J=8.8 Hz, 1H), 2.64-2.56 (m, 2H), 2.55-2.52 (m, 2H), 2.27 (s, 3H), 2.26-2.21 (m, 1H), 1.88-1.81 (m, 1H), 1.43 (s, 3H), 1.07 (d, J=6.8 Hz, 6H).

Example 36. Synthesis of Compound No. 40 (N-(7-(((1R,5S)-3-methyl-3-azabicyclo[3.1.0]hexan-1-yl) ethynyl)-4-((4-phenoxyphenyl)amino)quinazolin-6-yl)acrylamide) and Compound No. 41 (N-(7-(((1S, 5R)-3-methyl-3-azabicyclo[3.1.0]hexan-1-yl)ethynyl)-4-((4-phenoxyphenyl)amino)quinazolin-6-yl) acrylamide)

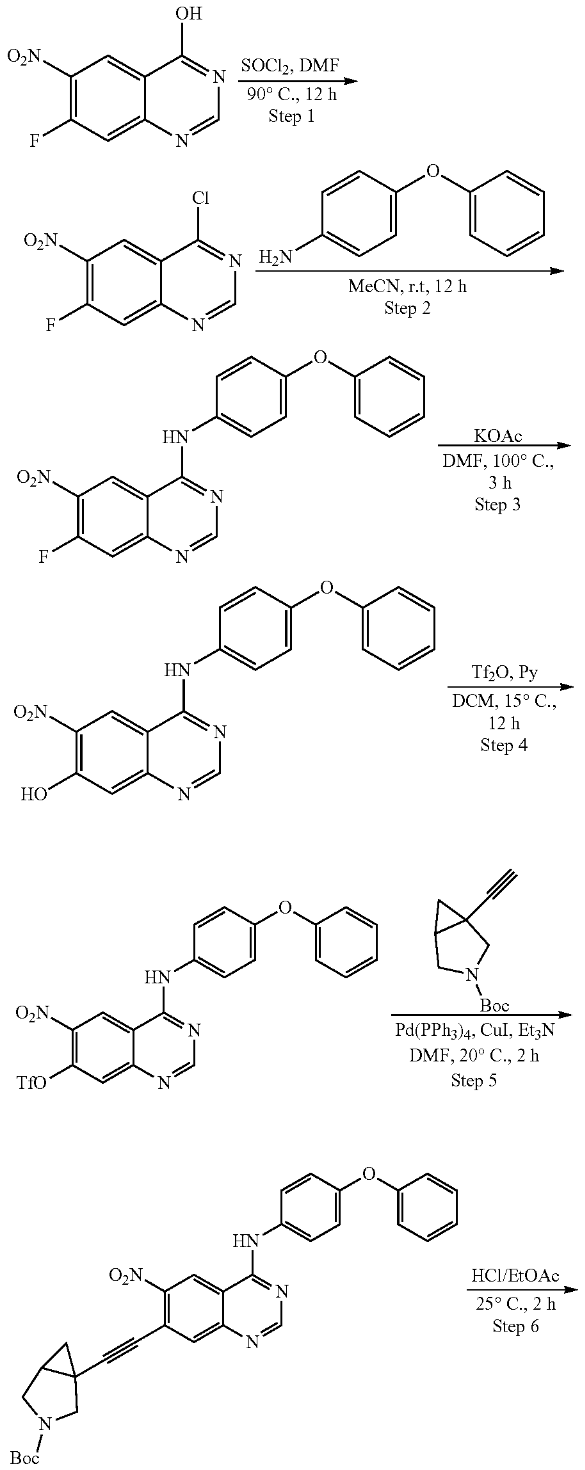

-continued
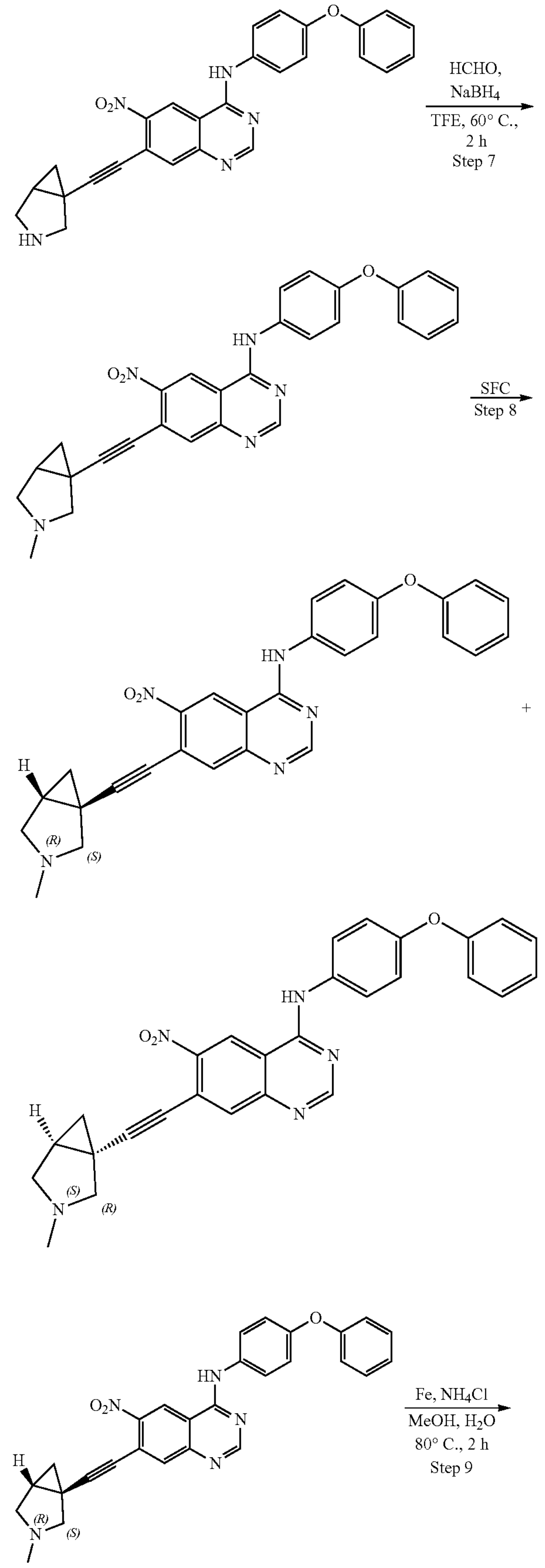
-continued
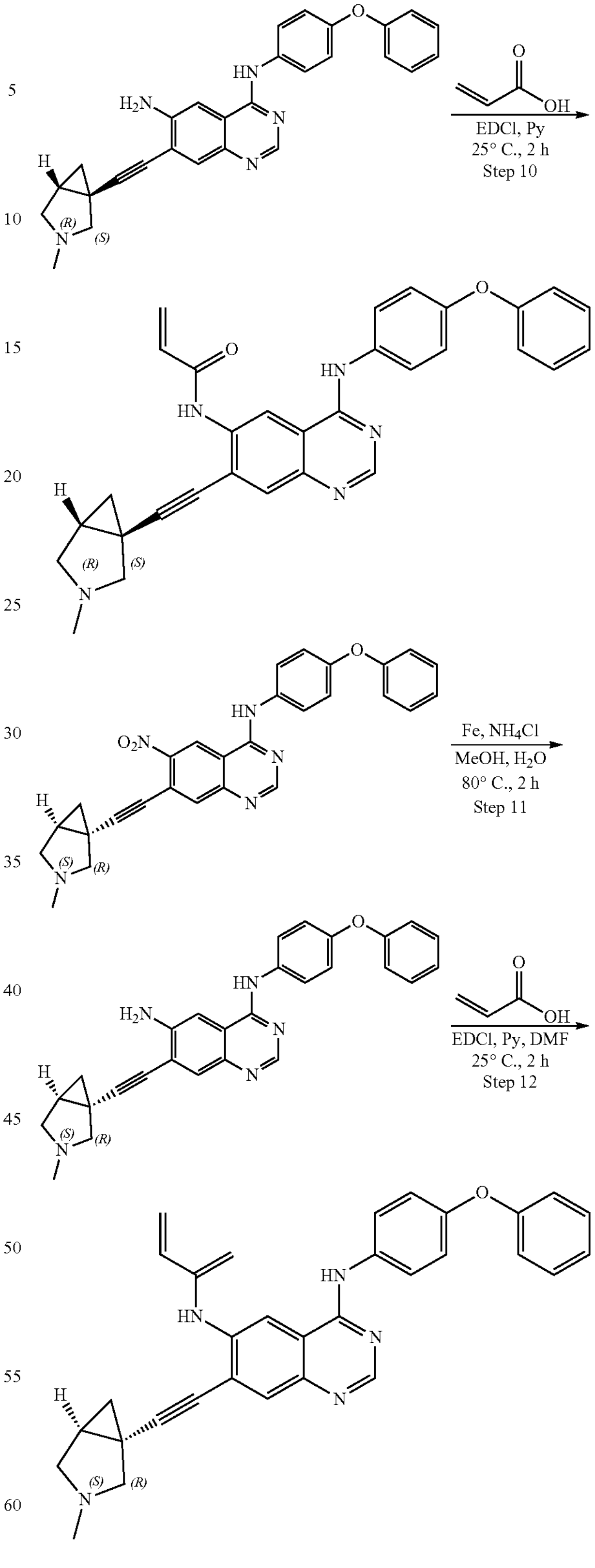
Step 1. To a solution of 7-fluoro-6-nitro-quinazolin-4-ol (5 g, 23.9 mmol) in $SOCl_2$ (50 mL) was added dimethylformamide (175 mg, 2.39 mmol). The mixture was stirred at 90° C. for 12 h. On completion, the reaction mixture was concentrated under reduced pressure to give 4-chloro-7-fluoro-6-nitroquinazoline (5.5 g, crude) as a yellow solid. m/z ES+ $[M+H]^+$ 228.0

Step 2. To a solution of 4-chloro-7-fluoro-6-nitro-quinazoline (5 g, 22.0 mmol) in $CH_3CN$ (60 mL) was added 4-phenoxyaniline (4.07 g, 22.0 mmol). The mixture was stirred at 20° C. for 12 h. On completion, the reaction mixture was concentrated under reduced pressure to give a residue. The crude product was triturated with ethyl acetate (500 mL) at 25° C. for 30 min to give 7-fluoro-6-nitro-N-(4-phenoxyphenyl)quinazolin-4-amine (9 g, crude) as a yellow solid. m/z ES+$[M+H]^+$ 377.2

Step 3. To a solution of 7-fluoro-6-nitro-N-(4-phenoxy-phenyl) quinazolin-4-amine (9 g, 23.9 mmol) in dimethyl-formamide (80 mL) was added KOAc (11.3 g, 115 mmol). The mixture was stirred at 100° C. for 3 h. On completion, the mixture was poured into water (150 mL). The resulting yellow precipitate was collected by filtration and dried in vacuo to give 6-nitro-4-((4-phenoxyphenyl) amino) quinazolin-7-ol (7 g, crude) as a yellow solid. m/z ES+ $[M+H]^+$ 375.2; $^1H$ NMR (400 MHz, DMSO-$d_6$) δ=12.11-11.77 (m, 1H), 10.14 (s, 1H), 9.24 (s, 1H), 8.52 (s, 1H), 7.80 (d, J=8.8 Hz, 2H), 7.46-7.36 (m, 2H), 7.18-6.98 (m, 6H).

Step 4. To a suspension of 6-nitro-4-(4-phenoxyanilino) quinazolin-7-ol (1.5 g, 4.01 mmol) in dichloromethane (20 mL) was added pyridine (1.58 g, 20.0 mmol) and $Tf_2O$ (2.26 g, 8.01 mmol). The mixture was stirred at 15° C. for 12 h. On completion, the reaction mixture was concentrated under reduced pressure to give a residue. The residue was purified by column chromatography ($SiO_2$, Petroleum ether/Ethyl acetate=5/1 to 1/1) to give 6-nitro-4-((4-phenoxyphenyl) amino) quinazolin-7-yl trifluoromethanesulfonate (1.1 g, 52.6% yield) as a yellow solid. m/z ES+ $[M+H]^+$ 507.2

Step 5. To a solution of [6-nitro-4-(4-phenoxyanilino) quinazolin-7-yl]trifluoromethanesulfonate (1 g, 1.97 mmol) and tert-butyl 1-ethynyl-3-azabicyclo[3.1.0]hexane-3-carboxylate (409 mg, 1.97 mmol) in dimethylformamide (12 mL) and triethylamine (600 mg, 5.92 mmol) was added $Pd(PPh_3)_4$ (228 mg, 197 umol) and CuI (75.2 mg, 395 umol) in one portion under nitrogen. The mixture was stirred at 20° C. for 2 h. On completion, the reaction mixture was diluted with $H_2O$ (100 mL) and extracted with ethyl acetate (50 mL×3). The combined organic layers were washed with brine (50 mL×2), dried over $Na_2SO_4$, filtered and concentrated under reduced pressure to give a residue. The residue was purified by column chromatography ($SiO_2$, Petroleum ether/Ethyl acetate=5/1 to 1/1) to give tert-butyl 1-((6-nitro-4-((4-phenoxyphenyl) amino) quinazolin-7-yl) ethynyl)-3-azabicyclo[3.1.0]hexane-3-carboxylate (1 g, 79.1% yield) as a yellow solid. m/z ES+ $[M+H]^+$ 564.4

Step 6. To a solution of tert-butyl 1-[2-[6-nitro-4-(4-phenoxyanilino) quinazolin-7-yl]ethynyl]-3-azabicyclo [3.1.0]hexane-3-carboxylate (1 g, 1.58 mmol) in ethyl acetate (10 mL) was added HCl/ethyl acetate (4 mL). The mixture was stirred at 25° C. for 2 h. On completion, the reaction mixture was concentrated under reduced pressure to give 7-(3-azabicyclo[3.1.0]hexan-1-ylethynyl)-6-nitro-N-(4-phenoxyphenyl) quinazolin-4-amine (1 g, crude, HCl) as a yellow solid. m/z ES+ $[M+H]^+$ 464.2

Step 7. A mixture of 7-[2-(3-azabicyclo[3.1.0]hexan-1-yl) ethynyl]-6-nitro-N-(4-phenoxyphenyl) quinazolin-4-amine (1.2 g, 2.40 mmol, HCl), HCHO (360 mg, 12.0 mmol) in trifluoroethanol (20 mL) was added $NaBH_4$ (185 mg, 4.90 mmol) at 25° C. The mixture was stirred at 60° C. for 2 h. On completion, the mixture was quenched by methanol (5.00 mL) and concentrated to dryness to give a residue. The residue was diluted with ethyl acetate (50.0 mL) and washed with water (50.0 mL). The organic layer was dried over anhydrous sodium sulfate, filtered and concentrated in vacuum. The residue was purified by prep-HPLC (column: Phenomenex luna C18 150*40 mm*15 um; mobile phase: [water (0.225% formic acid)-acetonitrile]; B %: 20%-50%, 11 min) to give 7-((3-methyl-3-azabicyclo[3.1.0]hexan-1-yl)ethynyl)-6-nitro-N-(4-phenoxyphenyl)quinazolin-4-amine (700 mg, 59.9% yield) as a white solid. m/z ES+ $[M+H]^+$ 478.3

Step 8. 7-[2-(3-methyl-3-azabicyclo[3.1.0]hexan-1-yl) ethynyl]-6-nitro-N-(4-phenoxyphenyl) quinazolin-4-amine (620 mg, 1.30 mmol) was purified by SFC (column: DAICEL CHIRALPAK AS (250 mm*30 mm, 10 um); mobile phase: [0.1% ammonium hydroxide methanol]; B %: 50%-50%, 4.8 min; 580 minmin) to give 7-(((1S,5R)-3-methyl-3-azabicyclo[3.1.0]hexan-1-yl) ethynyl)-6-nitro-N-(4-phenoxyphenyl) quinazolin-4-amine (250 mg, 40.3% yield, >99% ee, SFC retention time: 2.186 min) as a yellow solid and 7-(((1R,5S)-3-methyl-3-azabicyclo[3.1.0]hexan-1-yl) ethynyl)-6-nitro-N-(4-phenoxyphenyl) quinazolin-4-amine (260 mg, 41.9% yield, 98.4% ee, SFC retention time: 2.344 min) as a yellow solid.

Step 9. To a solution of 7-[2-[(1S,5R)-3-methyl-3-azabicyclo[3.1.0]hexan-1-yl]ethynyl]-6-nitro-N-(4-phenoxyphenyl)quinazolin-4-amine (220 mg, 460.72 umol) and $NH_4C_1$ (246 mg, 4.61 mmol) in MeOH (2.2 mL) and $H_2O$ (2.2 mL) was added Fe powder (129 mg, 2.30 mmol) and the mixture was stirred at 80° C. for 2 h. On completion, the reaction mixture was filtered and evaporated to afford 7-[2-[(1S,5R)-3-methyl-3-azabicyclo[3.1.0]hexan-1-yl]ethynyl]-N4-(4-phenoxyphenyl) quinazoline-4,6-diamine (230 mg, crude) as a yellow solid. m/z ES+ $[M+H]^+$ 448.3

Step 10. A solution of 7-[2-[(1S,5R)-3-methyl-3-azabicyclo[3.1.0]hexan-1-yl]ethynyl]-N4-(4-phenoxyphenyl) quinazoline-4,6-diamine (230 mg, 514 umol), acrylic acid (37.0 mg, 514 umol) and 1-ethyl-3-(3-dimethylaminopropyl)carbodiimide (394 mg, 2.06 mmol) in pyridine (2.5 mL) was stirred at 15° C. for 1 h. On completion, the reaction mixture was diluted with water (6 mL) and extracted with ethyl acetate (8 mL×3). The combined organic layers were washed with brine (5 mL×3), dried over $Na_2SO_4$ and evaporated. The residue was purified by prep-HPLC (column: Waters Xbridge 150*25 mm*5 um; mobile phase: [water (0.05% ammonium hydroxide v/v)-acetonitrile]; B %: 38%-71%, 10 min) to afford N-[7-[2-[(1S,5R)-3-methyl-3-azabicyclo[3.1.0]hexan-1-yl]ethynyl]-4-(4-phenoxyanilino)quinazolin-6-yl]prop-2-enamide (40.0 mg, 16% yield) as a yellow solid. m/z ES+ $[M+H]^+$ 502.3; $^1H$ NMR (400 MHz, DMSO-$d_6$) δ=9.89 (s, 2H), 8.69 (s, 1H), 8.52 (s, 1H), 7.83-7.74 (m, 3H), 7.42-7.37 (m, 2H), 7.13 (t, J=7.6 Hz, 1H), 7.07-7.01 (m, 4H), 6.59 (dd, J=10.4, 17.6 Hz, 1H), 6.33 (dd, J=2.0, 17.2 Hz, 1H), 5.89-5.81 (m, 1H), 3.09 (d, J=8.4 Hz, 1H), 2.92 (d, J=9.2 Hz, 1H), 2.43 (d, J=8.4 Hz, 1H), 2.39 (dd, J=3.6, 9.2 Hz, 1H), 2.25 (s, 3H), 1.94-1.89 (m, 1H), 1.36 (t, J=4.4 Hz, 1H), 1.00 (dd, J=4.0, 8.0 Hz, 1H).

Step 11. To a solution of 7-[2-[(1R,5S)-3-methyl-3-azabicyclo[3.1.0]hexan-1-yl]ethynyl]-6-nitro-N-(4-phenoxyphenyl)quinazolin-4-amine (260 mg, 544 umol) and $NH_4C_1$ (291 mg, 5.44 mmol) in MeOH (2.2 mL) and $H_2O$ (2.2 mL) was added Fe powder (152 mg, 2.72 mmol) and the mixture was stirred at 80° C. for 2 h. On completion, the reaction mixture was filtered and evaporated to afford 7-[2-[(1R,5S)-3-methyl-3-azabicyclo[3.1.0]hexan-1-yl]ethynyl]-N4-(4-phenoxyphenyl) quinazoline-4,6-diamine (260 mg, crude) as a yellow solid.

Step 12. A solution of 7-[2-[(1R,5S)-3-methyl-3-azabicyclo[3.1.0]hexan-1-yl]ethynyl]-N4-(4-phenoxyphenyl)quinazoline-4,6-diamine (260 mg, 581 umol), acrylic acid (41.9 mg, 581 umol) and 1-ethyl-3-(3-dimethylaminopropyl)carbodiimide (445 mg, 2.32 mmol) in pyridine (2.5 mL) was stirred at 15° C. for 1 h. On completion, the reaction mixture was evaporated. The residue was purified by prep-HPLC (column: Waters Xbridge 150*25 mm*5 um; mobile phase: [water (0.05% ammonium hydroxide v/v)-acetonitrile]; B %: 42%-72%, 10 min) to afford N-[7-[2-[(1R,5S)-3-methyl-3-azabicyclo[3.1.0]hexan-1-yl]ethynyl]-4-(4-phenoxyanilino) quinazolin-6-yl]prop-2-enamide (70.0 mg, 24% yield, 100% purity) as a yellow solid. m/z ES+ $[M+H]^+$ 502.3; $^1$H NMR (400 MHz, DMSO-$d_6$) δ=9.89 (d, J=4.0 Hz, 2H), 8.69 (s, 1H), 8.52 (s, 1H), 7.86-7.73 (m, 3H), 7.44-7.35 (m, 2H), 7.13 (t, J=7.6 Hz, 1H), 7.08-7.00 (m, 4H), 6.59 (dd, J=10.4, 17.2 Hz, 1H), 6.33 (dd, J=2.0, 17.2 Hz, 1H), 5.85 (dd, J=2.0, 10.4 Hz, 1H), 3.09 (d, J=8.8 Hz, 1H), 2.92 (d, J=9.2 Hz, 1H), 2.43 (d, J=8.4 Hz, 1H), 2.39 (dd, J=3.6, 9.2 Hz, 1H), 2.25 (s, 3H), 1.94-1.89 (m, 1H), 1.36 (t, J=4.4 Hz, 1H), 1.00 (dd, J=4.0, 8.0 Hz, 1H).

Example 37. Synthesis of Compound No. 42 (N-(4-((3-chloro-2-fluorophenyl)amino)-7-(((1S,5R)-3-isopropyl-3-azabicyclo[3.1.0]hexan-1-yl)ethynyl)quinazolin-6-yl)acrylamide)

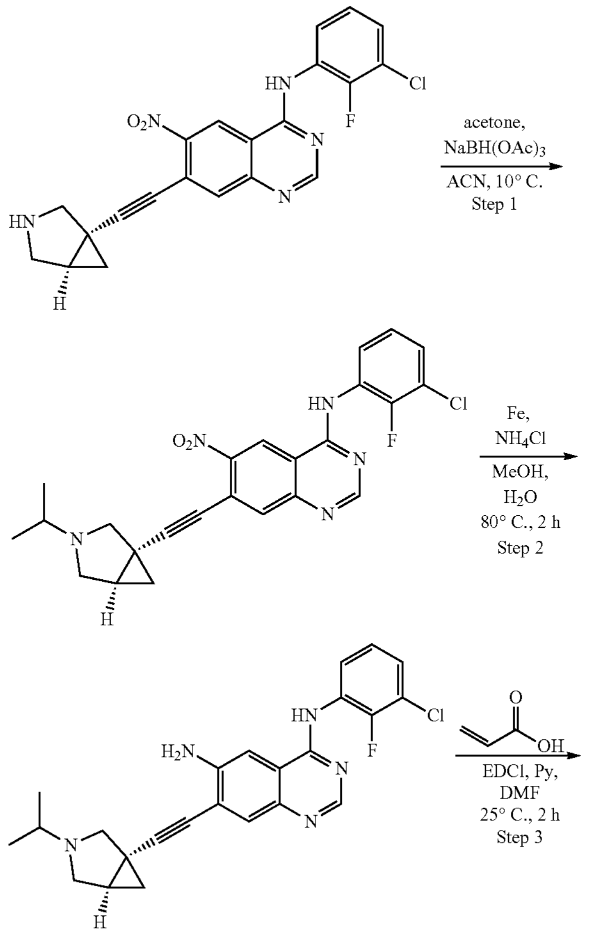

-continued

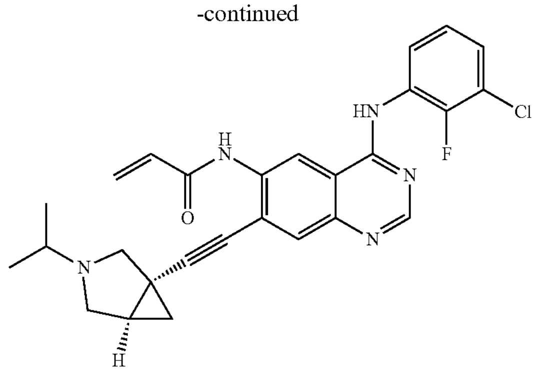

Step 1. To a solution of 7-[2-[(1S,5R)-3-azabicyclo[3.1.0]hexan-1-yl]ethynyl]-N-(3-chloro-2-fluoro-phenyl)-6-nitro-quinazolin-4-amine (500 mg, 1.18 mmol) in MeCN (5 mL) and acetone (5 mL) was added $NaBH(OAc)_3$ (1.25 g, 5.90 mmol) and HOAc (212.53 mg, 3.54 mmol) at 0° C. The mixture was stirred 20° C. for 16 h. On completion, the reaction was diluted with water (60 mL), and extracted with ethyl acetate (20 mL×3). The combined organic layers were washed with brine (30 mL), dried over $Na_2SO_4$, filtered and concentrated under vacuum. The crude product was purified by column chromatography (petroleum ether/ethyl acetate from 5/1 to 1/1) to give N-(3-chloro-2-fluoro-phenyl)-7-[2-[(1S,5R)-3-isopropyl-3-azabicyclo[3.1.0]hexan-1-yl]ethynyl]-6-nitro-quinazolin-4-amine (0.42 g, 68.77% yield) as a yellow solid. m/z ES+ $[M+H]^+$ 466.2

Step 2. To a mixture of N-(3-chloro-2-fluoro-phenyl)-7-[2-[(1S,5R)-3-isopropyl-3-azabicyclo[3.1.0]hexan-1-yl]ethynyl]-6-nitroquinazolin-4-amine (0.5 g, 1.07 mmol) in MeOH (6 mL) and $H_2O$ (2 mL) was added Fe powder (299.66 mg, 5.37 mmol) and $NH_4C_1$ (574.06 mg, 10.73 mmol) in one portion at 20° C. The mixture was then stirred at 80° C. for 2 h. On completion, the reaction mixture was filtered and concentrated under reduced pressure to give a residue. The residue was diluted with water (50 mL) and then extracted with ethyl acetate (50 mL×3). The combined organic layers were washed with brine (50 mL), dried over $Na_2SO_4$, filtered and concentrated under reduced pressure to give compound N4-(3-chloro-2-fluoro-phenyl)-7-[2-[(1S,5R)-3-isopropyl-3-azabicyclo[3.1.0]hexan-1-yl]ethynyl]quinazoline-4,6-diamine (0.4 g, 82.94% yield) as a yellow solid. m/z ES+ $[M+H]^+$ 436.2

Step 3. To a mixture of N4-(3-chloro-2-fluoro-phenyl)-7-[2-[(1S,5R)-3-isopropyl-3-azabicyclo[3.1.0]hexan-1-yl]ethynyl]quinazoline-4,6-diamine (300 mg, 688.19 umol) and acrylic acid (99.19 mg, 1.38 mmol) in dimethylformamide (3 mL) was added 1-ethyl-3-(3-dimethylaminopropyl)carbodiimide (395.78 mg, 2.06 mmol) and pyridine (272.18 mg, 3.44 mmol) in one portion at 20° C. The mixture was stirred at 20° C. for 2 h. On completion, the reaction mixture was quenched by water (10 mL) at 20° C., and then extracted with dichloromethane (10 mL×3). The combined organic layers were washed with water (10 mL×2), dried over $Na_2SO_4$, filtered and concentrated under reduced pressure to give a residue. The residue was purified by prep-HPLC (column: Shim-pack C18 150*25*10 um; mobile phase: [water (0.225% formic acid)-acetonitrile]; B %: 10%-40%, 10 min) and further purified by prep-HPLC (column: Waters Xbridge 150*25 mm*5 um; mobile phase: [water (10 mM NH4HCO3)-acetonitrile]; B %: 56%-86%, 5 min) to give compound N-[4-(3-chloro-2-fluoro-anilino)-7-[2-[(1S,5R)-3-isopropyl-3-azabicyclo[3.1.0]hexan-1-yl]ethynyl]quinazolin-6-yl]prop-2-enamide (21 mg, 6.23% yield) as a yellow solid. m/z ES+ $[M+H]^+$ 490.3; 41 NMR (400 MHz, DMSO-$d_6$) δ 10.07 (s, 1H), 9.87 (s, 1H), 8.68 (s, 1H), 8.48 (s, 1H), 7.81 (s, 1H), 7.50-7.48 (m, 2H), 7.30-7.27 (m, 1H), 6.64-6.57 (m, 1H), 6.36 (dd, J=1.2, 15.6 Hz, 1H), 5.84 (d, J=11.6 Hz, 1H), 3.16 (d, J=8.4 Hz, 1H), 2.98 (d, J=8.4 Hz 1H), 2.54-2.45 (m, 2H), 1.96-1.90 (m, 1H), 1.32 (t, J=4.4 Hz, 1H), 1.33-0.97 (m, 8H).

Example 38. Synthesis of Compound No. 43 (Methyl (4-((3-chloro-2-fluorophenyl)amino)-7-((1, 3-dimethylpyrrolidin-3-yl)ethynyl)quinazolin-6-yl) carbamate)

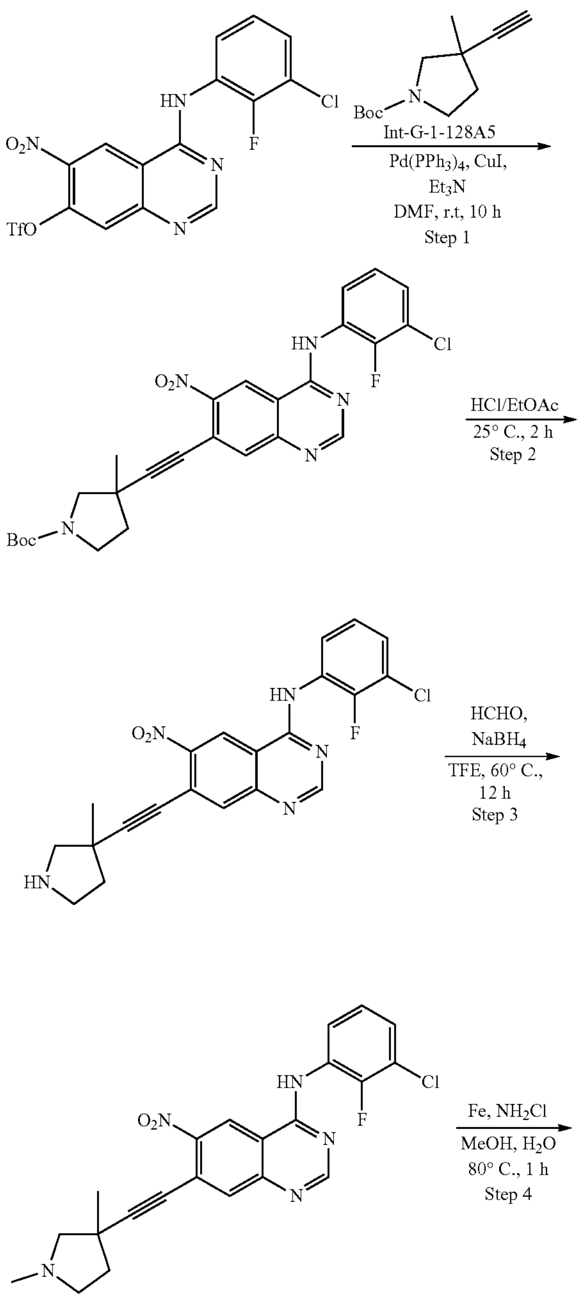

-continued

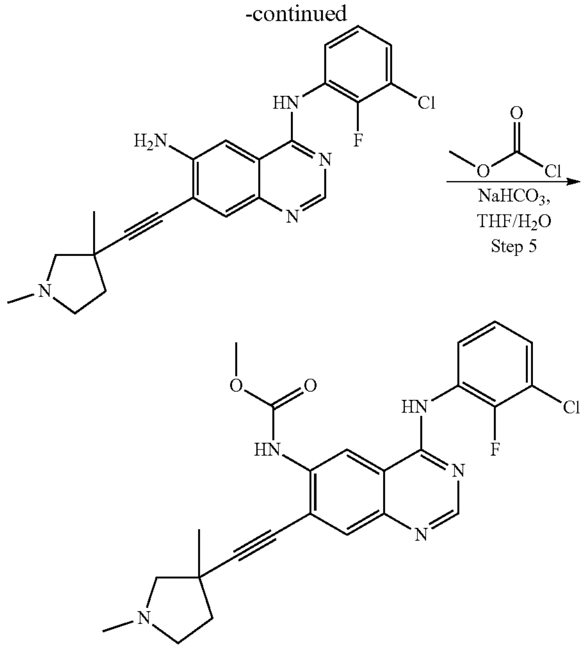

Step 1. A mixture of [4-(3-chloro-2-fluoro-anilino)-6-nitro-quinazolin-7-yl]trifluoromethanesulfonate (550 mg, 1.18 mmol), tert-butyl 3-ethynyl-3-methyl-pyrrolidine-1-carboxylate (271.27 mg, 1.30 mmol), $Pd(PPh_3)_4$ (136.17 mg, 117.84 umol), CuI (22.44 mg, 117.84 umol) in dimethylformamide (6 mL) and triethylamine (6 mL) was degassed and purged with $N_2$ for 3 times, and then the mixture was stirred at 50° C. for 1 h under $N_2$ atmosphere. On completion, the reaction mixture was diluted with $H_2O$ (70 mL) and extracted with ethyl acetate (50 mL×3). The combined organic layers were washed with brine (30 mL×3), dried over anhydrous $Na_2SO_4$, filtered and concentrated under reduced pressure to give a residue. The residue was purified by column chromatography ($SiO_2$, Petroleum ether/Ethyl acetate=3/1 to 1/1) to give tert-butyl 3-((4-((3-chloro-2-fluorophenyl)amino)-6-nitroquinazolin-7-yl)ethynyl)-3-methylpyrrolidine-1-carboxylate (300 mg, 39% yield) as an orange solid. m/z ES+ $[M+H]^+$ 526.3

Step 2. A solution of tert-butyl 3-((4-((3-chloro-2-fluorophenyl)amino)-6-nitroquinazolin-7-yl)ethynyl)-3-methylpyrrolidine-1-carboxylate (470 mg, 893.61 umol) in HCl/ethyl acetate (4 M, 5 mL) was stirred at 25° C. for 1 h. On completion, the reaction mixture was concentrated under reduced pressure to give N-(3-chloro-2-fluorophenyl)-7-((3-methylpyrrolidin-3-yl)ethynyl)-6-nitroquinazolin-4-amine (410 mg, crude, HCl) as a yellow solid. m/z ES+ $[M+H]^+$ 426.2

Step 3. To a solution of N-(3-chloro-2-fluorophenyl)-7-((3-methylpyrrolidin-3-yl)ethynyl)-6-nitroquinazolin-4-amine (410 mg, 962.80 umol, HCl) in trifluoroethanol (5 mL) was added triethylamine to adjust the mixture to pH=8. Then $(HCHO)_n$ (144.54 mg, 4.81 mmol) was added. The mixture was stirred at 60° C. for 30 min. Then $NaBH_4$ (72.85 mg, 1.93 mmol) was added and the mixture was stirred at 60° C. for 1 h. On completion, the reaction mixture was quenched by MeOH (12 ml), and concentrated under reduced pressure to give a residue. The crude product was purified by reverse-phase flash column (0.1% $NH_3 \cdot H_2O$) to give N-(3-chloro-2-fluorophenyl)-7-((1,3-dimethylpyrrolidin-3-yl)ethynyl)-6-nitroquinazolin-4-amine (210 mg, 44.6% yield) as a yellow solid. m/z ES+ $[M+H]^+$ 440.1

Step 4. To a solution of N-(3-chloro-2-fluoro-phenyl)-7-[2-(1,3-dimethylpyrrolidin-3-yl)ethynyl]-6-nitro-quinazolin-4-amine (180 mg, 409 umol) and $NH_4C_1$ (219 mg, 4.09 mmol) in MeOH (2 mL) and $H_2O$ (2 mL) was added Fe powder (114 mg, 2.05 mmol) and the mixture was stirred at 80° C. for 2 h. On completion, the reaction mixture was filtered and evaporated. The crude product was purified by reversed-phase HPLC (acetonitrile/0.1% $NH_3 \cdot H_2O$=80%) to afford N4-(3-chloro-2-fluoro-phenyl)-7-[2-(1,3-dimethylpyrrolidin-3-yl)ethynyl]quinazoline-4,6-diamine (90.0 mg, 54% yield) as a yellow solid. m/z ES+ $[M+H]^+$ 410.1

Step 5. To a solution of N4-(3-chloro-2-fluoro-phenyl)-7-[2-(1,3-dimethylpyrrolidin-3-yl)ethynyl]quinazoline-4,6-diamine (90 mg, 138 umol, 63% purity) in pyridine (1 mL) was added methyl carbonochloridate (26.1 mg, 277 umol) at 0° C. and the mixture was stirred at 15° C. for 1 h. On completion, the mixture was poured into water (0.5 mL) and filtered. The filter cake was washed with water (2 mLx3) and dried under vacuum to give a residue. The residue was purified by prep-HPLC (column: Waters Xbridge 150*25 mm*5 um; mobile phase: [water (10 mM NH4HCO3)-acetonitrile]; B %: 45%-75%, 10 min) to afford methyl N-[4-(3-chloro-2-fluoro-anilino)-7-[2-(1,3-dimethylpyrrolidin-3-yl)ethynyl]quinazol in-6-yl]carbamate (25.0 mg, 36% yield, 94% purity) as an off-white solid. m/z ES+ $[M+H]^+$ 468.3; $^1H$ NMR (400 MHz, DMSO-$d_6$) δ=10.03 (s, 1H), 9.02 (s, 1H), 8.57-8.41 (m, 2H), 7.76 (s, 1H), 7.49 (s, 2H), 7.27 (t, J=7.2 Hz, 1H), 3.72 (s, 3H), 2.78 (d, J=9.2 Hz, 1H), 2.64-2.60 (m, 2H), 2.53 (d, J=3.2 Hz, 1H), 2.29 (s, 3H), 2.25-2.19 (m, 1H), 1.90-1.80 (m, 1H), 1.43 (s, 3H).

Example 39. Synthesis of Compound No. 44 ((E)-N-(4-((3-chloro-2-fluorophenyl)amino)-7-((3-methyltetrahydrofuran-3-yl)ethynyl)quinazolin-6-yl)-4-(dimethylamino)but-2-enamide)

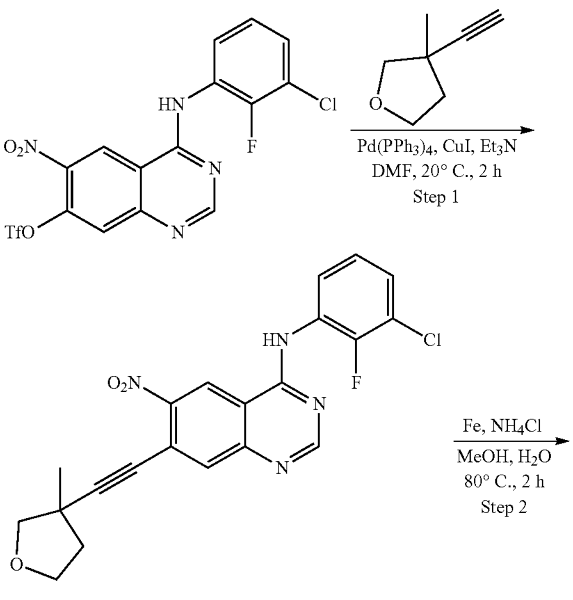

-continued

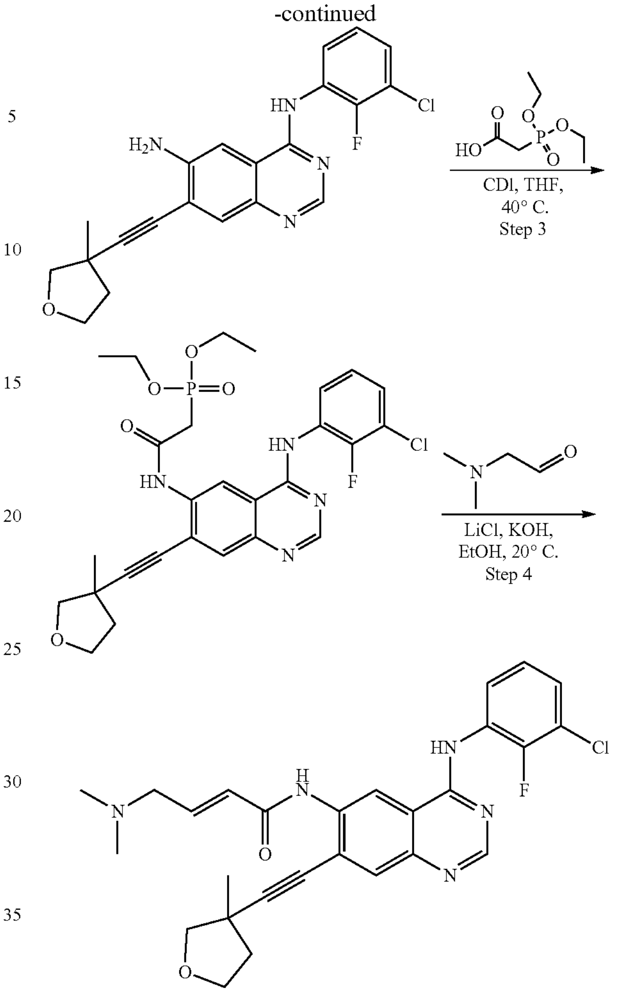

Step 1. To a solution of 4-((3-chloro-2-fluorophenyl)amino)-6-nitroquinazolin-7-yl trifluoromethanesulfonate (600 mg, 1.29 mmol), 3-ethynyl-3-methyltetrahydrofuran (170 mg, 1.54 mmol) in dimethyformamide (9.00 mL) and triethylamine (9.00 mL) was added CuI (48.9 mg, 257 umol) and tetrakis(triphenylphosphine)palladium(0) (149 mg, 129 umol) in one portion under nitrogen. The mixture was stirred at 20° C. for 2 h. The mixture was diluted with water (60.0 mL) and extracted with ethyl acetate (3×40.0 mL). The combined organic layer was washed with brine (20.0 mL), dried over sodium sulfate, filtered and concentrated in vacuum. The residue was purified by column chromatography (petroleum ether/ethyl acetate=2/1) to give N-(3-chloro-2-fluorophenyl)-7-((3-methyltetrahydrofuran-3-yl)ethynyl)-6-nitroquinazolin-4-amine (320 mg, 58% yield) as a yellow solid. $^1H$ NMR (400 MHz, DMSO-$d_6$) δ=10.62 (s, 1H), 9.40 (s, 1H), 7.99 (s, 1H), 7.57-7.52 (m, 3H), 7.35-7.25 (m, 1H), 3.94-3.86 (m, 3H), 3.62 (d, J=8.1 Hz, 1H), 2.34-2.24 (m, 1H), 2.05-1.95 (m, 1H), 1.44 (s, 3H).

Step 2. To a solution of N-(3-chloro-2-fluorophenyl)-7-((3-methyltetrahydrofuran-3-yl)ethynyl)-6-nitroquinazolin-4-amine (320 mg, 750 umol), ammonium chloride (281 mg, 5.25 mmol) in methanol (8.00 mL) and water (2.00 mL) was added iron powder (209 mg, 3.75 mmol) in portions. The mixture was stirred at 80° C. for 2 h. The mixture was filtered. The filtrate was concentrated in vacuum. The residue was diluted with water (50.0 mL) and extracted with ethyl acetate (3×40.0 mL). The combined organic layer was washed with brine (30.0 mL), dried over sodium sulfate, filtered and concentrated in vacuum. The residue was purified by reverse-phase chromatography (0.1% formic acid), then purified by column chromatography (petroleum ether/ethyl acetate=10/1 to 1/1) to give $N^4$-(3-chloro-2-fluorophenyl)-7-((3-methyltetrahydrofuran-3-yl)ethynyl)quinazoline-4,6-diamine (150 mg, 50% yield) as a yellow solid.

Step 3. A mixture of 1,1'-carbonyldiimidazole (24.5 mg, 151 umol) and 2-diethoxyphosphorylacetic acid (29.7 mg, 151 umol) in tetrahydrofuran (1 mL) were stirred at 40° C. for 30 min. Then a solution of N4-(3-chloro-2-fluoro-phenyl)-7-[2-(3-methyltetrahydrofuran-3-yl) ethynyl]quinazoline-4,6-diamine (50 mg, 126 umol) in tetrahydrofuran (0.5 mL) was added and the mixture was stirred at 40° C. for 12 h. On completion, the reaction mixture was diluted with $H_2O$ (20 mL) and extracted with ethyl acetate (20 mL×3). The combined organic layers were dried over $Na_2SO_4$, filtered and concentrated under reduced pressure to give diethyl (2-((4-((3-chloro-2-fluorophenyl) amino)-7-((3-methyltetrahydrofuran-3-yl) ethynyl) quinazolin-6-yl) amino)-2-oxoethyl) phosphonate (60 mg, crude) as a yellow oil. m/z ES+ $[M+H]^+$ 575.4

Step 4. To a solution of diethyl (2-((4-((3-chloro-2-fluorophenyl)amino)-7-((3-methyltetrahydrofuran-3-yl)ethynyl) quinazolin-6-yl)amino)-2-oxoethyl)phosphonate (60 mg, 104 umol) in ethanol (1 mL) was added LiCl (8.85 mg, 209 umol) and aqueous KOH solution (26.0 mg, 209 umol, 45 wt %) at 20° C. After 5 min, a solution of 2-(dimethylamino) acetaldehyde sulfate (35.1 mg, 209 umol) in $H_2O$ (0.5 mL) was added, and the mixture was stirred at 20° C. for 2 h. On completion, the reaction mixture was diluted with $H_2O$ (10 mL), and then adjusted to pH=7 by aqueous HCl solution (1 M). The mixture was extracted with ethyl acetate (10 mL×3). The combined organic layers were dried over $Na_2SO_4$, filtered and concentrated under reduced pressure to give a residue. The residue was purified by prep-HPLC (column: Phenomenex Synergi C18 150*25*10 um; mobile phase: [water (0.225% formic acid)-acetonitrile]; B %: 13%-43%, 8.5 min) to give N-(7-cyano-4-((4-phenoxyphenyl) amino) quinazolin-6-yl) acrylamide (15 mg, 25.4% yield, 100% purity, formic acid) as a yellow solid. m/z ES+ $[M+H]^+$ 508.3; $^1H$ NMR (400 MHz, DMSO-$d_6$) δ=10.07 (br s, 1H), 9.72 (s, 1H), 8.67 (s, 1H), 8.55-8.41 (m, 1H), 7.81 (s, 1H), 7.49 (s, 2H), 7.31-7.25 (m, 1H), 6.82 (td, J=6.0, 15.2 Hz, 1H), 6.40 (d, J=16.0 Hz, 1H), 3.92-3.87 (m, 3H), 3.59 (d, J=8.0 Hz, 1H), 3.09 (d, J=5.2 Hz, 2H), 2.32-2.25 (m, 1H), 2.18 (s, 6H), 1.97 (td, J=7.2, 12.0 Hz, 1H), 1.42 (s, 3H).

Example 40. Synthesis of Compound No. 45 (N-{4-[(3-chloro-2-fluorophenyl)amino]-7-{2-[(3S)-3-fluoro-1-methylpyrrolidin-3-yl] ethynyl}quinazolin-6-yl}prop-2-enamide) and Compound No. 46 (N-{4-[(3-chloro-2-fluorophenyl) amino]-7-{2-[(3R)-3-fluoro-1-methyl-pyrrolidin-3-yl]ethynyl}quinazolin-6-yl}prop-2-enamide)

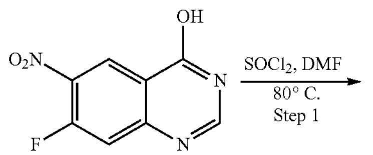

-continued

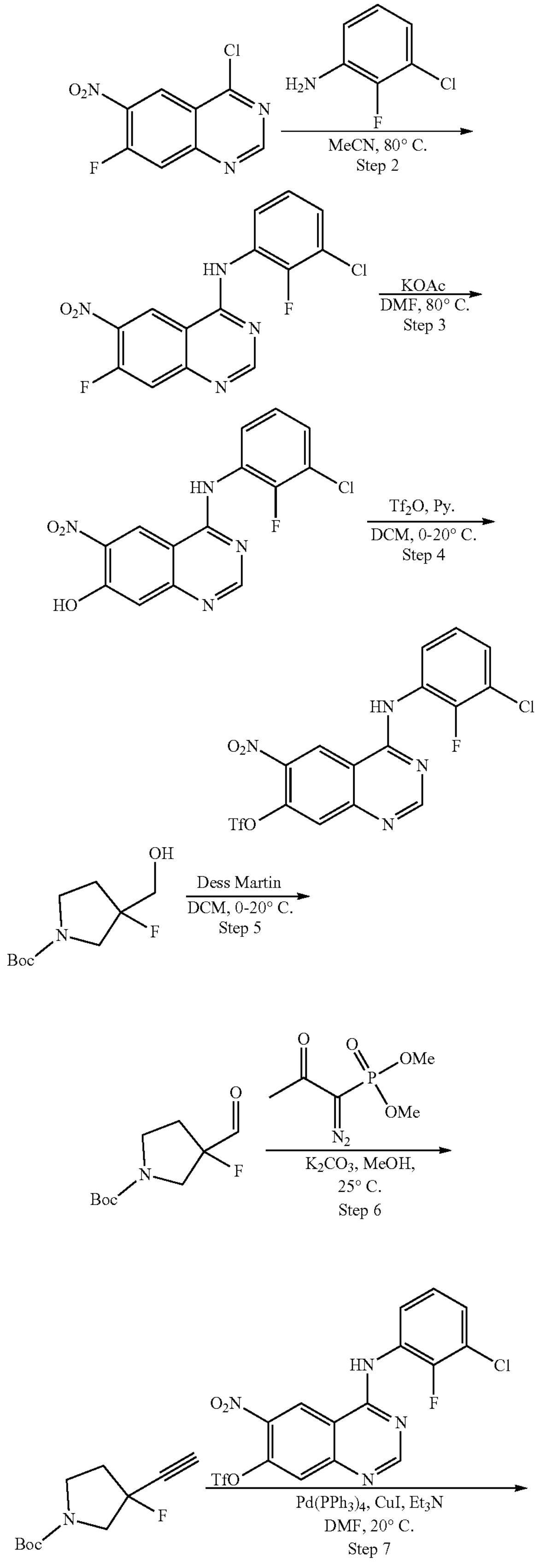

-continued
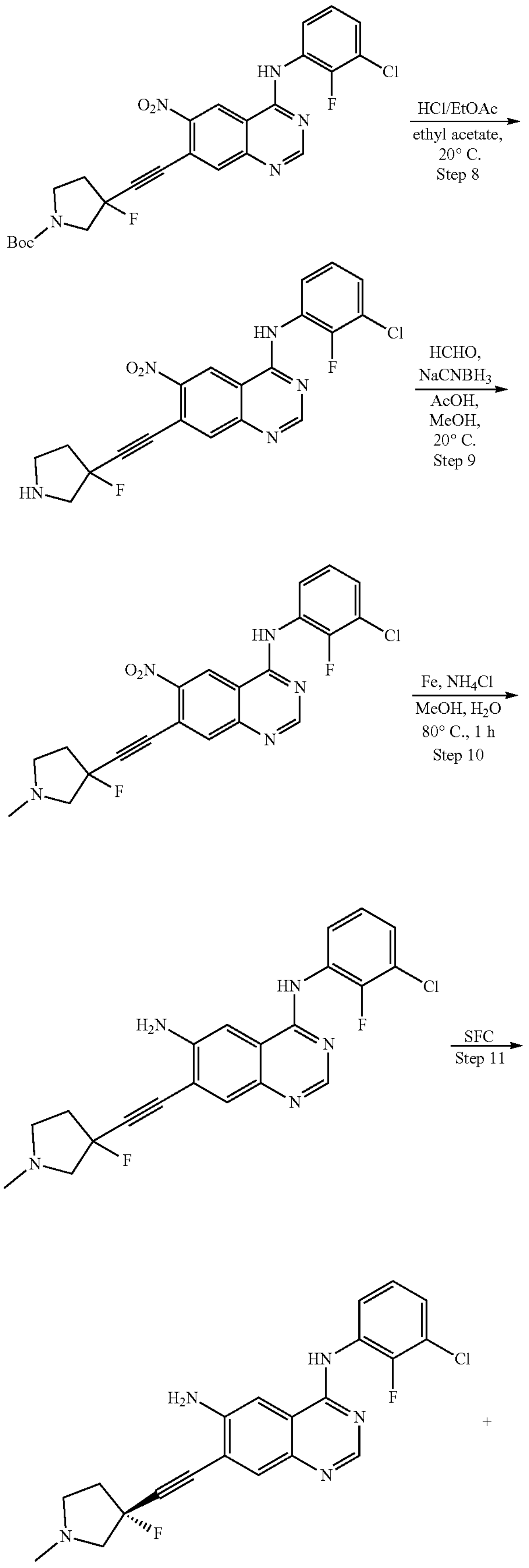
-continued
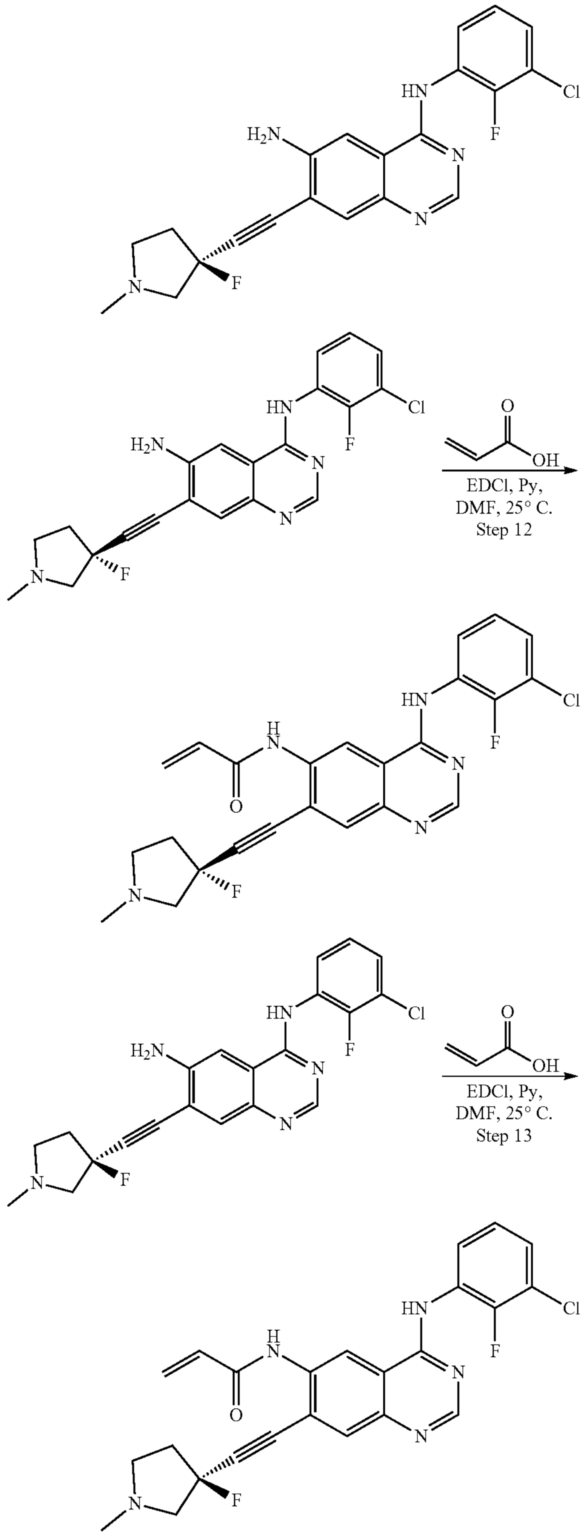
Step 1. To a solution of 7-fluoro-6-nitro-quinazolin-4-ol (100 g, 478 mmol) in $SOCl_2$ (400 mL) was added dimethylformamide (3.50 g, 47.8 mmol) dropwise. The mixture was stirred at 80° C. for 14 h. On completion, the reaction mixture was concentrated under vacuum to afford 4-chloro-7-fluoro-6-nitro-quinazoline (108 g, crude) as a yellow solid, which was used in the next step directly. $^1H$ NMR (400 MHz, DMSO-$d_6$) δ 8.73-8.70 (m, 1H), 8.33 (s, 1H), 7.79-7.75 (m, 1H).

Step 2. A solution of 4-chloro-7-fluoro-6-nitro-quinazoline (108 g, 475 mmol) and 3-chloro-2-fluoro-aniline (69 g, 475 mmol) in MeCN (1.5 L) was stirred at 80° C. for 2 h. On completion, the reaction mixture was concentrated to give N-(3-chloro-2-fluoro-phenyl)-7-fluoro-6-nitro-quinazolin-4-amine (180 g, crude) as a yellow solid, which was used for the next step without purification. $^1H$ NMR (400 MHz, DMSO-$d_6$) δ 9.67 (d, J=8.0 Hz, 1H), 8.75 (s, 1H), 7.93 (d, J=12.0 Hz, 1H), 7.61-7.50 (m, 2H), 7.35 (t, J=8.0 Hz, 1H).

Step 3. A solution of N-(3-chloro-2-fluoro-phenyl)-7-fluoro-6-nitro-quinazolin-4-amine (140 g, 416 mmol) and KOAc (204 g, 2.08 mol) in dimethylformamide (1.4 L) was stirred at 80° C. for 14 h. On completion, the mixture was diluted with ethanol (500 mL) and then filtered. The filtrate was concentrated under vacuum to give a residue. The residue was poured into the water (1.5 L), and then extracted with ethyl acetate (1.5 L×2). The combined organic layers were collected, dried over $Na_2SO_4$, filtered and concentrated under vacuum to give a residue. The residue was triturated with petroleum ether/ethyl acetate (10/1 v/v, 1.1 L) to give 4-(3-chloro-2-fluoro-anilino)-6-nitro-quinazolin-7-ol (140 g, crude) as a red solid, which was used for the next step without purification. m/z ES+ $[M+H]^+$ 335.2; $^1H$ NMR (400 MHz, DMSO-$d_6$) δ 10.33 (s, 1H), 9.16 (s, 1H), 8.48 (s, 1H), 7.60-7.40 (m, 2H), 7.40-7.10 (m, 3H).

Step 4. To a solution of 4-(3-chloro-2-fluoro-anilino)-6-nitro-quinazolin-7-ol (70 g, 142 mmol) and pyridine (56 g, 711 mmol) in dichloromethane (700 mL) was added trifluoromethylsulfonyl trifluoromethanesulfonate (60.2 g, 213 mmol) dropwise at 0° C. under $N_2$. The mixture was stirred at 20° C. for 2 h. On completion, the mixture was concentrated under vacuum. The residue was diluted with water (200 mL) and extracted with dichloromethane (200 mL×2). The combined organic layers were collected, dried over $Na_2SO_4$, filtered and concentrated to afford a residue. The residue was purified by column chromatography (petroleum ether/ethyl acetate=5:1-2:1) to afford a crude product. Then the crude product was triturated in petroleum ether (100 mL) to give [4-(3-chloro-2-fluoro-anilino)-6-nitro-quinazolin-7-yl]trifluoromethanesulfonate (40 g, 57% yield) as a yellow solid. m/z ES+ $[M+H]^+$ 466.9; $^1H$ NMR (400 MHz, DMSO-$d_6$) δ 9.03 (s, 1H), 8.90 (s, 1H), 8.15-8.10 (m, 1H), 7.95 (s, 1H), 7.33 (dd, J=5.6, 7.2 Hz, 1H), 7.21 (t, J=8.0 Hz, 1H).

Step 5. To a solution of tert-butyl 3-fluoro-3-(hydroxymethyl)pyrrolidine-1-carboxylate (54 g, 246 mmol) in dichloromethane (600 mL) was added DMP (157 g, 369 mmol) in portions at 0° C. The mixture was stirred at 20° C. for 1 h. On completion, the mixture was concentrated at room temperature to give a residue. The residue was diluted with ethyl acetate (200 mL) and then filtered. The filtrate was concentrated under vacuum to give a crude product. The crude product was purified by column chromatography ($SiO_2$, petroleum ether/ethyl acetate=5/1 to 1/2) to give tert-butyl 3-fluoro-3-formyl-pyrrolidine-1-carboxylate (50 g, crude) as a colorless oil. 41 NMR (400 MHz, $CDCl_3$) δ 9.87 (s, 1H), 3.80-3.40 (m, 4H), 2.33-2.20 (m, 2H), 1.46 (s, 9H).

Step 6. To a solution of tert-butyl 3-fluoro-3-formyl-pyrrolidine-1-carboxylate (50 g, 230 mmol) and $K_2CO_3$ (95.4 g, 690 mmol) in MeOH (500 mL) was added 1-diazo-1-dimethoxyphosphoryl-propan-2-one (57 g, 299 mmol) dropwise at 0° C. The mixture was stirred at 25° C. for 2 h until the color of the reaction solution turned from yellow to green. On completion, the mixture was diluted with water (1 L) and concentrated at room temperature to give a residue. The residue was then extracted with ethyl acetate (500 mL×3). The combined organic layers were collected, dried over $Na_2SO_4$ and concentrated under vacuum. The crude product was purified by column chromatography (petroleum ether/ethyl acetate=10/1) to give tert-butyl 3-ethynyl-3-fluoro-pyrrolidine-1-carboxylate (25 g, 51% yield) as a white solid. 41 NMR (400 MHz, $CDCl_3$) δ 3.84-3.46 (m, 4H), 2.77 (d, J=4.8 Hz, 1H), 2.45-2.21 (m, 2H), 1.47 (s, 9H).

Step 7. To a solution of [4-(3-chloro-2-fluoro-anilino)-6-nitro-quinazolin-7-yl]trifluoromethanesulfonate (22 g, 47.1 mmol) and tert-butyl 3-ethynyl-3-fluoro-pyrrolidine-1-carboxylate (10.1 g, 47.1 mmol) in dimethylformamide (200 mL) was added $Pd(PPh_3)_4$ (5.45 g, 4.71 mmol), CuI (1.80 g, 9.43 mmol) and triethylamine (145 g, 1.44 mol). The mixture was degassed and purged with $N_2$ for 3 times and then it was stirred at 20° C. for 2 h. Upon completion, the mixture was diluted with water (1 L) and extracted with ethyl acetate (3×300 mL). The combined organic layer was washed with brine (500 mL), dried over sodium sulfate, filtered and concentrated to give a crude product. The crude product was purified by column chromatography (petroleum ether/ethyl acetate=10/1 to 1/1) to give tert-butyl 3-[2-[4-(3-chloro-2-fluoro-anilino)-6-nitro-quinazolin-7-yl]ethynyl]-3-fluoro-pyrrolidine-1-carboxylate (24 g, 88% yield) as a brown oil. m/z ES+ $[M+H-56]^+$474.1

Step 8. To a solution of tert-butyl 3-[2-[4-(3-chloro-2-fluoro-anilino)-6-nitro-quinazolin-7-yl]ethynyl]-3-fluoro-pyrrolidine-1-carboxylate (27 g, 51 mmol) in ethyl acetate (50 mL) was added HCl/ethyl acetate (4 M, 306.82 mL). The mixture was stirred at 20° C. for 14 h. On completion, the mixture was filtered and the filter cake was washed with ethyl acetate (20 mL) to give a crude product. The crude product was purified by reverse-phase flash column (HCl conditions) to give N-(3-chloro-2-fluoro-phenyl)-7-[2-(3-fluoropyrrolidin-3-yl) ethynyl]-6-nitroquinazolin-4-amine (12 g, 44% yield) as a brown solid. m/z ES+ $[M+H]^+$ 430.0

Step 9. To a solution of N-(3-chloro-2-fluoro-phenyl)-7-[2-(3-fluoropyrrolidin-3-yl)ethynyl]-6-nitro-quinazolin-4-amine (10 g, 18.6 mmol) in MeOH (100 mL) was added AcOH (2.24 g, 37.2 mmol) and $(HCHO)_n$ (7.55 g, 93 mmol). The mixture was stirred at 20° C. for 0.2 h. Then $NaBH_3CN$ (5.00 g, 79.6 mmol) was added in portions. The mixture was stirred at 20° C. for 0.8 h. On completion, the reaction mixture was added dropwise to a stirred solution of ice water (800 mL) and ethyl acetate (100 mL), and then extracted with ethyl acetate (200 mL×3). The combined organic layers were collected, dried over $Na_2SO_4$, filtered and concentrated to give a residue. The residue was purified by Prep-HPLC (Neu:column: Phenomenex luna C18 250 mm*100 mm*10 um; mobile phase: [water (10 mM $NH_4HCO_3$)-acetonitrile]; B %: 40%-70%, 25 min) and Prep-HPLC (Base:column: Waters Xbridge C18 150*50 mm*10 um; mobile phase: [water (0.05% ammonium hydroxide v/v)-acetonitrile]; B %: 38%-68%, 11 min) to give N-(3-chloro-2-fluoro-phenyl)-7-[2-(3-fluoro-1-methyl-pyrrolidin-3-yl)ethynyl]-6-nitro-quinazolin-4-amine (5 g, 54% yield) as a brown oil. m/z ES+ $[M+H]^+$ 444.1; $^1H$ NMR (400 MHz, $CDCl_3$) δ 8.90 (s, 1H), 8.80 (s, 1H), 8.32 (t, J=7.6 Hz, 1H), 8.18 (s, 1H), 7.84 (s, 1H), 7.31-7.29 (m, 1H), 7.23-7.19 (m, 1H), 3.31-3.23 (m, 1H), 3.05-2.96 (m, 2H), 2.61-2.50 (m, 3H), 2.46 (s, 3H).

Step 10. To a solution of N-(3-chloro-2-fluoro-phenyl)-7-[2-(3-fluoro-1-methyl-pyrrolidin-3-yl)ethynyl]-6-nitro-quinazolin-4-amine (3.4 g, 6.82 mmol) in MeOH (60 mL) was added a solution of $NH_4C_1$ (3.65 g, 68.2 mmol) in $H_2O$ (12 mL). Then Fe (1.90 g, 34.1 mmol) was added in portions and the mixture was stirred at 80° C. for 1 h. Upon completion, the reaction mixture was added methanol (300 mL) and then filtered through Celite. The filtrate was concentrated to give a residue. The residue was diluted with saturated $NaHCO_3$ solution (500 mL) and extracted with ethyl acetate (3×200 mL). The combined organic layer was washed with brine (500 mL), dried over sodium sulfate, filtered and concentrated to give a crude product. The crude was triturated with a solution of petroleum ether/EA (10/1 v/v, 110 mL) at 20° C. for 30 min to give N4-(3-chloro-2-fluoro-phenyl)-7-[2-(3-fluoro-1-methyl-pyrrolidin-3-yl)ethynyl]-quinazoline-46-diamine (2.7 g, 86% yield) as a yellow solid. m/z ES+ $[M+H]^+$ 414.1

Step 11. N4-(3-chloro-2-fluoro-phenyl)-7-[2-(3-fluoro-1-methyl-pyrrolidin-3-yl)ethynyl]-quinazoline-46-diamine (3.1 g, 6.74 mmol) was purified by chial HPLC (column: Daicel ChiralPak IG (250*30 mm, 10 um); mobile phase: [0.1% ammonium hydroxide MeOH]; B %: 50%-50%, 5.1 min; 410 min) to give N4-(3-chloro-2-fluoro-phenyl)-7-[2-[(3R)-3-fluoro-1-methyl-pyrrolidin-3-yl]ethynyl]quinazoline-4,6-diamine (1.3 g, 46% yield, >99% ee, SFC rt: 0.939 min) as a yellow solid and N4-(3-chloro-2-fluoro-phenyl)-7-[2-[(3 S)-3-fluoro-1-methyl-pyrrolidin-3-yl]ethynyl]quinazoline-4,6-diamine (1.1 g, 39% yield, >99% ee, SFC rt: 1.384 min) as a yellow solid. m/z ES+$[M+H]^+$ 414.1

Step 12. To a mixture of N4-(3-chloro-2-fluoro-phenyl)-7-[2-[(3R)-3-fluoro-1-methyl-pyrrolidin-3-yl]ethynyl]quinazoline-4,6-diamine (1 g, 2.42 mmol) and pyridine (764 mg, 9.67 mmol) was added a solution of acrylic acid (200 mg, 2.78 mmol) in dimethylformamide (6 mL). Then 1-ethyl-3-(3-dimethylaminopropyl)carbodiimide (1.85 g, 9.67 mmol) was added and the mixture was stirred at 25° C. for 1 h. On completion, the reaction mixture was diluted with ethyl acetate (50 mL) and water (60 mL), then extracted with ethyl acetate (30 mL×2). The combined organic layers were collected, dried over $Na_2SO_4$, filtered and concentrated to give a residue. The residue was purified by Prep-HPLC (Neu:column: Waters Xbridge $C_{18}$ 150*50 mm*10 um; mobile phase: [water (10 mM $NH_4HCO_3$)-acetonitrile]; B %: 32%-62%, 11 min) to give N-[4-(3-chloro-2-fluoro-anilino)-7-[2-[(3R)-3-fluoro-1-methyl-pyrrolidin-3-yl]ethynyl]quinazolin-6-yl]prop-2-enamide (451 mg, 38% yield, >99% ee) as a yellow solid. m/z ES+ $[M+H]^+$ 468.2; $^1$H NMR (400 MHz, DMSO-$d_6$) δ 10.14 (s, 1H), 10.08 (s, 1H), 8.66 (s, 1H), 8.51 (s, 1H), 7.95 (s, 1H), 7.50 (s, 2H), 7.28 (t, J=8.0 Hz, 1H), 6.58 (dd, J=17.2, 10.0 Hz, 1H), 6.36-6.31 (m, 1H), 5.86 (d, J=10.4 Hz, 1H), 3.13 (dd, J=21.2, 11.6 Hz, 1H), 2.91-2.82 (m, 2H), 2.47-2.35 (m, 3H), 2.30 (s, 3H).

Step 13. To a mixture of N4-(3-chloro-2-fluoro-phenyl)-7-[2-[(3S)-3-fluoro-1-methyl-pyrrolidin-3-yl]ethynyl]quinazoline-4,6-diamine (1 g, 2.42 mmol) and pyridine (765 mg, 9.67 mmol) was added a solution of acrylic acid (200 mg, 2.78 mmol) in dimethylformamide (8 mL). Then 1-ethyl-3-(3-dimethylaminopropyl)carbodiimide (1.85 g, 9.67 mmol) was added and the mixture was stirred at 25° C. for 1 h. On completion, the reaction mixture was diluted with ethyl acetate (50 mL) and water (60 mL), then extracted with ethyl acetate (30 mL×2). The combined organic layers were collected, dried over $Na_2SO_4$, filtered and concentrated to give a residue. The residue was purified by Prep-HPLC (Neu:column: Waters Xbridge $C_{18}$ 150*50 mm*10 um; mobile phase: [water (10 mM $NH_4HCO_3$)-acetonitrile]; B %: 32%-62%, 11 min) to give N-[4-(3-chloro-2-fluoro-anilino)-7-[2-[(3 S)-3-fluoro-1-methyl-pyrrolidin-3-yl]ethynyl]quinazol in-6-yl]prop-2-enamide (554 mg, 47% yield, 99% ee) as a yellow solid. m/z ES+ $[M+H]^+$ 468.2; $^1$H NMR (400 MHz, DMSO-$d_6$) δ 10.14 (s, 1H), 10.09 (s, 1H), 8.66 (s, 1H), 8.51 (s, 1H), 7.96 (s, 1H), 7.50 (s, 2H), 7.28 (t, J=8.0 Hz, 1H), 6.58 (dd, J=17.2, 10.0 Hz, 1H), 6.36-6.32 (m, 1H), 5.86 (d, J=10.4 Hz, 1H), 3.13 (dd, J=21.2, 11.6 Hz, 1H), 2.91-2.82 (m, 2H), 2.47-2.45 (m, 3H), 2.30 (s, 3H).

Example 41. Synthesis of Compound No. 47 (N-(4-((3-chloro-2-fluorophenyl)amino)-7-((5,7-dimethyl-2-oxa-5-azaspiro[3.4]octan-7-yl)ethynyl)quinazolin-6-yl)acrylamide)

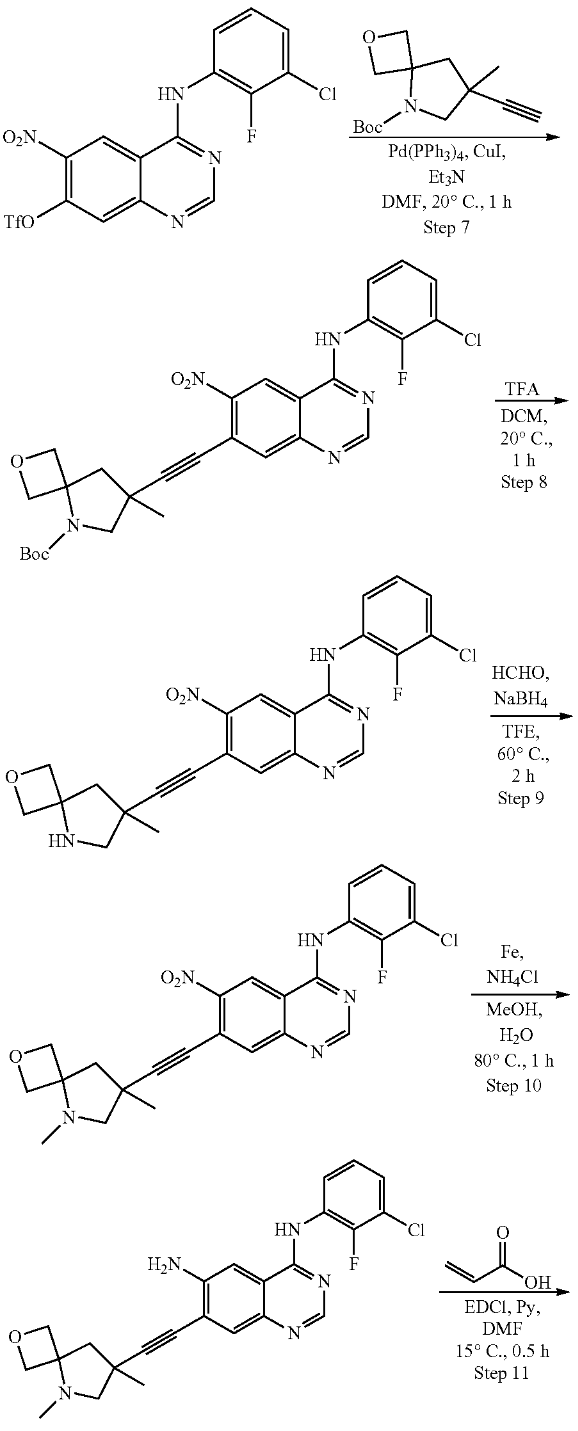

-continued

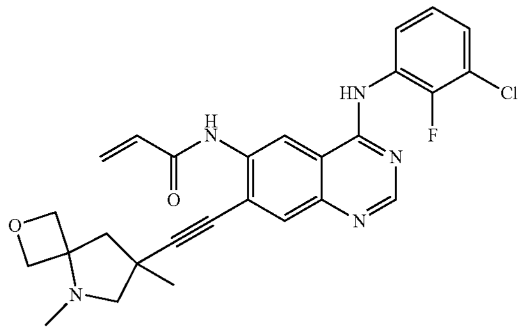

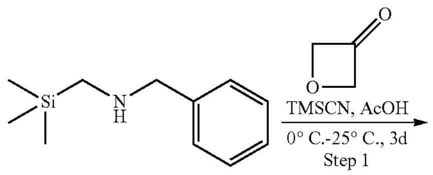

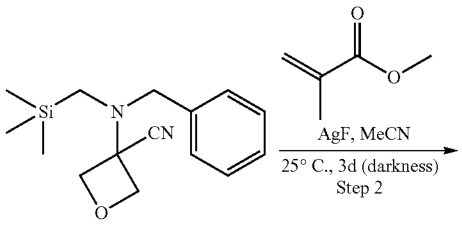

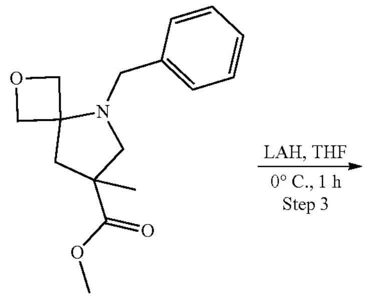

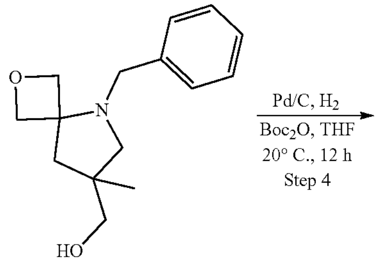

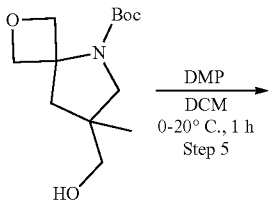

-continued

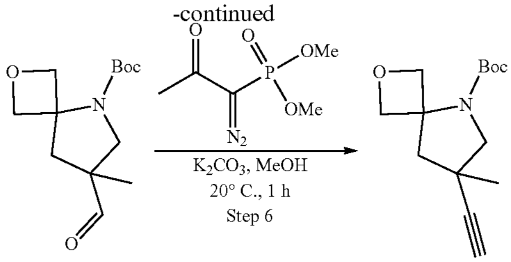

Step 1. To a mixture of N-benzyl-1-(trimethylsilyl)methanamine (80.5 g, 416 mmol) and oxetan-3-one (15.0 g, 208 mmol) in acetic acid (250 mL) was added TMSCN (22.7 g, 228 mmol, 28.6 mL) dropwise at 0° C. The mixture was stirred at 25° C. for 72 h. On completion, the mixture was poured into water (1.00 L) and extracted with ethyl acetate (2×300 mL). The combined organic phase was washed with acetic acid (5% in water, 500 mL) and brine (500 mL), dried with anhydrous sodium sulfate, filtered and concentrated in vacuum. The residue was purified by column chromatography (petroleum ether/ethyl acetate=10/1) to give 3-(benzyl((trimethylsilyl)methyl)amino)oxetane-3-carbonitrile (30.0 g, 52% yield) as a colorless oil. m/z ES+ $[M+H]^+$ 275.1

Step 2. A mixture of 3-(benzyl((trimethylsilyl)methyl)amino)oxetane-3-carbonitrile (12.0 g, 43.7 mmol), methyl methacrylate (21.8 g, 218 mmol) and AgF (16.6 g, 131 mmol) in acetonitrile (120 mL) was stirred at 25° C. in darkness for 72 h. On completion, the mixture was filtered and the filtrate was concentrated to dryness to give a residue. The residue was purified by column chromatography (petroleum ether/ethyl acetate=20/1 to 10/1) to give methyl 5-benzyl-7-methyl-2-oxa-5-azaspiro[3.4]octane-7-carboxylate (4.00 g, 33% yield) as a yellow oil. The structure was confirmed by 2D NMR.

Step 3. To a solution of methyl 5-benzyl-7-methyl-2-oxa-5-azaspiro[3.4]octane-7-carboxylate (500 mg, 1.82 mmol) in tetrahydrofuran (20.0 mL) was added lithium aluminum hydride (140 mg, 3.69 mmol). The mixture was stirred at 0° C. for 1 h. The mixture was quenched with sodium sulfate decahydrate (100 mg) and then filtered. The filtrate was concentrated under reduced pressure to give (5-benzyl-7-methyl-2-oxa-5-azaspiro[3.4]octan-7-yl)methanol (450 mg, crude) as a colorless oil.

Step 4. To a solution of (5-benzyl-7-methyl-2-oxa-5-azaspiro[3.4]octan-7-yl)methanol (450 mg, 1.82 mmol) in tetrahydrofuran (50.0 mL) was added di-tert-butyl dicarbonate (840 mg, 3.85 mmol, 884 uL) and palladium on activated carbon (100 mg, 10% loading). The mixture was stirred at 20° C. for 12 h under $H_2$ (15 Psi). The mixture was filtered and the filtrate was concentrated under reduced pressure to give a residue. The residue was purified by column chromatography (petroleum ether/ethyl acetate=1/1) to give tert-butyl 7-(hydroxymethyl)-7-methyl-2-oxa-5-azaspiro[3.4]octane-5-carboxylate (410 mg, 87% yield) as a colorless oil. $^1H$ NMR (400 MHz, $CDCl_3$) δ=5.45 (br s, 1H), 5.24 (br dd, J=5.2, 11.2 Hz, 1H), 4.59-4.44 (m, 2H), 3.47-3.29 (m, 3H), 3.22-3.07 (m, 1H), 2.49-2.31 (m, 1H), 2.17-2.07 (m, 1H), 1.66-1.47 (m, 9H), 1.05 (s, 3H).

Step 5. To a solution of tert-butyl 7-(hydroxymethyl)-7-methyl-2-oxa-5-azaspiro[3.4]octane-5-carboxylate (410 mg, 1.59 mmol) in dichloromethane (20.0 mL) was added DMP (1.64 g, 3.87 mmol) portionwise. The mixture was stirred at 20° C. for 1 h. The mixture was carefully concentrated under reduced pressure. The residue was purified by column chromatography (petroleum ether/ethyl acetate=1/1) to give tert-butyl 7-formyl-7-methyl-2-oxa-5-azaspiro[3.4]octane-5-carboxylate (400 mg, 98% yield) as a colorless oil. $^1$H NMR (400 MHz, $CDCl_3$) δ=9.52 (s, 1H), 5.55-5.27 (m, 1H), 5.27-5.07 (m, 1H), 4.57-4.44 (m, 2H), 3.93-3.73 (m, 1H), 3.28-3.12 (m, 1H), 2.93-2.72 (m, 1H), 1.61-1.52 (m, 9H), 1.23 (s, 3H).

Step 6. To a solution of tert-butyl 7-formyl-7-methyl-2-oxa-5-azaspiro[3.4]octane-5-carboxylate (520 mg, 2.04 mmol) in methanol (20.0 mL) was added potassium carbonate (1.13 g, 8.15 mmol) and dimethyl (1-diazo-2-oxopropyl) phosphonate (800 mg, 4.16 mmol). The mixture was stirred at 20° C. for 1 h. The mixture was concentrated under reduced pressure. The residue was purified by column chromatography (petroleum ether/ethyl acetate=1/1) to give tert-butyl 7-ethynyl-7-methyl-2-oxa-5-azaspiro[3.4]octane-5-carboxylate (420 mg, 82% yield) as a yellow oil.

Step 7. To a solution of 4-((3-chloro-2-fluorophenyl) amino)-6-nitroquinazolin-7-yl trifluoromethanesulfonate (500 mg, 1.07 mmol) and tert-butyl 7-ethynyl-7-methyl-2-oxa-5-azaspiro[3.4]octane-5-carboxylate (300 mg, 1.19 mmol) in dimethyl formamide (5.00 mL) and triethylamine (5.00 mL) was added copper(I) iodide (50.0 mg, 263 umol) and tetrakis(triphenylphosphine)palladium (130 mg, 113 umol). The mixture was stirred at 20° C. for 1 h under nitrogen. The mixture was added ethyl acetate (40.0 mL) and saturated sodium bicarbonate solution (20.0 mL). The organic phase was separated, washed with brine (2×20.0 mL), dried over anhydrous sodium sulfate, filtered and concentrated. The residue was purified by column chromatography ($SiO_2$, petroleum ether/ethyl acetate=3/1) to give tert-butyl 7-((4-((3-chloro-2-fluorophenyl)amino)-6-nitroquinazolin-7-yl)ethynyl)-7-methyl-2-oxa-5-azaspiro[3.4] octane-5-carboxylate (500 mg, 82% yield) as a brown solid. $^1$H NMR (400 MHz, $CDCl_3$) δ=9.39-9.31 (m, 1H), 8.83-8.66 (m, 1H), 8.09-7.90 (m, 2H), 7.75-7.60 (m, 3H), 7.58-7.51 (m, 1H), 7.50-7.41 (m, 2H), 7.24-7.08 (m, 1H), 5.62-5.38 (m, 1H), 5.37-5.21 (m, 1H), 4.79-4.61 (m, 1H), 4.57-4.44 (m, 1H), 4.16-4.08 (m, 1H), 3.93-3.74 (m, 1H), 3.40-3.23 (m, 1H), 2.99-2.92 (m, 3H), 2.91-2.84 (m, 4H), 2.56 (br d, J=1.9 Hz, 1H), 2.36-2.27 (m, 1H), 1.64-1.41 (m, 14H), 1.31-1.18 (m, 4H), 0.92-0.77 (m, 2H).

Step 8. To a solution of tert-butyl 7-((4-((3-chloro-2-fluorophenyl)amino)-6-nitro quinazolin-7-yl)ethynyl)-7-methyl-2-oxa-5-azaspiro[3.4]octane-5-carboxylate (360 mg, 633 umol) in dichloromethane (1.50 mL) was added trifluoroacetic acid (13.9 g, 122 mmol). The mixture was stirred at 20° C. for 1 h. On completion, the mixture was concentrated under reduced pressure to give N-(3-chloro-2-fluorophenyl)-7-((7-methyl-2-oxa-5-azaspiro[3.4]octan-7-yl)ethynyl)-6-nitroquinazolin-4-amine (350 mg, 94% yield, trifluoroacetic acid) as a brown solid. m/z ES+[M+H]$^+$ 468.1

Step 9. To a solution of N-(3-chloro-2-fluorophenyl)-7-((7-methyl-2-oxa-5-azaspiro[3.4]octan-7-yl)ethynyl)-6-nitroquinazolin-4-amine (350 mg, 601 umol, trifluoroacetic acid) in trifluoroethanol (5.00 mL) was added paraformaldehyde (54.5 mg, 1.82 mmol). The mixture was stirred at 60° C. for 1 h. Then sodium borohydride (22.8 mg, 601 umol) was added and the mixture was stirred at 60° C. for another 1 h. The mixture was filtered and the filtrate was concentrated under reduced pressure to give a residue. The residue was dissolved in dimethyl formamide (2.00 mL) and purified by prep-HPLC (column: Shim-pack C18 150*25*10 um; mobile phase: [water (0.225% formic acid)-acetonitrile]; B %: 23%-43%, 10 min) to give N-(3-chloro-2-fluorophenyl)-7-((5,7-dimethyl-2-oxa-5-azaspiro[3.4]octan-7-yl)ethynyl)-6-nitroquinazolin-4-amine (240 mg, 75% yield, formate) as a yellow solid. m/z ES+ [M+H]$^+$ 482.1; $^1$H NMR (400 MHz, DMSO-$d_6$) δ=9.33 (br s, 1H), 8.60 (br s, 1H), 7.91 (s, 1H), 7.56-7.46 (m, 2H), 7.33-7.27 (m, 1H), 4.83 (d, J=6.8 Hz, 1H), 4.76 (d, J=6.8 Hz, 1H), 4.50 (d, J=6.8 Hz, 1H), 4.46 (d, J=6.8 Hz, 1H), 2.99 (d, J=9.2 Hz, 1H), 2.79 (d, J=9.2 Hz, 1H), 2.63 (d, J=13.2 Hz, 1H), 2.55 (s, 3H), 2.28-2.22 (m, 1H), 1.41 (s, 3H).

Step 10. To a solution of N-(3-chloro-2-fluorophenyl)-7-((5,7-dimethyl-2-oxa-5-azaspiro[3.4]octan-7-yl)ethynyl)-6-nitroquinazolin-4-amine (240 mg, 454 umol, formate) in methanol (6.00 mL) and water (2.00 mL) was added iron powder (128 mg, 2.29 mmol) and ammonium chloride (197 mg, 3.67 mmol). The mixture was stirred at 80° C. for 1 h. The reaction mixture was concentrated under reduced pressure to give a residue. The mixture was diluted with ethyl acetate (40.0 mL) and water (20.0 mL). The organic phase was separated, dried over sodium sulfate, filtered and concentrated to give N$^4$-(3-chloro-2-fluorophenyl)-7-((5,7-dimethyl-2-oxa-5-azaspiro[3.4]octan-7-yl)ethynyl)quinazoline-4,6-diamine (110 mg, 53% yield) as a brown solid. m/z ES+[M+H]$^+$ 452.2

Step 11. To a solution of N$^4$-(3-chloro-2-fluorophenyl)-7-((5,7-dimethyl-2-oxa-5-azaspiro[3.4]octan-7-yl)ethynyl) quinazoline-4,6-diamine (110 mg, 243 umol) in dimethyl formamide (2.00 mL) was added acrylic acid (35.7 mg, 495 umol), pyridine (76.4 mg, 966 umol) and 1-(3-dimethylaminopropyl)-3-ethylcarbodiimide hydrochloride (94.0 mg, 490 umol). The mixture was stirred at 15° C. for 0.5 h. The reaction mixture was concentrated under reduced pressure to give a residue. The residue was diluted with dimethyl formamide (2.00 mL) and purified by prep-HPLC (column: Shim-pack C18 150*25*10 um; mobile phase: [water (0.225% formic acid)-acetonitrile]; B %: 18%-38%, 10 min), which was further purified by prep-HPLC (column: Waters Xbridge 150*25 mm*5 um; mobile phase: [water (10 mM $NH_4HCO_3$)-acetonitrile]; B %: 30%-60%, 9 min) to give N-(4-((3-chloro-2-fluorophenyl)amino)-7-((5,7-dimethyl-2-oxa-5-azaspiro[3.4]octan-7-yl)ethynyl)quinazolin-6-yl)acrylamide (9.98 mg, 8% yield, 99% purity) as a yellow solid. m/z ES+[M+H]$^+$ 506.2; $^1$H NMR (400 MHz, DMSO-$d_6$) δ=10.15 (br s, 1H), 9.75 (br s, 1H), 8.64 (s, 1H), 8.39 (s, 1H), 7.73 (br s, 1H), 7.44 (br d, J=5.6 Hz, 2H), 7.29-7.21 (m, 1H), 6.57 (dd, J=10.2, 17.2 Hz, 1H), 6.33 (dd, J=1.6, 17.2 Hz, 1H), 5.86 (dd, J=1.6, 10.4 Hz, 1H), 4.80 (d, J=6.8 Hz, 1H), 4.74 (d, J=6.8 Hz, 1H), 4.46 (d, J=6.8 Hz, 1H), 4.43 (d, J=6.7 Hz, 1H), 2.99 (d, J=9.2 Hz, 1H), 2.74 (d, J=9.2 Hz, 1H), 2.64 (d, J=13.2 Hz, 1H), 2.53 (s, 3H), 2.22 (d, J=13.2 Hz, 1H), 1.39 (s, 3H).

Example 42. Synthesis of Compound No. 48 (N-(4-((3-chloro-2-fluorophenyl)amino)-7-(((1S,5R)-3-(oxetan-3-yl)-3-azabicyclo[3.1.0]hexan-1-yl)ethynyl)quinazolin-6-yl)acrylamide)

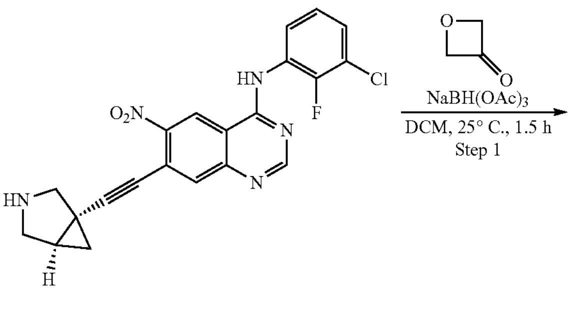

-continued

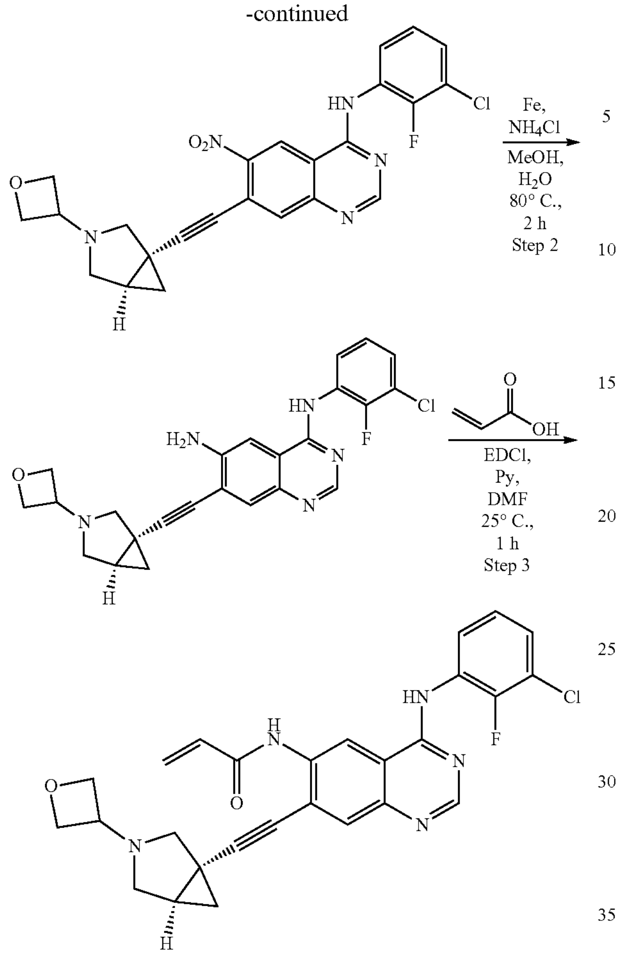

Step 1. To a solution of 7-((1S,5R)-3-azabicyclo[3.1.0]hexan-1-ylethynyl)-N-(3-chloro-2-fluorophenyl)-6-nitro-quinazolin-4-amine (1.20 g, 2.83 mmol) in dichloromethane (10.0 mL) was added oxetan-3-one (1.02 g, 14.2 mmol) dropwise. The mixture was stirred at 25° C. for 0.5 h. Then the mixture was added sodium triacetoxyborohydride (1.20 g, 5.66 mmol) in portions and stirred at 25° C. for 1 h. The mixture was diluted with water (30.0 mL) and extracted with ethyl acetate (3×30.0 mL). The combined organic layer was washed with brine (10.0 mL) and dried over anhydrous sodium sulfate, filtered and concentrated to give crude product. The crude product was purified by silica gel chromatography (petroleum ether/ethyl acetate=2/1 to 0/1) to give N-(3-chloro-2-fluorophenyl)-6-nitro-7-(((1S,5R)-3-(oxetan-3-yl)-3-azabicyclo[3.1.0]hexan-1-yl)ethynyl)quinazolin-4-amine (1.00 g, 74% yield) as a yellow solid. m/z ES+ [M+H]+ 480.0;

Step 2. To a solution of N-(3-chloro-2-fluorophenyl)-6-nitro-7-(41S,5R)-3-(oxetan-3-yl)-3-azabicyclo[3.1.0]hexan-1-yl)ethynyl)quinazolin-4-amine (1.00 g, 2.08 mmol), ammonium chloride (780 mg, 14.6 mmol) in methanol (12.0 mL) and water (3.00 mL) was added iron powder (582 mg, 10.4 mmol) in portions. The mixture was stirred at 80° C. for 2 h. The mixture was filtered. The filtrate was concentrated in vacuum. The residue was diluted with water (100 mL) and extracted with ethyl acetate (3×80.0 mL). The combined organic layer was washed with brine (40.0 mL), dried over anhydrous sodium sulfate, filtered and concentrated in vacuum to give $N^4$-(3-chloro-2-fluorophenyl)-7-(((1S,5R)-3-(oxetan-3-yl)-3-azabicyclo[3.1.0]hexan-1-yl)ethynyl)quinazoline-4,6-diamine (650 mg, crude) as a yellow solid. $^1$H NMR (400 MHz, DMSO-$d_6$) δ=9.70-9.43 (m, 1H), 8.34-8.15 (m, 1H), 7.78-7.46 (m, 3H), 7.46-7.33 (m, 2H), 7.28-7.20 (m, 1H), 5.65 (br s, 1H), 4.59-4.50 (m, 2H), 4.45 (q, J=6.0 Hz, 2H), 3.76 (br t, J=6.0 Hz, 1H), 3.32-3.25 (m, 1H), 3.17 (d, J=8.4 Hz, 1H), 2.95 (d, J=8.8 Hz, 1H), 2.57 (br d, J=8.4 Hz, 1H), 2.02 (td, J=4.0, 7.8 Hz, 1H), 1.37 (br t, J=4.0 Hz, 1H), 1.12 (br dd, J=4.0, 8.0 Hz, 1H).

Step 3. To a solution of $N^4$-(3-chloro-2-fluorophenyl)-7-4(1S,5R)-3-(oxetan-3-yl)-3-azabicyclo[3.1.0]hexan-1-yl) ethynyl)quinazoline-4,6-diamine (550 mg, 1.22 mmol), acrylic acid (106 mg, 1.47 mmol, 101 uL) and pyridine (387 mg, 4.89 mmol, 395 uL) in dimethyl formamide (6.00 mL) was added 1-ethyl-3-(3-dimethylamino-propyl)-carbodiimide hydrochloride (937 mg, 4.89 mmol) in portions. The mixture was stirred at 25° C. for 1 h. The mixture was diluted with water (30.0 mL) and extracted with ethyl acetate (3×30.0 mL). The combined organic layer was washed with brine (10.0 mL) and dried over anhydrous sodium sulfate, filtered and concentrated to give crude product. The crude product was purified by prep-HPLC (column: Waters Xbridge C18 150*50 mm*10 um; mobile phase: [water (10 mM $NH_4HCO_3$)-acetonitrile]; B %: 33%-63%, 11.5 min) and lyophilized to give N-(4-((3-chloro-2-fluorophenyl)amino)-7-(41S,5R)-3-(oxetan-3-yl)-3-azabicyclo[3.1.0]hexan-1-yl)ethynyl)quinazolin-6-yl)acrylamide (176.2 mg, 28% yield) as a yellow solid. m/z ES+ $[M+H]^+$ 504.3; $^1$H NMR (400 MHz, $CDCl_3$) δ=9.21 (s, 1H), 8.75 (s, 1H), 8.39 (dt, J=2.4, 7.3 Hz, 1H), 8.29 (s, 1H), 7.96 (s, 1H), 7.69 (br d, J=2.4 Hz, 1H), 7.26-7.14 (m, 2H), 6.57-6.47 (m, 1H), 6.39-6.25 (m, 1H), 6.00-5.87 (m, 1H), 4.78-4.68 (m, 2H), 4.63 (dt, J=4.0, 6.4 Hz, 2H), 3.85 (quin, J=6.4 Hz, 1H), 3.27 (d, J=8.4 Hz, 1H), 3.07 (d, J=8.8 Hz, 1H), 2.69-2.58 (m, 2H), 2.05-1.97 (m, 1H), 1.66 (t, J=4.8 Hz, 1H), 1.14 (dd, J=4.8, 8.0 Hz, 1H).

Example 43. Synthesis of Compound No. 49 (N-(4-((3-chloro-2-fluorophenyl)amino)-7-(((1S,5R)-3-methyl-3-azabicyclo[3.1.0]hexan-1-yl)ethynyl)quinazolin-6-yl)acrylamide)

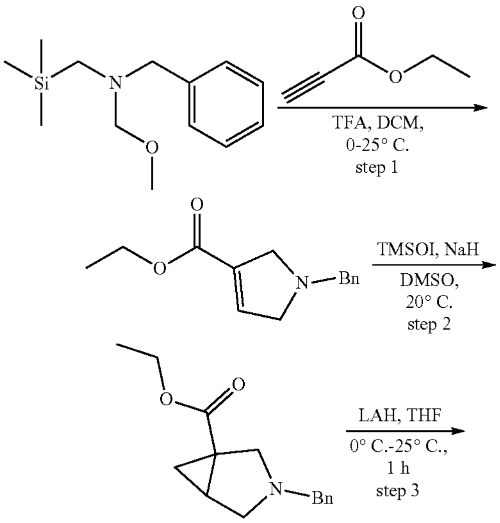

-continued
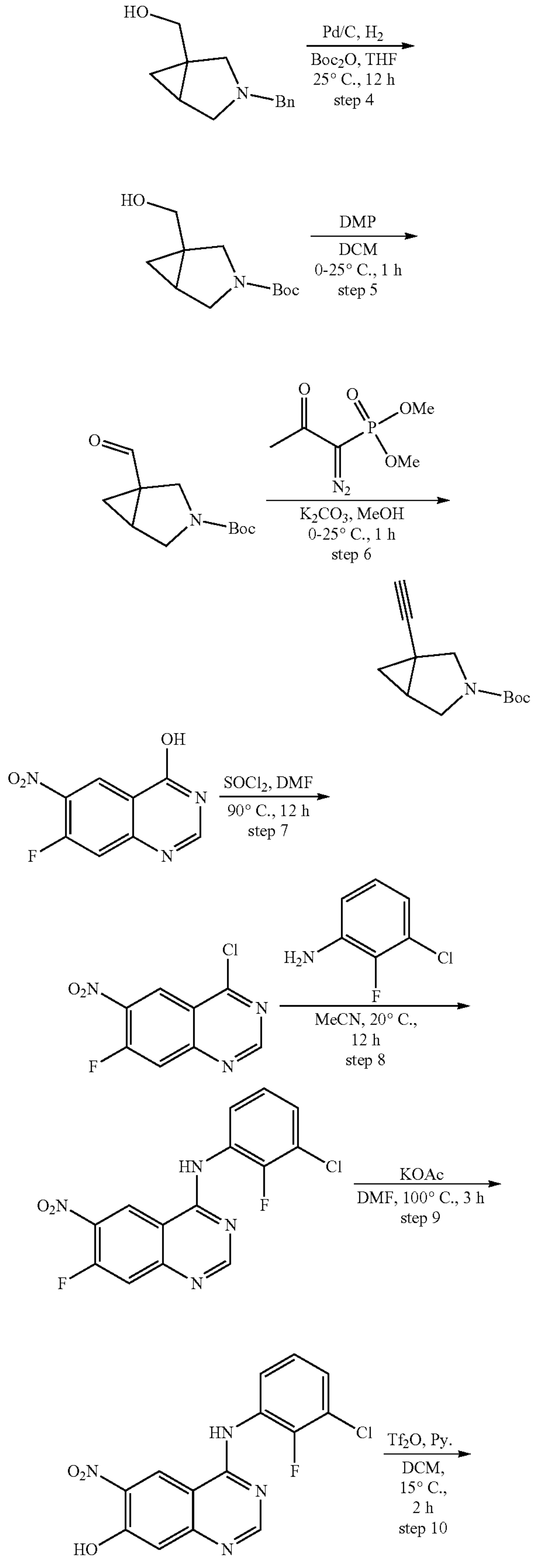
-continued
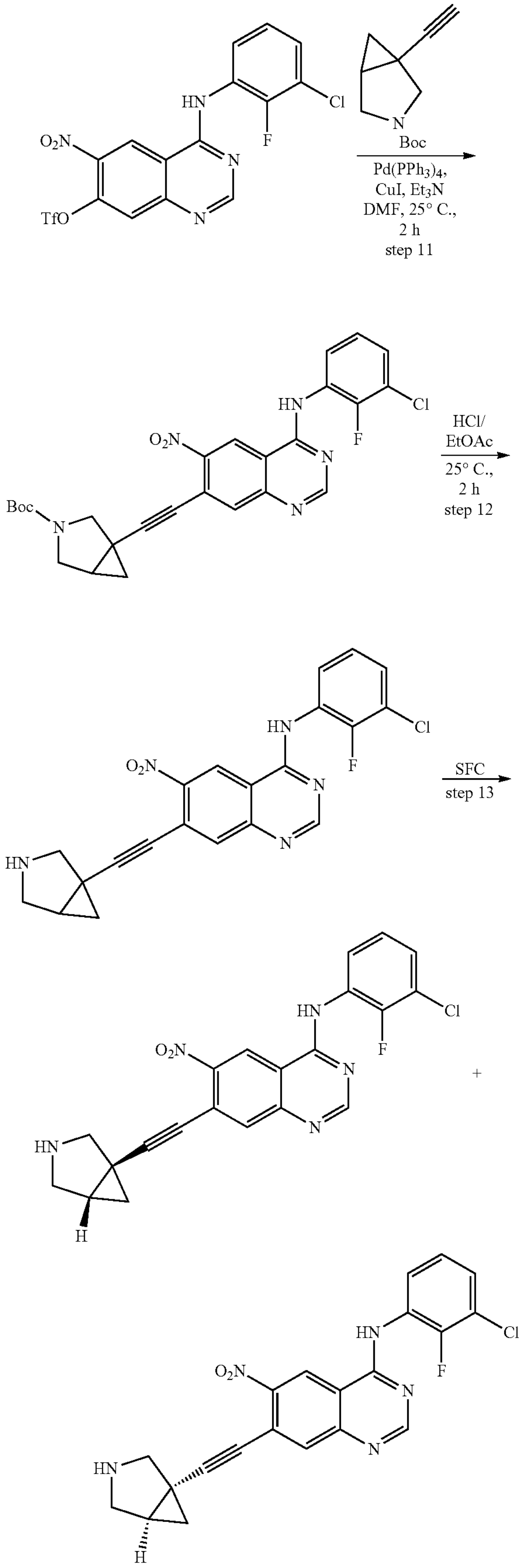

-continued

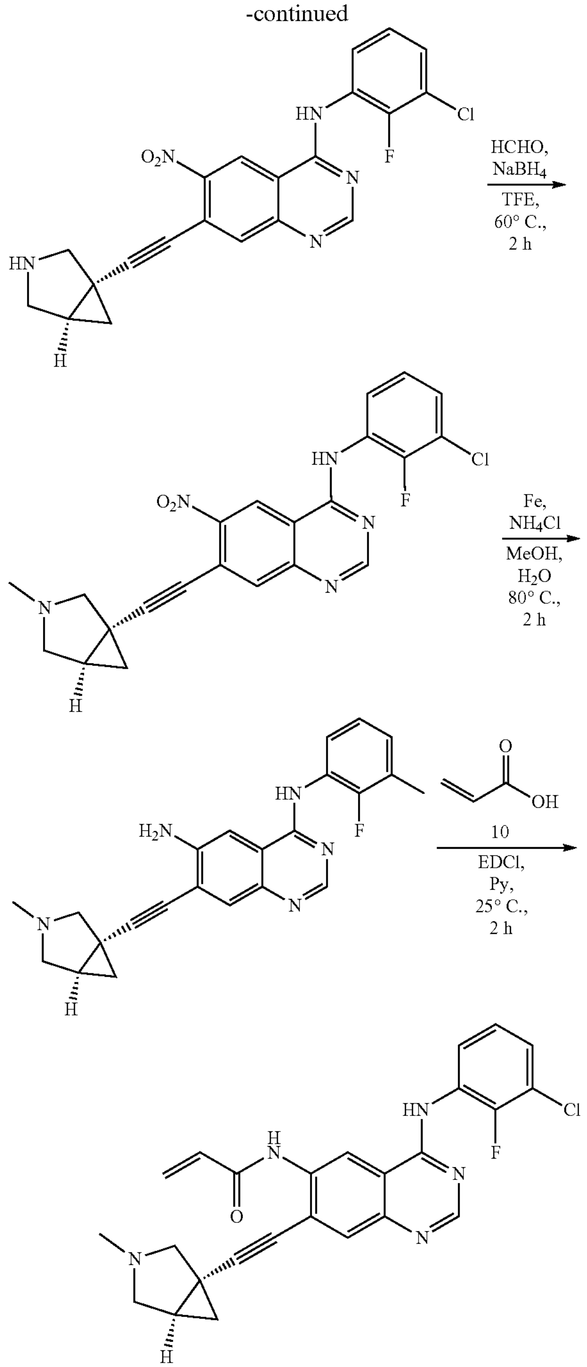

Step 1. To a solution of ethyl propiolate (43.4 g, 442 mmol, 43.4 mL) and N-benzyl-1-methoxy-N-((trimethylsilyl)methyl)methanamine (100 g, 421 mmol) in dichloromethane (1.00 L) was added trifluoroacetic acid (7.68 g, 67.4 mmol, 4.99 mL) dropwise at 0° C. The mixture was stirred at 25° C. for 2 h. The mixture was concentrated to give crude product. The crude product was purified by silica gel chromatography (petroleum ether/ethyl acetate=20/1 to 5/1) to give ethyl 1-benzyl-2,5-dihydro-1H-pyrrole-3-carboxylate (40.0 g, 41% yield) as yellow oil. 1H NMR (400 MHz, $CDCl_3$) δ=7.33-7.24 (m, 5H), 6.71-6.66 (m, 1H), 4.17-4.10 (m, 2H), 3.76 (s, 2H), 3.65-3.56 (m, 4H), 1.23-1.20 (m, 3H).

Step 2. To a solution of sodium hydride (13.5 g, 337 mmol, 60% purity) in dimethylsulfoxide (400 mL) was added trimethylsulfoxonium iodide (74.2 g, 337 mmol) in portions at 20° C. The mixture was added ethyl 1-benzyl-2,5-dihydro-1H-pyrrole-3-carboxylate (60.0 g, 259 mmol) dissolved in dimethylsulfoxide (200 mL) dropwise. The mixture was stirred at 20° C. for 1 h. The mixture was quenched with saturated ammonium chloride solution (500 mL) and extracted with ethyl acetate (3×200 mL). The combined organic layer was washed with brine (100 mL) and dried over sodium sulfate, filtered and concentrated to give crude product. The crude product was purified by silica gel chromatography (petroleum ether/ethyl acetate=20/1 to 10/1) to give ethyl 3-benzyl-3-azabicyclo[3.1.0]hexane-1-carboxylate (32.0 g, 130 mmol) as colorless oil. $^1H$ NMR (400 MHz, $CDCl_3$) δ=7.33-7.27 (m, 5H), 4.14 (q, J=7.2 Hz, 2H), 3.64 (d, J=2.0 Hz, 2H), 3.08 (d, J=8.8 Hz, 1H), 2.96 (d, J=8.8 Hz, 1H), 2.74 (d, J=8.8 Hz, 1H), 2.45 (dd, J=3.6, 8.8 Hz, 1H), 1.93 (ddd, J=3.6, 4.8, 8.3 Hz, 1H), 1.50 (t, J=4.4 Hz, 1H), 1.31 (dd, J=3.6, 8.8 Hz, 1H), 1.25 (t, J=7.2 Hz, 3H).

Step 3. To a solution of ethyl 3-benzyl-3-azabicyclo[3.1.0]hexane-1-carboxylate (32.0 g, 130 mmol) in tetrahydrofuran (300 mL) was added lithium aluminum hydride (9.90 g, 261 mmol) in portions at 0° C. The mixture was stirred at 25° C. for 1 h. The mixture was quenched with sodium sulfate decahydrate (20.0 g) and filtered. The filtrate was concentrated to give (3-benzyl-3-azabicyclo[3.1.0]hexan-1-yl)methanol (27.5 g, crude) as yellow oil. $^1H$ NMR (400 MHz, $CDCl_3$) δ=7.34-7.29 (m, 4H), 7.27-7.21 (m, 1H), 3.78-3.73 (m, 1H), 3.69-3.58 (m, 3H), 3.05 (d, J=8.4 Hz, 1H), 2.97 (d, J=8.8 Hz, 1H), 2.44 (br d, J=8.4 Hz, 2H), 1.28 (br d, J=3.6 Hz, 1H), 1.14 (t, J=4.0 Hz, 1H), 0.48 (dd, J=4.0, 8.0 Hz, 1H).

Step 4. To a solution of (3-benzyl-3-azabicyclo[3.1.0]hexan-1-yl)methanol (27.5 g, 135 mmol) and di-tert-butyl-dicarbonate (59.1 g, 271 mmol, 62.2 mL) in tetrahydrofuran (300 mL) was added palladium/carbon (4.00 g, 10% purity) in one portion under hydrogen. The mixture was stirred at 25° C. under hydrogen (15 Psi) for 12 h. The mixture was filtered and the filtrate was concentrated to give crude product. The residue was purified by silica gel chromatography (petroleum ether/ethyl acetate=10/1 to 3/1) to give tert-butyl 1-(hydroxymethyl)-3-azabicyclo[3.1.0]hexane-3-carboxylate (17.8 g, 62% yield) as colorless oil. $^1H$ NMR (400 MHz, $CDCl_3$) δ=3.69-3.40 (m, 4H), 3.37-3.28 (m, 2H), 1.37 (s, 9H), 1.34-1.31 (m, 1H), 0.71 (dd, J=5.2, 8.0 Hz, 1H), 0.47-0.37 (m, 1H).

Step 5. To a solution of tert-butyl 1-(hydroxymethyl)-3-azabicyclo[3.1.0]hexane-3-carboxylate (19.8 g, 92.8 mmol) in dichloromethane (200 mL) was added dess-martin periodinane (59.1 g, 139 mmol, 43.1 mL) in portions at 0° C. The mixture was stirred at 25° C. for 1 h. The mixture was quenched with saturated sodium sulfite solution (100 mL) and saturated sodium hydrogencarbonate solution (200 mL), and extracted with dichloromethane (3×200 mL). The combined organic layer was washed with brine (100 mL) and dried over sodium sulfate, filtered and concentrated to give tert-butyl 1-formyl-3-azabicyclo[3.1.0]hexane-3-carboxylate (18.0 g, crude) as colorless oil. $^1H$ NMR (400 MHz, $CDCl_3$) δ=9.23-8.89 (m, 1H), 3.86 (br d, J=11.2 Hz, 1H), 3.78-3.56 (m, 2H), 3.53-3.41 (m, 1H), 2.30-2.11 (m, 1H), 1.73-1.60 (m, 1H), 1.47 (s, 9H), 1.21-1.10 (m, 1H).

Step 6. To a solution of tert-butyl 1-formyl-3-azabicyclo[3.1.0]hexane-3-carboxylate (18.0 g, 85.2 mmol) and potassium carbonate (35.3 g, 256 mmol) in methanol (180 mL) was added dimethyl (1-diazo-2-oxopropyl)phosphonate (21.3 g, 111 mmol) dropwise at 0° C. The mixture was stirred at 25° C. for 1 h. The mixture was concentrated to give crude product. The crude product was purified by silica gel chromatography (petroleum ether/ethyl acetate=10/1 to 5/1) to give tert-butyl 1-ethynyl-3-azabicyclo[3.1.0]hexane-3-carboxylate (13.0 g, 74% yield) as a white solid. $^1H$ NMR (400 MHz, $CDCl_3$) δ=3.86-3.68 (m, 1H), 3.66-3.50 (m, 1H), 3.48-3.36 (m, 2H), 2.02 (s, 1H), 1.82 (br dd, J=4.0, 7.8 Hz, 1H), 1.46 (s, 9H), 1.17 (dd, J=5.2, 8.0 Hz, 1H), 0.74 (t, J=4.8 Hz, 1H).

Step 7. To a solution of 7-fluoro-6-nitroquinazolin-4-ol (50.0 g, 239 mmol) in thionyl chloride (820 g, 6.89 mol, 500 mL) was added dimethyl formamide (1.75 g, 23.9 mmol, 1.84 mL) dropwise. The mixture was stirred at 90° C. for 12 h. The mixture was concentrated to give 4-chloro-7-fluoro-6-nitroquinazoline (54.0 g, crude) as a yellow solid.

Step 8. To a solution of 4-chloro-7-fluoro-6-nitroquinazoline (54.0 g, 237 mmol) in acetonitrile (500 mL) was added 3-chloro-2-fluoroaniline (34.5 g, 237 mmol) dropwise. The mixture was stirred at 20° C. for 12 h. The mixture was concentrated to give crude product. The crude product was washed with ethyl acetate (800 mL) and filtered. The filter cake was dried to give N-(3-chloro-2-fluorophenyl)-7-fluoro-6-nitroquinazolin-4-amine (105 g, crude) as a yellow solid. m/z ES+ $[M+H]^+$ 337.0

Step 9. To a solution of N-(3-chloro-2-fluorophenyl)-7-fluoro-6-nitroquinazolin-4-amine (100 g, 297 mmol) in dimethyl formamide (500 mL) was added potassium acetate (140 g, 1.43 mol). The mixture was stirred at 100° C. for 3 h. After being cooled to room temperature, the mixture was poured into water (4.00 L). Yellow solid was precipitated from the mixture. The solid was collected by filtration and dried in vacuo to give 4-((3-chloro-2-fluorophenyl)amino)-6-nitroquinazolin-7-ol (75.0 g, crude) as a yellow solid. m/z ES+ $[M+H]^+$ 335.0

Step 10. To a suspension of 4-((3-chloro-2-fluorophenyl) amino)-6-nitroquinazolin-7-ol (30.0 g, 89.6 mmol) in dichloromethane (500 mL) was added pyridine (35.3 g, 446 mmol, 36.0 mL) and trifluoro methanesulfonic anhydride (51.3 g, 182 mmol, 30.0 mL). The mixture was stirred at 15° C. for 2 h. The mixture was diluted with dichloromethane (200 mL) and water (300 mL). The organic layer was separated and concentrated under reduced pressure. The residue was purified by column chromatography on silica gel (petroleum ether/ethyl acetate=10/1) to give 4-((3-chloro-2-fluorophenyl)amino)-6-nitroquinazolin-7-yl trifluoromethanesulfonate (14.0 g, 33% yield) as a yellow solid. m/z ES+ $[M+H]^+$ 466.9

Step 11. To a solution of 4-((3-chloro-2-fluorophenyl) amino)-6-nitroquinazolin-7-yl trifluoromethanesulfonate (15.5 g, 33.2 mmol) and tert-butyl 1-ethynyl-3-azabicyclo [3.1.0]hexane-3-carboxylate (7.23 g, 34.9 mmol) in dimethyl formamide (70.0 mL) and triethylamine (70.0 mL) was added tetrakis[triphenylphosphine]palladium(0) (1.92 g, 1.66 mmol) and copper(I) iodide (1.26 g, 6.64 mmol) in one portion under nitrogen. The mixture was stirred at 25° C. for 2 h. The mixture was diluted with water (300 mL) and extracted with ethyl acetate (3×80 mL). The combined organic layer was washed with brine (40 mL) and dried over sodium sulfate, filtered and concentrated to give crude product. The residue was purified by silica gel chromatography (petroleum ether/ethyl acetate=10/1 to 3/1) to give tert-butyl 14(4-((3-chloro-2-fluorophenyl)amino)-6-nitroquinazolin-7-yl)ethynyl)-3-azabicyclo[3.1.0]hexane-3-carboxylate (11.0 g, 63% yield) as a yellow solid. $^1H$ NMR (400 MHz, $CDCl_3$) δ=8.89 (s, 1H), 8.74 (s, 1H), 8.41-8.28 (m, 1H), 8.10 (s, 1H), 7.84 (br s, 1H), 7.33-7.29 (m, 1H), 7.25-7.18 (m, 1H), 3.98-3.80 (m, 1H), 3.76-3.61 (m, 1H), 3.60 (s, 1H), 3.55 (dd, J=4.0, 10.8 Hz, 1H), 2.11-2.07 (m, 1H), 1.48 (s, 9H), 1.43 (dd, J=5.2, 8.0 Hz, 1H), 1.00 (t, J=5.2 Hz, 1H).

Step 12. To a solution of tert-butyl 1-[2-[4-(3-chloro-2-fluoro-anilino)-6-nitro-quinazolin-7-yl]ethynyl]-3-azabicyclo[3.1.0]hexane-3-carboxylate (19.8 g, 37.8 mmol) in ethyl acetate (10 mL) was added HCl/ethyl acetate (4 M, 44 mL). The mixture was stirred at 20° C. for 2 h. On completion, the reaction was concentrated in vacuo to give a crude which was triturated with ethyl acetate (50 mL) at 25° C. for 30 min to afford 7-[2-(3-azabicyclo[3.1.0]hexan-1-yl)ethynyl]-N-(3-chloro-2-fluoro-phenyl)-6-nitro-quinazolin-4-amine (15 g, 84% yield) as a purple solid. m/z ES+ $[M+H]^+$ 424.2

Step 13. 7-[2-(3-azabicyclo[3.1.0]hexan-1-yl)ethynyl]-N-(3-chloro-2-fluoro-phenyl)-6-nitro-quinazolin-4-amine (15 g, 31.9 mmol, 90% purity) was separated by SFC (column: DAICEL CHIRALPAK AD (250 mm*30 mm, 10 um); mobile phase: [0.1% ammonium hydroxide ETOH]; B %: 45%-45%, 3.2 min; 3200 minmin) to afford 7-[2-[(1S,5R)-3-azabicyclo[3.1.0]hexan-1-yl]ethynyl]-N-(3-chloro-2-fluoro-phenyl)-6-nitro-quinazolin-4-amine (6.5 g, 41.5% yield) as a yellow solid. m/z ES+ $[M+H]^+$ 424.2; $^1H$ NMR (400 MHz, DMSO-$d_6$) δ=9.65-9.36 (m, 1H), 8.07 (br s, 1H), 7.63-7.53 (m, 2H), 7.37 (br t, J=8.0 Hz, 2H), 3.64 (d, J=11.2 Hz, 1H), 3.53-3.47 (m, 3H), 2.43-2.36 (m, 1H), 1.61 (t, J=5.6 Hz, 1H), 1.46-1.39 (m, 1H), 0.07-0.09 (m, 2H).

And 7-[2-[(1R,5S)-3-azabicyclo[3.1.0]hexan-1-yl]ethynyl]-N-(3-chloro-2-fluoro-phenyl)-6-nitro-quinazolin-4-amine (8.0 g, 49% yield) as a yellow solid. m/z ES+ $[M+H]^+$ 424.2; $^1H$ NMR (400 MHz, DMSO-$d_6$) δ=9.38 (s, 1H), 8.63 (s, 1H), 7.96 (s, 1H), 7.56 (td, J=6.8, 13.2 Hz, 2H), 7.39-7.32 (m, 1H), 3.49 (q, J=7.2 Hz, 1H), 3.13 (d, J=11.2 Hz, 1H), 2.94-2.87 (m, 3H), 1.98 (br dd, J=5.6, 7.2 Hz, 1H), 1.18 (t, J=4.8 Hz, 1H), 1.11 (t, J=6.8 Hz, 2H).

Step 14. To a solution of 7-[2-[(1S,5R)-3-azabicyclo [3.1.0]hexan-1-yl]ethynyl]-N-(3-chloro-2-fluoro-phenyl)-6-nitro-quinazolin-4-amine (6.5 g, 15.34 mmol) in trifluoroethanol (65 mL) was added HCHO (921 mg, 30.7 mmol). The mixture was stirred at 20° C. for 30 min. Then HCHO (1.34 g, 46 mmol) was added and the mixture was stirred at 20° C. for another 30 min. Then NaBH4 (580 mg, 15.3 mmol) was added, and the mixture was stirred at 60° C. for 30 min, followed by the addition of NaBH4 (580 mg, 15.3 mmol). The mixture was stirred at 60° C. for 1 h. On completion, the reaction was quenched with MeOH (200 mL) and then concentrated in vacuum. The residue was diluted with water (300 mL) and extracted with ethyl acetate (100 mL×3). The combined organic layers were washed with brine (100 mL), dried over $Na_2SO_4$, filtered and concentrated under vacuum to afford N-(3-chloro-2-fluoro-phenyl)-7-[2-[(1S,5R)-3-methyl-3-azabicyclo[3.1.0]hexan-1-yl]ethynyl]-6-nitro-quinazolin-4-amine (6.60 g, 78% yield) as a brown solid. m/z ES+ [M+H]+ 438.2

Step 15. To a solution of N-(3-chloro-2-fluoro-phenyl)-7-[2-[(1S,5R)-3-methyl-3-azabicyclo[3.1.0]hexan-1-yl] ethynyl]-6-nitro-quinazolin-4-amine (6.00 g, 13.7 mmol) in MeOH (120 mL) and $H_2O$ (30 mL) were added Fe (3.80 g, 68.5 mmol) and $NH_4C_1$ (3.7 g, 68.5 mmol). The mixture was stirred at 80° C. for 2 h. On completion, the reaction was filtered through celite and washed with MeOH (20 mL×3). The filtrate was concentrated in vacuum to give a crude product, which was purified by reversed-phase HPLC (0.1% formic acid condition) to afford N4-(3-chloro-2-fluoro-phenyl)-7-[2-[(1S,5R)-3-methyl-3-azabicyclo[3.1.0]hexan-1-yl]ethynyl]-quinazoline-4,6-diamine (4.7 g, 75% yield) as a yellow solid. m/z ES+ [M+H]+ 408.3; 1H NMR (400 MHz, DMSO-d6) δ 9.55 (s, 1H), 8.25 (s, 1H), 7.60 (s, 1H), 7.57-7.51 (m, 1H), 7.48-7.42 (m, 1H), 7.39 (s, 1H), 7.29-7.23 (m, 1H), 5.64 (s, 2H), 3.14 (d, J=8.4 Hz, 1H), 2.95-2.89 (m, 1H), 2.47 (s, 1H), 2.42 (dd, J=3.6, 8.8 Hz, 1H), 2.27 (s, 3H), 2.01-1.95 (m, 1H), 1.36 (t, J=4.2 Hz, 1H), 1.11-1.02 (m, 1H).

Step 16. To a solution of N4-(3-chloro-2-fluoro-phenyl)-7-[2-[(1S,5R)-3-methyl-3-azabicyclo[3.1.0]hexan-1-yl] ethynyl]quinazoline-4,6-diamine (3.7 g, 9.1 mmol) and acrylic acid (850 mg, 11.8 mmol) in pyridine (50 mL) was added 1-ethyl-3-(3-dimethylaminopropyl)carbodiimide (7.0 g, 36.3 mmol). The mixture was stirred at 25° C. for 1 h. On completion, the reaction was diluted with ethyl acetate (300 mL), then washed with water (100 mL×3) and brine (100 mL). The organic layer was dried over $Na_2SO_4$, filtered and concentrated under vacuum to give a crude product, which was purified by prep-HPLC (column: Phenomenex luna C18 150*40 mm*15 um; mobile phase: [water (0.225% formic acid)-acetonitrile]; B %: 5%-35%, 11 min) to afford N-[4-(3-chloro-2-fluoro-anilino)-7-[2-[(1 S, SR)-3-methyl-3 azabicyclo[3.1.0]hexan-1-yl]ethynyl]quinazolin-6-yl]prop-2-enamide (2.50 g, 51% yield) as a brown solid. m/z ES+ $[M+H]^+$ 462.2; $^1$H NMR (400 MHz, DMSO-$d_6$) δ 10.09 (s, 1H), 9.87 (s, 1H), 8.69 (s, 1H), 8.47 (s, 1H), 7.80 (s, 1H), 7.49 (br s, 2H), 7.28 (t, J=8.0 Hz, 1H), 6.61 (dd, J=16.8, 10.0 Hz, 1H), 6.37-6.30 (m, 1H), 5.86 (dd, J=10.4, 1.6 Hz, 1H), 3.11 (d, J=8.4 Hz, 1H), 2.93 (d, J=9.2 Hz, 1H), 2.45-2.35 (m, 2H), 2.26 (s, 3H), 1.96-1.90 (m, 1H), 1.38 (t, J=4.4 Hz, 1H), 1.03 (dd, J=8.0, 4.0 Hz, 1H).

Example 44. Synthesis of Compound No. 50 (N-(4-((3-chloro-2-fluorophenyl)amino)-7-(((1R,5S)-3-(oxetan-3-yl)-3-azabicyclo[3.1.0]hexan-1-yl)ethynyl)quinazolin-6-yl)acrylamide)

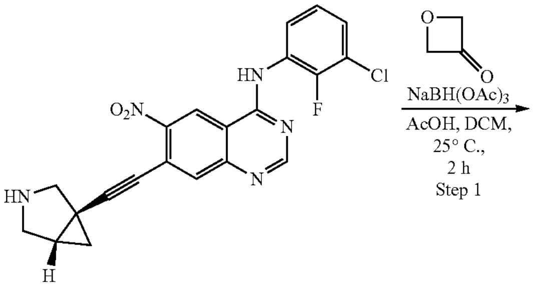

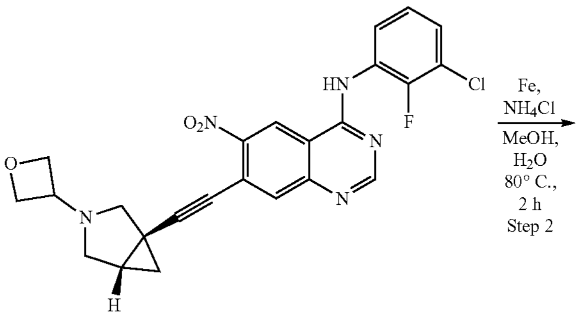

-continued

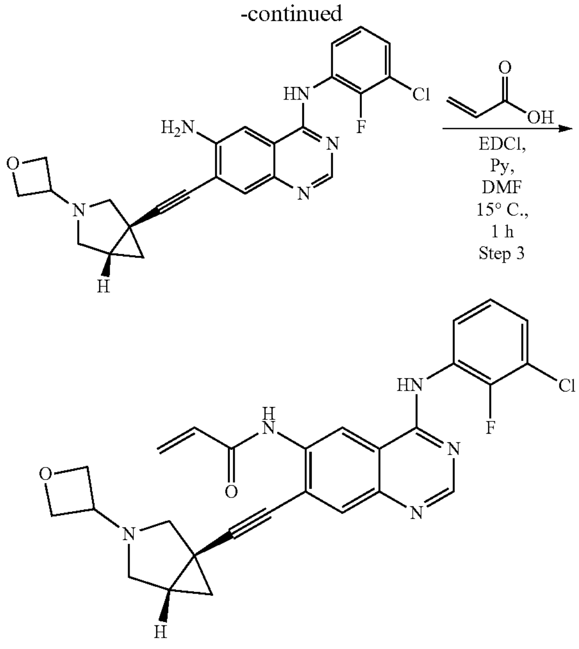

Step 1. A mixture of 7-((1R,5S)-3-azabicyclo[3.1.0] hexan-1-ylethynyl)-N-(3-chloro-2-fluorophenyl)-6-nitro-quinazolin-4-amine (1.35 g, 3.19 mmol), oxetan-3-one (1.38 g, 19.1 mmol) and acetic acid (105 mg, 1.75 mmol, 0.100 mL) in dichloromethane (10.0 mL) was added sodium triacetoxyhydroborate (4.05 g, 19.1 mmol) in portions at 25° C. The mixture was stirred at 25° C. for 2 h. The mixture was diluted with water (100 mL) and extracted with dichloromethane (3×80.0 mL). The combined organic layer was washed with brine (40.0 mL), dried over sodium sulfate, filtered and concentrated in vacuum. The residue was purified by silica gel chromatography (petroleum ether/ethyl acetate=0/1) to give N-(3-chloro-2-fluorophenyl)-6-nitro-7-4(1R,5S)-3-(oxetan-3-yl)-3-azabicyclo[3.1.0]hexan-1-yl) ethynyl)quinazolin-4-amine (500 mg, 33% yield) as a yellow solid. $^1$H NMR (400 MHz, DMSO-$d_6$) δ=10.60 (br s, 1H), 9.39 (br s, 1H), 8.64 (br s, 1H), 7.96 (br s, 1H), 7.54 (br d, J=7.2 Hz, 2H), 7.31 (br t, J=7.6 Hz, 1H), 4.55 (dt, J=2.8, 6.8 Hz, 2H), 4.47-4.43 (m, 2H), 4.09 (q, J=5.2 Hz, 1H), 3.76 (t, J=6.4 Hz, 1H), 3.17 (d, J=5.2 Hz, 2H), 2.97 (d, J=8.8 Hz, 1H), 2.09-2.00 (m, 1H), 1.45 (t, J=4.4 Hz, 1H), 1.09 (dd, J=4.0, 8.0 Hz, 1H).

Step 2. To a solution of N-(3-chloro-2-fluorophenyl)-6-nitro-7-(((1R,5S)-3-(oxetan-3-yl)-3-azabicyclo[3.1.0] hexan-1-yl)ethynyl)quinazolin-4-amine (500 mg, 1.04 mmol), ammonium chloride (390 mg, 7.29 mmol) in methanol (8.00 mL) and water (2.00 mL) was added iron powder (291 mg, 5.21 mmol) in portions. The mixture was stirred at 80° C. for 2 h. The mixture was filtered. The filtrate was concentrated in vacuum. The residue was diluted with water (80.0 mL) and extracted with ethyl acetate (3×80.0 mL). The combined organic layer was washed with brine (30.0 mL), dried over sodium sulfate, filtered and concentrated in vacuum to give $N^4$-(3-chloro-2-fluorophenyl)-7-(((1R,5S)-3-(oxetan-3-yl)-3-azabicyclo[3.1.0]hexan-1-yl)ethynyl)-quinazoline-4,6-diamine (480 mg, crude) as a yellow solid. m/z ES+ $[M+H]^+$ 424.2

Step 3. To a solution of $N^4$-(3-chloro-2-fluorophenyl)-7-(((1R,5S)-3-(oxetan-3-yl)-3-azabicyclo[3.1.0]hexan-1-yl) ethynyl)quinazoline-4,6-diamine (430 mg, 956 umol), acrylic acid (82.6 mg, 1.15 mmol, 78.7 uL), pyridine (302 mg, 3.82 mmol, 309 uL) in dimethyformamide (4.00 mL) was added 1-(3-dimethylaminopropyl)-3-ethylcarbodiimide hydrochloride (733 mg, 3.82 mmol) in portions. The mixture was stirred at 15° C. for 1 h. The mixture was filtered. The filtrate was purified by prep-HPLC (column: Waters Xbridge C18 150*50 mm*10 um; mobile phase: [water (10 mM $NH_4HCO_3$)-acetonitrile]; B %: 33%-63%, 11.5 min) and lyophilized to give N-(4-((3-chloro-2-fluorophenyl)amino)-7-(((1R,5 S)-3-(oxetan-3-yl)-3-azabicyclo[3.1.0]hexan-1-yl)ethynyl)quinazolin-6-yl)acrylamide (88.7 mg, 18% yield) as a yellow solid. m/z ES+ $[M+H]^+$ 504.3; $^1H$ NMR (400 MHz, $CDCl_3$) δ=9.17 (s, 1H), 8.72 (s, 1H), 8.44-8.15 (m, 2H), 7.93 (s, 1H), 7.82 (br s, 1H), 7.25-7.07 (m, 2H), 6.55-6.41 (m, 1H), 6.39-6.25 (m, 1H), 5.99-5.84 (m, 1H), 4.70 (td, J=3.2, 6.8 Hz, 2H), 4.62 (dt, J=4.0, 6.4 Hz, 2H), 3.83 (t, J=6.4 Hz, 1H), 3.41 (s, 1H), 3.25 (d, J=8.0 Hz, 1H), 3.05 (d, J=8.8 Hz, 1H), 2.66-2.54 (m, 2H), 2.00 (dd, J=4.0, 8.0 Hz, 1H), 1.64 (t, J=4.4 Hz, 1H), 1.12 (dd, J=4.4, 8.0 Hz, 1H).

Example 45. Synthesis of Compound No. 51 (N-(4-((3-chloro-2-fluorophenyl)amino)-7-(((1R,5S)-3-methyl-3-azabicyclo[3.1.0]hexan-1-yl)ethynyl)quinazolin-6-yl)acrylamide)

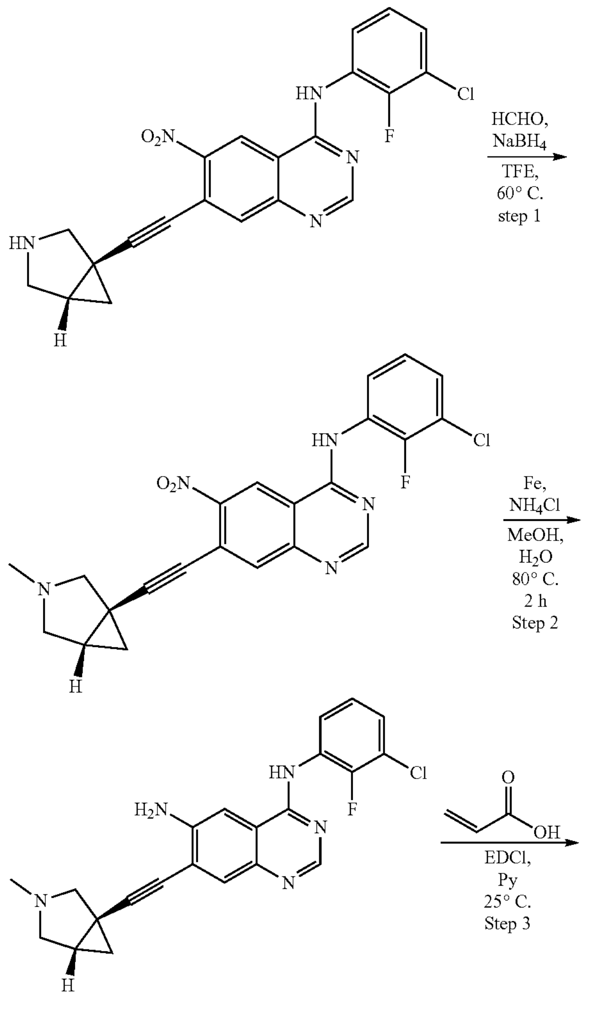

-continued

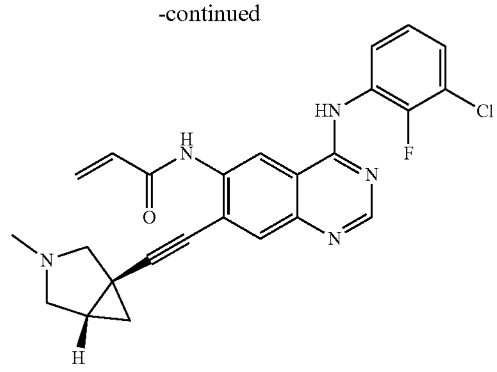

Step 1. To a solution of 7-[2-[(1R,5S)-3-azabicyclo[3.1.0]hexan-1-yl]ethynyl]-N-(3-chloro-2-fluoro-phenyl)-6-nitro-quinazolin-4-amine (6.60 g, 15.6 mmol) in trifluoroethanol (65 mL) was added HCHO (2.34 g, 77.9 mmol) in portions. The mixture was stirred at 60° C. for 0.5 h. Then the mixture was added $NaBH_4$ (1.18 g, 31.1 mmol) in portions at 60° C. and stirred at 60° C. for 13.5 h. On completion, the mixture was added methanol (100 mL) and concentrated to give a residue. The residue was diluted with water (300 mL) and extracted with ethyl acetate (3×200 mL). The combined organic layer was washed with brine (100 mL) and dried over anhydrous sodium sulfate, filtered and concentrated to give the N-(3-chloro-2-fluoro-phenyl)-7-[2-[(1R,5S)-3-methyl-3-azabicyclo[3.1.0]hexan-1-yl]ethynyl]-6-nitro-quinazolin-4-amine (6.20 g, crude) as a brown solid which was used for the next step without purification. m/z ES+ $[M+H]^+$ 438.2

Step 2. A solution of N-(3-chloro-2-fluoro-phenyl)-7-[2-[(1R,5S)-3-methyl-3-azabicyclo[3.1.0]hexan-1-yl]ethynyl]-6-nitro-quinazolin-4-amine (5.7 g, 11.2 mmol) and Fe (3.13 g, 56 mmol), $NH_4C_1$ (4.79 g, 90 mmol) in ethanol (100 mL) and $H_2O$ (25 mL) was stirred at 80° C. for 1 h. The mixture was quenched with methanol (50 mL) and concentrated to dryness to give a residue. The residue was diluted with ethyl acetate (200 mL) and washed with water (200 mL), dried over anhydrous sodium sulfate, filtered and concentrated in vacuum to give the crude. The crude was purified by reverse-phase flash (0.1% trifluoroacetic acid) to give N4-(3-chloro-2-fluoro-phenyl)-7-[2-[(1R,5S)-3-methyl-3-azabicyclo[3.1.0]hexan-1-yl]ethynyl]quinazoline-4,6-diamine (3.20 g, 68% yield) as a yellow solid. m/z ES+ $[M+H]^+$ 408.3; $^1H$ NMR (400 MHz, DMSO-$d_6$) δ 9.52 (s, 1H), 8.23 (s, 1H), 7.59 (s, 1H), 7.53-7.51 (m, 1H), 7.46-7.42 (m, 1H), 7.37 (s, 1H), 7.27-7.25 (m, 1H), 5.62 (s, 2H), 3.12 (d, J=8.4 Hz, 1H), 2.92 (d, J=9.2 Hz, 1H), 2.46-2.39 (m, 2H), 2.25 (s, 3H), 1.98-1.97 (m, 1H), 1.35-1.33 (m, 1H), 1.07-1.05 (m, 1H).

Step 3. A solution of N4-(3-chloro-2-fluoro-phenyl)-7-[2-[(1R,5S)-3-methyl-3-azabicyclo[3.1.0]hexan-1-yl]ethynyl]quinazoline-4,6-diamine (3.00 g, 7.36 mmol), acrylic acid (689 mg, 9.56 mmol), 1-ethyl-3-(3-dimethylaminopropyl)carbodiimide (5.64 g, 29.4 mmol) in pyridine (40 mL) was stirred at 10° C. for 0.5 h and then stirred at 25° C. for another 1 h. On completion, the reaction mixture was quenched with water (500 mL) and then extracted with ethyl acetate (500 mL×2). The organic layers were collected and then dried, filtered and concentrated to give the crude. The crude was purified by Prep-HPLC (formic acid:column: Phenomenex luna $C_{18}$ 150*40 mm*15 um; mobile phase: [water (0.225% formic acid)-acetonitrile]; B %: 5%-35%, 11 min) to give the first batch of product and another batch of product. Then the two batch of product were combined, and recrystallized with ethyl acetate (150 mL) to give the N-[4-(3-chloro-2-fluoro-anilino)-7-[2-[(1R,5S)-3-methyl-3-azabicyclo[3.1.0]hexan-1-yl]ethynyl]-quinazolin-6-yl]prop-2-enamide (1.34 g, 39% yield) as a yellow solid. m/z ES+ $[M+H]^+$ 462.1; $^1H$ NMR (400 MHz, DMSO-$d_6$) δ 9.20 (s, 1H), 8.74 (s, 1H), 8.42-8.32 (m, 2H), 7.95 (s, 1H), 7.65 (s, 1H), 7.20-7.16 (m, 2H), 6.53-6.49 (m, 1H), 6.35-6.28 (m, 1H), 5.93-5.91 (m, 1H), 3.27 (d, J=8.4 Hz, 1H), 3.06 (d, J=8.8 Hz, 1H), 2.58-2.53 (m, 2H), 2.38 (s, 3H), 1.96-1.94 (m, 1H), 1.60-1.57 (m, 1H), 1.10-1.07 (m, 1H).

Example 46. Synthesis of Compound No. 52 (N-(4-((3-chloro-2-fluorophenyl)amino)-7-((3-methoxy-1-methylpyrrolidin-3-yl)ethynyl)quinazolin-6-yl)acrylamide)

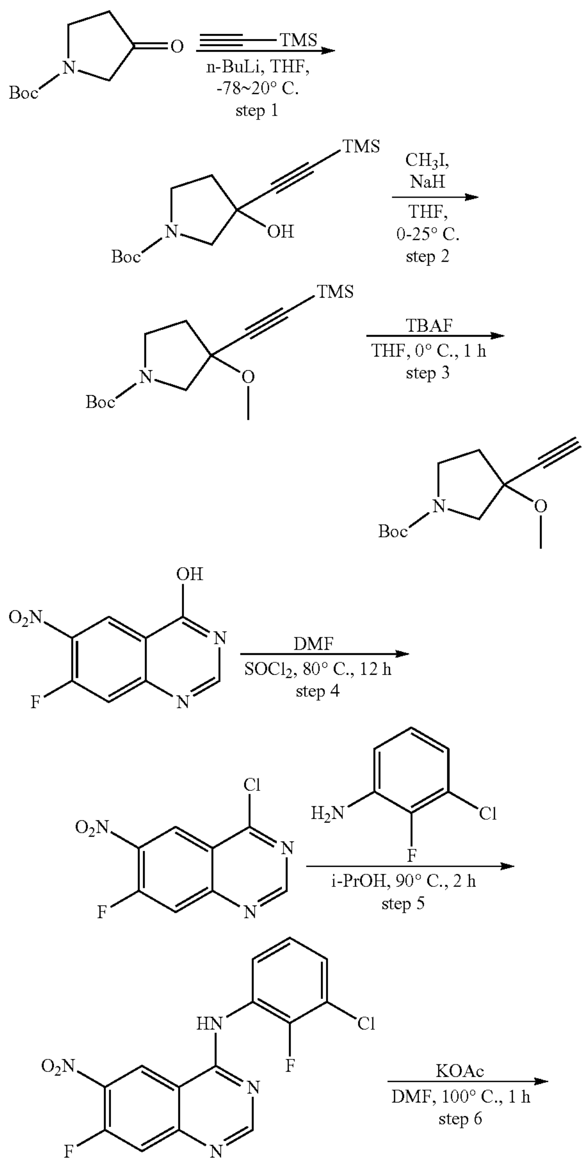

-continued

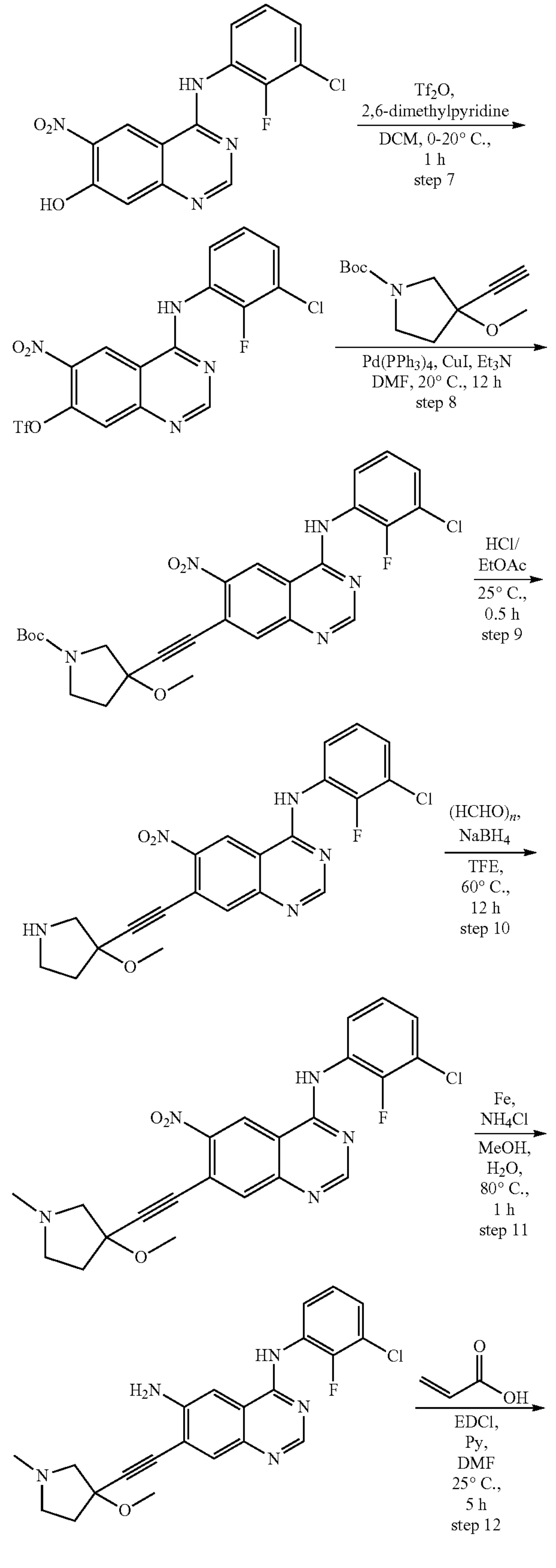

-continued

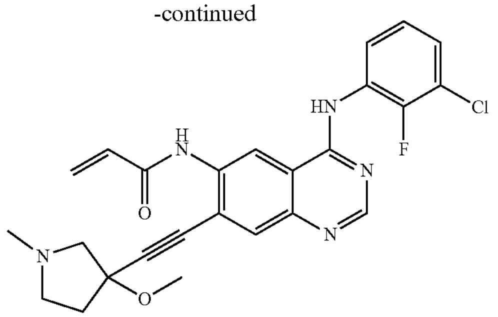

Step 1. To a solution of ethynyltrimethylsilane (1.59 g, 16.2 mmol, 2.24 mL) in tetrahydrofuran (70.0 mL) was added n-butyllithium (2.50 M, 6.48 mL). The mixture was stirred at −78° C. for 30 min. A solution of tert-butyl 3-oxopyrrolidine-1-carboxylate (2.50 g, 13.5 mmol) in tetrahydrofuran (10.0 mL) was added to the reaction through an addition funnel over 10 min. The mixture was stirred at 20° C. for 40 min. The reaction was quenched by addition of saturated ammonium chloride (15.0 mL), then extracted with ethyl acetate (3×50.0 mL). The combined organic layers were dried over anhydrous sodium sulfate, filtered and concentrated under reduced pressure to give a residue. The residue was purified by flash silica gel chromatography (ISCO®; 80 g SepaFlash® Silica Flash Column, Eluent of 0-4% Methanol/Dichloromethane @ 50 mL/min) to give tert-butyl 3-hydroxy-3-((trimethylsilyl)ethynyl) pyrrolidine-1-carboxylate (3.70 g, 97% yield) as a yellow oil. $^1$H NMR (400 MHz, $CDCl_3$) δ=5.31 (s, 1H), 3.64-3.54 (m, 2H), 3.53-3.39 (m, 2H), 2.24-2.09 (m, 2H), 1.48-1.41 (m, 9H), 0.26-0.07 (m, 9H).

Step 2. The tert-butyl 3-hydroxy-3-((trimethylsilyl)ethynyl)pyrrolidine-1-carboxylate (2.70 g, 9.53 mmol) was dissolved in tetrahydrofuran (50.0 mL) under an atmosphere of nitrogen and cooled to 0° C. in an ice bath. The sodium hydride (572 mg, 14.3 mmol, 60.0% purity) was added and the resulting suspension was stirred at 0° C. for 30 min. Iodomethane (4.06 g, 28.6 mmol, 1.78 mL) was then added and the reaction was allowed to slowly warm to 25° C. The mixture was stirred at 25° C. for 3 h. The reaction was quenched by addition of saturated ammonium chloride (50.0 mL), then extracted with ethyl acetate (3×50.0 mL). The combined organic layers were dried over anhydrous sodium sulfate, filtered and concentrated under reduced pressure to give a residue. The residue was purified by flash silica gel chromatography (ISCO®; 20 g SepaFlash® Silica Flash Column, Eluent of 0-4% methanol/dichloromethane gradient @ 30 mL/min) to give tert-butyl 3-methoxy-3-((trimethylsilyl)ethynyl) pyrrolidine-1-carboxylate (1.90 g, 67% yield) as a light yellow oil. $^1$H NMR (400 MHz, $CDCl_3$) δ=3.71-3.57 (m, 1H), 3.51-3.40 (m, 3H), 3.35 (s, 3H), 2.24-2.03 (m, 2H), 1.45 (s, 9H), 0.17 (s, 9H).

Step 3. To a solution of tert-butyl 3-methoxy-3-((trimethylsilyl)ethynyl)pyrrolidine-1-carboxylate (2.18 g, 7.33 mmol) in tetrahydrofuran (10.0 mL) was added tetrabutylammonium fluoride (1.00 M, 14.7 mL). The mixture was stirred at 0° C. for 1 h. The reaction mixture was extracted with water (20.0 mL) and ethyl acetate (2×30.0 mL), dried over anhydrous sodium sulfate, filtered and concentrated under reduced pressure to remove solvent. The residue was purified by flash silica gel chromatography (ISCO®; 40 g SepaFlash® Silica Flash Column, eluent of 0-4% Methanol/Dichloromethane gradient @ 30 mL/min) to give tert-butyl 3-ethynyl-3-methoxypyrrolidine-1-carboxylate (1.30 g, 79% yield) as a light yellow solid. $^1$H NMR (400 MHz, CD3OD) δ=3.62 (dd, J=8.4, 10.4 Hz, 1H), 3.50-3.40 (m, 2H), 3.37 (s, 3H), 3.35 (br d, J=3.6 Hz, 1H), 3.10 (s, 1H), 2.33-2.05 (m, 2H), 1.46 (s, 9H).

Step 4. To a solution of 7-fluoro-6-nitroquinazolin-4-ol (10.0 g, 47.8 mmol) in thionyl chloride (100 mL) was added dropwise dimethyl formamide (350 mg, 4.78 mmol, 368 uL) as catalyst. The mixture was heated to 80° C. and stirred for 12 h. Upon completion, the reaction mixture was concentrated under reduced pressure to remove thionyl chloride to give the crude product 4-chloro-7-fluoro-6-nitroquinazoline (12.5 g, crude) as a white solid and used for next step directly without purification.

Step 5. To a solution of 4-chloro-7-fluoro-6-nitroquinazoline (12.5 g, 54.9 mmol) in isopropanol (150 mL) was added 3-chloro-2-fluoroaniline (8.79 g, 60.4 mmol). The mixture was stirred at 90° C. for 2 h. The mixture was concentrated to afford a yellow solid which was triturated with ethyl acetate (100 mL). After filtration, the filter cake was washed with ethyl acetate (40.0 mL), dried in vacuum to afford N-(3-chloro-2-fluorophenyl)-7-fluoro-6-nitroquinazolin-4-amine (18.8 g, crude) as a yellow solid.

Step 6. To a solution of N-(3-chloro-2-fluorophenyl)-7-fluoro-6-nitroquinazolin-4-amine (18.8 g, 55.8 mmol) in dimethyl formamide (200 mL) was added potassium acetate (27.4 g, 279 mmol) at 15° C. The mixture was stirred at 100° C. for 1 h. The mixture was concentrated to afford a residue. The residue was triturated with water (20.0 mL). After filtration, the filter cake was washed with water (50.0 mL), dried in vacuum to remove solvent. The residue was purified by flash silica gel chromatography (ISCO®; 330 g SepaFlash® Silica Flash Column, Eluent of 0-4% Methanol/Dichloromethane gradient@ 100 mL/min) to give 4-((3-chloro-2-fluorophenyl)amino)-6-nitroquinazolin-7-ol (3.80 g, 13% yield) as a brown solid. $^1$H NMR (400 MHz, $CDCl_3$) δ=10.46 (br s, 1H), 8.96 (s, 1H), 8.78 (s, 1H), 8.30 (br t, J=7.2 Hz, 1H), 8.03 (s, 1H), 7.58 (s, 1H), 7.24-7.17 (m, 1H).

Step 7. To a solution of 4-((3-chloro-2-fluorophenyl) amino)-6-nitroquinazolin-7-ol (2.00 g, 5.98 mmol) and 2,6-dimethylpyridine (2.56 g, 23.9 mmol, 2.78 mL) in dichloromethane (40.0 mL) was added trifluoromethanesulfonic anhydride (3.37 g, 12.0 mmol, 1.97 mL) at 0° C. The mixture was stirred at 20° C. for 1 h. Upon completion, the reaction mixture was concentrated under reduced pressure to remove solvent. The residue was purified by flash silica gel chromatography (ISCO®; 80 g SepaFlash® Silica Flash Column, Eluent of 0100% Ethyl acetate/Petroleum ether gradient @ 60 mL/min) to give 4-((3-chloro-2-fluorophenyl) amino)-6-nitroquinazolin-7-yl trifluoromethanesulfonate (590 mg, 21% yield) as a yellow solid. $^1$H NMR (400 MHz, MeOD) δ=9.51 (s, 1H), 8.66 (br s, 1H), 7.91 (s, 1H), 7.58-7.52 (m, 1H), 7.46 (br t, J=7.2 Hz, 1H), 7.26 (dt, J=1.2, 8.0 Hz, 1H).

Step 8. To a solution of 4-((3-chloro-2-fluorophenyl) amino)-6-nitroquinazolin-7-yl trifluoromethanesulfonate (590 mg, 1.26 mmol), tert-butyl 3-ethynyl-3-methoxypyrrolidine-1-carboxylate (313 mg, 1.39 mmol), copper iodide (48.2 mg, 253 umol) and triethylamine (4.28 g, 42.4 mmol, 5.89 mL) in dimethyl formamide (5.00 mL) was added tetrakis(triphenylphosphine)palladium(0) (146 mg, 126 umol). The mixture was degassed and purged with nitrogen for 3 times, and then the mixture was stirred at 20° C. for 12 h under nitrogen atmosphere. Upon completion, the reaction mixture was concentrated under reduced pressure to remove solvent. The residue was purified by flash silica gel chromatography (ISCO®; 20 g SepaFlash® Silica Flash Column, Eluent of 0-50% Ethyl acetate/Petroleum ether gradient @ 30 mL/min) to give tert-butyl 3-((4-((3-chloro-2-fluorophenyl)amino)-6-nitroquinazolin-7-yl) ethynyl)-3-methoxypyrrolidine-1-carboxylate (480 mg, 58% yield) as a yellow solid. $^1$H NMR (400 MHz, $CDCl_3$) δ=8.90 (s, 1H), 8.82 (d, J=2.4 Hz, 1H), 8.35-8.24 (m, 1H), 8.17 (d, J=4.0 Hz, 1H), 7.98-7.85 (m, 1H), 7.25-7.17 (m, 1H), 3.87-3.56 (m, 3H), 3.53 (s, 3H), 3.52 (br s, 1H), 2.46-2.23 (m, 2H), 1.49 (s, 9H).

Step 9. To a solution of tert-butyl 3-((4-((3-chloro-2-fluorophenyl)amino)-6-nitroquinazolin-7-yl)ethynyl)-3-methoxypyrrolidine-1-carboxylate (480 mg, 886 umol) in hydrochloric acid/ethyl acetate (4.00 M, 5.00 mL) was stirred at 15° C. for 0.5 h. The reaction mixture was concentrated to afford product as a hydrochloride which was freed with saturated sodium carbonate (5.00 mL) and extracted with ethyl acetate (30.0 mL). The organic layer was washed with water (10.0 mL), dried over anhydrous sodium sulfate, filtered and concentrated under reduced pressure to afford N-(3-chloro-2-fluorophenyl)-7-((3-methoxypyrrolidin-3-yl)ethynyl)-6-nitroquinazolin-4-amine (400 mg, crude) as a yellow solid.

Step 10. To a solution of paraformaldehyde (125 mg, 4.18 mmol) and N-(3-chloro-2-fluorophenyl)-7-((3-methoxypyrrolidin-3-yl)ethynyl)-6-nitroquinazolin-4-amine (400 mg, 836 umol) in 2,2,2-trifluoroethanol (10.0 mL) was added sodium borohydride (63.3 mg, 1.67 mmol) at 60° C. The mixture was stirred at 60° C. for 12 h. The mixture was concentrated to afford a residue. The residue was diluted with saturated sodium carbonate (20.0 mL) and water (20.0 mL), extracted with ethyl acetate (3×20.0 mL). The combined organic layers were washed with water (20.0 mL), dried over anhydrous sodium sulfate, filtered and the filtrate was concentrated under reduced pressure to afford N-(3-chloro-2-fluorophenyl)-7-((3-methoxy-1-methylpyrrolidin-3-yl)ethynyl)-6-nitroquinazolin-4-amine (400 mg, crude) as a brown solid.

Step 11. To a solution of N-(3-chloro-2-fluorophenyl)-7-((3-methoxy-1-methylpyrrolidin-3-yl)ethynyl)-6-nitroquinazolin-4-amine (400 mg, 877 umol) and ammonium chloride (530 mg, 9.92 mmol) in methanol (5.00 mL) and water (5.00 mL) was added iron powder (429 mg, 7.68 mmol) at 20° C. The mixture was stirred at 80° C. for 1 h. The mixture was diluted with saturated sodium carbonate (10.0 mL) and water (20.0 mL), extracted with ethyl acetate (3×20.0 mL). The combined organic layers were dried over anhydrous sodium sulfate, filtered and the filtrate was concentrated under reduced pressure to afford $N^4$-(3-chloro-2-fluorophenyl)-7-((3-methoxy-1-methylpyrrolidin-3-yl)ethynyl)quinazoline-4,6-diamine (330 mg, 88% yield) as a brown solid.

Step 12. To a solution of $N^4$-(3-chloro-2-fluorophenyl)-7-((3-methoxy-1-methylpyrrolidin-3-yl)ethynyl)quinazoline-4,6-diamine (310 mg, 728 umol) and pyridine (230 mg, 2.91 mmol, 235 uL) in dimethyl formamide (4.00 mL) was added 1-(3-dimethylaminopropyl)-3-ethylcarbodiimide hydrochloride (279 mg, 1.46 mmol) and acrylic acid (78.7 mg, 1.09 mmol, 74.9 uL) at 0° C. The mixture was stirred at 25° C. for 5 h. Upon completion, the reaction mixture was concentrated under reduced pressure to remove solvent. The residue was purified by prep-HPLC (Xtimate C18 100*30 mm*3 um; water (0.04% ammonium hydroxide+10 mM $NH_4HCO_3$)-acetonitrile; B: 38° 4-68%) and further purified by prep-HPLC (column: Shim-pack C18 150*25*10 um; mobile phase: [water (0.225% formic acid)-acetonitrile]; B %: 15%-35%, 10 min). The eluent was concentrated to remove organic solvent and the residual aqueous solution was lyophilized to give N-(4-((3-chloro-2-fluorophenyl) amino)-7-((3-methoxy-1-methylpyrrolidin-3-yl)ethynyl)

quinazolin-6-yl) acrylamide (5.42 mg, 2% yield) as a yellow solid. m/z ES+ $[M+H]^+$ 480.0; $^1$H NMR (400 MHz, MeOD) δ=8.67 (s, 1H), 8.50 (br s, 2H), 7.98 (s, 1H), 7.57 (br t, J=6.4 Hz, 1H), 7.44 (br t, J=6.8 Hz, 1H), 7.25 (dt, J=1.6, 8.0 Hz, 1H), 6.67-6.56 (m, 1H), 6.53-6.46 (m, 1H), 5.92 (dd, J=2.0, 10.0 Hz, 1H), 3.50 (s, 3H), 3.48-3.43 (m, 1H), 3.40-3.35 (m, 1H), 3.29-3.16 (m, 2H), 2.75 (s, 3H), 2.57-2.49 (m, 2H).

Example 47. Synthesis of Compound No. 53 ((S)—N-(4-((3-chloro-2-fluorophenyl)amino)-7-((1,3-dimethylpiperidin-3-yl)ethynyl)quinazolin-6-yl)acrylamide)

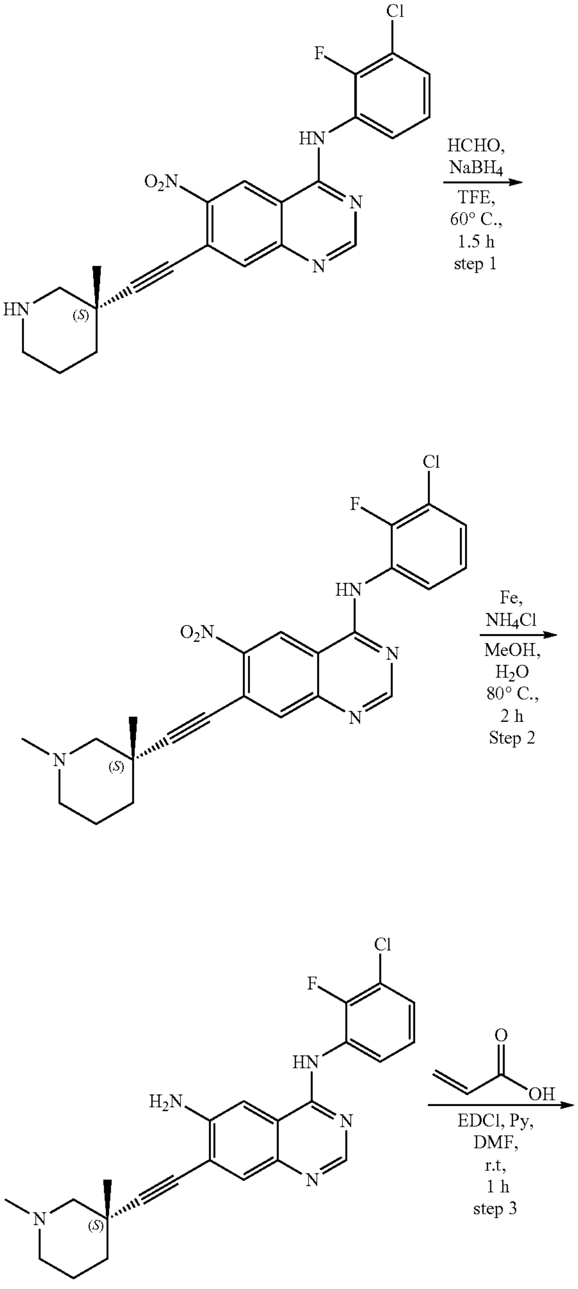

-continued

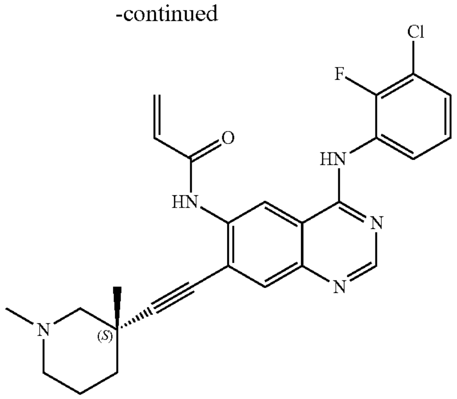

Step 1. To a solution of (S)—N-(3-chloro-2-fluorophenyl)-7-((3-methylpiperidin-3-yl)ethynyl)-6-nitroquinazolin-4-amine (650 mg, 1.48 mmol) in 2,2,2-trifluoroethanol (6.00 mL) was added paraformaldehyde (222 mg, 7.39 mmol, 204 uL) in portions and the mixture was stirred at 60° C. for 0.5 h. Then the mixture was added sodium borohydride (112 mg, 2.96 mmol) in portions at 60° C. The mixture was stirred at 60° C. for 1 h. The mixture was quenched with methanol (50.0 mL) and concentrated in vacuum. The residue was diluted with water (100 mL) and extracted with ethyl acetate (3×60.0 mL). The combined organic layer was washed with brine (40.0 mL), dried over sodium sulfate, filtered and concentrated in vacuum to give (S)—N-(3-chloro-2-fluorophenyl)-7-((1,3-dimethylpiperidin-3-yl)ethynyl)-6-nitroquinazolin-4-amine (720 mg, crude) as a yellow solid. $^1$H NMR (400 MHz, DMSO-$d_6$) δ=10.82-10.51 (m, 1H), 9.33 (br s, 1H), 8.60 (br s, 1H), 7.89 (s, 1H), 7.55-7.47 (m, 2H), 7.30 (t, J=8.0 Hz, 1H), 2.76-2.64 (m, 1H), 2.56 (br s, 1H), 2.17 (s, 3H), 1.99 (s, 2H), 1.86-1.76 (m, 2H), 1.60 (dt, J=4.4, 7.6 Hz, 1H), 1.39-1.32 (m, 1H), 1.31 (s, 3H).

Step 2. To a solution of (S)—N-(3-chloro-2-fluorophenyl)-7-((1,3-dimethylpiperidin-3-yl)ethynyl)-6-nitroquinazolin-4-amine (720 mg, 1.59 mmol), ammonium chloride (594 mg, 11.1 mmol) in methanol (8.00 mL) and water (2.00 mL) was added iron powder (443 mg, 7.93 mmol) in portions. The mixture was stirred at 80° C. for 2 h. The mixture was filtered. The filtrate was concentrated in vacuum. The residue was diluted with water (80.0 mL) and extracted with ethyl acetate (3×60.0 mL). The combined organic layer was washed with brine (30.0 mL), dried over sodium sulfate, filtered and concentrated in vacuum to give (S)—$N^4$-(3-chloro-2-fluorophenyl)-7-((1,3-dimethylpiperidin-3-yl)ethynyl) quinazoline-4,6-diamine (550 mg, crude) as a yellow solid. m/z ES+ $[M+H]^+$ 424.2

Step 3. To a solution of (S)—$N^4$-(3-chloro-2-fluorophenyl)-7-((1,3-dimethylpiperidin-3-yl)ethynyl)quinazoline-4,6-diamine (500 mg, 1.18 mmol), acrylic acid (93.5 mg, 1.30 mmol, 89.0 uL), pyridine (373 mg, 4.72 mmol, 381 uL) in dimethyformamide (3.00 mL) was added 1-(3-dimethylaminopropyl)-3-ethylcarbodiimide hydrochloride (904 mg, 4.72 mmol) in portions. The mixture was stirred at 20° C. for 1 h. The mixture was diluted with water (100 mL) and extracted with ethyl acetate (3×80.0 mL). The combined organic layer was washed with brine (40.0 mL), dried over sodium sulfate, filtered and concentrated in vacuum. The residue was purified by prep-HPLC (column: Waters Xbridge C18 150*50 mm*10 um; mobile phase: [water (10 mM $NH_4HCO_3$)-acetonitrile]; B %: 45%-75%, 11.5 min) to give crude product which purified by prep-HPLC (column: Shim-pack C18 150*25*10 um; mobile phase: [water (0.225% formic acid)-acetonitrile]; B %: 16%-36%, 9 min) and lyophilized to give (S)—N-(4-((3-chloro-2-fluorophenyl) amino)-7-((1,3-dimethylpiperidin-3-yl)ethynyl)quinazolin-6-yl)acrylamide (102.46 mg, 18% yield) as a yellow solid. m/z ES+$[M+H]^+$ 478.3; $^1$H NMR (400 MHz, $CDCl_3$) δ=9.72 (br s, 1H), 9.11 (s, 1H), 8.70 (s, 1H), 8.39 (s, 1H), 8.19 (br d, J=7.2 Hz, 1H), 8.11-7.95 (m, 1H), 7.92 (s, 1H), 7.93-7.86 (m, 1H), 7.21-7.08 (m, 2H), 6.54 (d, J=6.0 Hz, 2H), 5.85-5.79 (m, 1H), 3.25 (br d, J=7.2 Hz, 1H), 3.18 (br d, J=11.6 Hz, 1H), 2.53 (s, 3H), 2.19-2.08 (m, 3H), 2.03 (br d, J=14.8 Hz, 1H), 1.83-1.75 (m, 1H), 1.42 (s, 3H), 1.39-1.30 (m, 1H).

Example 48. Synthesis of Compound No. 54 ((R)—N-(4-((3-chloro-2-fluorophenyl)amino)-7-((1,3-dimethylpiperidin-3-yl)ethynyl)quinazolin-6-yl) acrylamide)

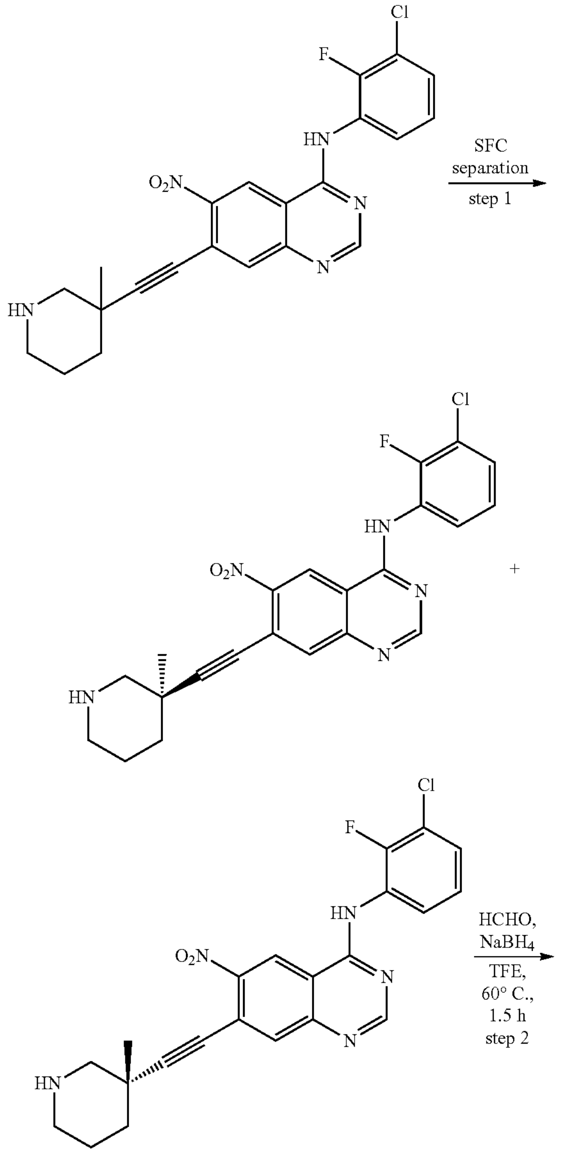

-continued

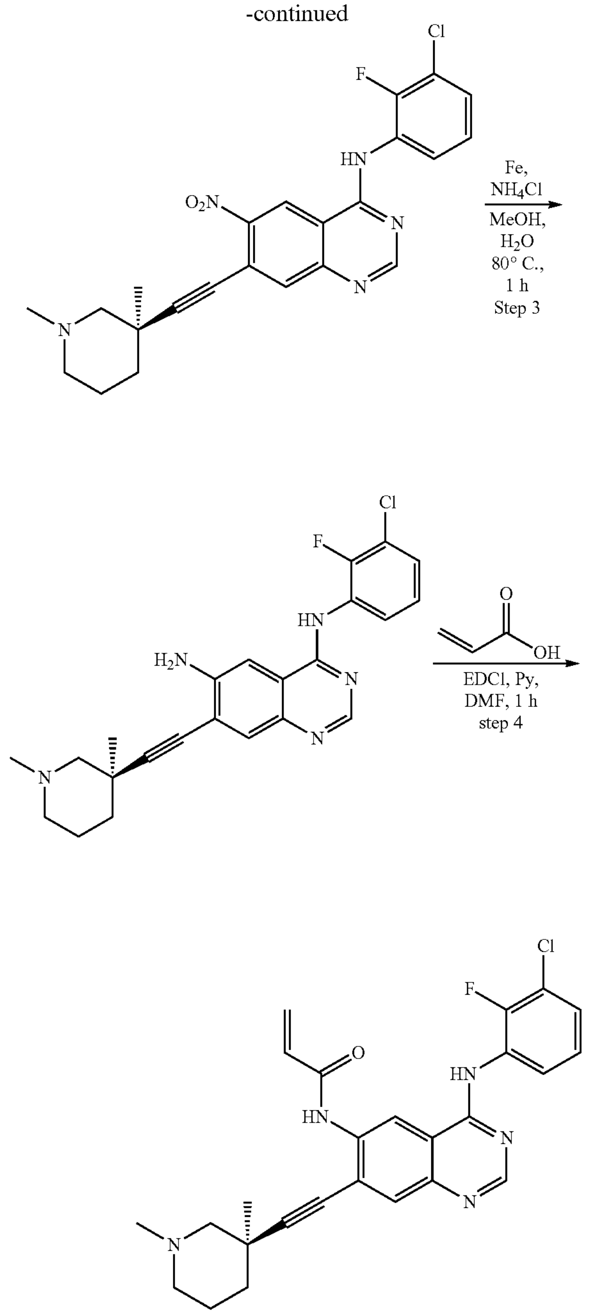

Step 1. The N-(3-chloro-2-fluorophenyl)-7-((3-methylpiperidin-3-yl)ethynyl)-6-nitroquinazolin-4-amine (1.70 g, 3.86 mmol) was separated by SFC separation (column: DAICEL CHIRALPAK AD (250 mm*30 mm, 10 um); mobile phase: [0.1% ammonium hydroxide in methanol]) and further separated by SFC separation (column: DAICEL CHIRALPAK AD-H (250 mm*30 mm, 5 um); mobile phase: [0.1% ammonium hydroxide IPA]; B %: 30%-30%, 7.5 min; 160 min) to give (R)—N-(3-chloro-2-fluorophenyl)-7-((3-methylpiperidin-3-yl)ethynyl)-6-nitroquinazolin-4-amine (800 mg, 47% yield, 94% ee) as a yellow solid and (S)—N-(3-chloro-2-fluorophenyl)-7-((3-methylpiperidin-3-yl)ethynyl)-6-nitroquinazolin-4-amine (700 mg, 41% yield, 98% ee) as a yellow solid. 41 NMR (400 MHz, DMSO-$d_6$) δ=10.81 (br s, 1H), 9.65-9.32 (m, 1H), 8.67 (br s, 1H), 8.28 (br s, 1H), 7.61-7.48 (m, 2H), 7.35-7.17 (m, 2H), 3.36 (br s, 1H), 3.22 (br d, J=12.4 Hz, 1H), 2.98 (br d, J=12.4 Hz, 1H), 2.83 (br t, J=11.2 Hz, 1H), 2.06-1.88 (m, 2H), 1.82 (br d, J=14.4 Hz, 1H), 1.71-1.60 (m, 1H), 1.38 (s, 3H).

Step 2. To a solution of (R)—N-(3-chloro-2-fluorophenyl)-7-((3-methylpiperidin-3-yl)ethynyl)-6-nitroquinazolin-4-amine (800 mg, 1.82 mmol) in trifluoroethanol (10.0 mL) was added paraformaldehyde (273 mg, 9.09 mmol, 251 uL) in portions. The mixture was stirred at 60° C. for 0.5 h. Then the mixture was added sodium borohydride (138 mg, 3.64 mmol) in portions at 60° C., and stirred at 60° C. for 1 h. The mixture was added methanol (20.0 mL) and concentrated to give residue. The residue was diluted with water (30.0 mL) and extracted with ethyl acetate (3×20.0 mL). The combined organic layer was washed with brine (10.0 mL) and dried over anhydrous sodium sulfate, filtered and concentrated to give (R)—N-(3-chloro-2-fluorophenyl)-7-((1,3-dimethylpiperidin-3-yl)ethynyl)-6-nitroquinazolin-4-amine (770 mg, crude) as a yellow solid. m/z ES+ $[M+H]^+$ 454.0.

Step 3. To a solution of (R)—N-(3-chloro-2-fluorophenyl)-7-((1,3-dimethylpiperidin-3-yl)ethynyl)-6-nitroquinazolin-4-amine (770 mg, 1.70 mmol) and ammonium chloride (454 mg, 8.48 mmol) in methanol (20.0 mL) and water (5.00 mL) was added iron powder (474 mg, 8.48 mmol) in portions. The mixture was stirred at 80° C. for 1 h. The mixture was added methanol (30.0 mL) and filtered. The filtrate was concentrated to give residue. The residue was diluted with saturated sodium bicarbonate solution (30.0 mL) and extracted with ethyl acetate (3×30.0 mL). The combined organic layer was washed with brine (10.0 mL) and dried over anhydrous sodium sulfate, filtered and concentrated to give (R)—$N^4$-(3-chloro-2-fluorophenyl)-7-((1,3-dimethylpiperidin-3-yl)ethynyl)quinazoline-4,6-diamine (700 mg, crude) as a yellow solid. $^1H$ NMR (400 MHz, DMSO-$d_6$) δ=9.57 (br s, 1H), 8.24 (br s, 1H), 7.62 (br d, J=6.7 Hz, 1H), 7.59-7.54 (m, 2H), 7.33-7.21 (m, 2H), 5.96 (br s, 2H), 2.84-2.70 (m, 2H), 2.23 (s, 3H), 1.91-1.87 (m, 2H), 1.80 (br d, J=13.6 Hz, 2H), 1.61 (br d, J=9.6 Hz, 2H), 1.29 (s, 3H).

Step 4. To a solution of (R)—$N^4$-(3-chloro-2-fluorophenyl)-7-((1,3-dimethylpiperidin-3-yl)ethynyl)quinazoline-4,6-diamine (600 mg, 1.42 mmol), acrylic acid (112 mg, 1.56 mmol, 107 uL) and pyridine (448 mg, 5.66 mmol, 457 uL) in dimethyl formamide (5.00 mL) was added 1-ethyl-3-(3-dimethylamino-propyl)-carbodiimide hydrochloride (1.09 g, 5.66 mmol) in portions at 20° C. The mixture was stirred at 20° C. for 1 h. The mixture was diluted with water (40.0 mL) and extracted with ethyl acetate (3×30.0 mL). The combined organic layer was washed with brine (10.0 mL) and dried over anhydrous sodium sulfate, filtered and concentrated to give crude product. The residue was purified by prep-HPLC (column: Waters Xbridge C18 150*50 mm*10 um; mobile phase: [water (10 mM $NH_4HCO_3$)-acetonitrile]; B %: 48%-78%, 11.5 min) and prep-HPLC (column: Phenomenex luna C18 150*25 mm*10 um; mobile phase: [water (0.225% formic acid)-acetonitrile]; B %: 7%-37%, 10 min) and lyophilized to give (R)—N-(4-((3-chloro-2-fluorophenyl)amino)-7-((1,3-dimethylpiperidin-3-yl)ethynyl)quinazolin-6-yl)acrylamide (89.95 mg, 12% yield) as a yellow solid. m/z ES+ $[M+H]^+$ 478.1; $^1H$ NMR (400 MHz, $CDCl_3$) δ=9.56 (br s, 1H), 9.17 (s, 1H), 8.74 (s, 1H), 8.40 (s, 1H), 8.35-8.26 (m, 1H), 7.95 (s, 1H), 7.84 (br s, 1H), 7.24-7.12 (m, 2H), 6.63-6.49 (m, 2H), 5.87-5.81 (m, 1H), 3.27-3.11 (m, 2H), 2.51 (s, 3H), 2.18-1.97 (m, 4H), 1.85-1.72 (m, 1H), 1.43 (s, 3H), 1.40-1.29 (m, 1H).

Example 49. Synthesis of Compound No. 55 (N-(4-((3-chloro-2-fluorophenyl)amino)-7-((4,4-difluoro-1,3-dimethylpyrrolidin-3-yl)ethynyl)quinazolin-6-yl)acrylamide)

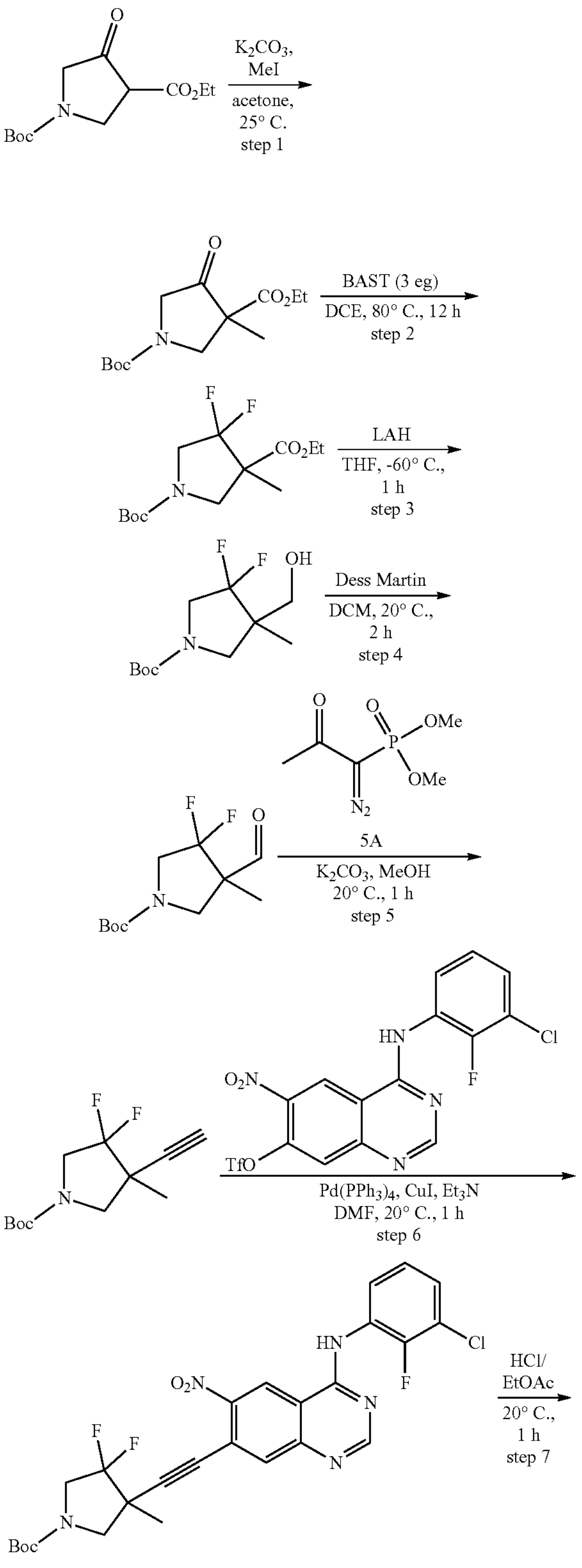

-continued

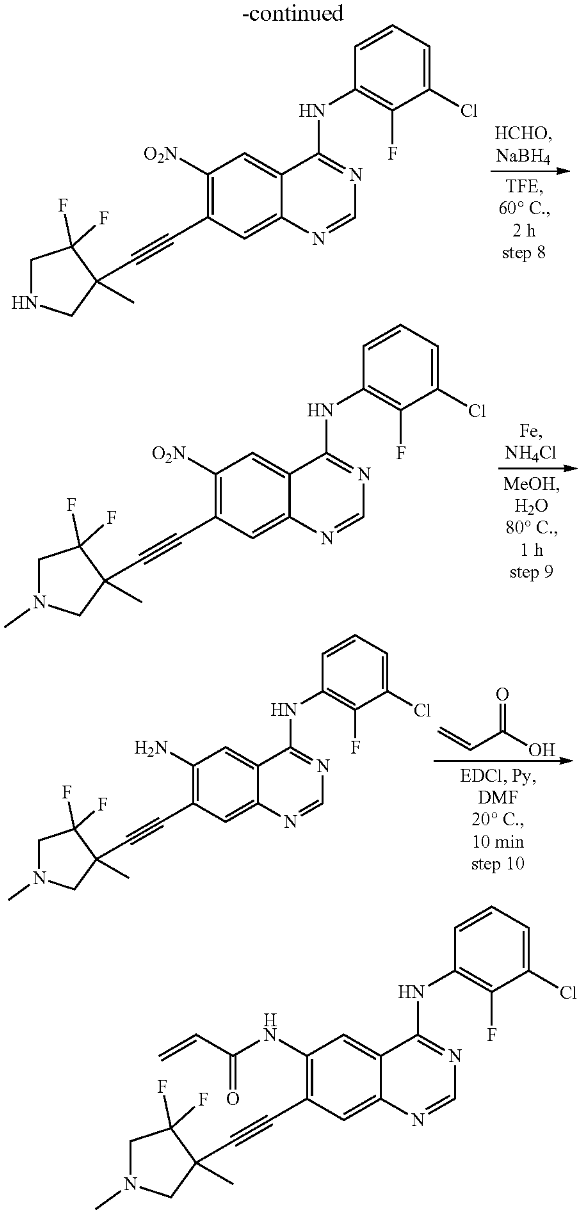

Step 1. To a solution of 1-tert-butyl 3-ethyl 4-oxopyrrolidine-1,3-dicarboxylate (20.0 g, 77.7 mmol) in acetone (100 mL) was added potassium carbonate (32.0 g, 231 mmol) and methyl iodide (31.9 g, 225 mmol, 14.0 mL). The mixture was stirred at 25° C. for 4 h. The mixture was diluted with water/ethyl acetate (1 L/1 L). The organic layer was concentrated under reduced pressure to give a residue. The residue was purified by column chromatography on silica gel (petroleum ether/ethyl acetate=1/0 to 10/1) to give 1-tert-butyl 3-ethyl 3-methyl-4-oxopyrrolidine-1,3-dicarboxylate (19.7 g, 93% yield) as a colorless oil.

Step 2. A solution of 1-tert-butyl 3-ethyl 3-methyl-4-oxopyrrolidine-1,3-dicarboxylate (2.00 g, 7.37 mmol) in 1,2-dichloroethane (40.0 mL) was added bis-(2-methoxyethyl)aminosulfur trifluoride (2.42 g, 10.9 mmol, 2.40 mL). The mixture was stirred at 80° C. for 12 h. The mixture was added dropwise to sodium bicarbonate (10%, 100 mL). The organic layer was separated and concentrated under reduced pressure. The residue was purified by column chromatography on silica gel (petroleum ether/ethyl acetate=20/1) to give 1-tert-butyl 3-ethyl 4,4-difluoro-3-methylpyrrolidine-1,3-dicarboxylate (530 mg, 24% yield) as a colorless oil. $^1$H NMR (400 MHz, DMSO-$d_6$) δ=4.30-4.22 (m, 2H), 3.95 (br t, J=10.4 Hz, 1H), 3.91-3.71 (m, 2H), 3.46 (br dd, J=11.2, 17.9 Hz, 1H), 1.49 (s, 9H), 1.45 (s, 3H), 1.34-1.29 (m, 3H).

Step 3. To a solution of 1-tert-butyl 3-ethyl 4,4-difluoro-3-methylpyrrolidine-1,3-dicarboxylate (450 mg, 1.53 mmol) in tetrahydrofuran (10.0 mL) was added lithium aluminum hydride (80.0 mg, 2.11 mmol) at −60° C. The mixture was stirred at −60° C. for 1 h. Sodium sulfate decahydrate (100 mg) was added to the mixture at −60° C. The mixture was stirred at this temperature for 10 min. Then the mixture was filtered and the filtrate was concentrated under reduced pressure to give tert-butyl 3,3-difluoro-4-(hydroxymethyl)-4-methylpyrrolidine-1-carboxylate (350 mg, crude) as a colorless oil. $^1$H NMR (400 MHz, DMSO-$d_6$) δ=3.78-3.66 (m, 4H), 3.62-3.55 (m, 1H), 3.34-3.26 (m, 1H), 1.48 (s, 9H), 1.22 (d, J=2.0 Hz, 3H).

Step 4. To a solution of tert-butyl 3,3-difluoro-4-(hydroxymethyl)-4-methylpyrrolidine-1-carboxylate (350 mg, 1.39 mmol) in dichloromethane (10.0 mL) was added Dess-Martin periodinane (1.18 g, 2.79 mmol). The mixture was stirred at 20° C. for 2 h. The mixture was concentrated under reduced pressure. The residue was purified by column chromatography on silica gel (petroleum ether/ethyl acetate=10/1) to give tert-butyl 3,3-difluoro-4-formyl-4-methylpyrrolidine-1-carboxylate (310 mg, 89% yield) as a yellow oil. $^1$H NMR (400 MHz, $CDCl_3$) δ=9.71 (s, 1H), 4.02-3.93 (m, 1H), 3.89-3.68 (m, 2H), 3.31 (br dd, J=12.0, 16.0 Hz, 1H), 1.49 (s, 9H), 1.37 (s, 3H).

Step 5. To a solution of tert-butyl 3,3-difluoro-4-formyl-4-methylpyrrolidine-1-carboxylate (310 mg, 1.24 mmol) in methanol (10.0 mL) was added potassium carbonate (520 mg, 3.76 mmol) and dimethyl (1-diazo-2-oxopropyl)phosphonate (360 mg, 1.87 mmol). The mixture was stirred at 20° C. for 1 h. The mixture was concentrated under reduced pressure. The residue was purified by column chromatography on silica gel (petroleum ether/ethyl acetate=30/1) to give tert-butyl 3-ethynyl-4,4-difluoro-3-methylpyrrolidine-1-carboxylate (180 mg, 59% yield) as a white solid. $^1$H NMR (400 MHz, $CDCl_3$) δ=3.90-3.63 (m, 3H), 3.46-3.37 (m, 1H), 2.32 (d, J=1.6 Hz, 1H), 1.48 (s, 9H), 1.42 (d, J=1.6 Hz, 3H).

Step 6. To a solution of 4-((3-chloro-2-fluorophenyl) amino)-6-nitroquinazolin-7-yl trifluoromethanesulfonate (300 mg, 643 umol) in dimethyl formamide (3.00 mL) and triethylamine (2.18 g, 21.6 mmol, 3.00 mL) was added tert-butyl 3-ethynyl-4,4-difluoro-3-methylpyrrolidine-1-carboxylate (160 mg, 652 umol), copper(I)iodide (25.0 mg, 131 umol) and tetrakis-(triphenylphosphine)palladium (75.0 mg, 64.9 umol). The mixture was stirred at 20° C. for 1 h. The mixture was diluted with ethyl acetate (100 mL) and water (100 mL). The organic layer was separated and concentrated under reduced pressure. The residue was purified by column chromatography on silica gel (petroleum ether/ethyl acetate=10/1 to 3/1) to give tert-butyl 3-((4-((3-chloro-2-fluorophenyl)amino)-6-nitroquinazolin-7-yl)ethynyl)-4,4-difluoro-3-methyl-pyrrolidine-1-carboxylate (300 mg, 83% yield) as a colorless oil. $^1$H NMR (400 MHz, DMSO-$d_6$) δ=10.69 (br s, 1H), 9.47 (br s, 1H), 8.69 (br s, 1H), 8.08 (br s, 1H), 7.47-7.40 (m, 1H), 7.33 (br t, J=6.4 Hz, 1H), 3.94-3.79 (m, 3H), 3.56 (br d, J=5.2 Hz, 1H), 1.53 (s, 3H), 1.44 (s, 9H).

Step 7. A solution of tert-butyl 3-((4-((3-chloro-2-fluorophenyl)amino)-6-nitroquinazolin-7-yl)ethynyl)-4,4-difluoro-3-methylpyrrolidine-1-carboxylate (300 mg, 534 umol) in ethyl acetate (10.0 mL) was added hydrogen chloride/ethyl acetate (4 M, 2.00 mL). The mixture was stirred at 20° C. for 1 h. The mixture was concentrated under reduced pressure to give N-(3-chloro-2-fluorophenyl)-7-((4,4-difluoro-3-methylpyrrolidin-3-yl)ethynyl)-6-nitroquinazolin-4-amine (260 mg, crude, hydrogen chloride) as a yellow solid.

Step 8. To a solution of N-(3-chloro-2-fluorophenyl)-7-((4,4-difluoro-3-methylpyrrolidin-3-yl)ethynyl)-6-nitroquinazolin-4-amine (260 mg, 521 umol, hydrogen chloride) in trifluoroethanol (10.0 mL) was added paraformaldehyde (60.0 mg, 2.00 mmol). The mixture was stirred at 60° C. for 1 h. Then sodium borohydride (40.0 mg, 1.06 mmol) was added to and the mixture was stirred at 60° C. for another 1 h. After being cooled to 20° C., the mixture was quenched with methanol (2.00 mL) and concentrated under reduced pressure to give N-(3-chloro-2-fluorophenyl)-7-((4,4-difluoro-1,3-dimethylpyrrolidin-3-yl)ethynyl)-6-nitroquinazolin-4-amine (250 mg, crude) as a brown solid. m/z ES+ $[M+H]^+$ 476.0

Step 9. To a solution of N-(3-chloro-2-fluorophenyl)-7-((4,4-difluoro-1,3-dimethyl-pyrrolidin-3-yl)ethynyl)-6-nitroquinazolin-4-amine (250 mg, 525 umol) in methanol (10.0 mL) and water (2.00 mL) was added iron powder (150 mg, 2.69 mmol) and ammonium chloride (230 mg, 4.30 mmol). The mixture was stirred at 80° C. for 1 h. The mixture was filtered and concentrated under reduced pressure. The residue was purified by column chromatography on silica gel (petroleum ether/ethyl acetate=1/1 to 0/1) to give $N^4$-(3-chloro-2-fluorophenyl)-7-((4,4-difluoro-1,3-dimethylpyrrolidin-3-yl)ethynyl)quinazoline-4,6-diamine (160 mg, 68% yield) as a yellow solid. m/z ES+ $[M+H]^+$ 446.0

Step 10. To a solution of $N^4$-(3-chloro-2-fluorophenyl)-7-((4,4-difluoro-1,3-dimethylpyrrolidin-3-yl)ethynyl) quinazoline-4,6-diamine (160 mg, 358 umol) in dimethyl formamide (1.00 mL) was added pyridine (157 mg, 1.98 mmol), 1-(3-dimethylaminopropyl)-3-ethylcarbodiimide hydrochloride (240 mg, 1.25 mmol) and acrylic acid (80.0 mg, 1.11 mmol). The mixture was stirred at 20° C. for 10 min. The mixture was filtered to give a solution. The solution was purified by prep-HPLC (column: Shim-pack C18 150*25*10 um; mobile phase: [water (0.225% formic acid)-acetonitrile]; B %: 15%-45%, 10 min). Further purified by prep-HPLC (column: Waters Xbridge 150*25 mm*5 um; mobile phase: [water (0.05% ammonium hydroxide v/v)-acetonitrile]; B %: 40%-70%, 8 min) to give crude product. Further purified by prep-HPLC (column: Shim-pack C18 150*25*10 um; mobile phase: [water (0.225% formic acid)-acetonitrile]; B %: 26%-46%, 9 min). The desired fraction was collected and lyophilized to give N-(44 (3-chloro-2-fluorophenyl)amino)-7-((4,4-difluoro-1,3-dimethylpyrrolidin-3-yl)ethynyl)-quinazolin-6-yl)acrylamide (4.10 mg, 2% yield, formate) as a yellow solid. m/z ES+ $[M+H]^+$ 500.0; $^1$H NMR (400 MHz, DMSO-$d_6$) δ=10.16 (br s, 1H), 9.79 (br s, 1H), 8.72 (s, 1H), 8.46 (br dd, J=5.6, 7.2 Hz, 1H), 7.83 (br s, 1H), 7.49 (br s, 2H), 7.34-7.23 (m, 1H), 6.55 (dd, J=10.0, 17.2 Hz, 1H), 6.40-6.28 (m, 1H), 5.86 (dd, J=1.6, 10.0 Hz, 1H), 3.13-3.02 (m, 3H), 2.84 (dd, J=1.2, 9.2 Hz, 1H), 2.31 (s, 3H), 1.49 (d, J=3.6 Hz, 3H).

Example 50. Synthesis of Compound No. 56 (N-(4-((3-chloro-2-fluorophenyl)amino)-7-((1-(2-fluoroethyl)-3-methylpyrrolidin-3-yl)ethynyl)quinazolin-6-yl)acrylamide)

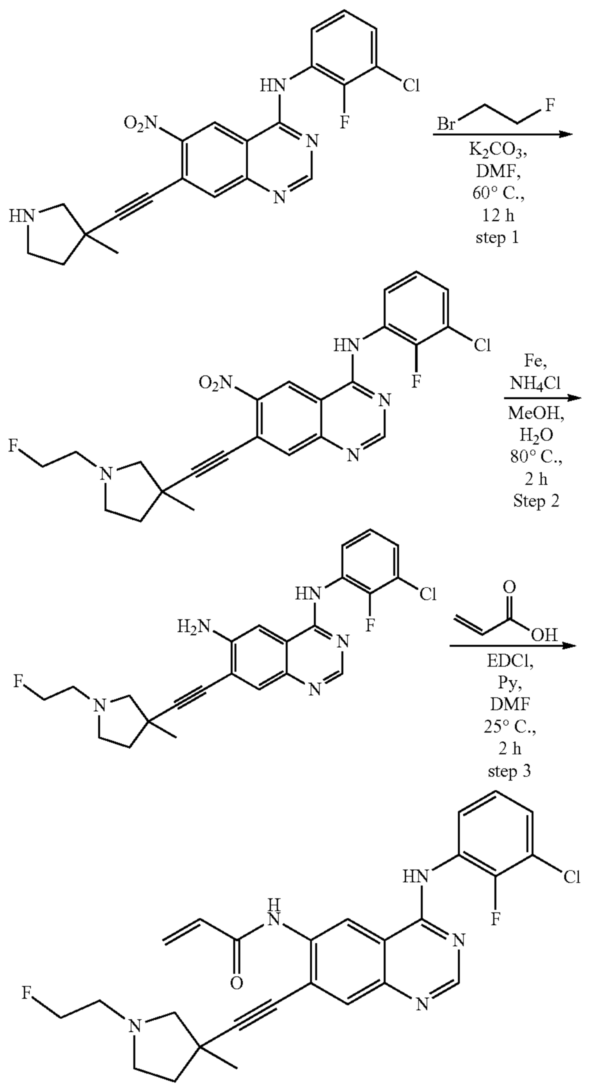

Step 1. To a mixture of (R)—N-(3-chloro-2-fluorophenyl)-7-((3-methylpyrrolidin-3-yl)ethynyl)-6-nitroquinazolin-4-amine (400 mg, 865 umol), potassium carbonate (478 mg, 3.46 mmol) in N,N-dimethylformamide (4.00 mL) was added 1-bromo-2-fluoroethane (165 mg, 1.30 mmol) at 25° C. The mixture was stirred at 60° C. for 12 h. The mixture was poured into water (50.0 mL) and extracted with ethyl acetate (3x20.0 mL). The combined organic phase was washed with brine (30.0 mL), dried over anhydrous sodium sulfate, filtered and concentrated in vacuum to give a residue. The residue was purified by silica gel chromatography (Petroleum ether/Ethyl acetate=3/1 to 1/1) to afford N-(3-chloro-2-fluorophenyl)-7-((1-(2-fluoroethyl)-3-methylpyrrolidin-3-yl)ethynyl)-6-nitroquinazolin-4-amine (300 mg, 73%) as a yellow solid. $^1$H NMR (400 MHz, $CDCl_3$) δ=8.88 (s, 1H), 8.76 (s, 1H), 8.35-8.28 (m, 1H), 8.11 (s, 1H), 7.31 (br d, J=1.6 Hz, 1H), 7.26-7.17 (m, 1H), 4.66 (t, J=5.2 Hz, 1H), 4.55 (t, J=5.2 Hz, 1H), 3.05 (d, J=9.2 Hz, 1H), 2.96-2.91 (m, 2H), 2.88-2.79 (m, 3H), 2.43-2.33 (m, 1H), 1.96 (td, J=7.2, 12.8 Hz, 1H), 1.55 (s, 3H).

Step 2. A mixture of N-(3-chloro-2-fluorophenyl)-7-((1-(2-fluoroethyl)-3-methylpyrrolidin-3-yl) ethynyl)-6-nitroquinazolin-4-amine (300 mg, 635 umol), iron powder (177 mg, 3.18 mmol) and ammonium chloride (170 mg, 3.18 mmol) in methanol (5.00 mL) and water (3.00 mL) was stirred at 80° C. for 2 h. The mixture was filtered and the filtrate was concentrated to dryness to give a residue. The residue was diluted with ethyl acetate (20.0 mL) and washed with saturated sodium bicarbonate solution (20.0 mL) and brine (15.0 mL), dried over anhydrous sodium sulfate, filtered and concentrated in vacuum to give $N^4$-(3-chloro-2-fluorophenyl)-7-((1-(2-fluoroethyl)-3-methylpyrrolidin-3-yl)ethynyl)quinazoline-4,6-diamine (210 mg, 75% yield) as a yellow solid. m/z ES+ $[M+H]^+$ 442.2

Step 3. To a mixture of $N^4$-(3-chloro-2-fluorophenyl)-7-((1-(2-fluoroethyl)-3-methylpyrrolidin-3-yl)ethynyl) quinazoline-4,6-diamine (150 mg, 339 umol), acrylic acid (29.4 mg, 407 umol) and pyridine (107 mg, 1.36 mmol) in dimethyl formamide (3.00 mL) was added 1-ethyl-3-(3-dimethylamino-propyl)-carbodiimide hydrochloride (260 mg, 1.36 mmol) at 25° C. The mixture was stirred at 25° C. for 2 h and then filtered. The filtrate was purified by prep-HPLC (column: Waters Xbridge 150*25 mm*5 um; mobile phase: [water (10 mM $NH_4HCO_3$)-acetonitrile]; B %: 37%-67%, 9 min) to give N-(4-((3-chloro-2-fluorophenyl)amino)-7-((1-(2-fluoroethyl)-3-methylpyrrolidin-3-yl) ethynyl) quinazolin-6-yl)acrylamide (25.4 mg, 15% yield) as a yellow solid. m/z ES+ $[M+H]^+$ 496.1; $^1$H NMR (400 MHz, $CDCl_3$) δ=9.22 (s, 1H), 8.76 (s, 1H), 8.52 (br s, 1H), 8.40 (dt, J=2.4, 7.2 Hz, 1H), 7.98 (s, 1H), 7.74 (br s, 1H), 7.25-7.13 (m, 2H), 6.60-6.50 (m, 1H), 6.44-6.33 (m, 1H), 5.90 (d, J=11.2 Hz, 1H), 4.69 (br t, J=4.8 Hz, 1H), 4.57 (br t, J=4.8 Hz, 1H), 3.20 (br d, J=7.6 Hz, 1H), 3.06 (br s, 1H), 2.95 (br s, 1H), 2.88 (br s, 1H), 2.80 (br d, J=5.2 Hz, 1H), 2.69 (br d, J=8.8 Hz, 1H), 2.45-2.35 (m, 1H), 2.07-1.97 (m, 1H), 1.59 (s, 3H).

Example 51. Synthesis of Compound No. 57 (1-(4-((3-chloro-2-fluorophenyl)amino)-7-((1,3-dimethylpyrrolidin-3-yl)ethynyl)quinazolin-6-yl)-3-methylurea)

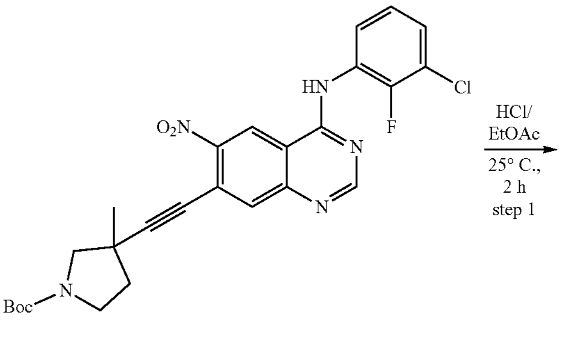

-continued

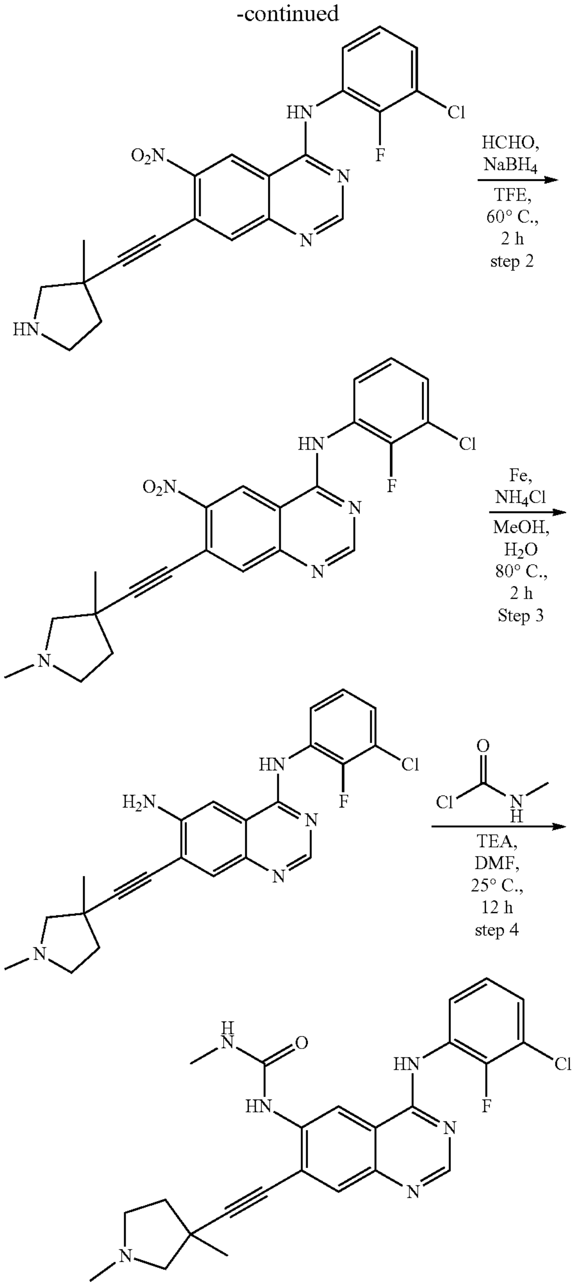

Step 1. To a solution of tert-butyl 3-((4-((3-chloro-2-fluorophenyl)amino)-6-nitroquinazolin-7-yl)ethynyl)-3-methylpyrrolidine-1-carboxylate (430 mg, 817 umol) in ethyl acetate (2.00 mL) was added hydrochloric acid/ethyl acetate (2.00 mL). The mixture was stirred at 25° C. for 2 h. The reaction mixture was concentrated in vacuum to give N-(3-chloro-2-fluorophenyl)-7-((3-methylpyrrolidin-3-yl)ethynyl)-6-nitroquinazolin-4-amine (340 mg, 97% yield) as a yellow solid. m/z ES+ $[M+H]^+$ 426.1

Step 2. A mixture of N-(3-chloro-2-fluorophenyl)-7-((3-methylpyrrolidin-3-yl)ethynyl)-6-nitroquinazolin-4-amine (290 mg, 681 umol) and formaldehyde (102 mg, 3.41 mmol, 93.8 uL) in tetrafluoroethylene (3.00 mL) was stirred at 60° C. for 0.5 h. Then the mixture was added sodium borohydride (51.5 mg, 1.36 mmol) in portions at 60° C. The mixture was stirred at 60° C. for 1.5 h. The mixture was quenched with methanol (10.0 mL) and concentrated to dryness to give a residue. The mixture was added ethyl acetate (20.0 mL) and saturated sodium bicarbonate solution (20.0 mL). The organic phase was separated, washed with brine (2×20.0 mL), dried over sodium sulfate, filtered and concentrated to give N-(3-chloro-2-fluorophenyl)-7-((1,3-dimethylpyrrolidin-3-yl)ethynyl)-6-nitroquinazolin-4-amine (360 mg, crude) as a yellow solid. m/z ES+ $[M+H]^+$ 440.0

Step 3. A mixture of N-(3-chloro-2-fluorophenyl)-7-((1,3-dimethylpyrrolidin-3-yl)ethynyl)-6-nitroquinazolin-4-amine (360 mg, 818 umol), iron powder (228 mg, 4.09 mmol) and ammonium chloride (218 mg, 4.09 mmol) in methanol (5.00 mL) and water (1.00 mL) was stirred at 80° C. for 2 h. The reaction mixture was added methanol (50.0 mL) and filtered, filtrate was concentrated on a rotary evaporator. Ethyl acetate (40.0 mL) and saturated sodium bicarbonate solution (40.0 mL) were added and organic layers were separated. The aqueous phase was extracted with ethyl acetate (2×20.0 mL). Combined organic phase was washed with brine (2×20.0 mL), dried over sodium sulfate, filtered, and concentrated to dryness to give $N^4$-(3-chloro-2-fluorophenyl)-7-((1,3-dimethylpyrrolidin-3-yl)ethynyl)quinazoline-4,6-diamine (300 mg, 89% yield) as a yellow solid. m/z ES+ $[M+H]^+$ 410.1

Step 4. To a solution of $N^4$-(3-chloro-2-fluorophenyl)-7-((1,3-dimethylpyrrolidin-3-yl)ethynyl)quinazoline-4,6-diamine (220 mg, 536 umol) in dimethyl formamide (2.00 mL) and triethylamine (162 mg, 1.61 mmol, 224 uL) was added methylcarbamic chloride (151 mg, 1.61 mmol). The mixture was stirred at 25° C. for 12 h. The reaction mixture was filtered to give filtrate. The filtrate was purified by prep-HPLC (column: Waters Xbridge 150*25 mm*5 um; mobile phase: [water (0.05% ammonium hydroxide v/v)-acetonitrile]; B %: 32%-62%, 10 min) to give 1444(3-chloro-2-fluorophenyl)amino)-7-((1,3-dimethylpyrrolidin-3-yl)ethynyl)-quinazolin-6-yl)-3-methylurea (34.57 mg, 14% yield) as a yellow solid. m/z ES+ $[M+H]^+$ 467.4; 41 NMR (400 MHz, $CDCl_3$) δ=8.96-8.89 (m, 1H), 8.73-8.66 (m, 1H), 8.41-8.33 (m, 1H), 8.09-8.02 (m, 1H), 7.86 (s, 1H), 7.76-7.67 (m, 1H), 7.22-7.18 (m, 1H), 7.18-7.13 (m, 1H), 5.97-5.87 (m, 1H), 3.36 (d, J=9.2 Hz, 1H), 3.31-3.24 (m, 1H), 2.94 (d, J=4.8 Hz, 3H), 2.50 (s, 3H), 2.47-2.36 (m, 2H), 2.30 (d, J=9.2 Hz, 1H), 2.06-1.97 (m, 1H), 1.53 (s, 3H).

Example 52. Synthesis of Compound No. 58 ((S)—N-(4-((3-chloro-2-fluorophenyl)amino)-7-((3-methyl-1-(oxetan-3-yl)pyrrolidin-3-yl)ethynyl)quinazolin-6-yl)acrylamide)

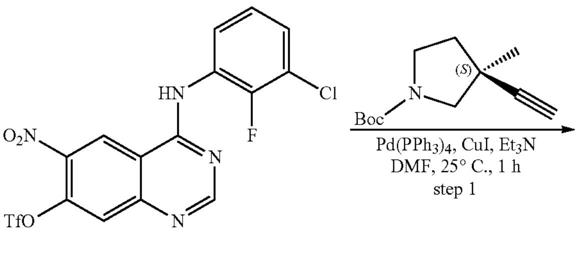

-continued

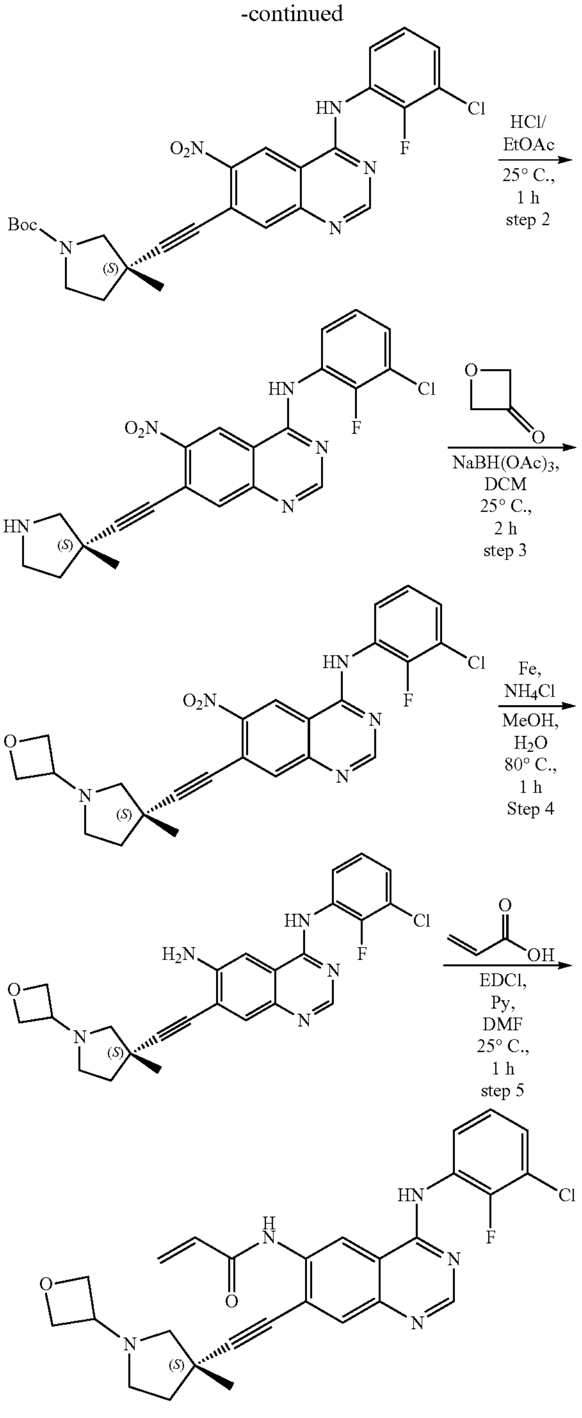

Step 1. To a solution of 4-((3-chloro-2-fluorophenyl) amino)-6-nitroquinazolin-7-yl trifluoromethanesulfonate (1.82 g, 3.91 mmol), (S)-tert-butyl 3-ethynyl-3-methylpyrrolidine-1-carboxylate (900 mg, 4.30 mmol) and triethylamine (2.65 g, 26.2 mmol, 3.65 mL) in dimethyl formamide (2.00 mL) was added etrakis(triphenylphosphine) palladium (0) (451 mg, 390 umol) and cuprous iodid (148 mg, 781 umol) under nitrogen, the mixture was stirred at 25° C. for 1 h. The reaction mixture was poured into water (120 mL) and stirred for 10 min. The aqueous phase was extracted with ethyl acetate (3×60.0 mL). The combined organic phase was washed with brine (100 mL), dried over anhydrous sodium sulfate, filtered and concentrated in vacuum to give a residue. The residue was purified by silica gel chromatography (Petroleum ether/Ethyl acetate=8/1 to 2/1) to afford (S)-tert-butyl 3-((4-((3-chloro-2-fluorophenyl)amino)-6-nitroquinazolin-7-yl)ethynyl)-3-methylpyrrolidine-1-carboxylate (1.50 g, 73% yield) as a yellow solid. m/z ES+ $[M+H]^+$ 526.1

Step 2. To a solution of (S)-tert-butyl 3-((4-((3-chloro-2-fluorophenyl)amino)-6-nitroquinazolin-7-yl)ethynyl)-3-methylpyrrolidine-1-carboxylate (1.50 g, 2.85 mmol) in ethyl acetate (10.0 mL) was added hydrochloric acid/ethyl acetate (4 M, 15.0 mL) at 25° C., the mixture was stirred at 25° C. for 1 h. The reaction mixture was concentrated to give a residue. The crude product was triturated with ethyl acetate (30.0 mL) at 25° C. for 30 min to afford (S)—N-(3-chloro-2-fluorophenyl)-7-((3-methylpyrrolidin-3-yl)ethynyl)-6-nitroquinazolin-4-amine (1.30 g, 98% yield, HCl) as a yellow solid. $^1$H NMR (400 MHz, DMSO-d$_6$) δ=9.94-9.78 (m, 1H), 9.67 (s, 2H), 8.79 (s, 1H), 8.16 (s, 1H), 7.54 (br t, J=6.8 Hz, 1H), 7.49-7.41 (m, 1H), 7.33-7.25 (m, 1H), 3.45-3.29 (m, 3H), 3.19-3.07 (m, 1H), 2.31-2.17 (m, 1H), 2.00 (td, J=8.0, 12.8 Hz, 1H), 1.45 (s, 3H). m/z ES+ $[M+H]^+$ 426.0

Step 3. A mixture of (S)—N-(3-chloro-2-fluorophenyl)-7-((3-methylpyrrolidin-3-yl)ethynyl)-6-nitroquinazolin-4-amine (1.00 g, 2.35 mmol) and oxetan-3-one (846 mg, 11.7 mmol) in dichloromethane (10.0 mL) was stirred at 25° C. for 0.5 h, then sodium triacetoxy borohydride (995 mg, 4.70 mmol) was added, the mixture was stirred at 25° C. for 1.5 h. The reaction mixture was poured into water (100 mL) and stirred for 10 min. The aqueous phase was extracted with ethyl acetate (3×40.0 mL). The combined organic phase was washed with brine (100 mL), dried over anhydrous sodium sulfate, filtered and concentrated in vacuum to give a residue. The residue was purified by reversed-phase HPLC (0.1% formic acid condition) to afford (S)—N-(3-chloro-2-fluorophenyl)-7-((3-methyl-1-(oxetan-3-yl)pyrrolidin-3-yl) ethynyl)-6-nitroquinazolin-4-amine (500 mg, 40% yield, formic acid) as a yellow solid. $^1$H NMR (400 MHz, CDCl$_3$) δ=8.87 (s, 1H), 8.75 (br s, 1H), 8.05 (br s, 1H), 7.99 (s, 1H), 7.23-7.20 (m, 1H), 7.14-7.07 (m, 1H), 4.80-4.68 (m, 4H), 4.15-3.95 (m, 1H), 3.25-3.14 (m, 1H), 3.14-3.07 (m, 1H), 3.06-2.89 (m, 2H), 2.35 (ddd, J=3.6, 6.8, 12.8 Hz, 1H), 2.02 (td, J=8.4, 12.8 Hz, 1H), 1.52 (s, 3H). m/z ES+ $[M+H]^+$ 482.1

Step 4. A mixture of (S)—N-(3-chloro-2-fluorophenyl)-7-((3-methyl-1-(oxetan-3-yl)pyrrolidin-3-yl)ethynyl)-6-nitroquinazolin-4-amine (500 mg, 947 umol, formic acid), iron powder (158 mg, 2.84 mmol) and ammonium chloride (253 mg, 4.74 mmol) in methanol (5.00 mL) and water (2.00 mL) was stirred at 80° C. for 1 h. The reaction mixture was filtered to give a filtrate, the filtrate was concentrated to give a residue. The residue was poured into water (100 mL) and stirred for 10 min. The aqueous phase was extracted with ethyl acetate (3×40.0 mL). The combined organic phase was washed with brine (100 mL), dried over anhydrous sodium sulfate, filtered and concentrated in vacuum to give (S)—N$^4$-(3-chloro-2-fluorophenyl)-7-((3-methyl-1-(oxetan-3-yl) pyrrolidin-3-yl)ethynyl)quinazoline-4,6-diamine (400 mg, 93% yield) as a yellow solid. m/z ES+ $[M+H]^+$ 452.2

Step 5. To a solution of (S)—N$^4$-(3-chloro-2-fluorophenyl)-7-((3-methyl-1-(oxetan-3-yl)pyrrolidin-3-yl)ethynyl) quinazoline-4,6-diamine (350 mg, 774 umol), acrylic acid (61.4 mg, 852 umol, 58.5 uL) and pyridine (306 mg, 3.87 mmol, 312 uL) in dimethyl formamide (4.00 mL) was added 1-ethyl-3-(3-dimethylamino-propyl)-carbodiimide hydrochloride (594 mg, 3.10 mmol) at 25° C., the mixture was stirred at 25° C. for 1 h. The reaction mixture was poured into water (100 mL) and stirred for 10 min. The aqueous phase was extracted with ethyl acetate (3×40.0 mL). The combined organic phase was washed with brine (90.0 mL), dried over anhydrous sodium sulfate, filtered and concentrated in vacuum to give a residue. The residue was purified by prep-HPLC (column: Waters Xbridge 150*25 mm*5 um; mobile phase: [water (0.05% ammonium hydroxide v/v)-acetonitrile]; B %: 40%-60%, 10 min) and prep-HPLC (column: Unisil 3-100 C18 Ultra 150*50 mm*3 um; mobile phase: [water (0.225% formic acid)-acetonitrile]; B %: 15%-35%, 10 min) to afford (S)—N-(4-((3-chloro-2-fluorophenyl)amino)-7-((3-methyl-1-(oxetan-3-yl) pyrrolidin-3-yl) ethynyl)quinazolin-6-yl)acrylamide (99.6 mg, 25% yield) as a yellow solid. m/z ES+ $[M+H]^+$ 506.2; $^1H$ NMR (400 MHz, DMSO-$d_6$) δ=10.26-10.00 (m, 1H), 9.81 (br s, 1H), 8.70 (s, 1H), 8.49 (br s, 1H), 8.21 (s, 1H), 7.81 (br s, 1H), 7.50 (br s, 2H), 7.36-7.22 (m, 1H), 6.59 (dd, J=10.0, 16.9 Hz, 1H), 6.34 (dd, J=1.2, 17.2 Hz, 1H), 5.86 (dd, J=1.2, 10.0 Hz, 1H), 4.58 (t, J=6.4 Hz, 2H), 4.48 (dt, J=1.2, 5.6 Hz, 2H), 3.71-3.67 (m, 1H), 2.85 (d, J=8.8 Hz, 1H), 2.73-2.64 (m, 2H), 2.59 (d, J=8.8 Hz, 1H), 2.25 (ddd, J=5.6, 7.2, 12.8 Hz, 1H), 1.87 (td, J=7.2, 12.4 Hz, 1H), 1.45 (s, 3H).

Example 53. Synthesis of Compound No. 59 ((R)—N-(4-((3-chloro-2-fluorophenyl)amino)-7-((3-methyl-1-(oxetan-3-yl)pyrrolidin-3-yl)ethynyl)quinazolin-6-yl)acrylamide)

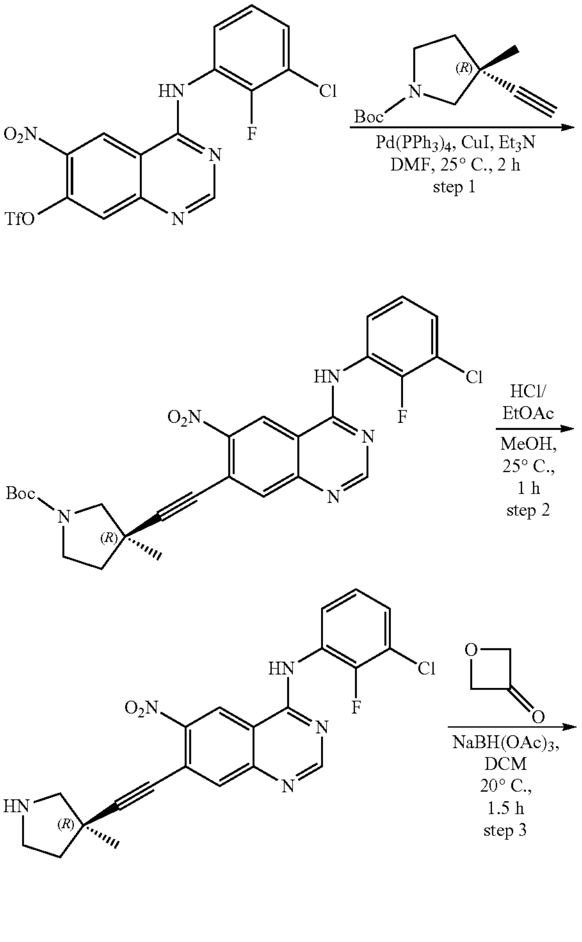

-continued

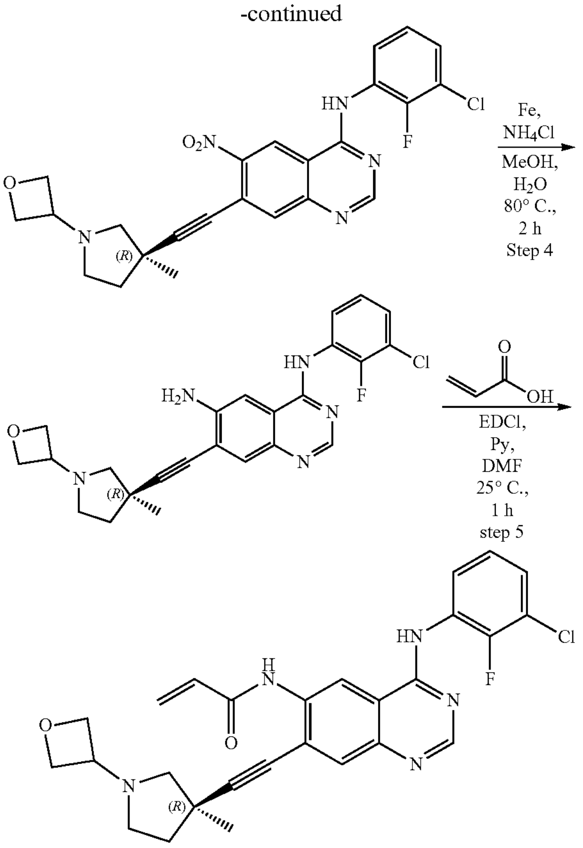

Step 1. To a solution of 4-((3-chloro-2-fluorophenyl) amino)-6-nitroquinazolin-7-yl trifluoromethanesulfonate (3.30 g, 7.07 mmol), (R)-tert-butyl 3-ethynyl-3-methylpyrrolidine-1-carboxylate (1.48 g, 7.07 mmol) in dimethylformamide (10.0 mL) and triethylamine (10.0 mL) was added copper iodide (269 mg, 1.41 mmol) and tetrakis(triphenylphosphine)palladium(0) (817 mg, 707 umol) in one portion under nitrogen. The mixture was stirred at 25° C. for 2 h. The mixture was diluted with water (200 mL) and extracted with ethyl acetate (3×150 mL). The combined organic layer was washed with brine (60.0 mL), dried over sodium sulfate, filtered and concentrated in vacuum. The residue was purified by silica gel chromatography (petroleum ether/ethyl acetate=3/1) to give (R)-tert-butyl 3-((4-((3-chloro-2-fluorophenyl) amino)-6-nitroquinazolin-7-yl) ethynyl)-3-methylpyrrolidine-1-carboxylate (3.00 g, 80% yield) as a yellow solid. 41 NMR (400 MHz, $CDCl_3$) δ=9.09 (s, 1H), 8.77 (br s, 1H), 8.03 (s, 1H), 7.85 (br s, 1H), 7.34 (br t, J=7.2 Hz, 1H), 7.27-7.23 (m, 1H), 7.14 (dt, J=0.8, 8.0 Hz, 1H), 3.77-3.68 (m, 1H), 3.61 (dt, J=3.6, 7.1 Hz, 1H), 3.56-3.48 (m, 1H), 3.29 (d, J=10.8 Hz, 1H), 2.32-2.19 (m, 1H), 1.98-1.83 (m, 1H), 1.47 (br d, J=4.0 Hz, 3H), 1.45 (s, 9H).

Step 2. To a solution of (R)-tert-butyl 3-((4-((3-chloro-2-fluorophenyl)amino)-6-nitroquinazolin-7-yl)ethynyl)-3-methylpyrrolidine-1-carboxylate (3.50 g, 6.65 mmol) in methanol (20.0 mL) was added hydrochloric acid/ethyl acetate (4 M, 5.00 mL) dropwise. The mixture was stirred at 25° C. for 1 h. The mixture was concentrated in vacuum to give (R)—N-(3-chloro-2-fluorophenyl)-7-((3-methylpyrrolidin-3-yl)ethynyl)-6-nitroquinazolin-4-amine (2.90 g, crude) as a yellow solid. $^1H$ NMR (400 MHz, DMSO-$d_6$) δ=9.86 (br d, J=4.0 Hz, 1H), 9.74 (s, 2H), 8.87 (s, 1H), 8.24

(s, 1H), 7.64-7.61 (m, 1H), 7.55-7.51 (m, 1H), 7.40-7.33 (m, 1H), 3.50-3.37 (m, 3H), 3.27-3.17 (m, 1H), 2.32 (td, J=6.4, 12.8 Hz, 1H), 2.08 (td, J=8.0, 12.8 Hz, 1H), 1.52 (s, 3H).

Step 3. To a solution of (R)—N-(3-chloro-2-fluorophenyl)-7-((3-methylpyrrolidin-3-yl)ethynyl)-6-nitroquinazolin-4-amine (1.20 g, 2.82 mmol) in dichloromethane (12.0 mL) was added oxetan-3-one (1.02 g, 14.1 mmol) in one portion for 0.5 h. Then the mixture was added sodium triacetoxyhydroborate (1.19 g, 5.64 mmol) and the mixture was stirred at 20° C. for 1 h. The mixture was diluted with water (150 mL) and extracted with ethyl acetate (3×80.0 mL). The combined organic layer was washed with brine (60.0 mL), dried over sodium sulfate, filtered and concentrated in vacuum. The residue was purified by reverse phase chromatography (0.1% formic acid) to give crude product. The crude product was purified by silica gel chromatography (petroleum ether/ethyl acetate=1/4) to give (R)—N-(3-chloro-2-fluorophenyl)-7-((3-methyl-1-(oxetan-3-yl)pyrrolidin-3-yl)ethynyl)-6-nitroquinazolin-4-amine (300 mg, 21% yield) as yellow oil. $^1$H NMR (400 MHz, DMSO-$d_6$) δ=10.78-10.53 (m, 1H), 9.35 (br s, 1H), 8.61 (br s, 1H), 7.93 (s, 1H), 7.64-7.41 (m, 2H), 7.37-7.14 (m, 1H), 4.58 (t, J=6.4 Hz, 2H), 4.48 (t, J=6.0 Hz, 2H), 3.70 (d, J=6.4 Hz, 1H), 2.83 (d, J=9.2 Hz, 1H), 2.74-2.60 (m, 3H), 2.23 (ddd, J=5.2, 7.6, 12.4 Hz, 1H), 1.89 (td, J=7.2, 12.4 Hz, 1H), 1.45 (s, 3H).

Step 4. To a solution of (R)—N-(3-chloro-2-fluorophenyl)-7-((3-methyl-1-(oxetan-3-yl)pyrrolidin-3-yl)ethynyl)-6-nitroquinazolin-4-amine (300 mg, 623 umol), ammonium chloride (167 mg, 3.11 mmol) in methanol (8.00 mL) and water (4.00 mL) was added iron powder (139 mg, 2.49 mmol) in portions. The mixture was stirred at 80° C. for 2 h. The mixture was filtered. The filtrate was concentrated in vacuum. The residue was diluted with water (80.0 mL) and extracted with ethyl acetate (3×60.0 mL). The combined organic layer was washed with brine (40.0 mL), dried over sodium sulfate, filtered and concentrated in vacuum to give (R)—$N^4$-(3-chloro-2-fluorophenyl)-7-((3-methyl-1-(oxetan-3-yl)pyrrolidin-3-yl)ethynyl)quinazoline-4,6-diamine (270 mg, crude) as a yellow solid. $^1$H NMR (400 MHz, DMSO-$d_6$) δ=9.83-9.38 (m, 1H), 7.67-7.47 (m, 3H), 7.42 (br s, 2H), 7.27-7.19 (m, 1H), 5.64 (br s, 2H), 4.58 (br t, J=6.4 Hz, 2H), 4.53-4.45 (m, 2H), 3.70 (td, J=6.0, 12.0 Hz, 1H), 2.88 (br d, J=8.8 Hz, 1H), 2.73-2.65 (m, 2H), 2.57 (br d, J=8.8 Hz, 1H), 2.32-2.22 (m, 1H), 1.94-1.81 (m, 1H), 1.46 (s, 3H).

Step 5. To a solution of (R)—$N^4$-(3-chloro-2-fluorophenyl)-7-((3-methyl-1-(oxetan-3-yl)pyrrolidin-3-yl)ethynyl)quinazoline-4,6-diamine (240 mg, 531 umol), acrylic acid (45.9 mg, 637 umol, 43.7 uL), pyridine (210 mg, 2.66 mmol, 214 uL) in dimethyformamide (2.00 mL) was added 1-(3-dimethylaminopropyl)-3-ethylcarbodiimide hydrochloride (407 mg, 2.12 mmol) in portions. The mixture was stirred at 20° C. for 1 h. The mixture was diluted with water (40.0 mL) and extracted with ethyl acetate (3×30.0 mL). The combined organic layer was washed with brine (20.0 mL), dried over sodium sulfate, filtered and concentrated in vacuum. The residue was purified by prep-HPLC (column: Waters Xbridge 150*25 mm*5 um; mobile phase: [water (10 mM $NH_4HCO_3$)-acetonitrile]; B %: 31%-61%, 9 min) to give a residue which was further purified by prep-HPLC (column: Unisil 3-100 C18 Ultra 150*50 mm*3 um; mobile phase: [water (0.225% formic acid)-acetonitrile]; B %: 8%-38%, 10 min) and lyophilized to give (R)—N-(4-((3-chloro-2-fluorophenyl)amino)-7-((3-methyl-1-(oxetan-3-yl)pyrrolidin-3-yl)ethynyl)-quinazolin-6-yl)acrylamide (46.28 mg, 17% yield) as a yellow solid. m/z ES+ $[M+H]^+$ 506.2; $^1$H NMR (400 MHz, DMSO-$d_6$) δ=10.21-9.97 (m, 1H), 9.79 (br s, 1H), 8.77-8.60 (m, 1H), 8.48 (br s, 1H), 8.21 (s, 1H), 7.80 (br s, 1H), 7.49 (br s, 2H), 7.36-7.17 (m, 1H), 6.59 (dd, J=10.2, 17.2 Hz, 1H), 6.34 (d, J=17.2 Hz, 1H), 5.85 (d, J=10.4 Hz, 1H), 4.62-4.54 (m, 2H), 4.52-4.41 (m, 2H), 3.68 (br t, J=6.0 Hz, 1H), 2.85 (d, J=9.2 Hz, 1H), 2.74-2.62 (m, 2H), 2.59 (d, J=8.8 Hz, 1H), 2.28-2.19 (m, 1H), 1.92-1.80 (m, 1H), 1.45 (s, 3H).

Example 54. Synthesis of Compound No. 60 (N-(4-((3-chloro-2-fluorophenyl)amino)-7-((3-fluoro-1-methylpyrrolidin-3-yl)ethynyl)quinazolin-6-yl)acrylamide)

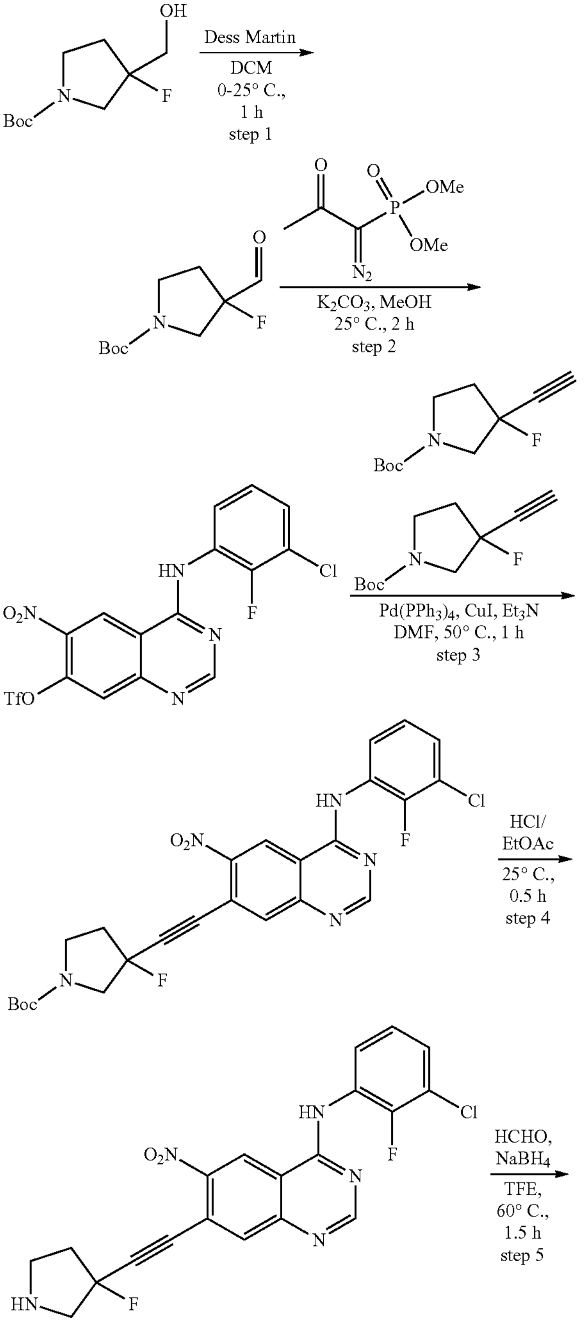

-continued

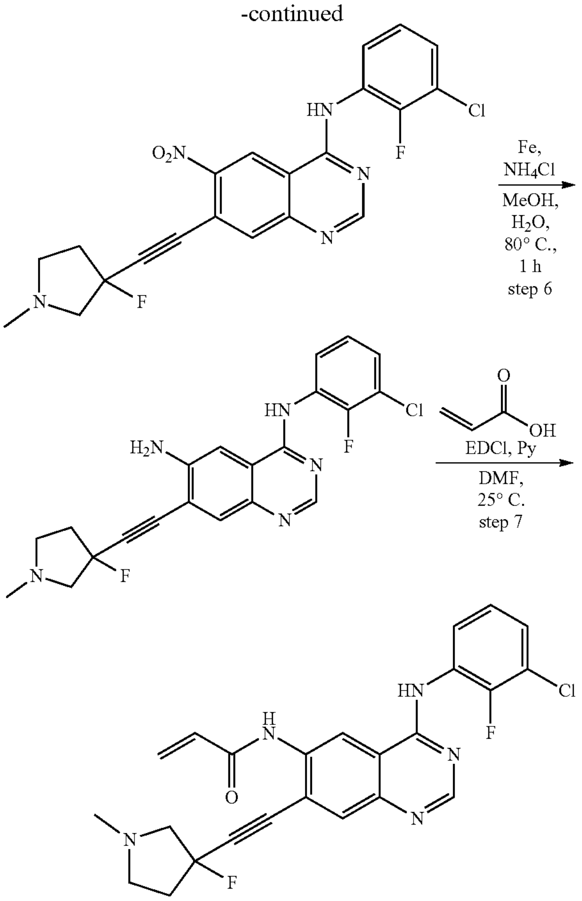

Step 1. To a solution of tert-butyl 3-fluoro-3-(hydroxymethyl)pyrrolidine-1-carboxylate (2.00 g, 9.12 mmol) in dichloromethane (25.0 mL) was added dess-martin periodinane (5.80 g, 13.7 mmol, 4.24 mL) in portions at 0° C. The mixture was stirred at 25° C. for 1 h. The mixture was filtered. The filtrate was concentrated to give crude product. The crude product was purified by silica gel chromatography (petroleum ether/ethyl acetate=5/1 to 1/1) to give tert-butyl 3-fluoro-3-formylpyrrolidine-1-carboxylate (2.50 g, crude) as colorless oil.

Step 2. To a solution of tert-butyl 3-fluoro-3-formylpyrrolidine-1-carboxylate (2.50 g, 11.5 mmol) and potassium carbonate (4.77 g, 34.5 mmol) in methanol (15.0 mL) was added dimethyl (1-diazo-2-oxopropyl)phosphonate (2.87 g, 15.0 mmol) dropwise. The mixture was stirred at 25° C. for 2 h. The mixture was concentrated to give crude product. The crude product was purified by silica gel chromatography (petroleum ether/ethyl acetate=10/1) to give tert-butyl 3-ethynyl-3-fluoropyrrolidine-1-carboxylate (980 mg, 40% yield) as a white solid. $^1$H NMR (400 MHz, $CDCl_3$) δ=3.97-3.79 (m, 1H), 3.73-3.44 (m, 3H), 2.78 (d, J=5.2 Hz, 1H), 2.45 (tddd, J=1.6, 6.8, 13.6, 15.2 Hz, 1H), 2.34-2.13 (m, 1H), 1.48 (s, 9H).

Step 3. To a solution of 4-((3-chloro-2-fluorophenyl)amino)-6-nitroquinazolin-7-yl trifluoromethanesulfonate (1.90 g, 4.07 mmol) and tert-butyl 3-ethynyl-3-fluoropyrrolidine-1-carboxylate (955 mg, 4.48 mmol) in triethylamine (5.00 mL) and dimethyl formamide (5.00 mL) was added tetrakis[triphenylphosphine]palladium(0) (470 mg, 407 umol) and copper(I) iodide (77.5 mg, 407 umol) in one portion under nitrogen. The mixture was stirred at 50° C. for 1 h. The mixture was diluted with water (30 mL) and extracted with ethyl acetate (3×30.0 mL). The combined organic layer was washed with brine (20 mL) and dried over sodium sulfate, filtered and concentrated to give crude product. The crude product was purified by silica gel chromatography (petroleum ether/ethyl acetate=10/1 to 3/1) to give tert-butyl 3-((4-((3-chloro-2-fluorophenyl)amino)-6-nitroquinazolin-7-yl)ethynyl)-3-fluoropyrrolidine-1-carboxylate (900 mg, 42% yield) as a yellow solid. $^1$H NMR (400 MHz, DMSO-$d_6$) δ=11.03-10.47 (m, 1H), 9.49 (br s, 1H), 8.68 (s, 1H), 8.16 (br s, 1H), 7.67-7.57 (m, 2H), 7.33 (t, J=7.6 Hz, 1H), 3.94-3.74 (m, 2H), 3.65-3.59 (m, 1H), 3.39-3.36 (m, 1H), 2.61-2.53 (m, 2H), 1.44 (s, 9H).

Step 4. A solution of tert-butyl 3-((4-((3-chloro-2-fluorophenyl)amino)-6-nitroquinazolin-7-yl)ethynyl)-3-fluoropyrrolidine-1-carboxylate (900 mg, 1.70 mmol) in hydrochloric acid/ethyl acetate (4 M, 5.00 mL) was stirred at 25° C. for 0.5 h. The mixture was concentrated to give N-(3-chloro-2-fluorophenyl)-7-((3-fluoropyrrolidin-3-yl) ethynyl)-6-nitroquinazolin-4-amine (800 mg, crude) as a yellow solid. m/z ES+ $[M+H]^+$ 430.0

Step 5. To a solution of N-(3-chloro-2-fluorophenyl)-7-((3-fluoropyrrolidin-3-yl)ethynyl)-6-nitroquinazolin-4-amine (800 mg, 1.86 mmol) in 2,2,2-trifluoroethanol (5.00 mL) was added paraformaldehyde (279 mg, 9.31 mmol, 256 uL) in one portion. The mixture was stirred at 60° C. for 0.5 h. Then the mixture was added sodium borohydride (141 mg, 3.72 mmol) in portions at 60° C. The mixture was stirred at 60° C. for 1 h. The reaction mixture was added methanol (10 mL) and concentrated to give residue. The residue was diluted with water (30 mL) and extracted with ethyl acetate (3×20.0 mL). The combined organic layer was washed with brine (10 mL) and dried over sodium sulfate, filtered and concentrated to give N-(3-chloro-2-fluorophenyl)-7-((3-fluoro-1-methylpyrrolidin-3-yl)ethynyl)-6-nitroquinazolin-4-amine (800 mg, crude) as a yellow solid. m/z ES+ $[M+H]^+$ 444.0

Step 6. To a solution of N-(3-chloro-2-fluorophenyl)-7-((3-fluoro-1-methylpyrrolidin-3-yl)ethynyl)-6-nitroquinazolin-4-amine (800 mg, 1.80 mmol) in methanol (12.0 mL) and water (3.00 mL) was added iron powder (503 mg, 9.01 mmol) and ammonium chloride (482 mg, 9.01 mmol) in portions. The mixture was stirred at 80° C. for 1 h. The mixture was added methanol (30 mL) and filtered. The filtrate was concentrated to give residue. The residue was diluted saturated sodium hydrogencarbonate solution (20 mL) and extracted with ethyl acetate (3×30 mL). The combined organic layer was washed with brine (10 mL) and dried over sodium sulfate, filtered and concentrated to give crude product. The crude product was purified by prep-HPLC (column: Phenomenex luna C18 150*40 mm*15 um; mobile phase: [water (0.225% formic acid)-acetonitrile]; B %: 2%-32%, 11 min) and lyophilized to give $N^4$-(3-chloro-2-fluorophenyl)-7-((3-fluoro-1-methylpyrrolidin-3-yl)ethynyl)quinazoline-4,6-diamine (120 mg, 16% yield) as a yellow solid. $^1$H NMR (400 MHz, CD3OD) δ=8.58 (s, 1H), 7.89 (s, 1H), 7.64 (s, 1H), 7.58-7.51 (m, 2H), 7.31 (dt, J=1.2, 8.0 Hz, 1H), 4.49-4.22 (m, 1H), 4.07-3.83 (m, 2H), 3.64-3.44 (m, 1H), 3.10 (s, 3H), 3.04-2.74 (m, 2H).

Step 7. To a solution of $N^4$-(3-chloro-2-fluorophenyl)-7-((3-fluoro-1-methylpyrrolidin-3-yl)ethynyl)quinazoline-4, 6-diamine (100 mg, 242 umol), acrylic acid (26.1 mg, 362 umol, 24.9 uL) and pyridine (76.5 mg, 967 umol, 78.0 uL) in dimethyl formamide (2.00 mL) was added 1-(3-dimethyl aminopropyl)-3-ethylcarbodiimide hydrochloride (185 mg, 967 umol) in portions. The mixture was stirred at 25° C. for 0.5 h. The mixture was filtered. The filtrate was purified by prep-HPLC (column: Unisil 3-100 C18 Ultra 150*50 mm*3 um; mobile phase: [water (0.225% formic acid)-acetonitrile]; B %: 12%-32%, 10 min) and lyophilized to give N-(4-((3-chloro-2-fluorophenyl)amino)-7-((3-fluoro-1-methylpyrrolidin-3-yl) ethynyl)quinazolin-6-yl)acrylamide (40.07 mg, 35% yield) as a yellow solid. m/z ES+ $[M+H]^+$ 468.3; $^1H$ NMR (400 MHz, DMSO-$d_6$) δ=10.29-10.01 (m, 2H), 8.67 (s, 1H), 8.59-8.39 (m, 1H), 8.29 (s, 1H), 7.96 (br s, 1H), 7.51 (br s, 2H), 7.35-7.23 (m, 1H), 6.59 (dd, J=10.4, 17.2 Hz, 1H), 6.35 (dd, J=1.6, 17.2 Hz, 1H), 5.87 (dd, J=1.6, 10.4 Hz, 1H), 3.22-3.09 (m, 2H), 2.93-2.83 (m, 2H), 2.45-2.33 (m, 2H), 2.31 (s, 3H).

Example 55. Synthesis of Compound No. 61 (N-(4-((3-chloro-4-((3-fluorobenzyl)oxy)-phenyl)amino)-7-((3-methyltetrahydrofuran-3-yl)ethynyl)quinazolin-6-yl)acrylamide)

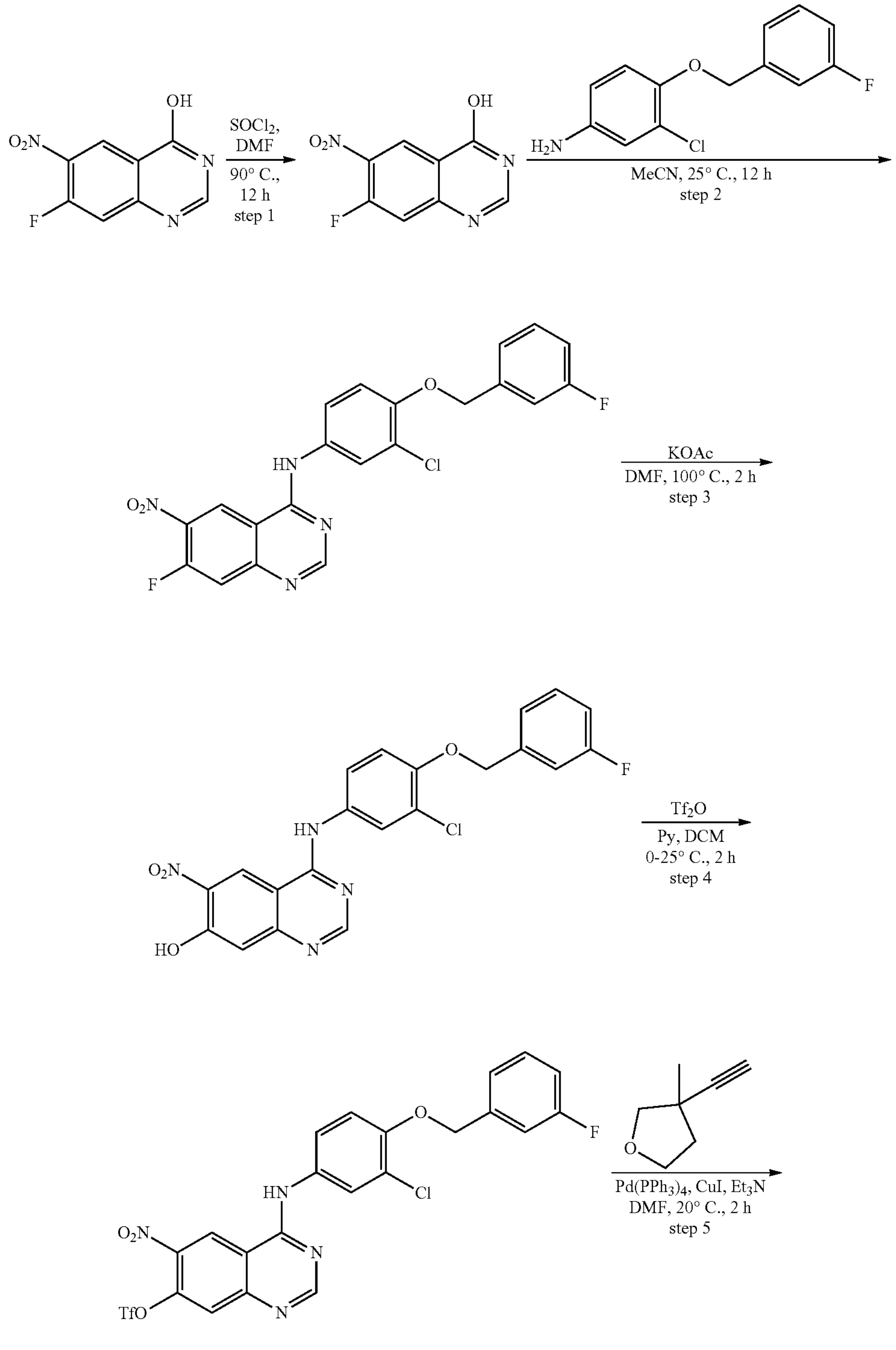

-continued

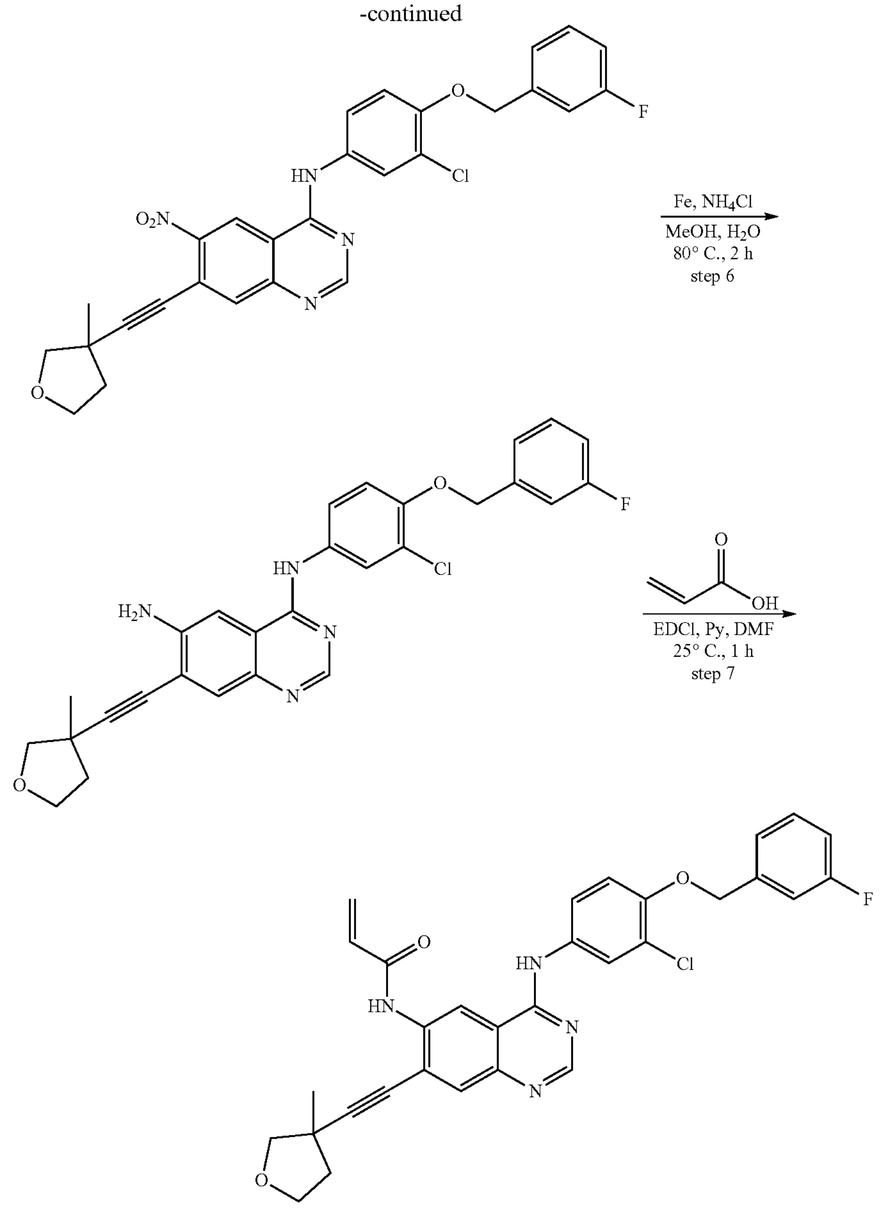

Step 1. To a solution of 7-fluoro-6-nitroquinazolin-4-ol (5.00 g, 23.9 mmol) in thionyl chloride (30 mL) was added dimethyformamide (190 mg, 2.60 mmol) dropwise. The mixture was stirred at 90° C. for 12 h. The mixture was concentrated in vacuum to give 4-chloro-7-fluoro-6-nitroquinazoline (5.40 g, crude) as a white solid.

Step 2. To a solution of 4-chloro-7-fluoro-6-nitroquinazoline (5.40 g, 23.7 mmol) in acetonitrile (50 mL) was added 3-chloro-4-((3-fluorobenzyl)oxy)aniline (5.97 g, 23.7 mmol) in portions. The mixture was stirred at 25° C. for 12 h. The mixture was concentrated in vacuum to give N-(3-chloro-4-((3-fluorobenzyl)oxy)phenyl)-7-fluoro-6-nitroquinazolin-4-amine (12.3 g, crude) as a yellow solid. m/z ES+ $[M+H]^+$ 443.1; $^1H$ NMR (400 MHz, DMSO-$d_6$) δ 11.99-11.47 (m, 1H), 9.85 (d, J=7.5 Hz, 1H), 8.91 (s, 1H), 8.01-7.88 (m, 2H), 7.69 (dd, J=2.6, 8.9 Hz, 1H), 7.48 (dt, J=6.1, 8.0 Hz, 1H), 7.38-7.28 (m, 3H), 7.24-7.14 (m, 1H), 5.29 (s, 2H).

Step 3. To a solution of N-(3-chloro-4-((3-fluorobenzyl)oxy)phenyl)-7-fluoro-6-nitroquinazolin-4-amine (12.3 g, 27.8 mmol) in dimethyformamide (150 mL) was added potassium acetate (13.6 g, 139 mmol) in portions. The mixture was stirred at 100° C. for 2 h. The mixture was added water (500 mL) and filtered. The filer cake was dried in vacuum to give 4-((3-chloro-4-((3-fluorobenzyl)oxy)phenyl)amino)-6-nitroquinazolin-7-ol (13.0 g, crude) as a red solid. m/z ES+ $[M+H]^+$ 441.0; $^1H$ NMR (400 MHz, DMSO-$d_6$) δ 9.16 (s, 1H), 8.58-8.32 (m, 1H), 7.99-7.94 (m, 2H), 7.69 (br d, J=9.0 Hz, 1H), 7.48-7.43 (m, 1H), 7.33-7.24 (m, 3H), 7.20-7.12 (m, 2H), 5.24 (s, 2H).

Step 4. To a solution of 4-((3-chloro-4-((3-fluorobenzyl)oxy)phenyl)amino)-6-nitroquinazolin-7-ol (2.00 g, 4.54 mmol), pyridine (1.79 g, 22.7 mmol) in dichloromethane (30 mL) was added trifluoromethanesulfonic anhydride (2.56 g, 9.07 mmol) dropwise at 0° C. The mixture was stirred at 25° C. for 2 h. The mixture was diluted with water (150 mL) and extracted with dichloromethane (3×80 mL). The combined organic layer was washed with brine (60 mL), dried over sodium sulfate, filtered and concentrated in vacuum. The residue was purified by silica gel chromatography (petroleum ether/ethyl acetate=10/1 to 3/1) to give 4-((3-chloro-4-((3-fluorobenzyl)oxy) phenyl)amino)-6-nitroquinazolin-7-yl trifluoromethanesulfonate (650 mg, 25% yield) as a yellow solid. $^1$H NMR (400 MHz, DMSO-$d_6$) δ 10.58 (s, 1H), 9.71 (s, 1H), 8.77 (s, 1H), 8.03 (s, 1H), 7.99-7.96 (m, 1H), 7.71-7.68 (m, 1H), 7.50-7.45 (m, 1H), 7.35-7.29 (m, 4H), 7.21-7.17 (m, 1H), 5.27 (s, 2H).

Step 5. To a solution of 4-((3-chloro-4-((3-fluorobenzyl) oxy)phenyl)amino)-6-nitroquinazolin-7-yl trifluoromethanesulfonate (600 mg, 1.05 mmol), 3-ethynyl-3-methyltetrahydrofuran (138 mg, 1.26 mmol) in dimethyformamide (9.00 mL) and triethylamine (9.00 mL) was added copper iodide (39.9 mg, 209 umol) and tetrakis(triphenylphosphine) palladium(0) (121 mg, 105 umol) in one portion. The mixture was stirred at 20° C. for 2 h. The mixture was diluted with water (100 mL) and extracted with ethyl acetate (3×80.0 mL). The combined organic layer was washed with brine (40.0 mL), dried over sodium sulfate, filtered and concentrated in vacuum. The residue was purified by silica gel chromatography (petroleum ether/ethyl acetate=3/1) to give N-(3-chloro-4-((3-fluorobenzyl)oxy) phenyl)-7-((3-methyltetrahydrofuran-3-yl)ethynyl)-6-nitroquinazolin-4-amine (290 mg, 52% yield) as a yellow solid. $^1$H NMR (400 MHz, DMSO-$d_6$) δ 10.35 (s, 1H), 9.42 (s, 1H), 8.70 (s, 1H), 8.00 (d, J=2.6 Hz, 1H), 7.94 (s, 1H), 7.71 (dd, J=2.6, 9.0 Hz, 1H), 7.47 (dt, J=6.0, 8.0 Hz, 1H), 7.35-7.28 (m, 3H), 7.18 (dt, J=2.3, 8.6 Hz, 1H), 5.27 (s, 2H), 4.11 (q, J=4.9 Hz, 2H), 3.94-3.88 (m, 3H), 2.31-2.21 (m, 1H), 2.00 (td, J=7.3, 12.2 Hz, 1H), 1.43 (s, 3H).

Step 6. To a solution of N-(3-chloro-4-((3-fluorobenzyl) oxy)phenyl)-7-((3-methyltetrahydrofuran-3-yl)ethynyl)-6-nitroquinazolin-4-amine (280 mg, 525 umol), ammonium chloride (197 mg, 3.68 mmol) in methanol (4.00 mL) and water (1.00 mL) was added iron powder (147 mg, 2.63 mmol) in portions. The mixture was stirred at 80° C. for 2 h. The mixture was filtered. The filtrate was concentrated in vacuum. The residue was diluted with saturated sodium bicarbonate solution (100 mL) and extracted with ethyl acetate (3×60.0 mL). The combined organic layer was washed with brine (40.0 mL), dried over sodium sulfate, filtered and concentrated in vacuum to give $N^4$-(3-chloro-4-((3-fluorobenzyl)oxy)phenyl)-7-((3-methyltetrahydrofuran-3-yl)ethynyl)quinazoline-4,6-diamine (250 mg, 95% yield) as a yellow solid. m/z ES+ $[M+H]^+$ 503.2; $^1$H NMR (400 MHz, DMSO-$d_6$) δ 9.47 (s, 1H), 8.33 (s, 1H), 8.03 (d, J=2.5 Hz, 1H), 7.71 (dd, J=2.5, 8.9 Hz, 1H), 7.59 (s, 1H), 7.47 (br t, J=2.9 Hz, 2H), 7.34-7.29 (m, 2H), 7.23 (d, J=9.0 Hz, 1H), 7.18 (dt, J=2.3, 8.7 Hz, 1H), 5.55 (s, 2H), 5.24 (s, 2H), 3.94-3.87 (m, 1H), 3.94-3.87 (m, 2H), 3.61 (d, J=7.9 Hz, 1H), 2.36-2.29 (m, 1H), 2.02-1.98 (m, 1H), 1.45 (s, 3H).

Step 7. To a mixture of $N^4$-(3-chloro-4-((3-fluorobenzyl) oxy)phenyl)-7-((3-methyltetrahydrofuran-3-yl)ethynyl) quinazoline-4,6-diamine (220 mg, 437 umol), acrylic acid (37.8 mg, 525 umol) and pyridine (138 mg, 1.75 mmol) in dimethyformamide (2.00 mL) was added 1-(3-dimethylaminopropyl)-3-ethylcarbodiimide hydrochloride (335 mg, 1.75 mmol) in portions. The mixture was stirred at 20° C. for 1 h. The mixture was filtered. The filtrate was purified by prep-HPLC (column: Waters Xbridge C18 150*50 mm*10 um; mobile phase: [water (10 mM $NH_4HCO_3$)-acetonitrile]; B %: 58%-78%, 10 min) and lyophilized to give N-(4-((3-chloro-4-((3-fluorobenzyl)oxy)phenyl)amino)-7-((3-methyltetrahydrofuran-3-yl)ethynyl)-quinazolin-6-yl)acrylamide (88.5 mg, 35% yield) as a yellow solid. m/z ES+ $[M+H]^+$ 557.4; $^1$H NMR (400 MHz, DMSO-$d_6$) δ 9.87 (s, 2H), 8.68 (s, 1H), 8.56 (s, 1H), 8.01 (d, J=2.4 Hz, 1H), 7.80 (s, 1H), 7.72 (dd, J=2.5, 9.0 Hz, 1H), 7.47 (dt, J=6.1, 8.0 Hz, 1H), 7.36-7.29 (m, 2H), 7.26 (d, J=9.2 Hz, 1H), 7.18 (dt, J=1.9, 8.6 Hz, 1H), 6.58 (br dd, J=10.2, 17.1 Hz, 1H), 6.34 (dd, J=1.8, 17.1 Hz, 1H), 5.85 (dd, J=1.8, 10.2 Hz, 1H), 5.25 (s, 2H), 3.93-3.82 (m, 3H), 3.59 (d, J=8.1 Hz, 1H), 2.33-2.23 (m, 1H), 1.96 (td, J=7.3, 12.2 Hz, 1H), 1.41 (s, 3H).

Example 56. Synthesis of Compound No. 62 (N-(4-((3-chloro-2-fluorophenyl)amino)-7-((1-methyl-3-(trifluoromethyl)pyrrolidin-3-yl)ethynyl)quinazolin-6-yl)acrylamide)

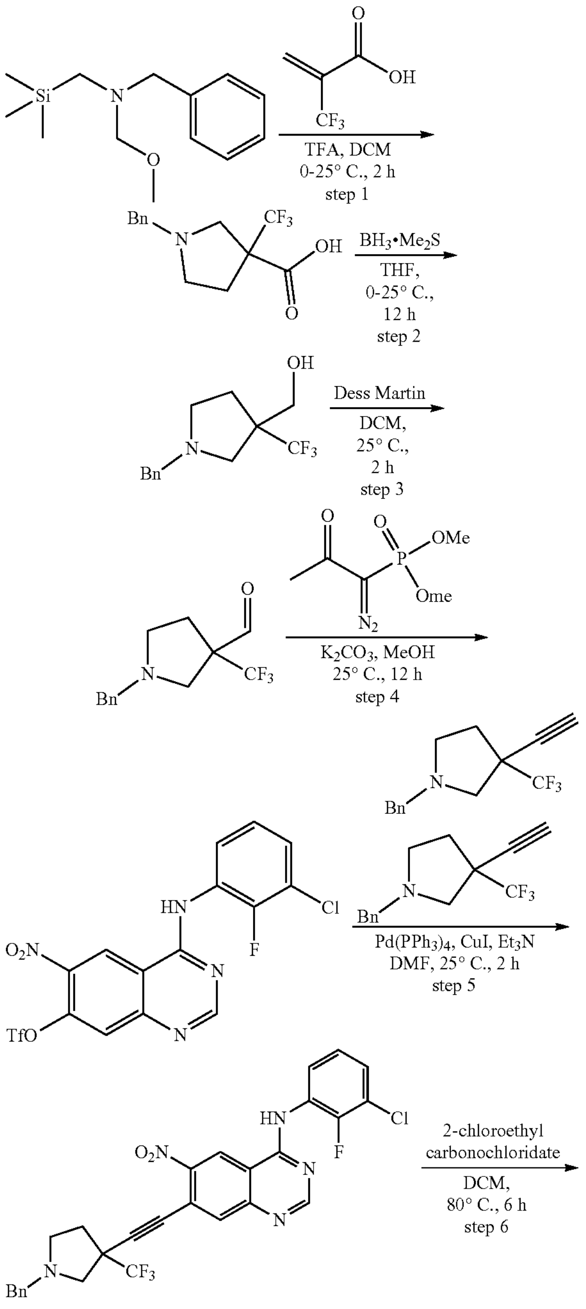

-continued

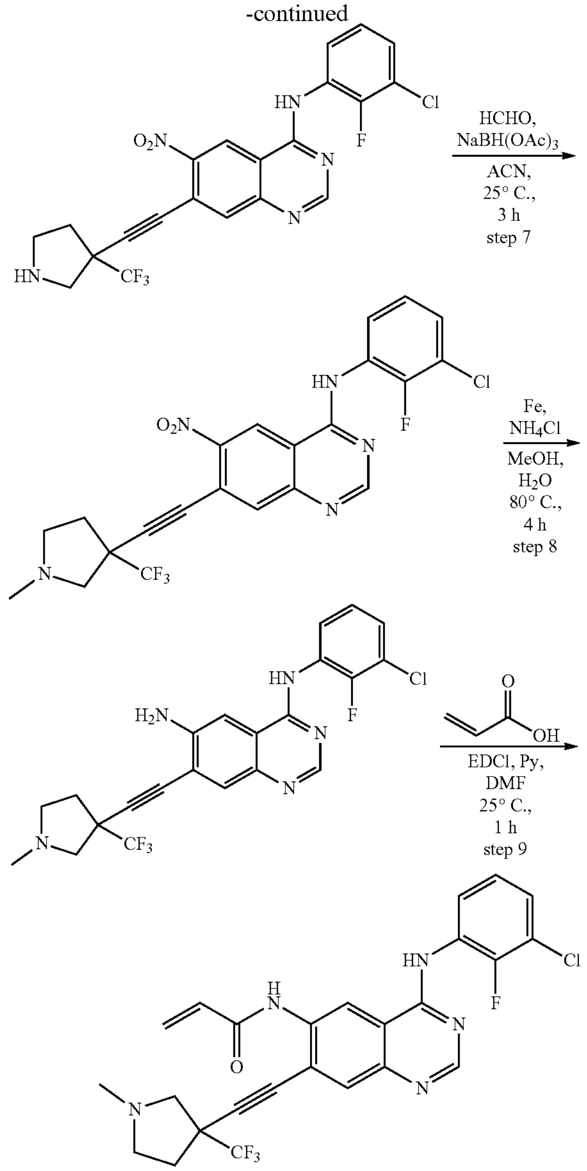

Step 1. To a solution of 2-(trifluoromethyl)acrylic acid (6.00 g, 42.8 mmol) in dichloromethane (100 mL) was slowly added N-benzyl-1-methoxy-N-((trimethylsilyl)methyl)methanamine (10.0 g, 42.1 mmol) and trifluoroacetic acid (770 mg, 6.75 mmol) at 0° C. The mixture was stirred at 25° C. for 2 h under nitrogen. The mixture was concentrated under reduced pressure to give a 1-benzyl-3-(trifluoromethyl)pyrrolidine-3-carboxylic acid (11.5 g, crude) as a white solid. m/z ES+ $[M+H]^+$ 274.0;

Step 2. To a solution of 1-benzyl-3-(trifluoromethyl)pyrrolidine-3-carboxylic acid (5.50 g, 20.1 mmol) in tetrahydrofuran (30 mL) was added borane dimethyl sulfide complex (10.0 M in tetrahydrofuran, 4.08 mL) at 0° C. The mixture was stirred at 25° C. for 12 h. The reaction mixture was quenched with methanol (50 mL). Then the mixture was concentrated under reduced pressure to give a residue. The residue was purified by column chromatography on silica gel (petroleum ether/ethyl acetate=20/1 to 4/1 to ethyl acetate/methanol=4/1). The desired fraction was collected and concentrated under reduced pressure to give (1-benzyl-3-(trifluoromethyl)pyrrolidin-3-yl)methanol (2.67 g, crude) as colorless oil. m/z ES+ $[M+H]^+$ 260.1;

Step 3. To a solution of (1-benzyl-3-(trifluoromethyl)pyrrolidin-3-yl)methanol (2.67 g, 10.3 mmol) in dichloromethane (100 mL) was added Dess-Martin (6.68 g, 15.7 mmol). The mixture was stirred at 25° C. for 2 h. The mixture was concentrated under reduced pressure to give a residue. The residue was purified by column chromatography on silica gel (petroleum ether/ethyl acetate=20/1 to 0/1). The desired fraction was collected and concentrated under reduced pressure to give 1-benzyl-3-(trifluoromethyl)pyrrolidine-3-carbaldehyde (2.60 g, crude) as yellow oil.

Step 4. To a solution of 1-benzyl-3-(trifluoromethyl)pyrrolidine-3-carbaldehyde (2.60 g, 10.1 mmol) in methanol (30.0 mL) was added dimethyl (1-diazo-2-oxopropyl)phosphonate (2.90 g, 15.1 mmol) and potassium carbonate (4.20 g, 30.3 mmol). The mixture was stirred at 25° C. for 12 h. The mixture was concentrated under reduced pressure to give a residue. The residue was purified by column chromatography on silica gel (petroleum ether/ethyl acetate=0/1). The desired fraction was collected and concentrated under reduced pressure to give 1-benzyl-3-ethynyl-3-(trifluoromethyl)pyrrolidine (1.05 g, 41% yield) as colorless oil. m/z ES+ $[M+H]^+$ 254.2; $^1H$ NMR (400 MHz, DMSO-$d_6$) δ 7.36-7.24 (m, 5H), 3.68-3.59 (m, 2H), 2.90 (d, J=9.9 Hz, 1H), 2.81-2.76 (m, 1H), 2.73-2.66 (m, 1H), 2.66-2.58 (m, 1H), 2.51-2.50 (m, 1H), 2.25 (td, J=6.8, 13.2 Hz, 1H), 2.17-2.09 (m, 1H).

Step 5. To a solution of 4-((3-chloro-2-fluorophenyl)amino)-6-nitroquinazolin-7-yl trifluoromethanesulfonate (1.80 g, 3.86 mmol) in dimethyl formamide (10 mL) was added 1-benzyl-3-ethynyl-3-(trifluoromethyl) pyrrolidine (950 mg, 3.75 mmol), triethylamine (7.27 g, 71.8 mmol), cuprous iodide (150 mg, 787 umol) and tetrakis(triphenylphosphine)palladium(0) (45.0 mg, 38.9 umol). The mixture was stirred at 25° C. for 2 h under nitrogen. The mixture was purified by column chromatography on silica gel (petroleum ether/ethyl acetate=10/1 to 4/1). The desired fraction was collected and concentrated under reduced pressure to give 7-((1-benzyl-3-(trifluoromethyl)pyrrolidin-3-yl)ethynyl)-N-(3-chloro-2-fluorophenyl)-6-nitroquinazolin-4-amine (1.67 g, 75% yield) as a yellow oil. m/z ES+ $[M+H]^+$ 570.2; $^1H$ NMR (400 MHz, DMSO-$d_6$) δ 10.69 (br s, 1H), 9.48 (br s, 1H), 8.69 (br s, 1H), 8.07 (br s, 1H), 7.55 (br s, 2H), 7.37-7.32 (m, 5H), 7.29 (br dd, J=4.8, 8.2 Hz, 1H), 3.75-3.67 (m, 2H), 3.08-2.99 (m, 2H), 2.84-2.78 (m, 1H), 2.77-2.70 (m, 1H), 2.42-2.35 (m, 2H).

Step 6. To a solution of 7-((1-benzyl-3-(trifluoromethyl)pyrrolidin-3-yl)ethynyl)-N-(3-chloro-2-fluorophenyl)-6-nitroquinazolin-4-amine (1.30 g, 2.28 mmol) in dichloromethane (6.0 mL) was added 2-chloroethyl carbonochloridate (8.34 g, 58.3 mmol). The mixture was stirred at 80° C. for 6 h under nitrogen. The mixture was concentrated under reduced pressure to give a residue. The residue was added methanol (20 mL) and stirred at 80° C. for 2 h. Then the mixture was concentrated under reduced pressure to give a residue. The residue was purified by reverse phase HPLC (0.1% formic acid condition). The desired fraction was concentrated and lyophilized to give a residue. The residue was purified by column chromatography on silica gel (ethyl acetate/methanol=1/0 to 20/1). The desired fraction was collected and concentrated to give N-(3-chloro-2-fluorophenyl)-6-nitro-7-((3-(trifluoromethyl)pyrrolidin-3-yl)ethynyl) quinazol in-4-amine (700 mg, crude) as a yellow solid. m/z ES+ $[M+H]^+$ 480.1;

Step 7. To a solution of N-(3-chloro-2-fluorophenyl)-6-nitro-7-((3-(trifluoromethyl)-pyrrolidin-3-yl)ethynyl) quinazolin-4-amine (700 mg, 1.46 mmol) in acetonitrile (20 mL) was added sodium triacetoxy borohydride (800 mg, 3.77 mmol) and paraformaldehyde (900 mg, 28.1 mmol). The mixture was stirred at 25° C. for 3 h. The mixture was concentrated under reduced pressure to give a residue. The residue was purified by column chromatography on silica gel (petroleum ether/ethyl acetate=1/1 to 0/1). The desired fraction was collected and concentrated to give N-(3-chloro-2-fluorophenyl)-7-((1-methyl-3-(trifluoromethyl)pyrrolidin-3-yl)ethynyl)-6-nitroquinazolin-4-amine (360 mg, crude) as a yellow solid. m/z ES+ $[M+H]^+$ 494.1; $^1H$ NMR (400 MHz, DMSO-$d_6$) δ 10.88-10.58 (m, 1H), 9.54-9.38 (m, 1H), 8.68 (br s, 1H), 8.06 (br s, 1H), 7.55 (br dd, J=5.7, 7.2 Hz, 2H), 7.32 (br s, 1H), 3.04-2.96 (m, 3H), 2.81-2.71 (m, 2H), 2.70-2.59 (m, 2H), 2.36 (br d, J=6.5 Hz, 2H).

Step 8. To a solution of N-(3-chloro-2-fluorophenyl)-7-((1-methyl-3-(trifluoromethyl)pyrrolidin-3-yl)ethynyl)-6-nitroquinazolin-4-amine (360 mg, 729 umol) in methanol (20 mL) and water (3.0 mL) was added iron powder (400 mg, 7.16 mmol) and ammonium chloride (600 mg, 11.2 mmol). The mixture was stirred at 80° C. for 4 h. The mixture was concentrated under reduced pressure to give a residue. The residue was purified by prep-HPLC (column: Phenomenex Synergi C18 150*25*10 um; mobile phase: [water (0.225% formic acid)-acetonitrile]; B %: 10%-40%, 8 min). The desired fraction was collected and lyophilized to give $N^4$-(3-chloro-2-fluorophenyl)-7-((1-methyl-3-(trifluoromethyl)pyrrolidin-3-yl)ethynyl) quinazoline-4,6-diamine (150 mg, 44% yield) as a yellow solid. m/z ES+ $[M+H]^+$ 464.1; $^1H$ NMR (400 MHz, DMSO-$d_6$) δ 9.79-9.47 (m, 1H), 8.27 (br s, 1H), 8.16 (s, 1H), 7.67 (br s, 1H), 7.53 (br d, J=2.9 Hz, 1H), 7.47 (br s, 1H), 7.26 (br t, J=7.9 Hz, 1H), 5.64 (br s, 2H), 3.08-3.03 (m, 1H), 2.99-2.94 (m, 1H), 2.82-2.75 (m, 1H), 2.65-2.55 (m, 1H), 2.45-2.35 (m, 2H), 2.33 (s, 3H).

Step 9. To a solution of $N^4$-(3-chloro-2-fluorophenyl)-7-((1-methyl-3-(trifluoromethyl)pyrrolidin-3-yl)ethynyl) quinazoline-4,6-diamine (120 mg, 258 umol) in dimethyl formamide (2.0 mL) was added 1-(3-dimethylaminopropyl)-3-ethylcarbodiimide hydrochloride (72.0 mg, 375 umol), pyridine (70.5 mg, 892 umol) and acrylic acid (20.0 mg, 277 umol). The mixture was stirred at 25° C. for 1 h. The mixture was filtered to give a solution. The solution was purified by prep-HPLC (column: Phenomenex Synergi C18 150*25*10 um; mobile phase: [water (0.225% formic acid)-acetonitrile]; B %: 12%-42%, 10 min). The desired fraction was concentrated and lyophilized to give N-(4-((3-chloro-2-fluorophenyl)amino)-7-((1-methyl-3-(trifluoromethyl)pyrrolidin-3-yl)ethynyl)quinazolin-6-yl)acrylamide (49.1 mg, 33% yield) as a yellow solid. m/z ES+ $[M+H]^+$ 518.1; $^1H$ NMR (400 MHz, DMSO-$d_6$) δ 10.14 (s, 1H), 10.02 (s, 1H), 8.64 (s, 1H), 8.53 (s, 1H), 8.14 (s, 1H), 7.92 (s, 1H), 7.52 (br t, J=7.3 Hz, 2H), 7.30 (br t, J=8.0 Hz, 1H), 6.59-6.50 (m, 1H), 6.34 (dd, J=1.7, 17.1 Hz, 1H), 5.86 (dd, J=1.6, 10.2 Hz, 1H), 3.07 (br s, 2H), 2.79-2.70 (m, 2H), 2.37 (br s, 3H), 2.37-2.34 (m, 2H).

Example 57. Synthesis of Compound No. 63 (N-(4-((3,4-dichloro-2-fluorophenyl)amino)-7-((3-methyltetrahydrofuran-3-yl)ethynyl)quinazolin-6-yl)acrylamide)

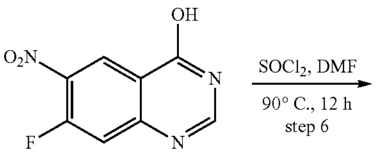

-continued

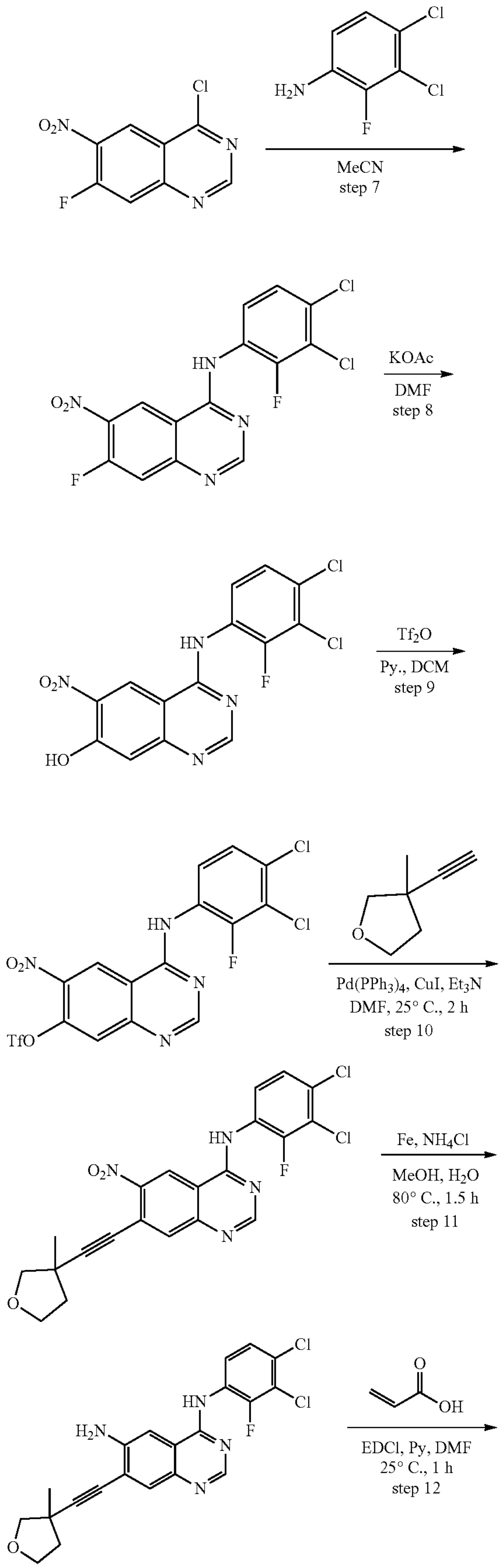

-continued

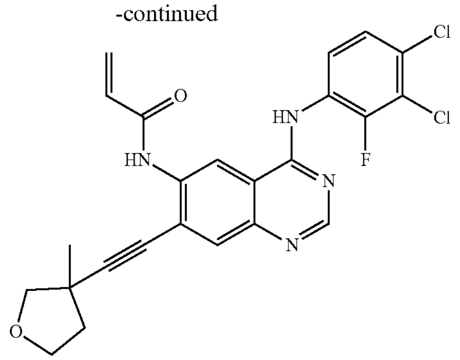

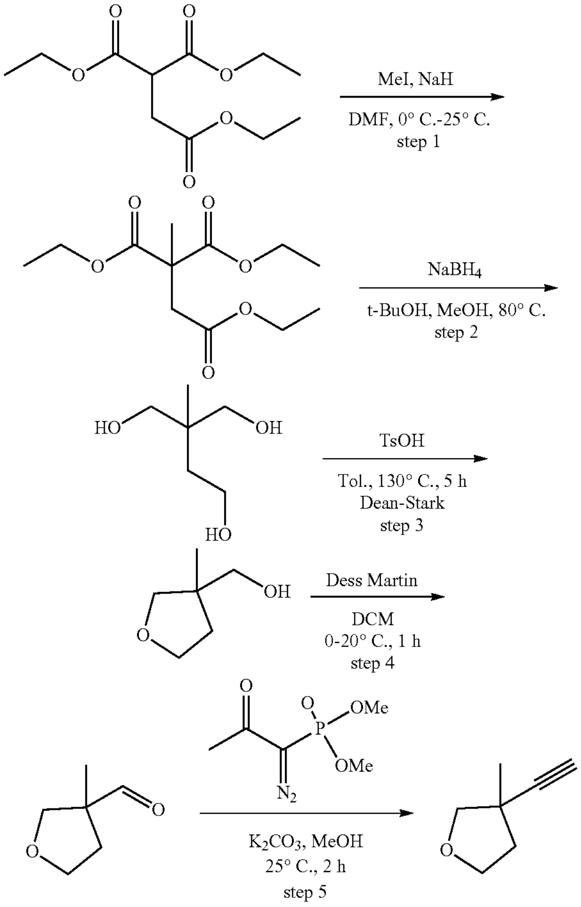

Step 1. To a solution of triethyl ethane-1,1,2-tricarboxylate (40.0 g, 162 mmol) in dimethyl formamide (300 mL) was added sodium hydride (9.10 g, 227 mmol, 60% purity) in portions at 0° C. The mixture was stirred at 0° C. for 0.5 h. Then the mixture was added iodomethane (30.0 g, 211 mmol) dropwise at 0° C. The mixture was stirred at 25° C. for 1 h. The mixture was quenched with saturated ammonium chloride solution (300 mL) and extracted with ethyl acetate (3×200 mL). The combined organic layer was washed with brine (100 mL) and dried over sodium sulfate, filtered and concentrated to give crude product. The crude product was purified by silica gel chromatography (petroleum ether/ethyl acetate=20/1 to 10/1) to give triethyl propane-1,2,2-tricarboxylate (45.0 g, crude) as colorless oil. $^1$H NMR (400 MHz, $CDCl_3$) δ 4.18-4.10 (m, 6H), 2.87-2.85 (m, 2H), 1.47 (s, 3H), 1.20-1.17 (m, 9H).

Step 2. Refluxing solution of triethyl propane-1,2,2-tricarboxylate (40.0 g, 154 mmol) and sodium borohydride (15.4 g, 407 mmol) in tert-butyl alcohol (400 mL) was added methanol (30.0 mL) dropwise over 0.5 h. The solution was boiled at 90° C. for a further 0.5 h and allowed to cool. 5 M hydrochloric acid was carefully added to neutralize the solution, which was then filtered. The residue was washed with ethanol (3×100 mL) and filtered. The solvent evaporated under reduced pressure to give a residue. The residue was purified by column chromatography (petroleum ether/ethyl acetate=10/1 to 1/1) to give 2-(hydroxymethyl)-2-methylbutane-1,4-diol (10.0 g, 49% yield) as light yellow oil. $^1$H NMR (400 MHz, DMSO-$d_6$) δ 4.47-4.43 (m, 1H), 4.39 (t, J=5.4 Hz, 2H), 3.46 (dt, J=4.9, 7.1 Hz, 2H), 3.18 (d, J=5.3 Hz, 4H), 1.40-1.35 (m, 2H), 0.74 (s, 3H).

Step 3. To a solution of 2-(hydroxymethyl)-2-methylbutane-1,4-diol (10.0 g, 74.5 mmol) in toluene (200 mL) was added 4-toluenesulfonic acid (1.28 g, 7.45 mmol) in portions. The mixture was stirred at 130° C. under Dean-Stark trap for 5 h. The mixture was concentrated to give residue. The residue was purified by silica gel chromatography (petroleum ether/ethyl acetate=10/1 to 2/1) to give (3-methyltetrahydrofuran-3-yl)methanol (6.00 g, 69% yield) as yellow oil. $^1$H NMR (400 MHz, $CDCl_3$) δ 3.85-3.76 (m, 2H), 3.66 (d, J=8.4 Hz, 1H), 3.44 (s, 2H), 3.32 (d, J=8.4 Hz, 1H), 1.82-1.75 (m, 1H), 1.61-1.57 (m, 1H), 1.06 (s, 3H)

Step 4. To a solution of (3-methyltetrahydrofuran-3-yl)methanol (600 mg, 5.17 mmol) in dichloromethane (8.0 mL) was added dess-martin periodinane (3.29 g, 7.75 mmol) in portions at 0° C. The mixture was stirred at 20° C. for 1 h. The mixture was concentrated to give crude product. The crude product was purified by silica gel chromatography (petroleum ether/ethyl acetate=10/1 to 2/1) to give 3-methyltetrahydrofuran-3-carbaldehyde (500 mg, crude) as colorless oil. $^1$H NMR (400 MHz, $CDCl_3$) δ 9.51 (s, 1H), 3.90-3.86 (m, 1H), 3.85-3.79 (m, 2H), 3.41 (d, J=9.1 Hz, 1H), 2.26 (ddd, J=6.8, 8.0, 12.7 Hz, 1H), 1.66 (ddd, J=5.6, 7.2, 12.8 Hz, 1H), 1.19 (s, 3H).

Step 5. To a solution of 3-methyltetrahydrofuran-3-carbaldehyde (500 mg, 4.38 mmol) and potassium carbonate (1.82 g, 13.1 mmol) in methanol (5.0 mL) was added dimethyl(1-diazo-2-oxopropyl) phosphonate (1.09 g, 5.69 mmol) dropwise. The mixture was stirred at 25° C. for 2 h. The mixture was diluted with water (40 mL) and extracted with petroleum ether (3×20 mL). The combined organic layer was washed with brine (10 mL) and dried over sodium sulfate, filtered. The organic layer was diluted with dimethyl formamide (10 mL) and concentrated to remove petroleum ether to give 3-ethynyl-3-methyl-tetrahydrofuran (~500 mg, crude) dissolved in dimethyl formamide (10 mL).

Step 6. To a solution of 7-fluoro-6-nitroquinazolin-4-ol (5.00 g, 23.9 mmol) in thionyl chloride (82.0 g, 689 mmol) was added dimethyl formamide (175 mg, 2.39 mmol) dropwise. The mixture was stirred at 90° C. for 12 h. The mixture was concentrated to give 4-chloro-7-fluoro-6-nitroquinazoline (5.40 g, crude) as a yellow solid.

Step 7. To a solution of 4-chloro-7-fluoro-6-nitroquinazoline (5.40 g, 23.7 mmol) in acetonitrile (50 mL) was added 3,4-dichloro-2-fluoroaniline (4.27 g, 23.7 mmol) in portions. The mixture was stirred at 25° C. for 1 h. The mixture was concentrated to give crude product. The crude product was washed with ethyl acetate (200 mL) and filtered, the filter cake was dried to give N-(3,4-dichloro-2-fluorophenyl)-7-fluoro-6-nitroquinazolin-4-amine (9.00 g, crude) as a white solid. 41 NMR (400 MHz, DMSO-$d_6$) δ 9.65 (br d, J=7.6 Hz, 1H), 8.74 (s, 1H), 7.93 (d, J=12.0 Hz, 1H), 7.68-7.62 (m, 1H), 7.61-7.54 (m, 1H)

Step 8. To a solution of N-(3,4-dichloro-2-fluorophenyl)-7-fluoro-6-nitroquinazolin-4-amine (9.00 g, 24.3 mmol) in dimethyl formamide (100 mL) was added potassium acetate (11.9 g, 121 mmol) in portions. The mixture was stirred at 100° C. for 2 h. The mixture was poured into water (500 mL) and filtered. The filter cake was dried to give 4-(3,4-dichloro-2-fluoro-anilino)-6-nitro-quinazolin-7-ol (8.00 g, crude) as a yellow solid. m/z ES+ $[M+H]^+$ 368.9;

Step 9. To a solution of 4-(3,4-dichloro-2-fluoro-anilino)-6-nitro-quinazolin-7-ol (5.00 g, 13.6 mmol) and pyridine (5.36 g, 67.7 mmol, 5.47 mL) in dichloromethane (40 mL) was added trifluoromethanesulfonic anhydride (7.64 g, 27.1 mmol) dropwise at 0° C. The mixture was stirred at 25° C. for 1 h. The mixture was diluted with water (30 mL) and extracted with dichloromethane (2×30 mL). The combined organic layer was washed with brine (20 mL) and dried over sodium sulfate, filtered and concentrated to give crude product. The crude product was purified by silica gel chromatography (petroleum ether/ethyl acetate=20/1 to 10/1) to give 4-((3,4-dichloro-2-fluorophenyl)amino)-6-nitroquinazolin-7-yl trifluoromethanesulfonate (3.50 g, 49% yield) as a yellow solid. m/z ES+ $[M+H]^+$ 500.9;

Step 10. To a solution of 4-((3,4-dichloro-2-fluorophenyl)amino)-6-nitroquinazolin-7-yl trifluoromethanesulfonate (400 mg, 798 umol) and 3-ethynyl-3-methyltetrahydrofuran (16.5 mg, 150 umol) in dimethyl formamide (5.0 mL) and triethylamine (5.0 mL) was added tetrakis[triphenylphosphine]palladium(0) (92.2 mg, 79.8 umol) and copper(I) iodide (15.2 mg, 79.8 umol) in one portion under nitrogen. The mixture was stirred at 25° C. for 2 h. The mixture was diluted with water (40 mL) and extracted with ethyl acetate (3×30 mL). The combined organic layer was washed with brine (10 mL) and dried over sodium sulfate, filtered and concentrated to give crude product. The crude product was purified by silica gel chromatography (petroleum ether/ethyl acetate=20/1 to 3/1) to give N-(3,4-dichloro-2-fluorophenyl)-7-((3-methyltetrahydrofuran-3-yl)ethynyl)-6-nitroquinazolin-4-amine (350 mg, 95% yield) as yellow oil. 41 NMR (400 MHz, $CDCl_3$) δ 8.89 (s, 1H), 8.75 (s, 1H), 8.34 (dd, J=8.0, 9.2 Hz, 1H), 8.13 (s, 1H), 7.88 (br s, 1H), 7.40 (dd, J=2.0, 9.2 Hz, 1H), 4.14-4.01 (m, 3H), 3.73 (d, J=8.4 Hz, 1H), 2.49-2.37 (m, 1H), 2.10-1.99 (m, 1H), 1.54 (s, 3H).

Step 11. To a solution of N-(3,4-dichloro-2-fluorophenyl)-7-((3-methyltetrahydrofuran-3-yl)ethynyl)-6-nitroquinazolin-4-amine (310 mg, 672 umol) and ammonium chloride (180 mg, 3.36 mmol) in methanol (8.0 mL) and water (2.0 mL) was added iron powder (188 mg, 3.36 mmol) in portions. The mixture was stirred at 80° C. for 1.5 h. The mixture was added methanol (50 mL) and filtered. The filtrate was concentrated to give crude product. The residue was diluted with saturated sodium hydrogencarbonate solution (30 mL) and extracted with ethyl acetate (3×30 mL). The combined organic layer was washed with brine (10 mL) and dried over sodium sulfate, filtered and concentrated to give $N^4$-(3,4-dichloro-2-fluorophenyl)-7-((3-methyltetrahydrofuran-3-yl)ethynyl)quinazoline-4,6-diamine (270 mg, crude) as a yellow solid. m/z ES+ $[M+H]^+$ 431.0;

Step 11. To a solution of $N^4$-(3,4-dichloro-2-fluorophenyl)-7-((3-methyltetrahydrofuran-3-yl)ethynyl)quinazoline-4,6-diamine (240 mg, 556 umol), acrylic acid (52.1 mg, 723 umol) and pyridine (176 mg, 2.23 mmol) in dimethyl formamide (3.0 mL) was added 1-(3-dimethylaminopropyl)-3-ethylcarbodiimide hydrochloride (427 mg, 2.23 mmol) in portions. The mixture was stirred at 25° C. for 1 h. The mixture was diluted with water (30 mL) and extracted with ethyl acetate (3×20 mL). The combined organic layer was washed with brine (10 mL) and dried over sodium sulfate, filtered and concentrated to give crude product. The crude product was purified by prep-HPLC (column: Waters Xbridge C18 150*50 mm*10 um; mobile phase: [water (10 mM $NH_4HCO_3$)-acetonitrile]; B %: 53%-73%, 10 min) and lyophilized to give N-(4-((3,4-di chloro-2-fluorophenyl)amino)-7-((3-methyltetrahydrofuran-3-yl)ethynyl)quinazol in-6-yl)acrylamide (67.7 mg, 25% yield) as a yellow solid. m/z ES+ $[M+H]^+$ 485.2; $^1H$ NMR (400 MHz, $CDCl_3$) δ 9.23 (s, 1H), 8.74 (s, 1H), 8.42 (s, 1H), 8.35 (dd, J=8.0, 9.2 Hz, 1H), 7.97 (s, 1H), 7.81 (br s, 1H), 7.34 (dd, J=2.0, 9.2 Hz, 1H), 6.61-6.52 (m, 1H), 6.49-6.37 (m, 1H), 5.92 (dd, J=1.2, 10.4 Hz, 1H), 4.19-4.06 (m, 3H), 3.69 (d, J=8.4 Hz, 1H), 2.51-2.37 (m, 1H), 2.15-2.03 (m, 1H), 1.59 (s, 3H).

Example 58. Synthesis of Compound No. 64 (N-(4-((3-chloro-2-fluorophenyl)amino)-7-((3-(oxetan-3-yl)-3-azabicyclo[3.1.0]hexan-1-yl)ethynyl)quinazolin-6-yl)acrylamide)

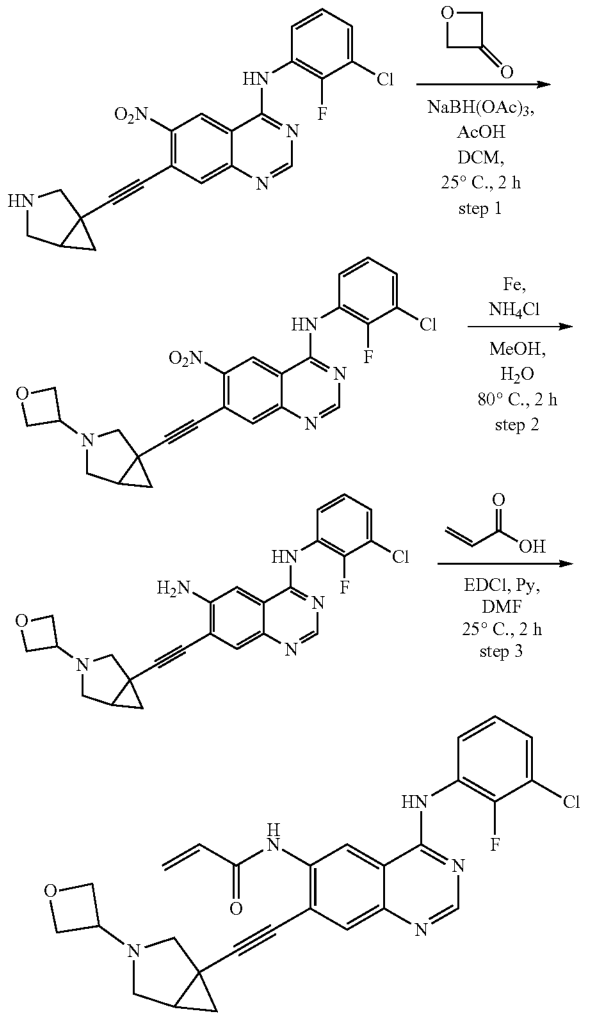

Step 1. A mixture of 7-(3-azabicyclo[3.1.0]hexan-1-ylethynyl)-N-(3-chloro-2-fluorophenyl)-6-nitroquinazolin-4-amine (400 mg, 869 umol), oxetan-3-one (376 mg, 5.21 mmol) and acetic acid (0.10 mL) in dichloromethane (10 mL) was added sodium borohydride acetate (1.11 g, 5.21 mmol) in portions at 25° C. The mixture was stirred at 25° C. for 2 h. The mixture was quenched with methanol (20 mL) and concentrated to dryness to give a residue. The residue was purified by silica gel chromatography (Petroleum ether/Ethyl acetate=0/1) to give N-(3-chloro-2-fluorophenyl)-6-nitro-7-((3-(oxetan-3-yl)-3-azabicyclo[3.1.0]hexan-1-yl)ethynyl) quinazolin-4-amine (350 mg, 84% yield) as a yellow solid. m/z ES+ $[M+H]^+$ 480.4; $^1H$ NMR (400 MHz, $CDCl_3$) δ 8.77 (s, 1H), 8.65 (s, 1H), 8.19 (br t, J=7.2 Hz, 1H), 7.98 (s, 1H), 7.22 (br s, 1H), 7.15-7.08 (m, 1H), 4.65-4.60 (m, 2H), 4.56-4.52 (m, 2H), 3.78-3.72 (m, 1H), 3.15 (d, J=8.4 Hz, 1H), 2.95 (d, J=8.8 Hz, 1H), 2.55 (d, J=8.4 Hz, 1H), 2.50 (dd, J=3.6, 8.8 Hz, 1H), 2.02 (s, 1H), 1.95-1.90 (m, 1H), 1.51 (t, J=4.8 Hz, 1H).

Step 2. A mixture of N-(3-chloro-2-fluorophenyl)-6-nitro-7-((3-(oxetan-3-yl)-3-azabicyclo[3.1.0]hexan-1-yl)ethynyl) quinazolin-4-amine (350 mg, 729 umol), iron powder (204 mg, 3.65 mmol) and ammonium chloride (195 mg, 3.65 mmol) in methanol (5.0 mL) and water (2.0 mL) was stirred at 80° C. for 2 h. The mixture was filtered and the filtrate was concentrated to dryness to give a residue. The residue was diluted with ethyl acetate (20 mL) and washed with saturated sodium bicarbonate solution (20 mL), brine (15 mL), dried with anhydrous sodium sulfate, filtered and concentrated in vacuum to give $N^4$-(3-chloro-2-fluorophenyl)-7-((3-(oxetan-3-yl)-3-azabicyclo[3.1.0]hexan-1-yl)ethynyl) quinazoline-4,6-diamine (210 mg, crude) as a yellow solid. m/z ES+ $[M+H]^+$ 450.1;

Step 3. To a mixture of $N^4$-(3-chloro-2-fluorophenyl)-7-((3-(oxetan-3-yl)-3-azabicyclo[3.1.0]hexan-1-yl)ethynyl) quinazoline-4,6-diamine (150 mg, 333 umol), acrylic acid (26.4 mg, 367 umol) and pyridine (105 mg, 1.33 mmol) in dimethyl formamide (2.0 mL) was added 1-ethyl-3-(3-dimethylamino-propyl)-carbodiimide hydrochloride (256 mg, 1.33 mmol) in portions at 25° C. The mixture was stirred at 25° C. for 2 h and then filtered. The filtrate was purified by prep-HPLC (column: Waters Xbridge 150*25 mm*5 um; mobile phase: [water (0.05% ammonium hydroxide v/v)-acetonitrile]; B %: 35%-65%, 10 min) and prep-HPLC (column: Unisil 3-100 C18 Ultra 150*50 mm*3 um; mobile phase: [water (0.225% formic acid)-acetonitrile]; B %: 10%-40%, 10 min) to give N-(4-((3-chloro-2-fluorophenyl) amino)-7-((3-(oxetan-3-yl)-3-azabicyclo[3.1.0]hexan-1-yl) ethynyl)quinazolin-6-yl)acrylamide (14.6 mg, 8% yield) as a yellow solid. m/z ES+ $[M+H]^+$ 504.4; $^1H$ NMR (400 MHz, $CDCl_3$) δ=9.19 (s, 1H), 8.74 (s, 1H), 8.36-8.27 (m, 2H), 7.96 (s, 1H), 7.86 (br s, 1H), 7.24-7.14 (m, 2H), 6.55-6.49 (m, 1H), 6.37-6.28 (m, 1H), 5.94 (d, J=10.4 Hz, 1H), 4.72 (dt, J=2.4, 6.4 Hz, 2H), 4.63 (dt, J=3.6, 6.0 Hz, 2H), 3.85 (quin, J=6.4 Hz, 1H), 3.27 (d, J=8.4 Hz, 1H), 3.07 (d, J=8.8 Hz, 1H), 2.67-2.60 (m, 2H), 2.01 (td, J=4.0, 8.0 Hz, 1H), 1.66 (t, J=4.4 Hz, 1H), 1.14 (dd, J=4.4, 8.4 Hz, 1H).

Example 59. Synthesis of Compound No. 65 (N-(4-((3-chloro-2-fluorophenyl)amino)-7-((3-methyl-3-azabicyclo[3.1.0]hexan-1-yl)ethynyl)quinazolin-6-yl)acrylamide)

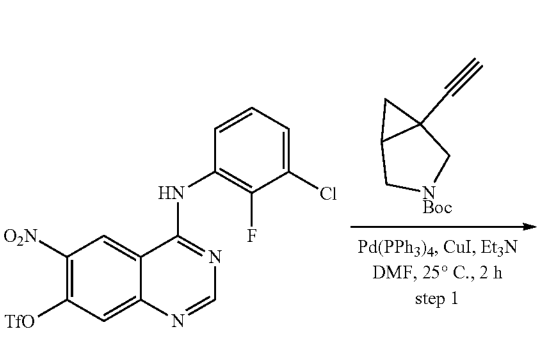

-continued

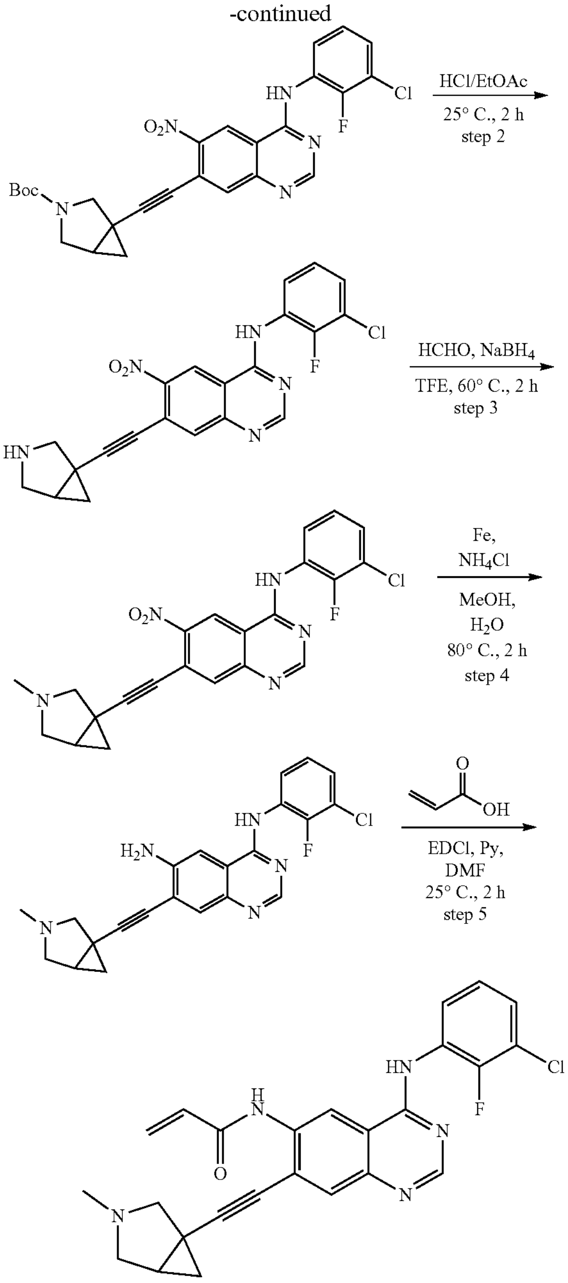

Step 1. To a mixture of 4-((3-chloro-2-fluorophenyl) amino)-6-nitroquinazolin-7-yl trifluoromethanesulfonate (1.80 g, 3.86 mmol), tert-butyl 1-ethynyl-3-azabicyclo [3.1.0]hexane-3-carboxylate (802 mg, 3.87 mmol) and cuprous iodide (147 mg, 772 umol) in dimethyl formamide (5.0 mL) and triethylamine (4.0 mL) was added tetrakis (triphenylphosphine) palladium (0) (446 mg, 386 umol) under nitrogen atmosphere. The mixture was stirred at 25° C. for 2 h. The mixture was concentrated to give a residue. The residue was purified by silica gel chromatography (Petroleum ether/Ethyl acetate=5/1-2/1) to give tert-butyl 1-((4-((3-chloro-2-fluorophenyl)amino)-6-nitroquinazolin-7-yl)ethynyl)-3-azabicyclo[3.1.0]hexane-3-carboxylate (2.00 g, 99% yield) as a yellow solid. m/z ES+ $[M+H]^+$ 524.0; $^1H$ NMR (400 MHz, $CDCl_3$) δ=8.87-8.79 (m, 2H), 8.23 (br t, J=6.8 Hz, 1H), 8.16 (br s, 1H), 8.06 (br d, J=14.3

Hz, 1H), 7.33-7.29 (m, 1H), 7.24-7.18 (m, 1H), 3.96-3.82 (m, 1H), 3.63-3.52 (m, 2H), 3.01-2.96 (m, 2H), 2.93-2.88 (m, 2H), 1.48 (s, 9H)

Step 2. To a mixture of tert-butyl 1-((4-((3-chloro-2-fluorophenyl)amino)-6-nitroquinazolin-7-yl)ethynyl)-3-azabicyclo[3.1.0]hexane-3-carboxylate (1.80 g, 3.44 mmol) in ethyl acetate (10 mL) was added hydrochloric acid/ethyl acetate (4.00 M, 4.00 mL), the mixture was stirred at 25° C. for 2 h. The mixture was concentrated to dryness to give a residue. The residue was triturated with ethyl acetate (10 mL). After filtration, the filter cake was washed with ethyl acetate (5.0 mL), dried in vacuum to give 7-(3-azabicyclo[3.1.0]hexan-1-ylethynyl)-N-(3-chloro-2-fluorophenyl)-6-nitroquinazolin-4-amine (1.40 g, 96% yield) as a yellow solid. m/z ES+$[M+H]^+$ 424.1; $^1$H NMR (400 MHz, DMSO-$d_6$) δ 9.86 (br s, 1H), 9.60-9.40 (m, 2H), 8.74 (br s, 1H), 8.08 (br s, 1H), 7.61-7.57 (m, 1H), 7.52 (br t, J=7.2 Hz, 1H), 7.38-7.31 (m, 1H), 3.63 (dd, J=6.0, 11.2 Hz, 1H), 3.56-3.44 (m, 2H), 3.38 (dd, J=6.0, 11.6 Hz, 1H), 2.41-2.35 (m, 1H), 1.60-1.51 (m, 1H), 1.47-1.39 (m, 1H).

Step 3. A mixture of 7-(3-azabicyclo[3.1.0]hexan-1-ylethynyl)-N-(3-chloro-2-fluorophenyl)-6-nitroquinazolin-4-amine (400 mg, 869 umol), paraformaldehyde (130 mg, 4.35 mmol) in trifluoroethanol (5.0 mL) was added sodium borohydride (65.8 mg, 1.74 mmol) at 25° C. The mixture was stirred at 60° C. for 1 h. The mixture was quenched with methanol (5.0 mL) and concentrated to dryness to give a residue. The residue was diluted with ethyl acetate (20 mL) and washed with water (20 mL), dried over anhydrous sodium sulfate, filtered and concentrated in vacuum to give N-(3-chloro-2-fluorophenyl)-7-((3-methyl-3-azabicyclo[3.1.0]hexan-1-yl)ethynyl)-6-nitroquinazolin-4-amine (350 mg, 92% yield) as a yellow solid. m/z ES+ $[M+H]^+$ 438.0;

Step 4. A mixture of N-(3-chloro-2-fluorophenyl)-7-((3-methyl-3-azabicyclo[3.1.0]hexan-1-yl)ethynyl)-6-nitroquinazolin-4-amine (350 mg, 799 umol), iron powder (223 mg, 4.00 mmol) and ammonium chloride (214 mg, 4.00 mmol) in methanol (5.0 mL) and water (2.0 mL) was stirred at 80° C. for 2 h. The mixture was filtered and the filtrate was concentrated to dryness to give a residue. The residue was diluted with ethyl acetate (20 mL) and washed with saturated sodium bicarbonate solution (20 mL), brine (15 mL), dried with anhydrous sodium sulfate, filtered and concentrated in vacuum to give $N^4$-(3-chloro-2-fluorophenyl)-7-((3-methyl-3-azabicyclo[3.1.0]hexan-1-yl)ethynyl)quinazoline-4,6-diamine (300 mg, crude) as a yellow solid. m/z ES+ $[M+H]^+$ 408.1.

Step 5. To a mixture of $N^4$-(3-chloro-2-fluorophenyl)-7-((3-methyl-3-azabicyclo[3.1.0]hexan-1-yl)ethynyl) quinazoline-4,6-diamine (250 mg, 613 umol), acrylic acid (57.4 mg, 796 umol) and pyridine (194 mg, 2.45 mmol) in dimethyl formamide (3.0 mL) was added 1-ethyl-3-(3-dimethylamino-propyl)-carbodiimide hydrochloride (470 mg, 2.45 mmol) at 25° C. The mixture was stirred at 25° C. for 2 h and then filtered. The filtrate was purified by prep-HPLC (column: Welch Xtimate C18 150*30 mm*5 um; mobile phase: [water (0.05% ammonium hydroxide v/v)-acetonitrile]; B %: 40%-70%, 10 min) and pre-HPLC (column: Unisil 3-100 C18 Ultra 150*50 mm*3 um; mobile phase: [water (0.225% formic acid)-acetonitrile]; B %: 8%-38%, 10 min) to give N-(4-((3-chloro-2-fluorophenyl)amino)-7-((3-methyl-3-azabicyclo[3.1.0]hexan-1-yl)ethynyl) quinazolin-6-yl) acrylamide (36.7 mg, 13% yield) as a yellow solid. m/z ES+$[M+H]^+$ 462.4; $^1$H NMR (400 MHz, $CDCl_3$) δ 9.18 (s, 1H), 8.72 (s, 1H), 8.38-8.30 (m, 2H), 7.94 (s, 1H), 7.78 (br s, 1H), 7.23-7.12 (m, 2H), 6.55-6.46 (m, 1H), 6.38-6.23 (m, 1H), 5.92 (d, J=10.4 Hz, 1H), 3.28 (br d, J=8.8 Hz, 1H), 3.08 (br d, J=9.2 Hz, 1H), 2.59 (br d, J=8.4 Hz, 2H), 2.39 (s, 3H), 1.96 (td, J=4.0, 8.4 Hz, 1H), 1.25 (s, 1H), 1.09 (br dd, J=4.0, 8.4 Hz, 1H).

Example 60. Synthesis of Compound No. 66 (N-(4-((3-chloro-2-fluorophenyl)amino)-7-((1,3-dimethylpiperidin-3-yl)ethynyl)quinazolin-6-yl)acrylamide)

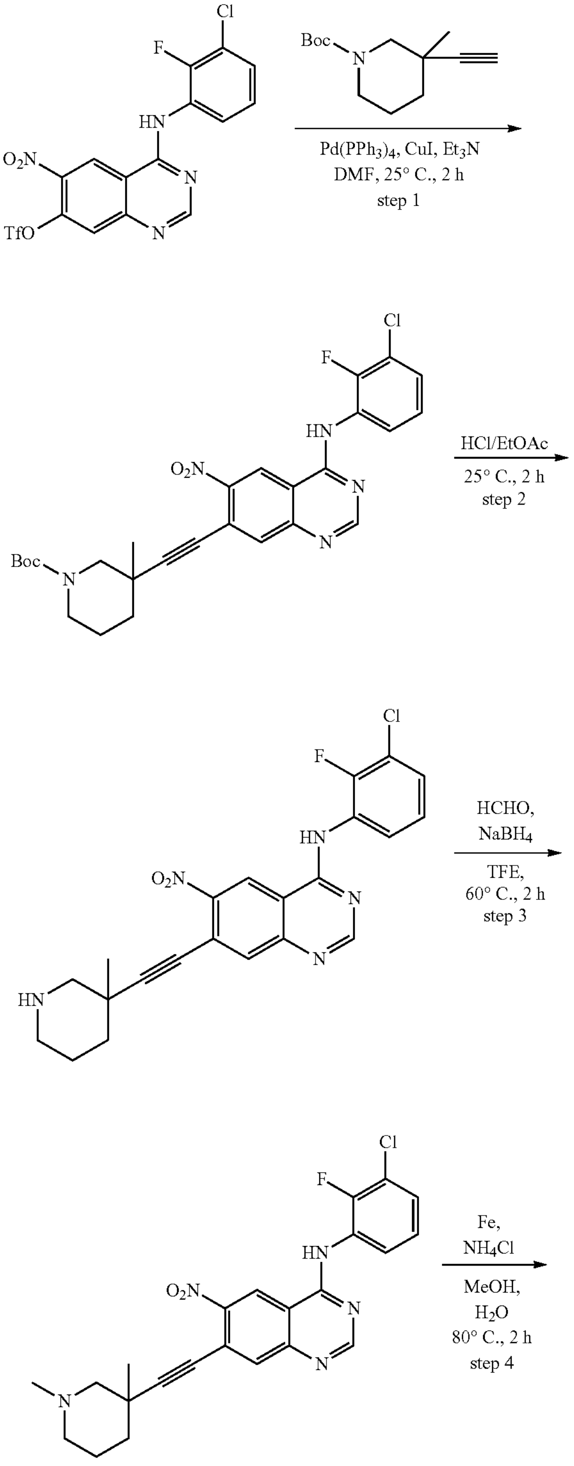

-continued

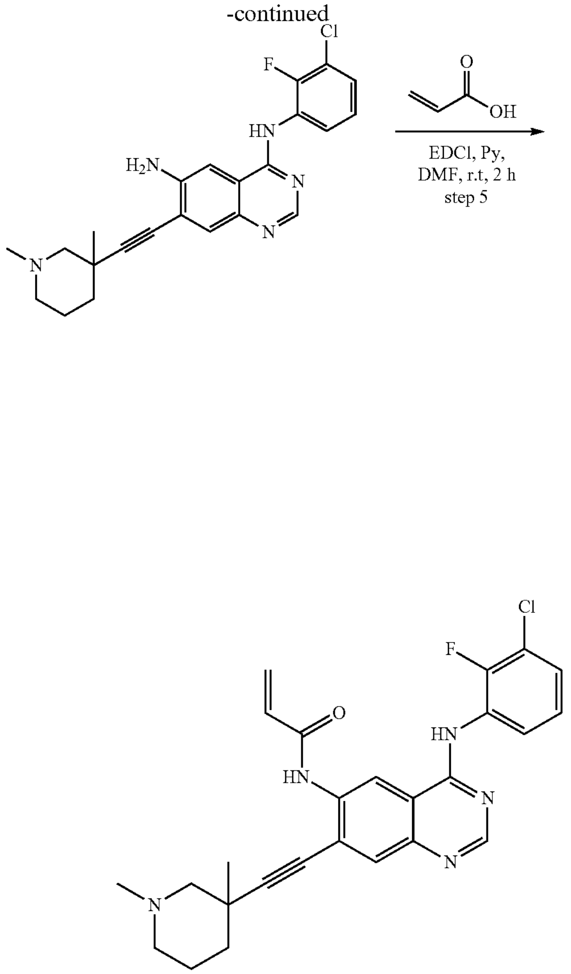

Step 1. To a mixture of 4-((3-chloro-2-fluorophenyl) amino)-6-nitroquinazolin-7-yl trifluoromethanesulfonate (1.50 g, 3.21 mmol), tert-butyl 3-ethynyl-3-methylpiperidine-1-carboxylate (789 mg, 3.54 mmol) and triethylamine (3.27 g, 32.3 mmol) in dimethyl formamide (3.0 mL) was added tetrakis(triphenylphosphine) palladium (0) (371 mg, 321 umol) and cuprous iodide (122 mg, 643 umol) at 25° C. The mixture was stirred under nitrogen atmosphere at 25° C. for 2 h. The mixture was concentrated to give a residue. The residue was purified by silica gel chromatography (Petroleum ether/Ethyl acetate=5/1-2/1) to afford tert-butyl 3-((4-((3-chloro-2-fluorophenyl) amino)-6-nitroquinazolin-7-yl) ethynyl)-3-methylpiperidine-1-carboxylate (1.5 g, crude) as a yellow solid. m/z ES+ $[M+H]^+$ 540.1; $^1H$ NMR (400 MHz, $CDCl_3$) δ 8.86 (s, 1H), 8.78 (br s, 1H), 8.29-8.22 (m, 1H), 8.09 (s, 2H), 7.46-7.35 (m, 1H), 7.23-7.18 (m, 1H), 3.91 (br d, J=13.2 Hz, 1H), 3.77 (br t, J=6.4 Hz, 1H), 2.99 (s, 2H), 1.97-1.85 (m, 2H), 1.73 (s, 3H), 1.67 (br s, 1H), 1.57 (br d, J=14.8 Hz, 1H), 1.44 (s, 9H), 1.37 (s, 3H).

Step 2. To a solution of tert-butyl 3-((4-((3-chloro-2-fluorophenyl)amino)-6-nitroquinazolin-7-yl)ethynyl)-3-methylpiperidine-1-carboxylate (1.00 g, 1.85 mmol) in ethyl acetate (5.0 mL) was added hydrochloric acid/ethyl acetate (4.00 M, 5.00 mL), the mixture was stirred at 25° C. for 1 h. The mixture was concentrated to dryness to give a residue. The residue was triturated with ethyl acetate (10 mL). After filtration, the filter cake was washed with ethyl acetate (5.0 mL), dried in vacuum to give N-(3-chloro-2-fluorophenyl)-7-((3-methylpiperidin-3-yl)ethynyl)-6-nitroquinazolin-4-amine (850 mg, 96% yield, HCl) as a yellow solid. m/z ES+$[M+H]^+$ 440.1; $^1H$ NMR (400 MHz, DMSO-$d_6$) δ 9.70-9.47 (m, 2H), 8.74 (br s, 1H), 8.37 (br s, 1H), 8.29 (br s, 1H), 7.59 (br d, J=6.4 Hz, 1H), 7.55-7.51 (m, 1H), 7.36-7.32 (m, 1H), 3.37 (br d, J=12.4 Hz, 1H), 3.24 (br d, J=12.0 Hz, 1H), 3.01 (br t, J=10.4 Hz, 1H), 2.91-2.81 (m, 1H), 1.98-1.90 (m, 2H), 1.84 (br d, J=14.4 Hz, 1H), 1.74-1.62 (m, 1H), 1.40 (s, 3H).

Step 3. A mixture of N-(3-chloro-2-fluorophenyl)-7-((3-methylpiperidin-3-yl)ethynyl)-6-nitroquinazolin-4-amine (550 mg, 1.15 mmol, HCl) and paraformaldehyde (173 mg, 5.77 mmol, 159 uL) in trifluoroethanol (5.0 mL) was stirred at 60° C. for 0.5 h. Then the mixture was added sodium borohydride (87.3 mg, 2.31 mmol) in portions at 60° C. The mixture was stirred at 60° C. for 1.5 h. The mixture was quenched with methanol (5.0 mL) and concentrated to dryness to give a residue. The residue was diluted with ethyl acetate (20 mL) and washed with water (10 mL), dried over anhydrous sodium sulfate, filtered and concentrated in vacuum to give N-(3-chloro-2-fluorophenyl)-7-((1,3-dimethylpiperidin-3-yl)ethynyl)-6-nitroquinazolin-4-amine (500 mg, crude) as a yellow solid. m/z ES+ $[M+H]^+$ 454.4; $^1H$ NMR (400 MHz, $CDCl_3$) δ 8.84 (br s, 1H), 8.74 (s, 1H), 8.28 (br s, 1H), 8.11 (s, 1H), 7.50-7.43 (m, 1H), 7.30 (br s, 1H), 7.21 (dd, J=1.2, 8.2 Hz, 1H), 2.88 (br d, J=11.2 Hz, 1H), 2.74 (br s, 1H), 2.31 (s, 3H), 2.01 (br s, 2H), 1.96 (br s, 2H), 1.75-1.68 (m, 2H), 1.39 (s, 3H).

Step 4. A mixture of N-(3-chloro-2-fluorophenyl)-7-((1,3-dimethylpiperidin-3-yl)ethynyl)-6-nitroquinazolin-4-amine (500 mg, 1.10 mmol), iron powder (308 mg, 5.51 mmol) and ammonium chloride (294 mg, 5.51 mmol) in methanol (8.0 mL) and water (3.0 mL) was stirred at 80° C. for 2 h. The mixture was filtered and the filtrate was concentrated to dryness to give a residue. The residue was diluted with ethyl acetate (20 mL) and washed with saturated sodium bicarbonate solution (20 mL), brine (20 mL), dried over anhydrous sodium sulfate, filtered and concentrated in vacuum to give $N^4$-(3-chloro-2-fluorophenyl)-7-((1,3-dimethylpiperidin-3-yl)ethynyl)quinazoline-4,6-diamine (400 mg, crude) as a yellow solid. m/z ES+ $[M+H]^+$ 424.1;

Step 5. To a mixture of $N^4$-(3-chloro-2-fluorophenyl)-7-((1,3-dimethylpiperidin-3-yl)ethynyl)quinazoline-4,6-diamine (300 mg, 708 umol), acrylic acid (61.2 mg, 849 umol, 58.3 uL) and pyridine (224 mg, 2.83 mmol) in dimethyl formamide (4.0 mL) was added 1-ethyl-3-(3-dimethylamino-propyl)-carbodiimide hydrochloride (543 mg, 2.83 mmol) at 25° C. The mixture was stirred at 25° C. for 2 h. The mixture was purified by pre-HPLC (column: Phenomenex Gemini NX—$C_{18}$ (75*30 mm*3 um); mobile phase: [water (0.05% ammonium hydroxide v/v)-acetonitrile]; B %: 50%-80%, 7 min) and (column: Unisil 3-100 C18 Ultra 150*50 mm*3 um; mobile phase: [water (0.225% formic acid)-acetonitrile]; B %: 10%-40%, 10 min) to give N-(4-((3-chloro-2-fluorophenyl)amino)-7-((1,3-dimethylpiperidin-3-yl)ethynyl)quinazolin-6-yl) acrylamide (55.4 mg, 15% yield) as a yellow solid. m/z ES+ $[M+H]^+$ 478.1; $^1H$ NMR (400 MHz, $CDCl_3$) δ 9.52 (br s, 1H), 9.19 (s, 1H), 8.75 (s, 1H), 8.38-8.34 (m, 1H), 7.96 (s, 1H), 7.80 (br s, 1H), 7.25-7.15 (m, 2H), 6.63-6.49 (m, 2H), 5.89-5.83 (m, 1H), 3.14 (br d, J=11.6 Hz, 2H), 2.50 (s, 3H), 2.14-2.01 (m, 4H), 1.79 (br dd, J=3.2, 10.8 Hz, 1H), 1.43 (s, 3H), 1.36 (br dd, J=3.6, 12.4 Hz, 1H).

Example 61. Synthesis of Compound No. 67 (N-(4-((3-chloro-4-(pyridin-2-ylmethoxy)phenyl)amino)-7-((1,3-dimethylpiperidin-3-yl)ethynyl)quinazolin-6-yl)acrylamide)
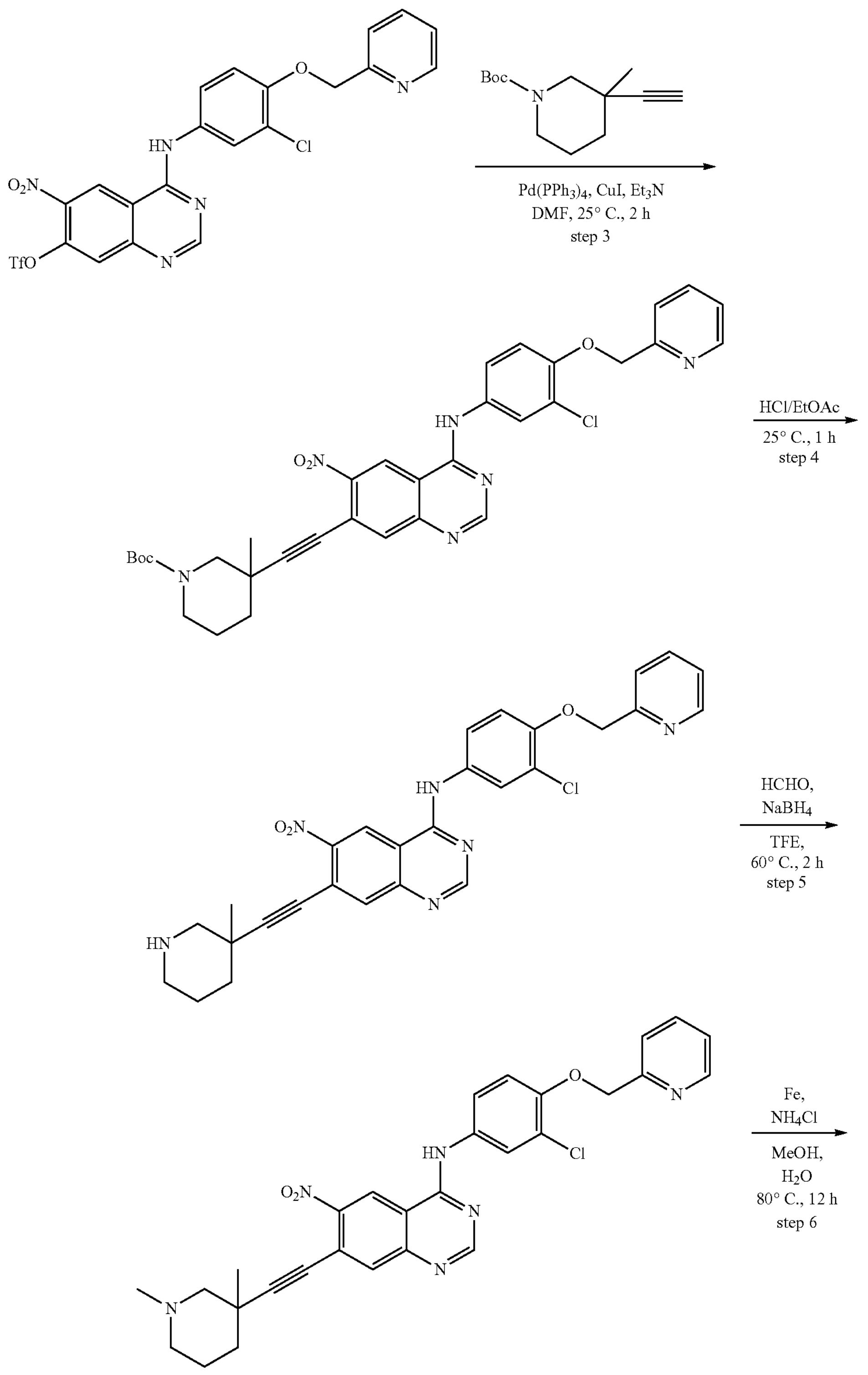

-continued

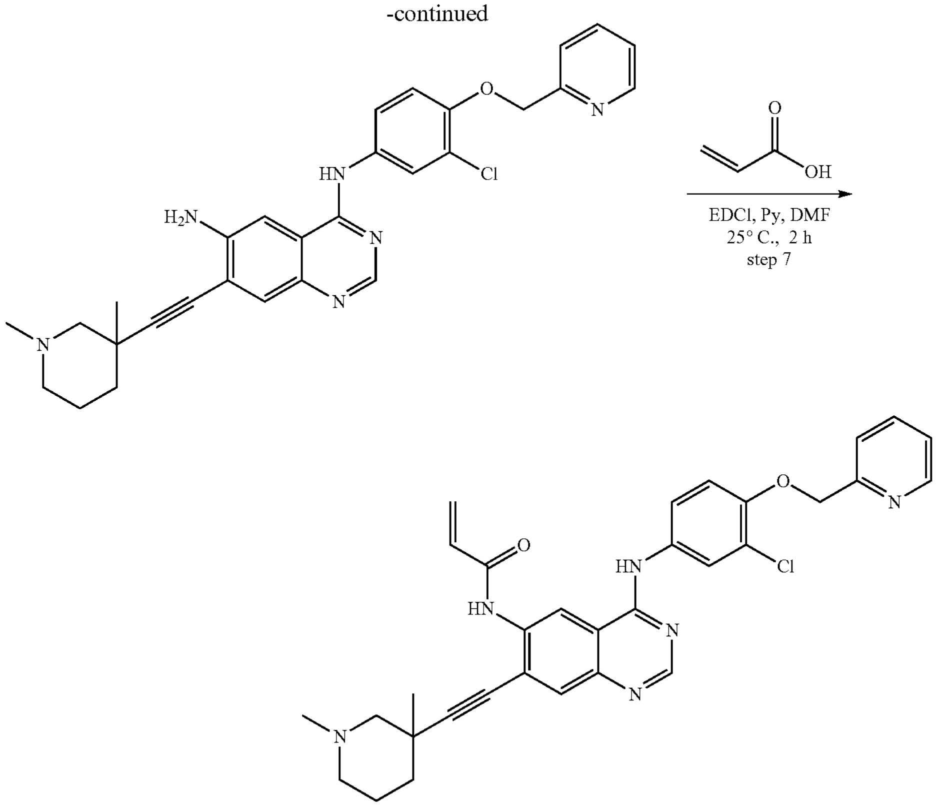

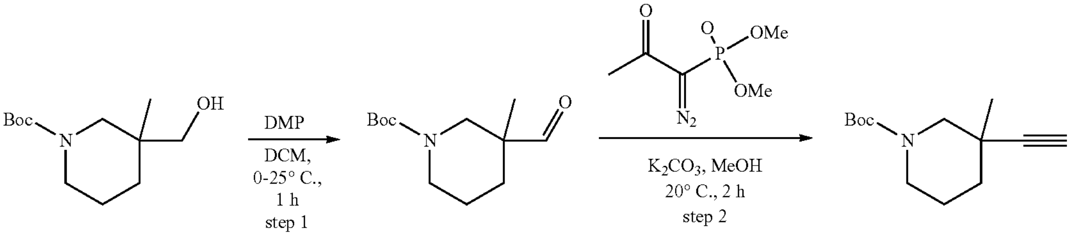

Step 1. To a solution of tert-butyl 3-(hydroxymethyl)-3-methylpiperidine-1-carboxylate (3.90 g, 17.0 mmol) in dichloromethane (20 mL) was added (1,1-diacetoxy-3-oxo-1,2-benziodoxol-1-yl) acetate (10.1 g, 23.8 mmol) at 0° C. in portions. The mixture was stirred at 25° C. for 1 h. The mixture was concentrated to afford a residue. The residue was purified by silica gel chromatography (Petroleum ether/Ethyl acetate=10/1) to give tert-butyl 3-formyl-3-methylpiperidine-1-carboxylate (3.10 g, 80% yield) as a colorless oil. $^1H$ NMR (400 MHz, $CDCl_3$) δ 3.80 (d, J=13.2 Hz, 1H), 3.46-3.37 (m, 1H), 3.17 (td, J=6.4, 12.8 Hz, 1H), 3.06 (d, J=13.2 Hz, 1H), 1.58-1.47 (m, 3H), 1.42 (s, 1H), 1.38 (s, 9H), 1.14 (s, 3H).

Step 2. To a mixture of tert-butyl3-formyl-3-methylpiperidine-1-carboxylate (3.00 g, 13.2 mmol) and potassium carbonate (3.65 g, 26.4 mmol) in methanol (20 mL) was added dimethyl (1-diazo-2-oxopropyl)phosphonate (3.30 g, 17.2 mmol) at 20° C. The mixture was stirred at 20° C. for 2 h. The mixture was concentrated to dryness to give a residue. The residue was purified by silica gel chromatography (Petroleum ether/Ethyl acetate=10/1) to give tert-butyl 3-ethynyl-3-methylpiperidine-1-carboxylate (2.60 g, 88% yield) as a colorless oil. $^1H$ NMR (400 MHz, $CDCl_3$) δ 3.91-3.67 (m, 2H), 2.86 (ddd, J=3.6, 9.6, 13.2 Hz, 1H), 2.78 (br d, J=12.4 Hz, 1H), 2.01 (s, 1H), 1.80-1.71 (m, 2H), 1.51-1.44 (m, 1H), 1.39 (s, 9H), 1.13 (s, 3H), 0.84-0.77 (m, 1H).

Step 3. To a mixture of 4-((3-chloro-4-(pyridin-2-ylmethoxy)phenyl)amino)-6-nitroquinazolin-7-yl trifluoromethane sulfonate (1.00 g, 1.80 mmol), tert-butyl 3-ethynyl-3-methylpiperidine-1-carboxylate (442 mg, 1.98 mmol) and triethylamine (1.09 g, 10.9 mmol) in dimethyl formamide (1.50 mL) was added tetrakis(triphenylphosphine) palladium (0) (208 mg, 180 umol) and cuprous iodide (68.5 mg, 360 umol) at 25° C. The mixture was stirred under nitrogen atmosphere at 25° C. for 2 h. The mixture was concentrated to give a residue. The residue was purified by silica gel chromatography (Petroleum ether/Ethyl acetate=5/1-2/1) to afford tert-butyl 3-((4-((3-chloro-4-(pyridin-2-ylmethoxy)phenyl)amino)-6-nitroquinazolin-7-yl)-ethynyl)-3-methylpiperidine-1-carboxylate (1.10 g, 97% yield) as a yellow solid. m/z ES+ $[M+H]^+$ 629.2; $^1H$ NMR (400 MHz, $CDCl_3$) δ 9.20 (br s, 1H), 9.02 (br s, 1H), 8.68 (s, 1H), 8.52 (dd, J=0.8, 4.8 Hz, 1H), 7.90 (s, 1H), 7.80 (d, J=2.4 Hz, 1H), 7.74-7.68 (m, 1H), 7.39-7.33 (m, 2H), 7.20-7.18 (m, 1H), 6.85 (d, J=8.8 Hz, 1H), 5.20 (s, 2H), 3.93-3.79 (m, 1H), 2.90 (s, 2H), 2.82 (s, 1H), 1.93 (br dd, J=4.4, 13.6 Hz, 1H), 1.82 (br d, J=6.4 Hz, 1H), 1.61-1.51 (m, 1H), 1.44 (br s, 1H), 1.34 (s, 9H), 1.26 (s, 3H).

Step 4. To a solution of tert-butyl 3-((4-((3-chloro-4-(pyridin-2-ylmethoxy)phenyl)amino)-6-nitroquinazolin-7-yl) ethynyl)-3-methylpiperidine-1-carboxylate (1.40 g, 2.23 mmol) in ethyl acetate (10 mL) was added hydrochloric acid/ethyl acetate (4.00 M, 10.0 mL), the mixture was stirred at 25° C. for 1 h. The mixture was concentrated to dryness to give a residue. The residue was triturated with ethyl acetate (20 mL). After filtration, the filter cake was washed with ethyl acetate (5.0 mL), dried in vacuum to give N-(3-chloro-4-(pyridin-2-ylmethoxy)phenyl)-7-((3-methylpiperidin-3-yl)ethynyl)-6-nitroquinazolin-4-amine (1.10 g, 87% yield, HCl) as a yellow solid. m/z ES+ $[M+H]^+$ 529.2; $^1H$ NMR (400 MHz, MeOD) δ 9.58 (s, 1H), 8.98-8.91 (m, 2H), 8.72 (t, J=8.0 Hz, 1H), 8.34-8.27 (m, 2H), 8.12 (t, J=6.8 Hz, 1H), 8.03 (d, J=2.4 Hz, 1H), 7.78 (dd, J=2.4, 8.8 Hz, 1H), 7.46 (d, J=9.2 Hz, 1H), 5.68 (s, 2H), 3.56 (br d, J=12.4 Hz, 1H), 3.46 (br d, J=12.4 Hz, 1H), 3.37 (s, 1H), 3.12 (d, J=12.8 Hz, 1H), 3.05 (dt, J=3.2, 12.8 Hz, 1H), 2.32-2.20 (m, 1H), 2.15 (br d, J=13.6 Hz, 1H), 2.05-1.97 (m, 1H), 1.78 (dt, J=3.6, 13.12 Hz, 1H), 1.52 (s, 3H).

Step 5. A mixture of N-(3-chloro-4-(pyridin-2-ylmethoxy)phenyl)-7-((3-methylpiperidin-3-yl)ethynyl)-6-nitroquinazolin-4-amine (500 mg, 884 umol, HCl) and paraformaldehyde (133 mg, 4.42 mmol) in trifluoroethanol (5.0 mL) was stirred at 60° C. for 0.5 h. Then the mixture was added sodium borohydride (56.1 mg, 1.48 mmol) in portions at 60° C. The mixture was stirred at 60° C. for 1.5 h. The mixture was quenched with methanol (5.0 mL) and concentrated to dryness to give a residue. The residue was diluted with ethyl acetate (20.0 mL) and washed with water (10 mL), dried over anhydrous sodium sulfate, filtered and concentrated in vacuum to give N-(3-chloro-4-(pyridin-2-ylmethoxy)phenyl)-7-((1,3-dimethylpiperidin-3-yl)ethynyl)-6-nitroquinazolin-4-amine (400 mg, crude) as a yellow solid. m/z ES+ $[M+H]^+$ 543.4; $^1H$ NMR (400 MHz, $CDCl_3$) δ 8.84 (s, 1H), 8.74 (s, 1H), 8.60 (br d, J=4.8 Hz, 1H), 8.02 (s, 1H), 7.89-7.82 (m, 1H), 7.78 (dd, J=1.6, 7.6 Hz, 1H), 7.67 (d, J=7.6 Hz, 1H), 7.51-7.46 (m, 1H), 7.26 (br s, 1H), 7.00-6.96 (m, 1H), 5.30 (s, 2H), 2.93-2.81 (m, 1H), 2.73 (br s, 1H), 2.29 (s, 3H), 2.02-1.90 (m, 4H), 1.73-1.64 (m, 1H), 1.37 (s, 3H), 1.32 (br s, 1H).

Step 6. A mixture of N-(3-chloro-4-(pyridin-2-ylmethoxy)phenyl)-7-((1,3-dimethylpiperidin-3-yl)ethynyl)-6-nitroquinazolin-4-amine (400 mg, 737 umol), iron powder (206 mg, 3.68 mmol) and ammonium chloride (197 mg, 3.68 mmol) in methanol (5.0 mL) and water (2.0 mL) was stirred at 80° C. for 2 h. The mixture was filtered and the filtrate was concentrated to dryness to give a residue. The residue was diluted with ethyl acetate (20 mL) and washed with saturated sodium bicarbonate solution (20 mL) and brine (20 mL), dried over anhydrous sodium sulfate, filtered and concentrated in vacuum to give $N^4$-(3-chloro-4-(pyridin-2-ylmethoxy)phenyl)-7-((1,3-dimethylpiperidin-3-yl)ethynyl) quinazoline-4,6-diamine (300 mg, crude) as a yellow solid. m/z ES+ $[M+H]^+$ 513.3.

Step 7. To a mixture of $N^4$-(3-chloro-4-(pyridin-2-ylmethoxy)phenyl)-7-((1,3-dimethylpiperidin-3-yl)ethynyl) quinazoline-4,6-diamine (300 mg, 585 umol), acrylic acid (59.0 mg, 818 umol) and pyridine (185 mg, 2.34 mmol) in dimethyl formamide (3.0 mL) was added 1-ethyl-3-(3-dimethylamino-propyl)-carbodiimide hydrochloride (448 mg, 2.34 mmol) at 25° C. The mixture was stirred at 25° C. for 2 h. The mixture was purified by pre-HPLC (column: Waters Xbridge 150*25 mm*5 um; mobile phase: [water (10 mM $NH_4HCO_3$)-acetonitrile]; B %: 42%-72%, 10 min) to give N-(4-((3-chloro-4-(pyridin-2-ylmethoxy)phenyl)amino)-7-((1,3-dimethylpiperidin-3-yl)ethynyl)quinazolin-6-yl)acrylamide (101 mg, 30% yield) as a yellow solid. m/z ES+ $[M+H]^+$ 567.2; $^1H$ NMR (400 MHz, $CDCl_3$) δ 9.70-9.47 (m, 2H), 8.74 (br s, 1H), 8.37 (br s, 1H), 8.29 (br s, 1H), 7.59 (br d, J=6.4 Hz, 1H), 7.55-7.51 (m, 1H), 7.36-7.32 (m, 1H), 3.37 (br d, J=12.4 Hz, 1H), 3.24 (br d, J=12.0 Hz, 1H), 3.01 (br t, J=10.4 Hz, 1H), 2.91-2.81 (m, 1H), 1.98-1.90 (m, 2H), 1.84 (br d, J=14.4 Hz, 1H), 1.74-1.62 (m, 1H), 1.40 (s, 3H).

Example 62. Synthesis of Compound No. 68 (N-(4-((3-chloro-4-(pyridin-2-ylmethoxy)phenyl)amino)-7-((1,3-dimethylpiperidin-3-yl)ethynyl)quinazolin-6-yl)acrylamide)

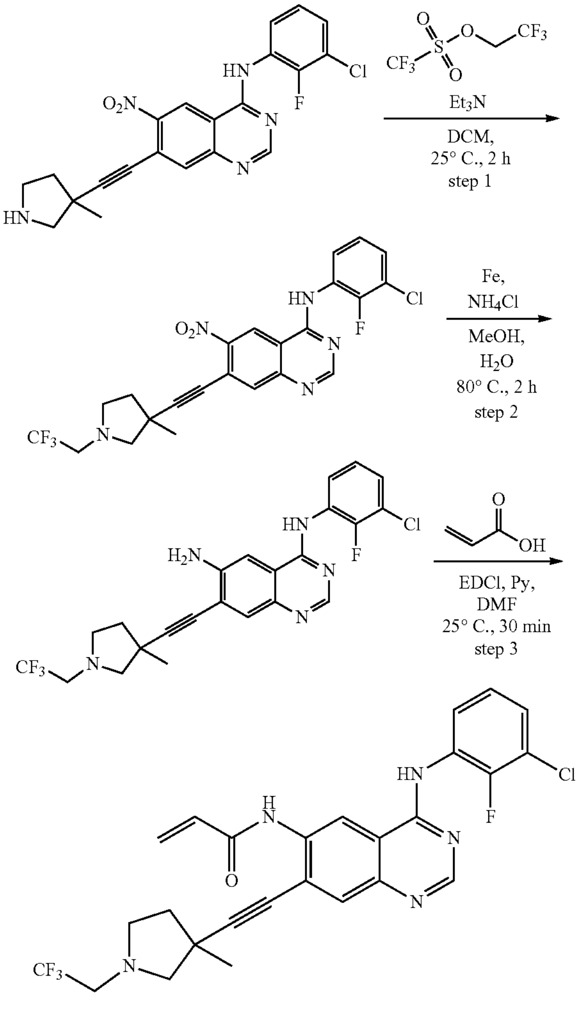

Step 1. A mixture of N-(3-chloro-2-fluorophenyl)-7-((3-methylpyrrolidin-3-yl)ethynyl)-6-nitroquinazolin-4-amine (500 mg, 1.17 mmol) and triethylamine (476 mg, 4.70 mmol) in dichloromethane (2.0 mL) was added 2,2,2-trifluoroethyl trifluoromethanesulfonate (545 mg, 2.35 mmol) at 25° C. The mixture was stirred at 25° C. for 2 h. The reaction mixture was partitioned between ethyl acetate (30 mL) and water (30 mL). The aqueous layer was washed by ethyl acetate (30 mL). The combined organic layers were dried over sodium sulfate, filtered and concentrated in vacuum to give N-(3-chloro-2-fluorophenyl)-7-((3-methyl-1-(2,2,2-trifluoroethyl)pyrrolidin-3-yl)ethynyl)-6-nitroquinazolin-4-amine (460 mg, 77% yield) as a yellow solid. $^1H$ NMR (400 MHz, $CDCl_3$) δ 9.42 (s, 1H), 8.68-8.61 (m, 2H), 8.56 (s, 1H), 8.02-7.97 (m, 2H), 7.85 (br d, J=7.6 Hz, 1H), 7.67-7.61 (m, 1H), 7.50-7.44 (m, 1H), 7.34 (d, J=9.6 Hz, 1H), 7.12 (d, J=8.8 Hz, 1H), 5.45 (s, 2H), 5.39 (br s, 1H), 3.88-3.74 (m, 1H), 3.72-3.60 (m, 1H), 3.50 (s, 2H), 3.19 (s, 3H), 2.36-2.26 (m, 1H), 2.23-2.12 (m, 1H), 1.50 (s, 9H). m/z ES+ $[M+H]^+$ 508.1.

Step 2. To a solution of N-(3-chloro-2-fluorophenyl)-7-((3-methyl-1-(2,2,2-trifluoroethyl)pyrrolidin-3-yl)ethynyl)-6-nitroquinazolin-4-amine (460 mg, 906 umol) and ammonium chloride (242 mg, 4.53 mmol) in water (2.0 mL) and methanol (5.0 mL) was added iron powder (253 mg, 4.53 mmol) at 25° C. The mixture was stirred at 80° C. for 2 h. The reaction mixture was poured into ethyl acetate (20 mL) and saturated sodium bicarbonate solution (20 mL) stirred for 10 min and filtered. The filtrate was extracted with ethyl acetate (20 mL). The combined organic phase was washed with brine (10 mL), dried over sodium sulfate, filtered and concentrated in vacuum to give $N^4$-(3-chloro-2-fluorophenyl)-7-((3-methyl-1-(2,2,2-trifluoroethyl)pyrrolidin-3-yl)ethynyl)quinazoline-4,6-diamine (420 mg, 97% yield) as a yellow solid. m/z ES+ $[M+H]^+$ 478.1.

Step 3. To a solution of $N^4$-(3-chloro-2-fluorophenyl)-7-((3-methyl-1-(2,2,2-trifluoroethyl)pyrrolidin-3-yl)ethynyl)quinazoline-4,6-diamine (170 mg, 356 umol), acrylic acid (25.6 mg, 356 umol) and pyridine (113 mg, 1.42 mmol) in dimethyl formamide (1.0 mL) was added 1-(3-dimethylaminopropyl)-3-ethylcarbodiimide hydrochloride (273 mg, 1.42 mmol) at 25° C. The reaction mixture was stirred at 25° C. for 30 min. The reaction mixture was filtered to give filtrate. The filtrate was purified by prep-HPLC (column: Phenomenex Gemini NX—C18 (75*30 mm*3 um); mobile phase: [water (0.05% ammonium hydroxide v/v)-acetonitrile]; B %: 46%-76%, 7 min) to give N-(4-((3-chloro-2-fluorophenyl)amino)-7-((3-methyl-1-(2,2,2-trifluoroethyl)-pyrrolidin-3-yl)ethynyl)quinazolin-6-yl)acrylamide (53.8 mg, 28% yield) as a yellow solid. m/z ES+ $[M+H]^+$ 532.2; $^1H$ NMR (400 MHz, $CDCl_3$) δ 9.14 (s, 1H), 8.66 (s, 1H), 8.31 (s, 1H), 8.19 (br t, J=7.2 Hz, 1H), 7.96 (s, 1H), 7.18-7.14 (m, 1H), 7.13-7.07 (m, 1H), 6.48-6.42 (m, 1H), 6.28-6.20 (m, 1H), 5.86-5.80 (m, 1H), 3.18-3.15 (m, 1H), 3.14-3.08 (m, 2H), 3.08-3.02 (m, 1H), 2.91-2.84 (m, 1H), 2.74 (d, J=9.2 Hz, 1H), 2.33-2.25 (m, 1H), 1.99-1.91 (m, 1H), 1.50 (s, 3H).

Example 63. Synthesis of Compound No. 69 (N-(4-((3-chloro-4-(pyridin-2-ylmethoxy)-phenyl)amino)-7-((1,3-dimethylpiperidin-3-yl)ethynyl)quinazolin-6-yl)acrylamide)

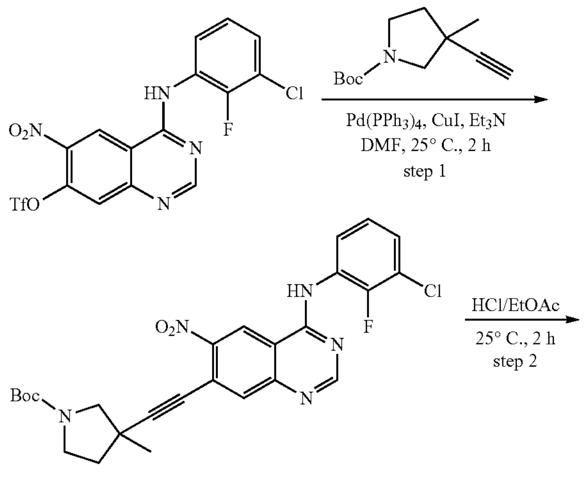

-continued

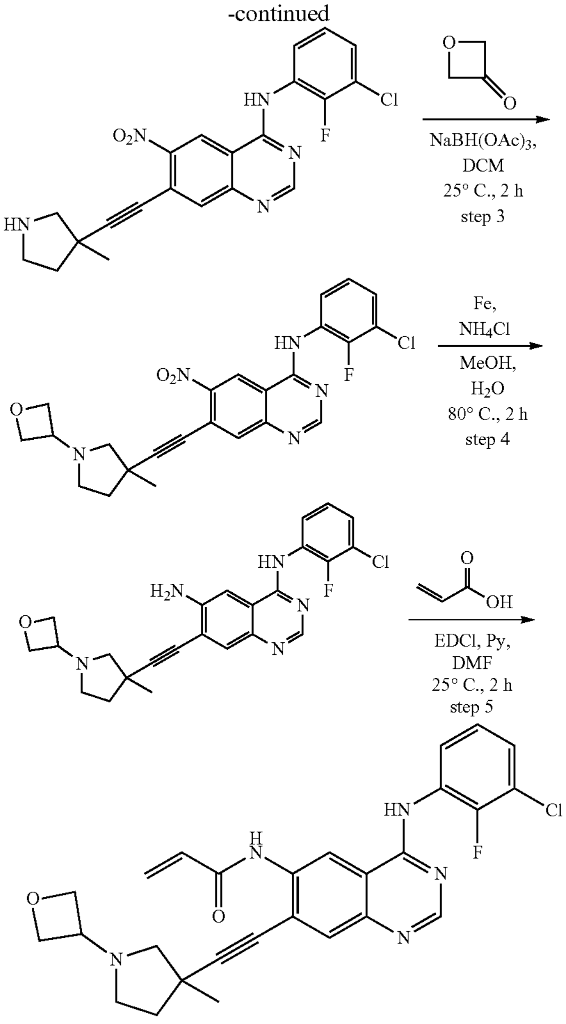

Step 1. To a mixture of 4-((3-chloro-4-(pyridin-2-ylmethoxy)phenyl)amino)-6-nitroquinazolin-7-yl trifluoromethane sulfonate (4.30 g, 9.21 mmol), tert-butyl 3-ethynyl-3-methylpyrrolidine-1-carboxylate (2.12 g, 10.1 mmol) and triethylamine (3.47 g, 34.3 mmol) in dimethyl formamide (5.0 mL) was added tetrakis(triphenylphosphine) palladium (0) (1.06 g, 921 umol) and cuprous iodide (351 mg, 1.84 mmol) at 25° C. The mixture was stirred under nitrogen atmosphere at 25° C. for 2 h. The mixture was concentrated to give a residue. The residue was purified by silica gel chromatography (Petroleum ether/Ethyl acetate=5/1-2/1) to afford tert-butyl 3-((4-(((3-chloro-2-fluorophenyl)amino)-6-nitro quinazolin-7-yl)ethynyl)-3-methylpyrrolidine-1-carboxylate (5.0 g, crude) as a yellow solid. m/z ES+ $[M+H]^+$ 526.1; $^1H$ NMR (400 MHz, $CDCl_3$) δ 8.81 (br d, J=7.2 Hz, 1H), 8.77 (s, 1H), 8.30 (br d, J=13.6 Hz, 1H), 8.08 (br s, 1H), 8.00 (s, 1H), 7.24-7.20 (m, 1H), 7.13-7.08 (m, 1H), 3.73-3.62 (m, 1H), 3.60-3.53 (m, 1H), 3.51-3.41 (m, 1H), 3.25 (br dd, J=7.2, 10.6 Hz, 1H), 2.26-2.16 (m, 1H), 1.92-1.82 (m, 1H), 1.43 (s, 3H), 1.41 (s, 9H).

Step 2. To a solution of tert-butyl 3-((4-((3-chloro-2-fluorophenyl)amino)-6-nitroquinazolin-7-yl)ethynyl)-3-methylpyrrolidine-1-carboxylate (7.00 g, 13.3 mmol) in ethyl acetate (20 mL) was added hydrochloric acid/ethyl acetate (4.00 M, 20.0 mL), the mixture was stirred at 25° C. for 2 h. The mixture was concentrated to dryness to give a residue. The residue was triturated with ethyl acetate (40 mL). After filtration, the filter cake was washed with ethyl acetate (10 mL), dried in vacuum to give N-(3-chloro-2-fluorophenyl)-7-((3-methylpyrrolidin-3-yl)ethynyl)-6-nitroquinazolin-4-amine (5.40 g, 88% yield) as a yellow solid. m/z ES+ $[M+H]^+$ 426.1

Step 3. To a mixture of N-(3-chloro-2-fluorophenyl)-7-((3-methylpyrrolidin-3-yl)ethynyl)-6-nitroquinazolin-4-amine (3.00 g, 6.49 mmol) and oxetan-3-one (2.34 g, 32.5 mmol) in dichloromethane (30 mL) was added sodium triacetoxy borohydride (6.88 g, 32.5 mmol) in portions. The mixture and stirred at 25° C. for 2 h. The reaction mixture was poured into saturated sodium bicarbonate solution (50 mL) and extracted with dichloromethane (2×30 mL). The combined organic phase was washed with brine (20 mL), dried over sodium sulfate, filtered and concentrated in vacuum to give a residue. The residue was purified by silica gel chromatography (Petroleum ether/Ethyl acetate=1/1-0/1) to afford N-(3-chloro-2-fluorophenyl)-7-((3-methyl-1-(oxetan-3-yl)pyrrolidin-3-yl)ethynyl)-6-nitroquinazolin-4-amine (1.50 g, 48% yield) as a yellow solid. m/z ES+ $[M+H]^+$ 482.2; $^1$H NMR (400 MHz, $CDCl_3$) δ 8.89 (s, 1H), 8.70 (s, 1H), 8.39-8.33 (m, 1H), 8.11 (s, 1H), 7.80 (br s, 1H), 7.32-7.29 (m, 1H), 7.25-7.19 (m, 1H), 4.78-4.73 (m, 2H), 4.72-4.67 (m, 2H), 3.84 (quin, J=6.4 Hz, 1H), 2.97 (d, J=9.2 Hz, 1H), 2.86 (dt, J=4.8, 8.4 Hz, 1H), 2.79-2.73 (m, 2H), 2.39 (ddd, J=4.8, 7.6, 12.6 Hz, 1H), 1.98 (td, J=7.6, 12.4 Hz, 1H), 1.56 (s, 3H).

Step 4. To a solution of N-(3-chloro-2-fluorophenyl)-7-((3-methyl-1-(oxetan-3-yl)pyrrolidin-3-yl)ethynyl)-6-nitroquinazolin-4-amine (1.50 g, 3.11 mmol) and ammonium chloride (833 mg, 15.6 mmol) in water (5.0 mL) and methanol (10 mL) was added iron powder (869 mg, 15.6 mmol) at 25° C. The mixture was stirred at 80° C. for 2 h. The reaction mixture was poured into ethyl acetate (50 mL) and saturated sodium bicarbonate solution (30 mL) stirred for 10 min and filtered. The filtrate was extracted with ethyl acetate (30 mL). The combined organic phase was washed with brine (30 mL), dried over sodium sulfate, filtered and concentrated in vacuum to give $N^4$-(3-chloro-2-fluorophenyl)-7-((3-methyl-1-(oxetan-3-yl)pyrrolidin-3-yl)ethynyl) quinazoline-4,6-diamine (1.30 g, crude) as a yellow solid. m/z ES+ $[M+H]^+$ 452.0;

Step 5. To a solution of $N^4$-(3-chloro-2-fluorophenyl)-7-((3-methyl-1-(oxetan-3-yl)pyrrolidin-3-yl)ethynyl) quinazoline-4,6-diamine (1.20 g, 2.66 mmol), acrylic acid (230 mg, 3.19 mmol) and pyridine (840 mg, 10.6 mmol) in dimethyl formamide (10 mL) was added 1-(3-dimethylaminopropyl)-3-ethylcarbodiimide hydrochloride (2.04 g, 10.6 mmol) at 25° C. The reaction mixture was stirred at 25° C. for 2 h. The reaction mixture was filtered to give filtrate. The filtrate was purified by prep-HPLC (column: Waters Xbridge 150*25 mm*5 um; mobile phase: [water (0.05% ammonium hydroxide v/v)-acetonitrile]; B %: 38%-68%, 10 min) to give N-(4-((3-chloro-2-fluorophenyl)amino)-7-((3-methyl-1-(oxetan-3-yl)pyrrolidin-3-yl)ethynyl) quinazolin-6-yl) acrylamide (280 mg, 21% yield) as a yellow solid. m/z ES+ $[M+H]^+$ 506.4; $^1$H NMR (400 MHz, $CDCl_3$) δ 9.22 (s, 1H), 8.75 (s, 1H), 8.51 (s, 1H), 8.39-8.31 (m, 1H), 7.98 (s, 1H), 7.86 (br s, 1H), 7.25-7.14 (m, 2H), 6.61-6.52 (m, 1H), 6.49-6.38 (m, 1H), 5.93 (dd, J=1.2, 10.0 Hz, 1H), 4.82-4.76 (m, 2H), 4.70 (dt, J=2.0, 6.0 Hz, 2H), 3.87-3.78 (m, 1H), 3.08 (d, J=8.8 Hz, 1H), 3.02-2.92 (m, 1H), 2.73 (dt, J=5.6, 8.8 Hz, 1H), 2.58 (d, J=8.8 Hz, 1H), 2.40 (ddd, J=5.6, 7.8, 13.2 Hz, 1H), 2.03 (ddd, J=6.4, 8.2, 12.8 Hz, 1H), 1.60 (s, 3H).

Example 64. Synthesis of Compound No. 70 N-(4-((3-chloro-4-(pyridin-2-ylmethoxy)phenyl)amino)-7-((1,3-dimethylpyrrolidin-3-yl)ethynyl)quinazolin-6-yl)but-2-ynamide

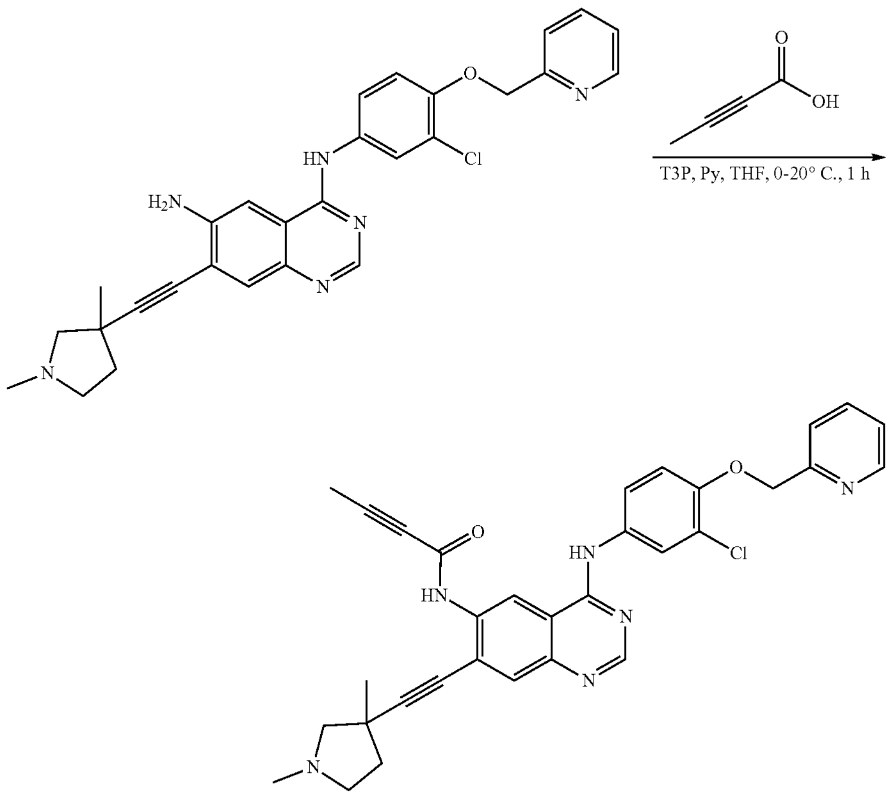

Step 1. To a suspension of $N^4$-(3-chloro-4-(pyridin-2-ylmethoxy)phenyl)-7-((1,3-dimethylpyrrolidin-3-yl) ethynyl)quinazoline-4,6-diamine (0.200 g, 0.40 mmol), but-2-ynoic acid (337 mg, 4.01 mmol) in pyridine (1.0 mL) and tetrahydrofuran (3.0 mL) was added propylphosphonic anhydride (1.79 g, 2.81 mmol, 50% purity) at 0° C. The mixture was stirred at 20° C. for 1 h. The mixture was concentrated under vacuum to give a residue. The residue was purified by prep-HPLC (column: Phenomenex Synergi C18 150*25*10 um; mobile phase: [water (0.225% formic acid)-acetonitrile]; B %: 5%-35%, 10 min) to give a residue which was further purified by prep-HPLC (column: Waters Xbridge 150*25 5 um; mobile phase: [water (10 mM $NH_4HCO_3$)-acetonitrile]; B %: 33%-63%, 10 min) to give N-(4-((3-chloro-4-(pyridin-2-ylmethoxy)phenyl)amino)-7-((1,3-dimethylpyrrolidin-3-yl)ethynyl)quinazolin-6-yl)but-2-ynamide (44.9 mg, 19% yield) as a white solid. m/z ES+ $[M+H]^+$ 565.1; $^1H$ NMR (400 MHz, $CD_3OD$) δ 8.58-8.55 (m, 2H), 8.48 (s, 1H), 7.93-7.91 (m, 2H), 7.78 (s, 1H), 7.72 (d, J=7.9 Hz, 1H), 7.58 (dd, J=2.8, 8.8 Hz, 1H), 7.39 (dd, J=5.2, 6.8 Hz, 1H), 7.16 (d, J=8.8 Hz, 1H), 5.27 (s, 2H), 3.09 (d, J=9.6 Hz, 1H), 3.02-2.91 (m, 1H), 2.74-2.63 (m, 1H), 2.57 (d, J=9.6 Hz, 1H), 2.45 (s, 3H), 2.42-2.37 (m, 1H), 2.09 (s, 3H), 2.03-1.97 (m, 1H), 1.53 (s, 3H).

Example 65. Synthesis of Compound No. 71 N-(4-((3-chloro-4-(pyridin-2-ylmethoxy) phenyl)amino)-7-((7-methyl-7-azabicyclo[2.2.1]heptan-1-yl)ethynyl)quinazolin-6-yl)acrylamide

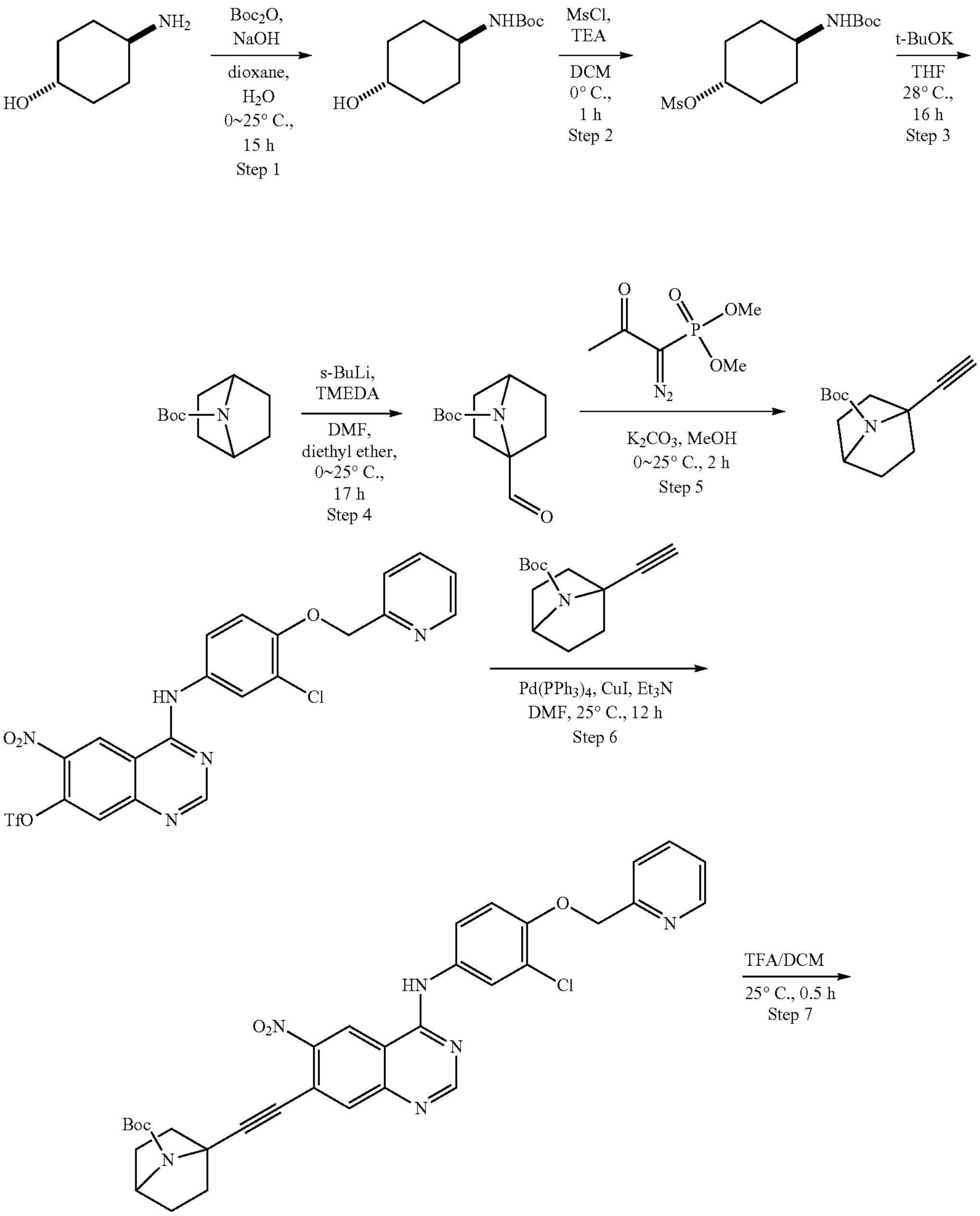

-continued
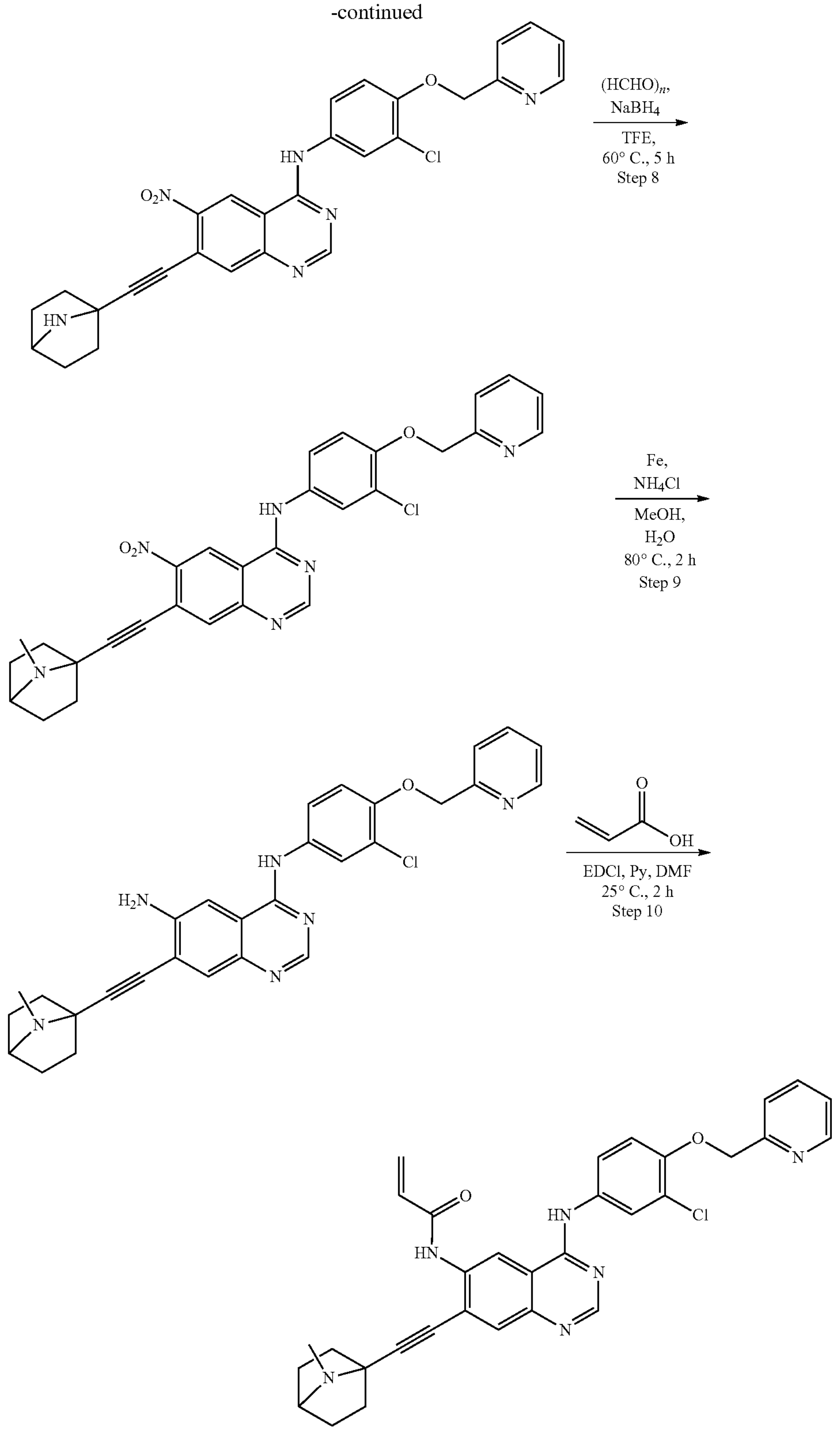
Step 1. To a 2 L the neck bottle was added (1r,4r)-4-aminocyclohexanol (40.0 g, 347 mmol) and 1,4-dioxane (1.00 L) with a thermometer. The resulting solution was cooled to 0° C. and a solution of sodium hydroxide (16.7 g, 417 mmol) in water (420 mL) was added dropwise. Then the mixture was stirred at 0° C. for 15 min and a solution of di-tert-butyl dicarbonate (83.4 g, 382 mmol, 87.8 mL) in 1,4-dioxane (250 mL) was added dropwise at 0° C. Finally the mixture was stirred at 25° C. for 15 h. The reaction was neutralized with 1 N hydrochloric acid and extracted with ethyl acetate (2×800 mL). The organic phases were combined, washed successively with 1 N hydrochloric acid (100 mL), saturated sodium bicarbonate (300 mL) and brine (300 mL) before being dried over sodium sulfate, filtered, and concentrated in vacuum to give tert-butyl ((1r,4r)-4-hydroxycyclohexyl)carbamate (68.0 g, 316 mmol, 90% yield) as a light yellow solid. $^1$H NMR (400 MHz, $CDCl_3$) δ=4.37 (br s, 1H), 3.66-3.53 (m, 1H), 3.42 (br s, 1H), 2.07-1.91 (m, 4H), 1.44 (s, 9H), 1.42-1.31 (m, 2H), 1.24-1.09 (m, 2H).

Step 2. To a solution of tert-butyl ((1r,4r)-4-hydroxycyclohexyl)carbamate (68.0 g, 316 mmol) in dichloromethane (2.00 L) was added triethylamine (47.9 g, 474 mmol, 66.0 mL). The resulting solution was then cooled to 0° C. and followed by the dropwise addition of methanesulfonyl chloride (54.3 g, 474 mmol, 36.7 mL). The mixture was stirred at 0° C. for 1 h. The reaction was quenched by the slow addition of saturated sodium bicarbonate solution (500 mL) with vigorous stirring. The reaction was then further diluted with dichloromethane (1.50 L) and saturated sodium bicarbonate solution (500 mL) and then separated. The organic layer was then washed with water (1.00 L) and dried over sodium sulfate before being concentrated in vacuum to give (1r,4r)-4-((tert-butoxycarbonyl)amino)cyclohexyl methanesulfonate (86.0 g, 293 mmol, 92% yield) as a white solid. $^1$H NMR (400 MHz, $CDCl_3$) δ=4.62 (tt, J=4.2, 10.6 Hz, 1H), 4.39 (br s, 1H), 3.57-3.39 (m, 1H), 3.01 (s, 3H), 2.21-2.01 (m, 4H), 1.76-1.61 (m, 2H), 1.44 (s, 9H), 1.32-1.17 (m, 2H).

Step 3. To a solution of (1r,4r)-4-((tert-butoxycarbonyl) amino)cyclohexyl methanesulfonate (43.0 g, 147 mmol) in tetrahydrofuran (1.50 L) was added potassium tert-butoxide (8.22 g, 73.3 mmol) at 28° C. under nitrogen atmosphere and the mixture was stirred at 28° C. for 2 h. Then potassium tert-butoxide (24.7 g, 220 mmol) was added and the mixture was stirred at 28° C. for 14 h under nitrogen atmosphere. The reaction was cooled to 0° C., quenched by the addition of 1 N hydrochloric acid (300 mL), and separated. The organic layer was then washed with saturated sodium bicarbonate solution (300 mL), dried over sodium sulfate, and concentrated in vacuum. The crude product was purified by chromatography on silica gel (petroleum ether/ethyl acetate=1/0 to 60/1) to give tert-butyl 7-azabicyclo[2.2.1] heptane-7-carboxylate (17.0 g, 86.2 mmol, 58% yield) as light yellow oil. $^1$H NMR (400 MHz, $CDCl_3$) δ=4.29-4.12 (m, 2H), 1.84-1.69 (m, 4H), 1.45 (s, 9H), 1.39 (d, J=7.2 Hz, 4H).

Step 4. To a dry flask was added a solution of tert-butyl 7-azabicyclo[2.2.1]heptane-7-carboxylate (10.0 g, 50.7 mmol) in diethyl ether (100 mL). Then 2,3-dimethylbutane-2,3-diamine (8.84 g, 76.0 mmol, 11.5 mL) was added to the solution at 25° C. The mixture was cooled to 0° C. After 15 min, sec-butyllithium (1.30 M, 58.5 mL) was added dropwise over 5 min. The reaction was maintained at 0° C. for 1 h. Then dimethyl formamide (7.41 g, 101 mmol, 7.80 mL) was added dropwise. This solution was warmed to 25° C. and stirred at 25° C. for 16 h. The mixture was quenched with saturated ammonium chloride aqueous solution (50 mL) and extracted with ethyl acetate (2×50.0 mL). The organic phases were combined, dried over anhydrous sodium sulfate and concentrated under vacuum to give a crude product. The crude product was purified by chromatography on silica gel (petroleum ether/ethyl acetate=200/1 to 30/1) to give tert-butyl 1-formyl-7-azabicyclo[2.2.1]heptane-7-carboxylate (10.0 g, 44.4 mmol, 87% yield) as colorless oil. $^1$H NMR (400 MHz, $CDCl_3$) δ=9.94 (s, 1H), 4.30 (s, 1H), 2.06-1.87 (m, 4H), 1.63-1.50 (m, 4H), 1.43 (s, 9H).

Step 5. To a solution of tert-butyl 1-formyl-7-azabicyclo [2.2.1]heptane-7-carboxylate (4.00 g, 17.8 mmol) in methanol (40 mL) was added potassium carbonate (4.91 g, 35.5 mmol) at 25° C., followed by dimethyl (1-diazo-2-oxopropyl)phosphonate (4.09 g, 21.3 mmol) dropwise at 0° C. and the mixture was stirred at 25° C. for 2 h. The mixture was concentrated under vacuum. The residue was purified by chromatography on silica gel (petroleum ether/ethyl acetate=1/0 to 20/1) to give tert-butyl 1-ethynyl-7-azabicyclo[2.2.1]heptane-7-carboxylate (6.80 g, 30.7 mmol, 86% yield) as a white solid. $^1$H NMR (400 MHz, DMSO-$d_6$) δ=4.27 (t, J=4.7 Hz, 1H), 2.64-2.52 (m, 1H), 2.15-1.99 (m, 2H), 1.92-1.76 (m, 4H), 1.47 (s, 9H), 1.45-1.39 (m, 2H).

Step 6. To a solution of 4-((3-chloro-4-(pyridin-2-ylmethoxy)phenyl)amino)-6-nitroquinazolin-7-yl trifluoromethanesulfonate (1.00 g, 1.80 mmol) and tert-butyl 1-ethynyl-7-azabicyclo[2.2.1]heptane-7-carboxylate (517 mg, 2.34 mmol) in dimethyl formamide (25 mL) was added copprous iodide (68.5 mg, 359 umol), tetrakis[triphenylphosphine]palladium(0) (207 mg, 179 umol) and triethylamine (1.82 g, 17.9 mmol, 2.50 mL) at 25° C. under nitrogen atmosphere. Then the mixture was stirred at 25° C. for 12 h. The reaction mixture was diluted with water (60 mL) and extracted with ethyl acetate (3×20 mL). The combined organic layers were washed with brine (3×10 mL), dried over sodium sulfate, filtered and concentrated under reduced pressure to give a residue. The residue was purified by column chromatography ($SiO_2$, Petroleum ether/Ethyl acetate=1/0 to 1/1) to give tert-butyl 1-((4-((3-chloro-4-(pyridin-2-ylmethoxy)phenyl)amino)-6-nitroquinazolin-7-yl)ethynyl)-7-azabicyclo[2.2.1]heptane-7-carboxylate (770 mg, 1.23 mmol, 68% yield) as a yellow solid. m/z ES+ $[M+H]^+$ 627.3

Step 7. To a solution of tert-butyl 1-((4-((3-chloro-4-(pyridin-2-ylmethoxy)phenyl)amino)-6-nitroquinazolin-7-yl)ethynyl)-7-azabicyclo[2.2.1]heptane-7-carboxylate (600 mg, 957 umol) in dichloromethane (20 mL) was added trifluoroacetic acid (4.36 g, 38.3 mmol, 2.83 mL) at 25° C. Then the mixture was stirred at 25° C. for 0.5 h. The reaction mixture was concentrated under reduced pressure to remove solvent. To the residue was added saturated sodium dicarbonate solution till pH=8. Then the mixture was filtered and the filter cake was triturated with ethyl acetate (10 mL). After filtered, the filter cake was dried to give 7-(7-azabicyclo[2.2.1]heptan-1-ylethynyl)-N-(3-chloro-4-(pyridin-2-ylmethoxy)phenyl)-6-nitroquinazolin-4-amine (500 mg, crude) as a yellow solid. m/z ES+ $[M+H]^+$ 527.2; $^1$H NMR (400 MHz, DMSO-$d_6$) δ=10.48 (s, 1H), 9.54 (s, 1H), 8.75 (s, 1H), 8.61 (br d, J=3.6 Hz, 1H), 8.09-7.95 (m, 2H), 7.90 (dt, J=1.6, 7.6 Hz, 1H), 7.71 (br dd, J=2.2, 8.8 Hz, 1H), 7.59 (d, J=7.8 Hz, 1H), 7.38 (dd, J=5.0, 7.0 Hz, 1H), 7.32 (d, J=9.0 Hz, 1H), 5.32 (s, 2H), 4.21 (br s, 1H), 2.26-2.06 (m, 4H), 2.02-1.95 (m, 2H), 1.79 (br d, J=8.4 Hz, 2H).

Step 8. A mixture of 7-(7-azabicyclo[2.2.1]heptan-1-ylethynyl)-N-(3-chloro-4-(pyridin-2-ylmethoxy)phenyl)-6-nitroquinazolin-4-amine (450 mg, 854 umol) and paraformaldehyde (128 mg, 4.27 mmol) in trifluoroethanol (15 mL) was refluxed at 60° C. for 0.5 h under nitrogen atmosphere. Then to the mixture was added sodium borohydride (64.6 mg, 1.71 mmol) in portions and the mixture was refluxed at 60° C. for 4.5 h. The reaction mixture was concentrated under reduced pressure to remove solvent. The residue was diluted with water (20 mL) and extracted with ethyl acetate (3×20 mL). The combined organic layers were washed with brine (3×20 mL), dried over sodium sulfate, filtered and concentrated under reduced pressure to give N-(3-chloro-4-(pyridin-2-ylmethoxy)phenyl)-7-((7-methyl-7-azabicyclo

[2.2.1]heptan-1-yl)ethynyl)-6-nitroquinazolin-4-amine (300 mg, crude) as a yellow solid. m/z ES+ $[M+H]^+$ 541.3

Step 9. A mixture of N-(3-chloro-4-(pyridin-2-ylmethoxy)phenyl)-7-((7-methyl-7-azabicyclo[2.2.1]heptan-1-yl)ethynyl)-6-nitroquinazolin-4-amine (300 mg, 555 umol), iron powder (158 mg, 2.77 mmol), ammonium chloride (148 mg, 2.77 mmol) in methanol (10 mL) and water (10 mL) was degassed and purged with nitrogen for 3 times, and then the mixture was refluxed at 80° C. for 2 h under nitrogen atmosphere. The reaction mixture was filtered and the filtrate was concentrated under reduced pressure. The residue was purified by reversed phase liquid chromatography (formic acid) to give $N^4$-(3-chloro-4-(pyridin-2-ylmethoxy)phenyl)-7-((7-methyl-7-azabicyclo[2.2.1]heptan-1-yl)ethynyl) quinazoline-4,6-diamine (70.0 mg, 136 umol, 24% yield) as a yellow solid. $^1H$ NMR (400 MHz, DMSO-$d_6$) δ=9.51 (br s, 1H), 8.60 (br d, J=4.2 Hz, 1H), 8.34 (s, 1H), 8.06 (d, J=2.4 Hz, 1H), 7.88 (br dd, J=1.7, 7.6 Hz, 1H), 7.72 (br dd, J=2.6, 8.9 Hz, 1H), 7.64-7.57 (m, 2H), 7.53 (s, 1H), 7.38 (br dd, J=5.0, 6.6 Hz, 1H), 7.25 (br d, J=9.0 Hz, 1H), 5.52 (br s, 2H), 5.29 (s, 2H), 3.30 (br t, J=4.3 Hz, 1H), 2.29 (s, 3H), 1.96 (br d, J=10.9 Hz, 2H), 1.84-1.77 (m, 4H), 1.44-1.37 (m, 2H).

Step 10. To a stirred solution of $N^4$-(3-chloro-4-(pyridin-2-ylmethoxy)phenyl)-7-((7-methyl-7-azabicyclo[2.2.1]heptan-1-yl)ethynyl)quinazoline-4,6-diamine (30.0 mg, 58.7 umol), acrylic acid (8.46 mg, 117 umol, 8.06 uL) and pyridine (9.29 mg, 117 umol, 9.48 uL) in dimethyl formamide (1.00 mL) was added 1-(3-dimethylaminopropyl)-3-ethylcarbodiimide hydrochloride (45.0 mg, 235 umol) at 25° C. in portions. The mixture was stirred at 25° C. for 2 h. The reaction was filtered and the filtrate was purified by prep-HPLC (column: X timate C18 150*25 mm*5 um; mobile phase: [water (0.05% ammonium hydroxide v/v)-acetonitrile]; B %: 42%-72%, 10 min) to give N-(4-((3-chloro-4-(pyridin-2-ylmethoxy)phenyl)amino)-7-((7-methyl-7-azabicyclo[2.2.1]-heptan-1-yl)ethynyl)quinazolin-6-yl) acrylamide (16.5 mg, 28.9 umol, 49% yield, 99% purity) as a yellow solid. m/z ES+ $[M+H]^+$ 565.4; $^1H$ NMR (400 MHz, $CDCl_3$) δ=9.11 (s, 1H), 8.69 (s, 1H), 8.62 (d, J=4.4 Hz, 1H), 8.54 (s, 1H), 8.00 (s, 1H), 7.92 (d, J=2.8 Hz, 1H), 7.84 (s, 1H), 7.80-7.75 (m, 1H), 7.72-7.66 (m, 1H), 7.59-7.51 (m, 1H), 7.26 (br d, J=6.4 Hz, 1H), 7.04 (d, J=9.2 Hz, 1H), 6.53 (d, J=5 Hz, 2H), 5.94-5.88 (m, 1H), 5.32 (s, 2H), 3.50 (s, 1H), 2.50 (s, 3H), 2.25-2.16 (m, 2H), 2.13-2.04 (m, 2H), 1.99-1.90 (m, 2H), 1.60-1.55 (m, 2H).

Example 66. Synthesis of Compound No. 72 N-(4-((3-chloro-4-(pyridin-2-ylmethoxy)phenyl)amino)-7-((1,4-dimethylpiperidin-4-yl)ethynyl)quinazolin-6-yl)acrylamide

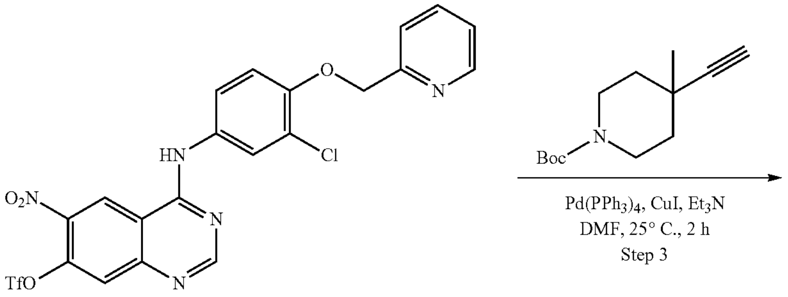

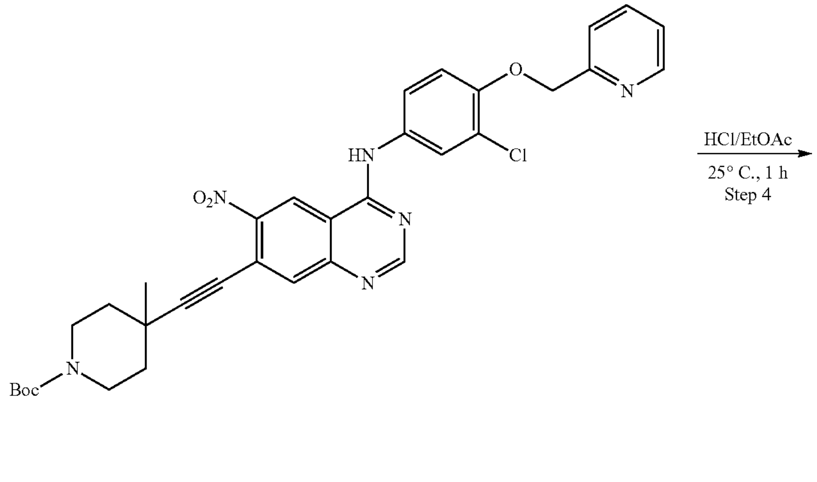

-continued
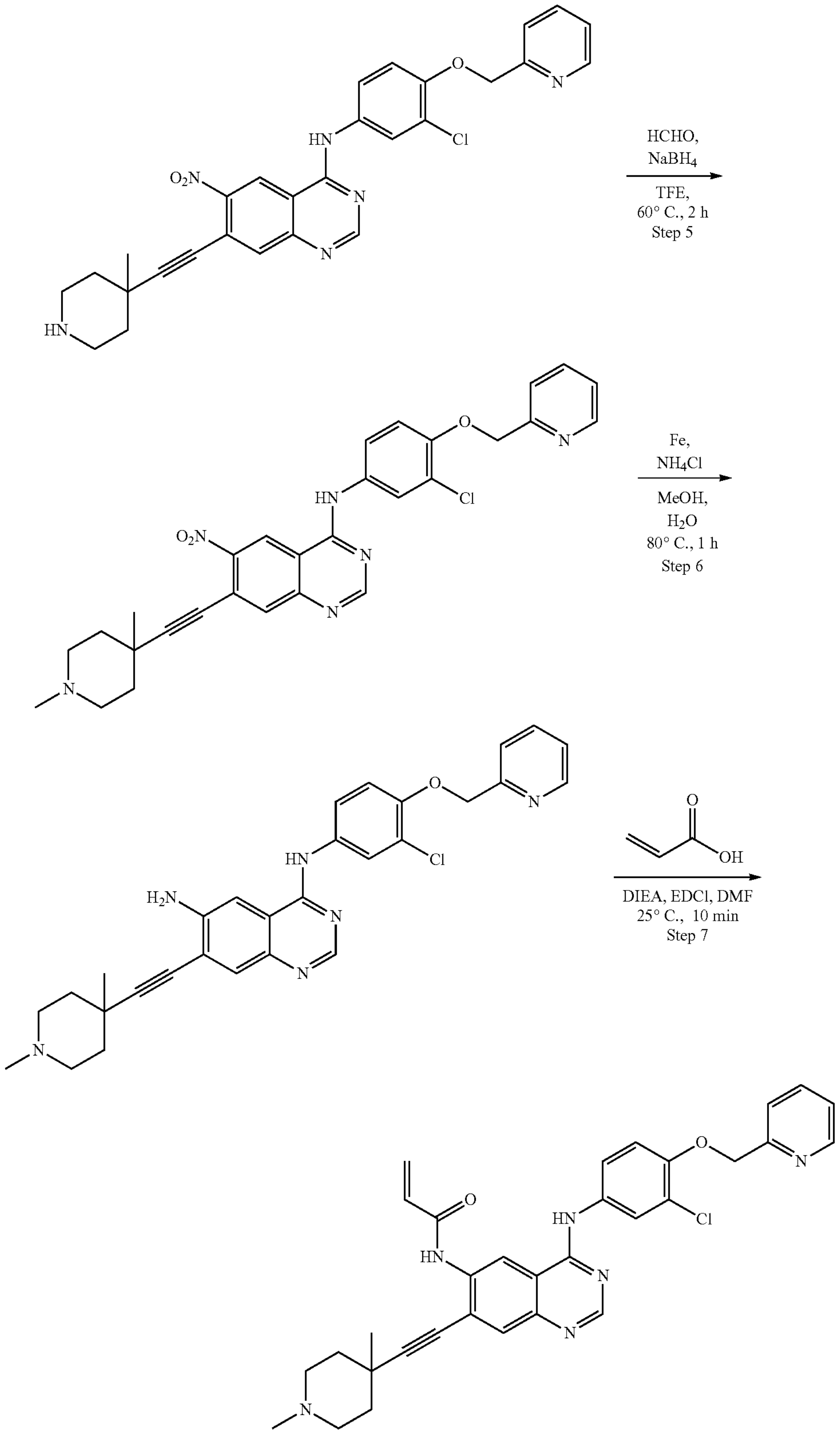

-continued

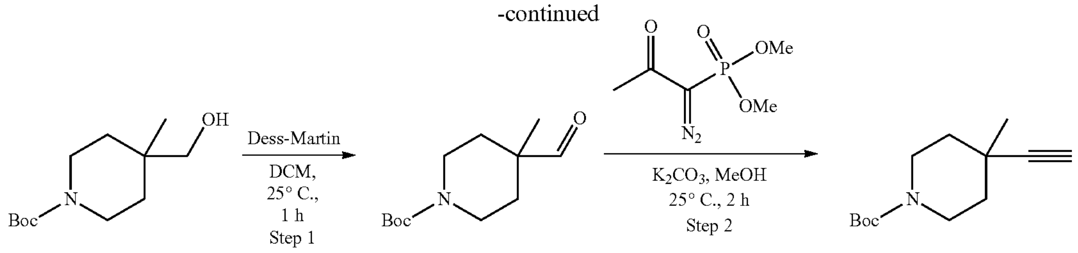

Step 1. To a solution of tert-butyl 4-(hydroxymethyl)-4-methylpiperidine-1-carboxylate (1.00 g, 4.36 mmol) in dichloromethane (20 mL) was added Dess-Martin periodinane (2.80 g, 6.60 mmol). The mixture was stirred at 25° C. for 1 h. The mixture was filtered and the filtrate was concentrated under reduced pressure to give a residue. The residue was purified by column chromatography on silica gel (petroleum ether/ethyl acetate=3/1) to give tert-butyl 4-formyl-4-methylpiperidine-1-carboxylate (1.20 g, crude) as colorless oil.

Step 2. To a solution of tert-butyl 4-formyl-4-methylpiperidine-1-carboxylate (1.40 g, 6.16 mmol) in methanol (40 mL) was added potassium carbonate (2.57 g, 18.6 mmol) and dimethyl (1-diazo-2-oxopropyl)phosphonate (1.78 g, 9.24 mmol). The reaction mixture was stirred at 25° C. for 1 h. The reaction mixture was filtered and the filtrate was concentrated in vacuum. The residue was purified by chromatography on silica gel (petroleum ether/ethyl acetate=5/1) to give tert-butyl 4-ethynyl-4-methylpiperidine-1-carboxylate (1.20 g, 5.37 mmol, 87% yield) as colorless oil. $^1$H NMR (400 MHz, DMSO-$d_6$) δ=3.83 (br d, J=12.1 Hz, 2H), 3.09 (s, 1H), 3.04-2.84 (m, 2H), 1.58 (br d, J=11.4 Hz, 2H), 1.41-1.39 (m, 9H), 1.29 (dt, J=4.2, 12.7 Hz, 2H), 1.20 (s, 3H).

Step 3. To a solution of 4-((3-chloro-4-(pyridin-2-ylmethoxy)phenyl)amino)-6-nitroquinazolin-7-yl trifluoromethane sulfonate (1.50 g, 2.70 mmol) in dimethyformamide (10 mL) and triethylamine (10 mL) was added tert-butyl 4-ethynyl-4-methylpiperidine-1-carboxylate (1.00 g, 4.48 mmol), copper iodine (120 mg, 630 umol) and tetrakis (triphenylphosphine)palladium(0) (330 mg, 285 umol). The reaction mixture was stirred at 25° C. for 2 h under nitrogen atmosphere. The reaction mixture was concentrated in vacuum. The residue was purified by chromatography on silica gel (petroleum ether/ethyl acetate=3/0 to 1/1) to give tert-butyl 4-((4-((3-chloro-4-(pyridin-2-ylmethoxy) phenyl) amino)-6-nitroquinazolin-7-yl)ethynyl)-4-methylpiperidine-1-carboxylate (1.20 g, 1.91 mmol, 71% yield) as a yellow solid. m/z ES+ $[M+H]^+$ 629.1; $^1$H NMR (400 MHz, DMSO-$d_6$) δ=10.35 (s, 1H), 9.43 (s, 1H), 8.71 (s, 1H), 8.61 (d, J=4.3 Hz, 1H), 8.02 (d, J=2.4 Hz, 1H), 8.00-7.94 (m, 1H), 7.89 (dt, J=1.8, 7.7 Hz, 1H), 7.72 (dd, J=2.4, 8.9 Hz, 1H), 7.66-7.55 (m, 3H), 7.38 (dd, J=5.1, 6.8 Hz, 1H), 7.31 (d, J=9.0 Hz, 1H), 5.31 (s, 2H), 4.00-3.86 (m, 2H), 3.17-3.00 (m, 2H), 1.78 (br d, J=12.6 Hz, 2H), 1.50-1.43 (m, 2H), 1.42 (s, 9H), 1.36 (s, 3H).

Step 4. A solution of tert-butyl 4-((4-((3-chloro-4-(pyridin-2-ylmethoxy)phenyl)amino)-6-nitroquinazolin-7-yl) ethynyl)-4-methylpiperidine-1-carboxylate (320 mg, 508 umol) in hydrochloric acid/ethyl acetate (4 M, 10 mL) was stirred at 25° C. for 1 h. The reaction mixture was concentrated under reduced pressure to give N-(3-chloro-4-(pyridin-2-ylmethoxy)phenyl)-7-((4-methylpiperidin-4-yl)ethynyl)-6-nitroquinazolin-4-amine (280 mg, crude) as a yellow solid. m/z ES+ $[M+H]^+$ 529.1

Step 5. To a solution of N-(3-chloro-4-(pyridin-2-ylmethoxy)phenyl)-7-((4-methylpiperidin-4-yl)ethynyl)-6-nitroquinazolin-4-amine (280 mg, 495 umol) in trifluoroethanol (10 mL) was added paraformaldehyde (70.0 mg, 2.33 mmol). The mixture was stirred at 60° C. for 1 h. Then sodium borohydride (40.0 mg, 1.06 mmol) was added and the mixture was stirred at 60° C. for another 1 h. The mixture was quenched with methanol (5 mL) and concentrated under reduced pressure to give N-(3-chloro-4-(pyridin-2-ylmethoxy)phenyl)-7-((1,4-dimethylpiperidin-4-yl)ethynyl)-6-nitroquinazolin-4-amine (350 mg, crude) as a yellow solid. m/z ES+ $[M+H]^+$ 543.5

Step 6. To a solution of N-(3-chloro-4-(pyridin-2-ylmethoxy)phenyl)-7-((1,4-dimethylpiperidin-4-yl)ethynyl)-6-nitroquinazolin-4-amine (350 mg, 644 umol) in methanol (10 mL) and water (3 mL) was added iron powder (180 mg, 3.22 mmol) and ammonium chloride (280 mg, 5.23 mmol). The mixture was stirred at 80° C. for 1 h. The mixture was concentrated under reduced pressure. The residue was purified by column chromatography on silica gel (ethyl acetate/methanol=10/1 to dichloromethane/methanol=4/1) to give $N^4$-(3-chloro-4-(pyridin-2-ylmethoxy)phenyl)-7-((1,4-dimethylpiperidin-4-yl) ethynyl)quinazoline-4,6-diamine (130 mg, 253 umol, 39% yield) as a yellow solid. m/z ES+ $[M+H]^+$ 513.6; $^1$H NMR (400 MHz, MeOD) δ=8.59 (d, J=4.8 Hz, 1H), 8.39 (d, J=7.7 Hz, 1H), 7.99-7.90 (m, 2H), 7.85-7.76 (m, 1H), 7.74 (br d, J=7.7 Hz, 1H), 7.64-7.50 (m, 2H), 7.42 (dd, J=5.2, 6.8 Hz, 1H), 7.21 (dd, J=2.8, 9.0 Hz, 1H), 5.31 (s, 2H), 3.60-3.37 (m, 4H), 2.96 (d, J=2.1 Hz, 3H), 2.35-2.17 (m, 2H), 2.06-1.89 (m, 2H), 1.56 (d, J=5.6 Hz, 3H).

Step 7. To a solution of $N^4$-(3-chloro-4-(pyridin-2-ylmethoxy)phenyl)-7-((1,4-dimethylpiperidin-4-yl)ethynyl) quinazoline-4,6-diamine (120 mg, 234 umol) in dimethyl formamide (2 mL) was added diisopropylethylamine (111 mg, 861 umol), 1-(3-dimethylaminopropyl)-3-ethylcarbodiimide hydrochloride (100 mg, 521 umol) and acrylic acid (42.0 mg, 583 umol). The mixture was stirred at 25° C. for 10 min. The mixture was filtered to give a solution which was purified by prep-HPLC (column: Waters Xbridge 150*25 mm*5 um; mobile phase: [water (10 mM $NH_4HCO_3$)-acetonitrile]; B %: 30%-60%, 10 min). The desired fraction was collected and lyophilized to give N-(4-((3-chloro-4-(pyridin-2-ylmethoxy)phenyl)amino)-7-((1,4-dimethylpiperidin-4-yl)ethynyl)quinazolin-6 yl)acrylamide (27.06 mg, 47.2 umol, 20% yield, 99% purity) as a yellow solid. m/z ES+ $[M+H]^+$ 567.1; $^1$H NMR (400 MHz, DMSO-$d_6$) δ=9.88 (d, J=6.0 Hz, 2H), 8.65 (s, 1H), 8.61 (d, J=4.8 Hz, 1H), 8.57 (s, 1H), 8.04 (d, J=2.4 Hz, 1H), 7.90-7.88 (m, 1H), 7.80 (s, 1H), 7.76-7.71 (m, 1H), 7.59 (d, J=8.0 Hz, 1H), 7.40-7.37 (m, 1H), 7.28 (d, J=9.2 Hz, 1H), 6.61-6.50 (m, 1H), 6.36-6.30 (m, 1H), 5.89-5.80 (m, 1H), 5.30 (s, 2H), 2.63-2.58 (m, 2H), 2.25 (t, J=11.6 Hz, 2H), 2.17 (s, 3H), 1.77 (d, J=12.8 Hz, 2H), 1.56-1.45 (m, 2H), 1.32 (s, 3H).

Example 67. Synthesis of Compound No. 73 N-(4-((3-chloro-4-hydroxyphenyl)amino)-7-(((1R,5S,6s)-3-methyl-3-azabicyclo[3.1.0]hexan-6-yl)ethynyl)quinazolin-6-yl)acrylamide

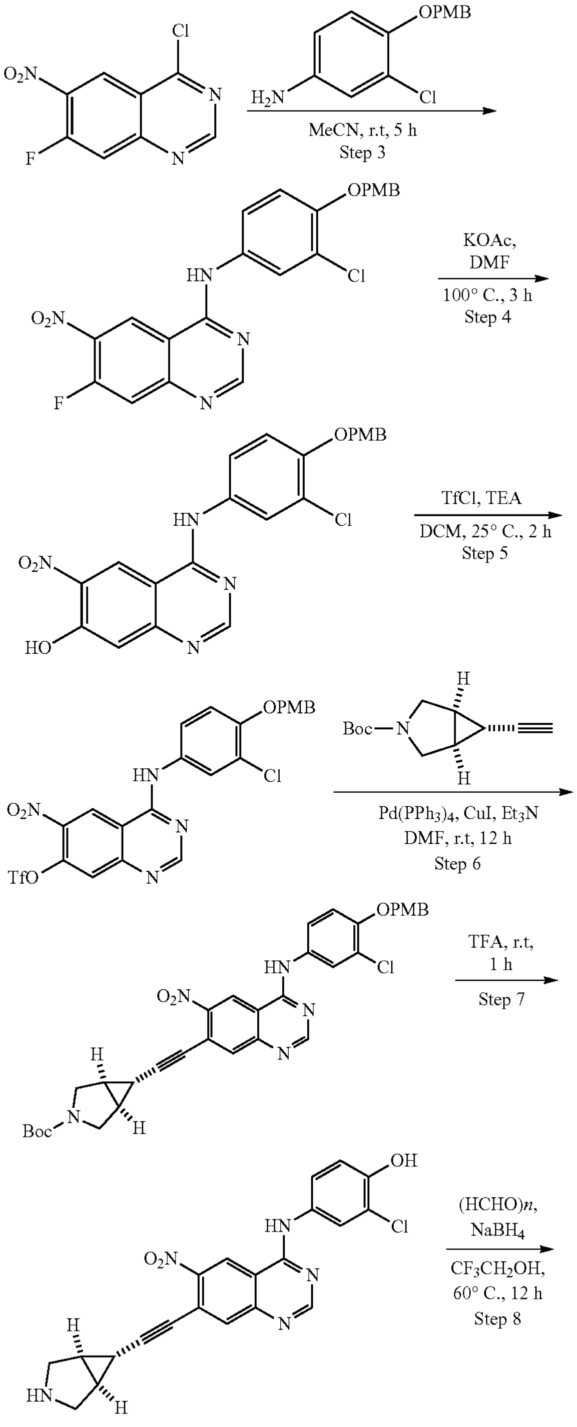

-continued

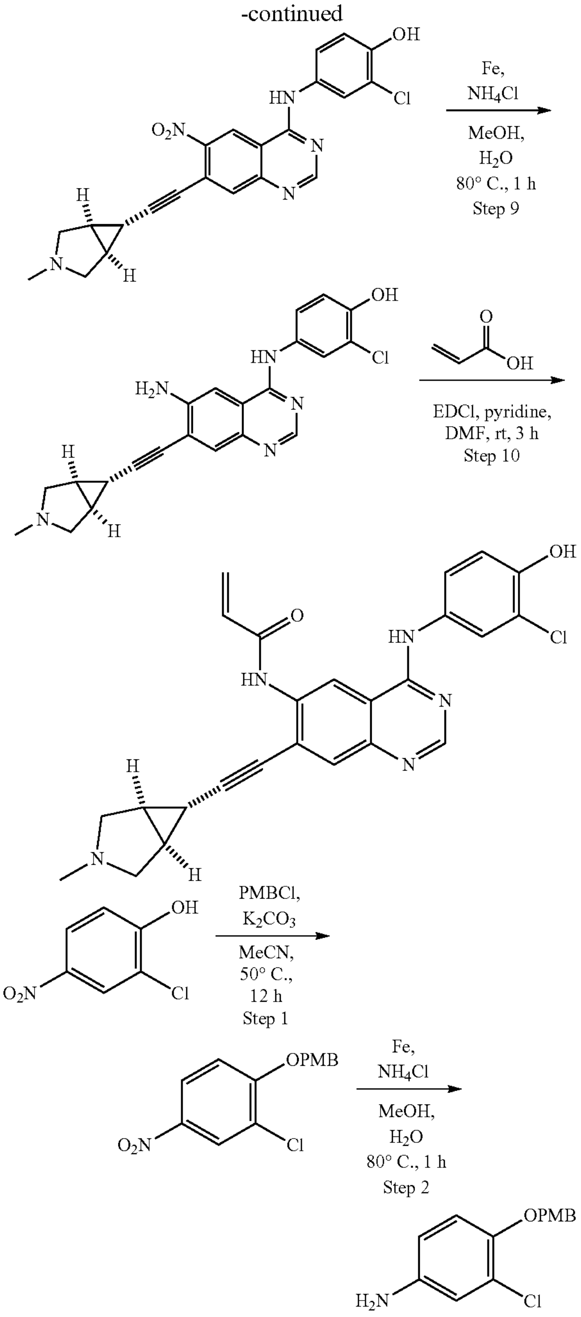

Step 1. To a solution of 2-chloro-4-nitro-phenol (5.00 g, 28.8 mmol) and potassium carbonate (5.97 g, 43.2 mmol) in acetonitrile (50 mL) was added 1-(chloromethyl)-4-methoxy-benzene (4.96 g, 31.7 mmol) dropwise at 25° C. The mixture was stirred at 50° C. for 12 h. The mixture was quenched by methanol (10 mL) and concentrated in vacuum. The residue was purified by silica gel chromatography (petroleum ether/ethyl acetate=10/1 to 5/1) to give 2-chloro-1-((4-methoxybenzyl)oxy)-4-nitrobenzene (7.40 g, 25.2 mmol, 87.5% yield) as a pink solid. m/z ES+$[M+H]^+$ 295.0; $^1$H NMR (400 MHz, $CDCl_3$) δ=8.23 (d, J=2.8 Hz, 1H), 8.05 (dd, J=2.8, 9.2 Hz, 1H), 7.33-7.27 (m, 2H), 6.97 (d, J=9.2 Hz, 1H), 6.89-6.84 (m, 2H), 5.12 (s, 2H), 3.75 (s, 3H).

Step 2. To a solution of 2-chloro-1-((4-methoxybenzyl)oxy)-4-nitrobenzene (3.20 g, 10.9 mmol) and ammonium chloride (2.91 g, 54.5 mmol) in methanol (15 mL) and water (7 mL) was added iron powder (1.83 g, 32.7 mmol) at 25° C. The mixture was heated to 80° C. and stirred at 80° C. for 1 h. The mixture was concentrated to afford a residue. The residue was diluted with water (10 mL), saturated sodium carbonate (10 mL), ethyl acetate (30 mL). The mixture was extracted with ethyl acetate (2×30 mL) and the combined organic layer was washed with water (20 mL), dried over anhydrous sodium sulfate and filtered. The filtrate was concentrated to afford 3-chloro-4-((4-methoxybenzyl)oxy) aniline (2.70 g, 10.2 mmol, 94.0% yield) as a brown solid. m/z ES+ $[M+H]^+$ 264.1

Step 3. A mixture of 4-chloro-7-fluoro-6-nitro-quinazoline (2.45 g, 10.8 mmol) and 3-chloro-4-((4-methoxybenzyl) oxy)aniline (2.70 g, 10.2 mmol) in acetonitrile (50 mL) was stirred at 25° C. for 5 h. The mixture was concentrated to give a residue. The residue was triturated with ethyl acetate (50 mL). After filtration, the filter cake was washed with ethyl acetate (20 mL), dried in vacuum to give N-(3-chloro-4-((4-methoxybenzyl)oxy)phenyl)-7-fluoro-6-nitroquinazolin-4-amine (4.40 g, 9.67 mmol, 94.4% yield) as a yellow solid. m/z ES+ $[M+H]^+$ 455.2; $^1H$ NMR (400 MHz, DMSO-$d_6$) δ=9.73 (d, J=7.6 Hz, 1H), 8.90-8.83 (m, 1H), 7.95-7.88 (m, 2H), 7.68 (dd, J=2.6, 8.8 Hz, 1H), 7.43 (d, J=8.6 Hz, 2H), 7.36 (d, J=9.0 Hz, 1H), 6.98 (d, J=8.8 Hz, 2H), 5.18 (s, 2H), 3.77 (s, 3H).

Step 4. To the solution of N-(3-chloro-4-((4-methoxybenzyl)oxy)phenyl)-7-fluoro-6-nitroquinazolin-4-amine (4.00 g, 8.79 mmol) in dimethylformamide (30 mL) was added potassium acetate (4.32 g, 44.0 mmol) at 25° C. The mixture was stirred at 100° C. for 3 h. The mixture was concentrated to afford a residue. The residue was diluted with water (50 mL). After filtration, the filter cake was washed with water (30 mL), dried in vacuum to give 4-((3-chloro-4-((4-methoxybenzyl)oxy)phenyl)amino)-6-nitroquinazolin-7-ol (3.50 g, 7.73 mmol, 87.9% yield) as a brown solid. m/z ES+ $[M+H]^+$ 453.0; $^1H$ NMR (400 MHz, DMSO-$d_6$) δ=10.07 (br s, 1H), 9.20 (s, 1H), 8.54 (s, 1H), 7.96 (d, J=2.2 Hz, 1H), 7.69 (dd, J=2.4, 8.8 Hz, 1H), 7.45-7.37 (m, 2H), 7.29 (d, J=9.0 Hz, 1H), 7.21 (br s, 1H), 7.01-6.94 (m, 2H), 5.21-5.08 (m, 2H), 3.81-3.73 (m, 3H).

Step 5. To the solution of 4-((3-chloro-4-((4-methoxybenzyl)oxy)phenyl)amino)-6-nitroquinazolin-7-ol (3.00 g, 6.62 mmol) and triethylamine (1.34 g, 13.3 mmol, 1.84 mL) in dichloromethane (15 mL) was added trifluoromethanesulfonyl chloride (1.67 g, 9.94 mmol, 1.05 mL, 1.50 eq) at 0° C. The mixture was warmed to 25° C. and stirred for 2 h. The mixture was concentrated to afford a residue. The residue was purified by silica gel chromatography (petroleum ether/Ethyl acetate=8/1) to afford 4-((3-chloro-4-((4-methoxybenzyl)oxy)phenyl)amino)-6-nitroquinazolin-7-yltrifluoromethanesulfonate (2.06 g, 3.52 mmol, 53.2% yield) as a yellow solid. m/z ES+ $[M+H]^+$ 584.9; $^1H$ NMR (400 MHz, DMSO-$d_6$) δ=10.64 (s, 1H), 9.77 (s, 1H), 8.83 (s, 1H), 8.10 (s, 1H), 8.00 (d, J=2.4 Hz, 1H), 7.75 (dd, J=2.4, 9.0 Hz, 1H), 7.48 (d, J=8.6 Hz, 2H), 7.39 (d, J=8.8 Hz, 1H), 7.04 (d, J=8.8 Hz, 2H), 5.22 (s, 2H), 3.83 (s, 3H).

Step 6. To the solution of 4-((3-chloro-4-((4-methoxybenzyl)oxy)phenyl)amino)-6-nitroquinazolin-7-yl trifluoromethanesulfonate (2.00 g, 3.42 mmol), (1R,5S,6s)-tert-butyl 6-ethynyl-3-azabicyclo[3.1.0]hexane-3-carboxylate (920 mg, 4.44 mmol), triethylamine (3.55 g, 35.1 mmol, 4.88 mL) and copper iodide (130 mg, 684 umol) in dimethylformamide (5.00 mL) was added tetrakis[triphenylphosphine]palladium(0) (395 mg, 342 umol) at 25° C. under nitrogen atmosphere. The mixture was stirred at 25° C. for 12 h. The mixture was concentrated to dryness to give a residue. The residue was purified by silica gel chromatography (petroleum ether/ethyl acetate=2/1 to 1/1) to afford (1R,5S,6s)-tert-butyl 6-((4-((3-chloro-4-((4-methoxybenzyl)oxy)phenyl)amino)-6-nitroquinazolin-7-yl)ethynyl)-3-azabicyclo[3.1.0]hexane-3-carboxylate (1.60 g, 2.49 mmol, 72.9% yield) as a yellow solid. m/z ES+ $[M+H]^+$ 642.5; $^1H$ NMR (400 MHz, DMSO-$d_6$) δ=10.35-10.29 (m, 1H), 9.39 (s, 1H), 8.67 (s, 1H), 7.97-7.88 (m, 2H), 7.69 (br dd, J=2.0, 9.0 Hz, 1H), 7.42 (br d, J=8.4 Hz, 2H), 7.30 (br d, J=9.0 Hz, 1H), 6.97 (d, J=8.6 Hz, 2H), 5.14 (s, 2H), 3.76 (s, 3H), 3.55 (br s, 2H), 3.17 (br d, J=3.6 Hz, 2H), 2.09 (br s, 2H), 1.47 (br s, 1H), 1.39 (s, 9H).

Step 7. The mixture of (1R,5S,6s)-tert-butyl 6-((4-((3-chloro-4-((4-methoxybenzyl)oxy)-phenyl)amino)-6-nitroquinazolin-7-yl)ethynyl)-3-azabicyclo[3.1.0]hexane-3-carboxylate (600 mg, 934 umol) in trifluoroacetic acid (7.70 g, 67.5 mmol, 5.00 mL) was stirred at 25° C. for 1 h. The mixture was concentrated to dryness to give crude product. The crude product was freed with saturated sodium carbonate (50 mL) and extracted with ethyl acetate (3×20 mL). The combined organic layers were washed with water (10 mL), dried over anhydrous sodium sulfate, filtered and concentrated to afford 4-((7-((1R,5S,6s)-3-azabicyclo[3.1.0]hexan-6-ylethynyl)-6-nitroquinazolin-4-yl)amino)-2-chlorophenol (300 mg, 711 umol, 76.1% yield) as a brown solid. m/z ES+ $[M+H]^+$ 422.1; $^1H$ NMR (400 MHz, $CD_3OD$) δ=9.10 (s, 1H), 8.49 (s, 1H), 7.77 (s, 1H), 7.68 (d, J=2.4 Hz, 1H), 7.37 (dd, J=2.6, 8.6 Hz, 1H), 6.87 (d, J=8.8 Hz, 1H), 3.04 (br d, J=11.4 Hz, 2H), 2.05 (br s, 2H), 1.52 (t, J=3.4 Hz, 1H), 1.27-1.21 (m, 2H).

Step 8. To the mixture of 4-((7-((1R,5S,6s)-3-azabicyclo[3.1.0]hexan-6-ylethynyl)-6-nitroquinazolin-4-yl)amino)-2-chlorophenol (340 mg, 806 umol) and paraformaldehyde (122 mg, 4.08 mmol) in trifluoroethanol (8.00 mL) was added sodium borohydride (92.0 mg, 2.42 mmol, 3.00 eq) at 25° C. The mixture was stirred at 60° C. for 2 h. The mixture was concentrated to dryness to give a residue. The residue was diluted with saturated sodium carbonate (5.00 mL) and water (10.0 mL), extracted with ethyl acetate (3×20 mL). The combined organic layer was washed with water (20 mL), dried over anhydrous sodium sulfate, filtered and the filtrate was concentrated to afford 2-chloro-4-((7-4(1R,5S,6s)-3-methyl-3-azabicyclo[3.1.0]hexan-6-yl)ethynyl)-6-nitroquinazolin-4-yl)amino)phenol (340 mg, 780 umol, 96.8% yield) as a brown solid. m/z ES+$[M+H]^+$ 436.1; $^1H$ NMR (400 MHz, $CD_3OD$) δ=9.18 (br s, 1H), 8.58 (br s, 1H), 7.88-7.77 (m, 2H), 7.47 (br d, J=7.6 Hz, 1H), 6.97 (br d, J=8.0 Hz, 1H), 3.15 (br d, J=9.6 Hz, 2H), 2.48 (br d, J=8.4 Hz, 2H), 2.35 (br s, 3H), 2.00 (br s, 2H), 1.97-1.91 (m, 1H).

Step 9. The mixture of 2-chloro-4-((7-(((1R,5S,6s)-3-methyl-3-azabicyclo[3.1.0]hexan-6-yl)ethynyl)-6-nitroquinazolin-4-yl)amino)phenol (190 mg, 436 umol), iron powder (76.0 mg, 1.36 mmol) and ammonium chloride (118 mg, 2.21 mmol) in methanol (10 mL) and water (5 mL) was stirred at 80° C. for 1 h. The mixture was concentrated to afford a residue. The residue was diluted with water (10 mL), saturated sodium carbonate (5 mL), ethyl acetate (30 mL). The mixture was extracted with ethyl acetate (2×30 mL) and the combined organic layer was washed with water (20 mL), dried over anhydrous sodium sulfate and filtered. The filtrate was concentrated to afford 4-((6-amino-7-(((1R,5S,6s)-3-methyl-3-azabicyclo[3.1.0]hexan-6-yl)ethynyl) quinazolin-4-yl)amino)-2-chlorophenol (150 mg, 370 umol, 84.8% yield) as a yellow solid. m/z ES+ $[M+H]^+$ 406.3; $^1H$ NMR (400 MHz, DMSO-$d_6$) δ=9.93 (br s, 1H), 9.32 (s, 1H), 8.27 (s, 1H), 7.86 (d, J=2.0 Hz, 1H), 7.55-7.50 (m, 2H), 7.42 (s, 1H), 6.96 (d, J=8.8 Hz, 1H), 5.51 (br s, 2H), 3.02 (br d, J=9.2 Hz, 2H), 2.34-2.23 (m, 6H), 1.97 (br s, 2H).

Step 10. To the solution of 4-((6-amino-7-(((1R,5S,6s)-3-methyl-3-azabicyclo[3.1.0]hexan-6-yl)ethynyl)quinazolin-4-yl)amino)-2-chlorophenol (90.0 mg, 222 umol), acrylic acid (32.0 mg, 443 umol, 30.4 uL) and pyridine (88.0 mg, 1.11 mmol, 89.8 uL) in dimethylformamide (2 mL) was added 1-(3-dimethylaminopropyl)-3-ethylcarbodiimide hydrochloride (212 mg, 1.11 mmol) at 25° C. The mixture was stirred at 25° C. for 2 h. The reaction mixture was filtered. The filtrate was purified by prep-HPLC (column: Phenomenex Gemini 150*25 mm*10 um; mobile phase: [water (0.04% ammonium hydroxide+10 mM $NH_4HCO_3$)-acetonitrile]; B %: 37%-67%, 10 min) and (column: Phenomenex Synergi C18 150*30 mm*4 um; mobile phase: [water (0.225% formic acid)-acetonitrile]; B %: 10%-30%, 10 min) and lyophilized to afford N-(4-((3-chloro-4-hydroxyphenyl)amino)-7-4(1R,5S,6s)-3-methyl-3-azabicyclo [3.1.0]hexan-6-yl)ethynyl)quinazolin-6-yl)acrylamide (16.4 mg, 32.4 umol, 14.6% yield, 100% purity, formic acid) as a yellow solid. m/z ES+ $[M+H]^+$ 406.2; $^1$H NMR (400 MHz, DMSO-$d_6$) δ=9.83 (s, 1H), 9.76 (s, 1H), 8.68 (s, 1H), 8.50 (s, 1H), 8.19 (s, 1H), 7.83 (d, J=2.4 Hz, 1H), 7.75 (s, 1H), 7.53 (dd, J=2.4, 8.8 Hz, 1H), 6.99 (d, J=8.8 Hz, 1H), 6.68-6.56 (m, 1H), 6.34 (dd, J=1.6, 16.8 Hz, 1H), 5.88-5.81 (m, 1H), 3.02 (d, J=9.2 Hz, 2H), 2.30 (d, J=8.8 Hz, 2H), 2.24 (s, 3H), 1.97-1.87 (m, 3H).

Example 68. Synthesis of Compound No. 74 N-(4-((3-chloro-2-fluorophenyl)amino)-7-(((1R,5S,6s)-3-methyl-3-azabicyclo[3.1.0]hexan-6-yl)ethynyl)quinazolin-6-yl)but-2-ynamide

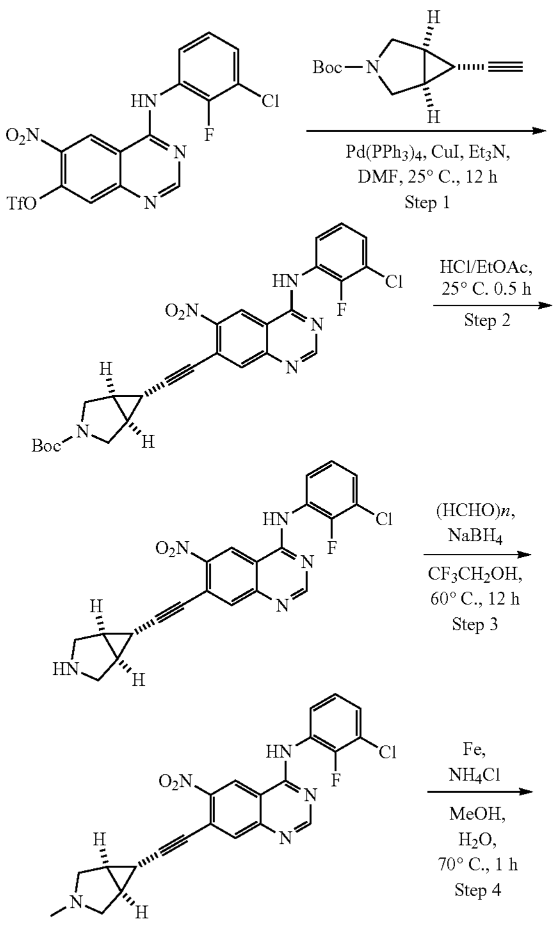

-continued

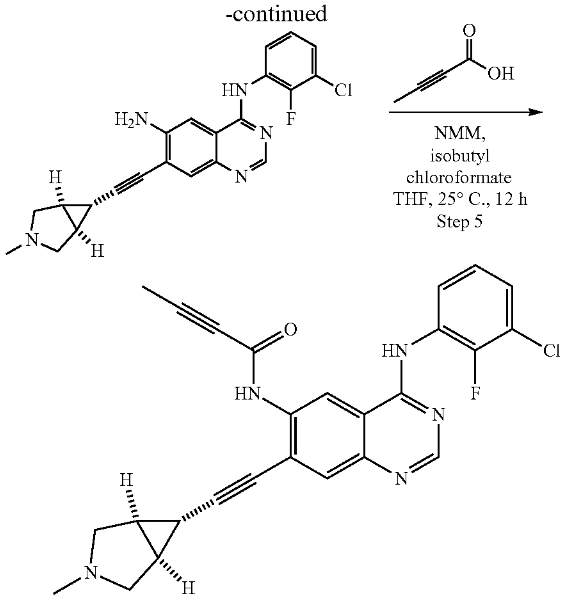

Step 1. A reaction mixture of 4-((3-chloro-2-fluorophenyl)amino)-6-nitroquinazolin-7-yl trifluoromethanesulfonate (1.00 g, 2.14 mmol), (1R,5S,6s)-tert-butyl 6-ethynyl-3-azabicyclo[3.1.0]hexane-3-carboxylate (666 mg, 3.21 mmol), tetrakis(triphenylphosphine)palladium(0) (495 mg, 428 umol), copper iodide (204 mg, 1.07 mmol), and triethylamine (650 mg, 6.43 mmol, 895 uL) in dimethyl formamide (5.00 mL) was stirred for 12 h at 25° C. The mixture was concentrated under vacuum to give the residue. The residue was purified by flash chromatography [silica gel column: 20 g, petroleum ether/ethyl acetate=10/1-1/1] to give (1R,5S,6s)-tert-butyl 6-((4-((3-chloro-2-fluorophenyl) amino)-6-nitroquinazolin-7-yl) ethynyl)-3-azabicyclo [3.1.0]hexane-3-carboxylate (550 mg, 1.05 mmol, 49% yield) as a light yellow solid. $^1$H NMR (400 MHz, DMSO-$d_6$) δ=9.39 (br s, 1H), 8.67 (br s, 1H), 7.99 (br s, 1H), 7.53 (br s, 2H), 7.36-7.26 (m, 1H), 3.57 (br d, J=11.00 Hz, 2H), 3.38 (br s, 2H), 2.11 (br s, 2H), 1.52-1.47 (m, 1H), 1.40 (s, 9H).

Step 2. A mixture of (1R,5S,6s)-tert-butyl 6-((4-((3-chloro-2-fluorophenyl)amino)-6-nitroquinazolin-7-yl)ethynyl)-3-azabicyclo[3.1.0]hexane-3-carboxylate (500 mg, 954 umol) in hydrochloric acid/ethyl acetate (4 M, 15.0 mL) was stirred at 25° C. for 0.5 h. The mixture was concentrated under vacuum to give 7-((1R,5S,6s)-3-azabicyclo[3.1.0] hexan-6-ylethynyl)-N-(3-chloro-2-fluorophenyl)-6-nitroquinazolin-4-amine (440 mg, crude, HCl) as a yellow solid, which was used to next step without purification. m/z ES+ $[M+H]^+$ 423.9

Step 3. A reaction mixture of 7-((1R,5S,6s)-3-azabicyclo [3.1.0]hexan-6-ylethynyl)-N-(3-chloro-2-fluorophenyl)-6-nitroquinazolin-4-amine (440 mg, 956 umol, HCl), sodium borohydride (72.3 mg, 1.91 mmol) and paraformaldehyde (144 mg, 4.78 mmol) in 2,2,2-trifluoroethanol (15 mL) was stirred for 12 h at 60° C. The mixture was concentrated under vacuum. The residue was purified by flash chromatography [silica gel column: 12 g, petroleum ether/ethyl acetate=10/1-1/2] to give N-(3-chloro-2-fluorophenyl)-7-4 (1R,5S,6s)-3-methyl-3-azabicyclo[3.1.0]hexan-6-yl)ethynyl)-6-nitroquinazolin-4-amine (210 mg, 480 umol, 50% yield) as a light brown solid. $^1$H NMR (400 MHz, DMSO-$d_6$) δ=10.63 (br s, 1H), 9.30 (br s, 1H), 8.56 (br s, 1H), 7.90

(s, 1H), 7.49 (q, J=8.11 Hz, 2H), 7.34-7.26 (m, 1H), 3.03 (d, J=9.17 Hz, 2H), 2.30 (br d, J=8.80 Hz, 2H), 2.24 (s, 3H), 1.96 (br s, 2H), 1.92 (br d, J=3.06 Hz, 1H).

Step 4. A mixture of N-(3-chloro-2-fluorophenyl)-7-(((1R,5S,6s)-3-methyl-3-azabicyclo[3.1.0]hexan-6-yl)ethynyl)-6-nitroquinazolin-4-amine (150 mg, 342 umol), iron power (95.7 mg, 1.71 mmol) and ammonium chloride (91.6 mg, 1.71 mmol) in methanol (5.00 mL) and water (2.00 mL) was stirred for 1 h at 70° C. The mixture was filtered to give the filtrate, which was concentrated under vacuum to give the residue. The residue was purified by prep-HPLC {column: Xtimate C18 150*25 mm*5 um; mobile phase: [water (0.05% ammonium hydroxide v/v)-acetonitrile]; B %: 35%-65%, 10 min.} to give $N^4$-(3-chloro-2-fluorophenyl)-7-(((1R,5S,6s)-3-methyl-3-azabicyclo[3.1.0]hexan-6-yl)ethynyl)quinazoline-4,6-diamine (65.0 mg, 159 umol, 47% yield) as a light yellow solid. $^1$H NMR (400 MHz, DMSO-$d_6$) δ=9.54 (s, 1H), 8.24 (s, 1H), 7.58 (s, 1H), 7.54 (br t, J=7.09 Hz, 1H), 7.45 (br t, J=7.21 Hz, 1H), 7.38 (s, 1H), 7.29-7.23 (m, 1H), 5.63 (br s, 2H), 3.02 (d, J=9.17 Hz, 2), 2.29 (br d, J=8.93 Hz, 2H), 2.24 (s, 3H), 1.98 (br s, 2H), 1.94 (br s, 1H).

Step 5. To a solution of but-2-ynoic acid (12.4 mg, 147 umol) in tetrahydrofuran (2.00 mL) was added N-methylmorpholine (14.9 mg, 147 umol) and isobutyl carbonochloridate (20.1 mg, 147 umol). The solution was stirred for 10 mins at 0° C. under nitrogen atmosphere, then $N^4$-(3-chloro-2-fluorophenyl)-7-(((1R,5S,6s)-3-methyl-3-azabicyclo[3.1.0]hexan-6-yl)ethynyl)-quinazoline-4,6-diamine (20.0 mg, 49.0 umol) was added to the solution and the resulting mixture was stirred for 12 h at 25° C. The mixture was concentrated under vacuum to give the residue. The residue was purified by prep-HPLC {column: Xtimate C18 150*25 mm*5 um; mobile phase: [water (0.05% ammonium hydroxide v/v)-acetonitrile]; B %: 49%-79%, 1 min. column: Phenomenex Gemini 150*25 mm*10 um; mobile phase: [water (10 mM $NH_4HCO_3$)-acetonitrile]; B %: 40%-70%, 10 min} to give N-(4-((3-chloro-2-fluorophenyl)amino)-7-(((1R,5S,6s)-3-methyl-3-azabicyclo[3.1.0]hexan-6-yl)ethynyl)quinazolin-6-yl)but-2-ynamide (1.6 mg, 3.24 umol, 6.61% yield, 96% purity) as a yellow solid. m/z ES+ $[M+H]^+$ 474.3; $^1$H NMR (400 MHz, DMSO-$d_6$) δ=10.23 (br s, 1H), 10.03 (s, 1H), 8.49 (br s, 1H), 8.47 (s, 1H), 7.77 (s, 1H), 7.53-7.47 (m, 2H), 7.28 (t, J=8.01 Hz, 1H), 3.03 (br d, J=9.17 Hz, 2H), 2.32 (br s, 2H), 2.25 (br s, 3H), 2.06 (br s, 3H), 1.95 (br s, 2H), 1.89 (br s, 1H).

Example 69. Synthesis of Compound No. 75 N-(4-((5-chloro-2-fluorophenyl)amino)-7-(((1R,5S,6s)-3-methyl-3-azabicyclo[3.1.0]hexan-6-yl)ethynyl)quinazolin-6-yl)acrylamide

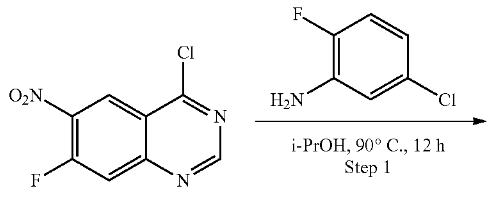

-continued

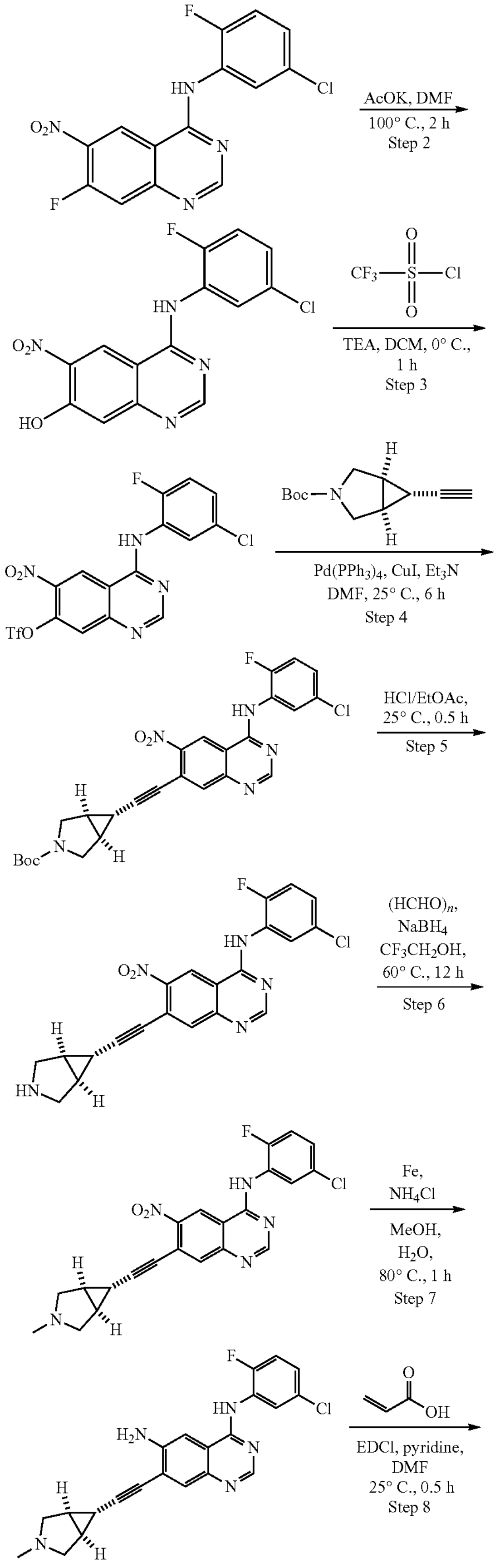

-continued

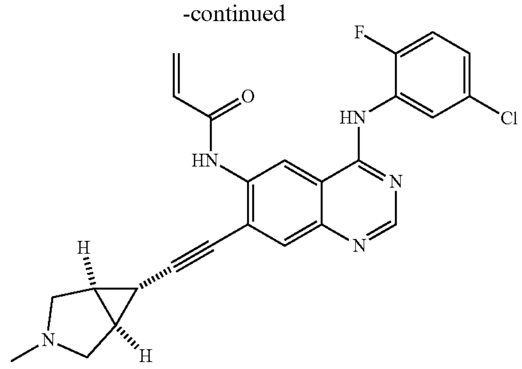

Step 1. A mixture of 4-chloro-7-fluoro-6-nitroquinazoline (5.00 g, 21.9 mmol) and 5-chloro-2-fluoroaniline (3.20 g, 21.9 mmol) in isopropanol (80.0 mL) was stirred at 80° C. for 12 h under nitrogen atmosphere. The reaction mixture was concentrated under reduced pressure to give N-(5-chloro-2-fluorophenyl)-7-fluoro-6-nitroquinazolin-4-amine (7.00 g, crude) as a yellow solid. m/z ES+ $[M+H]^+$ 337.1;

Step 2. A mixture of N-(5-chloro-2-fluorophenyl)-7-fluoro-6-nitroquinazolin-4-amine (6.50 g, 19.3 mmol), potassium acetate (9.47 g, 96.5 mmol) in dimethyl formamide (70.0 mL) was stirred at 100° C. for 2 h under nitrogen atmosphere. The reaction mixture was diluted with water (200 mL) and filtered. The filter cake was dried to give 4-((5-chloro-2-fluorophenyl)amino)-6-nitroquinazolin-7-ol (6.30 g, crude) as a yellow solid. m/z ES+ $[M+H]^+$ 335.0;

Step 3. To a solution of 4-((5-chloro-2-fluorophenyl) amino)-6-nitroquinazolin-7-ol (6.00 g, 17.9 mmol) and triethylamine (3.63 g, 35.8 mmol, 4.99 mL) in dichloromethane (80.0 mL) was added trifluoromethanesulfonyl chloride (3.93 g, 23.3 mmol, 2.47 mL at 0° C. The mixture was stirred at 0° C. for 1 h. The reaction mixture was concentrated under reduced pressure to give a residue. The residue was purified by flash silica gel chromatography (ISCO®; 20 g SepaFlash® Silica Flash Column, Eluent of 10100% Ethyl acetate/Petroleum ether gradient @ 80 mL/min) to give 4-((5-chloro-2-fluorophenyl)amino)-6-nitroquinazolin-7-yl trifluoromethanesulfonate (5.00 g, 10.7 mmol, 59% yield) as a yellow solid. m/z ES+ $[M+H]^+$ 467.1; $^1$H NMR (400 MHz, $CDCl_3$) δ 8.98-8.84 (m, 2H), 8.42 (dd, J=6.8, 1.8 Hz, 1H), 8.10-7.99 (m, 1H), 7.90 (s, 1H), 7.15-7.09 (m, 2H).

Step 4. A mixture of 4-((5-chloro-2-fluorophenyl)amino)-6-nitroquinazolin-7-yl trifluoromethanesulfonate (3.00 g, 6.43 mmol), (1R,5S,6s)-tert-butyl6-ethynyl-3-azabicyclo [3.1.0]hexane-3-carboxylate (1.73 g, 8.36 mmol), tetrakis [triphenylphosphine]-palladium (742 mg, 642 umol), copper iodide (245 mg, 1.29 mmol) in dimethyl formamide (25.0 mL) and triethylamine (5.00 mL) was degassed and purged with nitrogen for 3 times, and then the mixture was stirred at 25° C. for 6 h under nitrogen atmosphere. The reaction mixture was diluted with water (100 mL) and extracted with ethyl acetate (3×20 mL). The combined organic layers were washed with brine (3×20 mL), dried over sodium sulfate, filtered and concentrated under reduced pressure to give a residue. The residue was triturated with ethyl acetate (20 mL) and filtered to give (1R,5S,6s)-tert-butyl6-((4-((5-chloro-2-fluorophenyl)amino)-6-nitroquinazolin-7-yl) ethynyl)-3-azabicyclo[3.1.0]hexane-3-carboxylate (3.00 g, crude) as a yellow solid. m/z ES+$[M+H]^+$ 524.1; $^1$H NMR (400 MHz, DMSO-$d_6$) δ 10.63 (br s, 1H), 9.29 (br s, 1H), 8.89-8.16 (m, 1H), 7.66-7.58 (m, 2H), 7.34 (br d, J=10.8 Hz, 2H), 3.57 (br d, J=11.0 Hz, 2H), 3.37 (br d, J=11.4 Hz, 2H), 2.10 (br s, 2H), 1.48 (br s, 1H), 1.40 (s, 9H).

Step 5. A solution of (1R,5S,6s)-tert-butyl6-((4-((5-chloro-2-fluorophenyl)amino)-6-nitroquinazolin-7-yl)ethynyl)-3-azabicyclo[3.1.0]hexane-3-carboxylate (1.50 g, 2.86 mmol) in 4 M hydrochloride/ethyl acetate (10.0 mL) was stirred at 25° C. for 0.5 h under nitrogen atmosphere. The reaction mixture was concentrated under reduced pressure to remove solvent. The residue was diluted with water (50 mL) and extracted with ethyl acetate (3×10 mL). The combined organic layers were washed with brine (3×20 mL), dried over sodium sulfate, filtered and concentrated under reduced pressure to give 7-((1R,5S,6s)-3-azabicyclo[3.1.0]hexan-6-ylethynyl)-N-(5-chloro-2-luorophenyl)-6-nitroquinazolin-4-amine (1.20 g, crude) as a yellow solid. m/z ES+ $[M+H]^+$ 424.3;

Step 6. To a solution of 7-((1R,5S,6s)-3-azabicyclo[3.1.0] hexan-6-ylethynyl)-N-(5-chloro-2-fluorophenyl)-6-nitroquinazolin-4-amine (1.00 g, 2.36 mmol) and paraformaldehyde (353 mg, 11.8 mmol) in trifluoroethanol (30.0 mL) was added sodium borohydride (178 mg, 4.72 mmol) in portions at 60° C. The mixture was stirred at 60° C. for 12 h. The reaction mixture was concentrated under reduced pressure to remove solvent, diluted with water and extracted with ethyl acetate (3×20 mL). The combined organic layers were washed with brine (3×20 mL), dried over sodium sulfate, filtered and concentrated under reduced pressure to give a residue. The residue was purified by reversed-phase chromatography (FA) to give N-(5-chloro-2-fluorophenyl)-7-(((1R,5S,6s)-3-methyl-3-azabicyclo[3.1.0]hexan-6-yl)ethynyl)-6-nitroquinazolin-4-amine (170 mg, 388 umol, 16% yield) as a yellow solid. m/z ES+ $[M+H]^+$ 438.2; $^1$H NMR (400 MHz, $CDCl_3$) δ 8.83 (br s, 1H), 8.62-8.56 (m, 2H), 7.99 (s, 1H), 7.15-7.00 (m, 3H), 3.26-3.21 (m, 2H), 2.52-2.45 (m, 2H), 2.35 (s, 3H), 1.97 (m, J=3.2 Hz, 3H).

Step 7. A mixture of N-(5-chloro-2-fluorophenyl)-7-(((1R,5S,6s)-3-methyl-3-azabicyclo[3.1.0]hexan-6-yl)ethynyl)-6-nitroquinazolin-4-amine (150 mg, 342 umol), iron powder (95.6 mg, 1.71 mmol), ammonium chloride (91.6 mg, 1.71 mmol) in methanol (10.0 mL) and water (10.0 mL) was stirred at 80° C. for 1 h under nitrogen atmosphere. The reaction mixture was filtered and the filtrate was concentrated under reduced pressure to give a residue. The residue was purified by prep-HPLC (column: Phenomenex Gemini 150*25 mm*10 um; mobile phase: [water (0.04% $NH_3H_2O$+10 mM $NH_4HCO_3$)-ACN]; B %: 45%-78%, min) to give $N^4$-(5-chloro-2-fluorophenyl)-7-(((1R,5S,6s)-3-methyl-3-azabicyclo[3.1.0]hexan-6-yl)ethynyl)quinazoline-4,6-diamine (30.0 mg, 73.6 umol, 21% yield) as a blue solid. m/z ES+ $[M+H]^+$ 408.3;

Step 8. To a solution of $N^4$-(5-chloro-2-fluorophenyl)-7-4(1R,5S,6s)-3-methyl-3-azabicyclo[3.1.0]hexan-6-yl) ethynyl)quinazoline-4,6-diamine (10.0 mg, 24.0 umol), pyridine (3.88 mg, 49.0 umol, 3.96 uL) and acrylic acid (2.65 mg, 36.8 umol, 2.52 uL) in dimethyl formamide (3.00 mL) was added 1-(3-dimethylaminopropyl)-3-ethylcarbodiimide hydrochloride (18.8 mg, 98.1 umol) in portions at 25° C. The mixture was stirred at 25° C. for 0.5 h. The reaction mixture was filtered. The residue was purified by prep-HPLC (column: Xtimate C18 150*25 mm*5 um; mobile phase: [water (0.05% ammonia hydroxide v/v)-ACN]; B %: 48%-78%, 1 min) to give N-(4-((5-chloro-2-fluorophenyl)amino)-7-(((1R,5S,6s)-3-methyl-3-azabicyclo[3.1.0]hexan-6-yl)ethynyl)quinazolin-6-yl)acrylamide (5.91 mg, 12.8 umol, 52% yield, 100% purity) as a yellow solid. m/z ES+ $[M+H]^+$ 462.3; $^1$H NMR (400 MHz, DMSO-$d_6$) δ 9.98 (br s, 1H), 9.81 (br s, 1H), 8.72 (br s, 1H), 8.48 (s, 1H), 7.80 (s, 1H), 7.67 (br s, 1H), 7.38 (br d, J=6.2 Hz, 2H), 6.79-6.56 (m, 1H), 6.34 (br d, J=18.0 Hz, 1H), 5.86 (br d, J=10.0 Hz, 1H), 3.01 (br d, J=9.4 Hz, 2H), 2.30 (br d, J=8.8 Hz, 2H), 2.24 (br s, 3H), 1.98-1.97 (m, 3H).

Example 70. Synthesis of Compound No. 76 N-(4-((3-chloro-4-((3-fluorobenzyl)oxy)-phenyl)amino)-7-(((1R,5S,6s)-3-methyl-3-azabicyclo[3.1.0]hexan-6-yl)ethynyl)quinazolin-6-yl)acrylamide
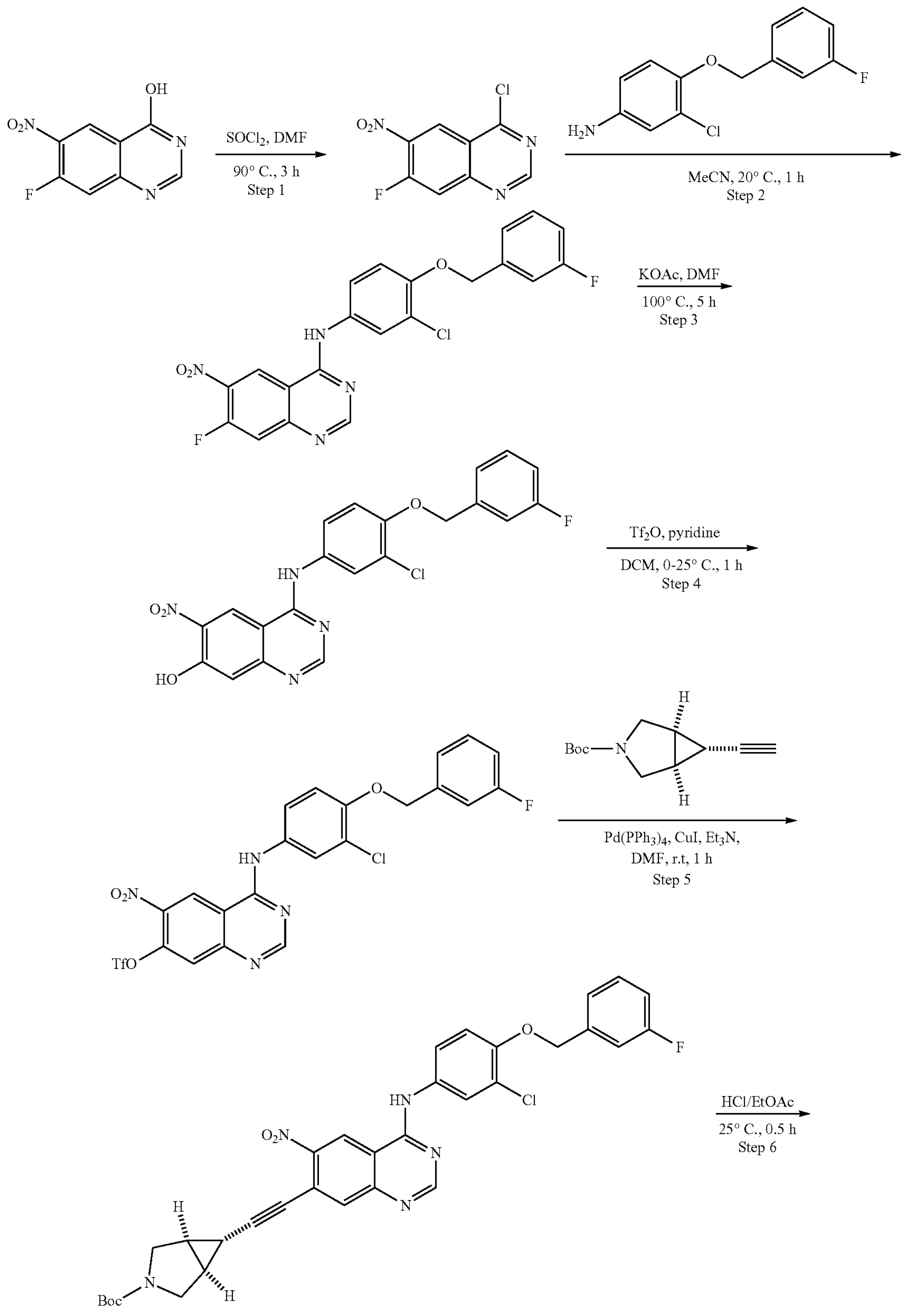

-continued
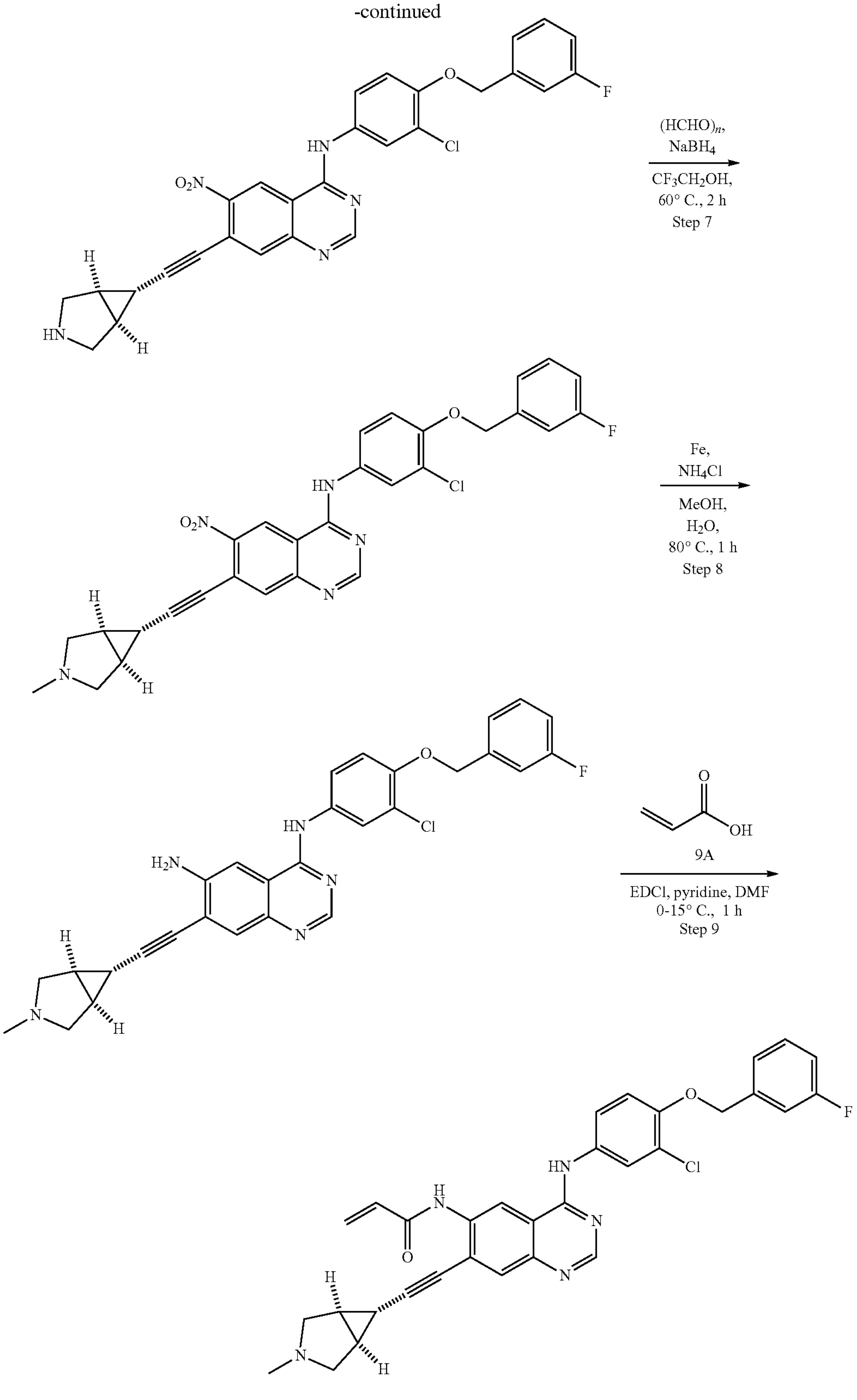
Step 1. A mixture of 7-fluoro-6-nitroquinazolin-4-ol (5.00 g, 23.9 mmol) and dimethyl formamide (87.3 mg, 1.20 mmol, 92.0 uL) in thionyl chloride (50.0 mL) was stirred at 90° C. for 3 h. The reaction mixture was concentrated to give 4-chloro-7-fluoro-6-nitroquinazoline (5.00 g, 21.9 mmol, 91.9% yield) as a white solid. m/z ES+ $[M+H]^+$ 227.9;

Step 2. A mixture of 4-chloro-7-fluoro-6-nitro-quinazoline (2.00 g, 8.74 mmol) and 3-chloro-4-((3-fluorobenzyl)oxy)aniline (2.00 g, 7.95 mmol) in acetonitrile (20.0 mL) was stirred at 20° C. for 1 h. The reaction mixture was concentrated to give a residue, the residue was poured into ethyl acetate (40.0 mL), stirred for 10 min, filtered and the filter cake was washed with ethyl acetate and concentrated in vaccum to give N-(3-chloro-4-((3-fluorobenzyl)oxy)phenyl)-7-fluoro-6-nitroquinazolin-4-amine (3.00 g, 6.78 mmol, 85% yield) as a yellow solid. m/z ES+ $[M+H]^+$ 443.1; $^1$H NMR (400 MHz, DMSO-$d_6$) δ 9.77 (br d, J=6.0 Hz, 1H), 8.87 (s, 1H), 7.98-7.90 (m, 2H), 7.69 (dd, J=2.4, 8.8 Hz, 1H), 7.49 (dt, J=6.0, 8.0 Hz, 1H), 7.38-7.30 (m, 3H), 7.24-7.14 (m, 1H), 5.30 (s, 2H).

Step 3. To a solution of N-(3-chloro-4-((3-fluorobenzyl)oxy)phenyl)-7-fluoro-6-nitroquinazolin-4-amine (3.00 g, 6.78 mmol) in dimethyl formamide (30.0 mL) was added potassium acetate (3.32 g, 33.9 mmol) at 25° C., the mixture was stirred at 100° C. for 5 h. The reaction mixture was poured into water (100 mL) and stirred for 10 min and filtered, the filter cake was washed with water (10.0 mL) and concentrated in vacuum to give a residue. The residue was poured into ethyl acetate (40.0 mL) and stirred, filtered, the filter cake was concentrated in vacuum to give 4-((3-chloro-4-((3-fluorobenzyl)oxy)phenyl)amino)-6-nitroquinazolin-7-ol (2.30 g, 5.22 mmol, 77% yield) as a yellow solid. m/z ES+ $[M+H]^+$ 441.1; $^1$H NMR (400 MHz, DMSO-$d_6$) δ=10.04 (br d, J=2.4 Hz, 1H), 9.17 (s, 1H), 8.51 (s, 1H), 8.01-7.93 (m, 2H), 7.70 (dd, J=2.0, 8.8 Hz, 1H), 7.52-7.45 (m, 1H), 7.33 (br d, J=7.2 Hz, 2H), 7.27 (d, J=9.0 Hz, 1H), 7.21-7.16 (m, 2H), 5.26 (s, 2H).

Step 4. To a solution of 4-((3-chloro-4-((3-fluorobenzyl)oxy)phenyl)amino)-6-nitroquinazolin-7-ol (1.00 g, 2.27 mmol) and pyridine (897 mg, 11.3 mmol, 915 uL) in dichloromethane (10.0 mL) was added trifluoro mesylate anhydride (1.28 g, 4.54 mmol, 748 uL) dropwise at 0° C., the mixture was stirred at 25° C. for 1 h. The reaction mixture was poured into ice water (100 mL) and stirred. The aqueous phase was extracted with ethyl acetate (3×40.0 mL). The combined organic phase was washed with brine (50.0 mL), dried over anhydrous sodium sulfate, filtered and concentrated in vacuum to give a residue. The residue was purified by silica gel chromatography (Petroleum ether/Ethyl acetate=5/1) to give 4-((3-chloro-4-((3-fluorobenzyl)oxy)phenyl)amino)-6-nitroquinazolin-7-yltrifluoromethanesulfonate (1.00 g, 1.75 mmol, 77% yield) as a yellow solid. m/z ES+ $[M+H]^+$ 573.1.

Step 5. To a solution of 4-((3-chloro-4-((3-fluorobenzyl)oxy)phenyl)amino)-6-nitroquinazolin-7-yltrifluoromethanesulfonate (700 mg, 1.22 mmol), tert-butyl 6-ethynyl-3-azabicyclo[3.1.0]hexane-3-carboxylate (252 mg, 1.22 mmol) and triethylamine (5.08 g, 50.0 mmol, 6.99 mL) in dimethyl formamide (5.00 mL) was added cuprous iodide (46.4 mg, 244 umol) and palladium tetraphenyl phosphate (140 mg, 122 umolq) at 15° C. under nitrogen atmosphere. The mixture was stirred at 15° C. for 1 h. The reaction mixture was poured into water (100 mL). The aqueous phase was extracted with ethyl acetate (3×40.0 mL). The combined organic phase was washed with brine (40.0 mL), dried over anhydrous sodium sulfate, filtered and concentrated in vacuum to give a residue. The residue was purified by silica gel chromatography (Petroleum ether/Ethyl acetate=6/1, 2/1) to afford (1R,5S,6s)-tert-butyl 6-((4-((3-chloro-4-((3-fluorobenzyl)oxy)phenyl)amino)-6-nitroquinazolin-7-yl)ethynyl)-3-azabicyclo[3.1.0]hexane-3-carboxylate (300 mg, 476 umol, 39% yield) as a yellow solid. $^1$H NMR (400 MHz, DMSO-$d_6$) δ 10.34 (s, 1H), 9.42 (s, 1H), 8.70 (s, 1H), 8.00 (d, J=2.4 Hz, 1H), 7.93 (s, 1H), 7.72 (dd, J=2.4, 9.0 Hz, 1H), 7.67-7.62 (m, 1H), 7.58-7.53 (m, 1H), 7.52-7.44 (m, 1H), 7.38-7.28 (m, 3H), 7.24-7.14 (m, 1H), 5.27 (s, 2H), 3.57 (br d, J=11.0 Hz, 2H), 3.43-3.36 (m, 2H), 2.11 (br s, 2H), 1.49 (t, J=3.2 Hz, 1H), 1.40 (s, 9H).

Step 6. To a solution of tert-butyl (1R,5S,6s)-tert-butyl 6-((4-((3-chloro-4-((3-fluorobenzyl)oxy)phenyl)amino)-6-nitro quinazolin-7-yl)ethynyl)-3-azabicyclo[3.1.0]hexane-3-carboxylate (450 mg, 714 umol) in ethyl acetate (4.00 mL) was added hydrochloric acid (4 M, 8.00 mL), the mixture was stirred at 25° C. for 0.5 h. The reaction mixture was concentrated to give a residue. The crude product was triturated with ethyl acetate (20.0 mL) at 10 min, filtered, the filter cake was washed with ethyl acetate (2.00 mL) and concentrated in vaccum to give 7-((1R,5S,6s)-3-azabicyclo[3.1]hexan-6-ylethynyl)-N-(3-chloro-4-((3-fluorobenzyl)oxy)phenyl)-6-nitroquinazolin-4-amine (300 mg, 566 umol, 79% yield) as a yellow solid. $^1$H NMR (400 MHz, DMSO-$d_6$) δ 10.87-10.62 (m, 1H), 9.51 (s, 1H), 9.45-9.29 (m, 1H), 9.10 (dt, J=3.2, 6.4 Hz, 1H), 8.78 (s, 1H), 8.06-7.85 (m, 2H), 7.71 (dd, J=2.4, 8.8 Hz, 1H), 7.48 (dt, J=6.0, 8.0 Hz, 1H), 7.24-7.13 (m, 1H), 5.29 (s, 2H), 3.37-3.32 (m, 2H), 3.17 (s, 1H), 2.32 (br d, J=3.4 Hz, 2H), 2.07 (t, J=3.6 Hz, 1H), 2.00 (s, 1H).

Step 7. To a solution of 7-((1R,5S,6s)-3-azabicyclo[3.1.0]hexan-6-ylethynyl)-N-(3-chloro-4-((3-fluorobenzyl)oxy)phenyl)-6-nitroquinazolin-4-amine (300.00 mg, 566 umol) and paraformaldehyde (85.0 mg, 2.83 mmol, 77.9 uL) in trifluoroethanol (3.00 mL) was added sodium borohydride (42.8 mg, 1.13 mmol, 2.00 eq) at 25° C., the mixture was stirred at 60° C. for 2 h. The reaction mixture was concentrated to give a residue. The residue was poured into methanol (30.0 mL) and concentrated in vaccum to give a yellow solid. The yellow solid was purified by prep-TLC (Ethyl acetate/Methanol=5/1) to afford N-(3-chloro-4-((3-fluorobenzyl)oxy)phenyl)-7-(((1R,5S,6s)-3-methyl-3-azabicyclo[3.1.0]hexan-6-yl)ethynyl)-6-nitroquinazolin-4-amine (150 mg, 275 umol, 48% yield) as a yellow solid. m/z ES+ $[M+H]^+$ 544.1; $^1$H NMR (400 MHz, DMSO-$d_6$) δ 10.34 (s, 1H), 9.42 (s, 1H), 8.70 (s, 1H), 8.00 (d, J=2.4 Hz, 1H), 7.93 (s, 1H), 7.72 (dd, J=2.4, 9.0 Hz, 1H), 7.67-7.62 (m, 1H), 7.58-7.53 (m, 1H), 7.52-7.44 (m, 1H), 7.38-7.28 (m, 3H), 7.24-7.14 (m, 1H), 5.27 (s, 2H), 3.57 (br d, J=11.0 Hz, 2H), 3.43-3.36 (m, 2H), 2.11 (br s, 2H), 1.49 (t, J=3.2 Hz, 1H), 1.40 (s, 9H).

Step 8. A mixture of N-(3-chloro-4-((3-fluorobenzyl)oxy)phenyl)-7-(((1R,5S,6s)-3-methyl-3-azabicyclo[3.1.0]hexan-6-yl)ethynyl)-6-nitroquinazolin-4-amine (150 mg, 275 umol), iron powder (46.2 mg, 827 umol) and ammonium chloride (73.7 mg, 1.38 mmol) in methanol (2.00 mL) and water (1.00 mL) was stirred at 80° C. for 1 h. The reaction mixture was poured into methanol (50.0 mL) and stirred for 10 min, filtered. The filtrate was concentrate to give a residue. The residue was poured into water (80.0 mL) and the aqueous phase was extracted with ethyl acetate (3×40.0 mL). The combined organic phase was washed with brine (60.0 mL), dried over anhydrous sodium sulfate, filtered and concentrated in vacuum to give $N^4$-(3-chloro-4-((3-fluorobenzyl)oxy)phenyl)-7-(((1R,5S,6s)-3-methyl-3-azabicyclo[3.1.0]hexan-6-yl)ethynyl)-quinazoline-4,6-diamine (90.0 mg, 175 umol, 63% yield) as a yellow solid. m/z ES+ $[M+H]^+$ 514.2;

Step 9. To a solution of $N^4$-(3-chloro-4-((3-fluorobenzyl)oxy)phenyl)-7-(((1R,5S,6s)-3-methyl-3-azabicyclo[3.1.0]hexan-6-yl)ethynyl)quinazoline-4,6-diamine (20.0 mg, 38.9 umol), acrylic acid (4.21 mg, 58.3 umol, 4.01 uL) and pyridine (12.3 mg, 155 umol, 12.5 uL) in dimethyl formamide (1.00 mL) was added 1-(3-dimethylaminopropyl)-3-ethylcarbodiimide hydrochloride (29.8 mg, 155 umol) at 15° C., the mixture was stirred at 15° C. for 1 h. The reaction mixture was filtered to give a filtrate. The filtrate was purified by prep-HPLC (column: Waters Xbridge 150*25 5 u; mobile phase: [water (10 mM NH4HCO3)-acetonitrile]; B %: 50%-80%, 10 min) to afford N-(4-((3-chloro-4-((3-fluorobenzyl)oxy)phenyl)amino)-7-(((1R,5S,6s)-3-methyl-3-azabicyclo[3.1.0]-hexan-6-yl)ethynyl)quinazolin-6-yl) acrylamide (1.78 mg, 3.13 umol, 8.0% yield) as a yellow solid. m/z ES+ $[M+H]^+$ 568.3; $^1$H NMR (400 MHz, $CDCl_3$) δ 9.10 (s, 1H), 8.68 (s, 1H), 8.35 (s, 1H), 7.90 (s, 2H), 7.69 (s, 1H), 7.54 (dd, J=2.4, 8.8 Hz, 1H), 7.44-7.34 (m, 1H), 7.28-7.21 (m, 2H), 7.08-7.02 (m, 1H), 6.99 (d, J=8.8 Hz, 1H), 6.55-6.45 (m, 1H), 6.41-6.27 (m, 1H), 5.93 (d, J=10.4 Hz, 1H), 5.18 (s, 2H), 3.18 (br d, J=9.4 Hz, 2H), 2.43 (br d, J=8.8 Hz, 2H), 2.37 (s, 3H), 2.11 (br s, 1H), 1.96 (br s, 2H).

Example 71. Synthesis of Compound No. 77 N-(4-((3-chloro-2-fluorophenyl)amino)-7-((1-methylpyrrolidin-3-yl)ethynyl)quinazolin-6-yl)acrylamide

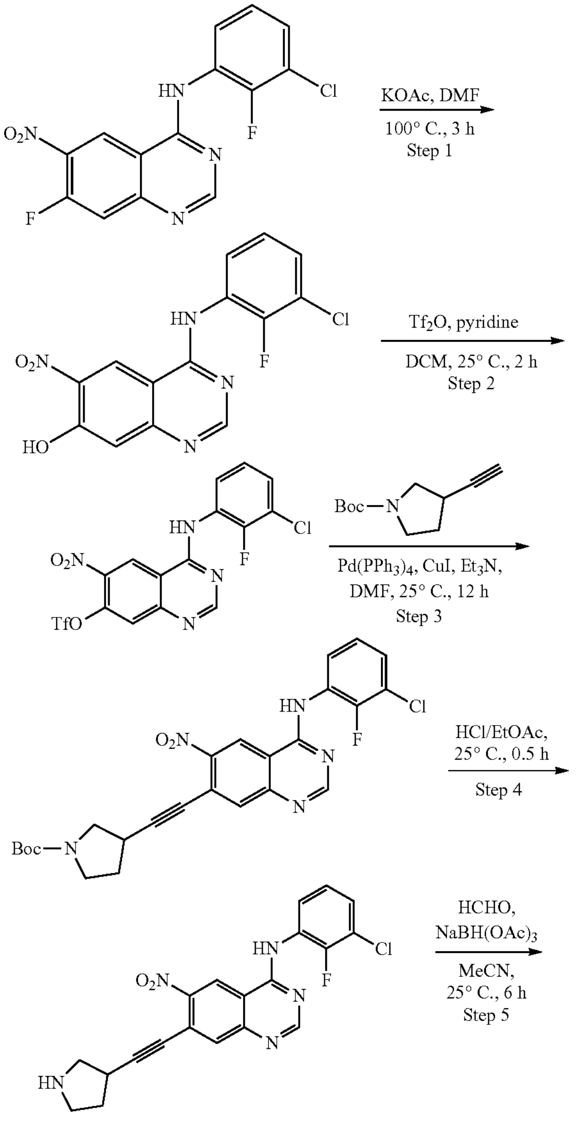

-continued

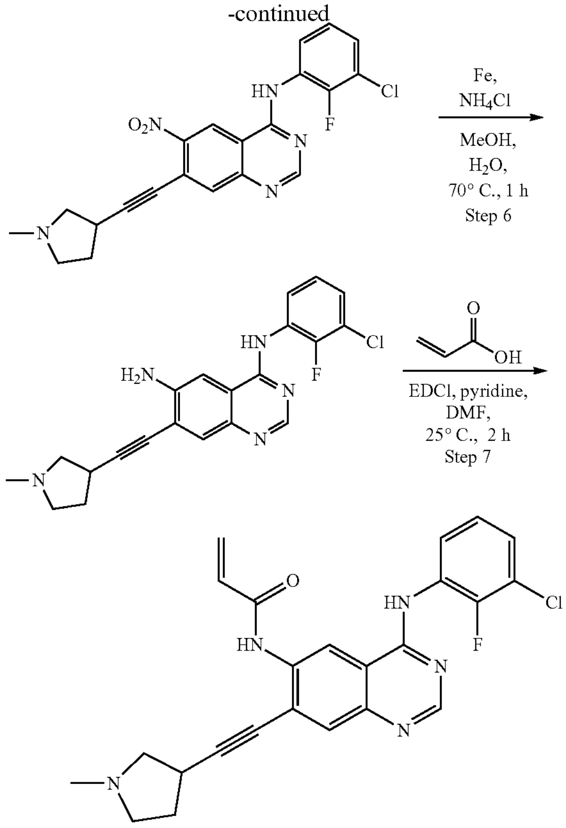

Step 1. A reaction mixture of N-(3-chloro-2-fluorophenyl)-7-fluoro-6-nitroquinazolin-4-amine (5.90 g, 17.5 mmol) and potassium acetate (8.60 g, 87.6 mmol) in dimethyl formamide (30.0 mL) was stirred for 3 h at 100° C. The mixture was concentrated under vacuum to give a residue. The residue was washed with water (3×20.0 mL) and dried under reduced pressure to give 4-((3-chloro-2-fluorophenyl) amino)-6-nitroquinazolin-7-ol (3.50 g, 10.5 mmol, 60% yield) as a light brown solid. m/z ES+ $[M+H]^+$ 335.1;

Step 2. A reaction mixture of 4-((3-chloro-2-fluorophenyl)amino)-6-nitroquinazolin-7-ol (3.50 g, 10.5 mmol), trifluoromethanesulfonic anhydride (5.90 g, 20.9 mmol, 3.45 mL) and pyridine (4.14 g, 52.3 mmol, 4.22 mL) in dichloromethane (50.0 mL) was stirred for 12 h at 25° C. The mixture was concentrated under vacuum to give a residue. The residue was purified by flash chromatography [silica gel column: 40 g, petroleum ether/ethyl acetate=10/1-1/2] to give 4-((3-chloro-2-fluorophenyl)amino)-6-nitroquinazolin-7-yltrifluoromethanesulfonate (1.39 g, 2.98 mmol, 28% yield) as a yellow solid. $^1$H NMR (400 MHz, DMSO-$d_6$) δ 9.39 (s, 1H), 8.77 (s, 1H), 7.63 (br t, J=6.91 Hz, 1H), 7.56-7.49 (m, 2H), 7.40-7.33 (m, 1H).

Step 3. A reaction mixture of 4-((3-chloro-2-fluorophenyl)amino)-6-nitroquinazolin-7-yl trifluoromethanesulfonate (690 mg, 1.48 mmol), tert-butyl 3-ethynylpyrrolidine-1-carboxylate (577 mg, 2.96 mmol), tetrakis (triphenylphosphine)palladium (342 mg, 296 umol), copper iodide (141 mg, 739 umol) and triethylamine (299 mg, 2.96 mmol, 411 uL) in dimethyl formamide (10.0 mL) was stirred for 12 h at 25° C. The mixture was concentrated under vacuum to give a residue. The residue was purified by flash chromatography [silica gel column: 40 g, petroleum ether/ethyl acetate=10/1 to 1/2] to give tert-butyl 3-((4-((3-chloro-2-fluorophenyl)amino)-6-nitroquinazolin-7-yl)ethynyl)pyrrolidine-1-carboxylate (450 mg, 879 umol, 68% yield) as a yellow solid. $^1H$ NMR (400 MHz, $CDCl_3$) δ 8.79 (s, 1H), 8.69 (s, 1H), 8.19 (br t, J=7.40 Hz, 1H), 8.03 (s, 1H), 7.93 (br s, 1H), 7.24-7.19 (m, 1H), 7.15-7.10 (m, 1H), 3.72-3.63 (m, 1H), 3.54 (br s, 1H), 3.48-3.34 (m, 2H), 3.23 (br s, 1H), 2.26-2.16 (m, 1H), 2.14-2.02 (m, 1H), 1.41 (s, 9H).

Step 4. A mixture of tert-butyl 3-((4-((3-chloro-2-fluorophenyl)amino)-6-nitroquinazolin-7-yl)ethynyl)pyrrolidine-1-carboxylate (900 mg, 1.76 mmol) in hydrochloric acid/ethyl acetate (4 M, 8.00 mL) was stirred at 25° C. for 0.5 h. The mixture was concentrated under vacuum to give N-(3-chloro-2-fluorophenyl)-6-nitro-7-(pyrrolidin-3-ylethynyl)quinazolin-4-amine (790 mg, crude, HCl) as a light brown solid, which was used to next step directly. m/z ES+ $[M+H]^+$ 412.2;

Step 5. To a solution of N-(3-chloro-2-fluorophenyl)-6-nitro-7-(pyrrolidin-3-ylethynyl)quinazolin-4-amine (780 mg, 1.74 mmol, HCl) in acetonitrile (20.0 mL) was added formaldehyde (1.41 g, 17.4 mmol, 1.30 mL, 37% purity) and sodium triacetoxyborohydride (1.18 g, 5.57 mmol). The mixture was stirred at 25° C. for 6 h. Sat. ammonium chloride (5.00 mL) was added to the mixture and the mixture was concentrated under reduced pressure to give a residue. The residue was purified by reversed-phase chromatography [Column: 80 g; $CH_3CN/H_2O$ ($NH_3 \cdot H_2O$: 0.1%)=0/1 to 1/1] to give N-(3-chloro-2-fluorophenyl)-7-((1-methylpyrrolidin-3-yl)ethynyl)-6-nitroquinazolin-4-amine (580 mg, 1.36 mmol, 78% yield) as a yellow solid. $^1H$ NMR (400 MHz, DMSO-$d_6$) δ 9.33 (s, 1H), 8.60 (s, 1H), 7.93 (s, 1H), 7.56-7.45 (m, 2H), 7.37-7.27 (m, 1H), 3.30-3.23 (m, 2H) 2.91 (t, J=8.38 Hz, 1H), 2.64-2.57 (m, 1H), 2.57-2.53 (m, 1H), 2.30 (s, 3H), 2.28-2.21 (m, 1H), 1.92 (dq, J=12.41, 6.34 Hz, 1H).

Step 6. A reaction mixture of N-(3-chloro-2-fluorophenyl)-7-((1-methylpyrrolidin-3-yl)ethynyl)-6-nitroquinazolin-4-amine (530 mg, 1.24 mmol), iron power (348 mg, 6.22 mmol) and ammonium chloride (333 mg, 6.22 mmol) in methanol (10.0 mL) and water (4.00 mL) was stirred for 1 h at 70° C. The mixture was filtered and the filtrate was concentrated under vacuum to give a residue. The residue was purified by reversed-phase chromatography [column: 80 g, $CH_3CN/H_2O$ (formic acid: 0.1%)=0/1-1/2] to give $N^4$-(3-chloro-2-fluorophenyl)-7-((1-methylpyrrolidin-3-yl)ethynyl)quinazoline-4,6-diamine (200 mg, 505 umol, 41% yield) as a yellow solid. $^1H$ NMR (400 MHz, DMSO-$d_6$) δ 9.56 (br s, 1H), 8.27 (br s, 1H), 7.62 (br s, 1H), 7.56 (br s, 1H), 7.45 (br d, J=6.60 Hz, 1H), 7.42 (s, 1H), 7.27 (br t, J=7.95 Hz, 1H), 5.66 (br s, 2H), 3.34 (br d, J=7.21 Hz, 1H), 3.00-2.88 (m, 1H), 2.66-2.58 (m, 3H), 2.34 (s, 3H), 2.30-2.22 (m, 1H), 2.06-1.91 (m, 1H).

Step 7. A mixture of $N^4$-(3-chloro-2-fluorophenyl)-7-((1-methylpyrrolidin-3-yl)ethynyl)quinazoline-4,6-diamine (180 mg, 455 umol), acrylic acid (39.3 mg, 546 umol, 37.5 uL), 1-(3-dimethylaminopropyl)-3-ethylcarbodiimide hydrochloride (174 mg, 909 umol) and pyridine (71.9 mg, 909 umol, 73.4 uL) in dimethyl formamide (5.00 mL) was stirred for 2 h at 25° C. The mixture was filtered. The filtrate was purified by prep-HPLC {column: Phenomenex Gemini 150*25 mm*10 um; mobile phase: [water (10 mM $NH_4HCO_3$)-acetonitrile]; B %: 42%-70%, 9 min.} to give N-(4-((3-chloro-2-fluorophenyl)amino)-7-((1-methylpyrrolidin-3-yl)ethynyl)quinazolin-6-yl)acrylamide (80 mg, 176.04 umol, 38.71% yield, 99% purity) as a yellow solid. m/z ES+ $[M+H]^+$ 450.3; $^1H$ NMR (400 MHz, DMSO-$d_6$) δ 10.09 (br s, 1H), 9.80 (br s, 1H), 8.73 (s, 1H), 8.46 (br s, 1H), 7.80 (br s, 1H), 7.48 (br s, 2H), 7.35-7.21 (m, 1H), 6.62 (dd, J=17.07, 10.19 Hz, 1H), 6.34 (dd, J=17.07, 1.81 Hz, 1H), 5.91-5.81 (m, 1H), 3.31-3.24 (m, 2H), 2.88 (t, J=8.32 Hz, 1H), 2.62-2.52 (m, 2H), 2.28 (s, 3H), 2.27-2.21 (m, 1H), 1.99-1.90 (m, 1H).

Example 72. Synthesis of Compound No. 78 N-(4-((3-chloro-2-fluorophenyl)amino)-7-(((1R,5S,6s)-3-methyl-3-azabicyclo[3.1.0]hexan-6-yl)ethynyl)quinazolin-6-yl)acrylamide

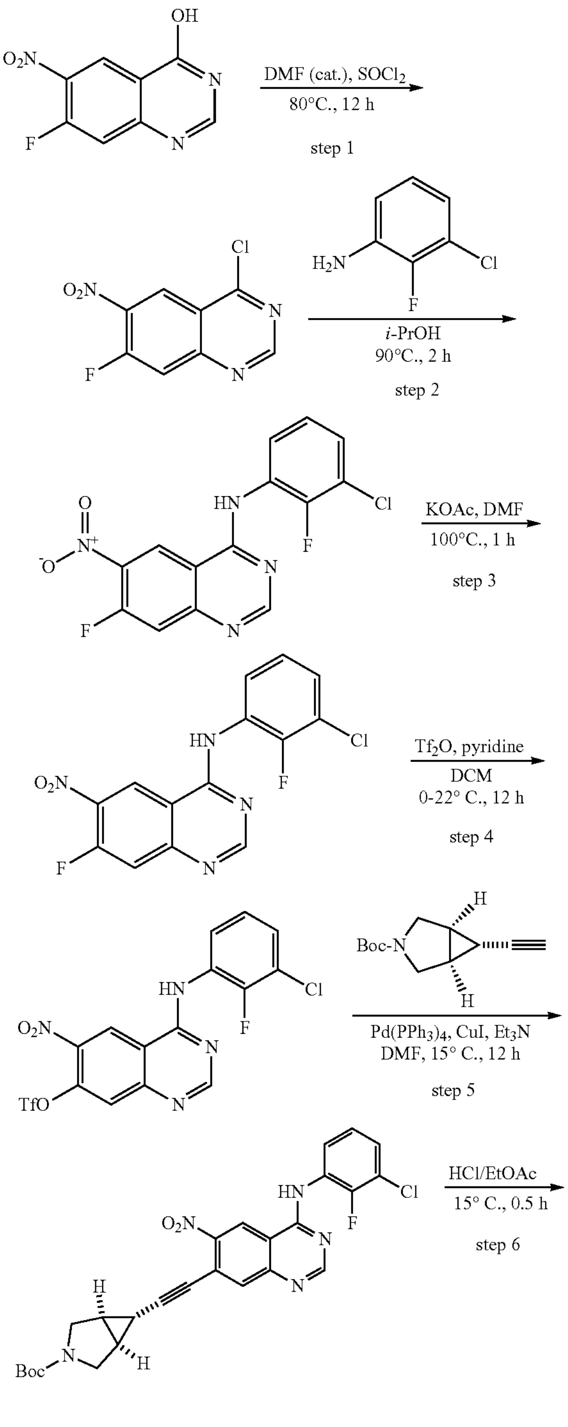

-continued

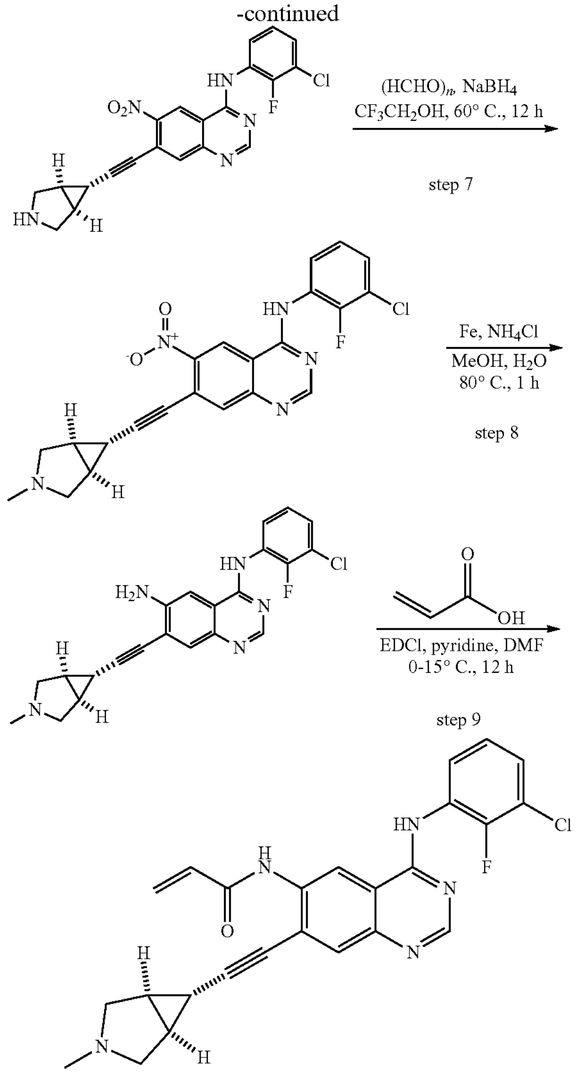

Step 1. To a solution of 7-fluoro-6-nitro-quinazolin-4-ol (5.00 g, 23.9 mmol, 1.00 eq) in thionyl chloride (82.0 g, 689 mmol, 50.0 mL, 28.8 eq) was added dropwise dimethylformamide (175 mg, 2.39 mmol, 184 uL, 0.100 eq) as catalyst. The mixture was heated to 80° C. and stirred for 12 h. The reaction mixture was concentrated to afford 4-chloro-7-fluoro-6-nitro-quinazoline (5.44 g, 23.9 mmol, 100% yield) as a white solid. The product was used in next step directly.

Step 2. To a solution of 4-chloro-7-fluoro-6-nitro-quinazoline (5.44 g, 23.9 mmol, 1.00 eq) in iso-propanol (100 mL) was added 3-chloro-2-fluoro-aniline (3.83 g, 26.3 mmol, 1.10 eq). The mixture was stirred at 90° C. for 2 h. The mixture was concentrated to afford a yellow solid which was triturated with ethyl acetate (50.0 mL). After filtration, the filter cake was washed with ethyl acetate (20.0 mL), dried in vacuum to afford N-(3-chloro-2-fluoro-phenyl)-7-fluoro-6-nitro-quinazolin-4-amine (8.40 g, crude) as a yellow solid. $^1$H NMR (400 MHz, DMSO-$d_6$) δ=12.5 (br s, 1H), 9.7-10.0 (m, 1H), 8.8-8.9 (m, 1H), 7.9-8.1 (m, 1H), 7.6 (td, J=7.46, 1.47 Hz, 1H), 7.5 (br t, J=7.34 Hz, 1H), 7.3-7.4 (m, 1H). MS (ESI) m/z 336.9 $[M+H]^+$ Step 3. To a solution of N-(3-chloro-2-fluorophenyl)-7-fluoro-6-nitroquinazolin-4-amine (8.40 g, 25.0 mmol, 1.00 eq) in dimethylformamide (100 mL) was added potassium acetate (12.2 g, 125 mmol, 5.00 eq) at 15° C. The mixture was stirred at 100° C. for 1 h. The mixture was concentrated to afford a residue. The residue was diluted with water (100 mL). After filtration, the filter cake was washed with water (30.0 mL), dried in vacuum to afford 4-((3-chloro-2-fluorophenyl)amino)-6-nitroquinazolin-7-ol (9.00 g, crude) as a brown solid. $^1$H NMR (400 MHz, DMSO-$d_6$) δ=9.0 (s, 1H), 8.3 (s, 1H), 7.4-7.5 (m, 2H), 7.2-7.3 (m, 1H), 7.0-7.1 (m, 1H). MS (ESI) m/z 335.2 $[M+H]^+$ Step 4. To a solution of 4-((3-chloro-2-fluorophenyl)amino)-6-nitroquinazolin-7-ol (9.00 g, 26.9 mmol, 1.00 eq) and pyridine (10.6 g, 134 mmol, 10.9 mL, 5.00 eq) in dichloromethane (200 mL) was added trifluoromethanesulfonic anhydride (15.2 g, 53.8 mmol, 8.87 mL, 2.00 eq) at 0° C. The mixture was stirred at 20° C. for 12 h. The mixture was concentrated to afford a residue. The residue was purified by silica gel chromatography (petroleum ether/ethyl acetate=1:1-0:1) to afford 4-((3-chloro-2-fluorophenyl)amino)-6-nitroquinazolin-7-yl trifluoromethanesulfonate (4.00 g, 7.97 mmol, 30% yield, 93% purity) as a yellow solid. $^1$H NMR (400 MHz, DMSO-$d_6$) δ=10.9 (br s, 1H), 9.7 (br s, 1H), 8.7 (br d, J=9.41 Hz, 1H), 8.1 (br s, 1H), 7.5-7.6 (m, 2H), 7.3-7.4 (m, 1H). MS (ESI) m/z 467.2 $[M+H]^+$ Step 5. To a solution of (1R,5S,6s)-tert-butyl 6-ethynyl-3-azabicyclo[3.1.0]hexane-3-carboxylate (244 mg, 1.18 mmol, 1.10 eq), 4-((3-chloro-2-fluorophenyl)amino)-6-nitroquinazolin-7-yl trifluoromethanesulfonate (500 mg, 1.07 mmol, 1.00 eq), copper iodide (40.8 mg, 214 umol, 0.200 eq) and triethylamine (3.63 g, 35.9 mmol, 4.99 mL, 33.5 eq) in dimethylformamide (5.00 mL) was added tetrakis[triphenylphosphine]palladium(0) (124 mg, 107 umol, 0.100 eq) at 15° C. The mixture was stirred at 15° C. for 12 h. The reaction was concentrated to afford a residue. The residue was triturated with ethyl acetate (5.00 mL). After filtration, the filter cake was dried in vacuum to afford crude product. The crude product was purified by silica gel chromatography (petroleum ether:ethyl acetate=1:1-0:1) to afford (1R,5S,6s)-tert-butyl 6-((4-((3-chloro-2-fluorophenyl)amino)-6-nitroquinazolin-7-yl)ethynyl)-3-azabicyclo[3.1.0]hexane-3-carboxylate (300 mg, 573 umol, 54% yield) as a yellow solid. $^1$H NMR (400 MHz, DMSO-$d_6$) δ=10.6 (s, 1H), 9.4 (s, 1H), 8.6 (s, 1H), 8.0 (s, 1H), 7.5-7.6 (m, 2H), 7.3 (br t, J=8.07 Hz, 1H), 3.6 (br d, J=10.88 Hz, 2H), 3.3-3.4 (m, 2H), 2.1 (br s, 2H), 1.5 (br s, 1H), 1.4 (s, 9H). MS (ESI) m/z 524.4 $[M+H]^+$ Step 6. A mixture of (1R,5S,6s)-tert-butyl 6-((4-((3-chloro-2-fluorophenyl)amino)-6-nitro quinazol in-7-yl) ethynyl)-3-azabicyclo[3.1.0]hexane-3-carb oxy late (300 mg, 573 umol, 1.00 eq) in 4 M hydrochloride/ethyl acetate (3.00 mL) was stirred at 15° C. for 0.5 h. The residue was concentrated to afford product as a hydrochloride which was freed with saturated sodium carbonate (5.00 mL) and extracted with ethyl acetate (30.0 mL). The organic layer was washed with water (10.0 mL), dried over anhydrous sodium sulfate, filtered and concentrated to afford 7-((1R,5S,6s)-3-azabicyclo[3.1.0]hexan-6-ylethynyl)-N-(3-chloro-2-fluorophenyl)-6-nitroquinazolin-4-amine (240 mg, 566 umol, 99% yield) as a yellow solid. $^1$H NMR (400 MHz, DMSO-$d_6$) δ=9.3 (s, 1H), 8.6 (s, 1H), 7.9 (s, 1H), 7.4-7.5 (m, 2H), 7.3 (t, J=7.89 Hz, 1H), 3.0 (d, J=11.62 Hz, 2H), 2.7 (br d, J=11.25 Hz, 2H), 1.9 (br s, 2H), 1.6 (t, J=3.24 Hz, 1H). MS (ESI) m/z 424.1 $[M+H]^+$ Step 7. To a solution of paraformaldehyde (70.8 mg, 2.36 mmol, 65.0 uL, 5.00 eq) and 7-((1R,5S,6s)-3-azabicyclo[3.1.0]hexan-6-ylethynyl)-N-(3-chloro-2-fluorophenyl)-6-nitroquinazolin-4-amine (200 mg, 472 umol, 1.00 eq) in trifluoroethanol (10.0 mL) was added sodium borohydride (35.7 mg, 944 umol, 2.00 eq) at 60° C. The mixture was stirred at 60° C. for 12 h. The mixture was concentrated to afford a residue. The residue was diluted with saturated sodium carbonate (1.00 mL) and water (5.00 mL), extracted with ethyl acetate (3×20.0 mL). The combined organic layers were washed with water (20.0 mL), dried over anhydrous sodium sulfate, filtered and the filtrate was concentrated to afford N-(3-chloro-2-fluorophenyl)-7-(((1R,5S,6s)-3-methyl-3-azabicyclo[3.1.0]hexan-6-yl)ethynyl)-6-nitroquinazolin-4-amine (270 mg, crude) as a yellow solid. $^1$H NMR (400 MHz, DMSO-$d_6$) δ=9.1 (br s, 1H), 8.2 (br s, 1H), 7.5-7.7 (m, 2H), 7.1-7.4 (m, 3H), 3.0 (br d, J=8.80 Hz, 2H), 2.3 (br d, J=8.56 Hz, 2H), 2.2 (br s, 3H), 1.9-2.0 (m, 3H). MS (ESI) m/z 438.3 $[M+H]^+$ Step 8. To a solution of N-(3-chloro-2-fluorophenyl)-7-(((1R,5S,6s)-3-methyl-3-azabicyclo[3.1.0]hexan-6-yl)ethynyl)-6-nitroquinazolin-4-amine (270 mg, 617 umol, 1.00 eq) and ammonium chloride (371 mg, 6.93 mmol, 242 uL, 11.3 eq) in methanol (13.0 mL) and water (13.0 mL) was added powder iron (301 mg, 5.40 mmol, 8.75 eq) at 20° C. The mixture was heated to 80° C. and stirred at 80° C. for 1 h. The combined mixture was concentrated to afford a residue. The residue was diluted with water (10.0 mL), saturated sodium carbonate (5.00 mL) and the mixture was stirred for 30 min. After filtration, the filter cake was washed with water (20.0 mL) and the filtrate was extracted with ethyl acetate (2×30.0 mL) to recover the product. The combined organic layer and the filter cake were concentrated to afford crude product. The crude product was purified by silica gel chromatography (petroleum ether/ethyl acetate=1/1-0/1, then ethyl acetate/methanol=5/1) to afford $N^4$-(3-chloro-2-fluorophenyl)-7-4(1R,5S,6s)-3-methyl-3-azabicyclo[3.1.0]hexan-6-yl)ethynyl)quinazoline-4,6-diamine (80.0 mg, 196 umol, 32% yield) as a brown oil. MS (ESI) m/z 408.1 [M+H]+

Step 9. To a solution of $N^4$-(3-chloro-2-fluorophenyl)-7-4(1R,5S,6s)-3-methyl-3-azabicyclo[3.1.0]hexan-6-yl) ethynyl)quinazoline-4,6-diamine (70.0 mg, 172 umol, 1.00 eq) and pyridine (0.500 M, 1.37 mL, 4.00 eq) in dimethylformamide (2.00 mL) was added 1-(3-dimethylaminopropyl)-3-ethylcarbodiimide hydrochloride (98.7 mg, 515 umol, 3.00 eq) and acrylic acid (0.500 M, 515 uL, 1.50 eq) at 0° C. The mixture was stirred at 25° C. for 5 h. The mixture was purified by prep-HPLC (column: Phenomenex Synergi C18 150*25*10 um; mobile phase: [water (0.225% formic acid)-acetonitrile]; B %: 10%-40%, 9 min) and lyophilized to afford N-(4-((3-chloro-2-fluorophenyl)amino)-7-(((1R,5S,6s)-3-methyl-3-azabicyclo[3.1.0]hexan-6-yl)ethynyl) quinazolin-6-yl)acrylamide (14.64 mg, 28.0 umol, 16% yield, 97% purity, formic acid) as a orange solid. MS (ESI) m/z 462.3 $[M+H]^+$; $^1$H NMR (400 MHz, DMSO-$d_6$) δ=10.1 (br s, 1H), 9.8 (br s, 1H), 8.7 (s, 1H), 8.5 (br s, 1H), 8.2 (s, 1H), 7.8 (br s, 1H), 7.5 (br s, 2H), 7.3 (br t, J=7.8 Hz, 1H), 6.6 (dd, J=17.2, 10.2 Hz, 1H), 6.3 (dd, J=17.2, 1.6 Hz, 1H), 5.8 (dd, J=10.4, 1.6 Hz, 1H), 3.0 (d, J=9.2 Hz, 2H), 2.3 (br d, J=9.2 Hz, 2H), 2.2 (s, 3H), 2.0-1.9 (m, 2H), 1.9-1.8 (m, 1H).

Example 73. Synthesis of Compound No. 79 N-(4-((3-chloro-4-(pyridin-2-ylmethoxy)phenyl)amino)-7-(((1R,5S,6r)-3-methyl-3-azabicyclo[3.1.0]hexan-6-yl)ethynyl)quinazolin-6-yl)acrylamide

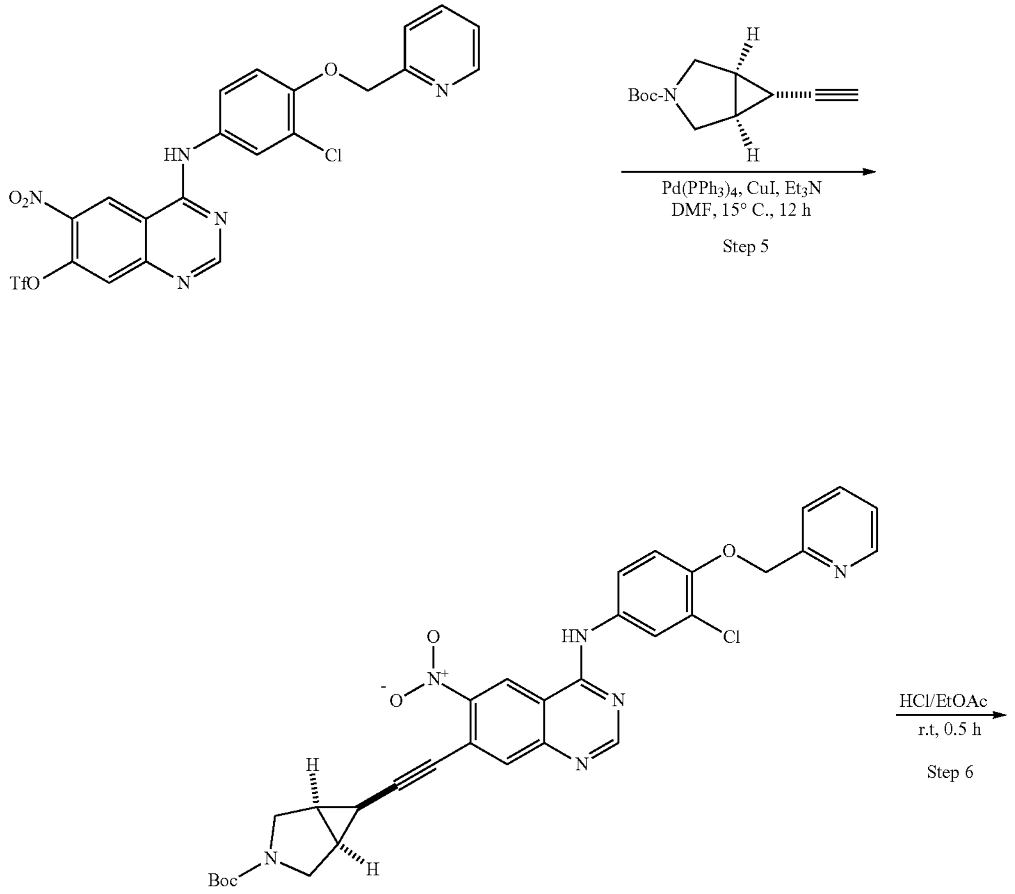

-continued
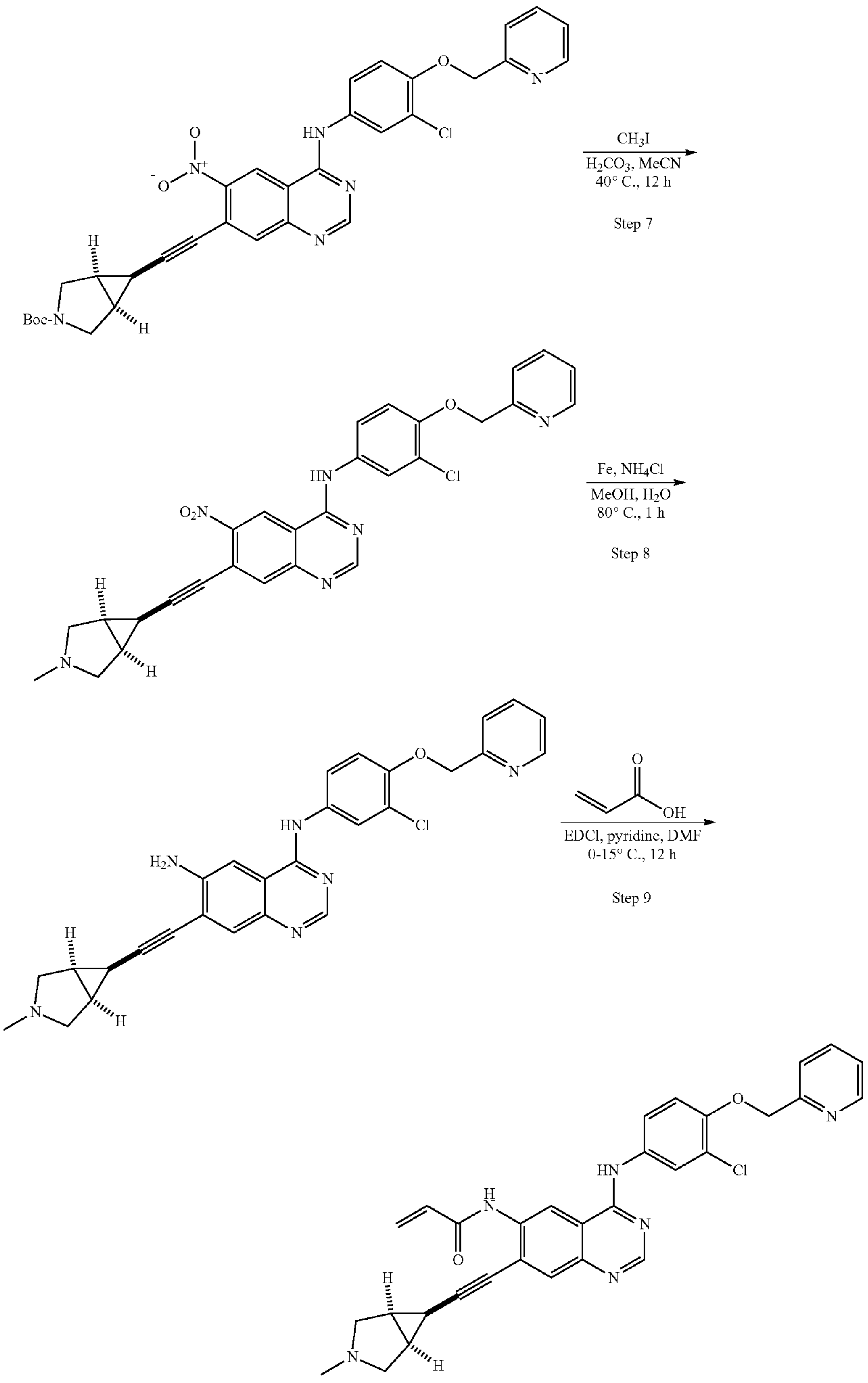

-continued

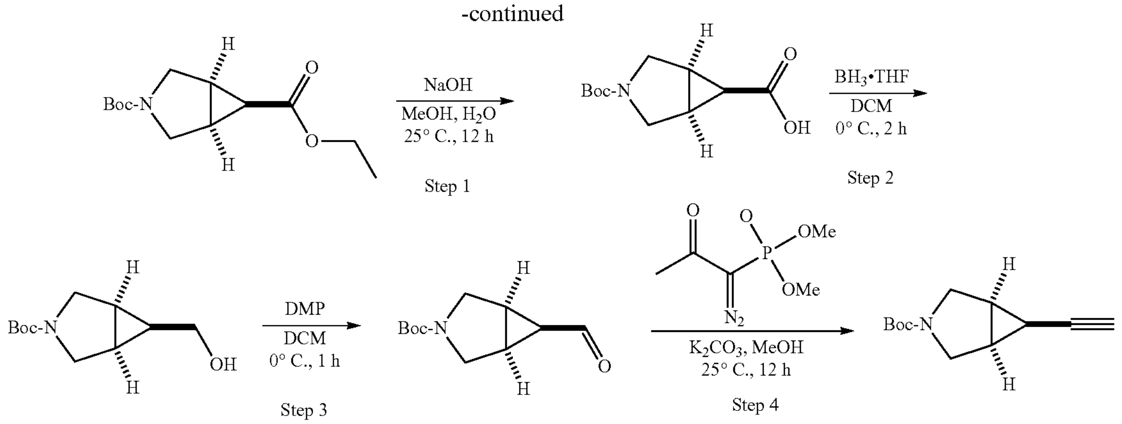

Step 1. The mixture of (1R,5S,6s)-3-tert-butyl 6-ethyl 3-azabicyclo[3.1.0]hexane-3,6-dicarboxylate (1.90 g, 7.44 mmol, 1.00 eq) in methanol (5.00 mL) and water (5.00 mL) was added sodium hydroxide (893 mg, 22.3 mmol, 3.00 eq) at 25° C. The mixture was stirred at 25° C. for 12 h. The mixture was concentrated to remove methanol, diluted with water (30.0 mL), acidified with conc. hydrochloric acid to PH=4-5. The mixture was extracted with ethyl acetate (3x30.0 mL). The combined organic layers were washed with water (30.0 mL), dried over anhydrous sodium sulfate, filtered and the filtrate was concentrated to afford (1R,5S,6s)-3-(tert-butoxycarbonyl)-3-azabicyclo[3.1.0]hexane-6-carboxylic acid (1.50 g, 6.60 mmol, 88% yield) as a white solid. $^1$H NMR (400 MHz, Chloroform-d) δ=3.7 (d, J=11.37 Hz, 2H), 3.5 (br d, J=11.62 Hz, 2H), 2.0 (br s, 1H), 2.0 (d, J=2.93 Hz, 1H), 1.7-1.8 (m, 1H), 1.4 (s, 9H).

Step 2. To a solution of (1R,5S,6s)-3-(tert-butoxycarbonyl)-3-azabicyclo[3.1.0]hexane-6-carboxylic acid (1.50 g, 5.94 mmol, 1.00 eq) in tetrahydrofuran (20.0 mL) was added dropwise a solution of borane in tetrahydrofuran (1.00 M, 11.9 mL, 2.00 eq) at 0° C. The mixture was stirred at 0° C. for 2 h. The reaction was quenched with methanol (5.00 mL) and concentrated to afford a residue. The residue was diluted with saturated sodium carbonate (10.0 mL), extracted with ethyl acetate (2x20.0 mL). The combined organic layers were washed with water, dried over anhydrous sodium sulfate, filtered and the filtrate was concentrated to afford (1R,5S,6s)-tert-butyl 6-(hydroxymethyl)-3-azabicyclo[3.1.0]hexane-3-carboxylate (1.20 g, 5.63 mmol, 95% yield) as a colorless oil. $^1$H NMR (400 MHz, Chloroform-d) δ=3.6-3.7 (m, 2H), 3.5-3.6 (m, 3H), 3.4 (t, J=11.00 Hz, 1H), 1.7-1.8 (m, 2H), 1.4 (s, 9H), 1.3 (br s, 1H), 1.2 (quin, J=7.86 Hz, 1H).

Step 3. To a solution of (1R,5S,6s)-tert-butyl 6-(hydroxymethyl)-3-azabicyclo[3.1.0]hexane-3-carboxylate (1.20 g, 5.63 mmol, 1.00 eq) in dichloromethane (30.0 mL) was added dess-martin periodinane (2.63 g, 6.19 mmol, 1.92 mL, 1.10 eq) at 0° C. The mixture was stirred at 0° C. for 1 h. The mixture was diluted with water (5.00 mL) and saturated sodium carbonate (5.00 mL), extracted with dichloromethane (2x20.0 mL). The combined organic layers were washed with water (20.0 mL), dried over anhydrous sodium sulfate, filtered. The filtrate was concentrated to afford a residue. The residue was purified by silica gel chromatography (petroleum ether/ethyl acetate=1/0~4/1) to afford tert-butyl 6-formyl-3-azabicyclo[3.1.0]hexane-3-carboxylate (0.950 g, 4.50 mmol, 80% yield) as a colorless oil. $^1$H NMR (400 MHz, Chloroform-d) δ=9.3 (d, J=6.24 Hz, 1H), 3.8-4.0 (m, 2H), 3.6-3.7 (m, 2H), 2.1-2.2 (m, 2H), 1.7-1.8 (m, 1H), 1.4 (s, 9H).

Step 4. To a solution of (1R,5S,6s)-tert-butyl 6-formyl-3-azabicyclo[3.1.0]hexane-3-carboxylate (0.850 g, 4.02 mmol, 1.00 eq) and potassium carbonate (1.11 g, 8.05 mmol, 2.00 eq) in methanol (20.0 mL) was added dimethyl (1-diazo-2-oxopropyl)phosphonate (0.930 g, 4.83 mmol, 1.20 eq) at 20° C. The mixture was stirred at 20° C. for 12 h. The mixture was filtered and concentrated to give a residue. The residue was purified by silica gel chromatography (petroleum ether/ethyl acetate=5/1) to afford (1R,5S,6r)-tert-butyl 6-ethynyl-3-azabicyclo[3.1.0]hexane-3-carboxylate (0.700 g, 3.38 mmol, 83% yield) as yellow oil. $^1$H NMR (400 MHz, Chloroform-d) 6=3.67 (d, J=11.2 Hz, 1H), 3.62-3.56 (m, 1H), 3.54-3.48 (m, 2H), 1.95 (d, J=2.1 Hz, 1H), 1.83-1.76 (m, 2H), 1.64-1.59 (m, 1H), 1.44 (s, 9H).

Step 5. To a solution of (1R,5S,6r)-tert-butyl 6-ethynyl-3-azabicyclo[3.1.0]hexane-3-carboxylate (223 mg, 1.08 mmol, 1.00 eq), 4-((3-chloro-4-(pyridin-2-ylmethoxy)phenyl)amino)-6-nitroquinazolin-7-yl trifluoro-methanesulfonate (600 mg, 1.08 mmol, 1.00 eq), copper iodide (41.1 mg, 215 umol, 0.200 eq) in triethylamine (5.00 mL) and dimethylformamide (10.0 mL) was added tetrakis[triphenylphosphine]palladium(0) (124 mg, 108 umol, 0.100 eq) at 15° C. The mixture was charged with nitrogen and stirred at 30° C. for 2 h. The mixture was diluted with saturated ammonium chloride (30.0 mL), extracted with ethyl acetate (3x30.0 mL), washed with brine (3x30.0 mL), dried over anhydrous sodium sulfate, filtered and concentrated. The crude product was purified by silica gel chromatography (petroleum ether/ethyl acetate=1/1 to 0/1) to afford (1R,5S,6r)-tert-butyl 6-((4-((3-chloro-4-(pyridin-2-ylmethoxy)phenyl)amino)-6-nitroquinazolin-7-yl)ethynyl)-3-azabicyclo[3.1.0]hexane-3-carboxylate (400 mg, 652 umol, 65% yield) as a yellow solid. $^1$H NMR (400 MHz, DMSO-$d_6$) δ=10.40 (s, 1H), 9.48 (s, 1H), 8.75 (s, 1H), 8.67 (br d, J=4.9 Hz, 1H), 8.08 (d, J=2.4 Hz, 1H), 7.98-7.92 (m, 2H), 7.78 (dd, J=2.6, 8.9 Hz, 1H), 7.65 (d, J=8.1 Hz, 1H), 7.47-7.42 (m, 1H), 7.37 (d, J=9.0 Hz, 1H), 5.37 (s, 2H), 3.62-3.55 (m, 3H), 2.16 (s, 3H), 1.29 (s, 9H).

Step 6. A mixture of (1R,5S,6r)-tert-butyl 6-((4-((3-chloro-4-(pyridin-2-ylmethoxy)phenyl)amino)-6-nitroquinazolin-7-yl)ethynyl)-3-azabicyclo[3.1.0]hexane-3-carboxylate (400 mg, 652 umol, 1.00 eq) in 4 M hydrochloride/ethyl acetate (10.0 mL) was stirred at 20° C. for 0.5 h. The mixture was concentrated to give a residue. The residue was added saturated sodium carbonate (5.00 mL) and filtered, the filter cake was recrystallized from methanol (5.00 mL) to give 7-((1R,5S,6r)-3-azabicyclo[3.1.0]hexan-6-ylethynyl)-N-(3-chloro-4-(pyridin-2-ylmethoxy)phenyl)-6-nitroquinazolin-4-amine (160 mg, crude) as a yellow solid. (Proton NMR looked abnormal) $^1$H NMR (400 MHz, DMSO-$d_6$) δ=10.19 (br s, 1H), 9.22 (br s, 1H), 8.67 (br s, 1H), 8.62 (br s, 1H), 8.43 (s, 1H), 8.06 (br s, 1H), 7.95-7.84 (m, 1H), 7.75 (br d, J=7.8 Hz, 1H), 7.60 (br d, J=7.9 Hz, 1H), 7.45-7.30 (m, 2H), 6.22 (s, 1H), 5.32 (br s, 2H), 2.59 (br s, 3H), 2.01-1.89 (m, 3H).

Step 7. To a solution of 7-((1R,5S,6r)-3-azabicyclo[3.1.0]hexan-6-ylethynyl)-N-(3-chloro-4-(pyridin-2-ylmethoxy)phenyl)-6-nitroquinazolin-4-amine (100 mg, 195 umol, 1.00 eq) and potassium carbonate (135 mg, 975 umol, 5.00 eq) in acetonitrile (1.00 mL) was added iodomethane (0.100 M, 3.00 mL, 1.54 eq) at 40° C. The mixture was stirred at 40° C. for 12 h. The mixture was filtered and the filtrate was concentrated to afford N-(3-chloro-4-(pyridin-2-ylmethoxy)phenyl)-7-(((1R,5S,6r)-3-methyl-3-azabicyclo[3.1.0]hexan-6-yl)ethynyl)-6-nitroquinazolin-4-amine (100 mg, crude) as a yellow solid. $^1$H NMR (400 MHz, DMSO-$d_6$) δ=8.6-8.7 (m, 2H), 8.1 (s, 1H), 8.0 (s, 1H), 7.9 (td, J=7.70, 1.71 Hz, 1H), 7.6 (d, J=7.83 Hz, 1H), 7.3-7.4 (m, 2H), 7.1-7.2 (m, 1H), 7.0-7.1 (m, 1H), 6.3 (s, 1H), 5.2 (s, 2H), 3.6 (s, 3H), 2.6-2.6 (m, 4H), 1.9-2.0 (m, 1H), 1.9-1.9 (m, 2H).

Step 8. To a solution of N-(3-chloro-4-(pyridin-2-ylmethoxy)phenyl)-7-(((1R,5S,6r)-3-methyl-3-azabicyclo[3.1.0]hexan-6-yl)ethynyl)-6-nitroquinazolin-4-amine (100 mg, 190 umol, 1.00 eq) and ammonium chloride (114 mg, 2.13 mmol, 74.6 uL, 11.3 eq) in methanol (10.0 mL) and water (10.0 mL) was added powder iron (92.8 mg, 1.66 mmol, 8.75 eq) at 20° C. The mixture was heated to 80° C. and stirred at 80° C. for 1 h. The mixture was concentrated to afford a residue. The residue was diluted with water (10.0 mL), saturated sodium carbonate (5.00 mL), ethyl acetate (30.0 mL). The mixture was extracted with ethyl acetate (2×30.0 mL) and the combined organic layer was washed with water (20.0 mL), dried over anhydrous sodium sulfate, filtered. The filtrate was concentrated to afford $N^4$-(3-chloro-4-(pyridin-2-ylmethoxy)phenyl)-7-(((1R,5S,6r)-3-methyl-3-azabicyclo[3.1.0]hexan-6-yl)ethynyl)quinazoline-4,6-diamine (90.0 mg, crude) as a yellow solid. MS (ESI) m/z 497.3 $[M+H]^+$ Step 9. To a solution of $N^4$-(3-chloro-4-(pyridin-2-ylmethoxy)phenyl)-7-(((1R,5S,6r)-3-methyl-3-azabicyclo[3.1.0]hexan-6-yl)ethynyl)quinazoline-4,6-diamine (90.0 mg, 181 umol, 1.00 eq) and pyridine (0.500 M, 1.09 mL, 3.00 eq) in dimethylformamide (1.80 mL) was added 1-(3-dimethylaminopropyl)-3-ethylcarbodiimide hydrochloride (69.4 mg, 362 umol, 2.00 eq) and acrylic acid (0.500 M in dimethylformamide, 435 uL, 1.20 eq) at 0° C. The mixture was stirred at 15° C. for 12 h. The mixture was purified by prep-HPLC (column: Phenomenex Gemini 150*25 mm*10 um; mobile phase: [water (10 mM $NH_4HCO_3$)-acetonitrile]; B %: 30%-80%, 10 min) to afford crude product. The crude product was purified by prep-TLC (ethyl acetate/ethanol=1:1) to afford crude product. Finally, the crude product was re-purified by prep-HPLC (column: Phenomenex Synergi C18 150*25*10 um; mobile phase: [water (0.225% formic acid)-acetonitrile]; B %: 15%-45%, 9 min) and lyophilized to afford N-(4-((3-chloro-4-(pyridin-2-ylmethoxy)phenyl)amino)-7-(((1R,5S,6r)-3-methyl-3-azabicyclo[3.1.0]hexan-6-yl) ethynyl) quinazolin-6-yl)acrylamide (21.89 mg, 39.3 umol, 22% yield, 99% purity) as an orange solid. (2D NMR didn't match the desired product reasonably and it was difficult to propose the real structure. Something may be happen during the de-Boc stage.) MS (ESI) m/z 551.4 $[M+H]^+$; $^1$H NMR (400 MHz, DMSO-$d_6$) δ=11.3 (br s, 1H), 8.7-8.4 (m, 2H), 8.1 (s, 1H), 8.1 (s, 1H), 8.0 (s, 1H), 7.9 (td, J=7.6, 1.6 Hz, 1H), 7.6 (d, J=7.6 Hz, 1H), 7.4 (dd, J=6.8, 5.2 Hz, 1H), 7.3 (d, J=2.2 Hz, 1H), 7.1 (d, J=8.8 Hz, 1H), 7.1-7.0 (m, 1H), 6.5 (dd, J=16.8, 10.2 Hz, 1H), 6.3 (dd, J=16.8, 2.0 Hz, 1H), 6.1 (s, 1H), 5.8-5.7 (m, 1H), 5.2 (s, 2H), 3.6 (s, 3H), 2.8-2.6 (m, 4H), 2.0-1.9 (m, 1H), 1.9-1.8 (m, 2H).

Example 74. Synthesis of Compound No. 80 N-(7-(3-oxabicyclo[3.1.0]hexan-6-ylethynyl)-4-((3,4-dichloro-2-fluorophenyl)amino)quinazolin-6-yl)acrylamide

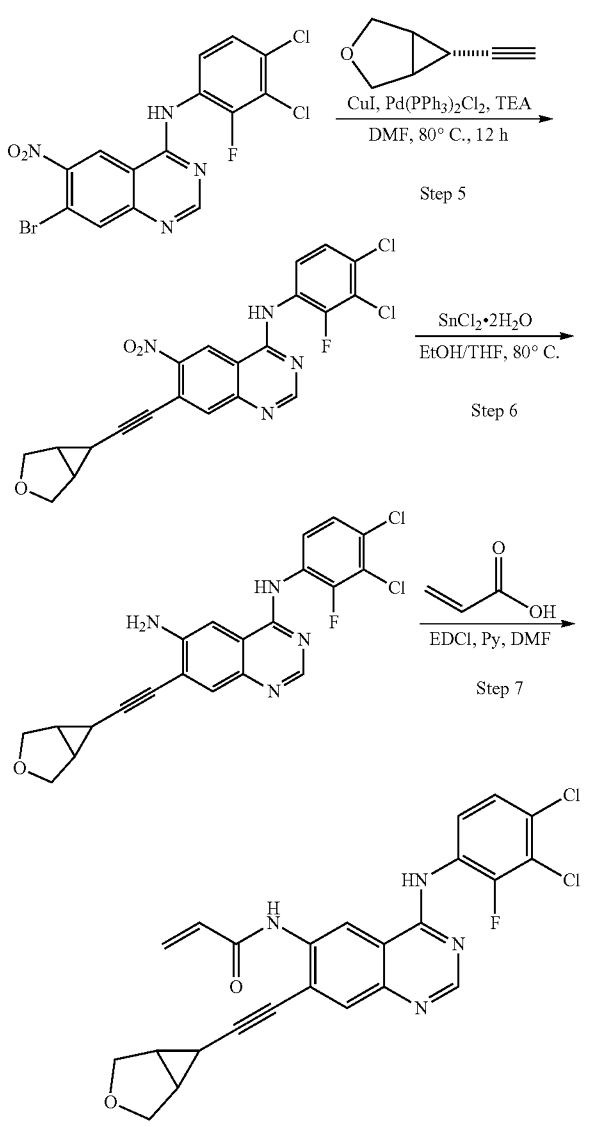

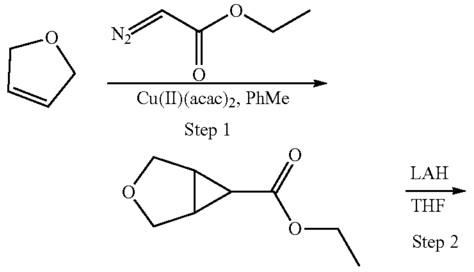

-continued

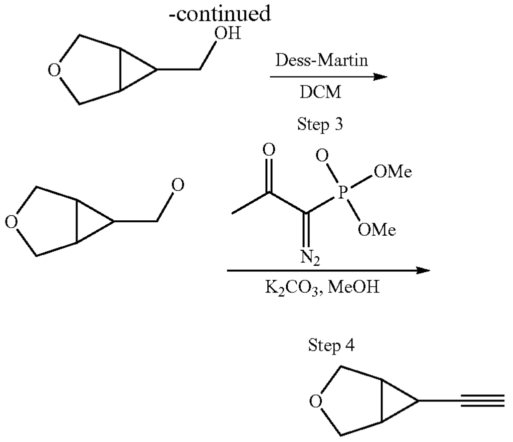

Step 1. To a stirred suspension of 2,5-dihydrofuran (10.0 g, 143 mmol, 10.8 mL, 1.00 eq) and copper(II) acetylacetonate (747 mg, 2.85 mmol, 0.02 eq) in toluene (100 mL) at 90° C. was added ethyl 2-diazoacetate (19.5 g, 171 mmol, 17.9 mL, 1.20 eq) over 0.5 h (color of the solution changed from blue to brown). After complete addition, the reaction was cooled to room temperature (25° C.) and stirred for 1.5 h. The solvent was removed under reduced pressure to give a residue. The residue was purified by column chromatography ($SiO_2$, Petroleum ether/Ethyl acetate=20/1 to 10/1) to give ethyl 3-oxabicyclo[3.1.0]hexane-6-carboxylate (8.00 g, 51.2 mmol, 35.90% yield) as a colorless oil. $^1H$ NMR (400 MHz, $CDCl_3$) δ=4.15 (q, J=7.2 Hz, 2H), 3.95 (d, J=8.8 Hz, 2H), 3.77 (d, J=8.8 Hz, 2H), 2.18 (dd, J=1.0, 1.6 Hz, 2H), 1.62 (t, J=3.2 Hz, 1H), 1.33 (t, J=7.2 Hz, 3H).

Step 2. To a solution of ethyl 3-oxabicyclo[3.1.0]hexane-6-carboxylate (8.00 g, 51.2 mmol, 1.00 eq) in tetrahydrofuran (100 mL) was added lithium aluminum hydride (1.94 g, 51.2 mmol, 1.00 eq) in portions at 0° C. After addition, the mixture was stirred at room temperature (25° C.) for 1 h. The reaction was quenched by slow portionwise addition of 10 g of sodium sulfate decahydrate, stirring was continued for additional 1 h after the vigorous reaction subsided. Sodium sulfate was added and solids were removed by filtration, rinsed with fresh tetrahydrofuran and solvents evaporated. The residue was purified by column chromatography ($SiO_2$, Petroleum ether/Ethyl acetate=10/1 to 2/1) to give 3-oxabicyclo[3.1.0]hexan-6-ylmethanol (3.00 g, 51.31% yield) as a colorless liquid. $^1H$ NMR (400 MHz, $CDCl_3$) δ=3.90 (d, J=8.2 Hz, 2H), 3.72 (d, J=8.2 Hz, 2H), 3.55 (d, J=6.9 Hz, 2H), 1.12 (tt, J=3.5, 7.1 Hz, 1H).

Step 3. To a solution of 3-oxabicyclo[3.1.0]hexan-6-ylmethanol (2.80 g, 24.5 mmol, 1.00 eq) in dichloromethane (200 mL) was added Dess-Martin periodinane (15.6 g, 36.8 mmol, 1.50 eq) in portions at 25° C. After addition, the mixture was stirred at room temperature (25° C.) for 4 h. The reaction mixture was filtered and concentrated under reduced pressure to give a residue. The residue was purified by column chromatography ($SiO_2$, Petroleum ether/Ethyl acetate=10/1 to 2/1) to give 3-oxabicyclo[3.1.0]hexane-6-carbaldehyde (2.10 g, 18.7 mmol, 76.35% yield) as a colorless liquid. 41 NMR (400 MHz, $CDCl_3$) δ=9.43 (d, J=4.4 Hz, 1H), 3.98 (d, J=8.8 Hz, 2H), 3.82 (d, J=8.8 Hz, 2H), 2.32 (dt, J=1.2, 2.2 Hz, 2H), 1.96 (q, J=3.2 Hz, 1H).

Step 4. To a solution of 3-oxabicyclo[3.1.0]hexane-6-carbaldehyde (0.300 g, 2.68 mmol, 1.00 eq) in methanol (5.00 mL) was added potassium carbonate (554 mg, 4.01 mmol, 1.50 eq) and dimethyl (1-diazo-2-oxopropyl)phosphonate (616 mg, 3.21 mmol, 1.20 eq) in portions at 25° C. After addition, the mixture was stirred at room temperature (25° C.) for 2 h. The reaction mixture was diluted with water (20 mL) and extracted with petroleum ether (2×20 mL). The combined organic layers were washed with brine (20 mL), dried over sodium sulfate, filtered and concentrated under reduced pressure to give the crude 6-ethynyl-3-oxabicyclo[3.1.0]hexane (50.0 mg, 462.37 umol, 17.28% yield) as a colorless liquid. 1H NMR (400 MHz, $CDCl_3$) δ=3.91 (d, J=8.8 Hz, 2H), 3.69 (d, J=8.8 Hz, 2H), 1.97-1.92 (m, 2H), 1.90 (d, J=2.0 Hz, 1H), 1.30-1.28 (m, 1H).

Step 5. To a solution of 7-bromo-N-(3,4-dichloro-2-fluorophenyl)-6-nitroquinazolin-4-amine (0.500 g, 1.16 mmol, 1.00 eq) and 6-ethynyl-3-oxabicyclo[3.1.0]hexane (375 mg, 3.47 mmol, 3.00 eq) in dimethyformamide (5.00 mL) was added cuprous iodide (44.1 mg, 231 umol, 0.20 eq), bis(triphenylphosphine)palladium(ii) dichloride (81.2 mg, 115 umol, 0.10 eq) and triethylamine (234 mg, 2.31 mmol, 322.17 uL, 2.00 eq) in portions at 25° C. After addition, the mixture was stirred at 80° C. for 12 h. The reaction mixture was diluted with water (30 mL) and extracted with ethyl acetate (2×30 mL). The combined organic layers were washed with brine (30 mL), dried over sodium sulfate, filtered and concentrated under reduced pressure to give a residue. The residue was purified by prep-HPLC (column: Phenomenex Synergi C18 150*30 mm*4 um; mobile phase: [water (0.225% formic acid)-acetonitrile]; B %: 50%-80%, 10.5 min) to give 7-(3-oxabicyclo[3.1.0]hexan-6-ylethynyl)-N-(3,4-dichloro-2-fluorophenyl)-6-nitroquinazolin-4-amine (0.3 g, 261.29 umol, 22.58% yield, 40% purity) as a yellow oil. MS (ESI) m/z 458.9 $[M+H]^+$ Step 6. To a stirring solution of 7-(3-oxabicyclo[3.1.0]hexan-6-ylethynyl)-N-(3,4-dichloro-2-fluorophenyl)-6-nitroquinazolin-4-amine (0.25 g, 544.36 umol, 1.00 eq) in ethyl alcohol (10 mL) and tetrahydrofuran (10 mL) was added dihydrate tin chloride (614.16 mg, 2.72 mmol, 5.00 eq) in portions at 25° C. The mixture was stirred at 80° C. for 12 h. The reaction mixture was concentrated under reduced pressure to give a residue. The residue was purified by reverse flash to give 7-(3-oxabicyclo[3.1.0]hexan-6-ylethynyl)-$N^4$-(3,4-dichloro-2-fluorophenyl)quinazoline-4,6-diamine (0.08 g, 186.36 umol, 34.24% yield) as a yellow solid. $^1H$ NMR (400 MHz, $CD_3OD$) δ=8.31 (br s, 1H), 7.53 (br t, J=8.2 Hz, 2H), 7.36 (br d, J=8.8 Hz, 1H), 7.30 (br s, 1H), 3.85 (d, J=8.8 Hz, 2H), 3.64 (d, J=8.6 Hz, 2H), 2.08 (br d, J=2.2 Hz, 2H), 1.47 (t, J=3.2 Hz, 1H)

Step 7. To a solution of 7-(3-oxabicyclo[3.1.0]hexan-6-ylethynyl)-$N^4$-(3,4-dichloro-2-fluorophenyl)quinazoline-4,6-diamine (50.0 mg, 116.48 umol, 1.00 eq) and acrylic acid (16.8 mg, 232.95 umol, 15.99 uL, 2.00 eq) in dimethyformamide (2.00 mL) was added 1-(3-dimethylaminopropyl)-3-ethylcarbodiimide hydrochloride (111.64 mg, 582.38 umol, 5.00 eq) and pyridine (46.07 mg, 582.38 umol, 47.01 uL, 5.00 eq) in portions at 25° C. Then the mixture was stirred at 25° C. for 0.5 h. The reaction mixture was diluted with sodium bicarbonate (20 mL) and extracted with ethyl acetate (2×20 mL). The combined organic layers were washed with brine (20 mL), dried over sodium sulfate, filtered and concentrated under reduced pressure to give a residue. The residue was purified by prep-HPLC (column: Phenomenex Synergi C18 150*30 mm*4 um; mobile phase: [water (0.225% formic acid)-acetonitrile]; B %: 35%-65%, 10.5 min) and further purified by prep-HPLC (column: Phenomenex Gemini 150*25 mm*10 um; mobile phase: [water (0.04% $NH_3 \cdot H_2O$+10 mM $NH_4HCO_3$)-acetonitrile]; B %: 50%-80%, 10 min) to give N-(7-(3-oxabicyclo[3.1.0]hexan-6-ylethynyl)-4-((3,4-dichloro-2-fluorophenyl)amino)quinazolin-6-yl)acrylamide (5.5 mg, 11.38 umol, 9.77% yield, 100% purity) as a white solid. m/z ES+ $[M+H]^+$ 483.0; $^1H$ NMR (400 MHz, $CDCl_3$) δ=9.21 (s, 1H), 8.74 (s, 1H), 8.39 (t, J=8.4 Hz, 1H), 8.30 (s, 1H), 7.97 (s, 1H), 7.72 (br s, 1H), 7.36 (dd, J=1.9, 9.0 Hz, 1H), 6.64-6.49 (m, 1H), 6.44-6.28 (m, 1H), 5.95 (d, J=10.3 Hz, 1H), 4.05 (d, J=8.8 Hz, 2H), 3.81 (d, J=8.8 Hz, 2H), 2.18 (d, J=3.2 Hz, 2H), 1.67 (t, J=3.2 Hz, 1H).

Example 75. Synthesis of Compound No. 81 ((R, E)-N-(4-((3-chloro-2-fluorophenyl)amino)-7-((1,3-dimethylpyrrolidin-3-yl)ethynyl)quinazolin-6-yl)-4-morpholinobut-2-enamide)

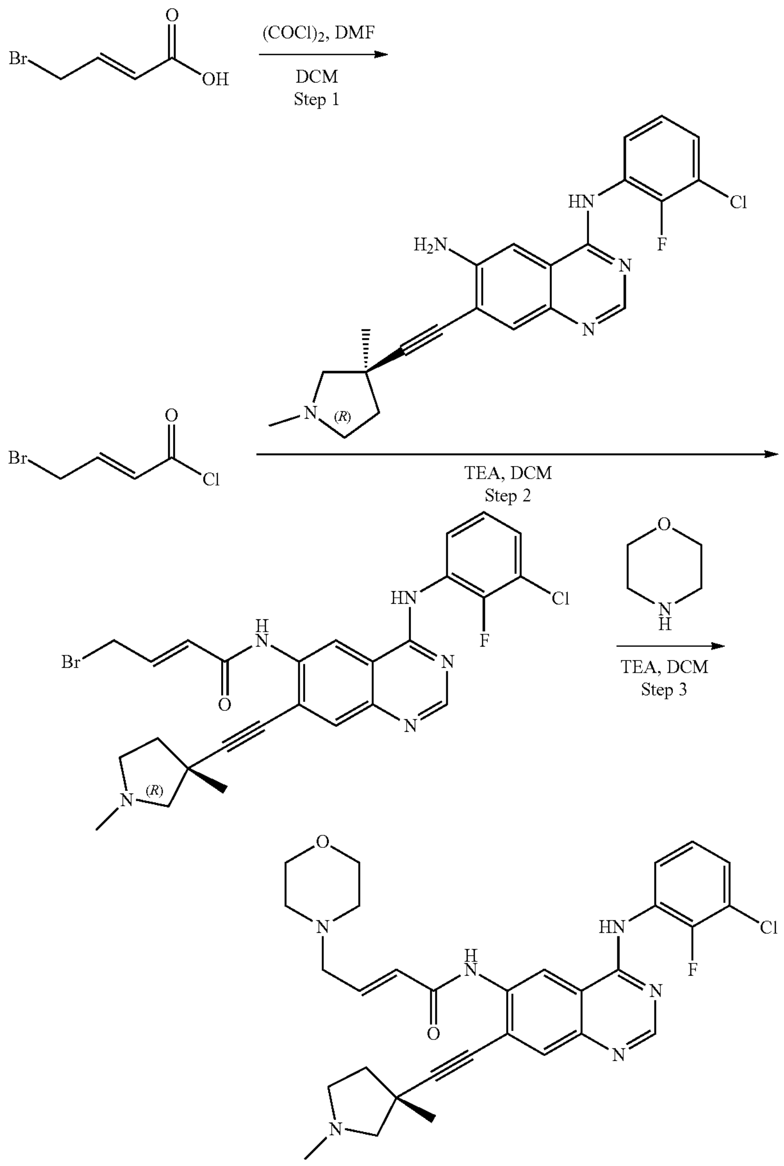

Step 1. To a mixture of (E)-4-bromobut-2-enoic acid (500 mg, 3.03 mmol) in dichloromethane (5.0 mL) and dimethylformamide (11.1 mg, 152 umol) was added oxalyl dichloride (769 mg, 6.06 mmol) at 20° C. under $N_2$. The mixture was stirred at 20° C. for 1 hour. On completion, the reaction mixture was concentrated to give (E)-4-bromobut-2-enoyl chloride (550 mg, 98% yield) as a yellow oil.

Step 2. To a mixture of N4-(3-chloro-2-fluoro-phenyl)-7-[2-[(3R)-1,3-dimethylpyrrolidin-3-yl]ethynyl]quinazoline-4,6-diamine (40.0 mg, 98 umol) in dichloromethane (1.0 mL) and triethylamine (29.6 mg, 293 umol) was added slowly (E)-4-bromobut-2-enoyl chloride (0.1 M, 1.95 mL) at 0° C. under $N_2$. The mixture was stirred at 0° C. for 10 min to give (E)-4-bromo-[4-(3-chloro-2-fluoro-anilino)-7-[2-[(3R)-1,3-dimethylpyrrolidin-3-yl]ethynyl]quinazolin-6-yl]but-2-enamide (54.3 mg, 99% yield) as a yellow solution. m/z ES+ $[M+H]^+$ 558.0;

Step 3. To a mixture of (E)-4-bromo-N-[4-(3-chloro-2-fluoro-anilino)-7-[2-[(3R)-1,3-dimethylpyrrolidin-3-yl]ethynyl]quinazolin-6-yl]but-2-enamide (54.3 mg, 97.5 umol) and morpholine (0.2 M, 975 uL) in dichloromethane (0.5 mL) was added triethylamine (19.7 mg, 195 umol) at 20° C. under $N_2$. The mixture was stirred at 20° C. for 12 hours. The reaction solvent was removed by nitrogen purge. The residue was purified by prep-HPLC (column: Phenomenex Gemini-NX C18 75*30 mm*3 um; mobile phase: [water (10 mM $NH_4HCO_3$)-acetonitrile]; B %: 30%-60%, 12 min) and further purified by prep-HPLC (column: Waters Xbridge BEH C18 100*30 mm*10 um; mobile phase: [water (10 mM$NH_4HCO_3$)-acetonitrile]; B %: 30%-60%, 8 min) to give (E)-N-[4-(3-chloro-2-fluoro-anilino)-7-[2-[(3R)-1,3-dimethylpyrrolidin-3-yl]ethynyl]quinazolin-6-yl]-4-morpholino-but-2-enamide (3.7 mg, 7% yield) as a white solid. m/z ES+ $[M+H]^+$ 563.2; $^1H$ NMR (400 MHz, DMSO-$d_6$) δ 8.84 (s, 1H), 8.38 (br d, J=10.4 Hz, 1H), 7.76-7.61 (m, 2H), 6.92-6.77 (m, 1H), 6.10 (dd, J=7.6, 16.4 Hz, 1H), 5.67 (dd, J=10.8, 18.0 Hz, 1H), 4.70 (d, J=13.2 Hz, 1H), 4.44 (d, J=12.0 Hz, 1H), 4.31 (d, J=13.2 Hz, 1H), 4.12 (br d, J=13.6 Hz, 1H), 3.61-3.41 (m, 1H), 3.21 (t, J=12.8 Hz, 1H), 3.04 (t, J=11.6 Hz, 1H), 2.83 (t, J=11.6 Hz, 1H), 2.79-2.71 (m, 1H), 2.18-2.06 (m, 1H), 2.04-1.79 (m, 2H), 1.65-1.48 (m, 1H), 1.58 (d, J=12.4 Hz, 1H).

Example 76. Synthesis of Compound No. 82 (N-(4-((3-chloro-2-fluorophenyl)amino)-7-(((1R,5S)-3-methyl-3-azabicyclo[3.1.0]hexan-1-yl)ethynyl)quinazolin-6-yl)-2-(methoxymethyl)acrylamide)

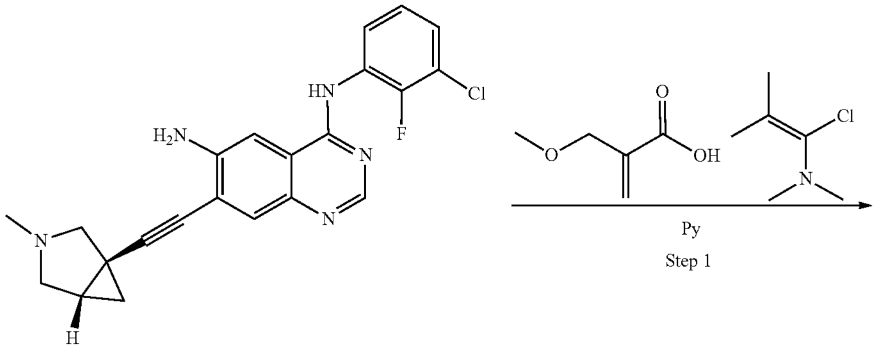

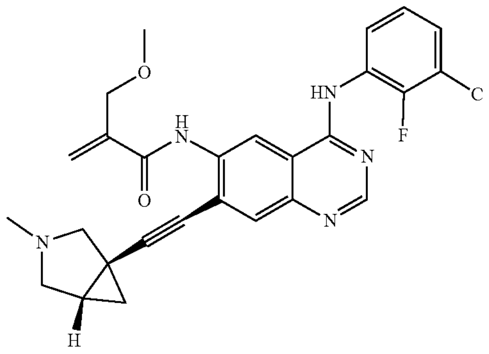

Step 1. To a mixture of 2-(methoxymethyl)prop-2-enoic acid (140 mg, 1.20 mmol) in dichloromethane (5 mL) was added 1-chloro-N,N,2-trimethyl-prop-1-en-1-amine (177.2 mg, 1.32 mmol) dropwise at 0° C. under $N_2$. The mixture was stirred at 25° C. for 1 h. The reaction solution was added slowly to a solution of $N^4$-(3-chloro-2-fluoro-phenyl)-7-[2-[(1R,5S)-3-methyl-3-azabicyclo[3.1.0]hexan-1-yl]ethynyl]quinazoline-4,6-diamine (100 mg, 245.2 umol) in pyridine (0.2 mL) under $N_2$. The mixture was stirred at 25° C. for 4 h. On completion, the reaction mixture was concentrated under reduced pressure to give a residue. The crude product was purified by reversed-phase HPLC (column: Phenomenex Gemini-NX C18 75*30 mm*3 um; mobile phase: [water (10 mM $NH_4HCO_3$)-acetonitrile]; B %: 40%-70%, 12 min) to give N-[4-(3-chloro-2-fluoro-anilino)-7-[2-[(1R,5S)-3-methyl-3-azabicyclo[3.1.0]hexan-1-yl]ethynyl]quinazolin-6-yl]-2-(methoxymethyl)prop-2-enamide (15 mg, 8.64% yield) as a yellow solid. m/z ES+ $[M+H]^+$ 506.2; $^1H$ NMR (400 MHz, DMSO-$d_6$) δ 10.11 (s, 1H), 9.74 (s, 1H), 8.85 (s, 1H), 8.47 (s, 1H), 7.83 (s, 1H), 7.52-7.47 (m, J=8.8 Hz, 2H), 7.30-7.26 (t, J=8.8 Hz, 1H), 6.24 (s, 1H), 5.84 (s, 1H), 4.29 (s, 2H), 3.35 (s, 3H), 3.12-3.10 (d, J=8.4 Hz, 1H), 2.94-2.92 (d, J=8.4 Hz, 1H), 2.46-2.40 (m, 1H), 2.39-2.35 (m, 1H), 2.25 (s, 3H), 1.97-1.93 (m, 1H), 1.39-1.30 (m, 1H), 1.04-1.00 (m, 1H).

Example 77. Synthesis of Compound No. 83 ((R)—N-(4-((3-chloro-2-fluorophenyl)amino)-7-((1,3-dimethylpyrrolidin-3-yl)ethynyl)quinazolin-6-yl)-2-(methoxymethyl)acrylamide)

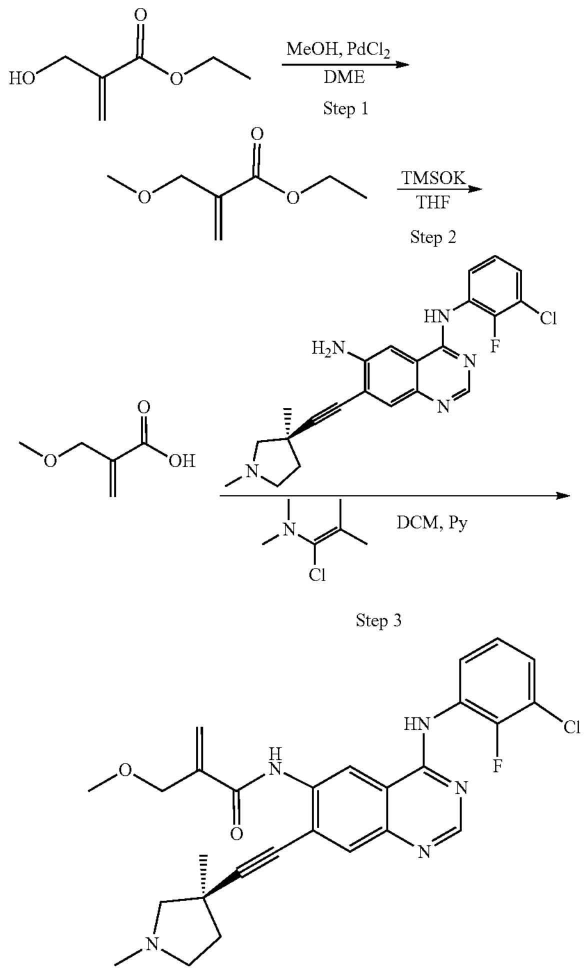

WX-G-1-56-1

Step 1. To a mixture of ethyl 2-(hydroxymethyl)prop-2-enoate (2 g, 15.37 mmol) and MeOH (2.46 g, 76.84 mmol) in DME (40 mL) was added $PdCl_2$ (272.51 mg, 1.54 mmol) in one portion at 25° C. under $N_2$. The mixture was stirred at 50° C. for 12 h under $N_2$. On completion, the reaction mixture was filtered and concentrated under reduced pressure to give a residue. The residue was purified by column chromatography ($SiO_2$, Petroleum ether) to give ethyl 2-(methoxymethyl)prop-2-enoate (1.2 g, 54.16% yield) as a colorless oil. $^1$H NMR (400 MHz, DMSO-$d_6$) δ 6.33 (s, 1H), 5.86 (s, 1H), 4.30-4.20 (m, 2H), 4.19 (s, 2H), 3.39 (s, 3H), 1.26 (t, J=8.0 Hz, 3H).

Step 2. To a mixture of ethyl 2-(methoxymethyl)prop-2-enoate (110 mg, 763.00 umol) in tetrahydrofuran (3 mL) was added TMSOK (195.77 mg, 1.53 mmol) in one portion at 25° C. under $N_2$. The mixture was stirred at 25° C. for 10 h. On completion, the reaction mixture was quenched by water 5 mL at 25° C., then adjusted to pH=8 with 0.1 N $NaHCO_3$ aqueous solution and washed with ethyl acetate (8 mL×2). The water layers were adjusted to pH=5 with 0.1 N HCl aqueous solution and extracted with ethyl acetate (8 mL×3), dried over with $Na_2SO_4$, filtered and concentrated under reduced pressure to give 2-(methoxymethyl)prop-2-enoic acid (73 mg, 628.69 umol, 82.40% yield) as a colorless oil. m/z ES+ $[M+H]^+$ 117.1;

Step 3. To a mixture of 2-(methoxymethyl)prop-2-enoic acid (70 mg, 602.85) in dichloromethane (2 mL) was added 1-chloro-N,N,2-trimethyl-prop-1-en-1-amine (88.61 mg, 663.14 umol) dropwise at 0° C. under $N_2$. The mixture was stirred at 25° C. for 1 h. The resulting solution was added slowly to a solution of $N^4$-(3-chloro-2-fluoro-phenyl)-7-[2-[(3R)-1,3-dimethylpyrrolidin-3-yl]ethynyl]quinazoline-4,6-diamine (200 mg, 487.94 umol) in pyridine (617.54 mg, 630.14 uL) at 25° C. The mixture was stirred at 50° C. for 4 h. On completion, the reaction mixture was filtered and concentrated under reduced pressure to give a residue. The crude product was purified by reversed-phase HPLC (column: Phenomenex Gemini-NX C18 75*30 mm*3 um; mobile phase: [water (10 mM $NH_4HCO_3$)-acetonitrile]; B %: 35%-60%, 12 min) to give N-[4-(3-chloro-2-fluoro-anilino)-7-[2-[(3R)-1,3-dimethylpyrrolidin-3-yl]ethynyl]-quinazolin-6-yl]-2-(methoxymethyl)prop-2-enamide (5.1 mg, 2.06% yield) as a brown solid. m/z ES+ $[M+H]^+$ 508.2; $^1$H NMR (400 MHz, DMSO-$d_6$) δ 10.11 (s, 1H), 9.64 (s, 1H), 8.82 (s, 1H), 8.48 (s, 1H), 7.82 (s, 1H), 7.51-7.48 (m, J=6.0 Hz, 2H), 7.30-7.20 (t, J=6.0 Hz, 1H), 6.25 (s, 1H), 5.83 (s, 1H), 4.27 (s, 2H), 3.42 (s, 3H), 2.80-2.70 (d, J=8.8 Hz, 1H), 2.62-2.56 (m, 2H), 2.55-2.52 (m, 1H), 2.53 (s, 3H), 2.25-2.20 (m, 1H), 1.90-1.80 (m, 1H), 1.44 (s, 3H).

Example 78. Synthesis of Compound No. 84 ((R)—N-(4-((3-chloro-2-fluorophenyl)amino)-7-((1,3-dimethylpyrrolidin-3-yl)ethynyl)quinazolin-6-yl)-2-cyanoacetamide)

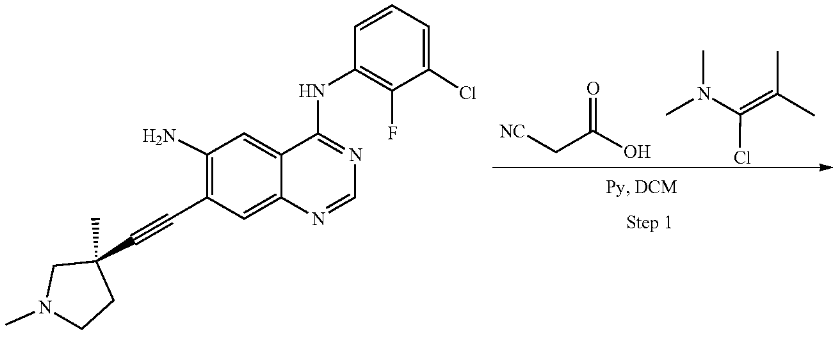

-continued

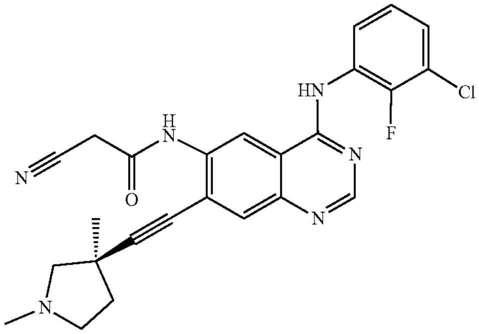

Step 1. To a solution of 2-cyanoacetic acid (125 mg, 1.46 mmol) in dichloromethane (2 mL) was added 1-chloro-N,N,2-trimethyl-prop-1-en-1-amine (196 mg, 1.46 mmol, 194 uL) at 25° C. under $N_2$. The mixture was stirred at 25° C. for 1 hour, then the mixture was added to a solution of N4-(3-chloro-2-fluoro-phenyl)-7-[2-[(3R)-1,3-dimethylpyrrolidin-3-yl]ethynyl]-quinazoline-4,6-diamine (200 mg, 488 umol) in dichloromethane (2 mL) and pyridine (38.6 mg, 488 umol, 39.4 uL) at 25° C. The mixture was stirred at 25° C. for 2 hours. On completion, the mixture was concentrated in vacuum to give a residue. The mixture was purified by prep-HPLC (column: Phenomenex Gemini-NX 80*40 mm*3 um; mobile phase: [water (10 mM $NH_4HCO_3$)-acetonitrile]; B %: 25%-45%, 8 min) to give (R)—N-(4-((3-chloro-2-fluorophenyl)amino)-7-((1,3-dimethylpyrrolidin-3-yl)ethynyl)quinazolin-6-yl)-2-cyanoacetamide (12 mg, 5.16% yield) as a brown solid. m/z ES+ $[M+H]^+$ 477.1; $^1H$ NMR (400 MHz, DMSO-$d_6$) δ 10.13 (s, 1H), 10.02 (br s, 1H), 8.60 (s, 1H), 8.50 (s, 1H), 7.82 (s, 1H), 7.55-7.46 (m, 2H), 7.29 (t, J=8.0 Hz, 1H), 4.03 (s, 2H), 2.88 (d, J=8.8 Hz, 1H), 2.70-2.62 (m, 2H), 2.55 (d, J=9.2 Hz, 1H), 2.32 (s, 3H), 2.29-2.23 (m, 1H), 1.93-1.83 (m, 1H), 1.46 (s, 3H).

Example 79. Synthesis of Compound D-1 (N-(7-(2-(1,3-bis(trideuteriomethyl)pyrrolidin-3-yl)ethynyl)-4-(3-chloro-2-fluoro-anilino)quinazolin-6-yl)prop-2-enamide)

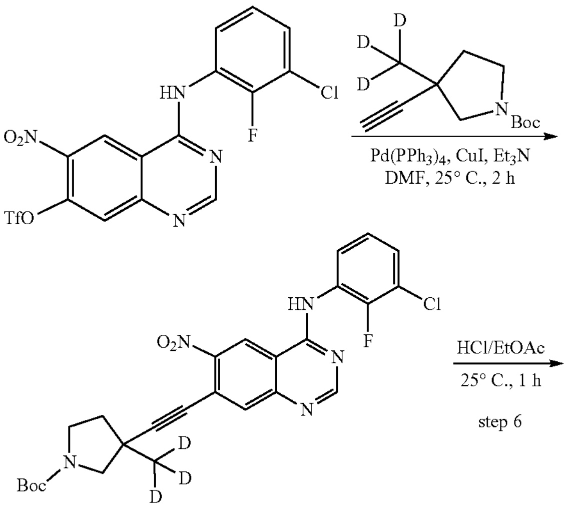

-continued

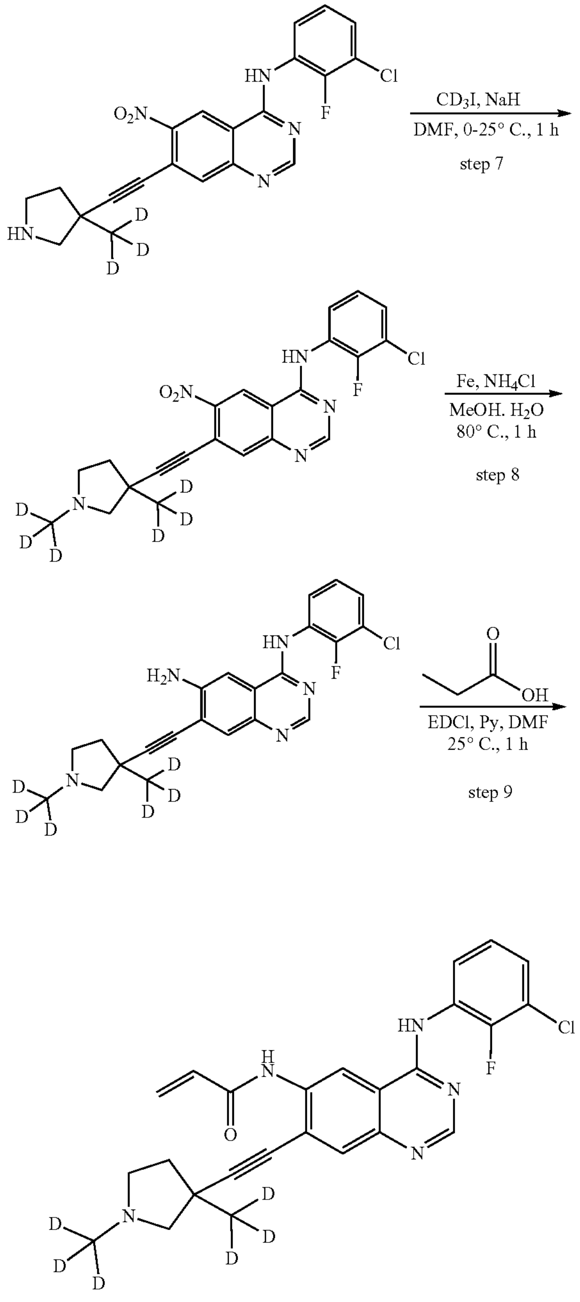

-continued

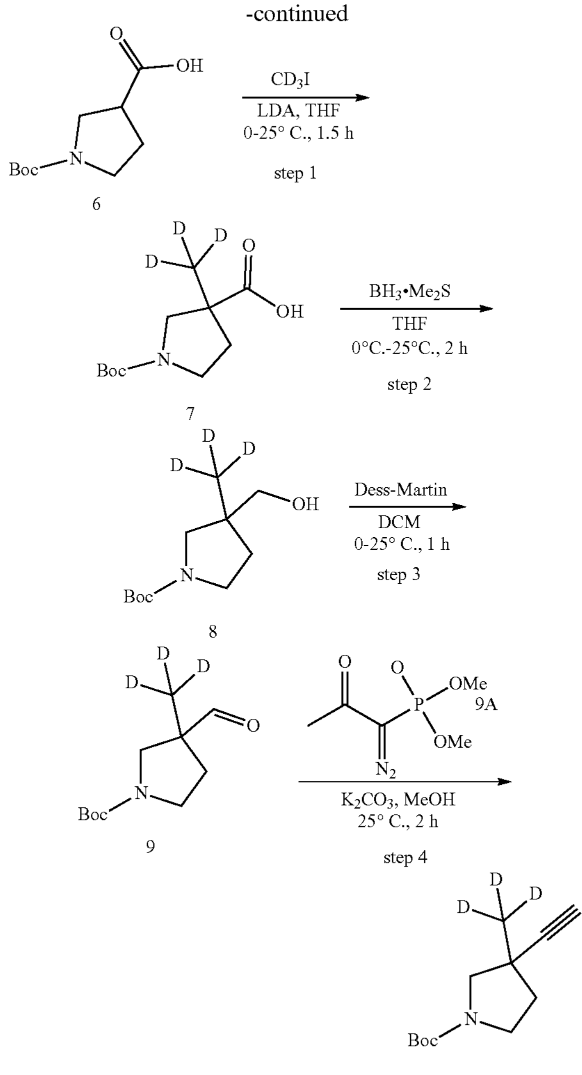

6, 7, 8, 9, 1A

Step 1. To a solution of 1-(tert-butoxycarbonyl)pyrrolidine-3-carboxylic acid (15.0 g, 69.7 mmol) in tetrahydrofuran (50 mL) was added Lithium diisopropylamide (2 M, 87.1 mL) dropwise at 0° C. The mixture was stirred at 0° C. for 0.5 h. Then the mixture was added iodomethane-$d_3$ (20.2 g, 139 mmol) dropwise at 0° C. The mixture was stirred at 25° C. for 1 h. The mixture was quenched with water (200 mL). Then the mixture was added saturated sodium hydrogencarbonate solution to pH=8-9 and diluted with ethyl acetate (100 mL). The aqueous phase was washed with ethyl acetate (2×200 mL) and then acidified with concentrated hydrochloric acid to pH=3-4, extracted with ethyl acetate (2×100 mL). The organic layers were dried over saturated sodium sulfate, filtered and concentrated to give 1-tert-butoxycarbonyl-3-(trideuteriomethyl)pyrrolidine-3-carboxylic acid (17.0 g, crude) as a yellow oil Step 2. To a solution of 1-tert-butoxycarbonyl-3-(trideuteriomethyl)pyrrolidine-3-carboxylic acid (17.0 g, 73.2 mmol) in tetrahydrofuran (200 mL) was added borane dimethyl sulfide complex (10 M, 11.0 mL) dropwise at 0° C. The mixture was stirred at 25° C. for 2 h. The mixture was quenched with methanol (200 mL) and concentrated to give crude product. The crude product was purified by silica gel chromatography (petroleum ether/ethyl acetate=10/1 to 3/1) to give tert-butyl 3-(hydroxymethyl)-3-(trideuteriomethyl)pyrrolidine-1-carboxylate (7.00 g, 44% yield) as a colorless oi. $^1$H NMR (400 MHz, $CDCl_3$) δ 3.41 (br d, J=4.8 Hz, 2H), 3.39-3.28 (m, 2H), 3.25-3.14 (m, 1H), 2.97 (br dd, J=11.2, 17.2 Hz, 1H), 1.84-1.69 (m, 1H), 1.50-1.45 (m, 1H), 1.39 (s, 9H).

Step 3. To a solution of tert-butyl 3-(hydroxymethyl)-3-(trideuteriomethyl)pyrrolidine-1-carboxylate (7.00 g, 32.1 mmol) in dichloromethane (50 mL) was added Dess-Martin Periodinane (20.4 g, 48.1 mmol) in portions at 0° C. The mixture was stirred at 25° C. for 1 h. The mixture was concentrated to give crude product. The crude product was purified by silica gel chromatography (petroleum ether/ethyl acetate=10/1 to 3/1) to give tert-butyl 3-formyl-3-(trideuteriomethyl)pyrrolidine-1-carboxylate (9.00 g, crude) as colorless oil.

Step 4. To a solution of tert-butyl 3-formyl-3-(trideuteriomethyl)pyrrolidine-1-carboxylate (9.00 g, 41.6 mmol, 1.00 eq) and potassium carbonate (17.3 g, 125 mmol) in methanol (60 mL) was added dimethyl (1-diazo-2-oxopropyl)phosphonate (10.4 g, 54.1 mmol) dropwise. The mixture was stirred at 25° C. for 2 h. The mixture was concentrated to give crude product. The crude product was purified by silica gel chromatography (petroleum ether/ethyl acetate=20/1 to 5/1) to give tert-butyl 3-ethynyl-3-(trideuteriomethyl)pyrrolidine-1-carboxylate (3.00 g, 34% yield) as colorless oil. $^1$H NMR (400 MHz, $CDCl_3$) δ 3.64-3.46 (m, 3H), 3.28-3.16 (m, 1H), 2.18 (s, 1H), 2.10 (td, J=6.4, 12.8 Hz, 1H), 1.87-1.77 (m, 1H), 1.49 (s, 9H)

Step 5. To a solution of 4-((3-chloro-2-fluorophenyl)amino)-6-nitroquinazolin-7-yl trifluoromethanesulfonate (2.00 g, 4.28 mmol), tert-butyl 3-ethynyl-3-(trideuteriomethyl)pyrrolidine-1-carboxylate (1.00 g, 4.71 mmol) in triethylamine (15.0 mL) and dimethyl formamide (15 mL) was added tetrakis[triphenylphosphine]palladium(0) (495 mg, 428 umol) and copper(I) iodide (81.6 mg, 429 umol) in one portion under nitrogen. The mixture was stirred at 25° C. for 2 h. The mixture was diluted with water (50 mL) and extracted with ethyl acetate (3×30.0 mL). The combined organic layer was washed with brine (20 mL) and dried over sodium sulfate, filtered and concentrated to give crude product. The crude product was purified by silica gel chromatography (petroleum ether/ethyl acetate=10/1 to 2/1) to give tert-butyl 3-(2-(4-(3-chloro-2-fluoro-anilino)-6-nitro-quinazol in-7-yl)ethynyl)-3-(trideuteriomethyl)pyrrolidine-1-carboxylate (1.12 g, 49% yield) as a yellow solid. $^1$H NMR (400 MHz, $CDCl_3$) δ 8.81 (s, 1H), 8.65 (d, J=2.4 Hz, 1H), 8.26 (br t, J=7.2 Hz, 1H), 8.03 (s, 1H), 7.81-7.66 (m, 1H), 7.22-7.19 (m, 1H), 7.16-7.10 (m, 1H), 3.75-3.61 (m, 1H), 3.59-3.43 (m, 2H), 3.29-3.19 (m, 1H), 2.30-2.15 (m, 1H), 1.93-1.80 (m, 1H), 1.41 (s, 9H). m/z ES+ $[M+H]^+$ 529.2.

Step 6. To a solution of tert-butyl 3-(2-(4-(3-chloro-2-fluoro-anilino)-6-nitro-quinazolin-7-yl)ethynyl)-3-(trideuteriomethyl)pyrrolidine-1-carboxylate (1.12 g, 2.12 mmol) in methanol (5.0 mL) was added hydrochloric acid/ethyl acetate (4 M, 5.00 mL) dropwise. The mixture was stirred at 25° C. for 1 h. The mixture was concentrated to give N-(3-chloro-2-fluoro-phenyl)-6-nitro-7-(2-(3-(trideuteriomethyl)pyrrolidin-3-yl)ethynyl)quinazolin-4-amine (900 mg, 99% yield) as a yellow solid. m/z ES+ $[M+H]^+$ 429.1;

Step 7. To a solution of N-(3-chloro-2-fluoro-phenyl)-6-nitro-7-(2-(3-(trideuteriomethyl)-pyrrolidin-3-yl)ethynyl) quinazolin-4-amine (900 mg, 2.10 mmol) in dimethyl formamide (10 mL) was added sodium hydride (252 mg, 6.30 mmol, 60% purity) in portions at 0° C. The mixture was stirred at 0° C. for 0.5 h. Then the mixture was added trideuterio(iodo)methane (365 mg, 2.52 mmol) dropwise at 0° C. The mixture was stirred at 25° C. for 1 h. The mixture was quenched with saturated ammonium chloride solution (30.0 mL) and extracted with ethyl acetate (3×30.0 mL). The combined organic layer was washed with brine (10 mL) and dried over sodium sulfate, filtered and concentrated to give crude product. The residue was purified by silica gel chromatography (petroleum ether/ethyl acetate=2/1 to ethyl acetate/methanol=10/1) to give 7-(2-(1,3-bis(trideuteriomethyl)pyrrolidin-3-yl)ethynyl)-N-(3-chloro-2-fluoro-phenyl)-6-nitro-quinazol in-4-amine (300 mg, 32% yield) as a yellow solid. m/z ES+ $[M+H]^+$ 446.3; $^1H$ NMR (400 MHz, DMSO-$d_6$) δ=10.92-10.31 (m, 1H), 9.47-9.19 (m, 1H), 8.74-8.47 (m, 1H), 7.92 (br s, 1H), 7.63-7.43 (m, 2H), 7.31 (br t, J=8.0 Hz, 1H), 2.78 (br d, J=8.8 Hz, 1H), 2.71-2.67 (m, 1H), 2.66-2.60 (m, 2H), 2.23 (ddd, J=5.6, 7, 12.8 Hz, 1H), 1.88 (td, J=7.2, 12.4 Hz, 1H).

Step 8. To a solution of 7-(2-(1,3-bis(trideuteriomethyl) pyrrolidin-3-yl)ethynyl)-N-(3-chloro-2-fluoro-phenyl)-6-nitro-quinazolin-4-amine (270 mg, 606 umol) and ammonium chloride (162 mg, 3.03 mmol) in methanol (8.0 mL) and water (2.0 mL) was added iron powder (169 mg, 3.03 mmol) in portions. The mixture was stirred at 80° C. for 1 h. The mixture was added methanol (50 mL) and filtered. The filtrate was concentrated to give residue. The residue was diluted with saturated sodium hydrogencarbonate solution (30 mL) and extracted with ethyl acetate (3×30 mL). The combined organic layer was washed with brine (10 mL) and dried over sodium sulfate, filtered and concentrated to give 7-(2-(1,3-bis(trideuteriomethyl)pyrrolidin-3-yl)ethynyl)-$N^4$-(3-chloro-2-fluoro-phenyl)quinazoline-4,6-diamine (270 mg, crude) as a yellow solid. m/z ES+$[M+H]^+$ 416.1;

Step 9. To a solution of 7-(2-(1,3-bis(trideuteriomethyl) pyrrolidin-3-yl)ethynyl)-$N^4$-(3-chloro-2-fluoro-phenyl) quinazoline-4,6-diamine (270 mg, 649 umol), acrylic acid (60.8 mg, 844 umol, 57.9 uL) and pyridine (205 mg, 2.60 mmol) in dimethyl formamide (4.0 mL) was added 1-(3-dimethyl aminopropyl)-3-ethylcarbodiimide hydrochloride (498 mg, 2.60 mmol) in portions. The mixture was stirred at 25° C. for 1 h. The mixture was filtered and the filtrate was purified by prep-HPLC (column: Waters Xbridge C18 150*50 mm*10 um; mobile phase: [water (10 mM $NH_4HCO_3$)-acetonitrile]; B %: 30%-60%, 10 min) and lyophilized to give N-(7-(2-(1,3-bis(trideuteriomethyl)pyrrolidin-3-yl) ethynyl)-4-(3-chloro-2-fluoro-anilino)quinazolin-6-yl)prop-2-enamide (31.0 mg, 10% yield) as a yellow solid. m/z ES+ $[M+H]^+$ 470.4; $^1H$ NMR (400 MHz, DMSO-$d_6$) δ 10.33-9.95 (m, 1H), 9.76 (br s, 1H), 8.71 (s, 1H), 8.47 (br s, 1H), 7.79 (br s, 1H), 7.49 (br s, 2H), 7.34-7.21 (m, 1H), 6.58 (dd, J=10.4, 17.2 Hz, 1H), 6.34 (dd, J=2.0, 17.2 Hz, 1H), 5.93-5.80 (m, 1H), 2.78 (d, J=8.8 Hz, 1H), 2.64-2.58 (m, 2H), 2.55-2.53 (m, 1H), 2.29-2.18 (m, 1H), 1.92-1.80 (m, 1H).

Example 80. Biological Activity of the Compounds of the Present Disclosure

The biological activity of the compounds of the present disclosure was determined utilising the assay described herein.

Retroviral Production: EGFR mutants were subcloned into pMXs-IRES-Blasticidin (RTV-016, Cell Biolabs, San Diego, CA). Retroviral expression vector retrovirus was produced by transient transfection of HEK 293T cells with the retroviral EGFR mutant expression vector pMXs-IRES-Blasticidin (RTV-016, Cell Biolabs), pCMV-Gag-Pol vector and pCMV-VSV-G-Envelope vector. Briefly, HEK 293T/17 cells were plated in 100 mm collagen coated plate (354450, Corning Life Sciences, Tewksbury, MA) ($4\times10^5$ per plate) and incubated overnight. The next day, retroviral plasmids (3 ng of EGFR mutant, 1.0 ng of pCMV-Gag-Pol and 0.5 ng pCMV-VSV-G) were mixed in 500 n1 of Optimem (31985, Life Technologies). The mixture was incubated at room temperature for 5 min and then added to Optimem containing transfection reagent Lipofectamine (11668, Invitrogen) and incubated for 20 minutes. Mixture was then added dropwise to HEK 293T cells. The next day the medium was replaced with fresh culture medium and retrovirus was harvested @ 24 and 48 hrs.

Generation of EGFR mutant stable cell lines: BaF3 cells (1.5E5 cells) were infected with 1 ml of viral supernatant supplemented with 8 ng/ml polybrene by centrifuging for 30 min at 1000 rpm. Cells were placed in a 37° C. incubator overnight. Cells were then spun for 5 minutes to pellet the cells. Supernatant was removed and cells re-infected a fresh 1 ml of viral supernatant supplemented with 8 ng/ml polybrene by centrifuging for 30 min at 1000 rpm. Cells were placed in 37° C. incubator overnight. Cells were then maintained in RPMI containing 10% Heat Inactivated FBS, 2% L-glutamine containing 10 ng/ml IL-3. After 48 hours cells were selected for retroviral infection in 10 ng/ml Blasticidin for one week. Blasticidin resistant populations were washed twice in phosphate buffered saline before plating in media lacking IL-3 to select for IL-3 independent growth.

Assay for cell proliferation: BaF3 cell lines were resuspended at 1.3E5 c/ml in RPMI containing 10% Heat Inactivated FBS, 2% L-glutamine and 1% Pen/Strep and dispensed in triplicate (17.5E4 c/well) into 96 well plates. To determine the effect of drug on cell proliferation, cells incubated for 3 days in the presence of vehicle control or test drug at varying concentrations. Inhibition of cell growth was determined by luminescent quantification of intracellular ATP content using CellTiterGlo (Promega), according to the protocol provided by the manufacturer. Comparison of cell number on day 0 versus 72 hours post drug treatment was used to plot dose-response curves. The number of viable cells was determined and normalized to vehicle-treated controls. Inhibition of proliferation, relative to vehicle-treated controls was expressed as a fraction of 1 and graphed using PRISM® software (Graphpad Software, San Diego, CA). $EC_{50}$ values were determined with the same application.

Cellular protein analysis: Cell extracts were prepared by detergent lysis (RIPA, R0278, Sigma, St Louis, MO) containing 10 mM Iodoacetamide (786-228, G-Biosciences, St, Louis, MO), protease inhibitor (P8340, Sigma, St. Louis, MO) and phosphatase inhibitors (P5726, P0044, Sigma, St. Louis, MO) cocktails. The soluble protein concentration was determined by micro-BSA assay (Pierce, Rockford IL). Protein immunodetection was performed by electrophoretic transfer of SDS-PAGE separated proteins to nitrocellulose, incubation with antibody, and chemiluminescent second step detection. Nitrocellulose membranes were blocked with 5% nonfat dry milk in TBS and incubated overnight with primary antibody in 5% bovine serum albumin. The following primary antibodies from Cell Signaling Technology were used at 1:1000 dilution: phospho-EGFR[Y1173] and total EGFR. 0-Actin antibody, used as a control for protein loading, was purchased from Sigma Chemicals. Horseradish peroxidase-conjugated secondary antibodies were obtained from Cell Signaling Technology and used at 1:5000 dilution. Horseradish peroxidase-conjugated secondary antibodies were incubated in nonfat dry milk for 1 hour. SuperSignal chemiluminescent reagent (Pierce Biotechnology) was used according to the manufacturer's directions and blots were imaged using the Alpha Innotech image analyzer and AlphaEaseFC software (Alpha Innotech, San Leandro CA).

The measured IC50 values of compounds of the present disclosure are shown in Table A below (A represents an IC50 value≤50 nM; B represents an IC50 value>50 nM and ≤100 nM; C represents an IC50 value>100 nM and ≤500 nM; and D represents an IC50 value>500 nM).

TABLE A

| | EFGR | | | | HER2 | |
|---|---|---|---|---|---|---|
| Compound No. | EGFR wt | EGFR V3 | EGFR SVD | EGFR NPH | HER2 S310F | HER2 YVMA |
| 1 | B | A | C | B | B | C |
| 2 | C | A | C | B | B | C |
| 3 | B | A | C | B | B | C |
| 4 | B | A | | | C | C |
| 5 | A | A | | | C | C |
| 6 | D | B | | | C | D |
| 7 | A | A | | | B | C |
| 8 | A | A | | | B | C |
| 10 | C | A | | | C | D |
| 11 | C | A | | | C | C |
| 12 | D | A | A | A | A | A |
| 13 | C | A | | | A | A |
| 14 | D | A | | | A | B |
| 16 | D | B | | | A | C |
| 17 | A | A | | | C | C |
| 18 | | A | | | A | |
| 19 | C | D | | | B | D |
| 20 | C | A | | | A | |
| 21 | A | C | | | C | D |
| 22 | | D | | | D | |
| 23 | B | D | | | C | |
| 24 | D | B | | | C | |
| 25 | C | D | | | D | D |
| 26 | B | A | | | B | C |
| 27 | C | D | | | | D |
| 28 | D | A | | | | A |
| 29 | C | C | | | | D |
| 30 | B | A | | | | B |
| 31 | A | B | | | | C |
| 32 | D | A | | | | D |
| 33 | A | A | | | | A |
| 34 | A | A | | | | A |
| 35 | A | A | | | | A |
| 36 | A | A | | | | A |
| 37 | A | A | | | C | C |
| 38 | B | A | | | | C |
| 39 | B | D | | | | D |
| 40 | C | A | | | | C |
| 41 | C | A | C | C | | A |
| 42 | A | A | | | | A |
| 43 | A | D | | | | D |
| 44 | A | A | | | | A |
| 45 | C | A | | | C | D |
| 46 | C | A | | | C | D |
| 47 | D | C | | | D | D |
| 48 | C | C | | | C | D |
| 49 | B | A | | | B | C |
| 50 | B | A | | | B | C |
| 51 | B | A | | | A | C |
| 52 | C | A | | | B | C |
| 53 | C | C | | | C | D |
| 54 | D | B | | | C | D |
| 55 | D | C | | | C | D |
| 56 | C | A | | | C | D |
| 57 | A | D | | | D | D |
| 58 | C | A | | | B | D |
| 59 | C | A | | | C | D |
| 60 | C | A | | | B | C |
| 61 | D | C | | | B | C |
| 62 | D | C | | | C | D |
| 63 | C | A | | | C | D |
| 64 | C | A | | | C | C |
| 65 | C | A | | | B | C |
| 66 | D | A | | | C | D |
| 67 | D | B | | | A | C |
| 68 | D | C | | | D | D |
| 69 | C | A | | | C | D |
| 70 | B | A | | | A | A |
| 71 | D | A | | | A | C |
| 72 | D | A | | | A | B |
| 73 | B | A | | | A | C |
| 74 | C | A | | | B | D |
| 75 | C | A | | | C | D |
| 76 | D | C | | | B | C |
| 77 | A | A | | | A | C |
| 78 | A | A | | | A | C |
| 79 | D | D | | | D | D |
| 80 | B | A | | | B | C |
| 81 | | C | | | D | D |
| 84 | D | D | | | | D |

The measured IC50 values of compounds of the present disclosure are also shown in Table B below (A represents an IC50 value≤10 nM; B represents an IC50 value>10 nM and ≤25 nM; C represents an IC50 value>25 nM and ≤50 nM; and D represents an IC50 value>50 nM).

TABLE B

| | EFGR | | | | | |
|---|---|---|---|---|---|---|
| Compound No. | EGFR wt | EGFR V3 | EGFR V2 | EGFR V6 | EGFR A289V | EGFR G598V |
| 37 | C | B | A | A | A | A |

EQUIVALENTS

The details of one or more embodiments of the disclosure are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference.

The foregoing description has been presented only for the purposes of illustration and is not intended to limit the disclosure to the precise form disclosed, but by the claims appended hereto.

The invention claimed is:
1. A compound selected from:
| Compound No. | Structure |
| --- | --- |
| 1 | 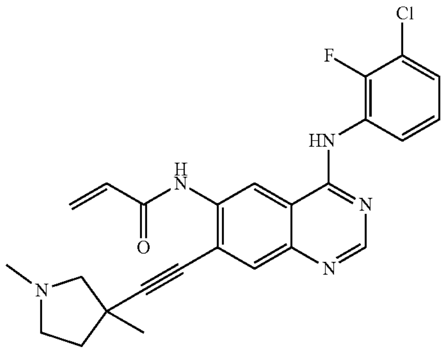 [SMILES: C=CC(=O)Nc1cc2c(Nc3cccc(Cl)c3F)ncnc2cc1C#CC1(C)CCN(C)C1] |
| 2 | 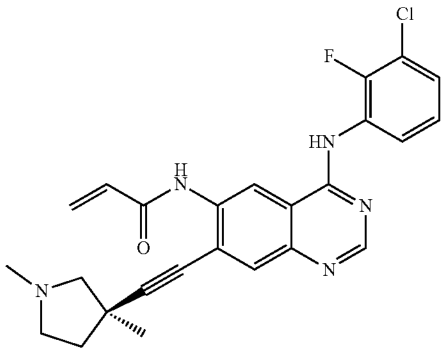 [SMILES: C=CC(=O)Nc1cc2c(Nc3cccc(Cl)c3F)ncnc2cc1C#C[C@@]1(C)CCN(C)C1] |
| 3 | 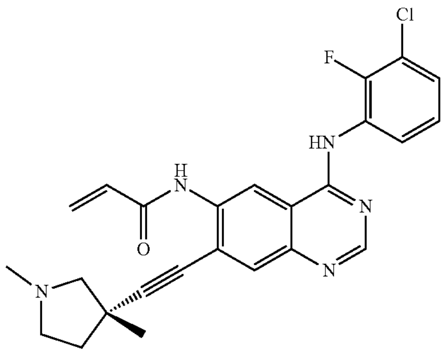 [SMILES: C=CC(=O)Nc1cc2c(Nc3cccc(Cl)c3F)ncnc2cc1C#C[C@]1(C)CCN(C)C1] |
| 4 | 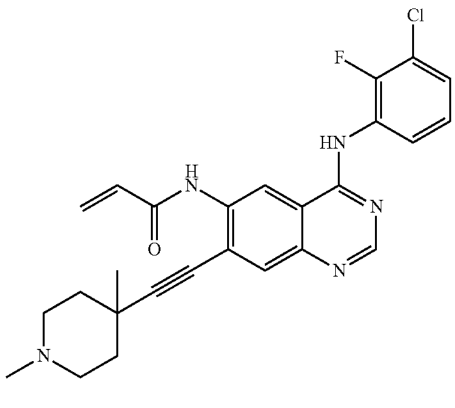 [SMILES: C=CC(=O)Nc1cc2c(Nc3cccc(Cl)c3F)ncnc2cc1C#CC1(C)CCN(C)CC1] |
-continued
| Compound No. | Structure |
| --- | --- |
| 5 | 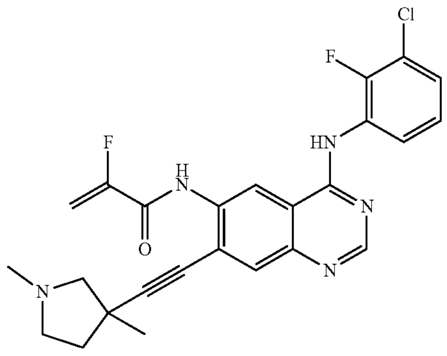 [SMILES: C=C(F)C(=O)Nc1cc2c(Nc3cccc(Cl)c3F)ncnc2cc1C#CC1(C)CCN(C)C1] |
| 6 | 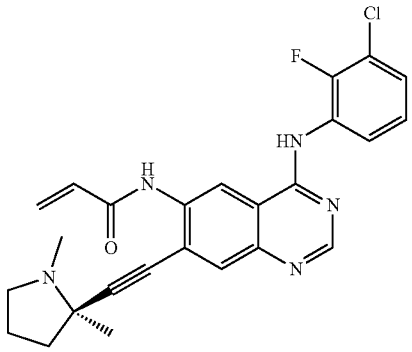 [SMILES: C=CC(=O)Nc1cc2c(Nc3cccc(Cl)c3F)ncnc2cc1C#C[C@@]1(C)CCCN1C] |
| 7 | 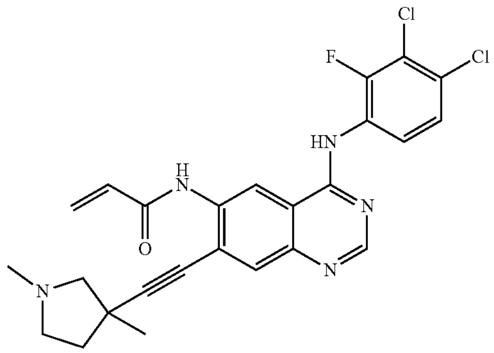 [SMILES: C=CC(=O)Nc1cc2c(Nc3ccc(Cl)c(Cl)c3F)ncnc2cc1C#CC1(C)CCN(C)C1] |
| 8 | 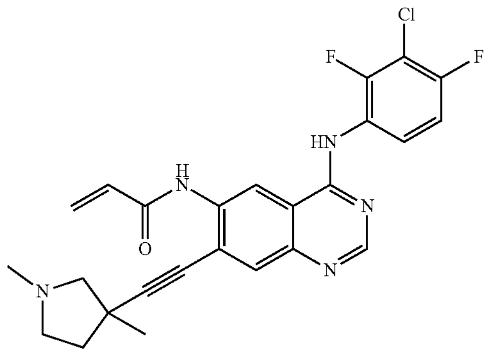 [SMILES: C=CC(=O)Nc1cc2c(Nc3ccc(F)c(Cl)c3F)ncnc2cc1C#CC1(C)CCN(C)C1] |

-continued
| Compound No. | Structure |
| --- | --- |
| 10 | 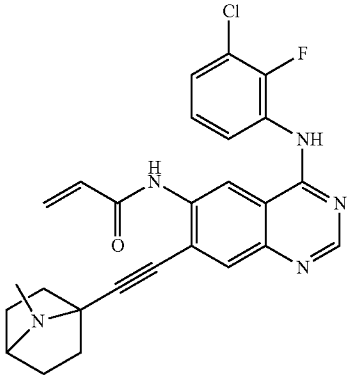 [SMILES: C=CC(=O)Nc1cc2c(Nc3cccc(Cl)c3F)ncnc2cc1C#CC12CCC(CC1)N2C] |
| 11 | 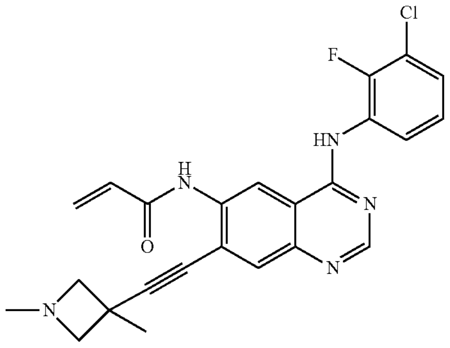 [SMILES: C=CC(=O)Nc1cc2c(Nc3cccc(Cl)c3F)ncnc2cc1C#CC1(C)CN(C)C1] |
| 12 | 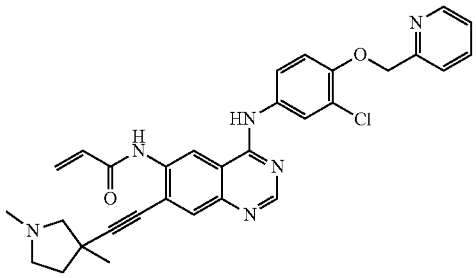 [SMILES: C=CC(=O)Nc1cc2c(Nc3ccc(OCc4ccccn4)c(Cl)c3)ncnc2cc1C#CC1(C)CCN(C)C1] |
| 13 | 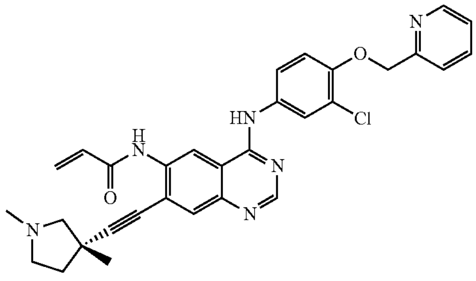 [SMILES: C=CC(=O)Nc1cc2c(Nc3ccc(OCc4ccccn4)c(Cl)c3)ncnc2cc1C#C[C@]1(C)CCN(C)C1] |
-continued
| Compound No. | Structure |
| --- | --- |
| 14 | 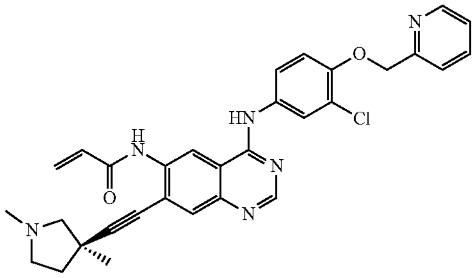 [SMILES: C=CC(=O)Nc1cc2c(Nc3ccc(OCc4ccccn4)c(Cl)c3)ncnc2cc1C#C[C@@]1(C)CCN(C)C1] |
| 16 | 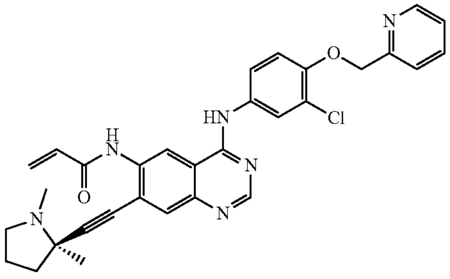 [SMILES: C=CC(=O)Nc1cc2c(Nc3ccc(OCc4ccccn4)c(Cl)c3)ncnc2cc1C#C[C@@]1(C)CCCN1C] |
| 17 | 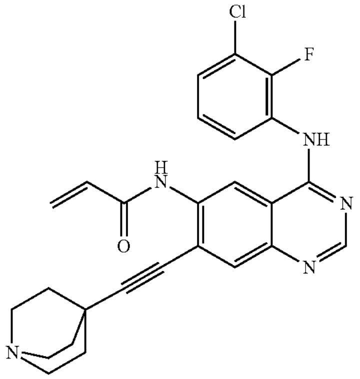 [SMILES: C=CC(=O)Nc1cc2c(Nc3cccc(Cl)c3F)ncnc2cc1C#CC12CCN(CC1)CC2] |
| 18 | 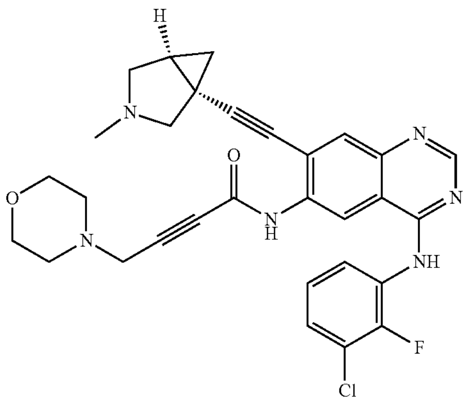 [SMILES: CN1C[C@H]2C[C@@]2(C#Cc2cc3ncnc(Nc4cccc(Cl)c4F)c3cc2NC(=O)C#CCN2CCOCC2)C1] |

-continued
| Compound No. | Structure |
|---|---|
| 19 | 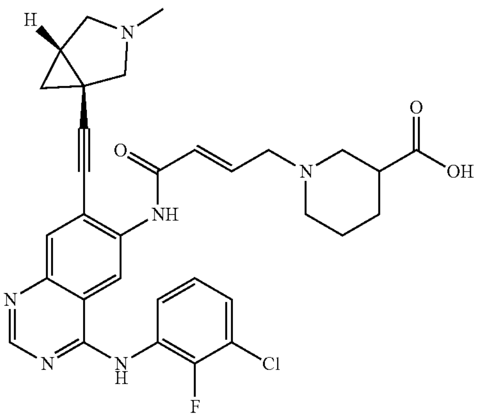 [SMILES: CN1C[C@H]2C[C@@]2(C#Cc2cc3ncnc(Nc4cccc(Cl)c4F)c3cc2NC(=O)/C=C/CN2CCCC(C(=O)O)C2)C1] |
| 20 | 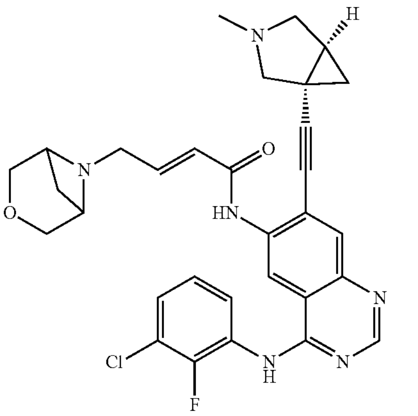 [SMILES: CN1C[C@H]2C[C@@]2(C#Cc2cc3ncnc(Nc4cccc(Cl)c4F)c3cc2NC(=O)/C=C/CN2C3COCC2C3)C1] |
| 21 | 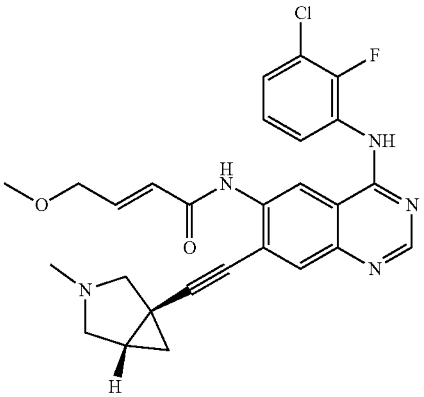 [SMILES: COC/C=C/C(=O)Nc1cc2c(Nc3cccc(Cl)c3F)ncnc2cc1C#C[C@@]12C[C@@H]1CN(C)C2] |
-continued
| Compound No. | Structure |
|---|---|
| 22 | 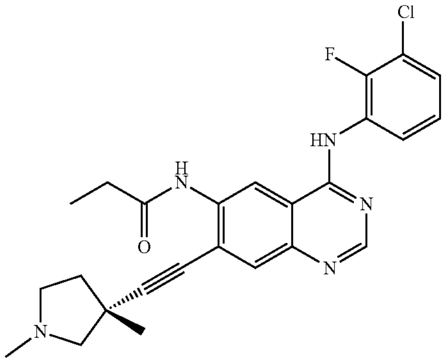 [SMILES: CCC(=O)Nc1cc2c(Nc3cccc(Cl)c3F)ncnc2cc1C#C[C@@]1(C)CCN(C)C1] |
| 23 | 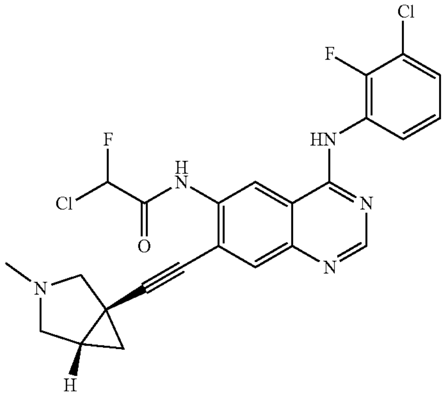 [SMILES: CN1C[C@H]2C[C@@]2(C#Cc2cc3ncnc(Nc4cccc(Cl)c4F)c3cc2NC(=O)C(F)Cl)C1] |
| 24 | 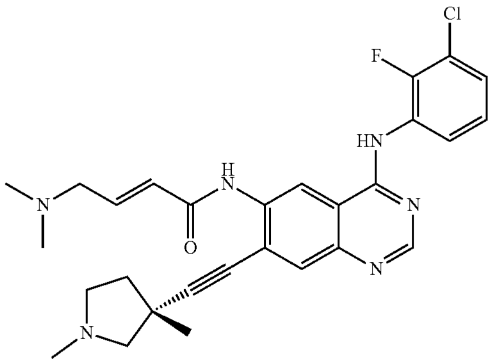 [SMILES: CN(C)C/C=C/C(=O)Nc1cc2c(Nc3cccc(Cl)c3F)ncnc2cc1C#C[C@@]1(C)CCN(C)C1] |
| 25 | 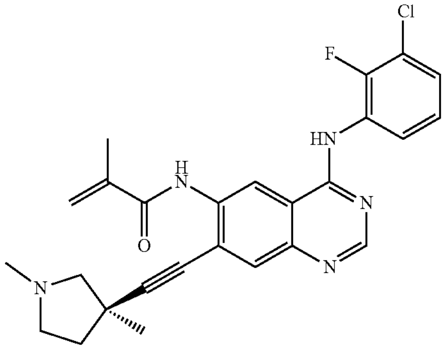 [SMILES: C=C(C)C(=O)Nc1cc2c(Nc3cccc(Cl)c3F)ncnc2cc1C#C[C@@]1(C)CCN(C)C1] |

-continued
| Compound No. | Structure |
| --- | --- |
| 26 | 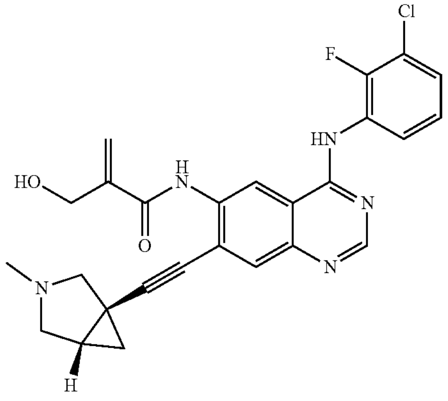 [SMILES: C=C(CO)C(=O)Nc1cc2c(Nc3cccc(Cl)c3F)ncnc2cc1C#C[C@@]12C[C@@H]1CN(C)C2] |
| 27 | 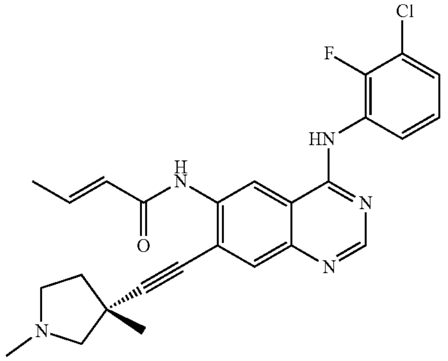 [SMILES: C/C=C/C(=O)Nc1cc2c(Nc3cccc(Cl)c3F)ncnc2cc1C#C[C@@]1(C)CCN(C)C1] |
| 28 | 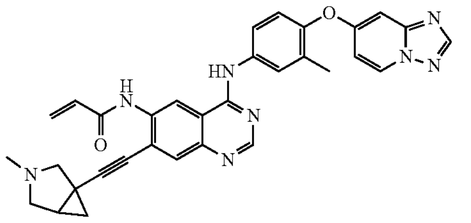 [SMILES: C=CC(=O)Nc1cc2c(Nc3ccc(Oc4ccn5ncnc5c4)c(C)c3)ncnc2cc1C#CC12CC1CN(C)C2] |
| 29 | 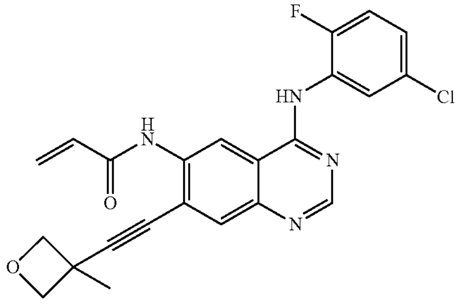 [SMILES: C=CC(=O)Nc1cc2c(Nc3cc(Cl)ccc3F)ncnc2cc1C#CC1(C)COC1] |
-continued
| Compound No. | Structure |
| --- | --- |
| 30 | 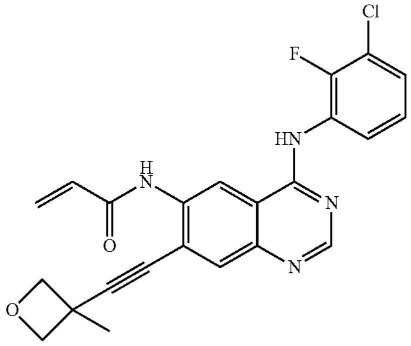 [SMILES: C=CC(=O)Nc1cc2c(Nc3cccc(Cl)c3F)ncnc2cc1C#CC1(C)COC1] |
| 31 | 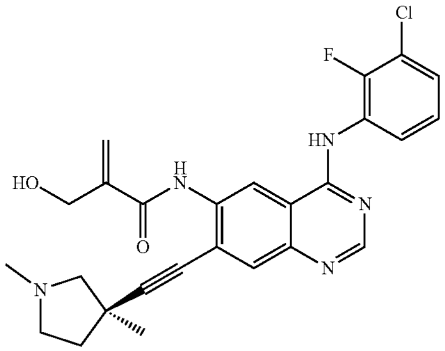 [SMILES: C=C(CO)C(=O)Nc1cc2c(Nc3cccc(Cl)c3F)ncnc2cc1C#C[C@@]1(C)CCN(C)C1] |
| 32 | 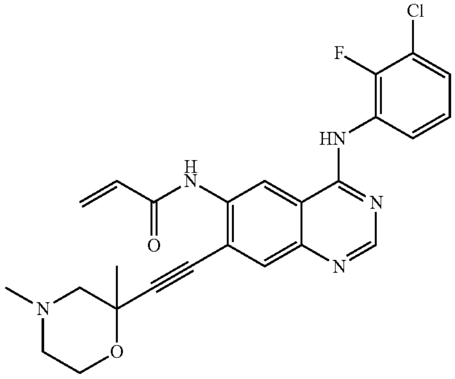 [SMILES: C=CC(=O)Nc1cc2c(Nc3cccc(Cl)c3F)ncnc2cc1C#CC1(C)CN(C)CCO1] |
| 33 | 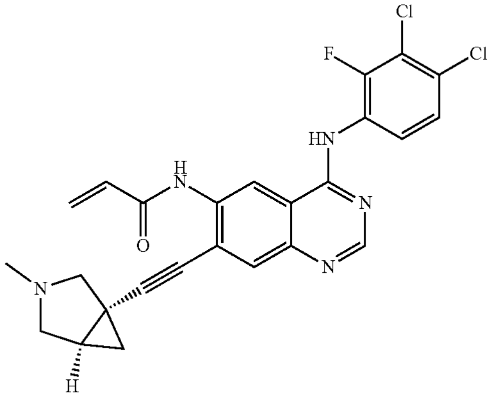 [SMILES: C=CC(=O)Nc1cc2c(Nc3ccc(Cl)c(Cl)c3F)ncnc2cc1C#C[C@]12C[C@H]1CN(C)C2] |

| Compound No. | Structure |
|---|---|
| 34 | 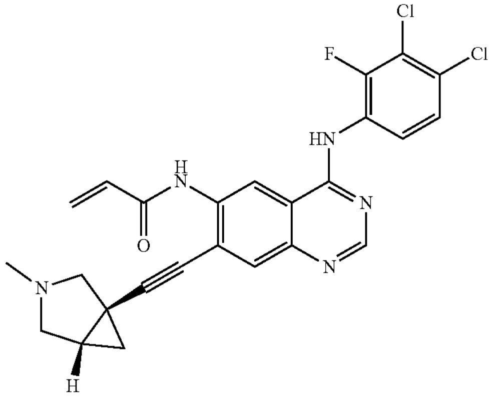 [SMILES: C=CC(=O)Nc1cc2c(Nc3ccc(Cl)c(Cl)c3F)ncnc2cc1C#C[C@@]12C[C@@H]1CN(C)C2] |
| 35 | 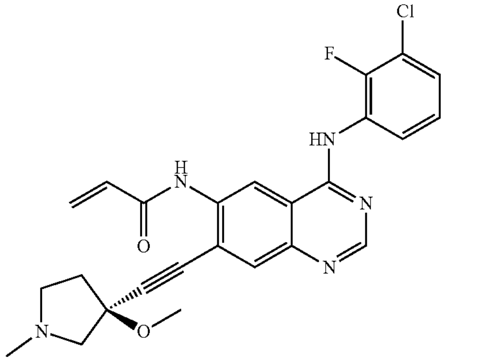 [SMILES: C=CC(=O)Nc1cc2c(Nc3cccc(Cl)c3F)ncnc2cc1C#C[C@@]1(OC)CCN(C)C1] |
| 36 | 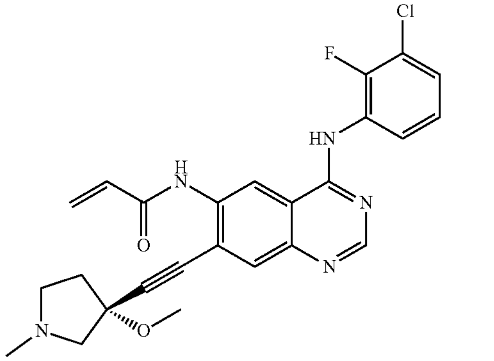 [SMILES: C=CC(=O)Nc1cc2c(Nc3cccc(Cl)c3F)ncnc2cc1C#C[C@]1(OC)CCN(C)C1] |
| 37 | 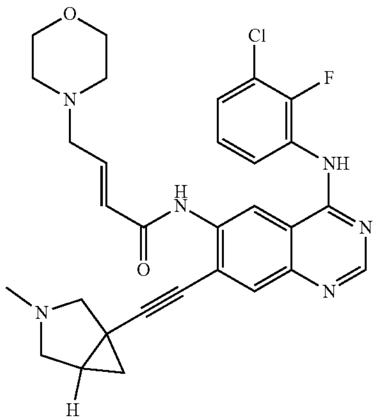 [SMILES: CN1CC2CC2(C#Cc2cc3ncnc(Nc4cccc(Cl)c4F)c3cc2NC(=O)/C=C/CN2CCOCC2)C1] |
| Compound No. | Structure |
|---|---|
| 37A | 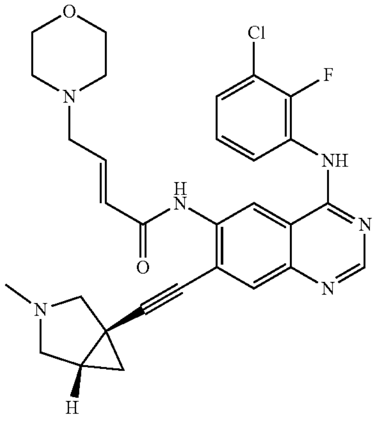 [SMILES: CN1C[C@H]2C[C@@]2(C#Cc2cc3ncnc(Nc4cccc(Cl)c4F)c3cc2NC(=O)/C=C/CN2CCOCC2)C1] |
| 37B | 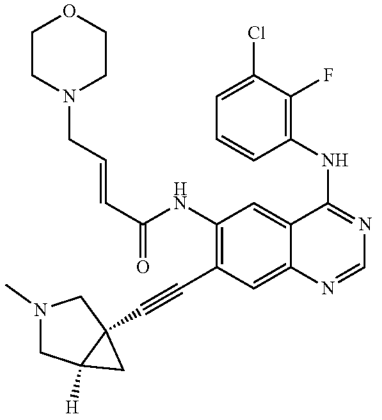 [SMILES: CN1C[C@@H]2C[C@]2(C#Cc2cc3ncnc(Nc4cccc(Cl)c4F)c3cc2NC(=O)/C=C/CN2CCOCC2)C1] |
| 38 | 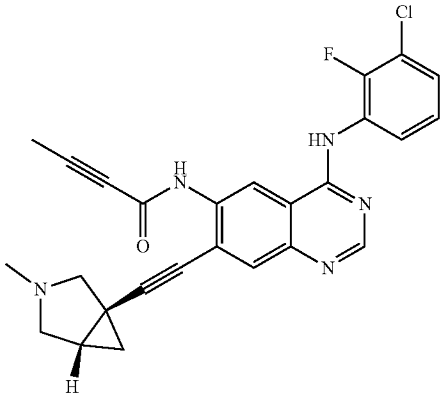 [SMILES: CC#CC(=O)Nc1cc2c(Nc3cccc(Cl)c3F)ncnc2cc1C#C[C@@]12C[C@@H]1CN(C)C2] |

-continued
| Compound No. | Structure |
| --- | --- |
| 39 | 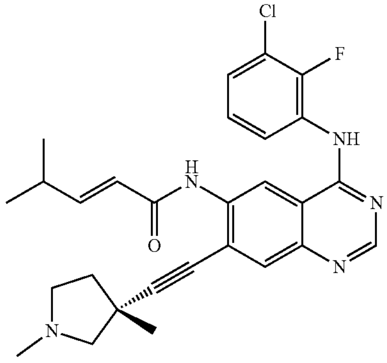 [SMILES: CC(C)/C=C/C(=O)Nc1cc2c(Nc3cccc(Cl)c3F)ncnc2cc1C#C[C@@]1(C)CCN(C)C1] |
| 40 | 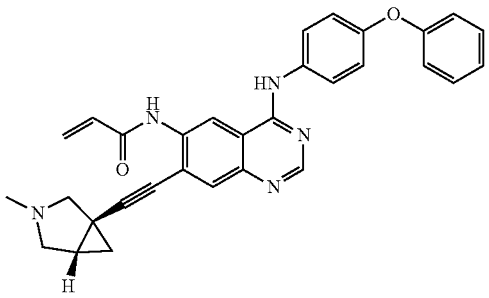 [SMILES: C=CC(=O)Nc1cc2c(Nc3ccc(Oc4ccccc4)cc3)ncnc2cc1C#C[C@@]12C[C@@H]1CN(C)C2] |
| 41 | 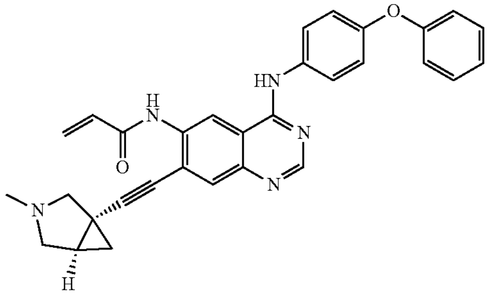 [SMILES: C=CC(=O)Nc1cc2c(Nc3ccc(Oc4ccccc4)cc3)ncnc2cc1C#C[C@]12C[C@H]1CN(C)C2] |
| 42 | 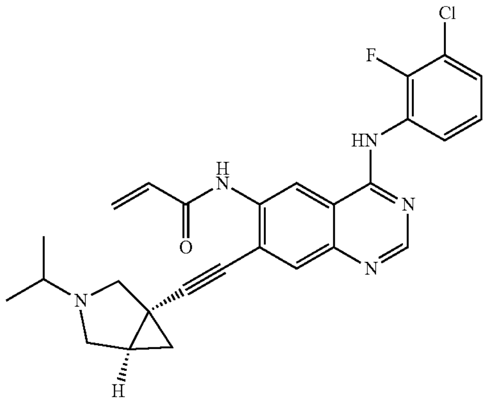 [SMILES: C=CC(=O)Nc1cc2c(Nc3cccc(Cl)c3F)ncnc2cc1C#C[C@]12C[C@H]1CN(C(C)C)C2] |
| 43 | 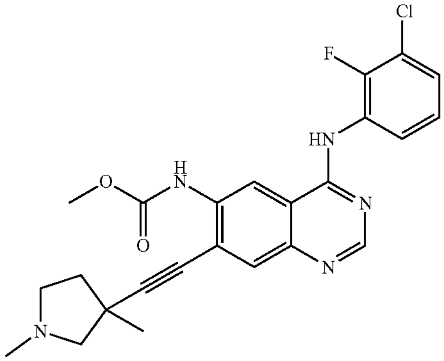 [SMILES: COC(=O)Nc1cc2c(Nc3cccc(Cl)c3F)ncnc2cc1C#CC1(C)CCN(C)C1] |
| 44 | 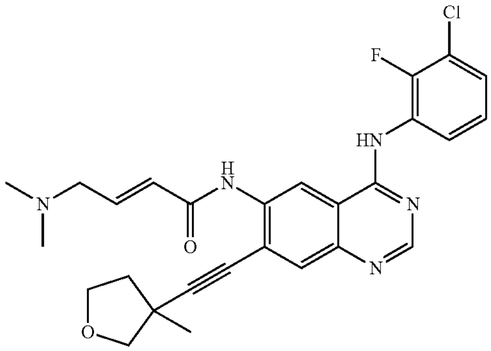 [SMILES: CN(C)C/C=C/C(=O)Nc1cc2c(Nc3cccc(Cl)c3F)ncnc2cc1C#CC1(C)CCOC1] |
| 45 | 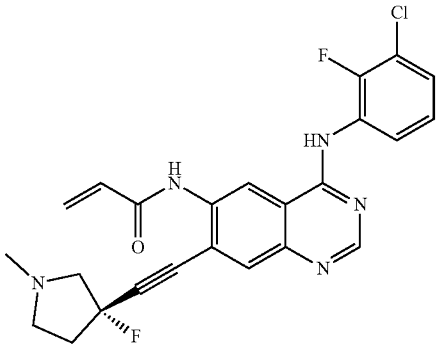 [SMILES: C=CC(=O)Nc1cc2c(Nc3cccc(Cl)c3F)ncnc2cc1C#C[C@@]1(F)CCN(C)C1] |
| 46 | 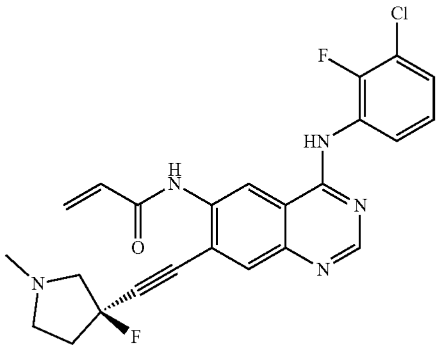 [SMILES: C=CC(=O)Nc1cc2c(Nc3cccc(Cl)c3F)ncnc2cc1C#C[C@]1(F)CCN(C)C1] |

-continued
| Compound No. | Structure |
|---|---|
| 47 | 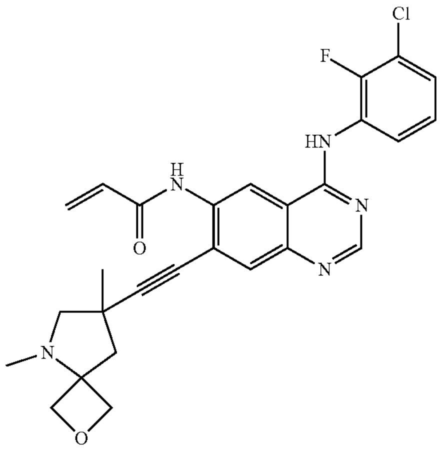 [SMILES: C=CC(=O)Nc1cc2c(Nc3cccc(Cl)c3F)ncnc2cc1C#CC1(C)CN(C)C2(COC2)C1] |
| 48 | 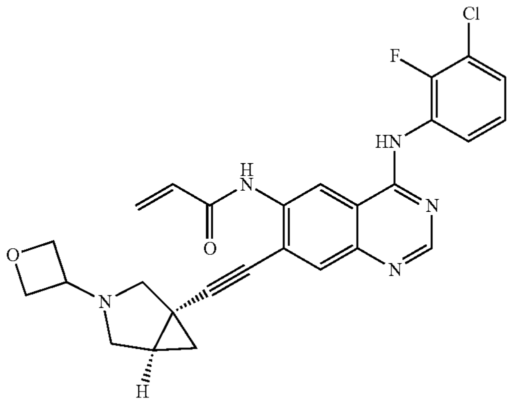 [SMILES: C=CC(=O)Nc1cc2c(Nc3cccc(Cl)c3F)ncnc2cc1C#C[C@]12C[C@H]1CN(C1COC1)C2] |
| 49 | 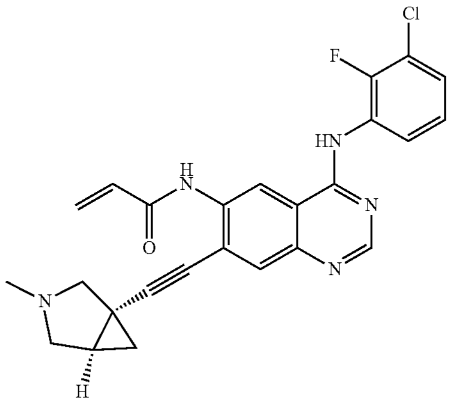 [SMILES: C=CC(=O)Nc1cc2c(Nc3cccc(Cl)c3F)ncnc2cc1C#C[C@]12C[C@H]1CN(C)C2] |
-continued
| Compound No. | Structure |
|---|---|
| 50 | 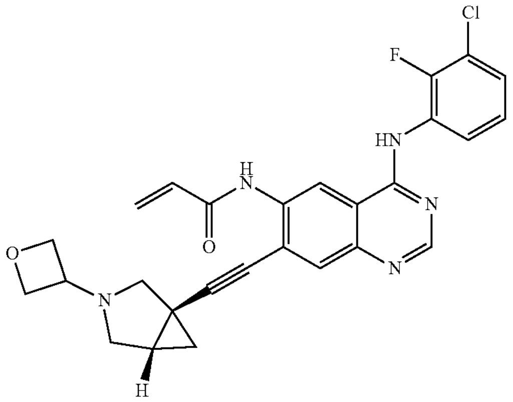 [SMILES: C=CC(=O)Nc1cc2c(Nc3cccc(Cl)c3F)ncnc2cc1C#C[C@@]12C[C@@H]1CN(C1COC1)C2] |
| 51 | 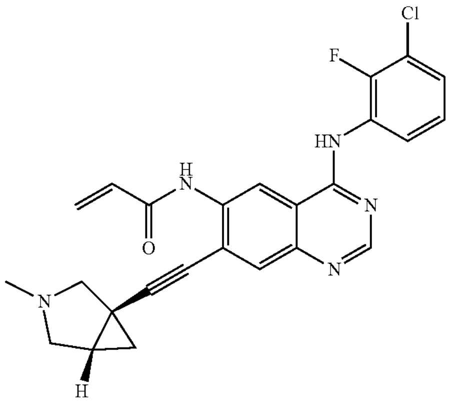 [SMILES: C=CC(=O)Nc1cc2c(Nc3cccc(Cl)c3F)ncnc2cc1C#C[C@@]12C[C@@H]1CN(C)C2] |
| 52 | 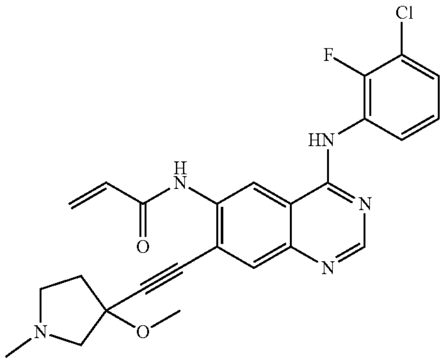 [SMILES: C=CC(=O)Nc1cc2c(Nc3cccc(Cl)c3F)ncnc2cc1C#CC1(OC)CCN(C)C1] |
| 53 | 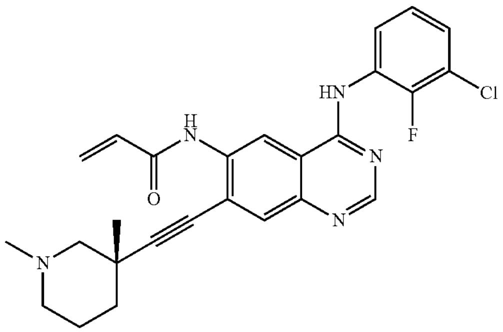 [SMILES: C=CC(=O)Nc1cc2c(Nc3cccc(Cl)c3F)ncnc2cc1C#C[C@]1(C)CCCN(C)C1] |

-continued
| Compound No. | Structure |
| --- | --- |
| 54 | 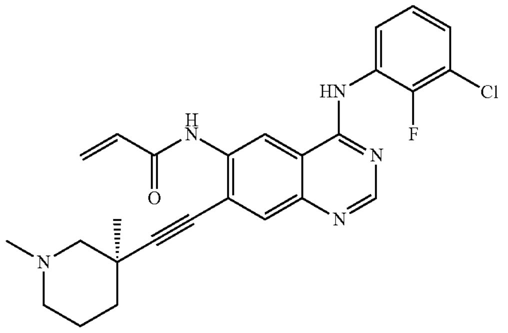 [SMILES: C=CC(=O)Nc1cc2c(Nc3cccc(Cl)c3F)ncnc2cc1C#C[C@@]1(C)CCCN(C)C1] |
| 55 | 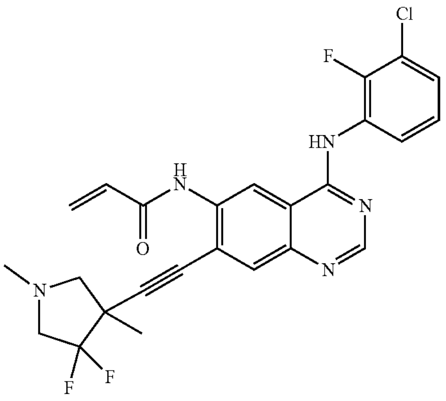 [SMILES: C=CC(=O)Nc1cc2c(Nc3cccc(Cl)c3F)ncnc2cc1C#CC1(C)CN(C)CC1(F)F] |
| 56 | 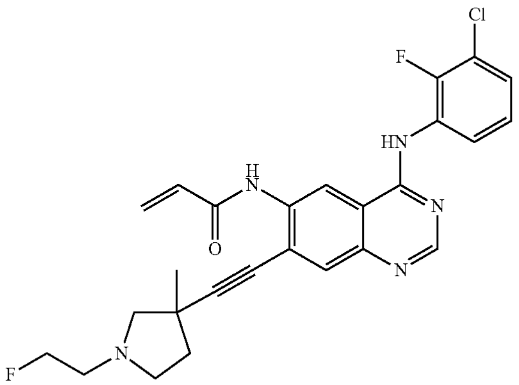 [SMILES: C=CC(=O)Nc1cc2c(Nc3cccc(Cl)c3F)ncnc2cc1C#CC1(C)CCN(CCF)C1] |
| 57 | 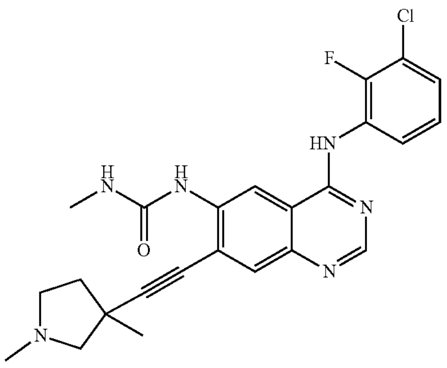 [SMILES: CNC(=O)Nc1cc2c(Nc3cccc(Cl)c3F)ncnc2cc1C#CC1(C)CCN(C)C1] |
-continued
| Compound No. | Structure |
| --- | --- |
| 58 | 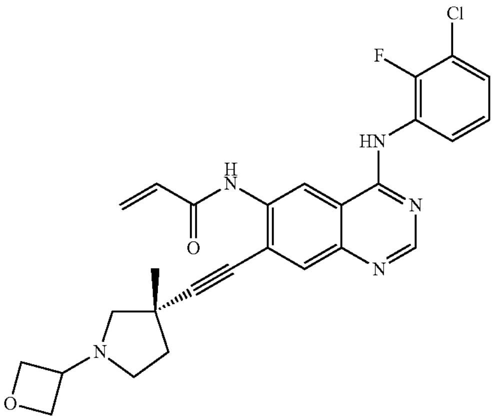 [SMILES: C=CC(=O)Nc1cc2c(Nc3cccc(Cl)c3F)ncnc2cc1C#C[C@]1(C)CCN(C2COC2)C1] |
| 59 | 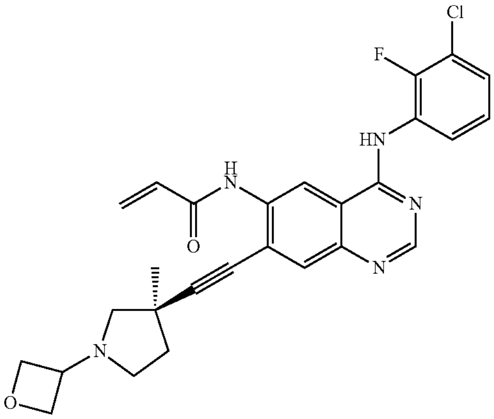 [SMILES: C=CC(=O)Nc1cc2c(Nc3cccc(Cl)c3F)ncnc2cc1C#C[C@@]1(C)CCN(C2COC2)C1] |
| 60 | 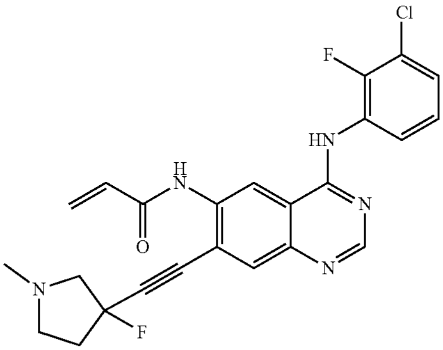 [SMILES: C=CC(=O)Nc1cc2c(Nc3cccc(Cl)c3F)ncnc2cc1C#CC1(F)CCN(C)C1] |
| 61 | 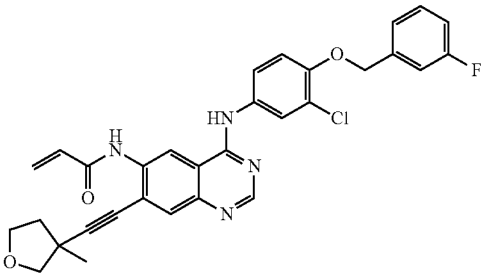 [SMILES: C=CC(=O)Nc1cc2c(Nc3ccc(OCc4cccc(F)c4)c(Cl)c3)ncnc2cc1C#CC1(C)CCOC1] |

-continued
| Compound No. | Structure |
| --- | --- |
| 62 | 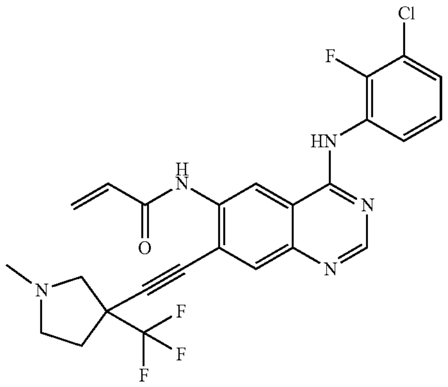 [SMILES: C=CC(=O)Nc1cc2c(Nc3cccc(Cl)c3F)ncnc2cc1C#CC1(C(F)(F)F)CCN(C)C1] |
| 63 | 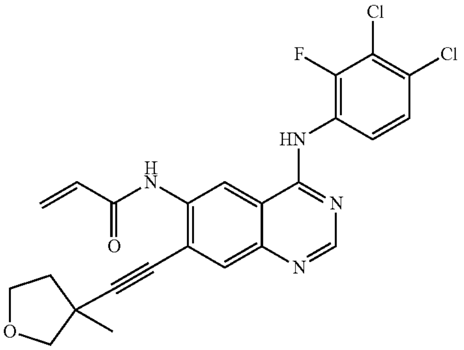 [SMILES: C=CC(=O)Nc1cc2c(Nc3ccc(Cl)c(Cl)c3F)ncnc2cc1C#CC1(C)CCOC1] |
| 64 | 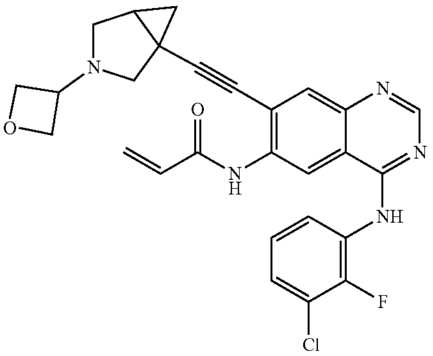 [SMILES: C=CC(=O)Nc1cc2c(Nc3cccc(Cl)c3F)ncnc2cc1C#CC12CC1CN(C1COC1)C2] |
| 65 | 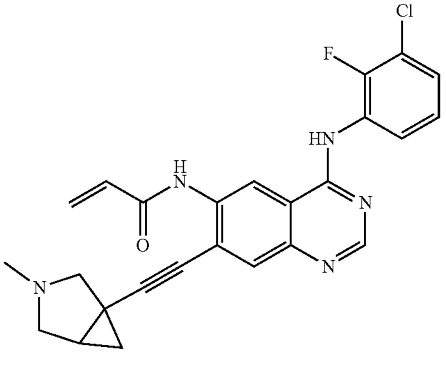 [SMILES: C=CC(=O)Nc1cc2c(Nc3cccc(Cl)c3F)ncnc2cc1C#CC12CC1CN(C)C2] |
-continued
| Compound No. | Structure |
| --- | --- |
| 66 | 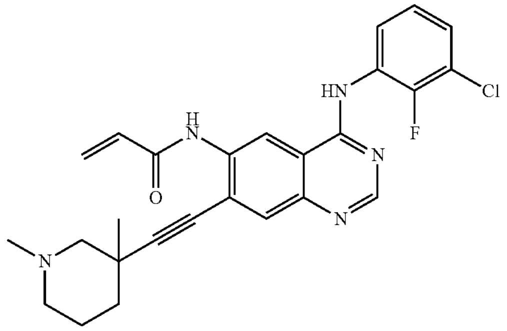 |
| 67 | 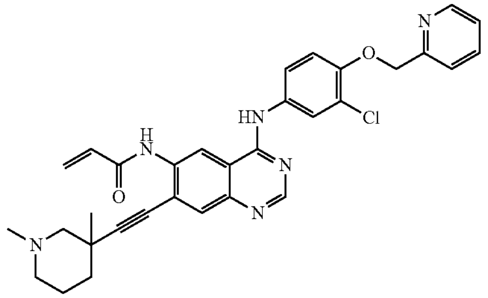 [SMILES: C=CC(=O)Nc1cc2c(Nc3ccc(OCc4ccccn4)c(Cl)c3)ncnc2cc1C#CC1(C)CCCN(C)C1] |
| 68 | 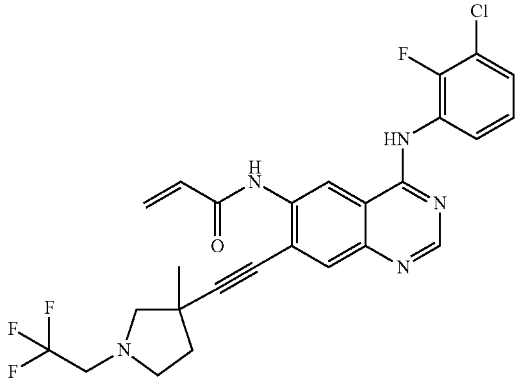 [SMILES: C=CC(=O)Nc1cc2c(Nc3cccc(Cl)c3F)ncnc2cc1C#CC1(C)CCN(CC(F)(F)F)C1] |
| 69 | 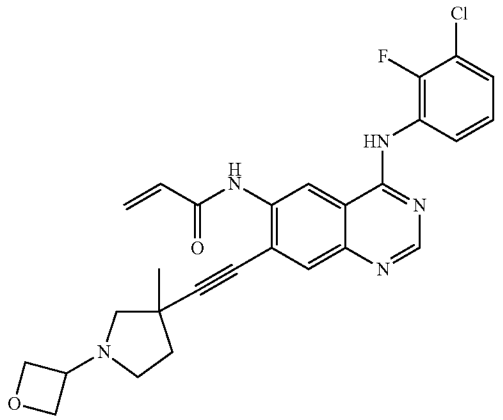 [SMILES: C=CC(=O)Nc1cc2c(Nc3cccc(Cl)c3F)ncnc2cc1C#CC1(C)CCN(C2COC2)C1]

-continued
| Compound No. | Structure |
|---|---|
| 70 | 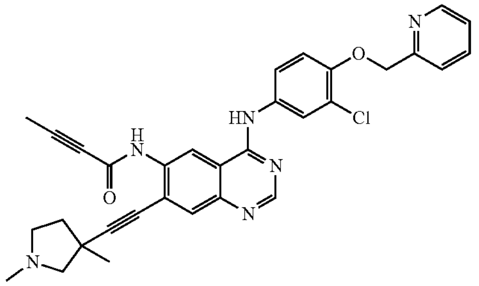 [SMILES: CC#CC(=O)Nc1cc2c(Nc3ccc(OCc4ccccn4)c(Cl)c3)ncnc2cc1C#CC1(C)CCN(C)C1] |
| 71 | 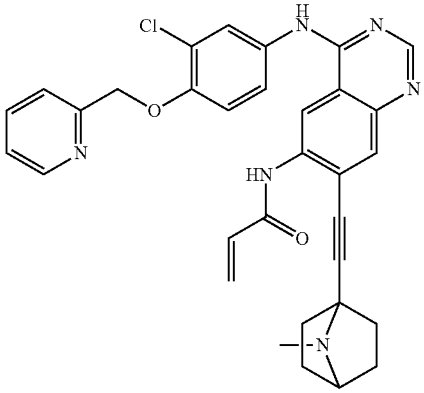 [SMILES: C=CC(=O)Nc1cc2c(Nc3ccc(OCc4ccccn4)c(Cl)c3)ncnc2cc1C#CC12CCC(CC1)N2C] |
| 72 | 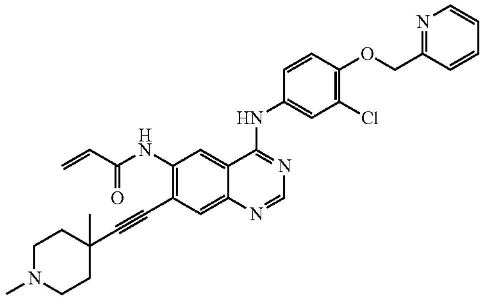 [SMILES: C=CC(=O)Nc1cc2c(Nc3ccc(OCc4ccccn4)c(Cl)c3)ncnc2cc1C#CC1(C)CCN(C)CC1] |
| 73 | 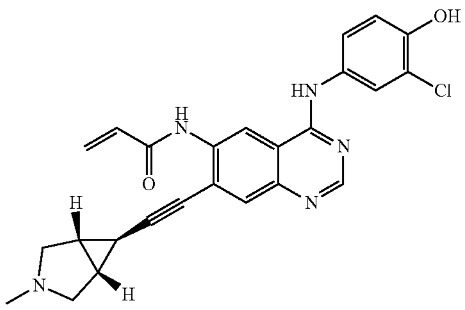 [SMILES: C=CC(=O)Nc1cc2c(Nc3ccc(O)c(Cl)c3)ncnc2cc1C#C[C@@H]1[C@H]2CN(C)C[C@@H]12] |
-continued
| Compound No. | Structure |
|---|---|
| 74 | 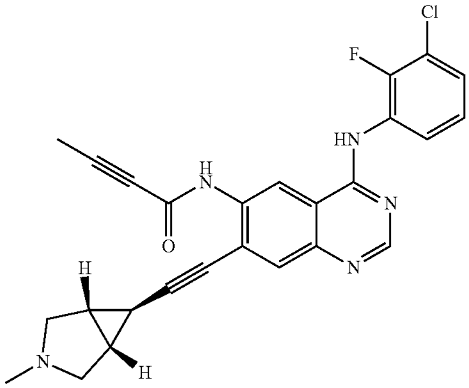 [SMILES: CC#CC(=O)Nc1cc2c(Nc3cccc(Cl)c3F)ncnc2cc1C#C[C@@H]1[C@H]2CN(C)C[C@@H]12] |
| 75 | 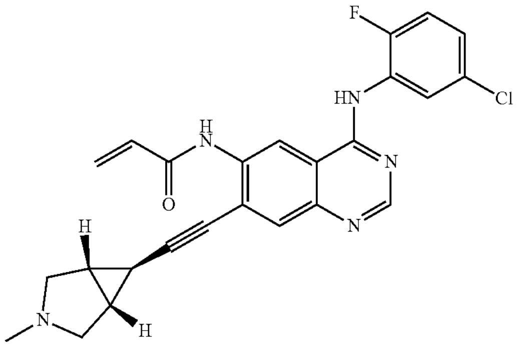 [SMILES: C=CC(=O)Nc1cc2c(Nc3cc(Cl)ccc3F)ncnc2cc1C#C[C@@H]1[C@H]2CN(C)C[C@@H]12] |
| 76 | 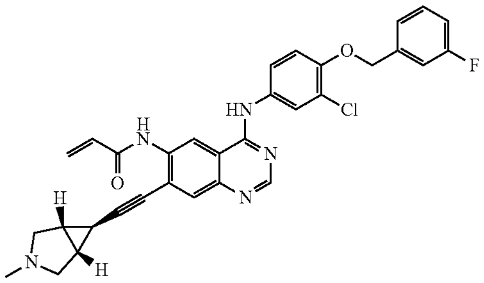 [SMILES: C=CC(=O)Nc1cc2c(Nc3ccc(OCc4cccc(F)c4)c(Cl)c3)ncnc2cc1C#C[C@@H]1[C@H]2CN(C)C[C@@H]12] |
| 77 | 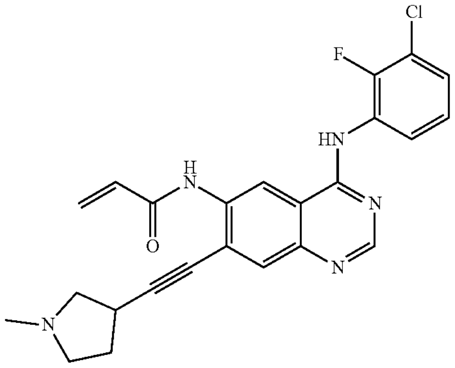 [SMILES: C=CC(=O)Nc1cc2c(Nc3cccc(Cl)c3F)ncnc2cc1C#CC1CCN(C)C1] |

-continued
| Compound No. | Structure |
| --- | --- |
| 78 | 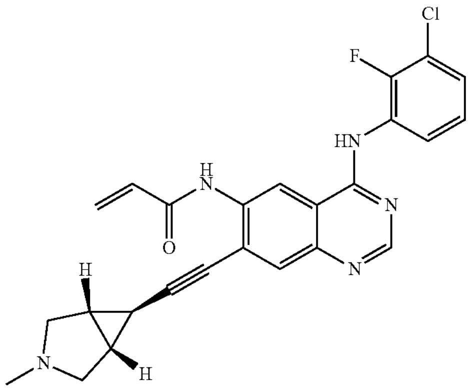 [SMILES: C=CC(=O)Nc1cc2c(Nc3cccc(Cl)c3F)ncnc2cc1C#C[C@@H]1[C@H]2CN(C)C[C@@H]12] |
| 79 | 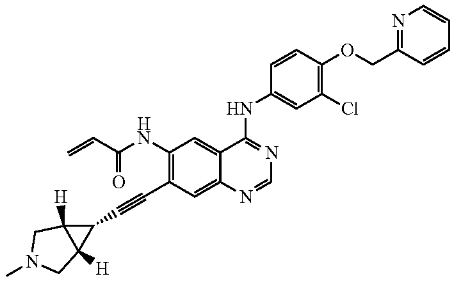 [SMILES: C=CC(=O)Nc1cc2c(Nc3ccc(OCc4ccccn4)c(Cl)c3)ncnc2cc1C#C[C@H]1[C@H]2CN(C)C[C@@H]12] |
| 80 | 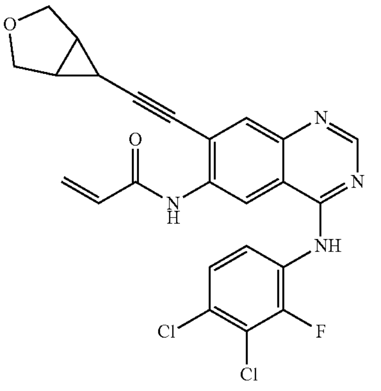 [SMILES: C=CC(=O)Nc1cc2c(Nc3ccc(Cl)c(Cl)c3F)ncnc2cc1C#CC1C2COCC12] |
| 81 | 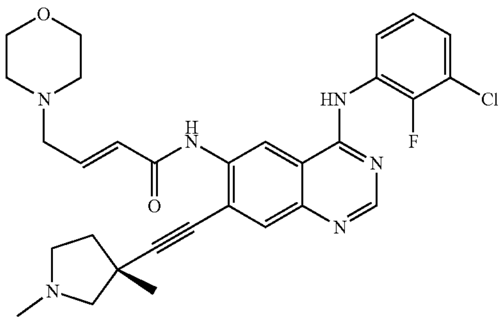 [SMILES: CN1CC[C@](C)(C#Cc2cc3ncnc(Nc4cccc(Cl)c4F)c3cc2NC(=O)/C=C/CN2CCOCC2)C1] |
| 82 | 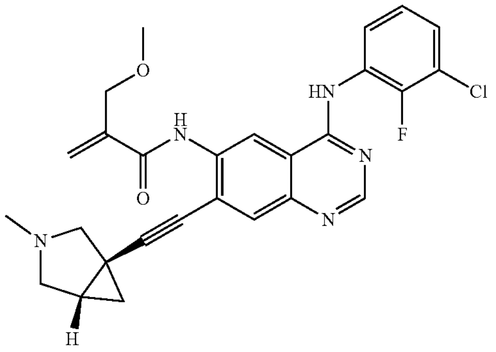 [SMILES: C=C(COC)C(=O)Nc1cc2c(Nc3cccc(Cl)c3F)ncnc2cc1C#C[C@@]12C[C@@H]1CN(C)C2] |
| 83 | 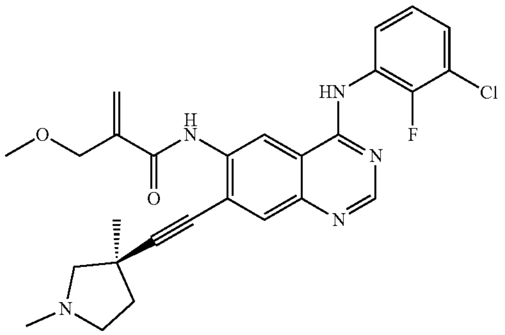 [SMILES: C=C(COC)C(=O)Nc1cc2c(Nc3cccc(Cl)c3F)ncnc2cc1C#C[C@@]1(C)CCN(C)C1] |
| 84 | 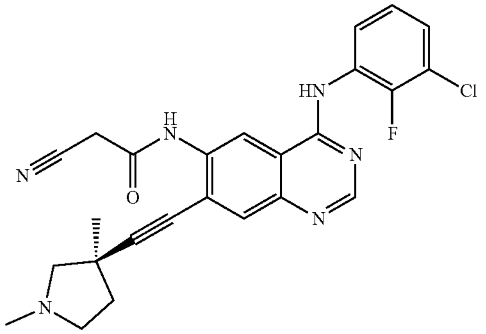 [SMILES: CN1CC[C@](C)(C#Cc2cc3ncnc(Nc4cccc(Cl)c4F)c3cc2NC(=O)CC#N)C1] |
and pharmaceutically acceptable salts thereof.
2. A composition comprising a compound of claim 1, and a pharmaceutically acceptable carrier.

3. A compound of which is (Compound No. 37)

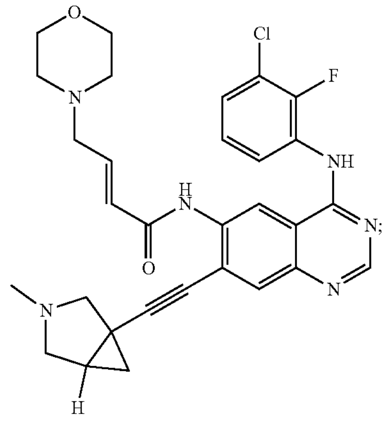

or a pharmaceutically acceptable salt thereof.

4. A composition comprising the compound of claim 3, and a pharmaceutically acceptable carrier.

5. A compound of which is (Compound No. 37A)

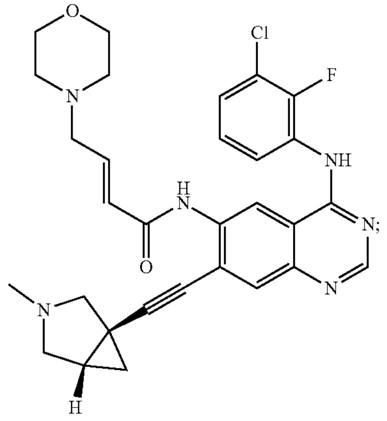

or a pharmaceutically acceptable salt thereof.

6. A composition comprising the compound of claim 5, and a pharmaceutically acceptable carrier.

7. The compound of claim 1, being which is (Compound No. 37B)

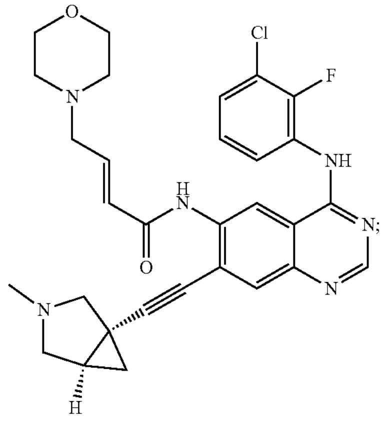

or a pharmaceutically acceptable salt thereof.

8. A composition comprising the compound of claim 7, and a pharmaceutically acceptable carrier.

9. A method of inhibiting an oncogenic variant of an ErbB receptor, comprising administering to a subject in need thereof a compound of claim 1.

10. A method of treating cancer, comprising administering to the subject a compound of claim 1.

11. The method of claim 10, wherein the cancer is a bladder cancer, a breast cancer, a cervical cancer, a colorectal cancer, an endometrial cancer, a gastric cancer, a glioblastoma (GBM), a head and neck cancer, a lung cancer, a non-small cell lung cancer (NSCLC), or any subtype thereof.

12. A method of inhibiting an oncogenic variant of an ErbB receptor, comprising administering to the subject in need thereof the compound of claim 3.

13. A method of treating cancer, comprising administering to the subject in need thereof the compound of claim 3.

14. The method of claim 13, wherein the cancer is a bladder cancer, a breast cancer, a cervical cancer, a colorectal cancer, an endometrial cancer, a gastric cancer, a glioblastoma (GBM), a head and neck cancer, a lung cancer, a non-small cell lung cancer (NSCLC), or any subtype thereof.

15. A method of inhibiting an oncogenic variant of an ErbB receptor, comprising administering to the subject in need thereof the compound of claim 5.

16. A method of treating cancer, comprising administering to the subject in need thereof the compound of claim 5.

17. The method of claim 16, wherein the cancer is a bladder cancer, a breast cancer, a cervical cancer, a colorectal cancer, an endometrial cancer, a gastric cancer, a glioblastoma (GBM), a head and neck cancer, a lung cancer, a non-small cell lung cancer (NSCLC), or any subtype thereof.

18. A method of inhibiting an oncogenic variant of an ErbB receptor, comprising administering to the subject in need thereof the compound of claim 7.

19. A method of treating cancer, comprising administering to the subject in need thereof the compound of claim 7.

20. The method of claim 19, wherein the cancer is a bladder cancer, a breast cancer, a cervical cancer, a colorectal cancer, an endometrial cancer, a gastric cancer, a glioblastoma (GBM), a head and neck cancer, a lung cancer, a non-small cell lung cancer (NSCLC), or any subtype thereof.

* * * * *